US012473331B2

(12) United States Patent
Lin et al.

(10) Patent No.: US 12,473,331 B2
(45) Date of Patent: *Nov. 18, 2025

(54) MACROCYCLIC COMPOUNDS AS PROTEASOME INHIBITORS

(71) Applicants: CORNELL UNIVERSITY, Ithaca, NY (US); TRI-INSTITUTIONAL THERAPEUTICS DISCOVERY INSTITUTE, New York, NY (US)

(72) Inventors: Gang Lin, Forest Hills, NY (US); Carl Nathan, Larchmont, NY (US); Laura Kirkman, New York, NY (US); Wenhu Zhan, Elmhurst, NY (US); Trevor Morgan, Royston (GB); Kenjiro Sato, Kanagawa (JP); Ryoma Hara, Tokyo (JP); Masanori Kawasaki, Tokyo (JP); Toshihiro Imaeda, Kanagawa (JP); Akinori Toita, Kanagawa (JP); Rei Okamoto, Kanagawa (JP); Takafumi Yukawa, Kanagawa (JP); Kazuyoshi Aso, Kanagawa (JP); Tzu-Tshin Wong, Acton, MA (US); John D. Ginn, New Milford, CT (US); Michael A. Foley, New York, NY (US)

(73) Assignees: CORNELL UNIVERSITY, Ithaca, NY (US); TRI-INSTITUTIONAL THERAPEUTICS DISCOVERY INSTITUTE, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/473,846

(22) Filed: Sep. 25, 2023

(65) Prior Publication Data

US 2024/0043470 A1 Feb. 8, 2024

Related U.S. Application Data

(63) Continuation of application No. 16/755,482, filed as application No. PCT/US2018/055493 on Oct. 11, 2018, now Pat. No. 11,834,515.

(Continued)

(51) Int. Cl.
*C07K 5/02* (2006.01)
*A61P 37/06* (2006.01)

(Continued)

(52) U.S. Cl.
CPC ............ *C07K 5/0215* (2013.01); *A61P 37/06* (2018.01); *C07K 11/02* (2013.01); *A61K 38/00* (2013.01)

(58) Field of Classification Search
CPC ....... C07K 5/0215; C07K 11/02; A61P 37/06; A61K 38/00
See application file for complete search history.

(56) References Cited

U.S. PATENT DOCUMENTS 11,834,515 B2 * 12/2023 Lin .......................... A61P 35/00
2009/0170878 A1 7/2009 Machauer (Continued)

FOREIGN PATENT DOCUMENTS

WO 01/81325 A2 11/2001
WO 2017/066763 A1 4/2017

OTHER PUBLICATIONS

Boger (Bioorganic & Medicinal Chemistry Letters (1993), 3(2), 245-250). (Year: 1993).*

(Continued)

*Primary Examiner* — Sudhakar Katakam
(74) *Attorney, Agent, or Firm* — Troutman Pepper Locke LLP

(57) ABSTRACT

The compounds of the present invention are represented by the following compounds having Formula I and Formula (I'):

(I)

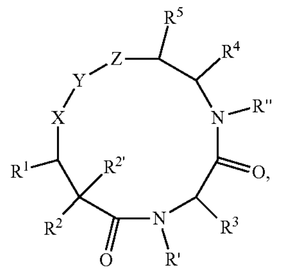

where the substituents $R^1$, $R^2$, $R^{2'}$, $R^3$, $R^4$, $R^5$, R', R'', X, Y, and Z are as defined herein and (I')

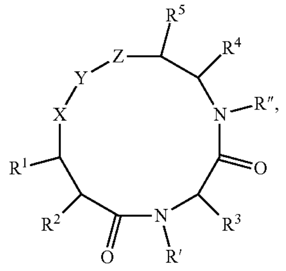

where the substituents $R^1$, $R^2$, $R^3$, $R^4$, $R^5$, R', R'', X, Y, and Z are as defined herein. These compounds are used in the treatment of bacterial infections, parasite infections, fungal infections, cancer, immunologic disorders, autoimmune disorders, neurodegenerative diseases and disorders, inflamma- (Continued)

tory disorders, or muscular dystrophy or for providing immunosuppression for transplanted organs or tissues.

14 Claims, 1 Drawing Sheet

Related U.S. Application Data

(60) Provisional application No. 62/571,163, filed on Oct. 11, 2017.

(51) Int. Cl.
*C07K 11/02* (2006.01)
*A61K 38/00* (2006.01)

(56) References Cited

U.S. PATENT DOCUMENTS

| | | | |
|---|---|---|---|
| 2010/0022500 | A1 | 1/2010 | Auberson et al. |
| 2014/0287992 | A1 | 9/2014 | Chen et al. |
| 2016/0130257 | A1 | 5/2016 | Sello |

OTHER PUBLICATIONS

Li (Journal of the American Chemical Society, 2014, 136(39), 13562-13565). (Year: 2014).*
International Search Report and Written Opinion for Application No. PCT/US2018/055493 (mailed Feb. 5, 2019).
International Preliminary Report on Patentability for Application No. PCT/US2018/055493 (Apr. 14, 2020).
Partial Supplementary European Search Report for Application No. 18866475.9 (Jul. 9, 2021).
Li et al., "Identification of Potent and Selective Non-Covalent Inhibitors of the Plasmodium Falciparum Proteasome," J. Am. Chem. Soc. 136(39):13562-13565 (2014).
Extended European Search Report for Application No. 18866475.9 (Oct. 21, 2021).
Patani et al., "Bioisosterism: A Rational Approach in Drug Design," Chem. Rev. 96:3147-3176 (1996).
Stella V.J., "Prodrugs: Some Thoughts and Current Issues," Journal of Pharmaceutical Sciences 99:4755-4765 (2010).

* cited by examiner

MACROCYCLIC COMPOUNDS AS PROTEASOME INHIBITORS

This application is a continuation of U.S. patent application Ser. No. 16/755,482, filed Apr. 10, 2020, which is a national stage application under 35 U.S.C. § 371 of PCT Application No. PCT/US2018/055493, filed Oct. 11, 2018, which claims the priority benefit of U.S. Provisional Patent Application Ser. No. 62/571,163, filed Oct. 11, 2017, which is hereby incorporated by reference in its entirety.

This invention was made with government support under R21 AI23794 awarded by National Institutes of Health. The government has certain rights in the invention.

FIELD OF THE INVENTION

The present invention relates to macrocyclic compounds as proteasome inhibitors.

BACKGROUND OF THE INVENTION

The proteasome is an ATP-dependent, self-compartmentalized protease in the cytosol and nucleus of eukaryotic cells, and is responsible for the degradation of the majority of cellular proteins (Baumeister et al., "The Proteasome: Paradigm of a Self-Compartmentalizing Protease," *Cell* 92:367-380 (1998); Goldberg, "Functions of the Proteasome: From Protein Degradation and Immune Surveillance to Cancer Therapy," *Biochem. Soc. Trans.* 35:12-17 (2007)). The proteasome controls many critical cellular checkpoints such as transcription factor activation and cell cycle progression and generates peptides for antigen presentation (Goldberg, "Functions of the Proteasome: From Protein Degradation and Immune Surveillance to Cancer Therapy," *Biochem. Soc. Trans.* 35:12-17 (2007); Rock et al., "Inhibitors of the Proteasome Block the Degradation of Most Cell Proteins and the Generation of Peptides Presented on MHC Class I Molecules," *Cell* 78:761-771 (1994)). Recently, proteasomes have shown to splice protein substrates to produce antigenic peptides (Liepe et al., "A Large Fraction of HLA Class I Ligands are Proteasome-Generated Spliced Peptides," *Science* 354:354-358 (2016)). Proteasome inhibitors limit the overall supply of peptides for MHC class I molecules and thus block antigen presentation (Rock et al., "Protein Degradation and the Generation of MHC Class I-Presented Peptides," *Adv. Immunol.* 80:1-70 (2002)). Inside c-20S reside two copies of each of three proteases with distinct specificities, β1c (caspase-like), β2c (tryptic-like), and β5c (chymotryptic-like) (Bedford et al., "Ubiquitin-Like Protein Conjugation and the Ubiquitin-Proteasome System as Drug Targets," *Nat. Rev. Drug Discov.* 10:29-46 (2011)). However, lymphocytes, cells at sites of inflammation and cells that have responded to interferon-γ (IFN-γ) express variable proportions of immunoproteasome (i-20S) subunits, in which the β1c, β2c, and/or β5c are replaced by β1i, β2i, and/or β5i, respectively (Tanaka, "Role of Proteasomes Modified by Interferon-Gamma in Antigen Processing," *J. Leukoc. Biol.* 56:571-575 (1994); Kim et al., "A Draft Map of the Human Proteome," *Nature* 509:575-581 (2014); Wilhelm et al., "Mass-Spectrometry-Based Draft of the Human Proteome," *Nature* 509:582-587 (2014); Van den Eynde et al., "Differential Processing of Class-I-Restricted Epitopes by the Standard Proteasome and the Immunoproteasome," *Curr. Opin. Immunol.* 13:147-153 (2001); Foss et al., "Interferon Regulatory Factor 1 Mediates the Interferon-Gamma Induction of the Human Immunoproteasome Subunit Multicatalytic Endopeptidase Complex-Like 1," *J. Biol. Chem.* 274:35196-35202 (1999); Griffin et al., "Immunoproteasome Assembly: Cooperative Incorporation of Interferon Gamma (IFN-Gamma)-Inducible Subunits," *J Exp. Med.* 187:97-104 (1998)). Recently, there have been reports that cells in retina and muscle can express high level of i-20S under certain conditions (Kimura et al., "New Insights into the Function of the Immunoproteasome in Immune and Nonimmune Cells," *J. Immunol. Res.* 2015: 541984 (2015)). I-20S principally functions at the interface between the innate and adaptive immune responses (Kruger et al., "Immunoproteasomes at the Interface of Innate and Adaptive Immune Responses: Two Faces of One Enzyme," *Curr. Opin. Immunol.* 24:77-83 (2012); Morel, "Processing of Some Antigens by the Standard Proteasome but not by the Immunoproteasome Results in Poor Presentation by Dendritic Cells," *Immunity* 12:107-117 (2000)). Intermediate proteasomes that contain mixed β subunits are found in many cells, for example in the mucosa of the colon and small bowel (Guillaume et al., "Two Abundant Proteasome Subtypes That Uniquely Process Some Antigens Presented by HLA Class I Molecules," *Proc. Natl. Acad. Sci. USA.* 107:18599-18604 (2010)). The difference between i-20S and c-20S include increased proteolytic activity and altered peptide preferences of the active sites (Rock et al., "Proteases in MHC Class I Presentation and Cross-Presentation," *J. Immunol.* 184: 9-15 (2010); Huber et al., "Immuno- and Constitutive Proteasome Crystal Structures Reveal Differences in Substrate and Inhibitor Specificity," *Cell* 148:727-738 (2012)). Mice with combined deficiency of β1i, β2i, and β5i are viable, fertile, and healthy but express a different antigenic peptide repertoire than wild type mice, as evidenced by their rejection of syngeneic wild type splenocytes (Kincaid et al., "Mice Completely Lacking Immunoproteasomes Show Major Changes in Antigen Presentation," *Nat. Immunol.* 13:129-135 (2012)). Mice lacking i-20S subunits are immunocompetent, though they have enhanced susceptibility to coxsackievirus B3 (Opitz et al., "Impairment of Immunoproteasome Function by beta5i/LMP7 Subunit Deficiency Results in Severe Enterovirus Myocarditis," *PLoS Pathog.* 7:e1002233 (2011)), *Toxoplasma gondii* (Tu et al., "Critical Role for the Immunoproteasome Subunit LMP7 in the Resistance of Mice to *Toxoplasma gondii* Infection," *Eur. J. Immunol.* 39:3385-3394 (2009)), and *Listeria monocytogenes* (Strehl et al., "Immunoproteasomes are Essential for Clearance of *Listeria Monocytogenes* in Nonlymphoid Tissues but not for Induction Of Bacteria-Specific Cd8+ T Cells," *J. Immunol.* 177:6238-44 (2006)). Proteasomes control activation of NF-κB, co-translocation of TLR9 and Unc93B1 to endosomes (Hirai et al., "Bortezomib Suppresses Function and Survival of Plasmacytoid Dendritic Cells by Targeting Intracellular Trafficking of Toll-like Receptors and Endoplasmic Reticulum Homeostasis," *Blood* 117:500-509 (2011)). They also control diverse cellular functions, among them signal transduction for inflammatory cytokine release, antigen presentation, and the ability of plasma cells to secrete antibodies without dying from accumulation of misfolded immunoglobulins (Goldberg, "Functions of the Proteasome: From Protein Degradation and Immune Surveillance to Cancer Therapy," *Biochem. Soc. Trans.* 35:12-17 (2007); Bedford et al., "Ubiquitin-Like Protein Conjugation and the Ubiquitin-Proteasome System as Drug Targets," *Nat. Rev. Drug Discov.* 10:29-46 (2011); Neubert et al., "The Proteasome Inhibitor Bortezomib Depletes Plasma Cells and Protects Mice With Lupus-Like Disease From Nephritis," *Nat. Med* 14:748-755 (2008)). Thus, the proteasome could be an attractive target for treating autoimmune and inflammatory diseases. However, c-20S is essential and its inhibition leads to apoptosis. Inhibitors that do not discriminate between c-20S and i-20S can be expected to be toxic and this has been borne out in the clinic. Selective inhibition of the i-20S impacts the immune system but otherwise is far less toxic than combined inhibition of both c-20S and i-20S (Fan et al., "Oxathiazolones Selectively Inhibit the Human Immunoproteasome over the Constitutive Proteasome," *ACS Med Chem. Lett.* 5:405-410 (2014); Muchamuel et al., "A Selective Inhibitor of the Immunoproteasome Subunit LMP7 Blocks Cytokine Production and Attenuates Progression of Experimental Arthritis," *Nat. Med* 15:781-787 (2009); Sula et al., "Brief Treatment With a Highly Selective Immunoproteasome Inhibitor Promotes Long-Term Cardiac Allograft Acceptance in Mice," *PNAS* 113(52): E8425-E8432 (2016)).

There are many chemical classes of proteasome inhibitors (Huber et al., "Inhibitors for the Immuno- and Constitutive Proteasome: Current and Future Trends in Drug Development," *Angew. Chem. Int. Ed. Engl.* 51:8708-8720 (2012); Kisselev, "Joining the Army of Proteasome Inhibitors," *Chem. Biol.* 15:419-421 (2008); Kisselev et al., "Proteasome Inhibitors: an Expanding Army Attacking a Unique Target," *Chem. Biol.* 19:99-115 (2012)). The FDA has approved three proteasome inhibitors, Bortezomib (BTZ), Carfilzomib (CFZ), and Ixazomib (IXZ), for treatment of hematologic neoplasms (Moreau et al., "Proteasome Inhibitors in Multiple Myeloma: 10 years later," *Blood* 120:947-59 (2012)). All three equally potently inhibit β5c and β5i (Huber et al., "Inhibitors for the Immuno- and Constitutive Proteasome: Current and Future Trends in Drug Development," *Angew. Chem. Int. Ed. Engl.* 51:8708-8720 (2012)). BTZ and IXZ are dipeptidyl boronates, which are covalent, slow-binding, reversible inhibitors. CFZ is a peptide with an epoxyketone warhead that inhibits proteasomes irreversibly (Huber et al., "Inhibitors for the Immuno- and Constitutive Proteasome: Current and Future Trends in Drug Development," *Angew. Chem. Int. Ed. Engl.* 51:8708-8720 (2012)). BTZ has been effective in mouse models of IBD, SLE, GvHD, antibody-mediated graft rejection, RA, and MS, where its efficacy has been attributed to inhibition of immunoproteasomes (Neubert et al., "The Proteasome Inhibitor Bortezomib Depletes Plasma Cells and Protects Mice With Lupus-Like Disease From Nephritis," *Nat. Med.* 14:748-755 (2008); Raghavan et al., "Bortezomib in Kidney Transplantation," *J. Transplant.* 2010: 698594 (2010); Frohlich et al., "Successful Use of Bortezomib in a Patient With Systemic Lupus Erythematosus and Multiple Myeloma," *Ann. Rheum. Dis.* 70:1344-1345 (2011)). However, BTZ is toxic to nerves, bone marrow, and other organs.

Species selective proteasome inhibitors have been reported (Hu et al., "Structure of the *Mycobacterium Tuberculosis* Proteasome and Mechanism of Inhibition by a Peptidyl Boronate," *Mol. Microbiol.* 59:1417-1428 (2006); Li et al., "Structural Basis for the Assembly and Gate Closure Mechanisms of the *Mycobacterium Tuberculosis* 20S Proteasome," *Embo J.* 29:2037-2047 (2010); Lin et al., "N,C-Capped Dipeptides With Selectivity for Mycobacterial Proteasome Over Human Proteasomes: Role of S3 and S1 Binding Pockets," *J Am Chem Soc.* 135:9968-9971 (2013); Lin et al., "*Mycobacterium Tuberculosis* prcBA Genes Encode a Gated Proteasome With Broad Oligopeptide Specificity," *Mol. Microbiol.* 59:1405-1416 (2006); Lin et al., "Fellutamide B is a Potent Inhibitor of the *Mycobacterium Tuberculosis* Proteasome," *Arch. Biochem. Biophys.* 501:214-220 (2010); Lin et al., "Inhibitors Selective for Mycobacterial Versus Human Proteasomes," *Nature* 461 (7264):621-626 (2009); Lin et al., "Distinct Specificities of *Mycobacterium Tuberculosis* and Mammalian Proteasomes for N-Acetyl Tripeptide Substrates," *J. Biol. Chem.* 283: 34423-31 (2008)).

Several macrocyclic compounds were reported as 20S proteasome inhibitors. For example, Wilson et al., "Synthesis and Evaluation of Macrocyclic Peptide Aldehydes as Potent and Selective Inhibitors of the 20S Proteasome," *ACS Med. Chem. Lett.* 7:250-5 (2016) reported macrocyclic peptide aldehydes as β5 inhibitor of human constitutive proteasome. Chiba et al., "Total Synthesis of Syringolin A and Improvement of its Biological Activity," *Angew. Chem. Int. Ed.* 53:4836-9 (2014), Clerc et al., "The Natural Product Hybrid of Syringolin A and Glidobactin A Synergizes Proteasome Inhibition Potency with Subsite Selectivity," *Chem. Commun.* 47:385-7 (2011), Clerc et al., "Synthetic and Structural Studies on Syringolin A and B Reveal Critical Determinants of Selectivity and Potency of Proteasome Inhibition," *Proc. Natl. Acad. Sci. U.S.A.* 106: 6507-6512 (2009), and Clerc et al., "Syringolin A Selectively Labels the 20S Proteasome in Murine EL4 and Wild-Type and Bortezomib-Adapted Leukaemic Cell Lines," *ChemBioChem* 10:2638-2643 (2009) reported syringolin A that selectively inhibits β5 and β2 of human proteasome acting as a Michael acceptor. Koguchi et al., "TMC-95A, B, C, and D, Novel Proteasome Inhibitors Produced by Apiospora Montagnei Sacc. TC 1093. Taxonomy, Production, Isolation, and Biological Activities," *J. Antibiot.* (*Tokyo*) 53:105-109 (2000) reported the discovery of TMC-95A, a novel human proteasome inhibitor, from fermentation broth of Apiospora montagnei Sacc. TC1093. Li et al., "Identification of Potent and Selective Non-Covalent Inhibitors of the *Plasmodium Falciparum* Proteasome," *J. Am. Chem. Soc.* 136(39): 13562-13565(2014) reported a macrocyclic peptide that is highly selective for malarial proteasome.

As shown by the above references, the proteasome represents an important target for therapeutic intervention of various disorders. Thus, there is an ongoing need for new and/or improved proteasome inhibitors.

The present invention is directed to overcoming these and other deficiencies in the art.

SUMMARY OF THE INVENTION

A first aspect of the present invention relates to a compound of Formula (I):

(I)

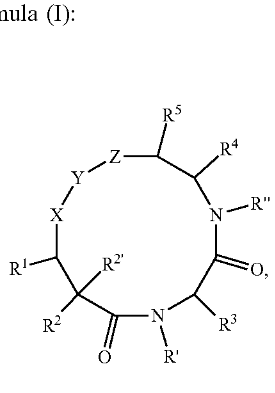

wherein

X is $-(CH_2)_m-$; $-CH_2-CH{=}CH-$, or

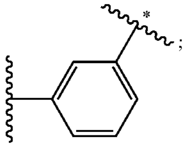 [SMILES: *c1cccc(*)c1]

Y is $-CH_2-$ or O;

Z is $-(CH_2)_m-$,

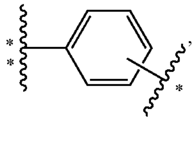

$-CH_2-CH_2-O-$, $CH_2-CH{=}CH-$, or O;

is the point of attachment to $-C(R^1)-$ moiety;

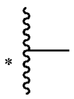

is the point of attachment to Y;

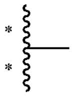

is the point of attachment to $-C(R^5)-$ moiety;

$R^1$ is H;

$R^2$ is independently selected at each occurrence thereof from the group consisting of H, $C_{1-6}$ alkyl, arylalkyl, $-NR^6R^7$, $-NHC(O)R^8$, $-NHS(O)_2R^8$, and $-NHC(O)(CH_2)_nNR^6R^7$;

$R^{2'}$ is H or $C_{1-6}$ alkyl;

$R^3$ is independently selected at each occurrence thereof from the group consisting of H, $C_{1-6}$ alkyl, $-(CH_2)_nNR^6R^7$, $-CH_2C(O)NR^6R^7$, $-CH_2C(O)OH$, and arylalkyl, wherein $C_{1-6}$ alkyl or arylalkyl can be optionally substituted from 1 to 3 times with halogen, $C_{1-6}$ alkoxy, —O-aryl, and $CF_3$;

$R^4$ is selected from the group consisting of $R^9$, $-C(O)R^9$, $-C(O)NH(CR^aR^b)_nR^8$, $-C(O)N(Me)(CR^aR^b)_nR^8$, $-C(O)OH$, $-C(O)CH_2Ph$, $-C(O)OR^9$, $-CH_2NHR^8$, and $-C(O)NR^6R^7$;

$R^5$ is H;

$R^6$ and $R^7$ are each independently selected from the group consisting of H, $C_{1-6}$ alkyl, $C_{3-8}$ cycloalkyl, and $C_{3-12}$ cycloalkylalkyl, or, wherein $C_{3-8}$ cycloalkyl and $C_{3-12}$ cycloalkylalkyl can be optionally substituted from 1 to 3 times with $CF_3$;

or $R^6$ and $R^7$ are taken together with the nitrogen to which they are attached to form a piperidine, pyrrolidine, morpholine ring, piperazine, oxazolidine, or isothiazolidine, wherein piperidine, pyrrolidine, morpholine, piperazine, oxazolidine, or isothiazolidine ring can be optionally substituted 1 to 3 times with halogen, $C_{1-6}$ alkyl, aryl, =O, $C_{3-8}$ cycloalkyl, or non-aromatic heterocycle;

$R^8$ is selected from the group consisting of H, OH, $CF_3$, $CHF_2$, $C_{1-12}$ alkyl, $C_{3-8}$ cycloalkyl, $C_{3-12}$ cycloalkylalkyl, $C_{1-12}$ alkoxy, monocyclic or bicyclic aryl, arylalkyl, and heteroaryl, heterocyclyl, and non-aromatic heterocycle, wherein $C_{1-12}$ alkyl, $C_{3-8}$ cycloalkyl, $C_{3-12}$ cycloalkylalkyl, monocyclic or bicyclic aryl, arylalkyl, and heteroaryl, heterocyclyl, and non-aromatic heterocycle can be optionally substituted from 1 to 3 times with OH, halogen, $C_{1-6}$ alkyl, $C_{1-6}$ alkoxy, $CHF_2$, $CF_3$, $-S(O)_2Me$;

$R^9$ is selected from the group consisting of OH, $CF_3$, $CHF_2$, $C_{1-12}$ alkyl, $C_{3-8}$ cycloalkyl, $C_{3-12}$ cycloalkylalkyl, $C_{1-12}$ alkoxy, monocyclic or bicyclic aryl, and heteroaryl, wherein $C_{1-12}$ alkyl, $C_{3-8}$ cycloalkyl, $C_{3-12}$ cycloalkylalkyl, monocyclic or bicyclic aryl, arylalkyl, and heteroaryl, can be optionally substituted from 1 to 3 times with OH, halogen, $C_{1-6}$ alkyl, $C_{1-6}$ alkoxy, $CHF_2$, $CF_3$, $-S(O)_2Me$;

$R^a$ and $R^b$ are each independently selected from the group consisting of H and $C_{1-6}$ alkyl;

R' and R" are each independently selected from the group consisting of H and $C_{1-6}$ alkyl;

n is 0, 1, 2, 3, or 4; and m is independently selected at each occurrence from the group consisting of 2, 3, 4, and 5, with the proviso that i) $R^2$ is not $NH_2$, ii) $R^4$ is not

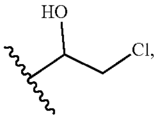 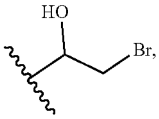 or 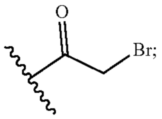

iii) when $R^4$ is COOH, then $R^3$ is not

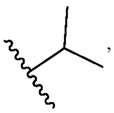, 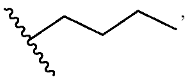, or

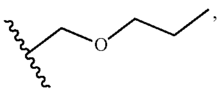, and iv) when $R^4$ is COOMe, then $R^3$ is not

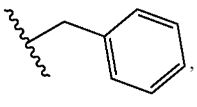 [SMILES: *Cc1ccccc1], or an oxide thereof, a pharmaceutically acceptable salt thereof, a solvate thereof, or a prodrug thereof.

A second aspect of the present invention relates to a compound of Formula (II):

(II)

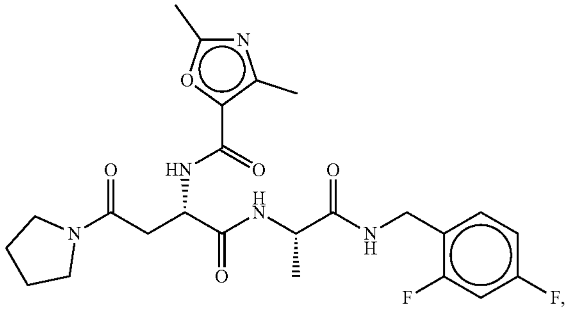

or an oxide thereof, a pharmaceutically acceptable salt thereof, a solvate thereof, or a prodrug thereof.

A third aspect of the present invention relates to a compound of Formula (III):

(III)

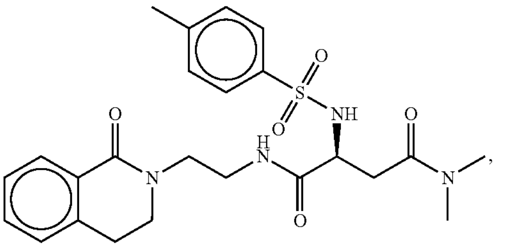

or an oxide thereof, a pharmaceutically acceptable salt thereof, a solvate thereof, or a prodrug thereof.

A fourth aspect of the present invention relates to a method of treating bacterial infections, parasite infections, fungal infections, cancer, immunologic disorders, autoimmune disorders, neurodegenerative diseases and disorders, inflammatory disorders, or muscular dystrophy, in a subject or for achieving immunosuppression in transplanted organs or tissues in a subject. This method includes administering to the subject in need thereof a compound according to any aspect of the present invention.

A fifth aspect of the present invention relates to a method of inhibiting proteasome activity. This method includes contacting a proteasome with a compound according to any aspect of the present invention under conditions effective to inhibit proteasome activity.

DETAILED DESCRIPTION OF THE INVENTION

Figures 1A, 1B:
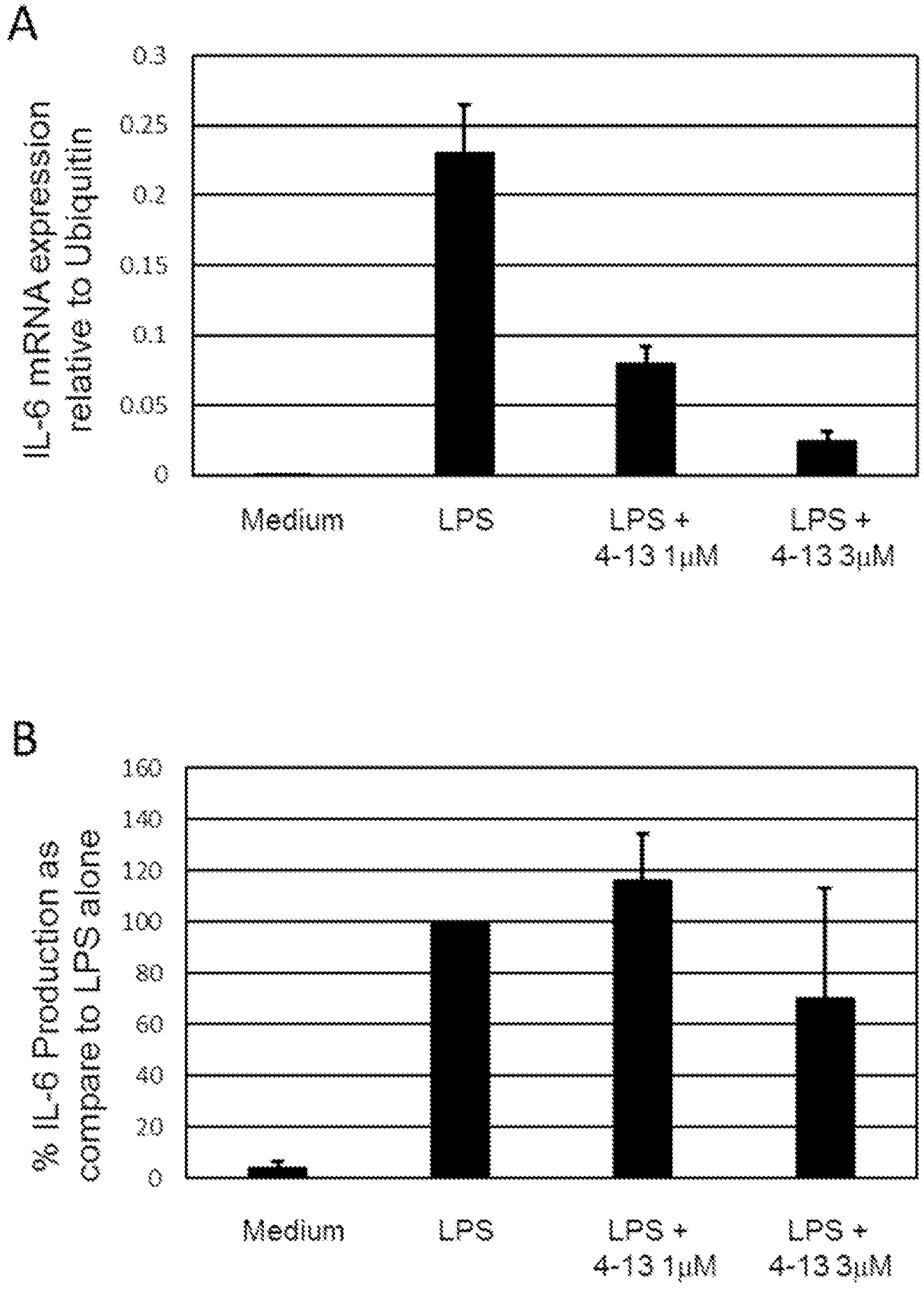
FIGS. 1A-1B are graphs showing inhibition of IL-6 in LPS-stimulated human macrophages by compound 4-13.

A first aspect of the present invention relates to a compound of Formula (I):

(I)

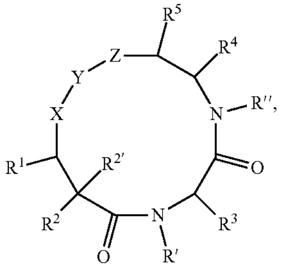

wherein

X is $-(CH_2)_m-$; $-CH_2-CH=CH-$, or

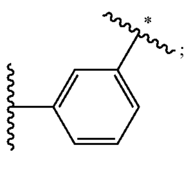 [SMILES: *c1cccc(*)c1]

Y is $-CH_2-$ or O;

Z is $-(CH_2)_m-$,

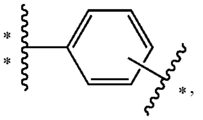

$-CH_2-CH_2-O-$, $CH_2-CH=CH-$, or O;

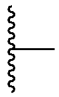

is the point of attachment to $-C(R^1)-$ moiety;

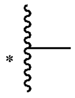

is the point of attachment to Y;

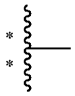

is the point of attachment to —C($R^5$)— moiety;

$R^1$ is H;

$R^2$ is independently selected at each occurrence thereof from the group consisting of H, $C_{1-6}$ alkyl, arylalkyl, —$NR^6R^7$, —NHC(O)$R^8$, —NHS$(O)_2R^8$, and —NHC(O)$(CH_2)_nNR^6R^7$;

$R^{2'}$ is H or $C_{1-6}$ alkyl;

$R^3$ is independently selected at each occurrence thereof from the group consisting of H, $C_{1-6}$ alkyl, —$(CH_2)_nNR^6R^7$, —$CH_2C(O)NR^6R^7$, —$CH_2C(O)OH$, and arylalkyl, wherein $C_{1-6}$ alkyl or arylalkyl can be optionally substituted from 1 to 3 times with halogen, $C_{1-6}$ alkoxy, —O-aryl, and $CF_3$;

$R^4$ is selected from the group consisting of $R^9$, —C(O)$R^9$, —C(O)NH$(CR^aR^b)_nR^8$, —C(O)N(Me)$(CR^aR^b)_nR^8$, —C(O)OH, —C(O)$CH_2$Ph, —C(O)O$R^9$, —$CH_2NHR^8$, and —C(O)$NR^6R^7$;

$R^5$ is H;

$R^6$ and $R^7$ are each independently selected from the group consisting of H, $C_{1-6}$ alkyl, $C_{3-8}$ cycloalkyl, and $C_{3-12}$ cycloalkylalkyl, or, wherein $C_{3-8}$ cycloalkyl and $C_{3-12}$ cycloalkylalkyl can be optionally substituted from 1 to 3 times with $CF_3$;

or $R^6$ and $R^7$ are taken together with the nitrogen to which they are attached to form a piperidine, pyrrolidine, morpholine ring, piperazine, oxazolidine, or isothiazolidine, wherein piperidine, pyrrolidine, morpholine, piperazine, oxazolidine, or isothiazolidine ring can be optionally substituted 1 to 3 times with halogen, $C_{1-6}$ alkyl, aryl, =O, $C_{3-8}$ cycloalkyl, or non-aromatic heterocycle;

$R^8$ is selected from the group consisting of H, OH, $CF_3$, $CHF_2$, $C_{1-12}$ alkyl, $C_{3-8}$ cycloalkyl, $C_{3-12}$ cycloalkylalkyl, $C_{1-12}$ alkoxy, monocyclic or bicyclic aryl, arylalkyl, and heteroaryl, heterocyclyl, and non-aromatic heterocycle, wherein $C_{1-12}$ alkyl, $C_{3-8}$ cycloalkyl, $C_{3-12}$ cycloalkylalkyl, monocyclic or bicyclic aryl, arylalkyl, and heteroaryl, heterocyclyl, and non-aromatic heterocycle can be optionally substituted from 1 to 3 times with OH, halogen, $C_{1-6}$ alkyl, $C_{1-6}$ alkoxy, $CHF_2$, $CF_3$, —$S(O)_2$Me;

$R^9$ is selected from the group consisting of OH, $CF_3$, $CHF_2$, $C_{1-12}$ alkyl, $C_{3-8}$ cycloalkyl, $C_{3-12}$ cycloalkylalkyl, $C_{1-12}$ alkoxy, monocyclic or bicyclic aryl, and heteroaryl, wherein $C_{1-12}$ alkyl, $C_{3-8}$ cycloalkyl, $C_{3-12}$ cycloalkylalkyl, monocyclic or bicyclic aryl, arylalkyl, and heteroaryl, can be optionally substituted from 1 to 3 times with OH, halogen, $C_{1-6}$ alkyl, $C_{1-6}$ alkoxy, $CHF_2$, $CF_3$, —$S(O)_2$Me;

$R^a$ and $R^b$ are each independently selected from the group consisting of H and $C_{1-6}$ alkyl;

R' and R" are each independently selected from the group consisting of H and $C_{1-6}$ alkyl;

n is 0, 1, 2, 3, or 4; and m is independently selected at each occurrence from the group consisting of 2, 3, 4, and 5, with the proviso that i) $R^2$ is not $NH_2$, ii) $R^4$ is not

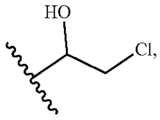, 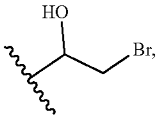, or 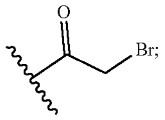;

iii) when $R^4$ is COOH, then $R^3$ is not

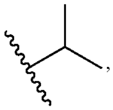, 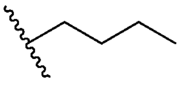, or 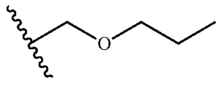, and iv) when $R^4$ is COOMe, then $R^3$ is not

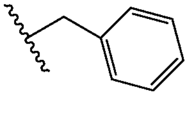, or an oxide thereof, a pharmaceutically acceptable salt thereof, a solvate thereof, or a prodrug thereof.

As used above, and throughout the description herein, the following terms, unless otherwise indicated, shall be understood to have the following meanings. If not defined otherwise herein, all technical and scientific terms used herein have the same meaning as is commonly understood by one of ordinary skill in the art to which this technology belongs. In the event that there is a plurality of definitions for a term herein, those in this section prevail unless stated otherwise.

The term "alkyl" means an aliphatic hydrocarbon group which may be straight or branched having about 1 to about 12 carbon atoms in the chain. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, and 3-pentyl.

The term "cycloalkyl" means a non-aromatic mono- or multicyclic ring system of about 3 to about 12 carbon atoms, preferably of about 3 to about 8 carbon atoms. Exemplary monocyclic cycloalkyls include cyclopentyl, cyclohexyl, cycloheptyl, bicyclo[1.1.1]pentyl, and the like.

The term "cycloalkylalkyl" means a cycloalkyl-alkyl-group in which the cycloalkyl and alkyl are as defined herein. Exemplary cycloalkylalkyl groups include cyclopropylmethyl, cyclobutylmethyl, cyclopentylmethyl, cyclopropylethyl, cyclobutylethyl, and cyclopentylethyl. The alkyl radical and the cycloalkyl radical may be optionally substituted as defined herein.

The term "aryl" means an aromatic monocyclic or multicyclic ring system of 6 to about 14 carbon atoms, preferably of 6 to about 10 carbon atoms. Representative aryl groups include phenyl and naphthyl.

The term "arylalkyl" means an alkyl substituted with one or more aryl groups, wherein the alkyl and aryl groups are as herein described. One particular example is an arylmethyl or arylethyl group, in which a single or a double carbon spacer unit is attached to an aryl group, where the carbon spacer and the aryl group can be optionally substituted as described herein. Representative arylalkyl groups include

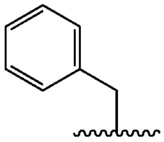, 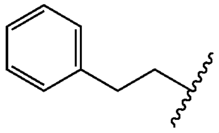, and

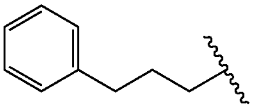

The term "heteroaryl" means an aromatic monocyclic or multicyclic ring system of about 5 to about 14 ring atoms, preferably about 5 to about 10 ring atoms, in which one or more of the atoms in the ring system is/are element(s) other than carbon, for example, nitrogen, oxygen, or sulfur. In the case of multicyclic ring system, only one of the rings needs to be aromatic for the ring system to be defined as "Heteroaryl". Preferred heteroaryls contain about 5 to 6 ring atoms. The prefix aza, oxa, thia, or thio before heteroaryl means that at least a nitrogen, oxygen, or sulfur atom, respectively, is present as a ring atom. A nitrogen atom of a heteroaryl is optionally oxidized to the corresponding N-oxide. Representative heteroaryls include pyridyl, 2-oxo-pyridinyl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, 2-oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, and the like.

As used herein, "heterocyclyl" refers to a stable 3- to 18-membered ring (radical) which consists of carbon atoms and from one to five heteroatoms selected from the group consisting of nitrogen, oxygen and sulfur. For purposes of this application, the heterocycle may be a monocyclic, or a polycyclic ring system, which may include fused, bridged, or spiro ring systems; and the nitrogen, carbon, or sulfur atoms in the heterocycle may be optionally oxidized; the nitrogen atom may be optionally quaternized; and the ring may be partially or fully saturated. Examples of such heterocycles include, without limitation, azepinyl, azocanyl, pyranyl dioxanyl, dithianyl, 1,3-dioxolanyl, tetrahydrofuryl, dihydropyrrolidinyl, decahydroisoquinolyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, 2-oxoazepinyl, oxazolidinyl, oxiranyl, piperidinyl, piperazinyl, 4-piperidonyl, pyrrolidinyl, pyrazolidinyl, thiazolidinyl, tetrahydropyranyl, thiamorpholinyl, thiamorpholinyl sulfoxide, and thiamorpholinyl sulfone. Further heterocycles and heteroaryls are described in Katritzky et al., eds., *Comprehensive Heterocyclic Chemistry: The Structure, Reactions, Synthesis and Use of Heterocyclic Compounds*, Vol. 1-8, Pergamon Press, N.Y. (1984), which is hereby incorporated by reference in its entirety.

The term "non-aromatic heterocycle" means a non-aromatic monocyclic or multicyclic system containing 3 to 10 atoms, preferably 4 to about 7 carbon atoms, in which one or more of the atoms in the ring system is/are element(s) other than carbon, for example, nitrogen, oxygen, or sulfur. Representative non-aromatic heterocycle groups include pyrrolidinyl, 2-oxopyrrolidinyl, piperidinyl, 2-oxopiperidinyl, azepanyl, 2-oxoazepanyl, 2-oxooxazolidinyl, morpholino, 3-oxomorpholino, thiomorpholino, 1,1-dioxothiomorpholino, piperazinyl, tetrohydro-2H-oxazinyl, and the like.

The term "monocyclic" used herein indicates a molecular structure having one ring.

The term "polycyclic" or "multi-cyclic" used herein indicates a molecular structure having two or more rings, including, but not limited to, fused, bridged, or spiro rings.

Terminology related to "protecting", "deprotecting," and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes described herein, the person of ordinary skill can readily envision those groups that would be suitable as "protecting groups." Suitable groups for that purpose are discussed in standard textbooks in the field of chemistry, such as Greene, *Protective Groups in Organic Synthesis*, John Wiley & Sons, New York (1991), which is hereby incorporated by reference in its entirety.

The term "alkoxy" means groups of from 1 to 12 carbon atoms of a straight, branched, or cyclic configuration and combinations thereof attached to the parent structure through an oxygen. Examples include methoxy, ethoxy, propoxy, isopropoxy, cyclopropyloxy, cyclohexyloxy, and the like. Lower-alkoxy refers to groups containing one to four carbons. For the purposes of the present patent application, alkoxy also includes methylenedioxy and ethylenedioxy in which each oxygen atom is bonded to the atom, chain, or ring from which the methylenedioxy or ethylenedioxy group is pendant so as to form a ring. Thus, for example, phenyl substituted by alkoxy may be, for example,

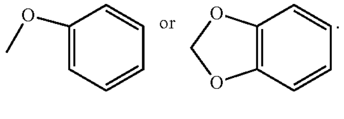

A compound with a hydroxy group drawn next to a nitrogen on a heterocycle can exist as the "keto" form. For example, 3-(2-hydroxy-[1,2,4]triazolo[1,5-a]pyridin-6-yl) propanoic acid can exist as 3-(2-oxo-2,3-dihydro-[1,2,4]triazolo[1,5-a]pyridin-6-yl)propanoic acid.

The term "halogen" means fluoro, chloro, bromo, or iodo.

The term "substituted" or "substitution" of an atom means that one or more hydrogen on the designated atom is replaced with a selection from the indicated group, provided that the designated atom's normal valency is not exceeded.

"Unsubstituted" atoms bear all of the hydrogen atoms dictated by their valency. When a substituent is keto (i.e., =O), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The term "optionally substituted" is used to indicate that a group may have a substituent at each substitutable atom of the group (including more than one substituent on a single atom), provided that the designated atom's normal valency is not exceeded and the identity of each substituent is independent of the others. Up to three H atoms in each residue are replaced with alkyl, halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy.

The term "method of treating" means amelioration or relief from the symptoms and/or effects associated with the disorders described herein. As used herein, reference to "treatment" of a patient is intended to include prophylaxis.

The term "compounds of the invention", and equivalent expressions, are meant to embrace compounds of general Formula (I), Formula (I'), Formula (I'a), Formula (I'b), Formula (I'c), Formula (II), and Formula (III) as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

The term "pharmaceutically acceptable salts" means the relatively non-toxic, inorganic, and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulphamates, malonates, salicylates, propionates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates and quinateslaurylsulphonate salts, and the like (see, for example, Berge et al., "Pharmaceutical Salts," *J. Pharm. Sci.,* 66:1-9 (1977) and Remington's Pharmaceutical Sciences, 17th ed., Mack Publishing Company, Easton, Pa., 1985, p. 1418, which are hereby incorporated by reference in their entirety). Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include, for example, sodium hydride, sodium hydroxide, potassium hydroxide, calcium hydroxide, aluminium hydroxide, lithium hydroxide, magnesium hydroxide, and zinc hydroxide. Suitable amine base addition salts are prepared from amines which have sufficient basicity to form a stable salt, and preferably include those amines which are frequently used in medicinal chemistry because of their low toxicity and acceptability for medical use, such as ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylarnine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, dicyclohexylamine, and the like.

The term "pharmaceutically acceptable prodrugs" as used herein means those prodrugs of the compounds useful according to the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" means compounds that are rapidly transformed in vivo to yield the parent compound of the above formula, for example by hydrolysis in blood. Functional groups which may be rapidly transformed, by metabolic cleavage, in vivo form a class of groups reactive with the carboxyl group of the compounds of this invention. They include, but are not limited to, such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: *Design of Prodrugs*, H. Bundgaard, ed., Elsevier (1985); *Methods in Enzymology*, K. Widder et al, Ed., Academic Press, 42, p. 309-396 (1985); *A Textbook of Drug Design and Development*, Krogsgaard-Larsen and H. Bundgaard, ed., Chapter 5; "Design and Applications of Prodrugs" p. 113-191 (1991); *Advanced Drug Delivery Reviews*, H. Bundgard, 8, p. 1-38 (1992); *J. Pharm. Sci.,* 77:285 (1988); Nakeya et al, *Chem. Pharm. Bull.,* 32:692 (1984); Higuchi et al., "Pro-drugs as Novel Delivery Systems," Vol. 14 of the *A.C.S. Symposium Series, and Bioreversible Carriers in Drug Design*, Edward B. Roche, ed., American Pharmaceutical Association and Pergamon Press (1987), which are incorporated herein by reference in their entirety. Examples of prodrugs include, but are not limited to, acetate, formate, and benzoate derivatives of alcohol and amine functional groups in the compounds of the invention.

The term "solvate" refers to a compound of Formula (I), Formula (I'), Formula (I'a), Formula (I'b), Formula (I'c), Formula (II), and Formula (III) in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

The term "therapeutically effective amounts" is meant to describe an amount of compound of the present invention effective to produce the desired therapeutic effect. Such amounts generally vary according to a number of factors well within the purview of ordinarily skilled artisans given the description provided herein to determine and account for. These include, without limitation: the particular subject, as well as its age, weight, height, general physical condition, and medical history; the particular compound used, as well as the carrier in which it is formulated and the route of administration selected for it; and, the nature and severity of the condition being treated.

The term "pharmaceutical composition" means a composition comprising a compound of Formula (I), Formula (I'), Formula (I'a), Formula (I'b), Formula (I'c), Formula (II), and Formula (III) and at least one component comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifingal agents, lubricating agents and dispensing agents, depending on the nature of the mode of administration and dosage forms. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monosterate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgement, suitable for use in contact with the cells of humans and lower animals without undue toxicity, irritation, allergic response and the like, and are commensurate with a reasonable benefit/risk ratio.

The term "pharmaceutically acceptable dosage forms" means dosage forms of the compound of the invention, and includes, for example, tablets, dragees, powders, elixirs, syrups, liquid preparations, including suspensions, sprays, inhalants tablets, lozenges, emulsions, solutions, granules, capsules, and suppositories, as well as liquid preparations for injections, including liposome preparations. Techniques and formulations generally may be found in Remington's Pharmaceutical Sciences, Mack Publishing Co., Easton, Pa., latest edition.

Compounds described herein may contain one or more asymmetric centers and may thus give rise to enantiomers, diastereomers, and other stereoisomeric forms. Each chiral center may be defined, in terms of absolute stereochemistry, as (R)- or (S)-. This technology is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

This technology also envisions the "quaternization" of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

In the characterization of some of the substituents, it is recited that certain substituents may combine to form rings. Unless stated otherwise, it is intended that such rings may exhibit various degrees of unsaturation (from fully saturated to fully unsaturated), may include heteroatoms and may be substituted with lower alkyl or alkoxy.

The general scheme for the synthesis of compounds of the present invention is shown in Scheme 1.

Scheme 1

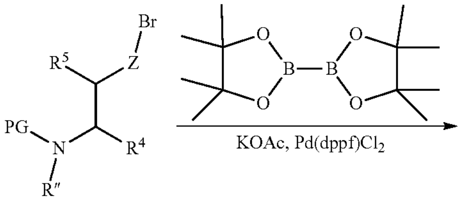

1

PG and PG* are protrcting groups

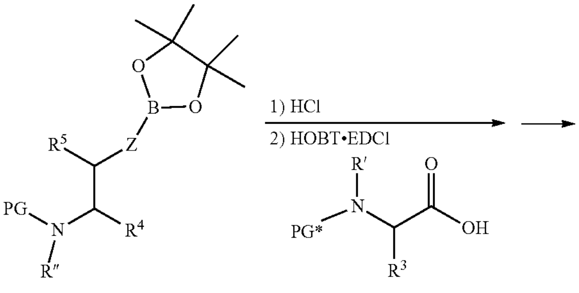

2

(3)

3) HCl

-continued

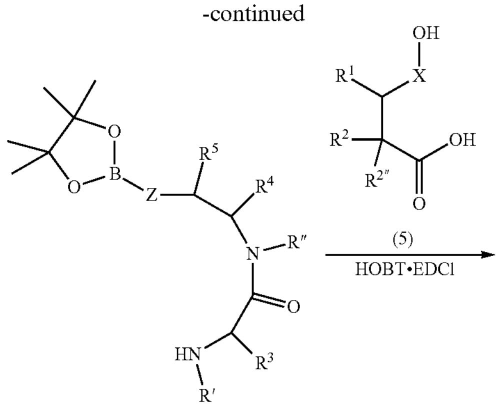

4

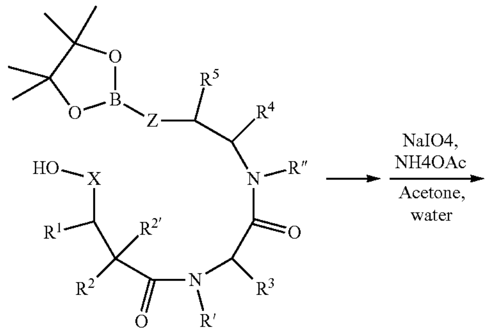

6

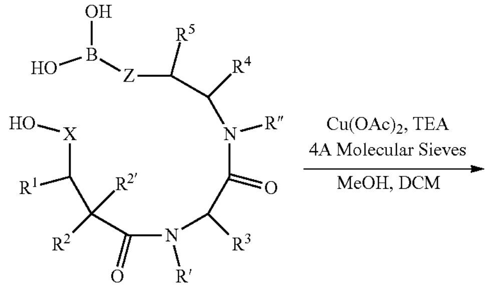

7

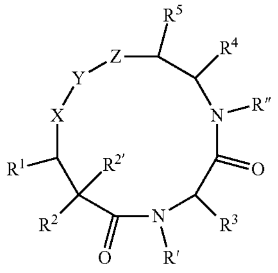

I

Borylation of compound 1 leads to formation of boronic ester 2. Following the deprotection, amine 2 was reacted with acid 3. The reaction can be carried out in a variety of solvents, for example in methylene chloride ($CH_2Cl_2$), tetrahydrofuran (THF), dimethylformamide (DMF), or other such solvents or in the mixture of such solvents. During the reaction process, the non-participating carboxylic acids or amines on the reacting set of amino acids or peptide fragments can be protected by a suitable protecting group (PG) which can be selectively removed at a later time if desired. A detailed description of these groups and their selection and chemistry is contained in "The Peptides, Vol. 3", Gross and Meinenhofer, Eds., Academic Press, New York, 1981, which is hereby incorporated by reference in its entirety. Thus, useful protective groups for the amino group are benzyloxycarbonyl (Cbz), t-butyloxycarbonyl (t-BOC), 2,2,2-trichloroethoxycarbonyl (Troc), t-amyloxycarbonyl, 4-methoxybenzyloxycarbonyl, 2-(trichlorosilyl)ethoxycarbonyl, 9-fluorenylmethoxycarbonyl (Fmoc), phthaloyl, acetyl (Ac), formyl, trifluoroacetyl, and the like. Deprotection of the formed product gave amino boronic-ester 4. Coupling of 4 with acid 5 leads to formation of hydroxyl-boronic ester 6. The reaction can be carried out in a variety of solvents, for example in methylene chloride ($CH_2Cl_2$), tetrahydrofuran (THF), dimethylformamide (DMF), or other such solvents or in the mixture of such solvents. During the reaction process, the non-participating carboxylic acids or amines on the reacting set of amino acids or peptide fragments can be protected by a suitable protecting group (PG) which can be selectively removed at a later time if desired. Reduction of boronic ester leads to formation of boronic acid 7. Intramolecular Chan-Lam coupling affords macrocycle of Formula (I).

The general scheme for the synthesis of compounds of the present invention with generalized structure A10 is shown in Scheme 1-1.

Scheme 1-1

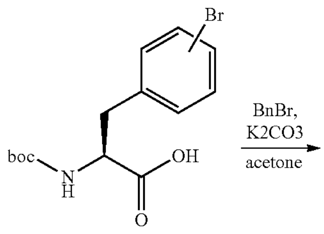

A1

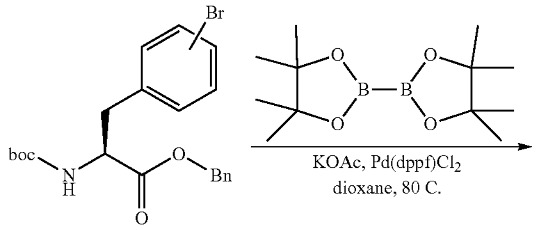

A2

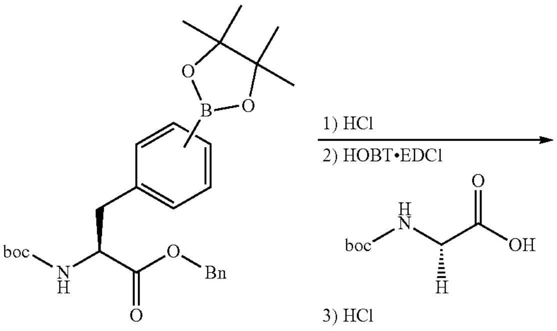

A3

-continued

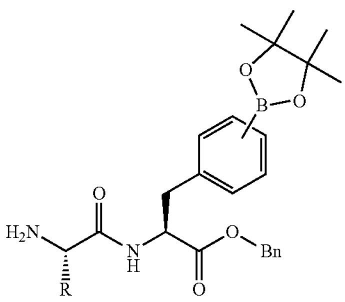

A4

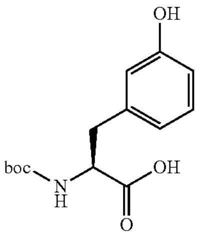

HOBT•EDCl

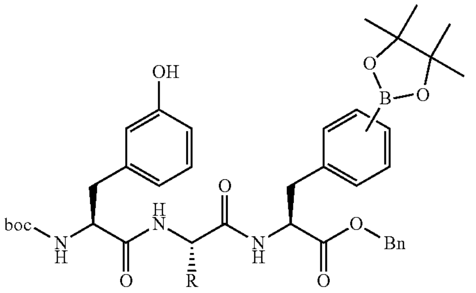

A5

NaIO4,
NH4OAc
Acetone,
water

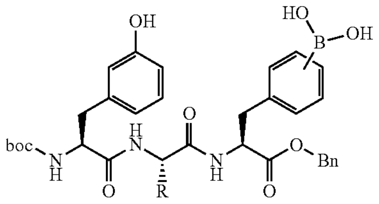

A6

Cu(OAc)2,
TEA
4A Molecular Sieves
MeOH, DCM

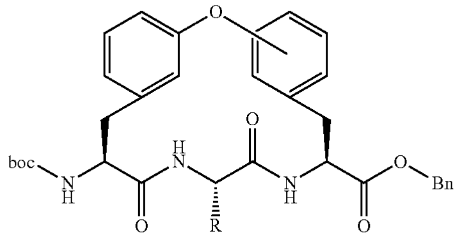

A7

NaIO4,
NH4OAc

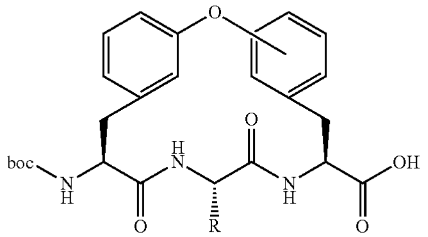

A8

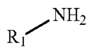

EDCl,
HOBT

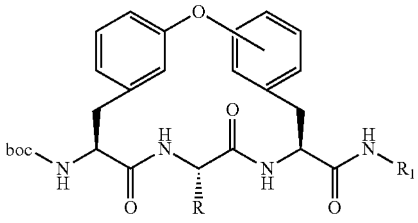

A9

1) HCl
2) TEA

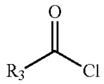

-continued

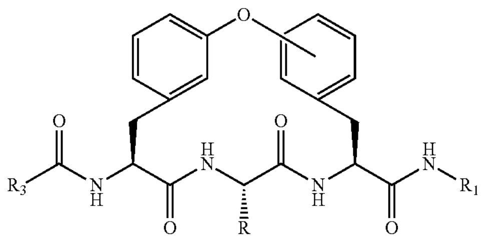

A10
(R = $CH_2CH_2Ph$)

Acid A1 was benzylated to give benzylester A2. Borylation of A2 afforded boronic ester A3. Boc deprotection and amide coupling with amino acid (with R side chain) followed by deprotection gave amino boronic-ester A4. Coupling of A4 with (S)-2-((tert-butoxycarbonyl)amino)-3-(3-hydroxyphenyl)propanoic acid led to formation of hydroxyl-boronic ester A5. Boronic ester was reduced to boronic acid and intramolecular Chan-Lam coupling afforded macrocycle A7. Debenzylation and amide coupling produced compound A9. Boc deprotection and amidation afforded product A10.

The general scheme for the synthesis of compounds of the present invention with generalized structure A12 is shown in Scheme 1a.

Scheme 1a

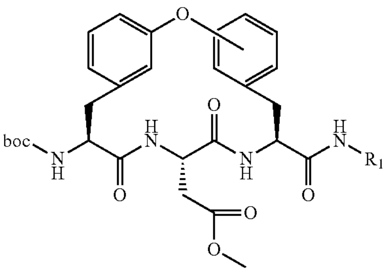

A9
(R = $CH_2CO_2Me$)

1) LiOH
2) EDCl, HOBT

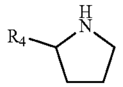

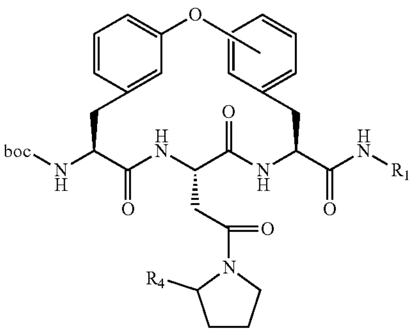

A11

1) HCl
2) TEA

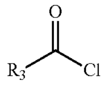

-continued

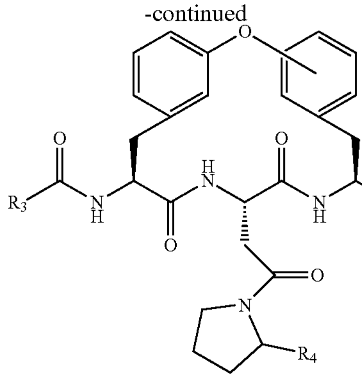

A12

Ester with general structure A9 was hydrolyzed. Resulting acid was coupled with amine to give amide A11. Deprotection and amide coupling afforded compounds with general structure A12.

Compounds of the present invention can also be prepared according to Scheme 2.

Scheme 2

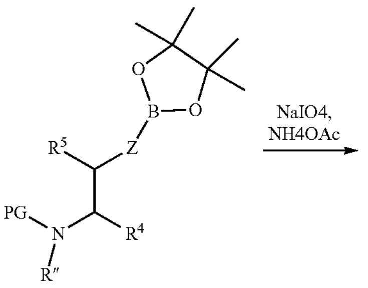

2
PG and PG*
are protrcting groups

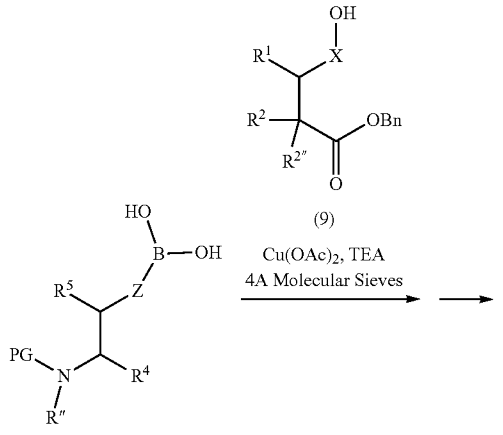

8

-continued

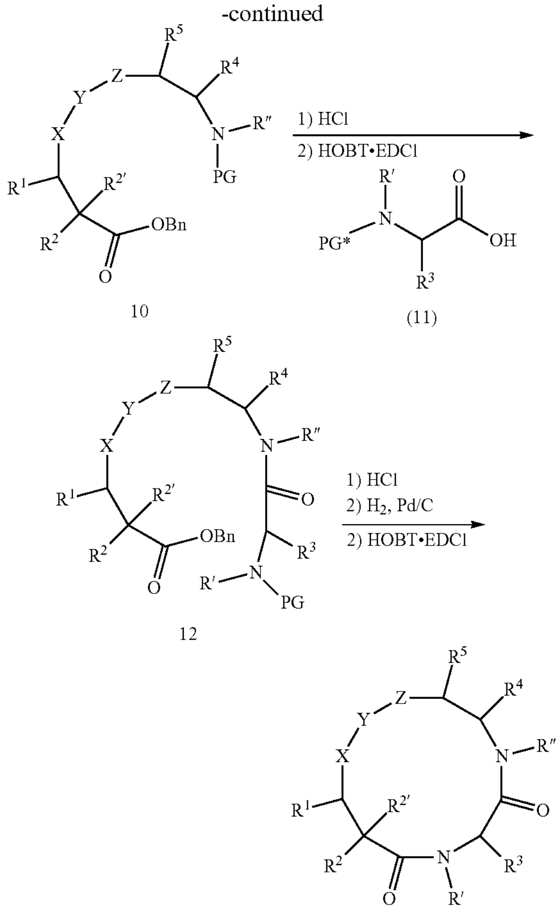

I

Hydrolysis of the boronic ester 2 leads to formation of boronic acid 8. Chan Lam reaction affords dibenzyl ether 10. Deprotection and amide coupling reactions lead to formation of compound 12. The reaction can be carried out in a variety of solvents, for example in methylene chloride ($CH_2Cl_2$), tetrahydrofuran (THF), dimethylformamide (DMF), or other such solvents or in the mixture of such solvents. During the synthetic sequence, the non-participating carboxylic acids or amines on the reacting set of amino acids or peptide fragments can be protected by a suitable protecting group (PG) which can be selectively removed at a later time if desired. A detailed description of these groups and their selection and chemistry is contained in "The Peptides, Vol. 3", Gross and Meinenhofer, Eds., Academic Press, New York, 1981, which is hereby incorporated by reference in its entirety. Thus, useful protective groups for the amino group are benzyloxycarbonyl (Cbz), t-butyloxycarbonyl (t-BOC), 2,2,2-trichloroethoxycarbonyl (Troc), t-amyloxycarbonyl, 4-methoxybenzyloxycarbonyl, 2-(trichlorosilyl)ethoxycarbonyl, 9-fluorenylmethoxycarbonyl (Fmoc), phthaloyl, acetyl (Ac), formyl, trifluoroacetyl, and the like. Stepwise deprotection followed by amide coupling affords macrocycle of Formula (I). The reaction can be carried out in a variety of solvents, for example in methylene chloride ($CH_2Cl_2$), tetrahydrofuran (THF), dimethylformamide (DMF), or other such solvents or in the mixture of such solvents.

The general scheme for the synthesis of compounds of the present invention with generalized structure A17 is shown in Scheme 2-1.

Scheme 2-1

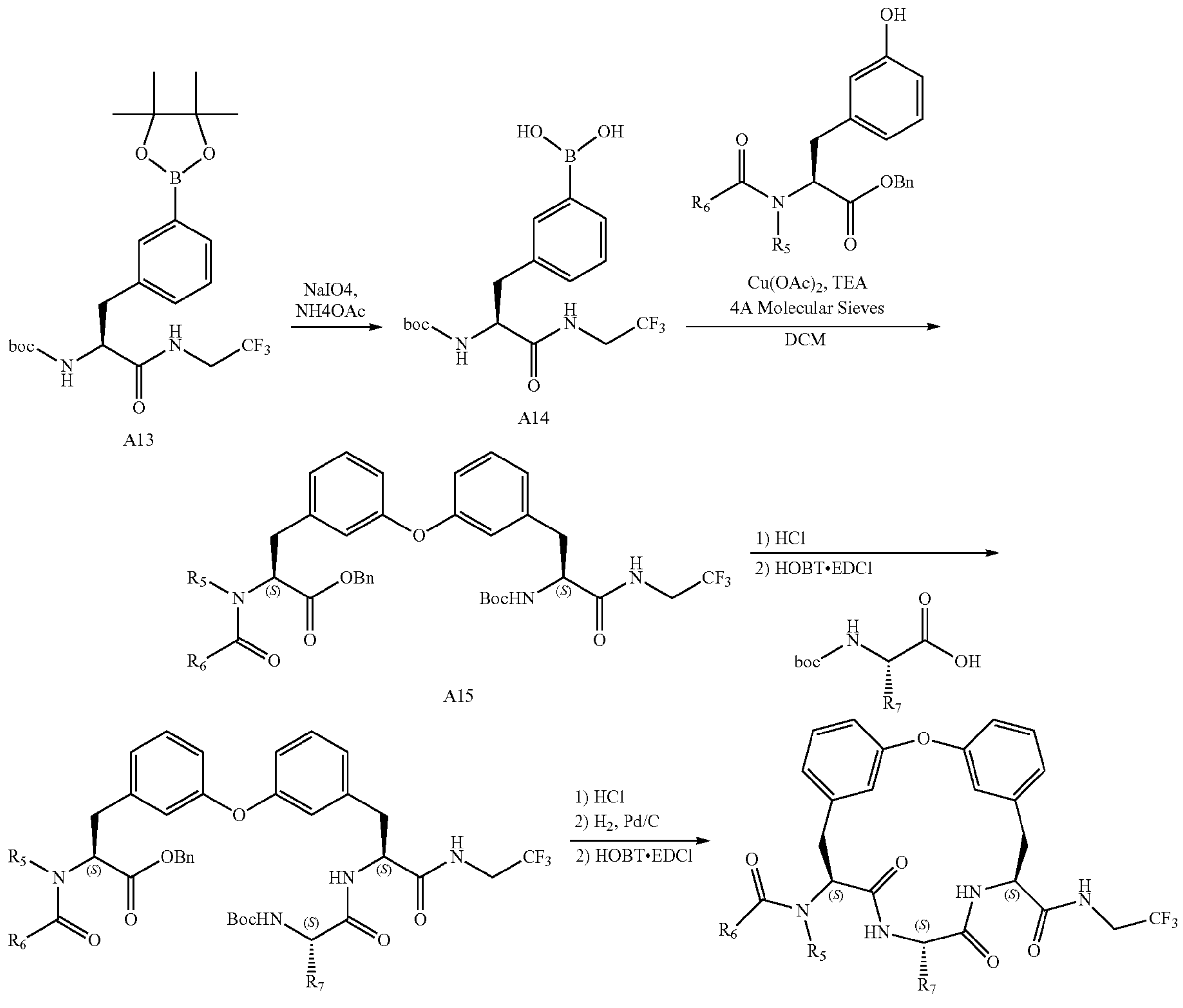

A13 A14 A15 A16 A17

Boronic ester A13 was hydrolized to boronic acid A14. Chan Lam reaction afforded dibenzyl ether A15. Boc deprotection and amide coupling reaction gave compound A16. Stepwise Boc and benzyl ester deprotection followed by amide coupling afforded product A17.

The general scheme for the synthesis of compounds of the present invention with generalized structure A20 is shown in Scheme 3a.

Scheme 3a

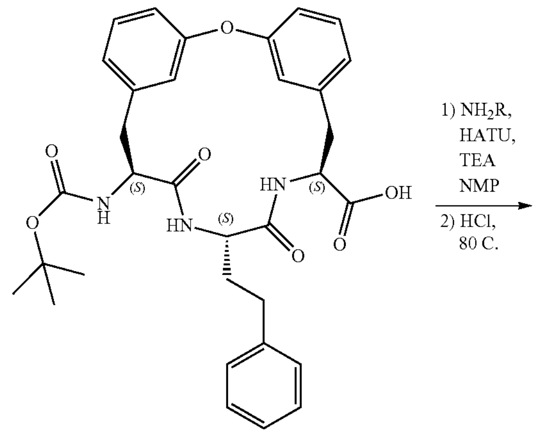

A18

-continued

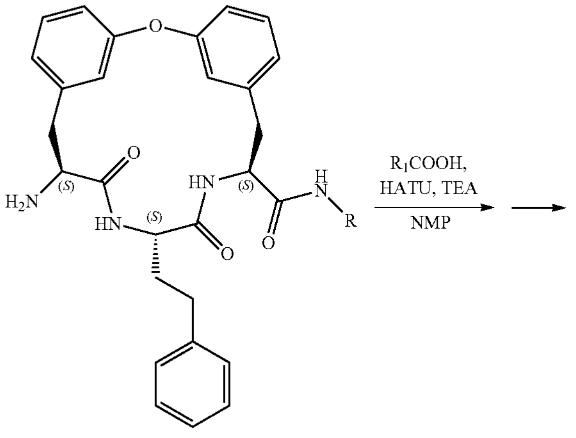

A19

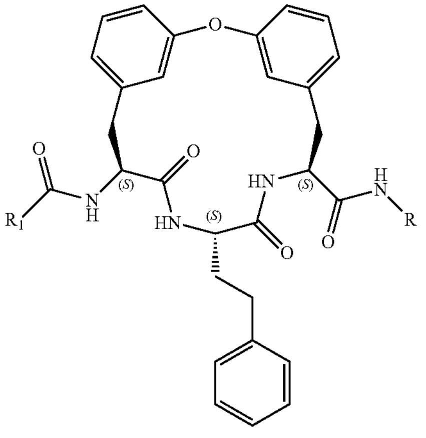

A20

NMP (0.4 ml) was added to (5S,8S,11S)-11-((tert-butoxy-carbonyl)amino)-7,10-dioxo-8-phenethyl-2-oxa-6,9-diaza-1,3(1,3)-dibenzenacyclododecaphane-5-carboxylic acid (A18) (10 mg, 0.017 mmol). Amine (0.017 mmol) and HATU (0.020 mmol) were then added followed by TEA (0.020 mmol). The reaction mixture was stirred at room temperature for 30 minutes. 4M HCl/dioxane (0.255 ml, 1.021 mmol) was added and the reaction mixture was heated to 80° C. for 3 hours. Intermediate A19 was isolated by passing through scx-2 (5 g), washing with MeOH (3*8 ml), and eluting with 2N ammonia MeOH (3*8 ml). Solvent was removed by evaporation. NMP (0.4 ml) and TEA (0.085 mmol) were then added. Carboxylic acid (0.068 mmol) and HATU (0.068 mmol) were then added and the reaction mixture was stirred for 60 minutes. The reaction mixture was then filtered through cotton wool to give crude product A20 in solution.

The general scheme for the synthesis of compounds of the present invention with generalized structure A21 is shown in Scheme 3b.

Scheme 3b

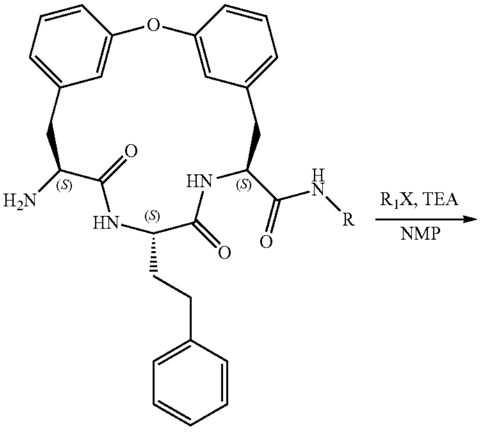

A19

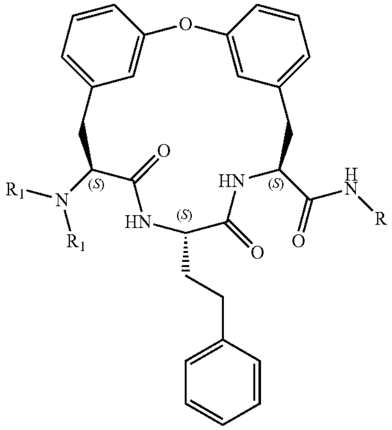

A21

NMP and TEA (0.104 mmol) were added to the crude A19. Alkyl halide (0.085 mmol) was then added and the reaction mixture was heated to 80° C. for 120 minutes. Reaction mixture was cooled to room temperature and filtered through cotton wool to give the crude product A21 in solution.

The general scheme for the synthesis of compounds of the present invention with generalized structure A22 is shown in Scheme 3c.

Scheme 3c

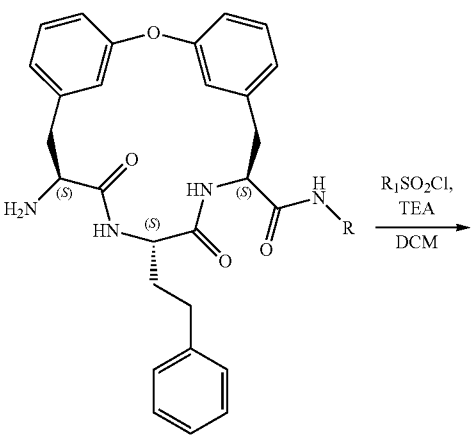

A19

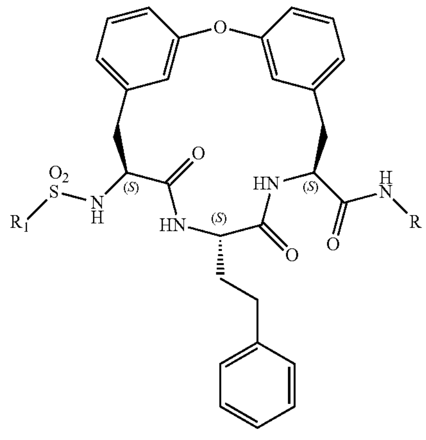

A22

DCM (1 mL) and TEA (0.85 mmol) were added to the crude A19. Sulfonyl chloride (0.068 mmol) was then added and the reaction mixture was stirred for 60 minutes. Solvent was removed by evaporation. NMP (0.4 ml) was then added and the mixture was filtered through cotton wool to give crude product A22 in solution.

The general scheme for the synthesis of compounds of the present invention with generalized structure A23 is shown in Scheme 3d.

Scheme 3d

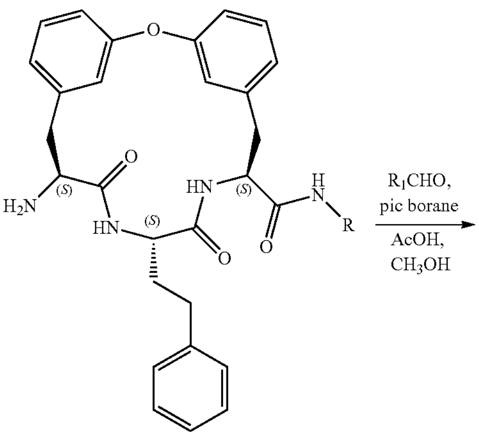

A19

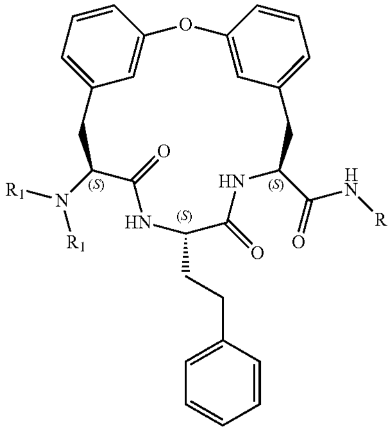

A23

MeOH (2 mL) was added to the crude A19 followed by addition of acetaldehyde (35 mg, 0.796 mmol), pic borane (36 mg, 0.332 mmol), and a drop of AcOH. The reaction mixture was stirred overnight. Solvent was removed by evaporation. NMP (0.4 ml) was added and the mixture was filtered through cotton wool to give crude product A23 in solution.

Compounds of the present invention can also be prepared according to Scheme 4.

Scheme 4

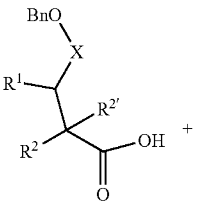

13

-continued

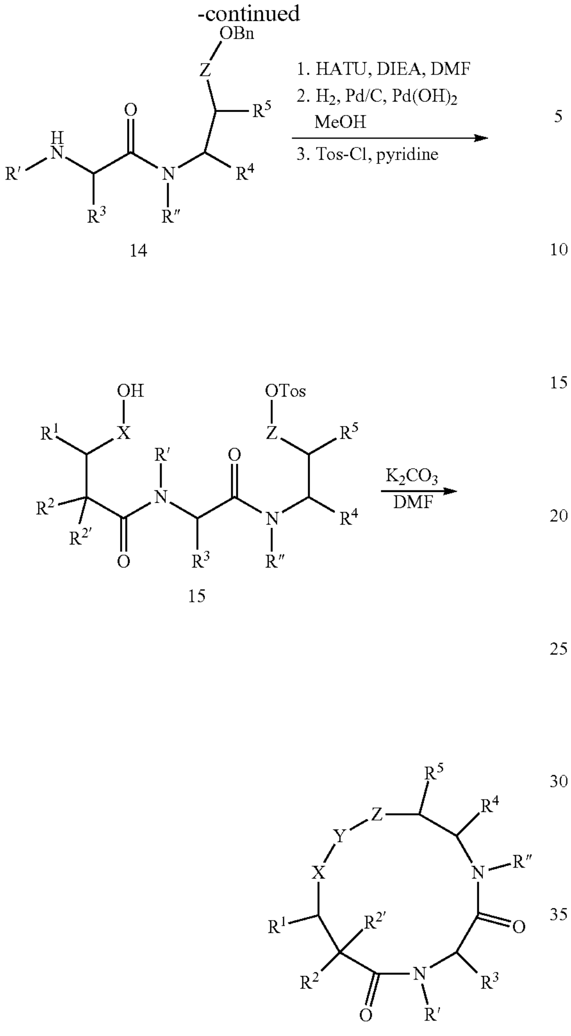

14

15

I

Scheme 4-1

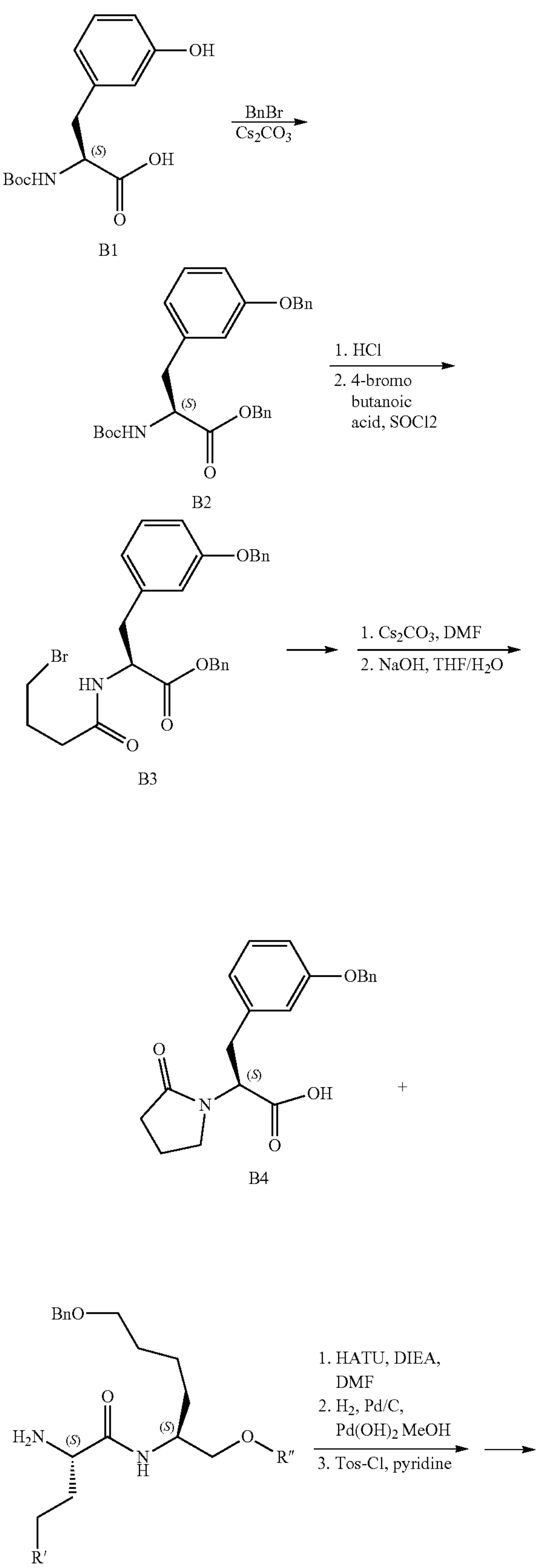

B1

B2

B3

B4

B5

Amide coupling of carboxylic acid derivative (13) with amine (14), followed by hydrogenation of the benzyl ethers and reaction with tosyl chloride leads to formation of the compound (15). The reactions can be carried out in a variety of solvents, for example in methylene chloride ($CH_2Cl_2$), tetrahydrofuran (THF), dimethylformamide (DMF), or other such solvents or in the mixture of such solvents. During the reaction process, the non-participating carboxylic acids or amines on the reacting set of amino acids or peptide fragments can be protected by a suitable protecting group (PG) which can be selectively removed at a later time if desired. A detailed description of these groups and their selection and chemistry is contained in "The Peptides, Vol. 3", Gross and Meinenhofer, Eds., Academic Press, New York, 1981, which is hereby incorporated by reference in its entirety. Thus, useful protective groups for the amino group are benzyloxycarbonyl (Cbz), t-butyloxycarbonyl (t-BOC), 2,2,2-trichloroethoxycarbonyl (Troc), t-amyloxycarbonyl, 4-methoxybenzyloxycarbonyl, 2-(trichlorosilyl)ethoxycarbonyl, 9-fluorenylmethoxycarbonyl (Fmoc), phthaloyl, acetyl (Ac), formyl, trifluoroacetyl, and the like. Macrocyclolization of compound (15) by tosyl displacement affords macrocycles of Formula (I).

The general scheme for the synthesis of compounds of the present invention with generalized structure B8 is shown in Scheme 4-1.

-continued

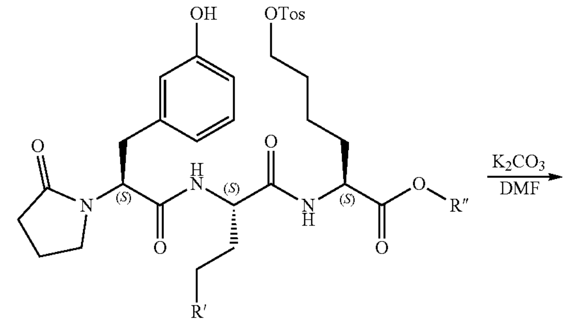

B6

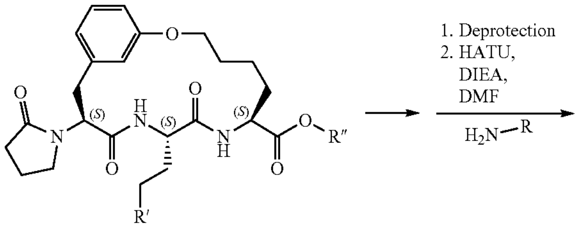

B7

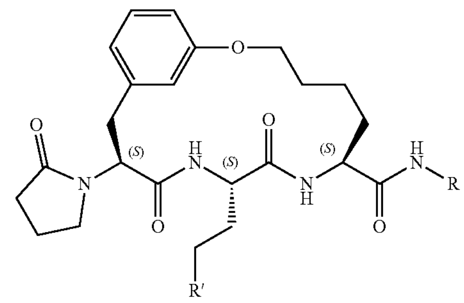

B8

Phenolic acid B1 was protected to produce benzyl protected B2. Boc deprotection and amide coupling gave amide B3, which was cyclized and deprotected to afford acid B4. Coupling of B4 and B5 gave tribenzyl-ether that was deprotected and monoprotected as tosylate to give compound B6. Macrocyclolization by tosyl displacement afforded compound B7. Deprotection and amide coupling afforded product B8.

Alternative scheme for compounds with generalized structure B8 is shown in Scheme 4a.

Scheme 4a

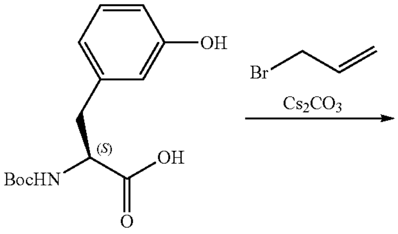

B1

-continued

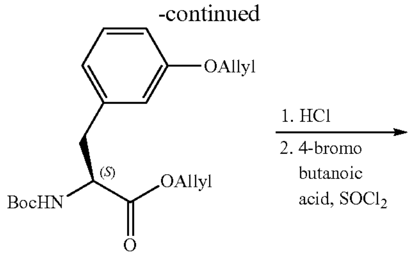

B9

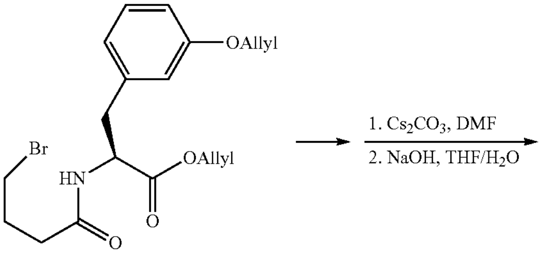

B10

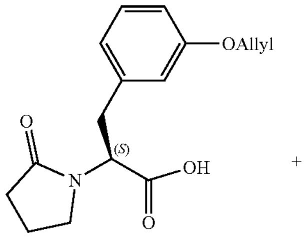

B11

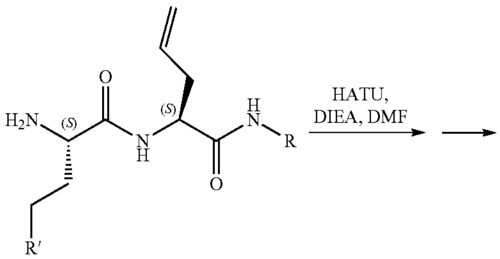

B12

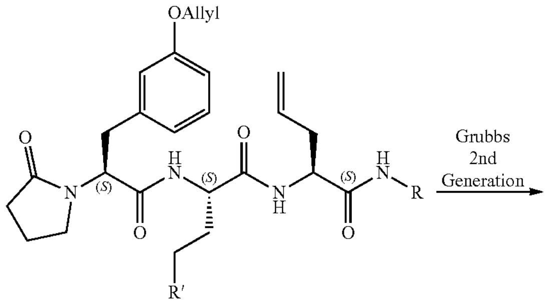

B13

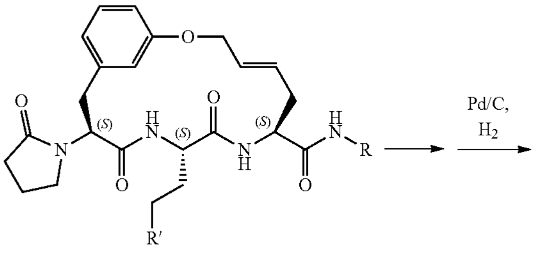

B14

-continued

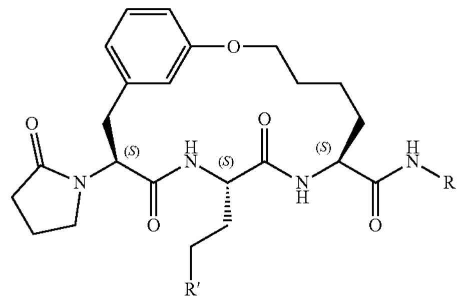

B8

Phenolic acid B1 was protected to produce allyl protected compound B9. Boc deprotection and amide coupling gave amide B10, which was cyclized and deprotected to afford acid B11. Coupling of B11 and B12 provided compound B13 that was treated with Grubb's $2^{nd}$ generation catalyst to afford the ring closing metathesis product B14. Hydrogenation then afforded product B8.

The general scheme for the synthesis of compounds of the present invention with generalized structure C6 is shown in Scheme 5.

Scheme 5

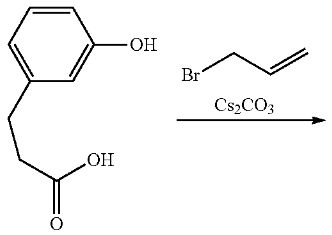

C1

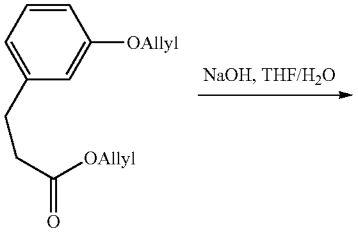

C2

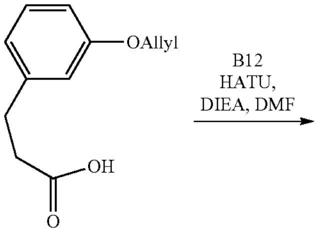

C3

-continued

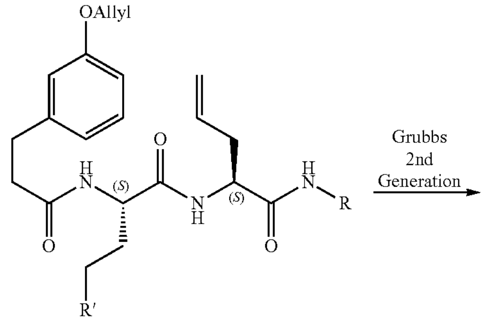

C4

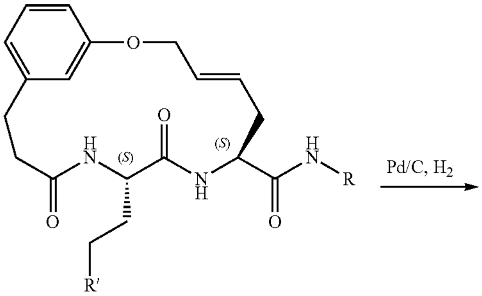

C5

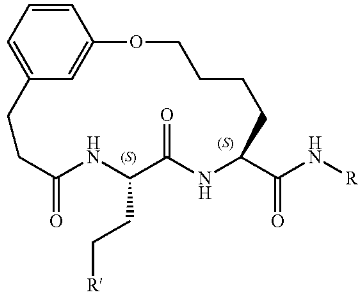

C6

Phenolic acid C1 was protected to produce allyl protected compound C2. Deprotection afforded acid C3 which was coupled with compound B12 to provide compound C4. Compound C4 was treated with Grubb's $2^{nd}$ generation catalyst affording the ring closing metathesis product C5. Hydrogenation then afforded final product C6.

The general scheme for the synthesis of compounds of the present invention with generalized structure D8 is shown in Scheme 6.

Scheme 6

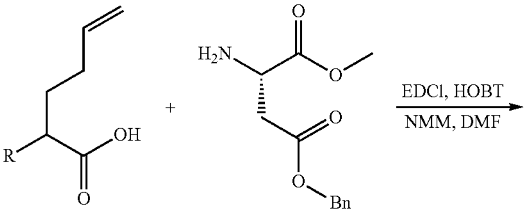

D1 D2

-continued

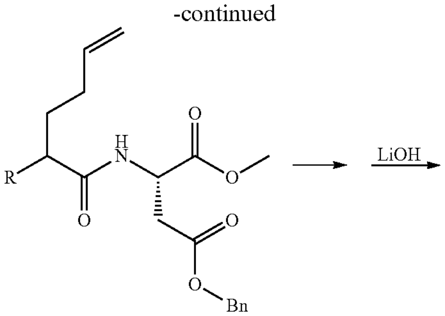

D3

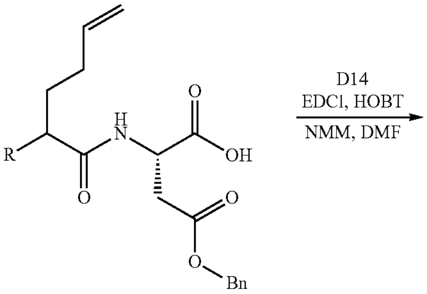

D4

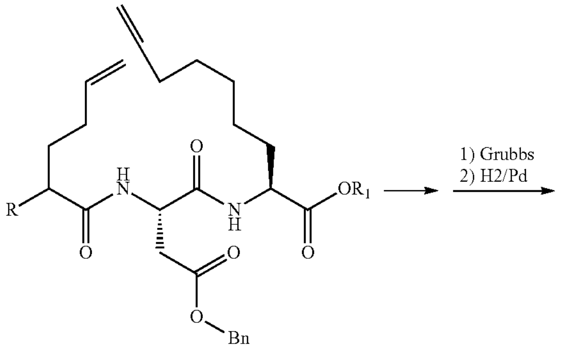

D5

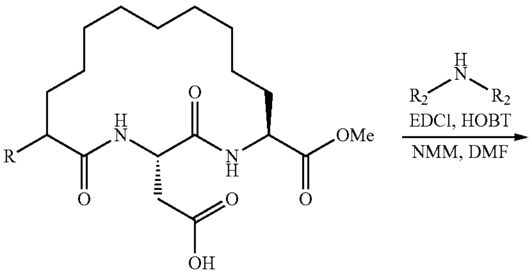

D6

-continued

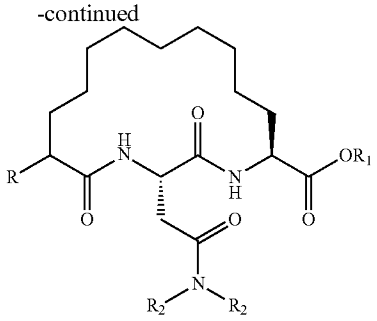

D7

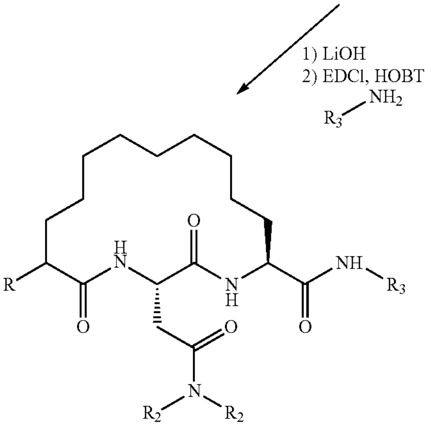

D8

Acid D1 was coupled with amine D2 to afford ester D3. Methyl ester hydrolysis afforded acid D4 which was coupled with intermediate D14 to afford diallyl D5. Ring closing metathesis and benzyl ester deprotection gave macrocycle D6. Amide coupling afforded ester D7. Ester hydrolysis and amide coupling resulted in product D8.

The general scheme for the synthesis of intermediate D14 is shown in Scheme 6a.

Scheme 6a

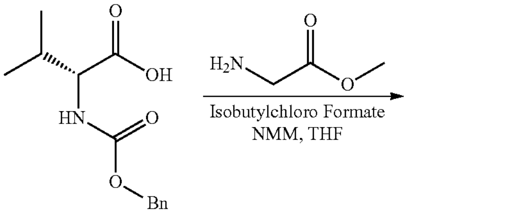

D9

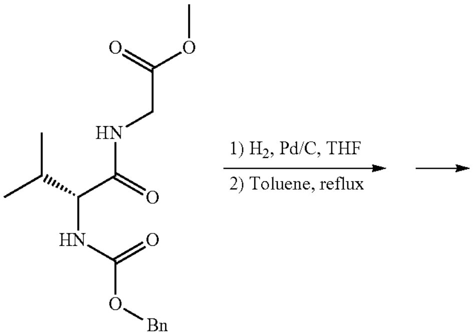

D10

-continued

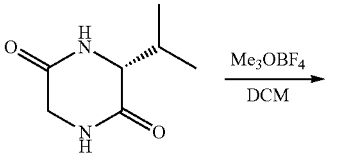

D11

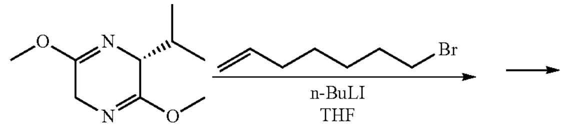

D12

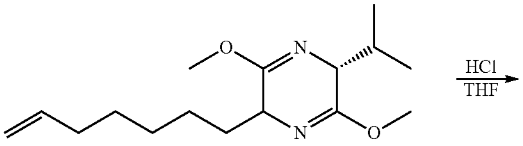

D13

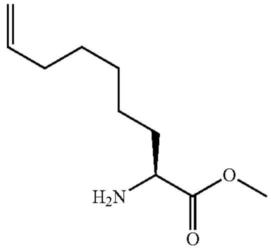

D14

Amino acid D9 was coupled with glycine methyl ester to give compound D10. Cbz deprotection followed by intramolecular methyl ester displacement afforded compound D11. Oxidation of D11 gave dimetoxy compound D12. Alkylation of D12 resulted in compound D13. HCl ring opening gave amino acid D14.

One embodiment relates to the compound of Formulae (I) where $R^2$ is selected from the group consisting of H, $CH_3$,

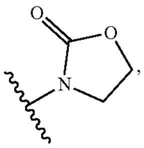
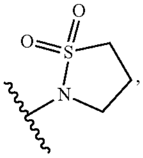
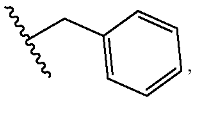
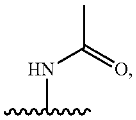
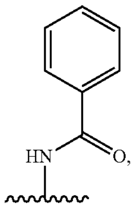
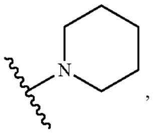
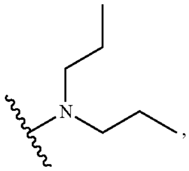
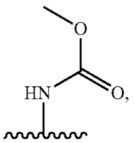
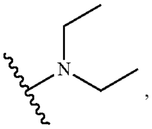

-continued

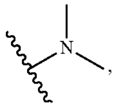
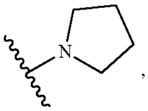
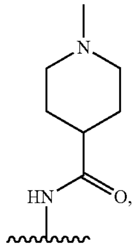
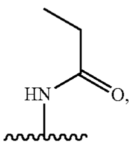
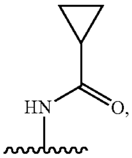
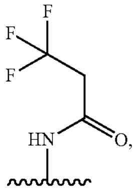
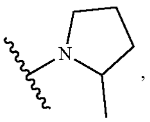
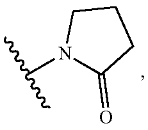
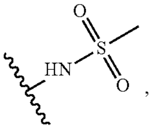
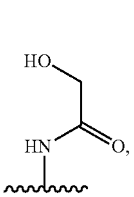
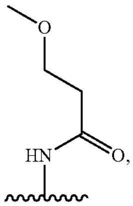
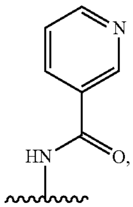
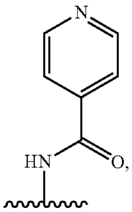
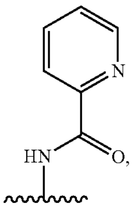
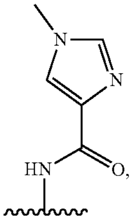
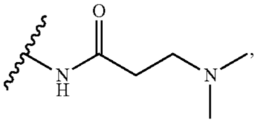
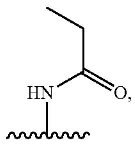
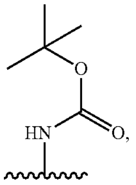
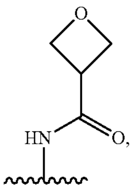
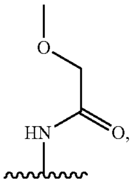

and

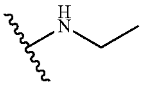

, wherein

is the point of attachment to the corresponding carbon atom of the structure of Formula (I).

Another embodiment relates to the compound of Formulae (I) where $R^3$ is selected from the group consisting of H,

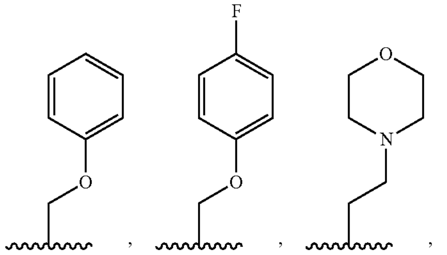

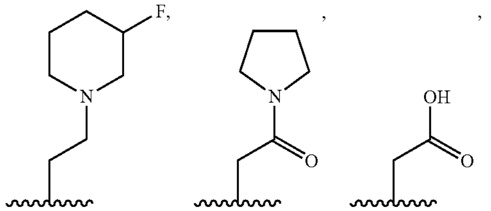

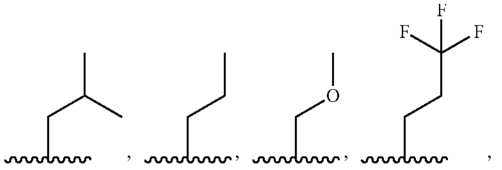

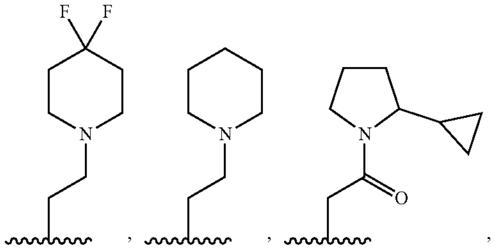

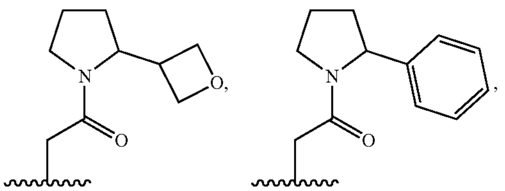

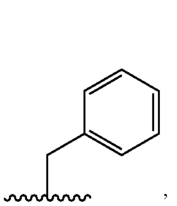

and

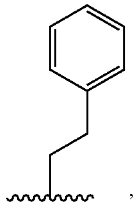

wherein

is the point of attachment to the corresponding carbon atom of the structure of Formula (I).

Another embodiment relates to the compound of Formulae (I) where $R^4$ is selected from the group consisting of

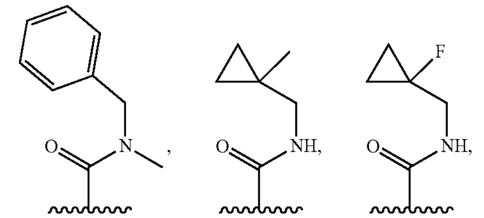

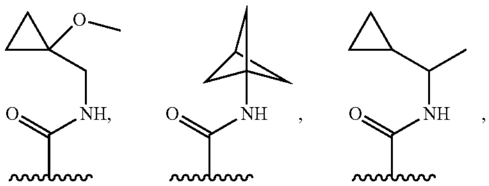

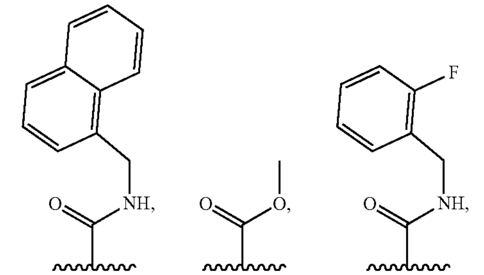

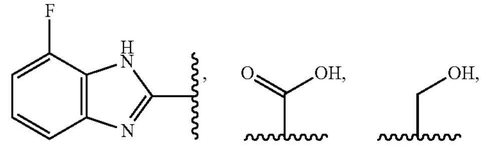

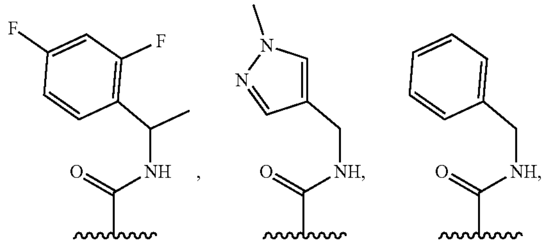

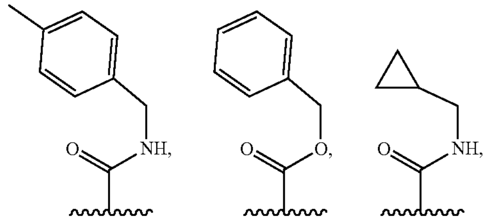

-continued

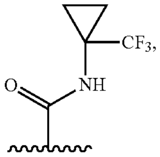
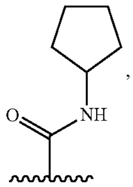,
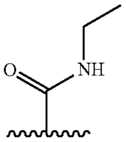,
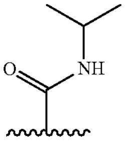,
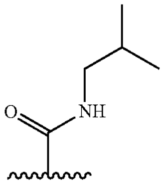,
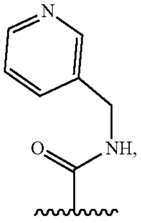
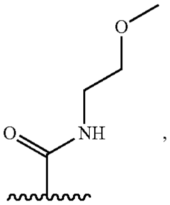,
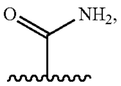
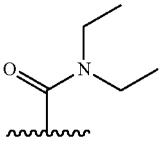
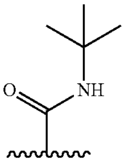,
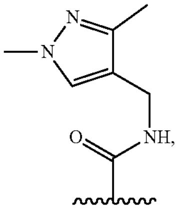
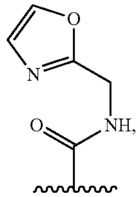
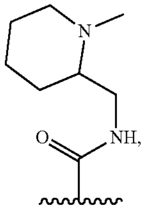
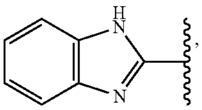
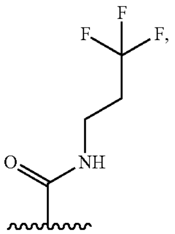
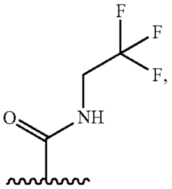
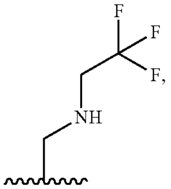
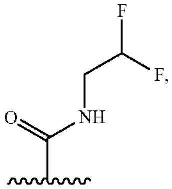
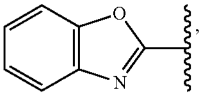
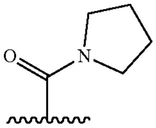, -continued

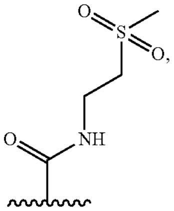
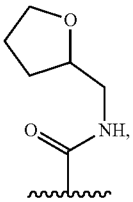
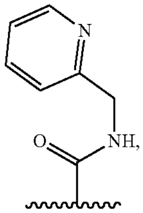
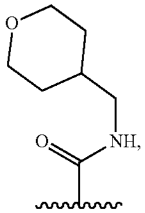
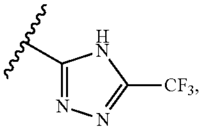
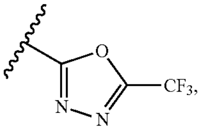
and
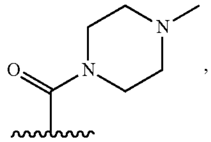, wherein

is the point of attachment to the corresponding carbon atom of the structure of Formula (I).

Yet another embodiment relates to the compound of Formulae (I) where X is selected from the group consisting of $—(CH_2)_3—$, $—CH_2—CH═CH—$,

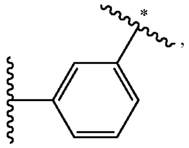 [SMILES: *c1cccc(*)c1]

and $—(CH_2)_5—$.

Another embodiment relates to the compound of Formulae (I) where Z is selected from the group consisting of $—(CH_2)_3—$, $—(CH_2)_2—$,

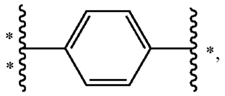
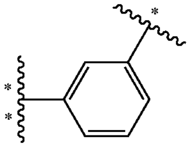, $—CH_2—CH_2—O—$, $—CH_2—CH═CH—$, and O.

A further embodiment relates to the compound of Formulae (I) where the compound has a structure selected from the group consisting of:

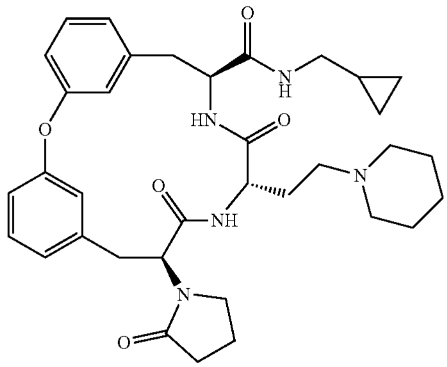
,
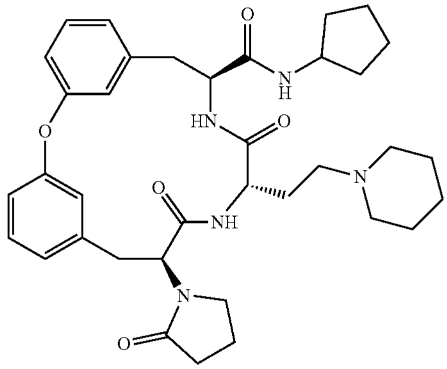
,
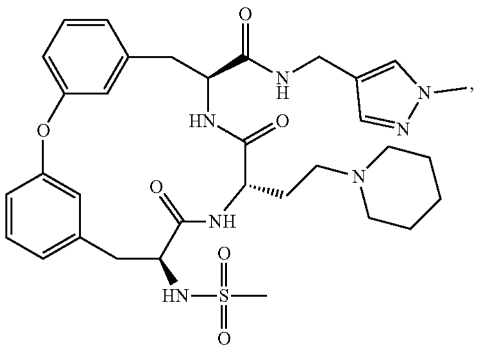
,
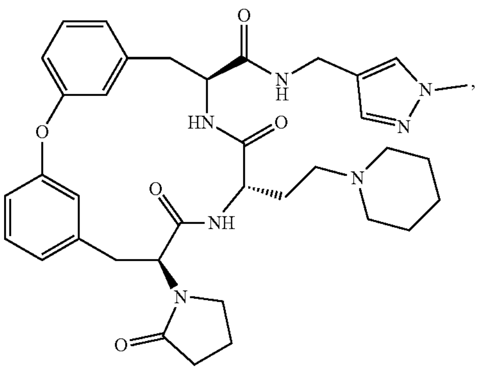
,
-continued
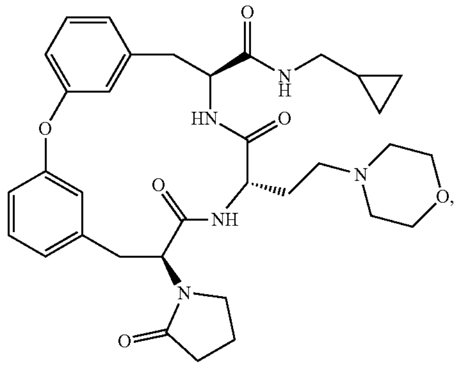
,
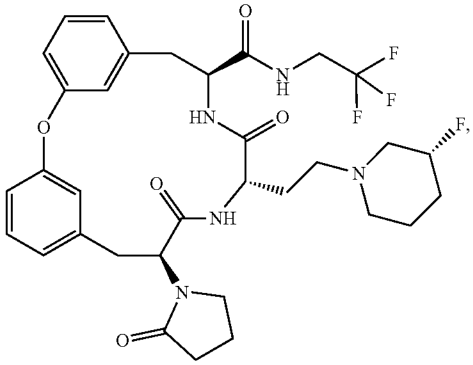
,
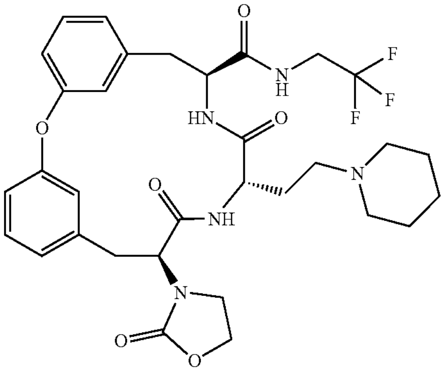
,
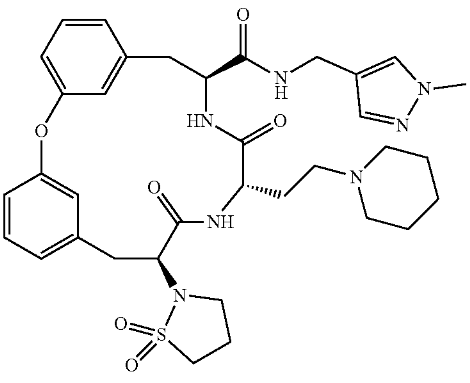
, -continued
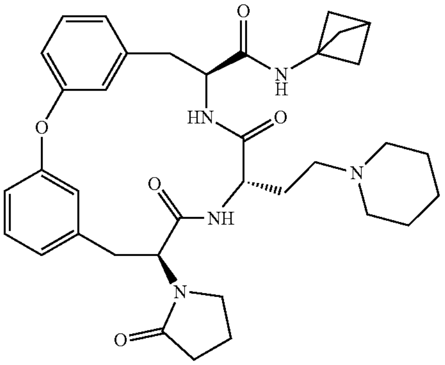
,
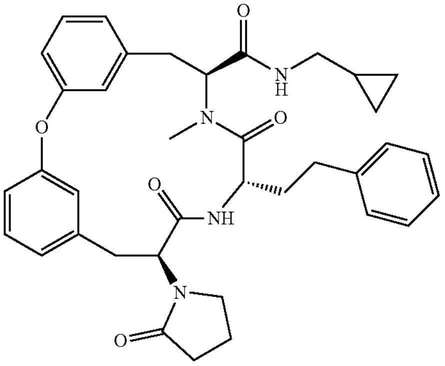
,
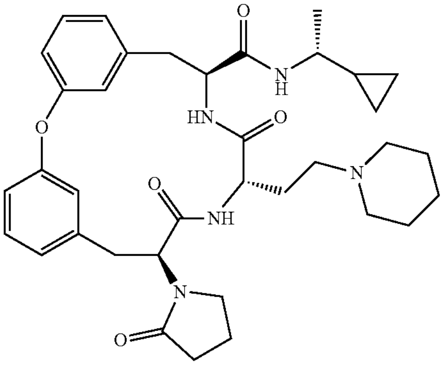
,
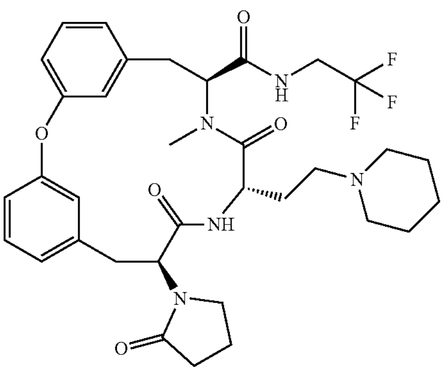
,
-continued
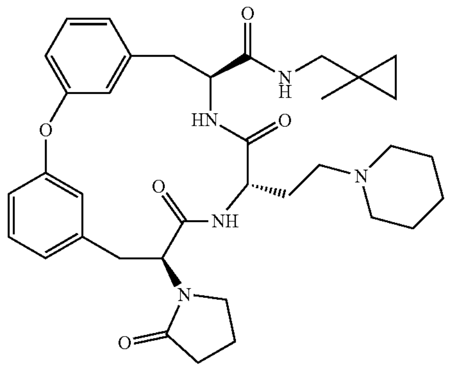
,
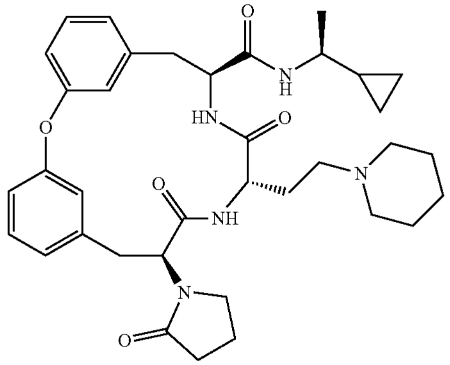
,
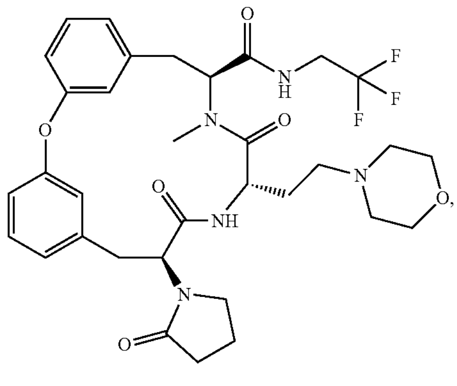
,
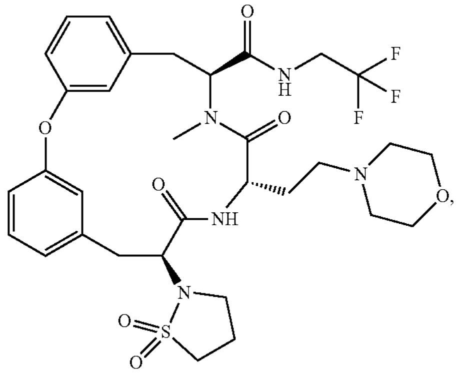
, -continued
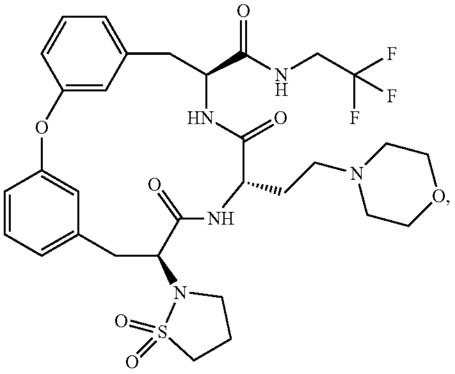
,
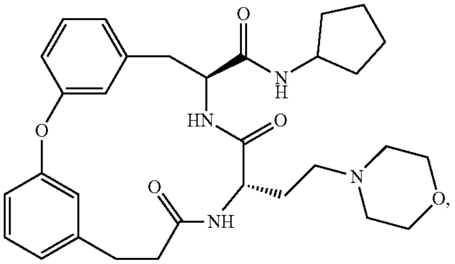
,
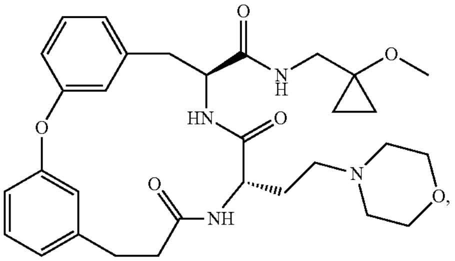
,
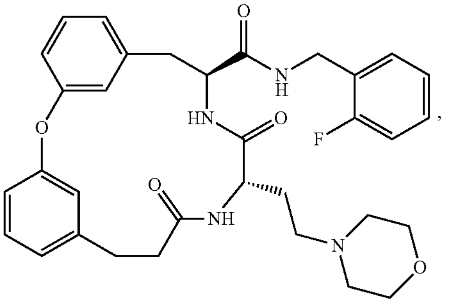
,
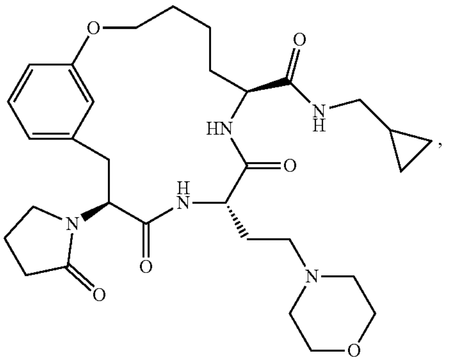
,
-continued
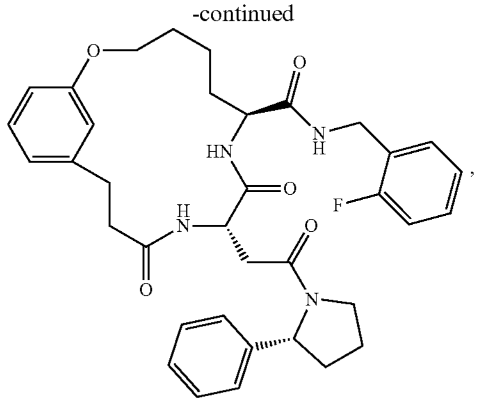
,
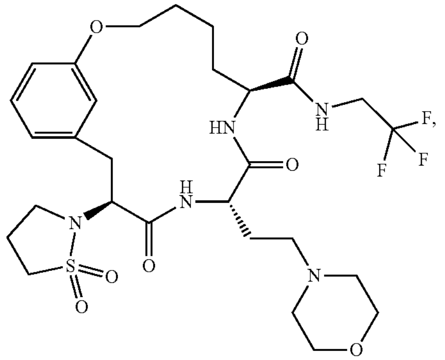
,
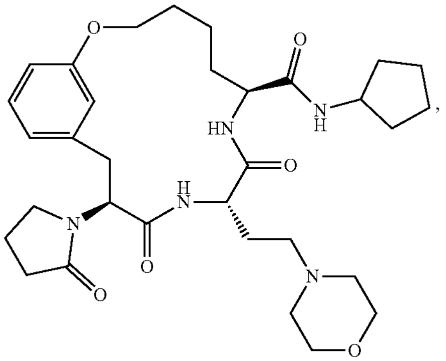
,
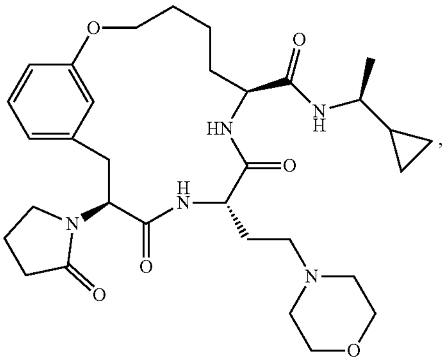
, -continued
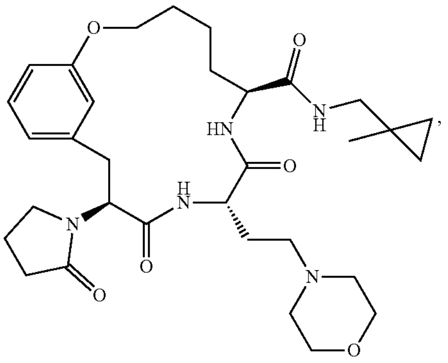
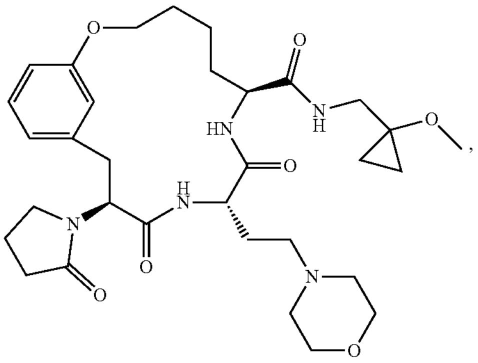
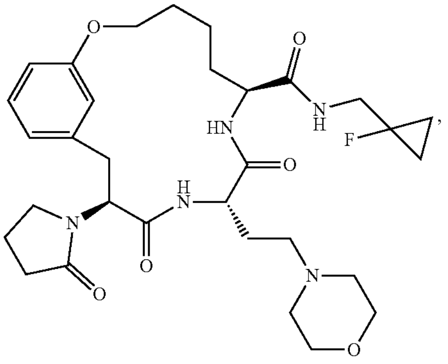
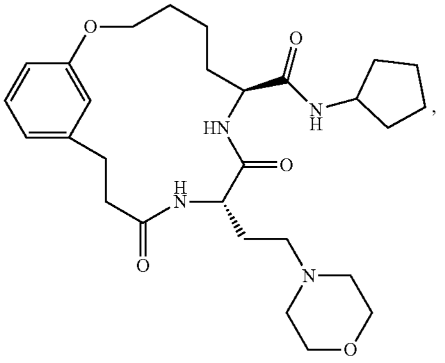
-continued
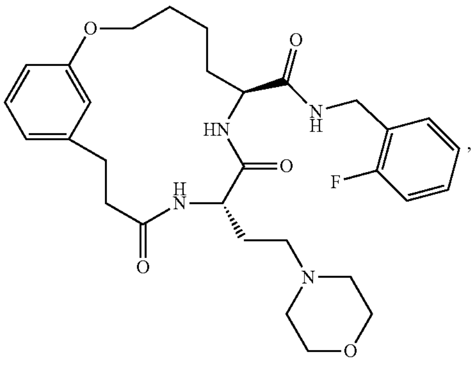
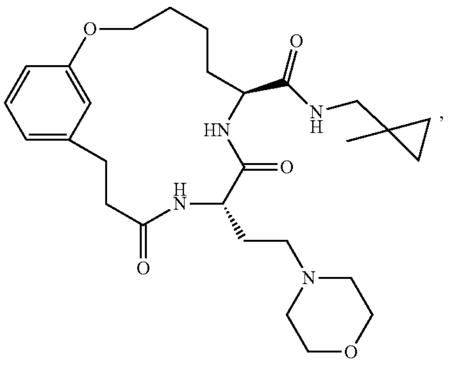
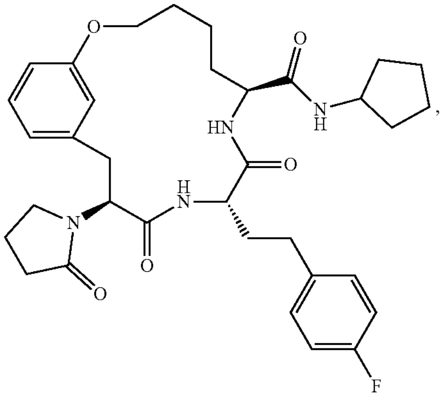
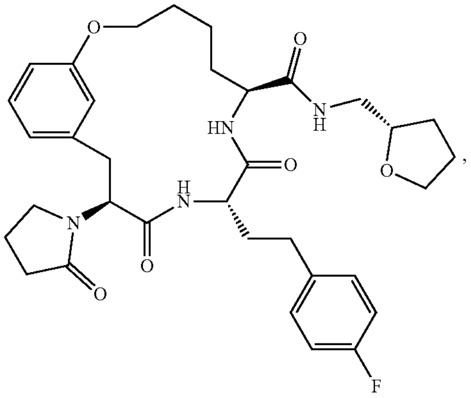

-continued
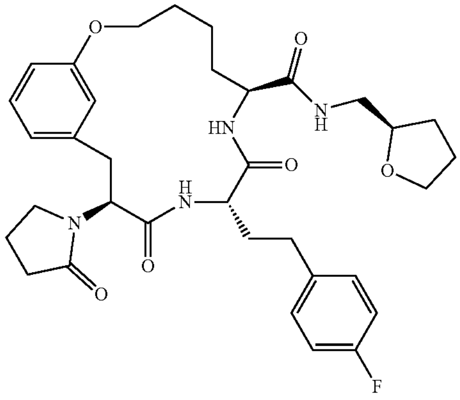
,
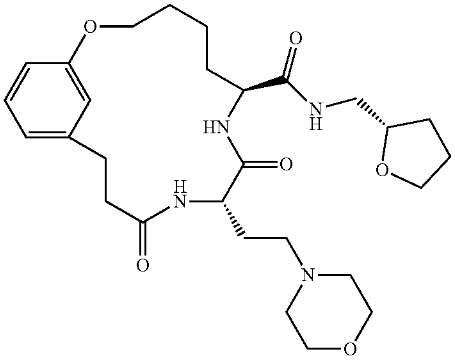
,
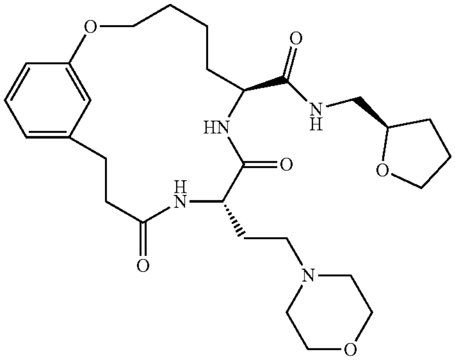
,
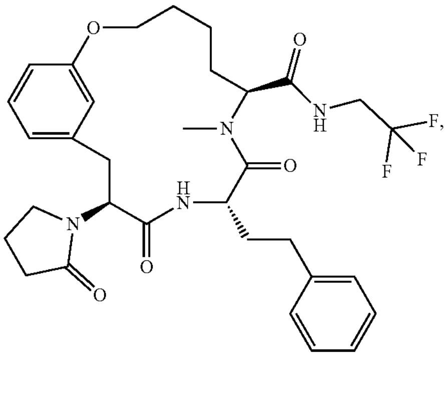
,
-continued
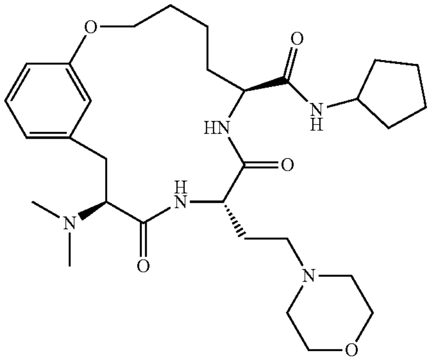
,
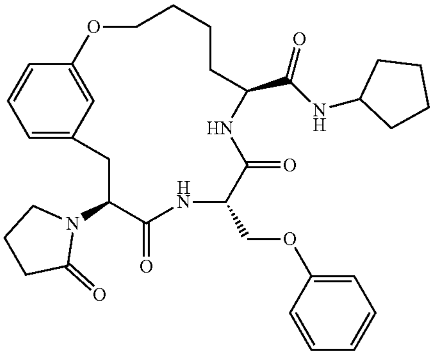
,
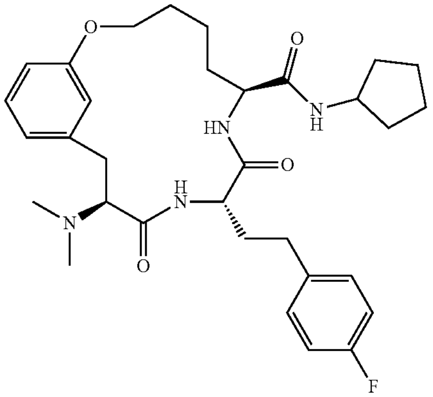
,
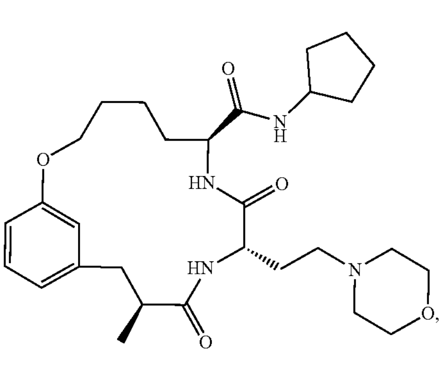
, -continued
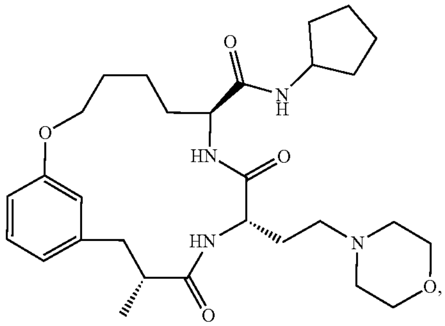
,
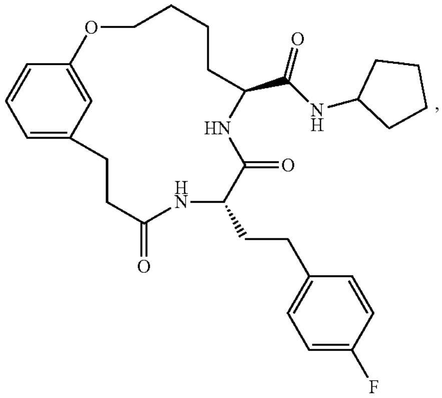
,
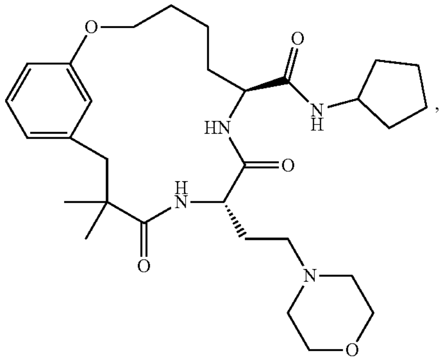
,
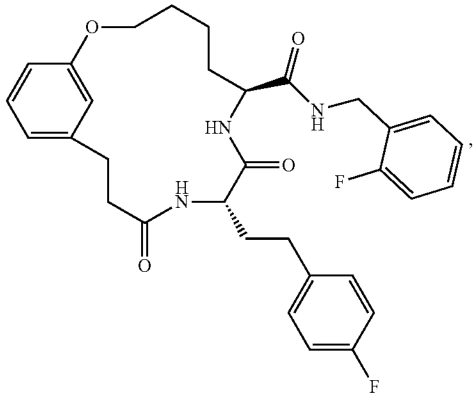
,
-continued
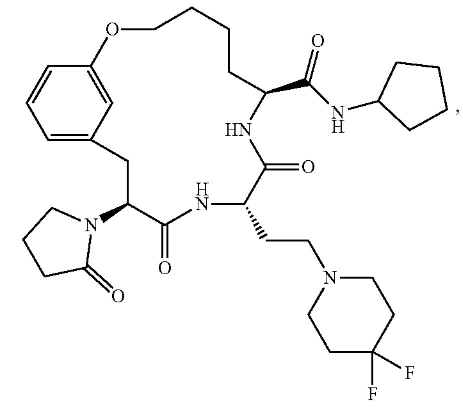
,
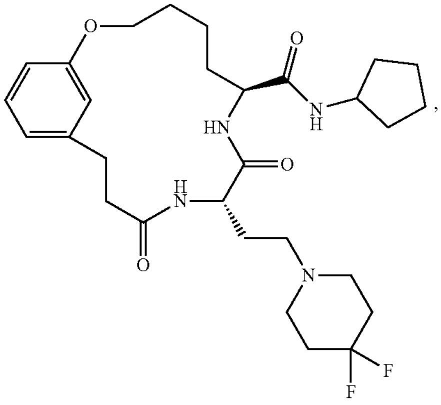
,
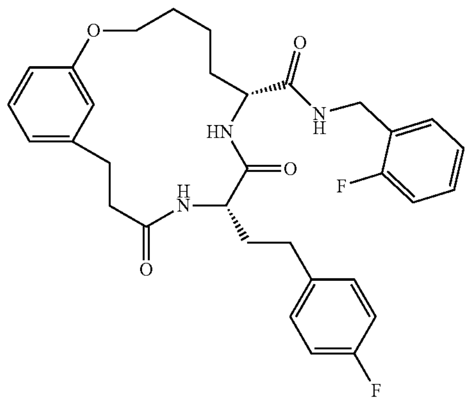
,
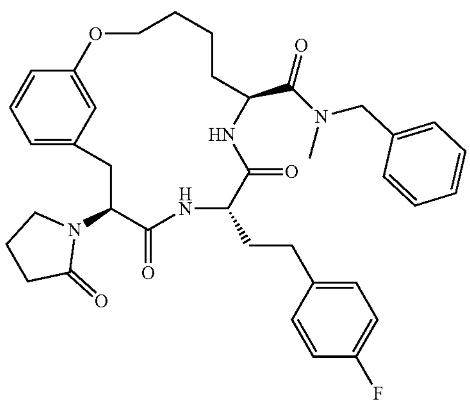
, -continued
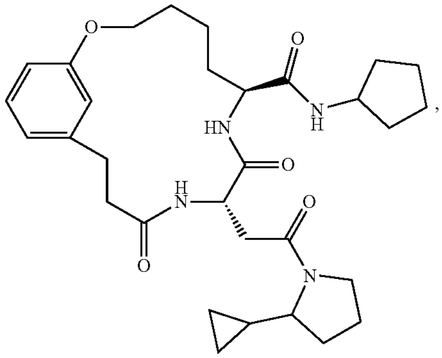
,
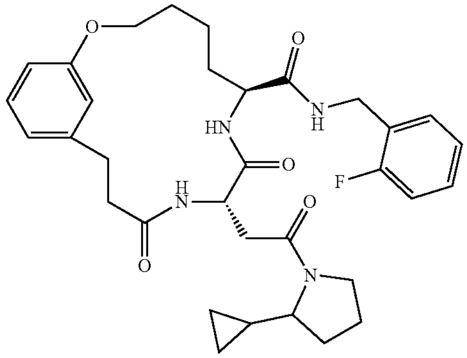
,
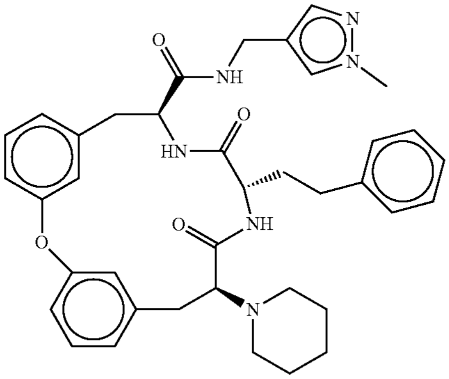
,
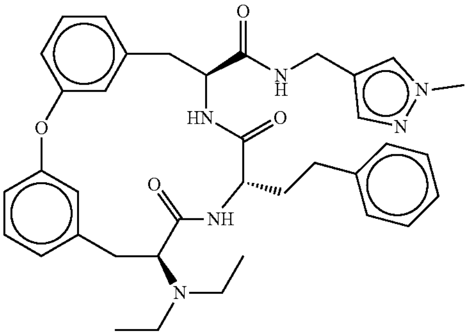
,
-continued
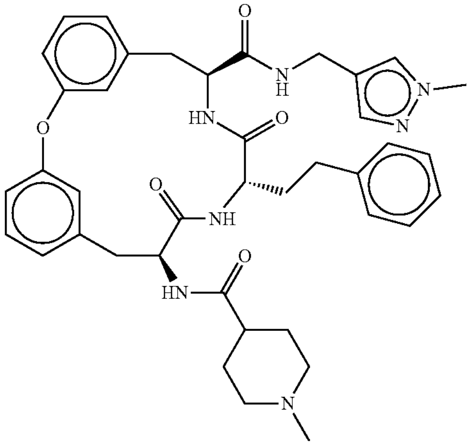
,
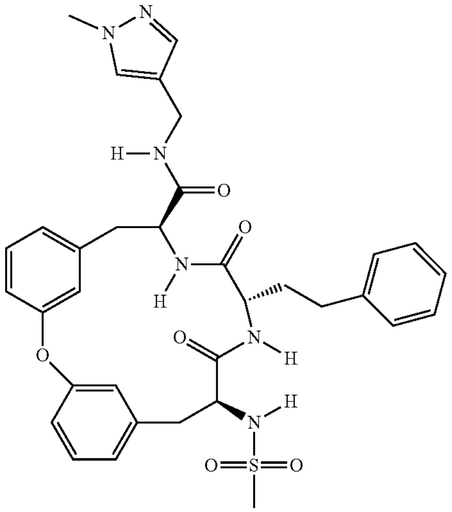
,
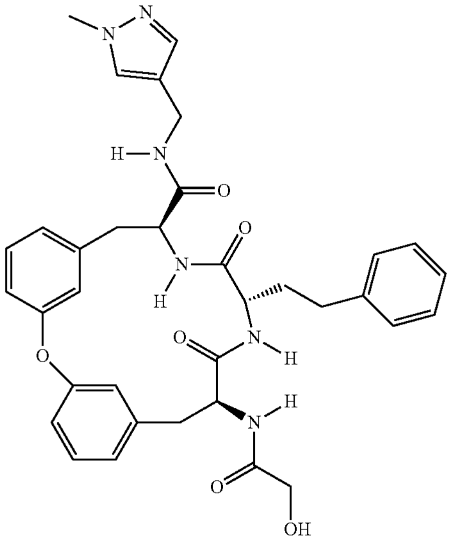
, -continued
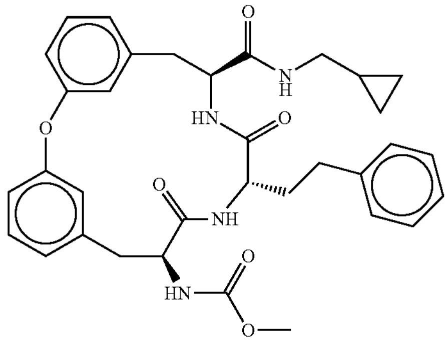
,
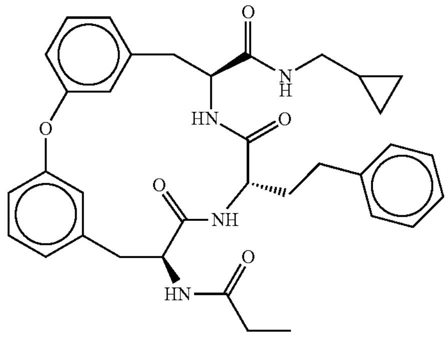
,
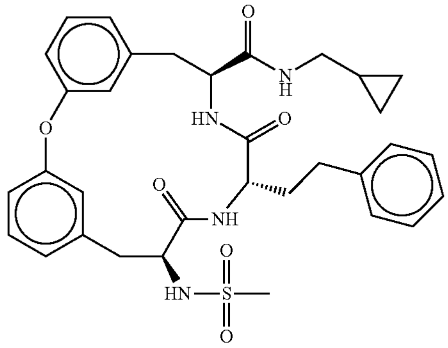
,
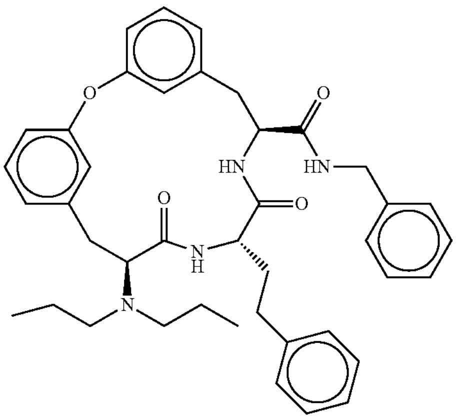
,
-continued
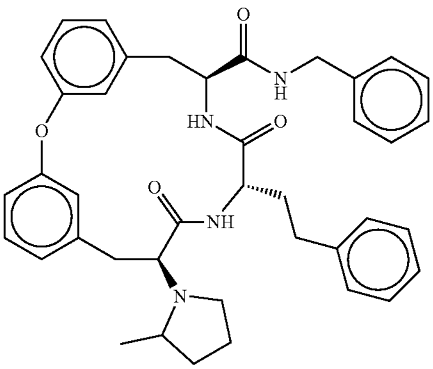
,
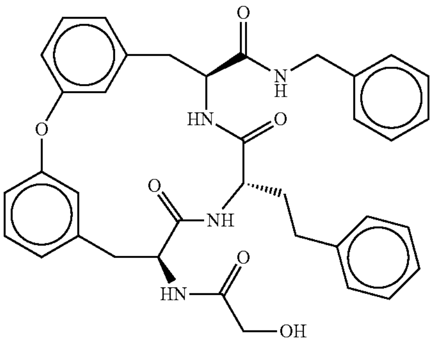
,
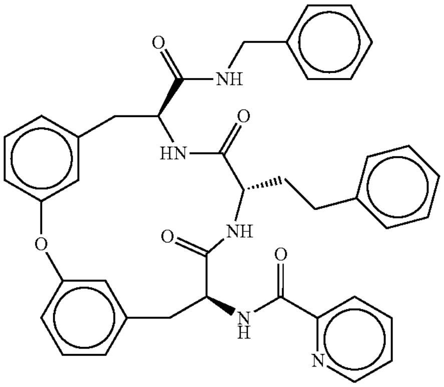
,
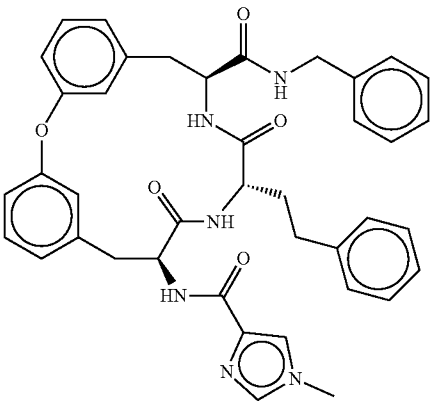

-continued
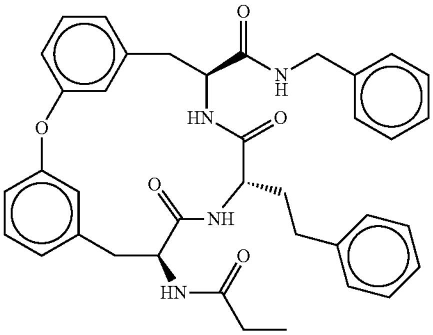
,
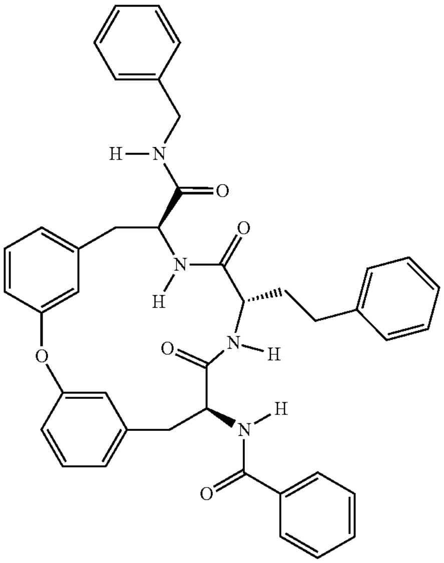
,
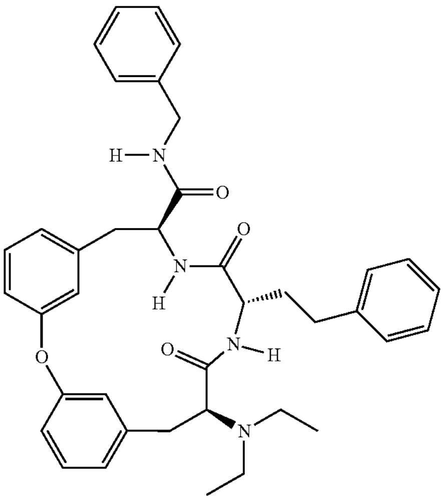
,
-continued
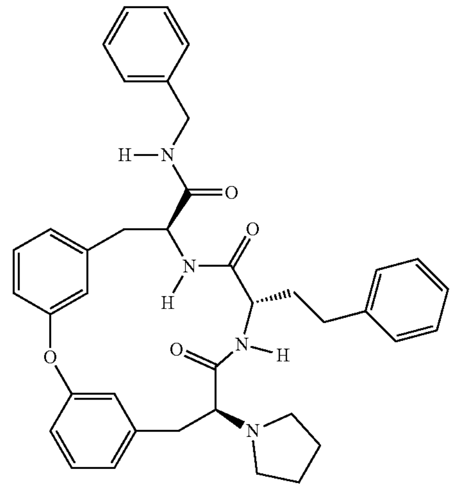
,
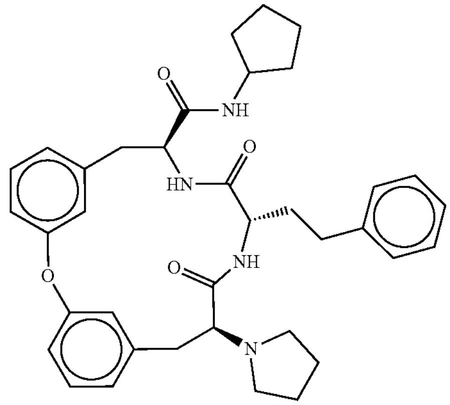
,
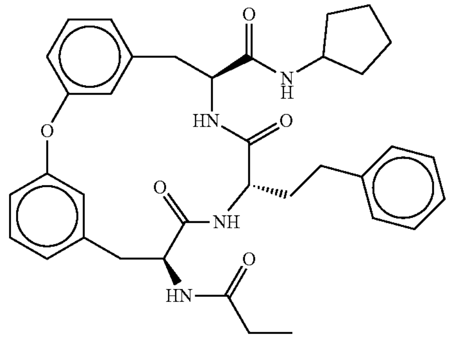
,
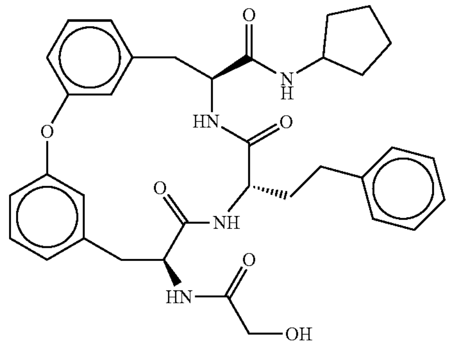
, -continued
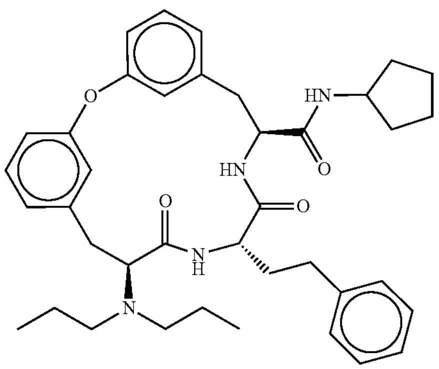
,
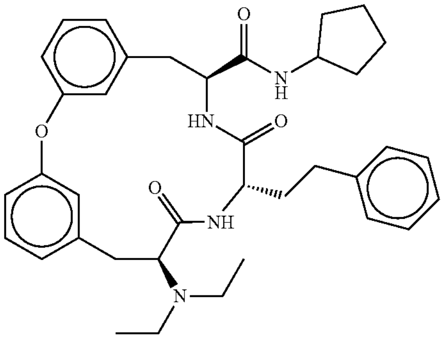
,
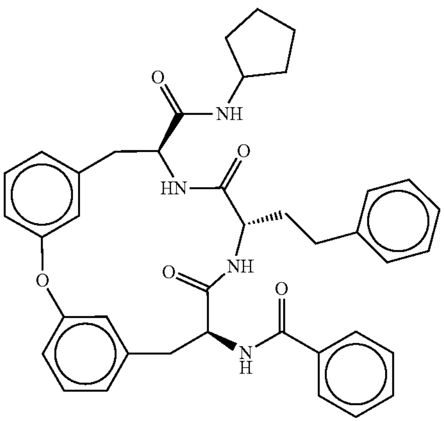
,
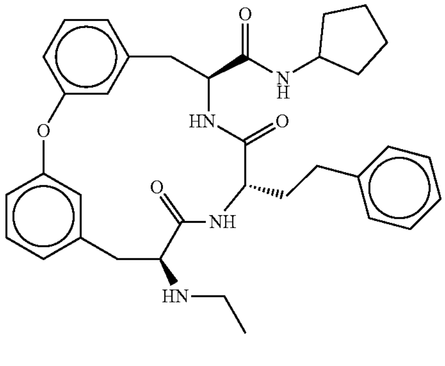
,
-continued
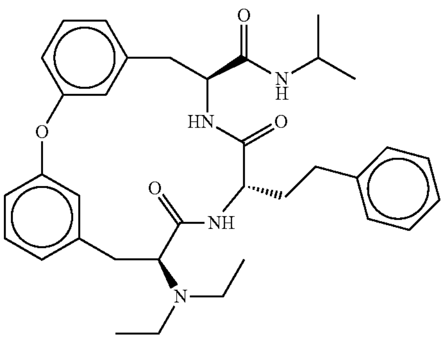
,
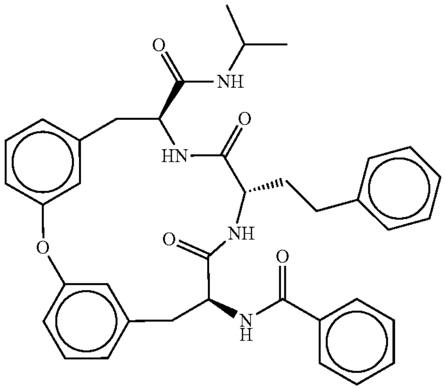
,
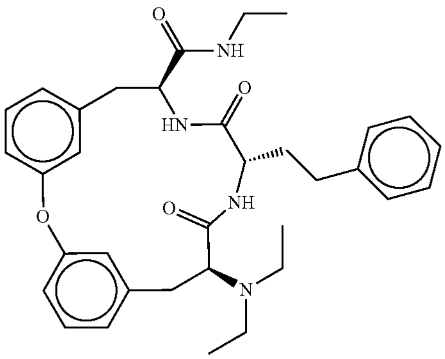
,
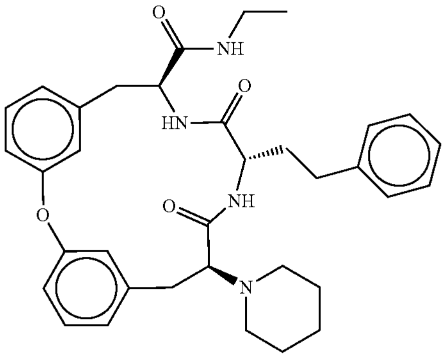
, -continued
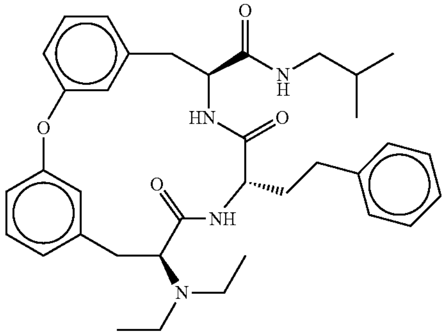
,
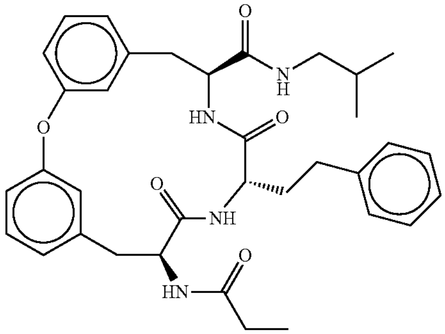
,
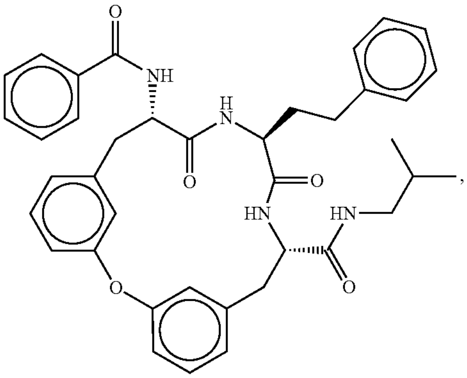
,
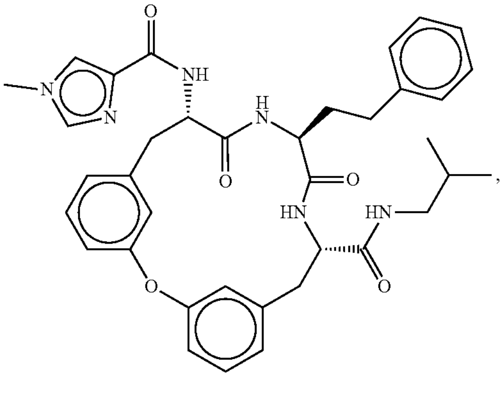
,
-continued
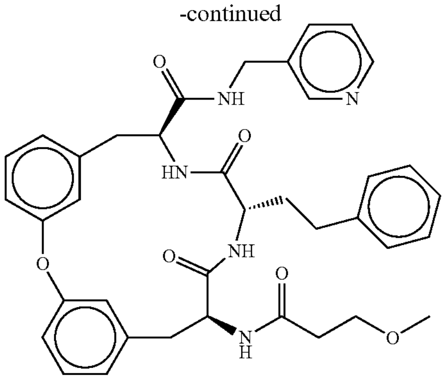
,
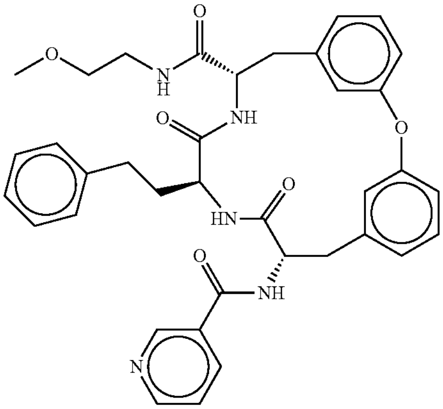
,
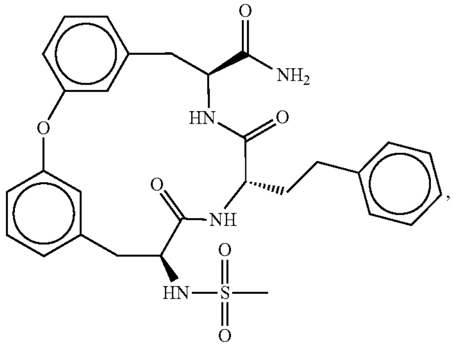
,
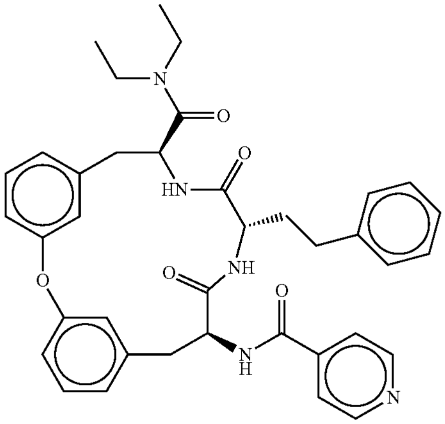
, -continued
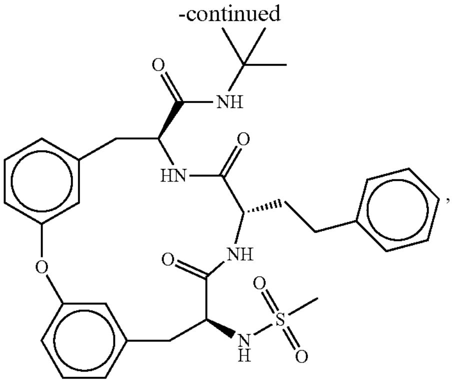,
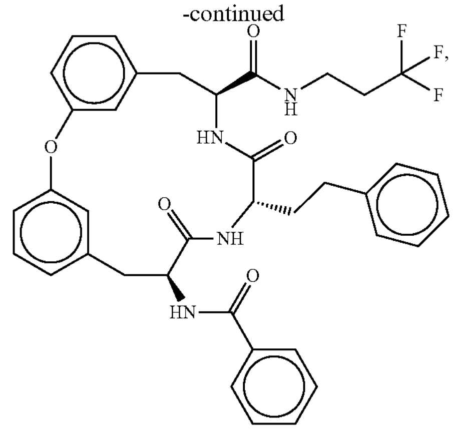,
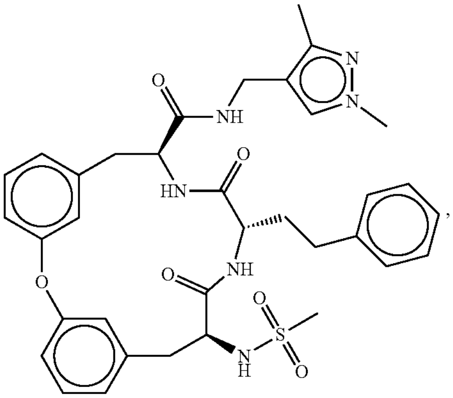,
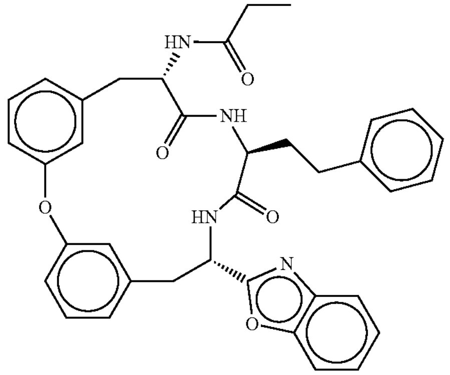,
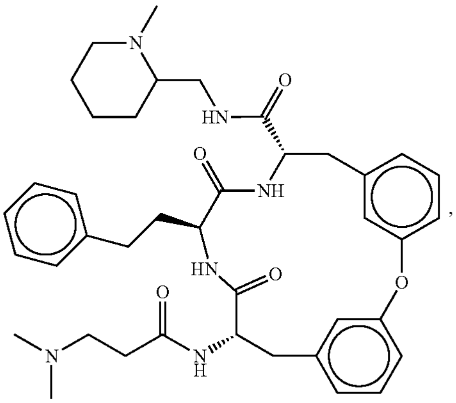,
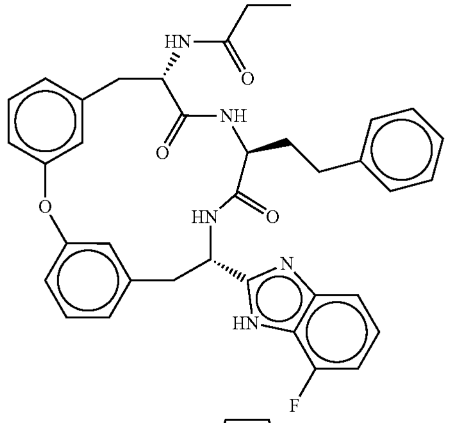,
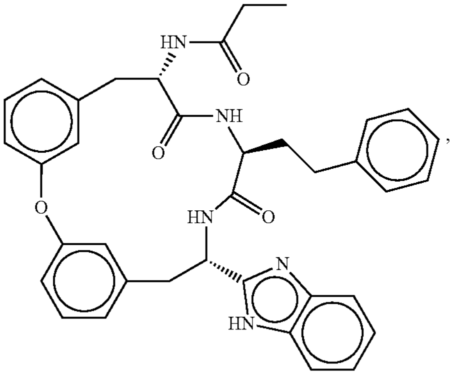,
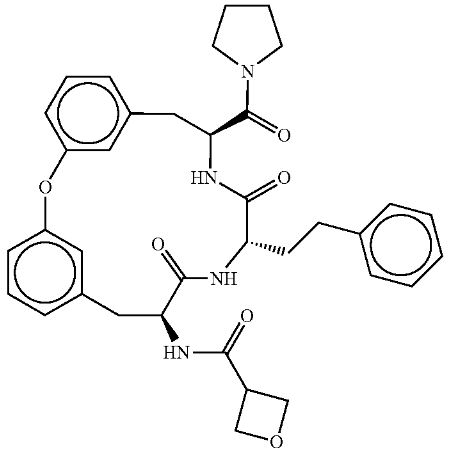, -continued
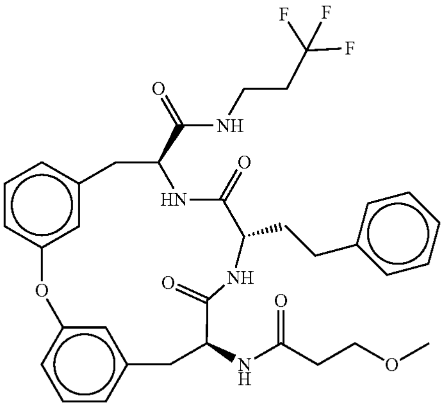,
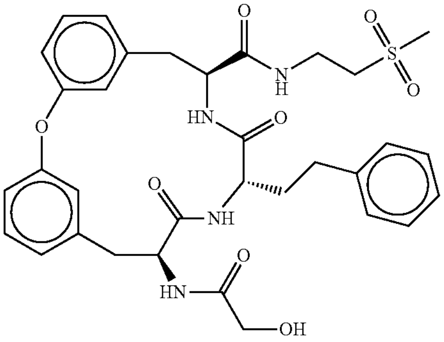,
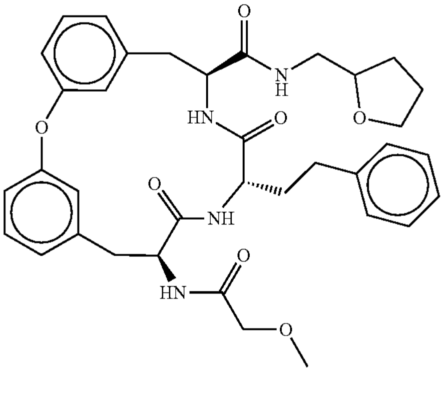,
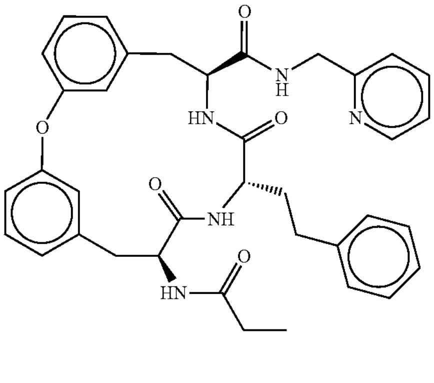,
-continued
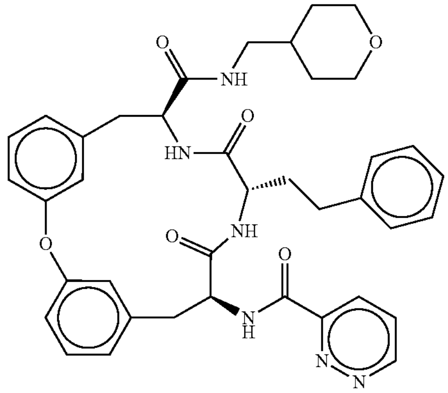,
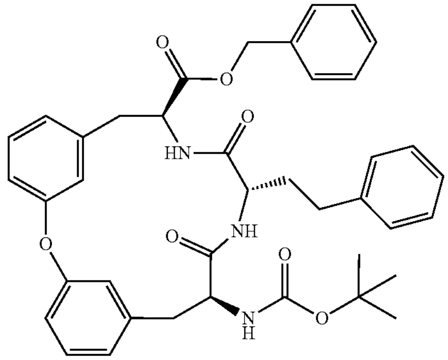,
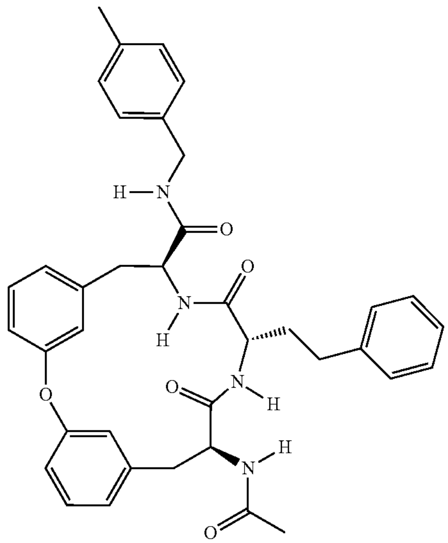,
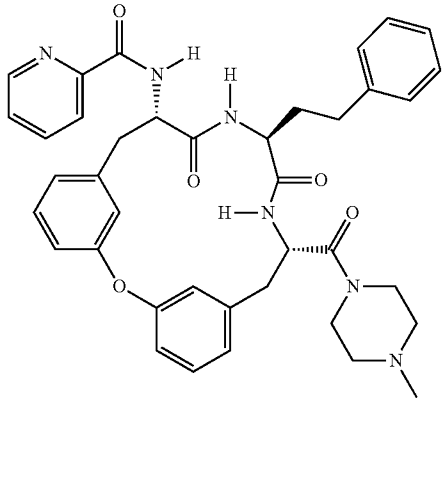, -continued
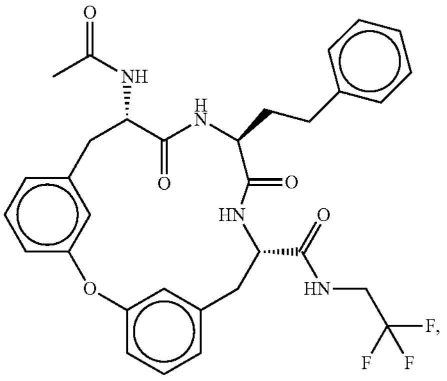
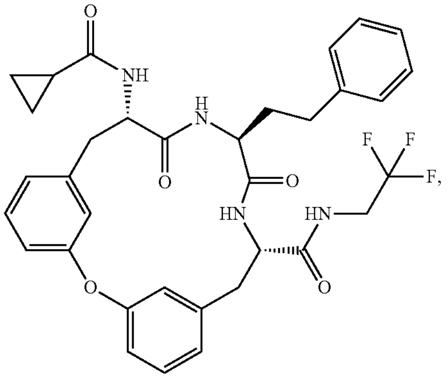
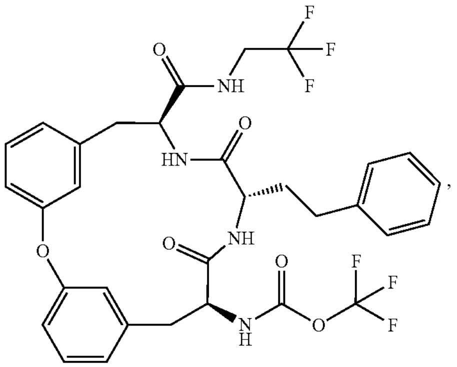
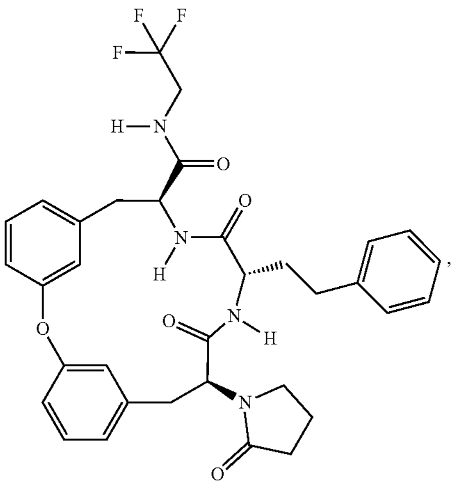
-continued
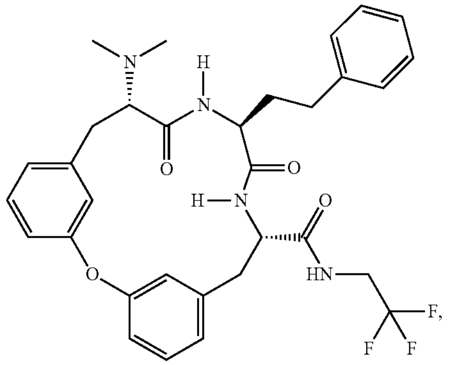
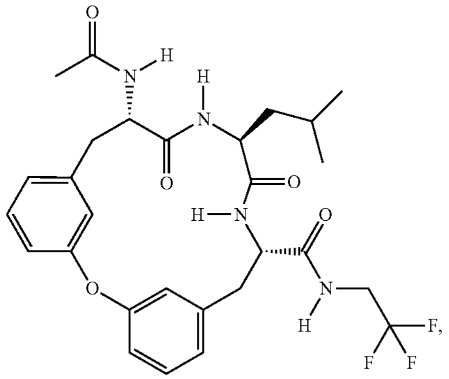
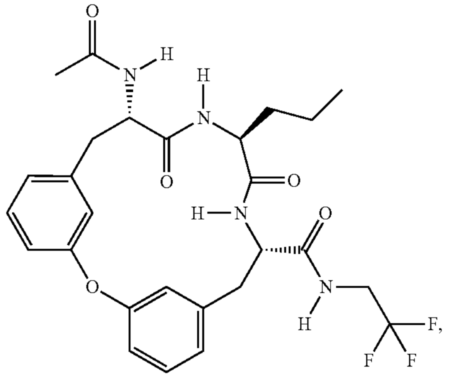
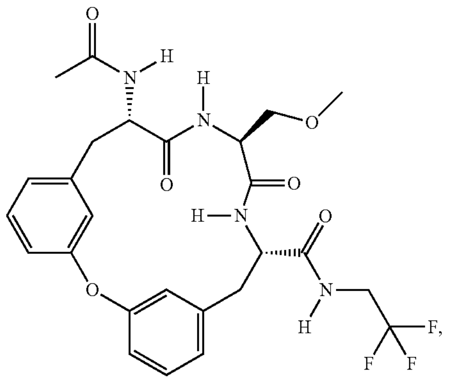

-continued
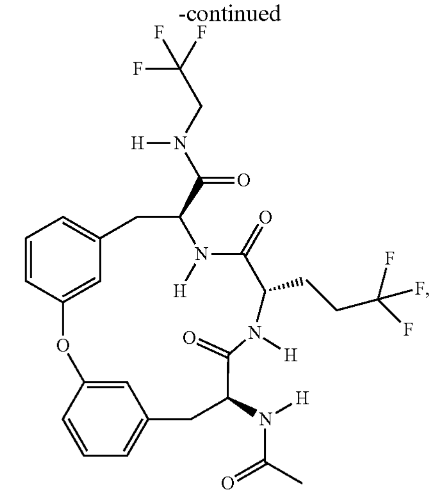
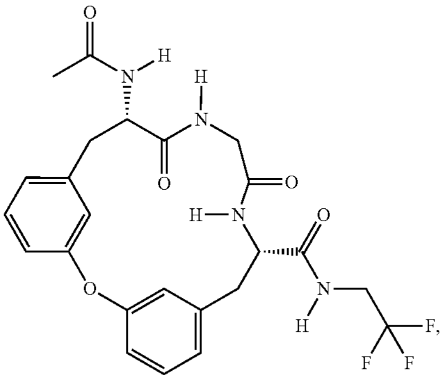
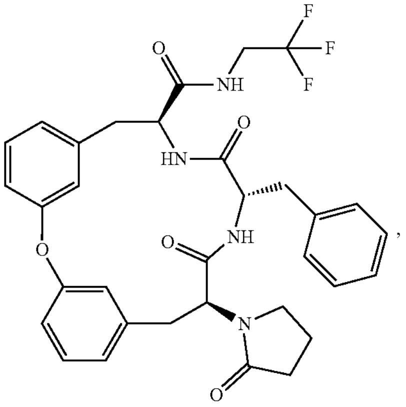
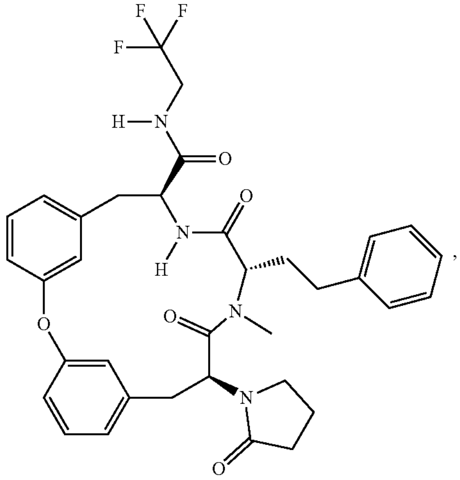
-continued
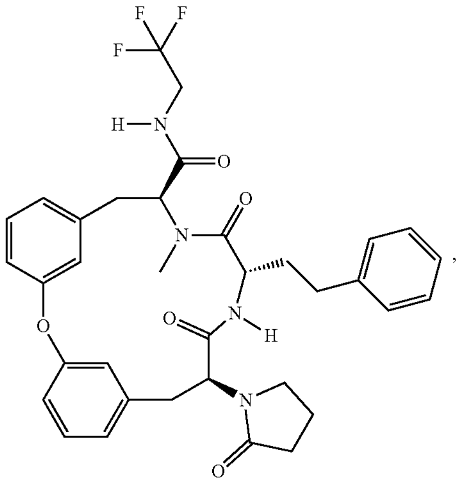
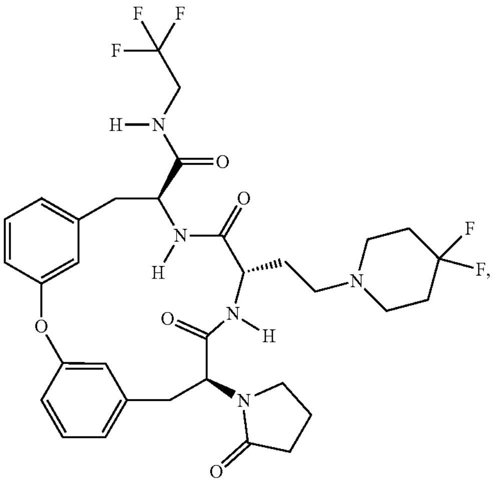
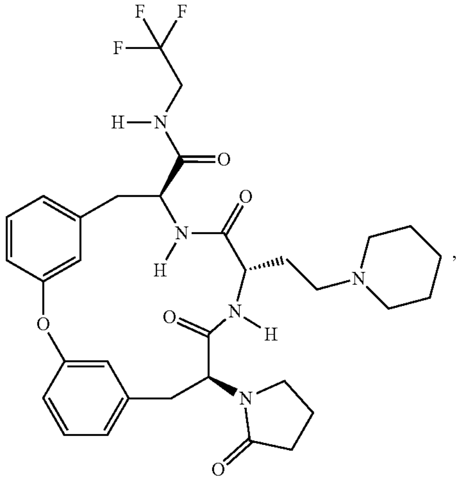

-continued
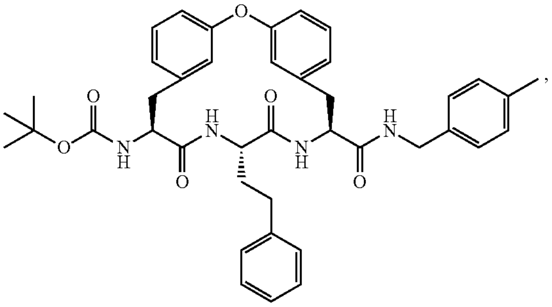
,
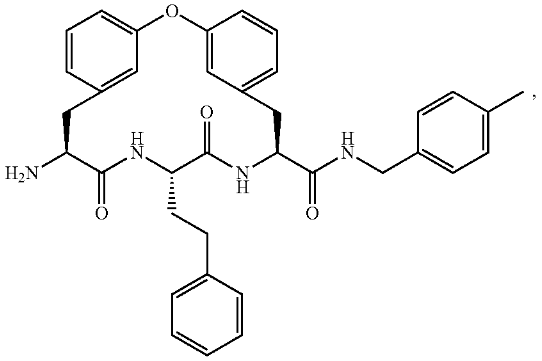
,
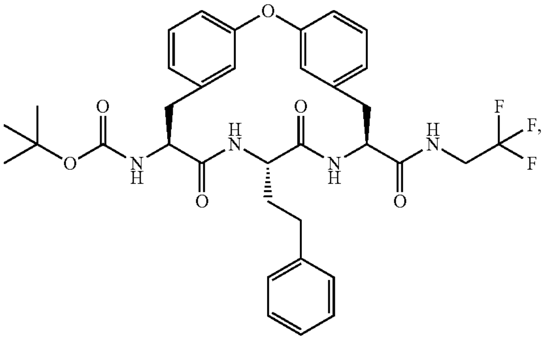
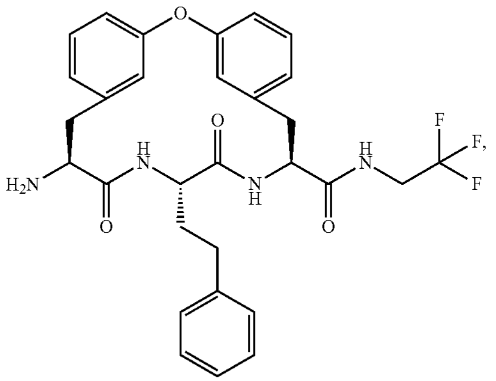
-continued
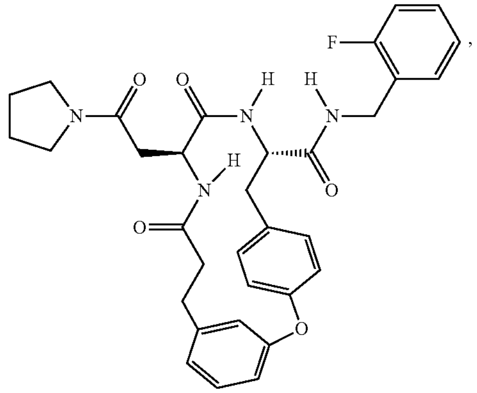
,
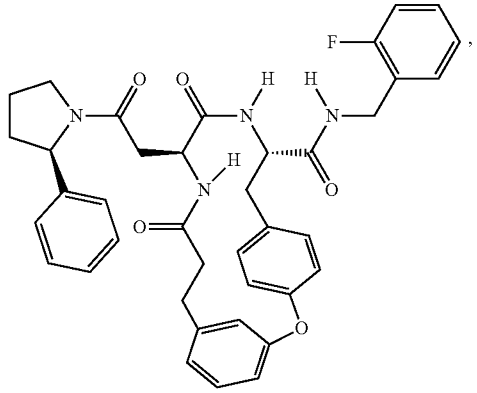
,
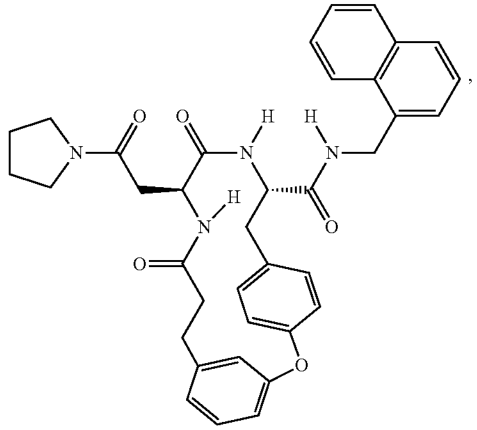
,
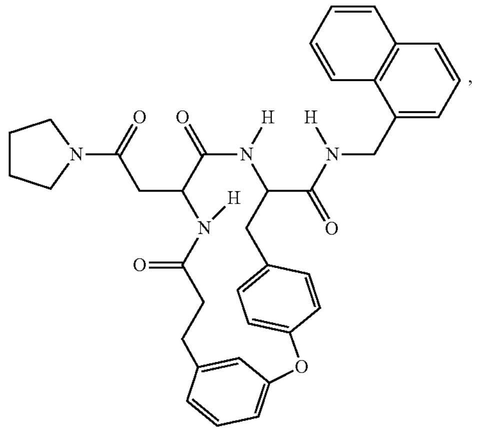
, -continued
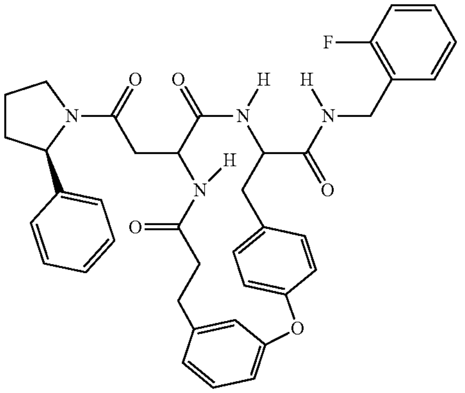,
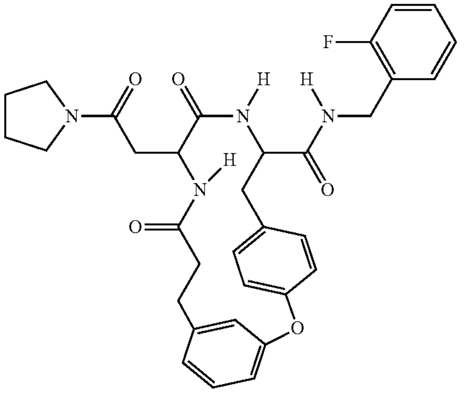,
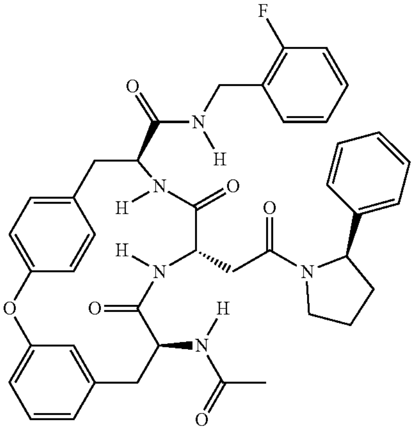,
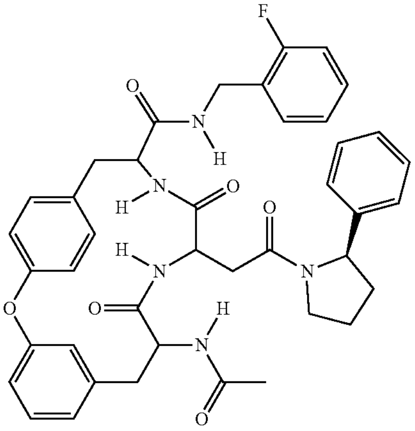,
-continued
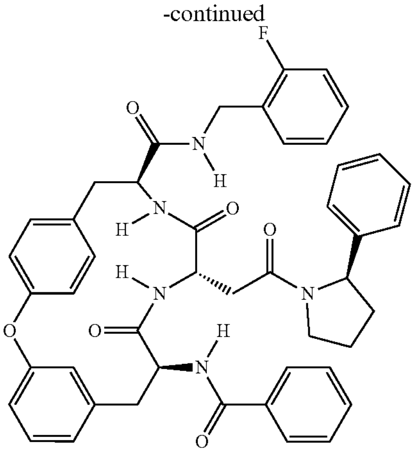,
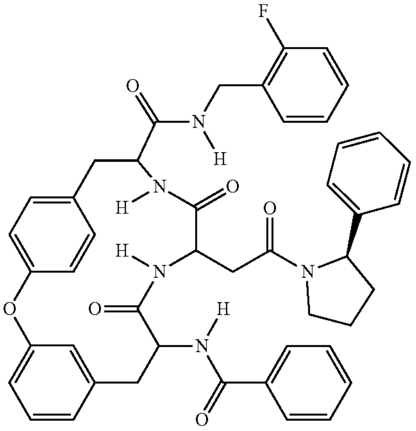,
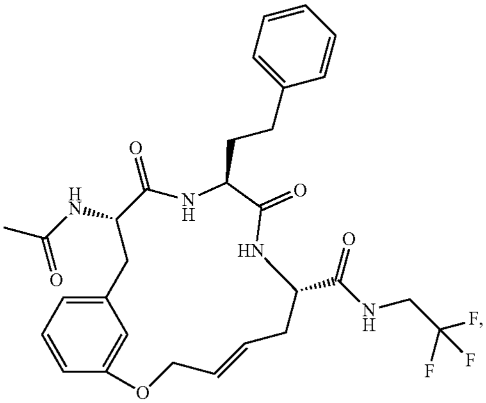,
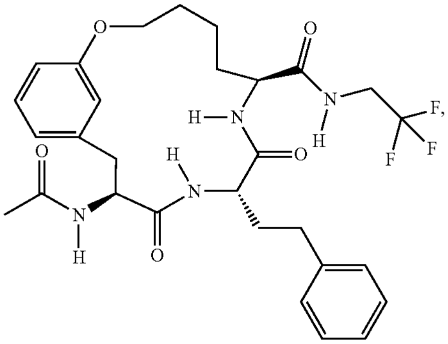

-continued
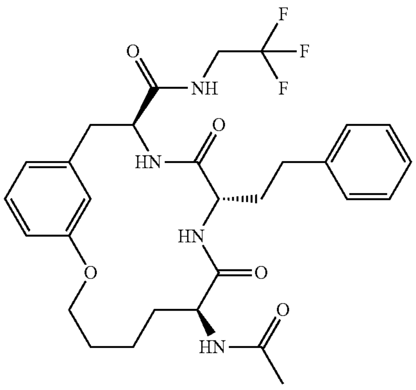
,
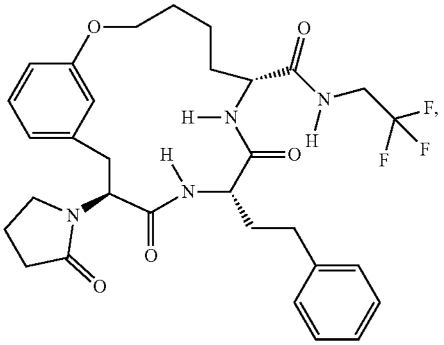
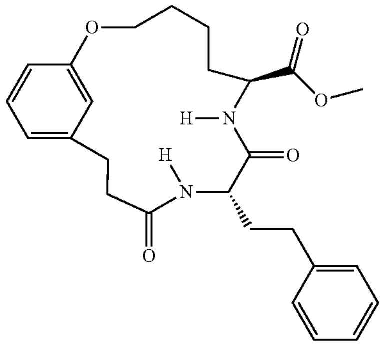
,
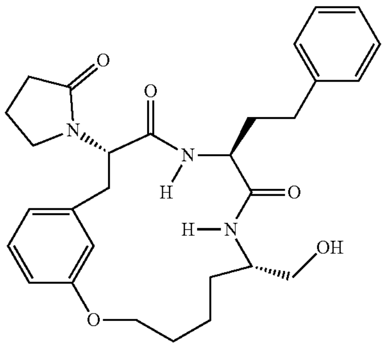
,
-continued
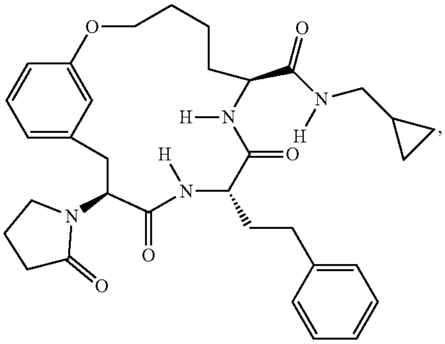
,
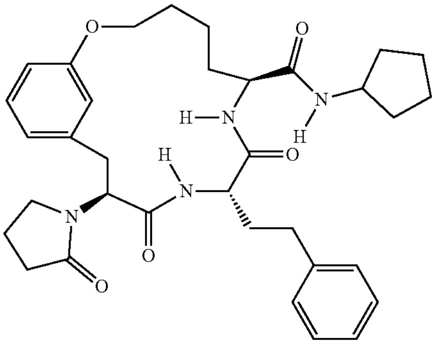
,
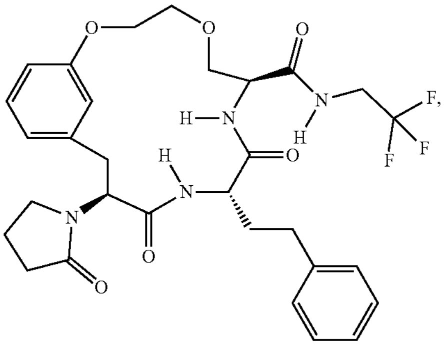
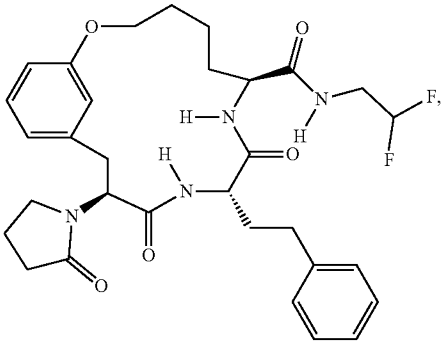
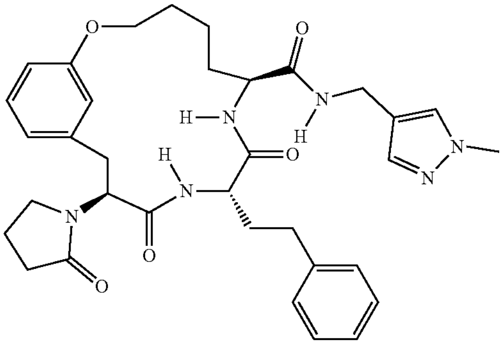
, -continued
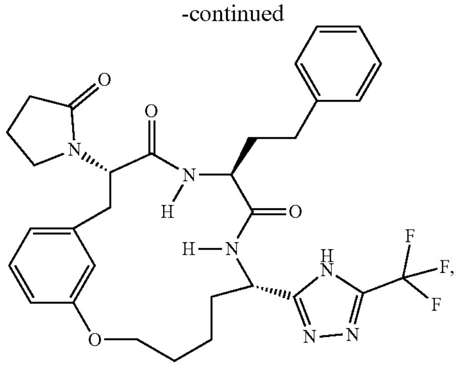
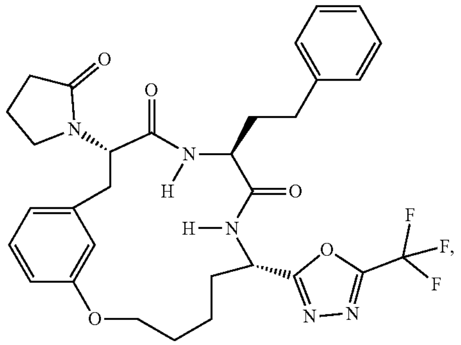
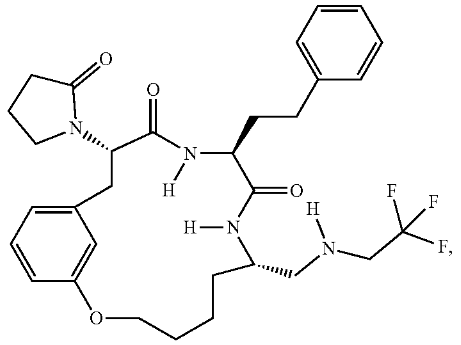
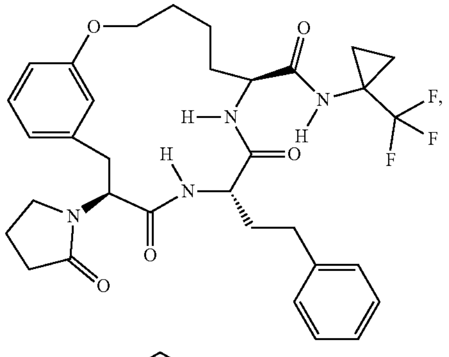
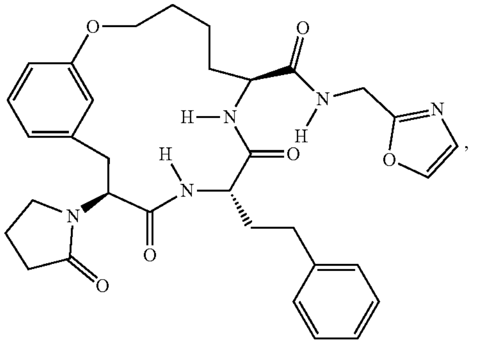
-continued
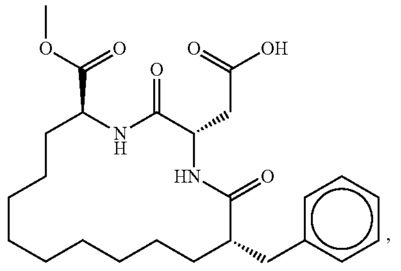
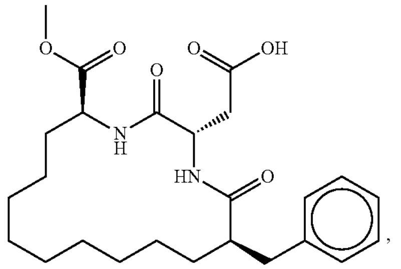
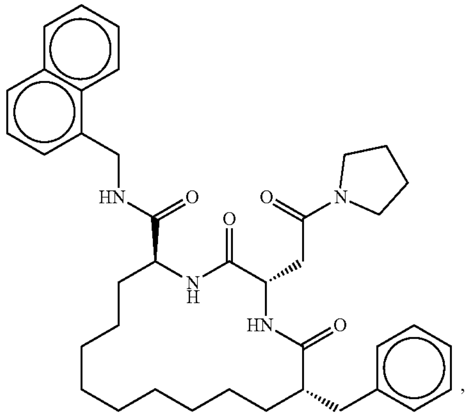
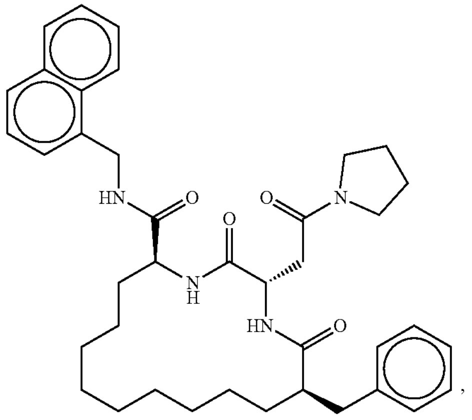

-continued
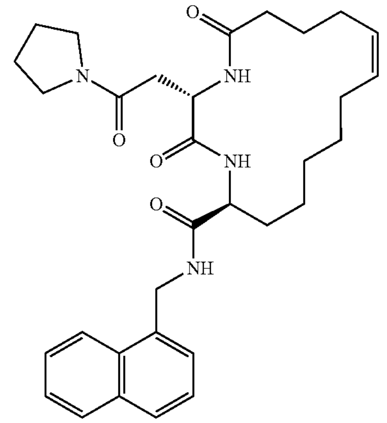
,
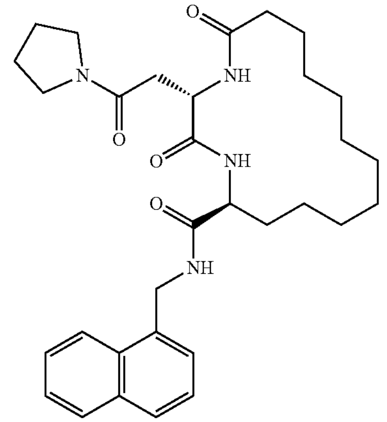
,
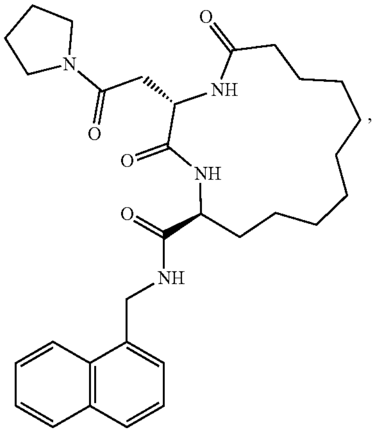
,
-continued
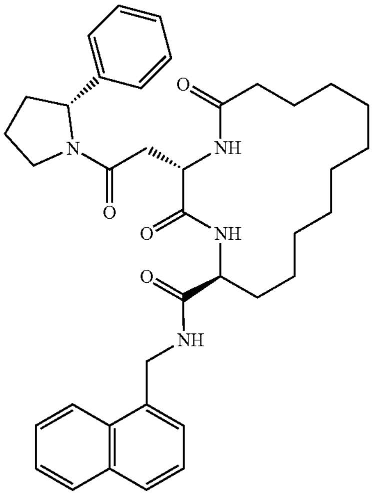
,
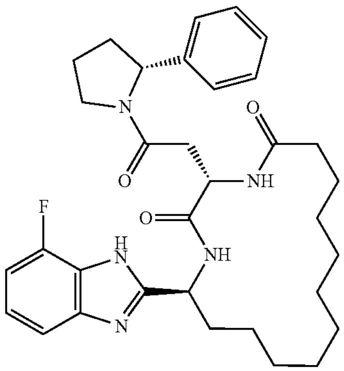
,
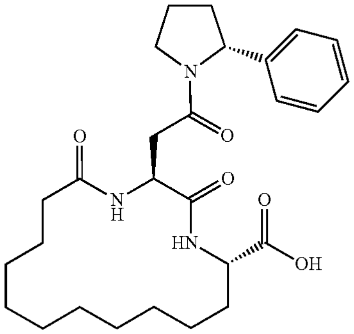
,
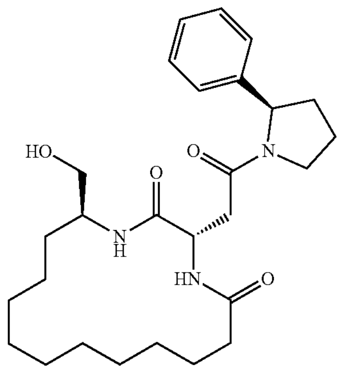
, -continued
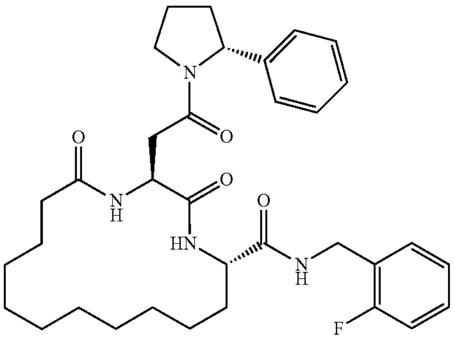
,
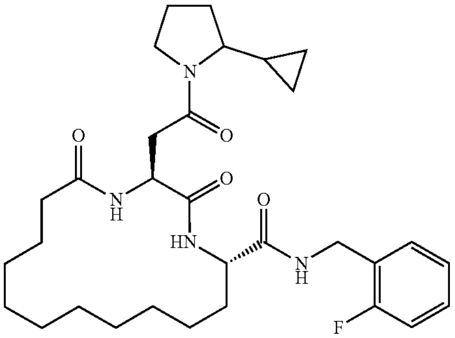
,
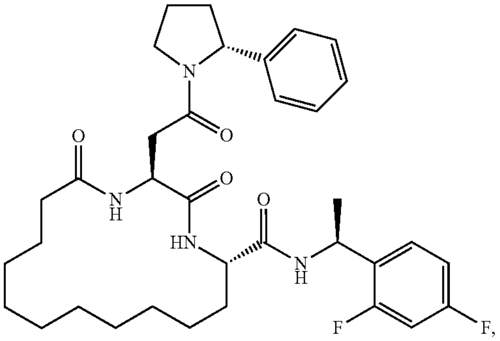
,
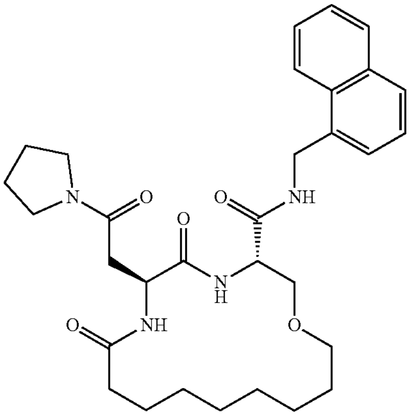
,
-continued
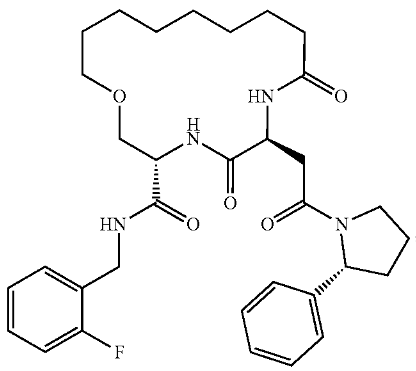
, and
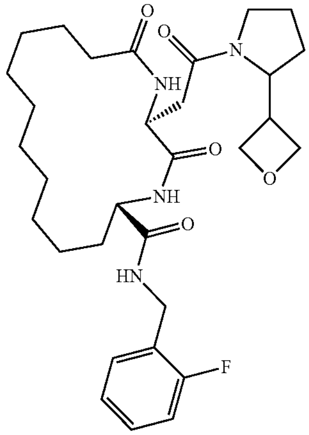
.
In one embodiment, compound has the Formula (I'):
(I')
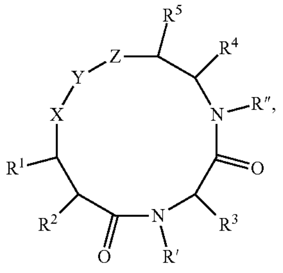
wherein
X is $-(CH_2)_m-$; $-CH_2-CH{=}CH-$, or
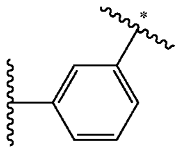
;

Y is a $-CH_2-$ or O;

Z is $-(CH_2)_m-$,

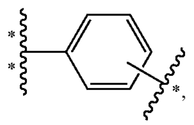

$-CH_2-CH_2-O-$, or O;

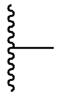

is the point of attachment to $-C(R^1)-$ moiety;

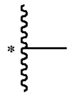

is the point of attachment to Y;

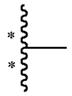

is the point of attachment to $-C(R^5)-$ moiety;

$R^1$ is H;

$R^2$ is independently selected at each occurrence thereof from the group consisting of H, arylalkyl, $-NR^6R^7$, $-NHC(O)R^8$, $-NHS(O)_2R^8$, and $-NHC(O)(CH_2)_nNR^6R^7$;

$R^3$ is independently selected at each occurrence thereof from the group consisting of H, $C_{1-6}$ alkyl, $-(CH_2)_nNR^6R^7$, $-CH_2C(O)NR^6R^7$, $-CH_2C(O)OH$, and arylalkyl, wherein $C_{1-6}$ alkyl can be optionally substituted from 1 to 3 times with $C_{1-6}$ alkoxy and $CF_3$;

$R^4$ is selected from the group consisting of $R^8$, $-C(O)R^8$, $-C(O)NH(CR^aR^b)_nR^8$, $-C(O)OR^8$, $-CH_2NHR^8$, and $-C(O)NR^6R^7$;

$R^5$ is H;

$R^6$ and $R^7$ are each independently selected from the group consisting of H, $C_{1-6}$ alkyl, $C_{3-8}$ cycloalkyl, and $C_{3-12}$ cycloalkylalkyl, or, wherein $C_{3-8}$ cycloalkyl and $C_{3-12}$ cycloalkylalkyl can be optionally substituted from 1 to 3 times with $CF_3$; or $R^6$ and $R^7$ are taken together with the nitrogen to which they are attached to form a piperidine, pyrrolidine, or morpholine ring, wherein piperidine, pyrrolidine, or morpholine ring can be optionally substituted 1 to 3 times with halogen, $C_{1-6}$ alkyl, aryl, =O, $C_{3-8}$ cycloalkyl, or non-aromatic heterocycle;

$R^8$ is selected from the group consisting of H, OH, $CF_3$, $CHF_2$, $C_{1-12}$ alkyl, $C_{3-8}$ cycloalkyl, $C_{3-12}$ cycloalkylalkyl, $C_{1-12}$ alkoxy, monocyclic or bicyclic aryl, arylalkyl, heteroaryl, heterocyclyl, and non-aromatic heterocycle, wherein $C_{1-12}$ alkyl, monocyclic or bicyclic aryl, arylalkyl, heteroaryl, heterocyclyl, and non-aromatic heterocycle can be optionally substituted from 1 to 3 times with OH, halogen, $C_{1-6}$ alkyl, $C_{1-6}$ alkoxy, $CHF_2$, $CF_3$, $-S(O)_2Me$;

$R^a$ and $R^b$ are each independently selected from the group consisting of H and $C_{1-6}$ alkyl;

R' and R" are each independently selected from the group consisting of H and $C_{1-6}$ alkyl;

n is 0, 1, 2, 3, or 4; and m is 2, 3, 4, or 5.

In another embodiment, compound has the Formula (I'a):

(I'a)

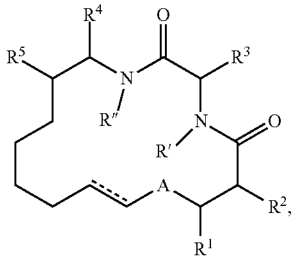

wherein $\equiv$ a single or a double bond, and

A is optional and, if present, is $CH_2$ or O.

In another embodiment, compound has the Formula (I'b):

(I'b)

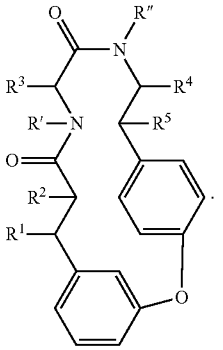

In yet another embodiment, compound has the Formula (I'c):

(I'c)

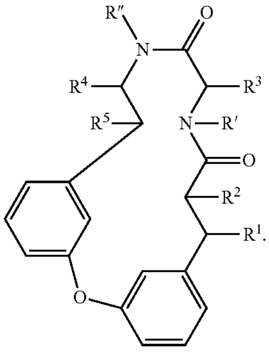

One embodiment relates to the compound of Formulae (I') where $R^2$ is selected from the group consisting of H,
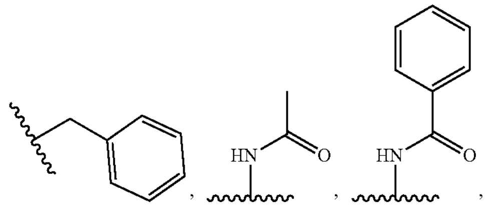
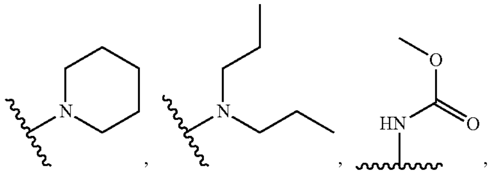
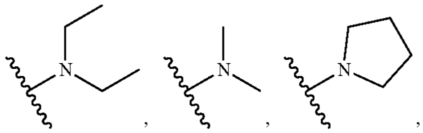
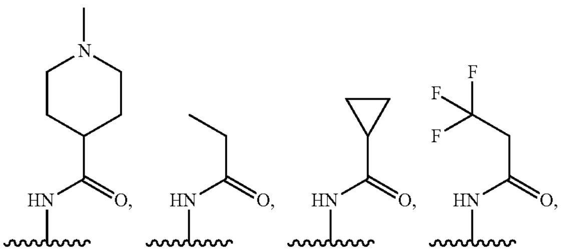
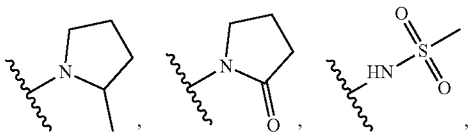
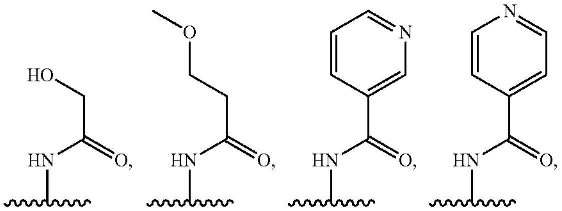
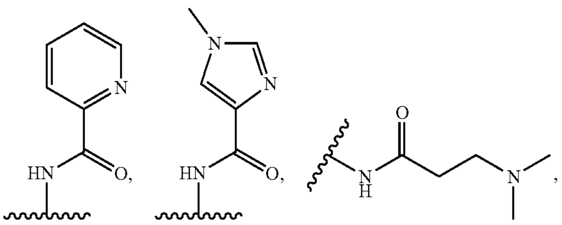
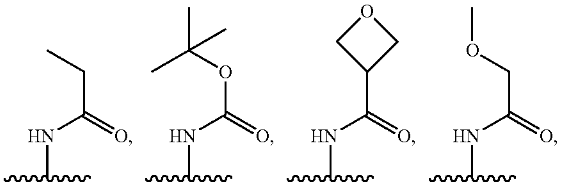
-continued
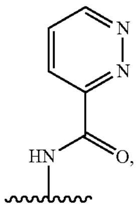
and
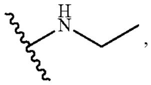
wherein
is the point of attachment to the corresponding carbon atom of the structure of Formula (I).
Another embodiment relates to the compound of Formulae (I') where $R^3$ is selected from the group consisting of H,
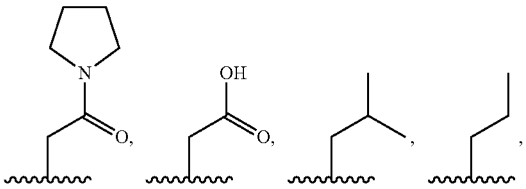
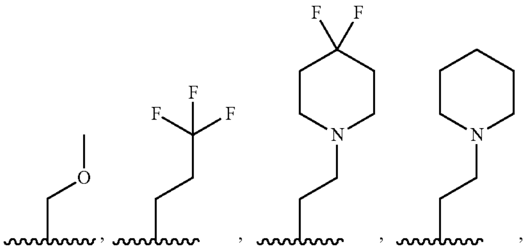
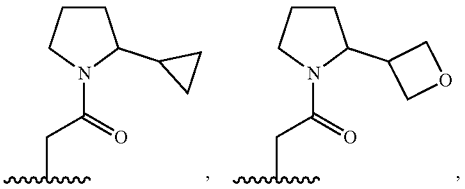
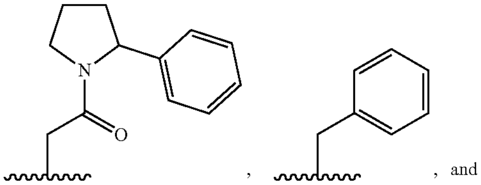
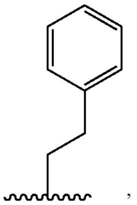

wherein
is the point of attachment to the corresponding carbon atom of the structure of Formula (I).
Another embodiment relates to the compound of Formulae (I') where $R^4$ is selected from the group consisting of
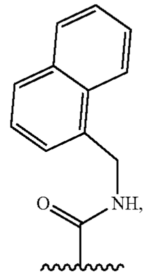
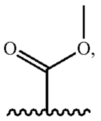
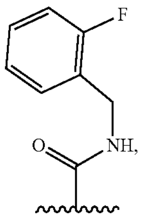
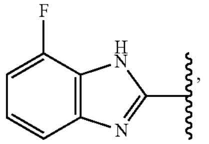
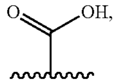
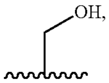
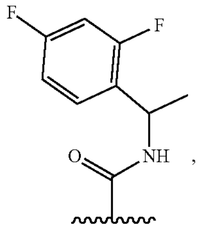
,
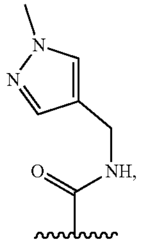
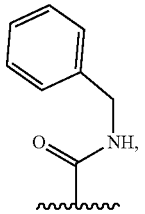
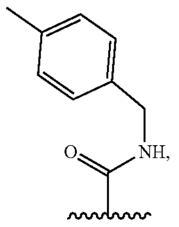
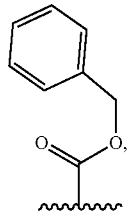
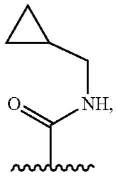
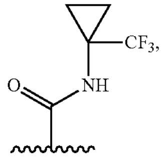
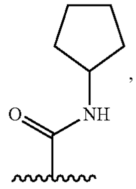
,
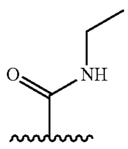
,
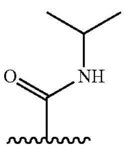
,
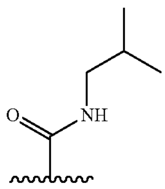
,
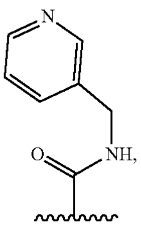
-continued
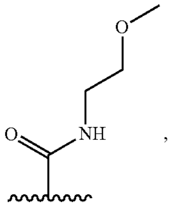
,
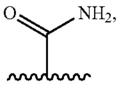
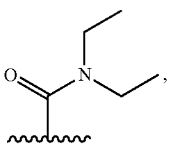
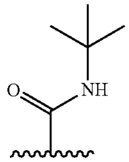
,
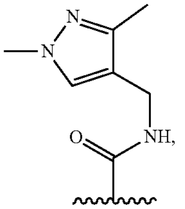
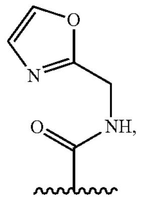
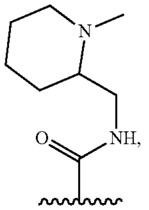
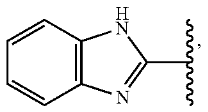
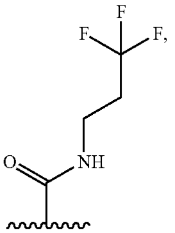
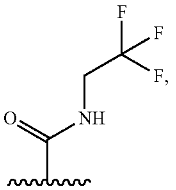
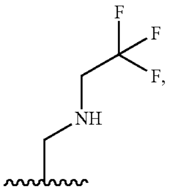
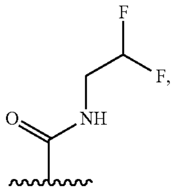
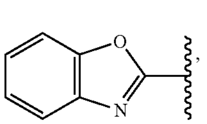
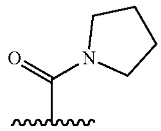
,
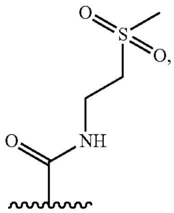
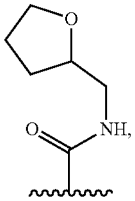
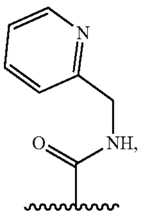
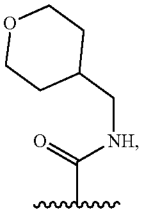
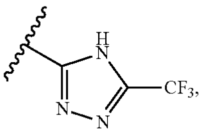

-continued

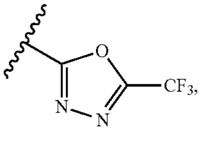

and

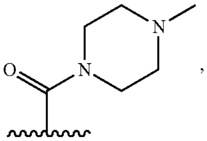

, wherein

is the point of attachment to the corresponding carbon atom of the structure of Formula (I).

Yet another embodiment relates to the compound of Formulae (I') where X is selected from the group consisting of —$(CH_2)_3$—, —$CH_2$—CH═CH—,

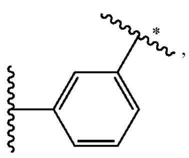

and —$(CH_2)_5$—.

A further embodiment relates to the compound of Formulae (I') where Z is selected from the group consisting of —$(CH_2)_3$—, —$(CH_2)_2$—,

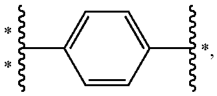

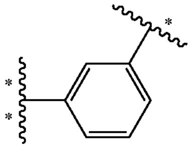

,

—CH—$CH_2$—O—, and O.

Another embodiment relates to the compound of Formulae (I') where the compound has a structure selected from the group consisting of.

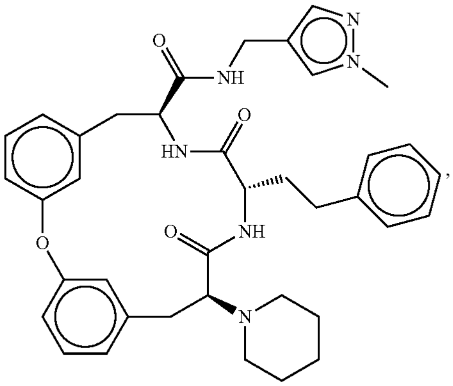

-continued

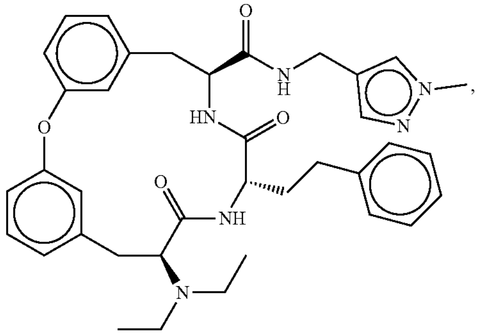

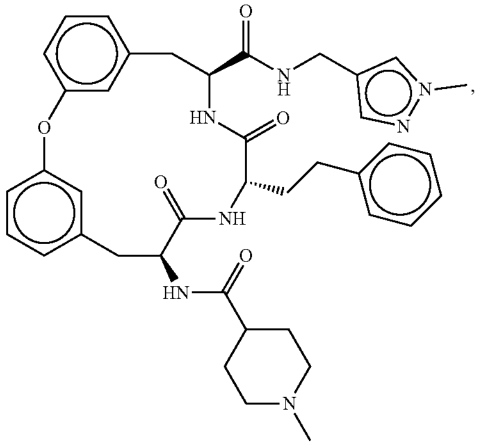

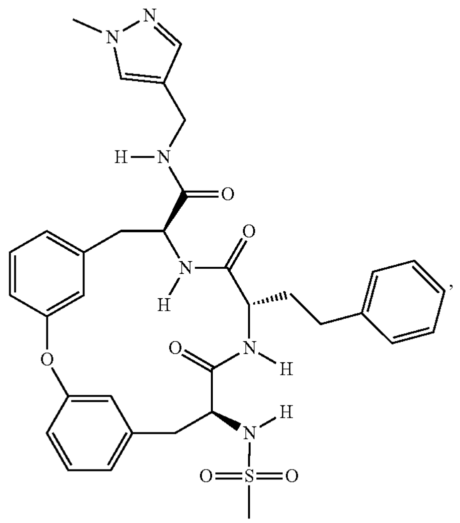

-continued
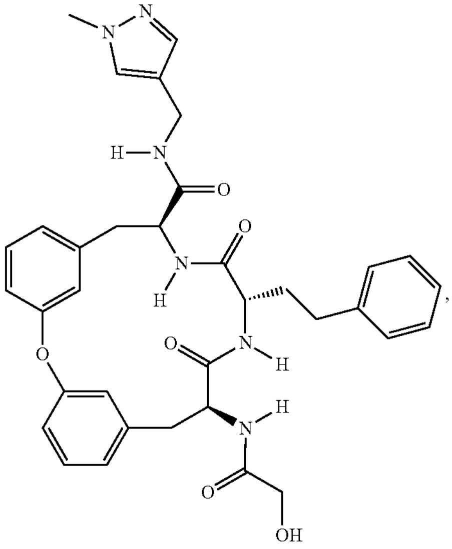
,
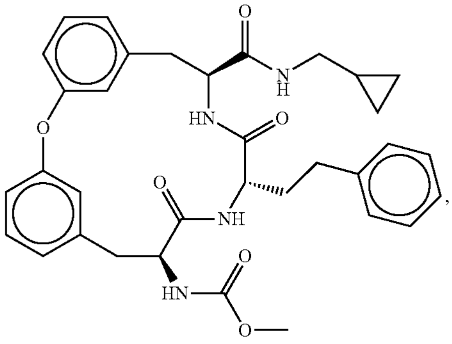
,
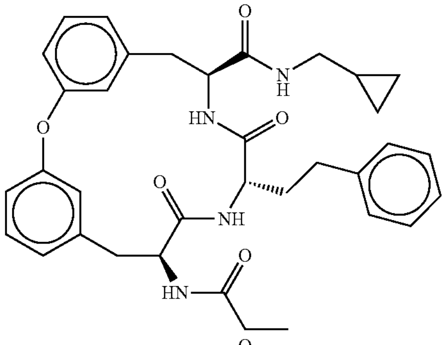
,
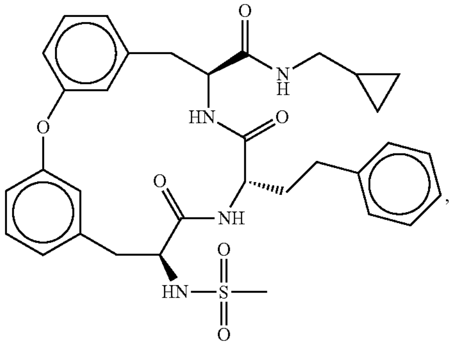
,
-continued
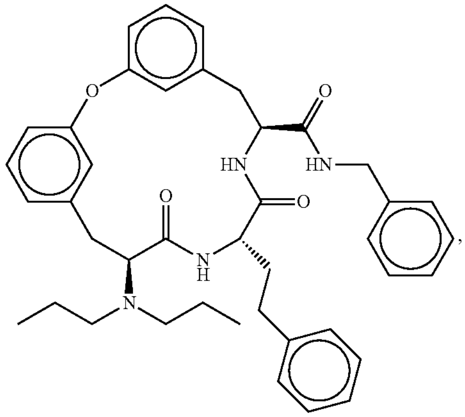
,
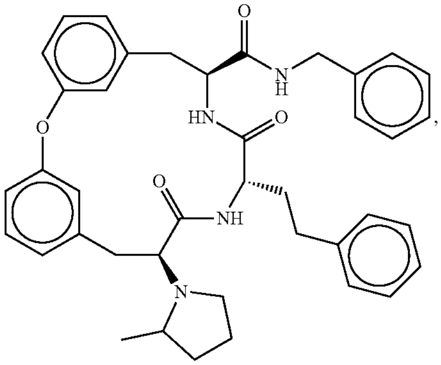
,
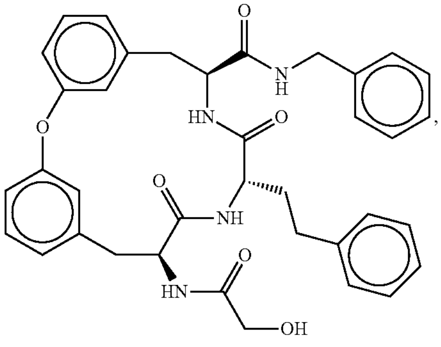
,
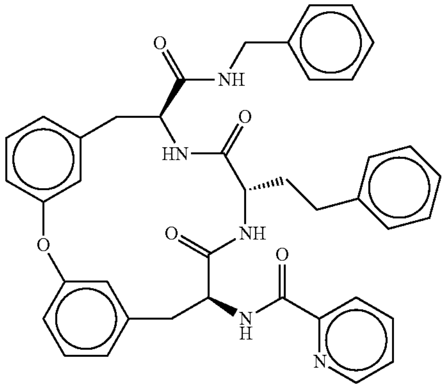
, -continued
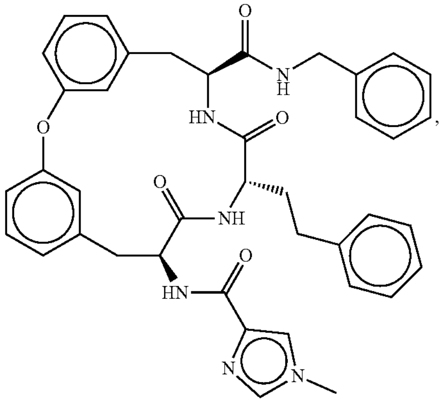
,
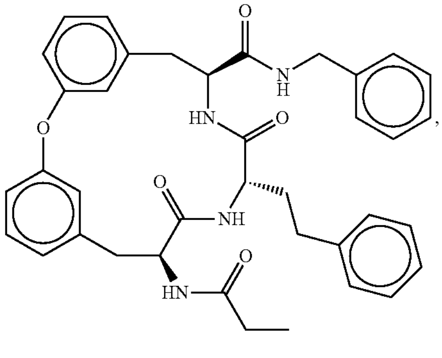
,
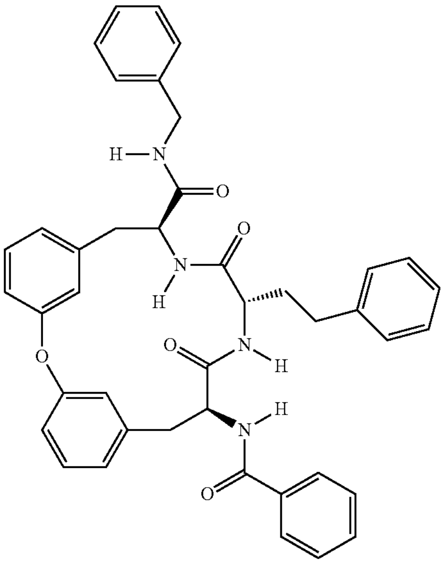
,
-continued
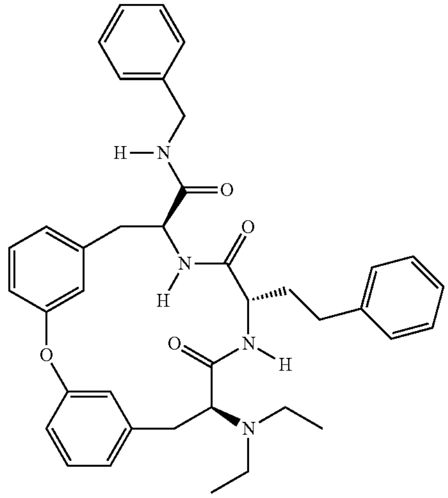
,
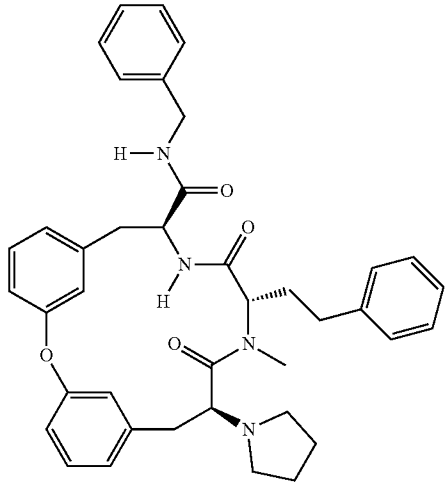
,
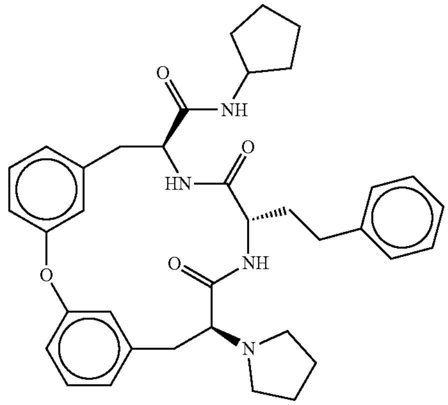
,
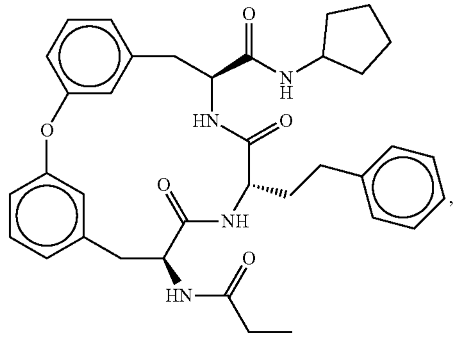
, -continued
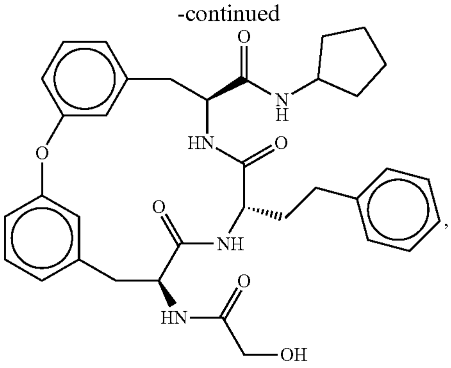
,
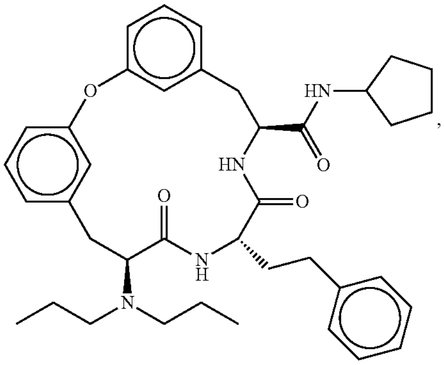
,
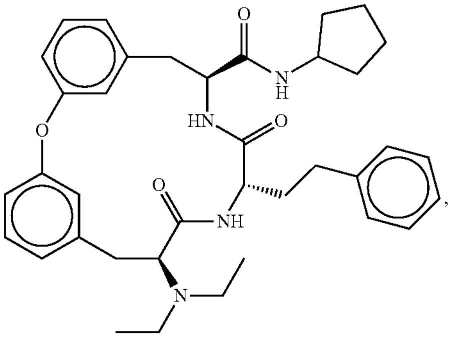
,
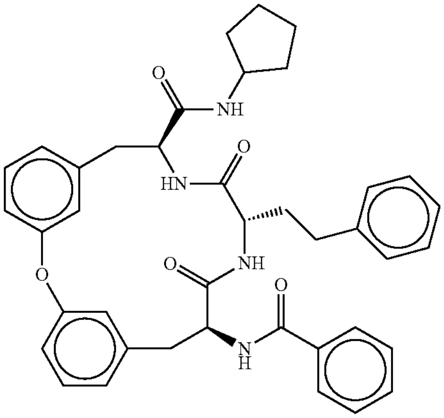
,
-continued
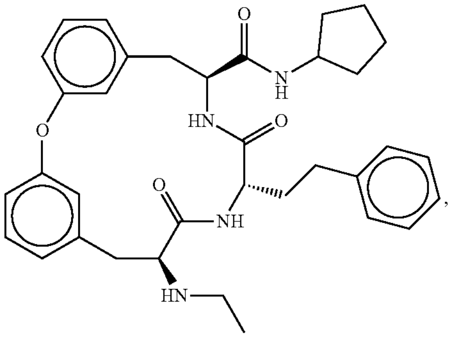
,
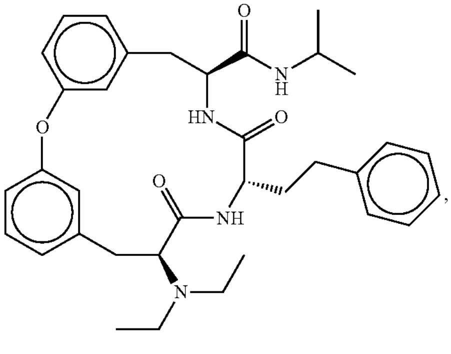
,
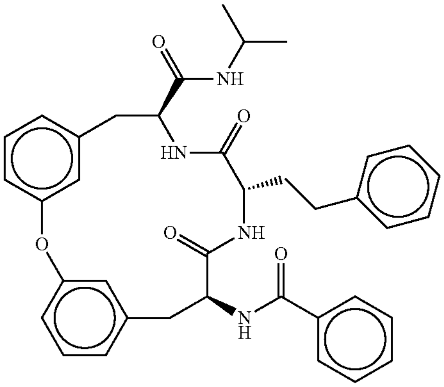
,
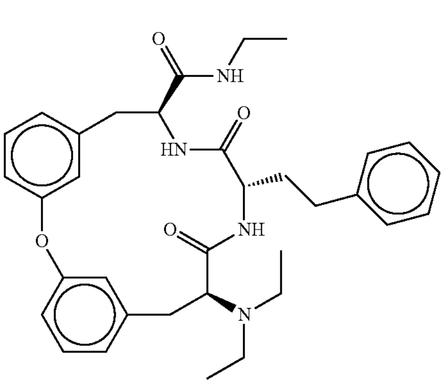
, -continued
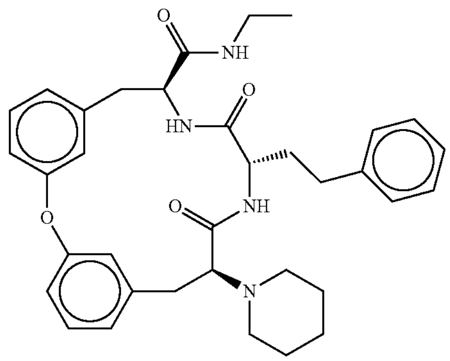
,
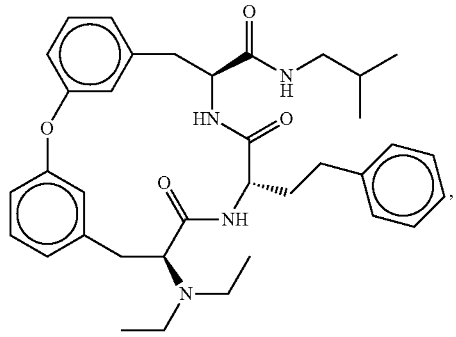
,
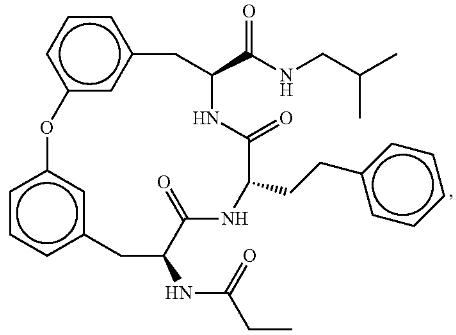
,
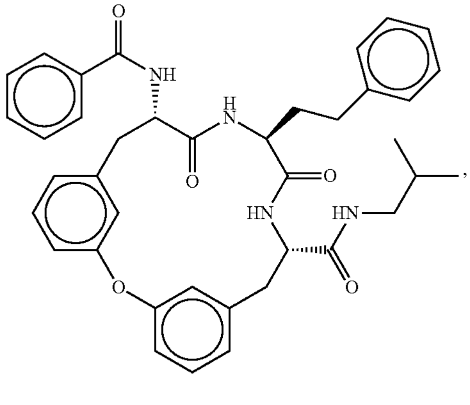
,
-continued
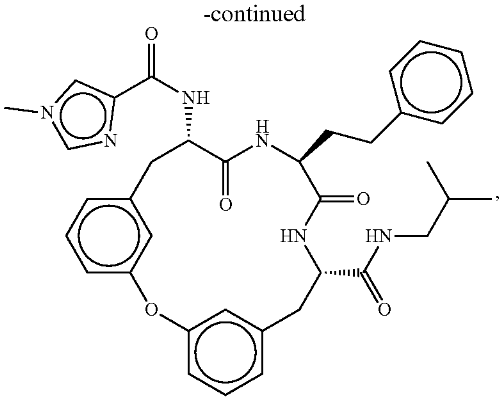
,
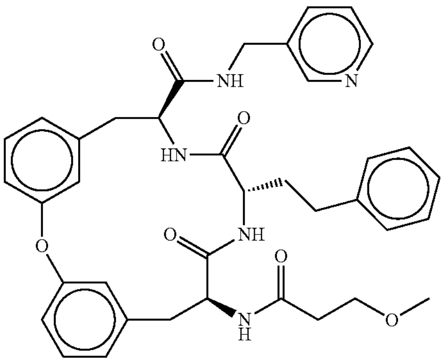
,
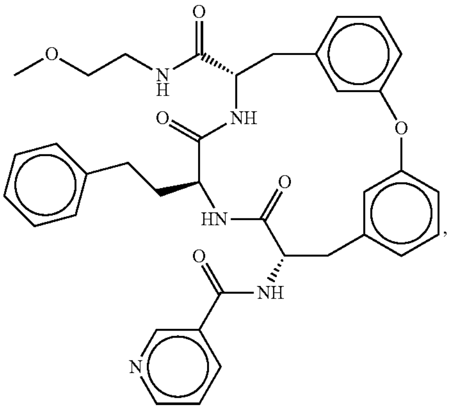
,
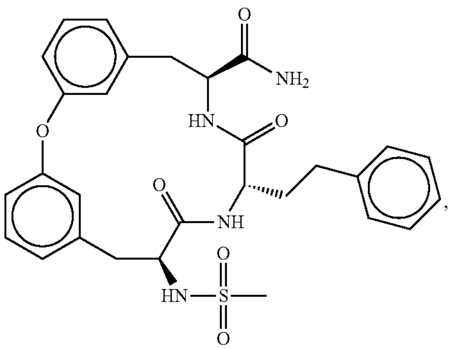
, -continued
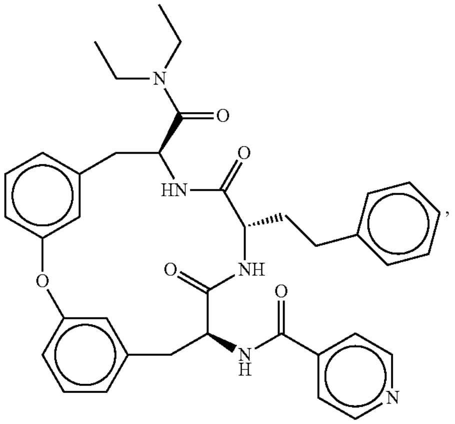
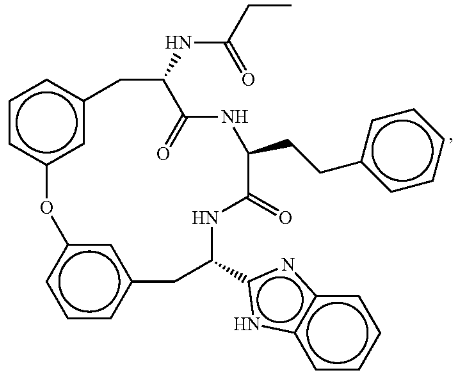
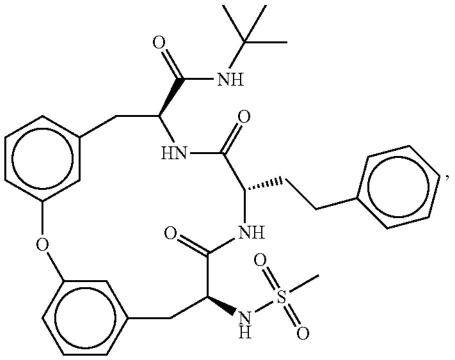
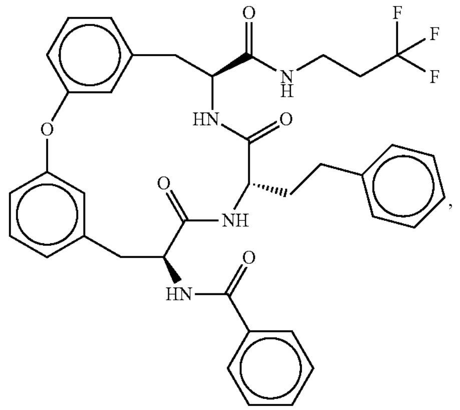
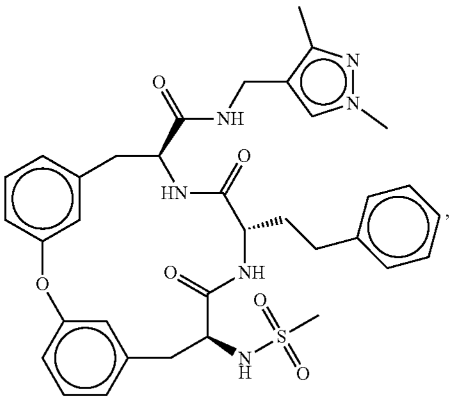
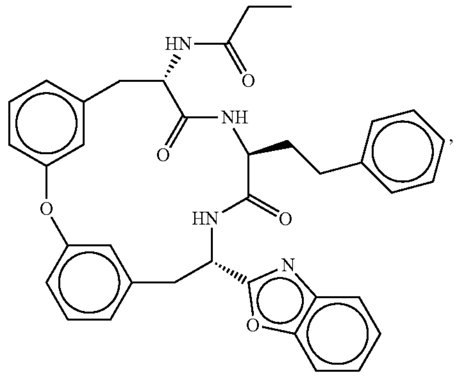
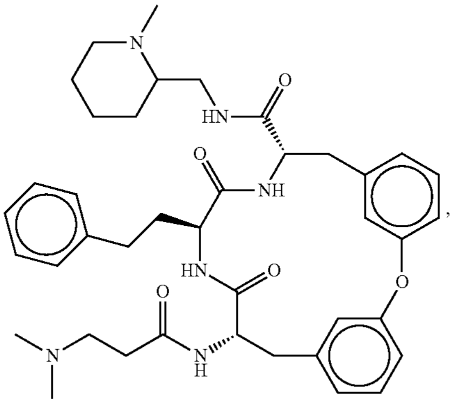
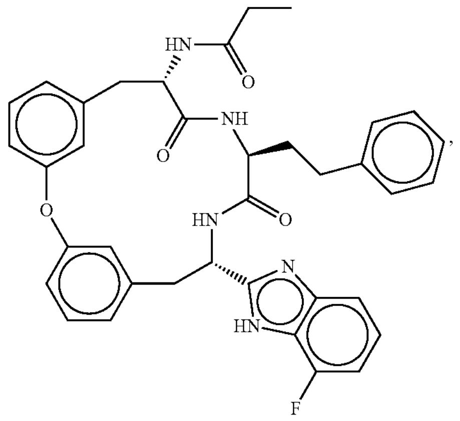

-continued
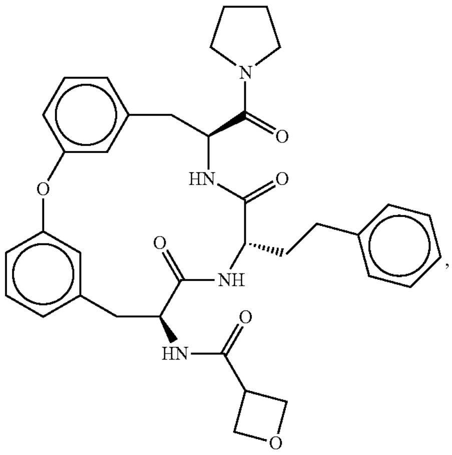
,
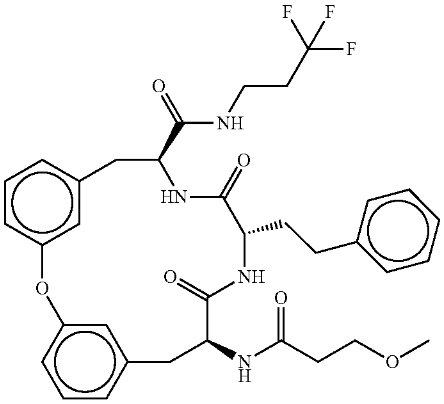
,
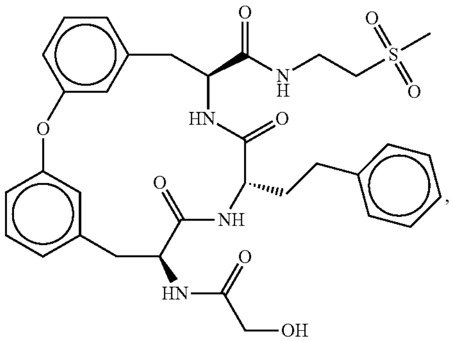
,
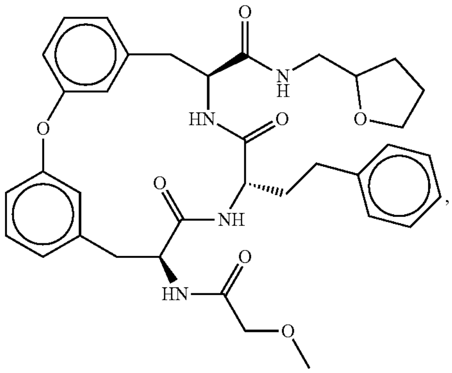
,
-continued
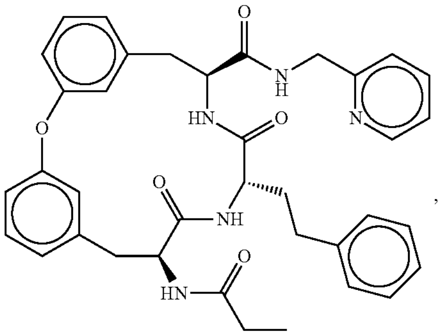
,
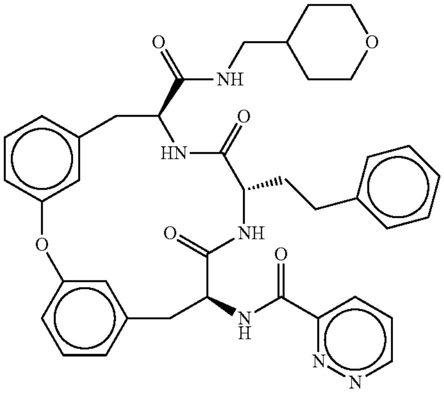
,
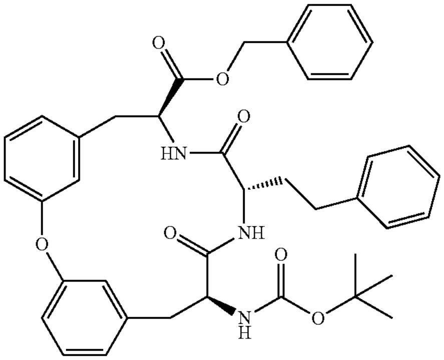
,
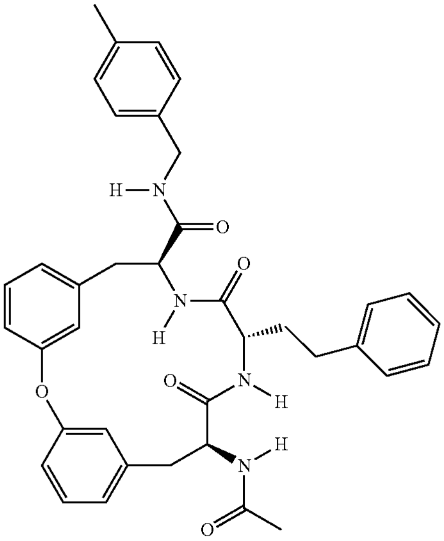
, -continued
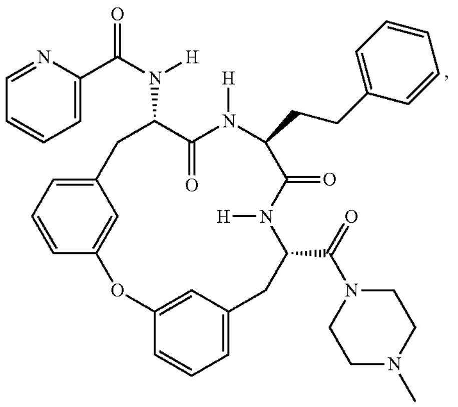
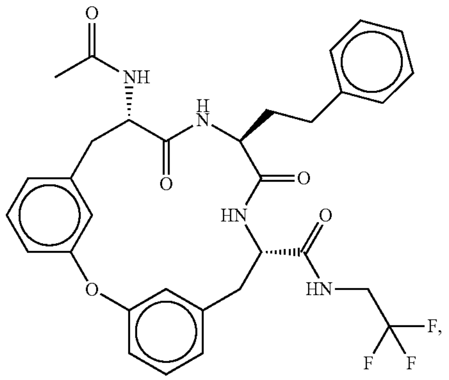
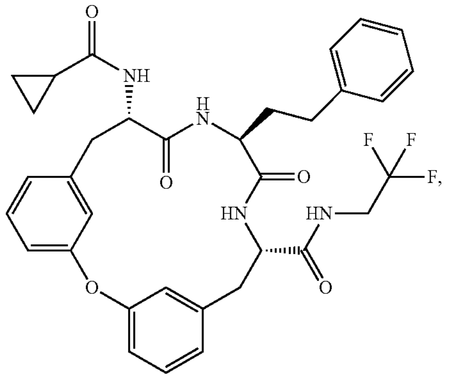
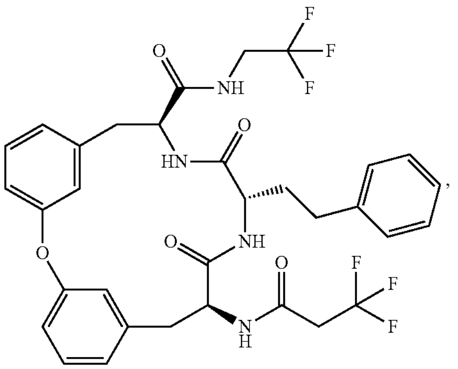
-continued
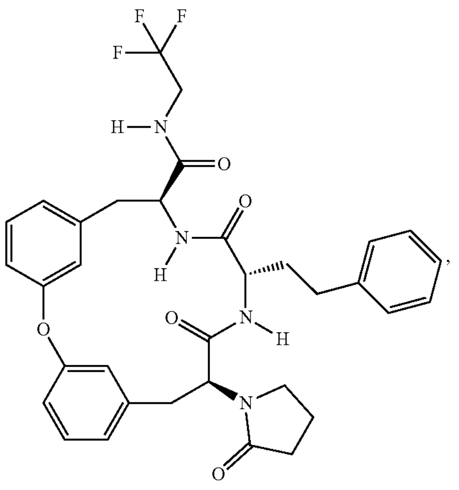
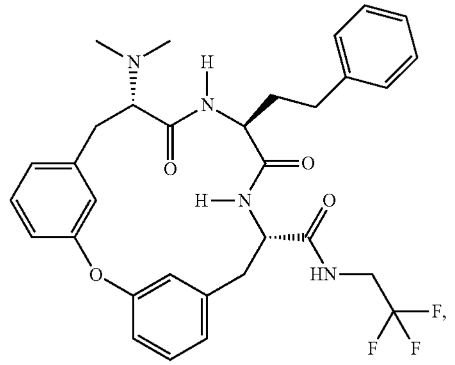
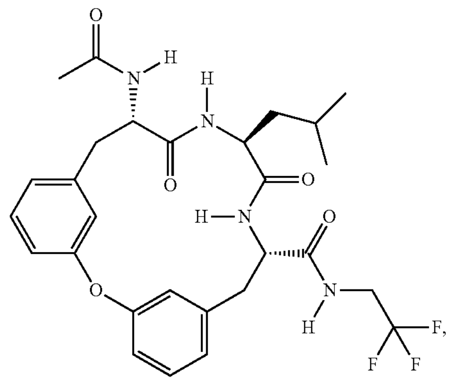
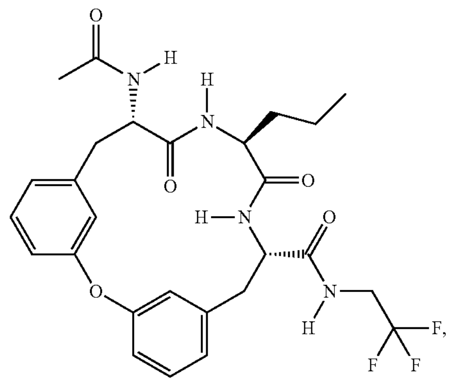

-continued
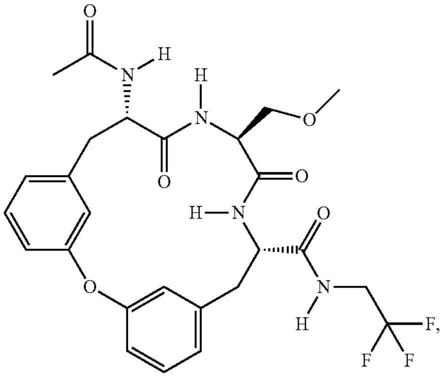
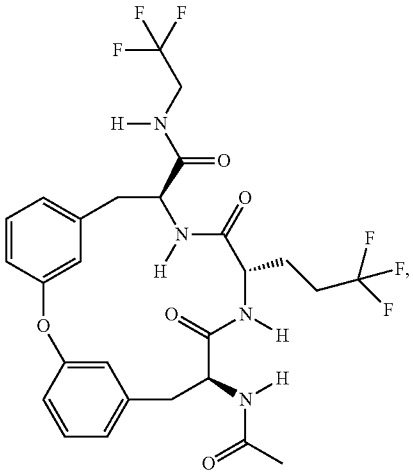
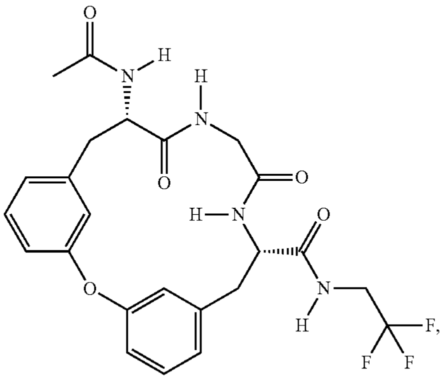
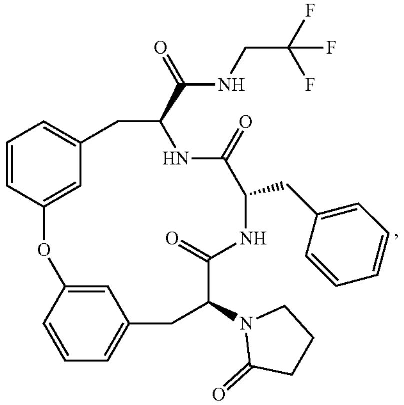
-continued
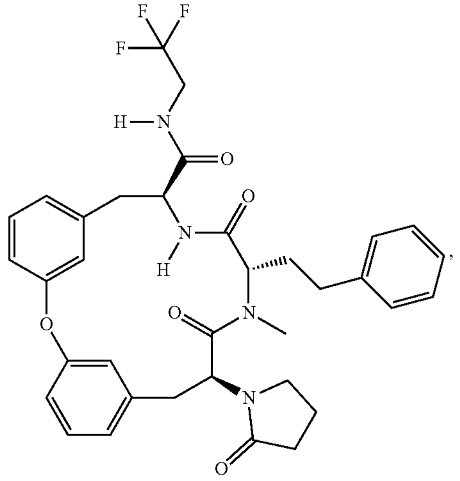
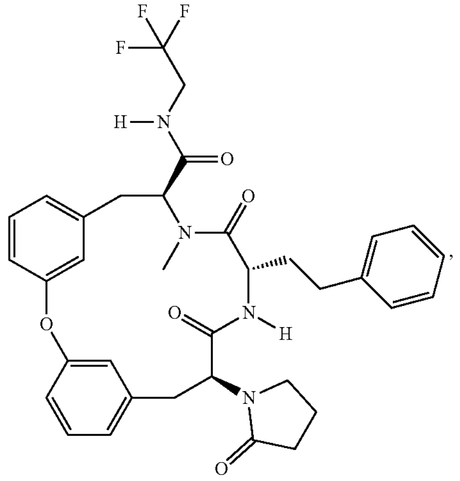
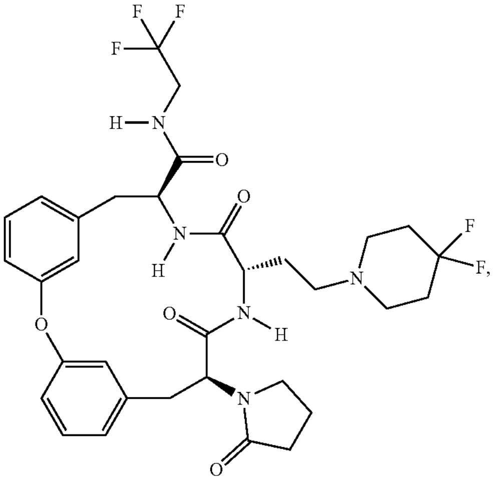

-continued
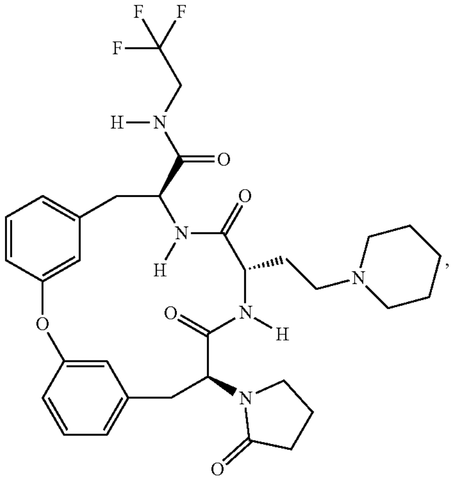
,
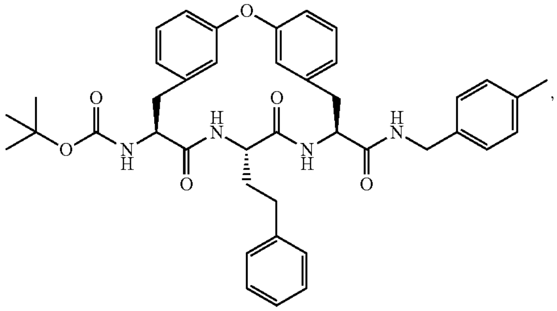
,
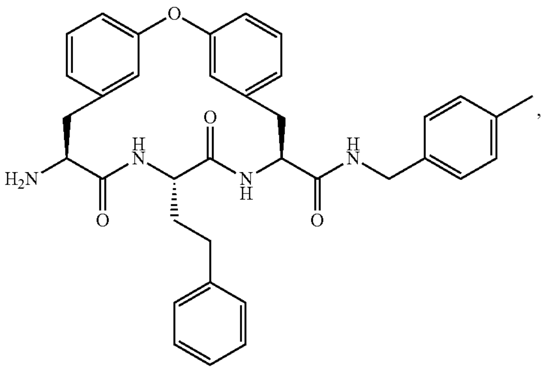
,
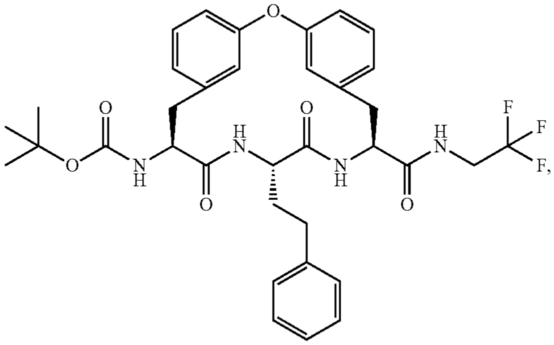
,
-continued
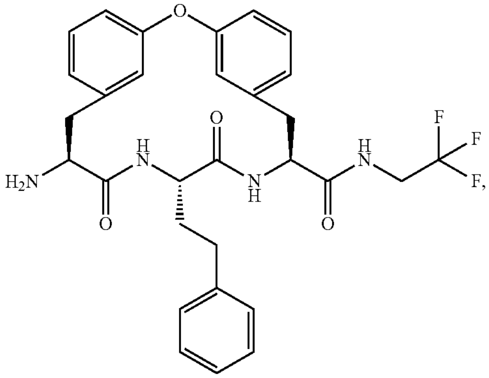
,
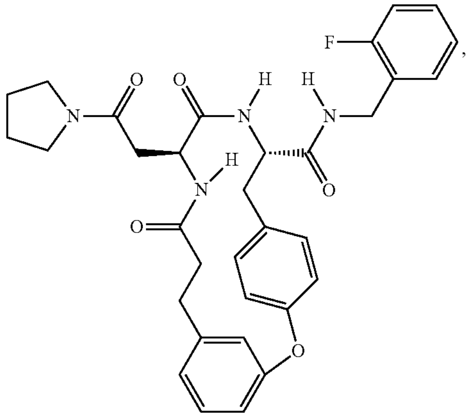
,
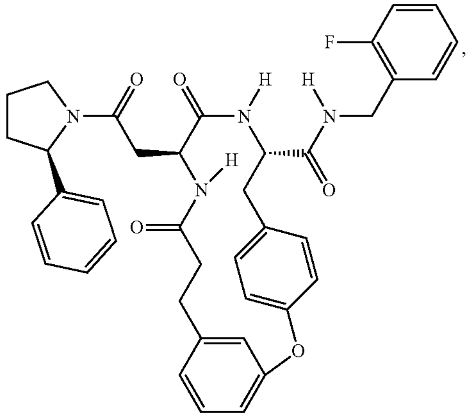
,
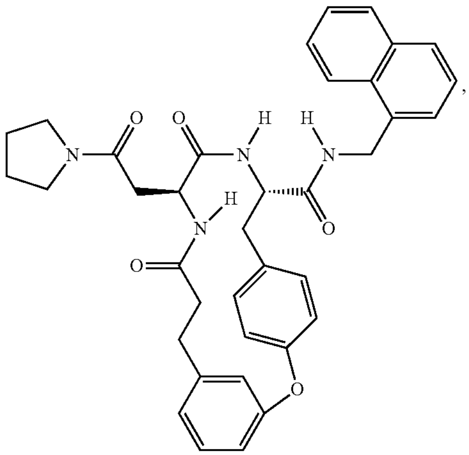
,

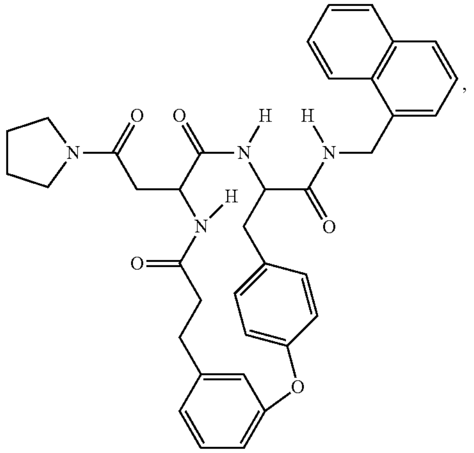
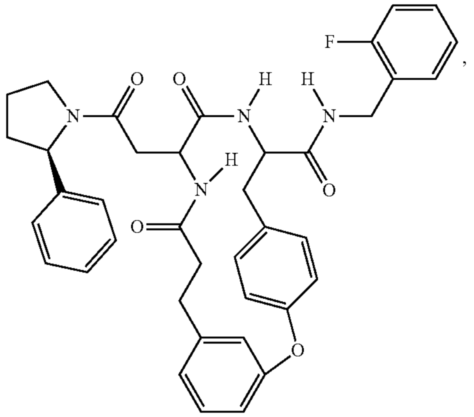
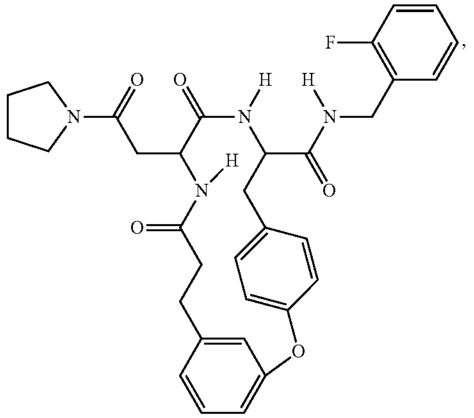
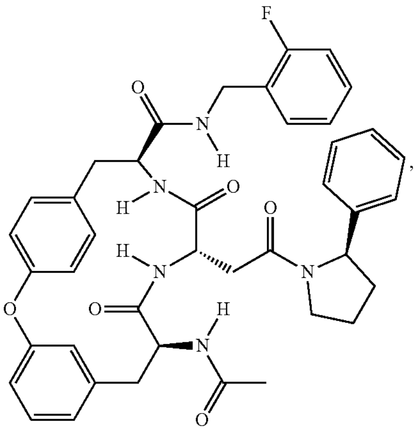
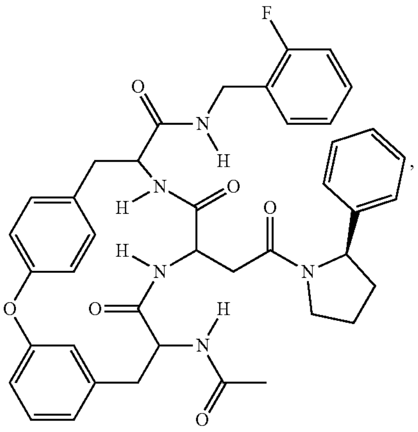
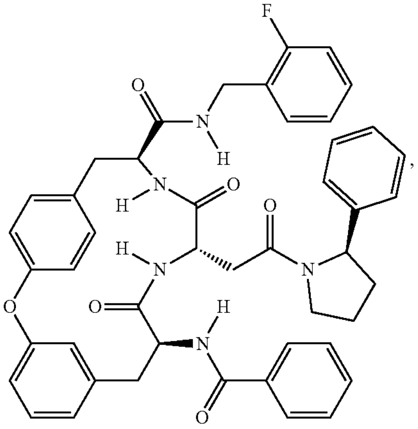
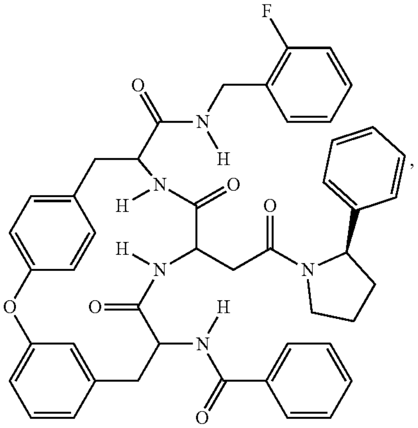
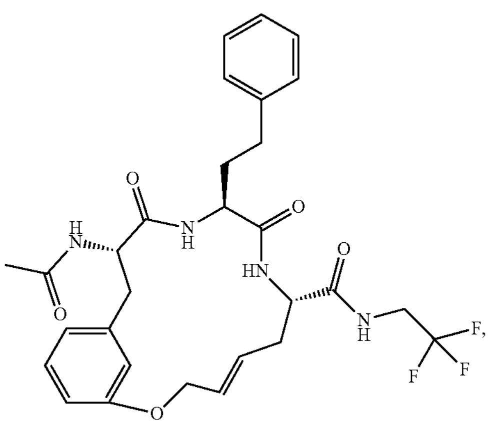

-continued
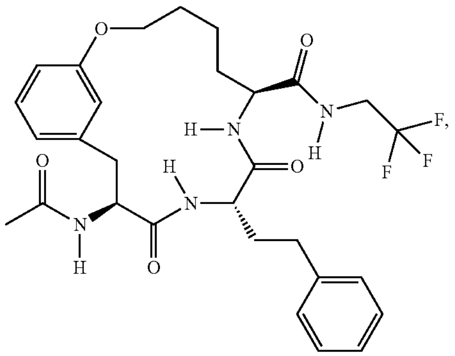
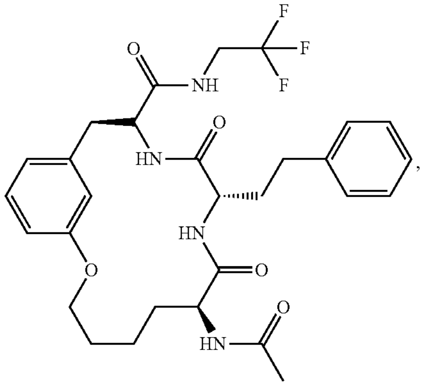
,
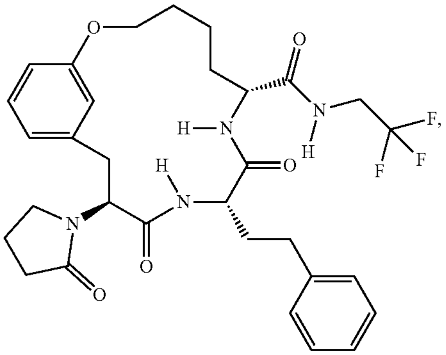
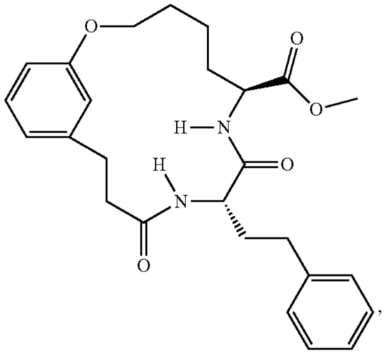
,
-continued
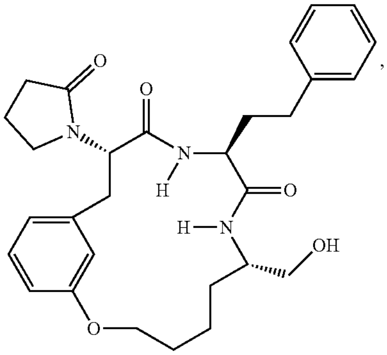
,
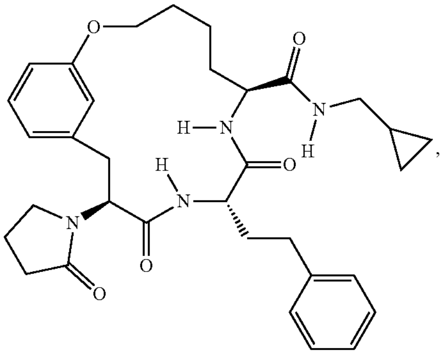
,
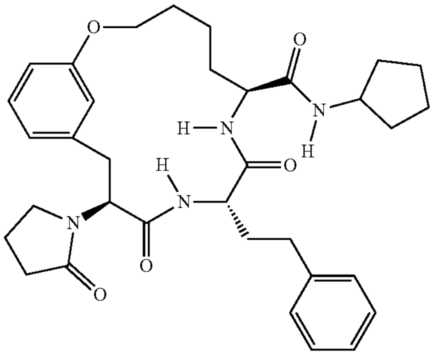
,
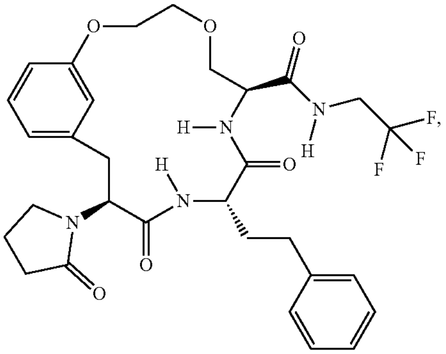

-continued
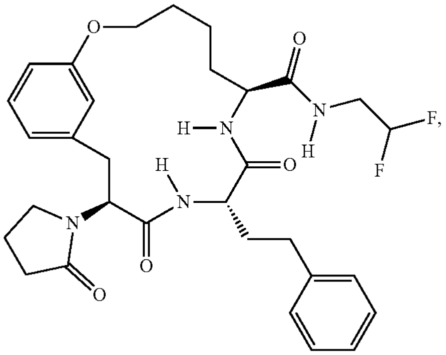
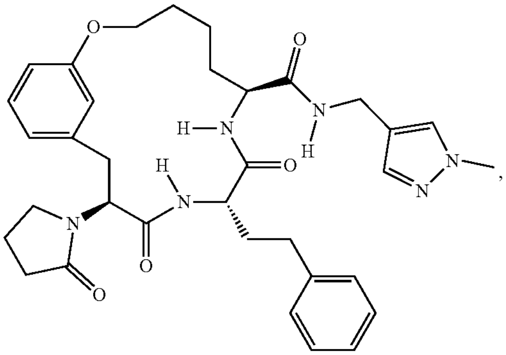
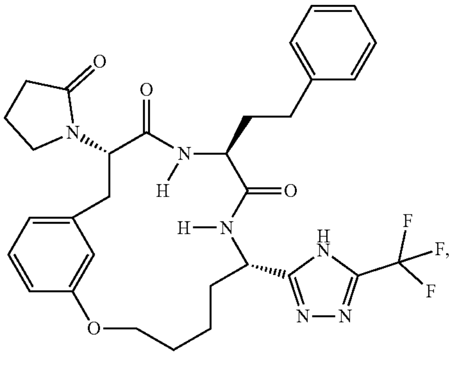
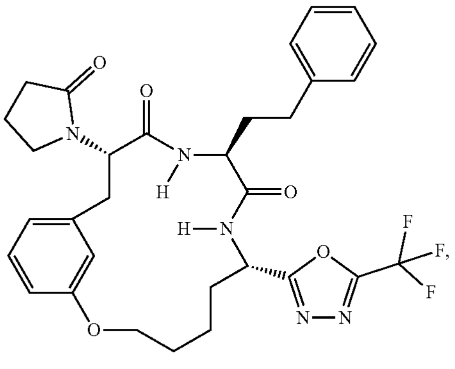
-continued
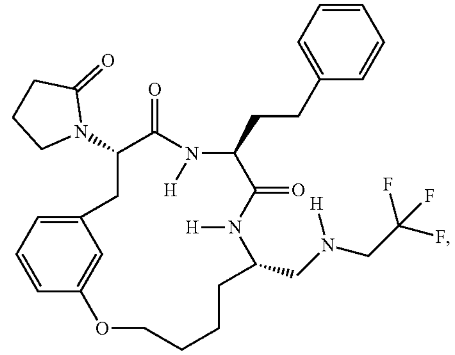
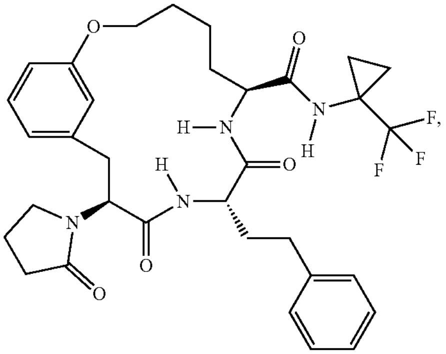
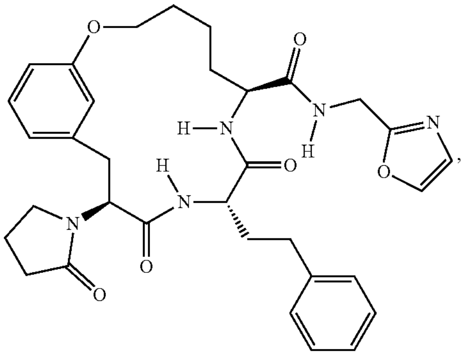
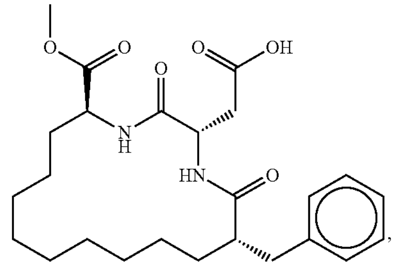
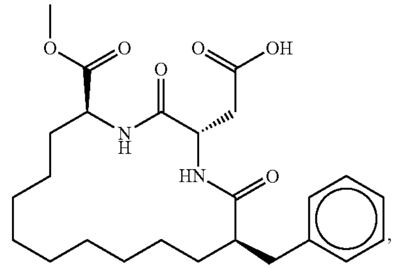

-continued
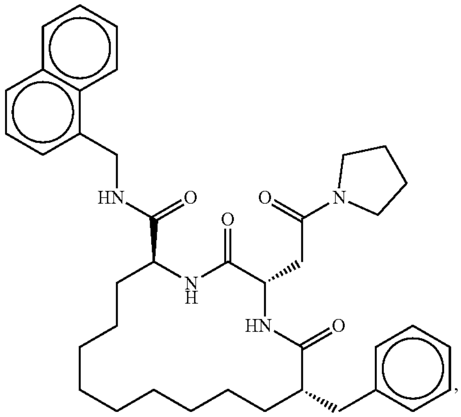
,
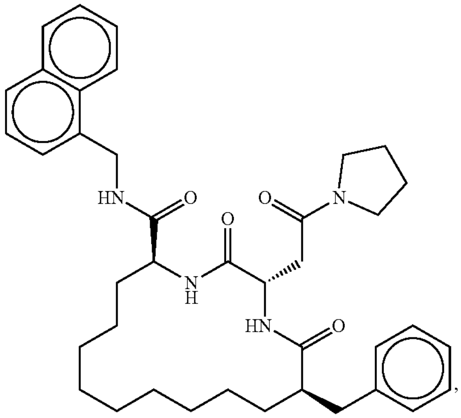
,
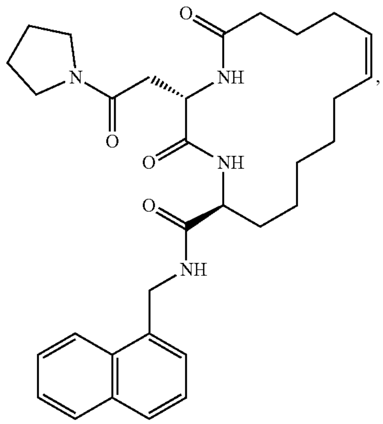
,
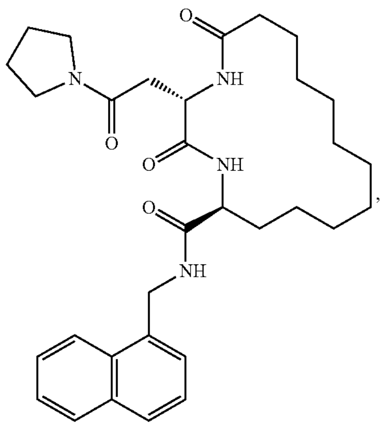
,
-continued
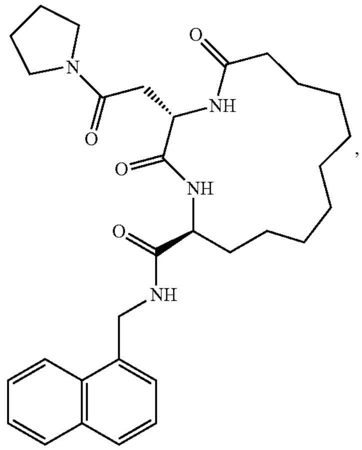
,
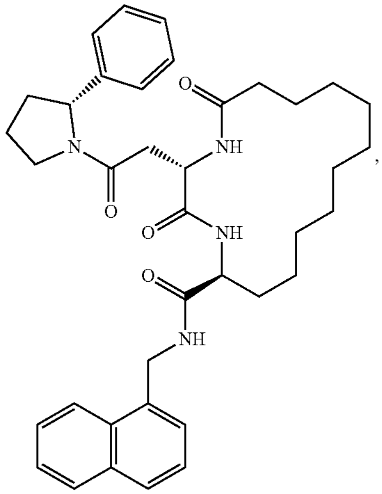
,
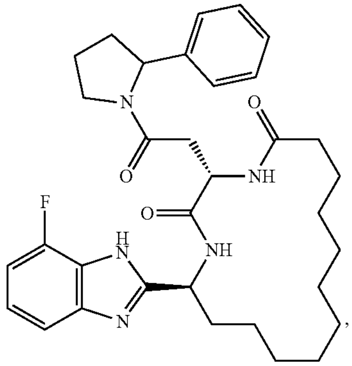
,
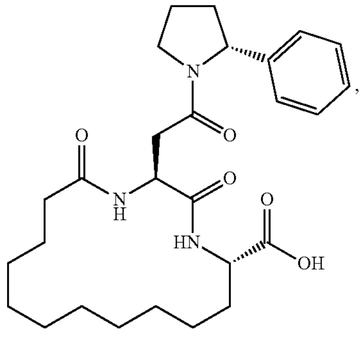
, -continued
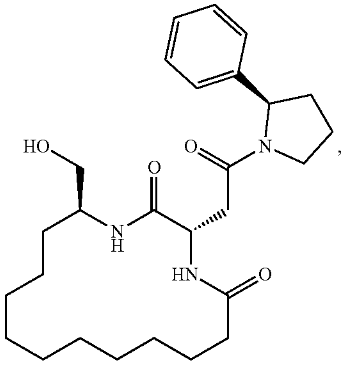
,
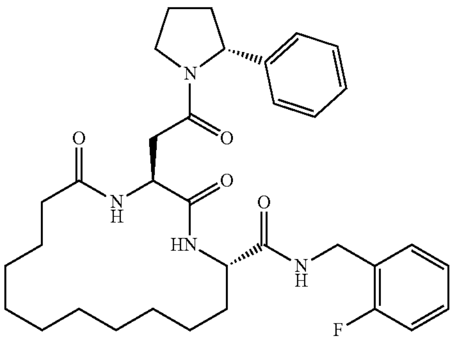
,
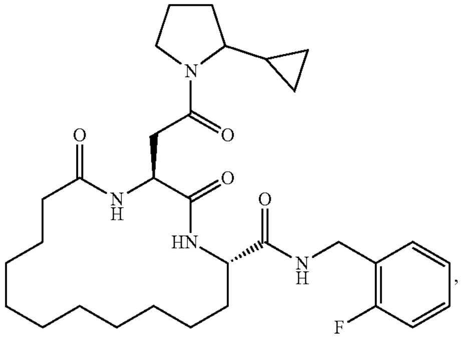
,
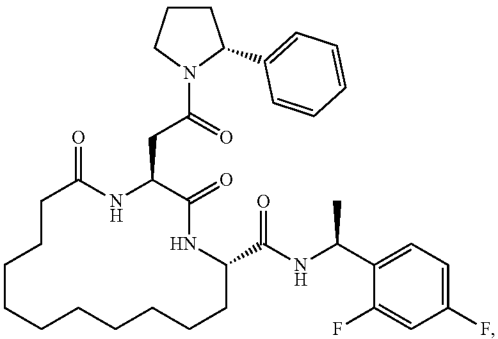
-continued
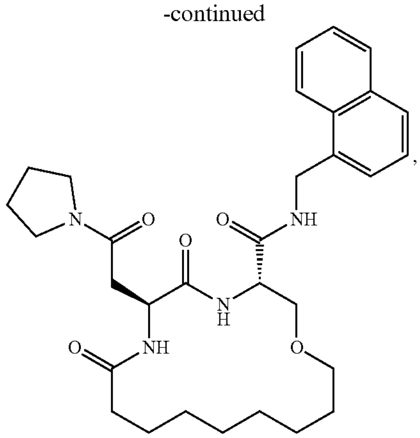
,
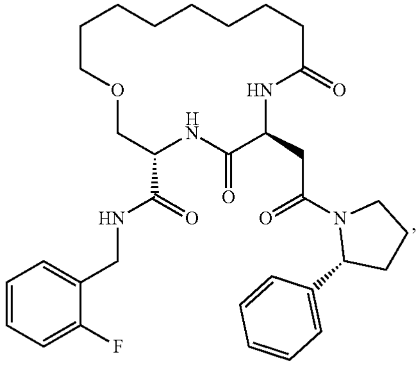
, and
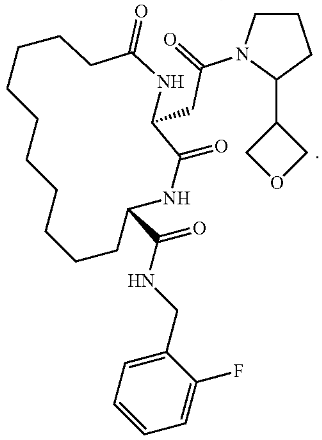
.
A second aspect of the present invention relates to a compound of Formula (II):
(II)
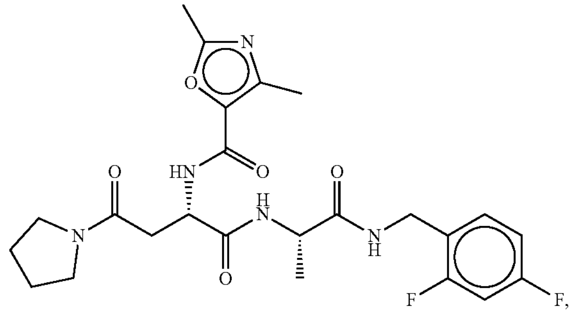

or an oxide thereof, a pharmaceutically acceptable salt thereof, a solvate thereof, or a prodrug thereof.

A third aspect of the present invention relates to a compound of Formula (III):

(III)

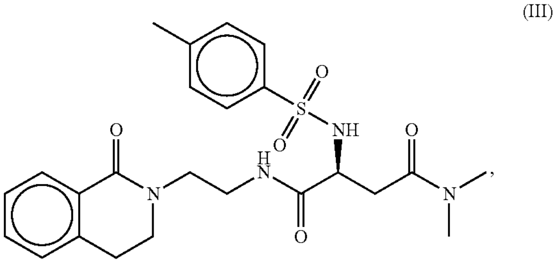

or an oxide thereof, a pharmaceutically acceptable salt thereof, a solvate thereof, or a prodrug thereof.

Another aspect of the present invention relates to a method of treating bacterial infections, parasite infections, fungal infections, cancer, immunologic disorders, autoimmune disorders, neurodegenerative diseases and disorders, inflammatory disorders, or muscular dystrophy, in a subject or for achieving immunosuppression in transplanted organs or tissues in a subject. This method includes administering to the subject in need thereof a compound of Formula (I):

(I)

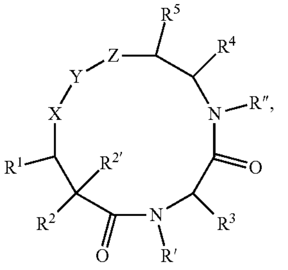

wherein

X is $—(CH_2)_m—$; $—CH_2—CH{=}CH—$, or

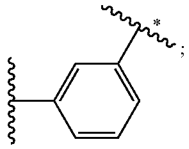 [SMILES: *c1cccc(*)c1]

Y is $—CH_2—$ or O;

Z is $—(CH_2)_m—$,

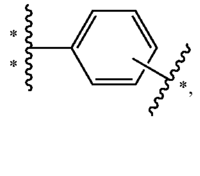

$—CH_2—CH_2—O—$, $CH_2—CH{=}CH—$, or O;

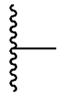

is the point of attachment to $—C(R^1)—$ moiety;

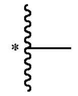

is the point of attachment to Y;

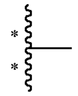

is the point of attachment to $—C(R^5)—$ moiety;

$R^1$ is H;

$R^2$ is independently selected at each occurrence thereof from the group consisting of H, $C_{1-6}$ alkyl, arylalkyl, $—NR^6R^7$, $—NHC(O)R^8$, $—NHS(O)_2R^8$, and $—NHC(O)(CH_2)_nNR^6R^7$;

$R^{2'}$ is H or $C_{1-6}$ alkyl;

$R^3$ is independently selected at each occurrence thereof from the group consisting of H, $C_{1-6}$ alkyl, $—(CH_2)_nNR^6R^7$, $—CH_2C(O)NR^6R^7$, $—CH_2C(O)OH$, and arylalkyl, wherein $C_{1-6}$ alkyl or arylalkyl can be optionally substituted from 1 to 3 times with halogen, $C_{1-6}$ alkoxy, —O-aryl, and $CF_3$;

$R^4$ is selected from the group consisting of $R^9$, $—C(O)R^9$, $—C(O)NH(CR^aR^b)_nR^8$, $—C(O)N(Me)(CR^aR^b)_nR^8$, $—C(O)OH$, $—C(O)CH_2Ph$, $—C(O)OR^9$, $—CH_2NHR^8$, and $—C(O)NR^6R^7$;

$R^5$ is H;

$R^6$ and $R^7$ are each independently selected from the group consisting of H, $C_{1-6}$ alkyl, $C_{3-8}$ cycloalkyl, and $C_{3-12}$ cycloalkylalkyl, or, wherein $C_{3-8}$ cycloalkyl and $C_{3-12}$ cycloalkylalkyl can be optionally substituted from 1 to 3 times with $CF_3$;

or $R^6$ and $R^7$ are taken together with the nitrogen to which they are attached to form a piperidine, pyrrolidine, morpholine ring, piperazine, oxazolidine, or isothiazolidine, wherein piperidine, pyrrolidine, morpholine, piperazine, oxazolidine, or isothiazolidine ring can be optionally substituted 1 to 3 times with halogen, $C_{1-6}$ alkyl, aryl, =O, $C_{3-8}$ cycloalkyl, or non-aromatic heterocycle;

$R^8$ is selected from the group consisting of H, OH, $CF_3$, $CHF_2$, $C_{1-12}$ alkyl, $C_{3-8}$ cycloalkyl, $C_{3-12}$ cycloalkylalkyl, $C_{1-12}$ alkoxy, monocyclic or bicyclic aryl, arylalkyl, and heteroaryl, heterocyclyl, and non-aromatic heterocycle, wherein $C_{1-12}$ alkyl, $C_{3-8}$ cycloalkyl, $C_{3-12}$ cycloalkylalkyl, monocyclic or bicyclic aryl, arylalkyl, and heteroaryl, heterocyclyl, and non-aromatic heterocycle can be optionally substituted from 1 to 3 times with OH, halogen, $C_{1-6}$ alkyl, $C_{1-6}$ alkoxy, $CHF_2$, $CF_3$, $—S(O)_2Me$;

$R^9$ is selected from the group consisting of OH, $CF_3$, $CHF_2$, $C_{1-12}$ alkyl, $C_{3-8}$ cycloalkyl, $C_{3-12}$ cycloalkylalkyl, $C_{1-12}$ alkoxy, monocyclic or bicyclic aryl, and heteroaryl, wherein $C_{1-12}$ alkyl, $C_{3-8}$ cycloalkyl, $C_{3-12}$ cycloalkylalkyl, monocyclic or bicyclic aryl, arylalkyl, and heteroaryl, can be optionally substituted from 1 to 3 times with OH, halogen, $C_{1-6}$ alkyl, $C_{1-6}$ alkoxy, $CHF_2$, $CF_3$, —$S(O)_2Me$;

$R^a$ and $R^b$ are each independently selected from the group consisting of H and $C_{1-6}$ alkyl;

R' and R" are each independently selected from the group consisting of H and $C_{1-6}$ alkyl;

n is 0, 1, 2, 3, or 4; and m is independently selected at each occurrence from the group consisting of 2, 3, 4, or 5, with the proviso that i) $R^2$ is not $NH_2$, ii) $R^4$ is not

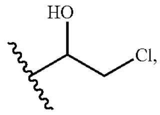 , 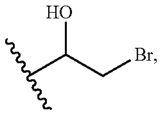 , or 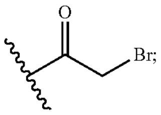 ;

iii) when $R^4$ is COOH, then $R^3$ is not

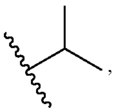 , 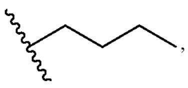 , or 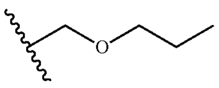 , and iv) when $R^4$ is COOMe, then $R^3$ is not

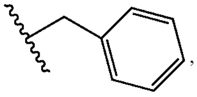 [SMILES: *Cc1ccccc1] , or an oxide thereof, a pharmaceutically acceptable salt thereof, a solvate thereof, or a prodrug thereof.

One embodiment of the present invention relates to a method of treating bacterial infections, parasite infections, fungal infections, cancer, immunologic disorders, autoimmune disorders, neurodegenerative diseases and disorders, inflammatory disorders, or muscular dystrophy, in a subject or for achieving immunosuppression in transplanted organs or tissues in a subject. This method includes administering to the subject in need thereof a compound of Formula (I'):

(I')

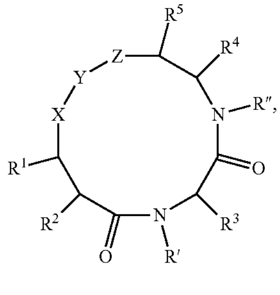

wherein

X is —$(CH_2)_m$—; —$CH_2$—CH═CH—, or

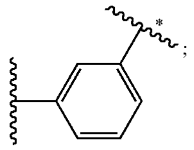 [SMILES: *c1cccc(*)c1] ;

Y is a —$CH_2$— or O;

Z is —$(CH_2)_m$—,

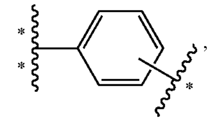 ,

—$CH_2$—$CH_2$—O—, or O;

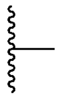

is the point of attachment to —C($R^1$)— moiety;

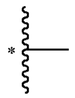

is the point of attachment to Y;

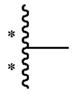

is the point of attachment to —C($R^5$)— moiety;

$R^1$ is H;

$R^2$ is independently selected at each occurrence thereof from the group consisting of H, arylalkyl, —$NR^6R^7$, —$NHC(O)R^8$, —$NHS(O)_2R^8$, and —NHC(O)$(CH_2)_nNR^6R^7$;

$R^3$ is independently selected at each occurrence thereof from the group consisting of H, $C_{1-6}$ alkyl, —$(CH_2)_nNR^6R^7$, —$CH_2C(O)NR^6R^7$, —$CH_2C(O)OH$, and arylalkyl, wherein $C_{1-6}$ alkyl can be optionally substituted from 1 to 3 times with $C_{1-6}$ alkoxy and $CF_3$;

$R^4$ is selected from the group consisting of $R^8$, —$C(O)R^8$, —$C(O)NH(CR^aR^b)_nR^8$, —$C(O)OR^8$, —$CH_2NHR^8$, and —$C(O)NR^6R^7$;

$R^5$ is H;

$R^6$ and $R^7$ are each independently selected from the group consisting of H, $C_{1-6}$ alkyl, $C_{3-8}$ cycloalkyl, and $C_{3-12}$ cycloalkylalkyl, or, wherein $C_{3-8}$ cycloalkyl and $C_{3-12}$ cycloalkylalkyl can be optionally substituted from 1 to 3 times with $CF_3$;

or $R^6$ and $R^7$ are taken together with the nitrogen to which they are attached to form a piperidine, pyrrolidine, or morpholine ring, wherein piperidine, pyrrolidine, or morpholine ring can be optionally substituted 1 to 3 times with halogen, $C_{1-6}$ alkyl, aryl, =O, $C_{3-8}$ cycloalkyl, or non-aromatic heterocycle;

$R^8$ is selected from the group consisting of H, OH, $CF_3$, $CHF_2$, $C_{1-12}$ alkyl, $C_{3-8}$ cycloalkyl, $C_{3-12}$ cycloalkylalkyl, $C_{1-12}$ alkoxy, monocyclic or bicyclic aryl, arylalkyl, heteroaryl, heterocyclyl, and non-aromatic heterocycle, wherein $C_{1-12}$ alkyl, monocyclic or bicyclic aryl, arylalkyl, heteroaryl, heterocyclyl, and non-aromatic heterocycle can be optionally substituted from 1 to 3 times with OH, halogen, $C_{1-6}$ alkyl, $C_{1-6}$ alkoxy, $CHF_2$, $CF_3$, $-S(O)_2Me$;

$R^a$ and $R^b$ are each independently selected from the group consisting of H and $C_{1-6}$ alkyl;

R' and R" are each independently selected from the group consisting of H and $C_{1-6}$ alkyl;

n is 0, 1, 2, 3, or 4; and m is 2, 3, 4, or 5.

Another aspect of the present invention relates to a method of treating bacterial infections, parasite infections, fungal infections, cancer, immunologic disorders, autoimmune disorders, neurodegenerative diseases and disorders, inflammatory disorders, or muscular dystrophy, in a subject or for achieving immunosuppression in transplanted organs or tissues in a subject. This method includes administering to the subject in need thereof a compound of Formula (II):

(II)

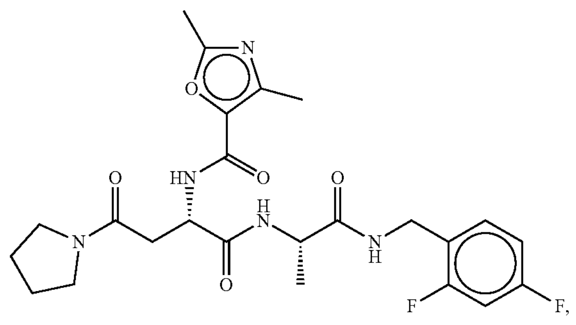

or an oxide thereof, a pharmaceutically acceptable salt thereof, a solvate thereof, or a prodrug thereof.

Another aspect of the present invention relates to a method of treating bacterial infections, parasite infections, fungal infections, cancer, immunologic disorders, autoimmune disorders, neurodegenerative diseases and disorders, inflammatory disorders, or muscular dystrophy, in a subject or for achieving immunosuppression in transplanted organs or tissues in a subject. This method includes administering to the subject in need thereof a compound of Formula (III):

(III)

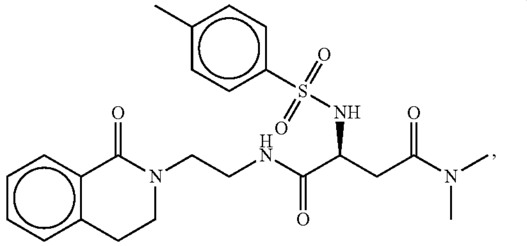

or an oxide thereof, a pharmaceutically acceptable salt thereof, a solvate thereof, or a prodrug thereof.

In one embodiment, bacterial infection is treated. The bacterial infection is *Mycobacterium tuberculosis.*

In another embodiment, parasite infection is treated. The parasite infection is selected from, but not limited to, the group consisting of malaria, leishmaniasis, river blindness, Chagas disease, sleeping disease, cryptosporidiosis, amebiasis, cyclosporiasis, giardiasis, and toxoplasmosis.

In yet another embodiment, parasite infection is veterinary parasite infection. The veterinary parasite infection is caused by protozoan parasites, helminth parasites, arachnids, insects, or custaceans. Exemplary protozoan parasites include, but are not limited to, *Babesia divergens, Balantidium coli, Eimeria tenella, Giardia lamblia* (*Giardia duodenalis*), *Hammondia hammondi, Histomonas meleagridis, Isospora canis, Leishmania donovani, Leishmania infantum, Neospora caninum, Toxoplasma gondii, Trichomonas gallinae, Tritrichomonas foetus, Trypanosoma brucei*, and *Trypanosoma equiperdum*. Exemplary helminth parasites include, but are not limited to, *Ancylostoma duodenale, Ascaris suum, Dicrocoelium dendriticum, Dictyocaulus viviparus, Dipylidium caninum, Echinococcus granulosus, Fasciola hepatica, Fascioloides magna, Habronema species, Haemonchus contortus, Metastrongylus, Muellerius capillaris, Ostertagia ostertagi, Paragonimus westermani, Schistosoma bovis, Strongyloides species, Strongylus vulgaris, Syngamus trachea* (Gapeworm), *Taenia pisiformis, Taenia saginata, Taenia solium, Toxocara canis, Trichinella spiralis, Trichobilharzia regenti, Trichostrongylus species*, and *Trichuris suis*. Exemplary arachnids, insects, and custaceans include, but are not limited to, *Caligus* species, *Cimex colombarius, Cimex lectularius, Culex pipiens, Culicoides imicola, Demodex bovis, Dermacentor reticulatus, Gasterophilus intestinalis, Haematobia irritans, Hypoderma bovis, Ixodes ricinus, Knemidocoptes mutans, Lepeophtheirus salmonis, Lucilia sericata, Musca domestica, Nosema apis, Notoedres cati, Oestrus ovis, Otodectes cynotis, Phlebotomus species, Psoroptes ovis, Pulex irritans, Rhipicephalus sanguineus, Sarcoptes equi, Sarcophaga carnaria, Tabanus atratus, Triatoma species, Ctenocephalides canis*, and *Ctenocephalides felis.*

In another embodiment, an autoimmune disorder is treated. The autoimmune disorder is selected from the group consisting of arthritis, colitis, multiple sclerosis, lupus, Sjogren Syndrome, Systemic Lupus Erythematosus and lupus nephritis, glomerulonephritis, Rheumatoid Arthritis, Inflammatory bowel disease (IBD), ulcerative colitis, Crohn's diseases, Psoriasis, and asthma.

In yet another embodiment, immunosuppression is provided for transplanted organs or tissues. The immunosuppression is used to prevent transplant rejection and graft-verse-host disease.

In a further embodiment, an inflammatory disorder is treated. The inflammatory disorder is Crohn's disease.

The compounds and pharmaceutical compositions of the present invention are particularly useful for the treatment of cancer. As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and bloodborne tumors. The term "cancer" encompasses diseases of skin, tissues, organs, bone, cartilage, blood, and vessels. The term "cancer" further encompasses primary and metastatic cancers.

Non-limiting examples of solid tumors that can be treated with the disclosed proteasome inhibitors include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma.

In one embodiment, cancer is treated. The cancer is selected from the group consisting of neoplastic disorders, hematologic malignances, lymphocytic malignancies, mantel cell lymphoma, leukemia, Waldenstrom Macroglobulinemia, pancreatic cancer, bladder cancer, colorectal cancer, breast cancer, metastatic breast cancer, prostate cancer, androgen-dependent and androgen-independent prostate cancer, renal cancer, metastatic renal cell carcinoma, hepatocellular cancer, lung cancer, non-small cell lung cancer (NSCLC), bronchioloalveolar carcinoma (BAC), and adenocarcinoma of the lung, ovarian cancer, progressive epithelial or primary peritoneal cancer, cervical cancer, gastric cancer, esophageal cancer, head and neck cancer, squamous cell carcinoma of the head and neck, melanoma, neuroendocrine cancer, metastatic neuroendocrine tumors, brain tumors, glioma, anaplastic oligodendroglioma, adult glioblastoma multiforme, and adult anaplastic astrocytoma, bone cancer, and soft tissue sarcoma.

In another embodiment, a neurodegenerative disease or disorder is treated. The neurodegenerative disease or disorder is Amyotrophic Lateral Sclerosis (ALS) or Multiple Sclerosis (MS).

Another aspect of the present invention relates to a method of inhibiting proteasome activity. This method includes contacting a proteasome with a compound of Formula (I):

(I)

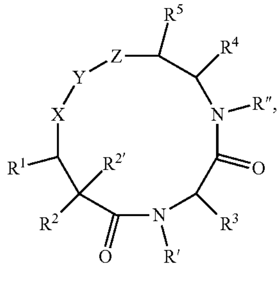

wherein

X is $—(CH_2)_m—$; $—CH_2—CH{=}CH—$, or

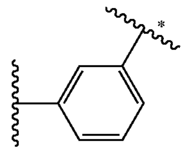

;

Y is $—CH_2—$ or O;

Z is $—(CH_2)_m—$,

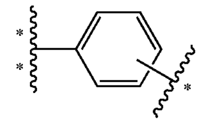

, $—CH_2—CH_2—O—$, $CH_2—CH{=}CH—$, or O;

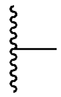

is the point of attachment to $—C(R^1)—$ moiety;

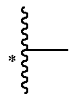

is the point of attachment to Y;

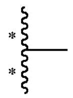

is the point of attachment to $—C(R^5)—$ moiety;

$R^1$ is H;

$R^2$ is independently selected at each occurrence thereof from the group consisting of H, $C_{1-6}$ alkyl, arylalkyl, $—NR^6R^7$, $—NHC(O)R^8$, $—NHS(O)_2R^8$, and $—NHC(O)(CH_2)_nNR^6R^7$;

$R^2$ is H or $C_{1-6}$ alkyl;

$R^3$ is independently selected at each occurrence thereof from the group consisting of H, $C_{1-6}$ alkyl, $—(CH_2)_nNR^6R^7$, $—CH_2C(O)NR^6R^7$, $—CH_2C(O)OH$, and arylalkyl, wherein $C_{1-6}$ alkyl or arylalkyl can be optionally substituted from 1 to 3 times with halogen, $C_{1-6}$ alkoxy, —O-aryl, and $CF_3$;

$R^4$ is selected from the group consisting of $R^9$, $—C(O)R^9$, $—C(O)NH(CR^aR^b)_nR^8$, $—C(O)N(Me)(CR^aR^b)_nR^8$, $—C(O)OH$, $—C(O)CH_2Ph$, $—C(O)OR^9$, $—CH_2NHR^8$, and $—C(O)NR^6R^7$;

$R^5$ is H;

$R^6$ and $R^7$ are each independently selected from the group consisting of H, $C_{1-6}$ alkyl, $C_{3-8}$ cycloalkyl, and $C_{3-12}$ cycloalkylalkyl, or, wherein $C_{3-8}$ cycloalkyl and $C_{3-12}$ cycloalkylalkyl can be optionally substituted from 1 to 3 times with $CF_3$;

or $R^6$ and $R^7$ are taken together with the nitrogen to which they are attached to form a piperidine, pyrrolidine, morpholine ring, piperazine, oxazolidine, or isothiazolidine, wherein piperidine, pyrrolidine, morpholine, piperazine, oxazolidine, or isothiazolidine ring can be optionally substituted 1 to 3 times with halogen, $C_{1-6}$ alkyl, aryl, =O, $C_{3-8}$ cycloalkyl, or non-aromatic heterocycle;

$R^8$ is selected from the group consisting of H, OH, $CF_3$, $CHF_2$, $C_{1-12}$ alkyl, $C_{3-8}$ cycloalkyl, $C_{3-12}$ cycloalkylalkyl, $C_{1-12}$ alkoxy, monocyclic or bicyclic aryl, arylalkyl, and heteroaryl, heterocyclyl, and non-aromatic heterocycle, wherein $C_{1-12}$ alkyl, $C_{3-8}$ cycloalkyl, $C_{3-12}$ cycloalkylalkyl, monocyclic or bicyclic aryl, arylalkyl, and heteroaryl, heterocyclyl, and non-aromatic heterocycle can be optionally substituted from 1 to 3 times with OH, halogen, $C_{1-6}$ alkyl, $C_{1-6}$ alkoxy, $CHF_2$, $CF_3$, $—S(O)_2Me$;

$R^9$ is selected from the group consisting of OH, $CF_3$, $CHF_2$, $C_{1-12}$ alkyl, $C_{3-8}$ cycloalkyl, $C_{3-12}$ cycloalkylalkyl, $C_{1-12}$ alkoxy, monocyclic or bicyclic aryl, and heteroaryl, wherein $C_{1-12}$ alkyl, $C_{3-8}$ cycloalkyl, $C_{3-12}$ cycloalkylalkyl, monocyclic or bicyclic aryl, arylalkyl, and heteroaryl, can be optionally substituted from 1 to 3 times with OH, halogen, $C_{1-6}$ alkyl, $C_{1-6}$ alkoxy, $CHF_2$, $CF_3$, $—S(O)_2Me$;

$R^a$ and $R^b$ are each independently selected from the group consisting of H and $C_{1-6}$ alkyl;

R' and R" are each independently selected from the group consisting of H and $C_{1-6}$ alkyl;

n is 0, 1, 2, 3, or 4; and m is independently selected at each occurrence from the group consisting of 2, 3, 4, and 5, with the proviso that i) $R^2$ is not $NH_2$, ii) $R^4$ is not

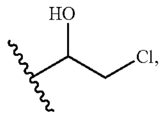

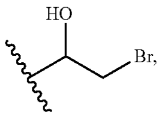

or

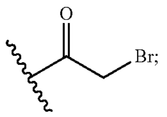

iii) when $R^4$ is COOH, then $R^3$ is not

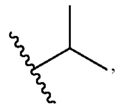

,

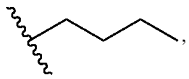

, or

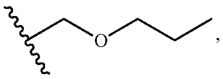

, and iv) when $R^4$ is COOMe, then $R^3$ is not,

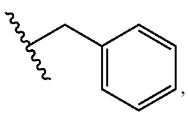 [SMILES: *Cc1ccccc1]

, or an oxide thereof, a pharmaceutically acceptable salt thereof, a solvate thereof, or a prodrug thereof under conditions effective to inhibit proteasome activity.

One embodiment of the present invention relates to a method of inhibiting proteasome activity. This method includes contacting a proteasome with a compound of Formula (I'):

(I')

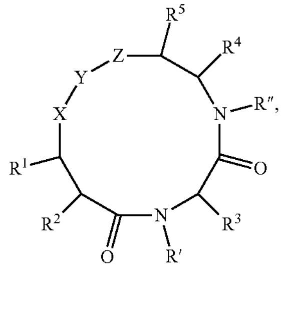

wherein

X is $—(CH_2)_m—$; $—CH_2—CH{=}CH—$, or

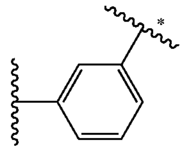

;

Y is a $—CH_2—$ or O;

Z is $—(CH_2)_m—$,

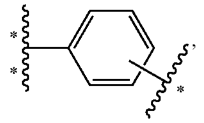

, $—CH_2—CH_2—O—$, or O;

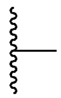

is the point of attachment to $—C(R^1)—$ moiety;

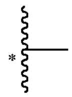

is the point of attachment to Y;

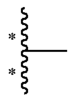

is the point of attachment to $—C(R^5)—$ moiety;

$R^1$ is H;

$R^2$ is independently selected at each occurrence thereof from the group consisting of H, arylalkyl, $—NR^6R^7$, $—NHC(O)R^8$, $—NHS(O)_2R^8$, and $—NHC(O)(CH_2)_nNR^6R^7$;

$R^3$ is independently selected at each occurrence thereof from the group consisting of H, $C_{1-6}$ alkyl, $—(CH_2)_nNR^6R^7$, $—CH_2C(O)NR^6R^7$, $—CH_2C(O)OH$, and arylalkyl, wherein $C_{1-6}$ alkyl can be optionally substituted from 1 to 3 times with $C_{1-6}$ alkoxy and $CF_3$;

$R^4$ is selected from the group consisting of $R^8$, —C(O)$R^8$, —C(O)NH($CR^aR^b$)$_n R^8$, —C(O)O$R^8$, —$CH_2$NH$R^8$, and —C(O)N$R^6R^7$;

$R^5$ is H;

$R^6$ and $R^7$ are each independently selected from the group consisting of H, $C_{1-6}$ alkyl, $C_{3-8}$ cycloalkyl, and $C_{3-12}$ cycloalkylalkyl, or, wherein $C_{3-8}$ cycloalkyl and $C_{3-12}$ cycloalkylalkyl can be optionally substituted from 1 to 3 times with $CF_3$;

or $R^6$ and $R^7$ are taken together with the nitrogen to which they are attached to form a piperidine, pyrrolidine, or morpholine ring, wherein piperidine, pyrrolidine, or morpholine ring can be optionally substituted 1 to 3 times with halogen, $C_{1-6}$ alkyl, aryl, =O, $C_{3-8}$ cycloalkyl, or non-aromatic heterocycle;

$R^8$ is selected from the group consisting of H, OH, $CF_3$, $CHF_2$, $C_{1-12}$ alkyl, $C_{3-8}$ cycloalkyl, $C_{3-12}$ cycloalkylalkyl, $C_{1-12}$ alkoxy, monocyclic or bicyclic aryl, arylalkyl, heteroaryl, heterocyclyl, and non-aromatic heterocycle, wherein $C_{1-12}$ alkyl, monocyclic or bicyclic aryl, arylalkyl, heteroaryl, heterocyclyl, and non-aromatic heterocycle can be optionally substituted from 1 to 3 times with OH, halogen, $C_{1-6}$ alkyl, $C_{1-6}$ alkoxy, $CHF_2$, $CF_3$, —S(O)$_2$Me;

$R^a$ and $R^b$ are each independently selected from the group consisting of H and $C_{1-6}$ alkyl;

R' and R" are each independently selected from the group consisting of H and $C_{1-6}$ alkyl;

n is 0, 1, 2, 3, or 4; and m is 2, 3, 4, or 5, or an oxide thereof, a pharmaceutically acceptable salt thereof, a solvate thereof, or a prodrug thereof under conditions effective to inhibit proteasome activity.

Another aspect of the present invention relates to a method of inhibiting proteasome activity. This method includes contacting a proteasome with a compound of Formula (II):

(II)

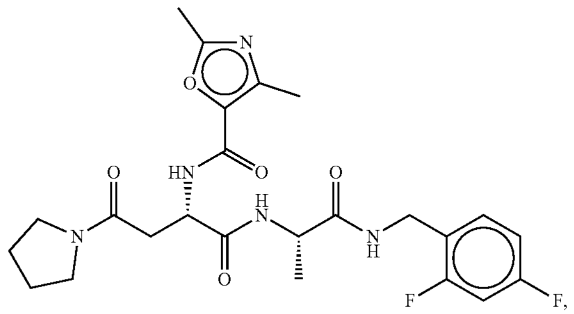

or an oxide thereof, a pharmaceutically acceptable salt thereof, a solvate thereof, or a prodrug thereof under conditions effective to inhibit proteasome activity.

Another aspect of the present invention relates to a method of inhibiting proteasome activity. This method includes contacting a proteasome with a compound of Formula (III):

(III)

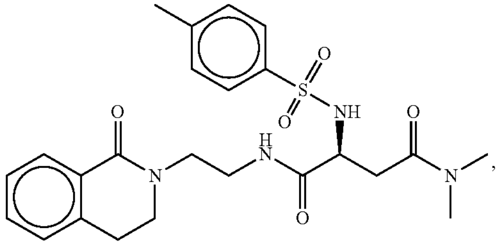

or an oxide thereof, a pharmaceutically acceptable salt thereof, a solvate thereof, or a prodrug thereof under conditions effective to inhibit proteasome activity.

While it may be possible for compounds of Formula (I), Formula (I'), Formula (I'a), Formula (I's), Formula (I'c), Formula (II), or Formula (III), to be administered as raw chemicals, it will often be preferable to present them as a part of a pharmaceutical composition. Accordingly, another aspect of the present invention is a pharmaceutical composition containing a therapeutically effective amount of the compound of Formula (I), Formula (I'), Formula (I'a), Formula (I's), Formula (I'c), Formula (II), or Formula (III), or a pharmaceutically acceptable salt or solvate thereof, and a pharmaceutically acceptable carrier. The carrier must be "acceptable" in the sense of being compatible with the other ingredients of the formulation and not deleterious to the recipient thereof.

In practicing the method of the present invention, agents suitable for treating a subject can be administered using any method standard in the art. The agents, in their appropriate delivery form, can be administered orally, intradermally, intramuscularly, intraperitoneally, intravenously, subcutaneously, or intranasally. The compositions of the present invention may be administered alone or with suitable pharmaceutical carriers, and can be in solid or liquid form, such as tablets, capsules, powders, solutions, suspensions, or emulsions.

The agents of the present invention may be orally administered, for example, with an inert diluent, or with an assimilable edible carrier, or it may be enclosed in hard or soft shell capsules, or it may be compressed into tablets, or they may be incorporated directly with the food of the diet. Agents of the present invention may also be administered in a time release manner incorporated within such devices as time-release capsules or nanotubes. Such devices afford flexibility relative to time and dosage. For oral therapeutic administration, the agents of the present invention may be incorporated with excipients and used in the form of tablets, capsules, elixirs, suspensions, syrups, and the like. Such compositions and preparations should contain at least 0.1% of the agent, although lower concentrations may be effective and indeed optimal. The percentage of the agent in these compositions may, of course, be varied and may conveniently be between about 2% to about 60% of the weight of the unit. The amount of an agent of the present invention in such therapeutically useful compositions is such that a suitable dosage will be obtained.

Also specifically contemplated are oral dosage forms of the agents of the present invention. The agents may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. (Abuchowski and Davis, "Soluble Polymer-Enzyme Adducts," In: *Enzymes as Drugs*, Hocenberg and Roberts, eds., Wiley-Interscience, New York, N.Y., pp. 367-383 (1981), which are hereby incorporated by reference in their entirety). Other polymers that could be used are poly-1,3-dioxolane and poly-1,3,6-tioxocane. Preferred for pharmaceutical usage, as indicated above, are polyethylene glycol moieties.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, sucralose, or saccharin. When the dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

The agents of the present invention may also be administered parenterally. Solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

When it is desirable to deliver the agents of the present invention systemically, they may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Intraperitoneal or intrathecal administration of the agents of the present invention can also be achieved using infusion pump devices such as those described by Medtronic, Northridge, CA. Such devices allow continuous infusion of desired compounds avoiding multiple injections and multiple manipulations.

In addition to the formulations described previously, the agents may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The agents of the present invention may also be administered directly to the airways in the form of an aerosol. For use as aerosols, the agent of the present invention in solution or suspension may be packaged in a pressurized aerosol container together with suitable propellants, for example, hydrocarbon propellants like propane, butane, or isobutane with conventional adjuvants. The agent of the present invention also may be administered in a non-pressurized form such as in a nebulizer or atomizer.

Effective doses of the compositions of the present invention, for the treatment of cancer or pathogen infection vary depending upon many different factors, including type and stage of cancer or the type of pathogen infection, means of administration, target site, physiological state of the patient, other medications or therapies administered, and physical state of the patient relative to other medical complications. Treatment dosages need to be titrated to optimize safety and efficacy.

The percentage of active ingredient in the compositions of the present invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.01 to about 100 mg/kg body weight, preferably about 0.01 to about 10 mg/kg body weight per day by inhalation, from about 0.01 to about 100 mg/kg body weight, preferably 0.1 to 70 mg/kg body weight, more especially 0.1 to 10 mg/kg body weight per day by oral administration, and from about 0.01 to about 50 mg/kg body weight, preferably 0.01 to 10 mg/kg body weight per day by intravenous administration. In each particular case, the doses will be determined in accordance with the factors distinctive to the subject to be treated, such as age, weight, general state of health, and other characteristics which can influence the efficacy of the medicinal product.

The products according to the present invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

EXAMPLES
Example 1—Synthesis of (5S,8S,11S)-N-((1-Methyl-1H-pyrazol-4-yl)methyl)-7,10-dioxo-8-phenethyl-11-(piperidin-1-yl)-2-oxa-6,9-diaza-1,3(1,3)-dibenzenacyclododecaphane-5-carboxamide (1-01)
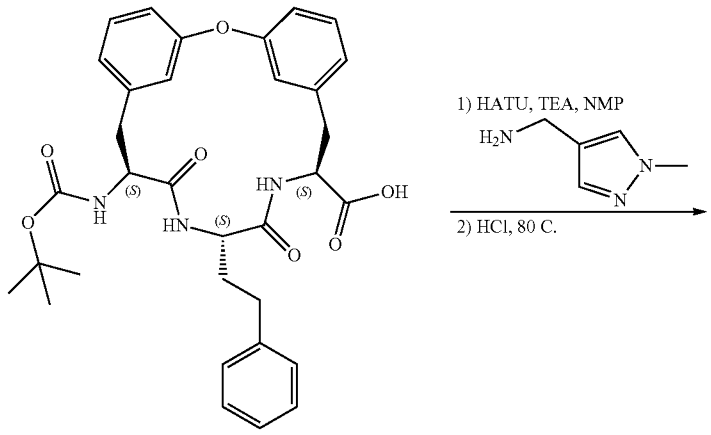
1-68-1
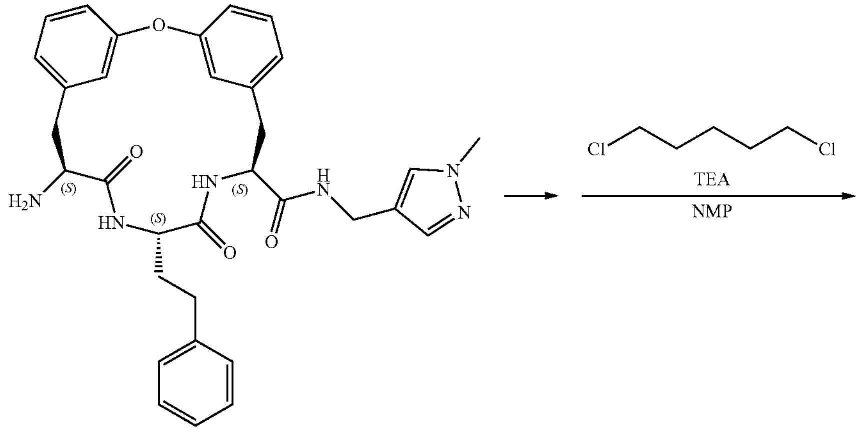
1-01-1
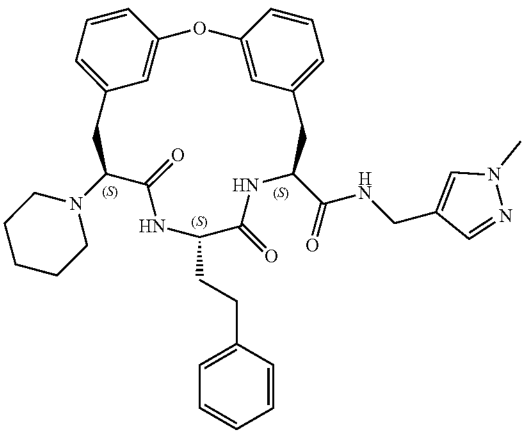
1-01

To a mixture of 1-68-1 (10 mg, 0.017 mmol) and NMP (0.4 mlL) (1-methyl-1H-pyrazol-4-yl)methanamine (0.017 mmol) was added followed by HATU (0.020 mmol) and TEA (0.020 mmol). The mixture was stirred at room temperature for 30 minutes and a 4M solution of HCl in dioxane (0.255 mL, 1.021 mmol) was added. The mixture was heated to 80° C. for 3 hours then cooled to room temperature and passed through a solid phase extraction column (scx-2 5 g), washed with MeOH (3*8 mL), and eluted with 2N ammonia MeOH (3*8 mL). Volatile organics were removed by evaporation to provide 1-01-1 which was used immediately without purification.

To the isolated 1-01-1 NMP (0.4 mL) was added followed by TEA (0.104 mmol). Then 1,5-dichloropentane (0.085 mmol) was added and the mixture was heated to 80° C. for 120 minutes. The reaction mixture was cooled to room temperature and filtered through cotton wool. The product was purified by reverse phase HPLC to provide 1-01. LCMS of 1-01: RT=7.67 min, m/z 649.34 $[M+H]^+$ The following compounds were made using a similar synthetic route as described for compound 1-01:

Compound 1-02; LCMS: RT=6.71 min, m/z 637.34 $[M+H]^+$

Compound 1-09; LCMS: RT=9.77 min, m/z 661.37 $[M+H]^+$

Compound 1-10; LCMS: RT=8.64 min, m/z 645.35 $[M+H]^+$

Compound 1-17; LCMS: RT=5.06 min, m/z 631.77 $[M+H]^+$

Compound 1-18; LCMS: RT=8.29 min, m/z 609.34 $[M+H]^+$

Compound 1-21; LCMS: RT=9.77 min, m/z 639.38 $[M+H]^+$

Compound 1-22; LCMS: RT=9.09 min, m/z 611.35 $[M+H]^+$

Compound 1-25; LCMS: RT=8.66 min, m/z 585.34 $[M+H]^+$

Compound 1-27; LCMS: RT=8.26 min, m/z 571.32 $[M+H]^+$

Compound 1-28; LCMS: RT=8.09 min, m/z 583.32 $[M+H]^+$

Compound 1-29; LCMS: RT=8.97 min, 599.35 m/z $[M+H]^+$

Example 2—Synthesis of (5S,8S,11S)-N-((1-Methyl-1H-pyrazol-4-yl)methyl)-11-(1-methylpiperidine-4-carboxamido)-7,10-dioxo-8-phenethyl-2-oxa-6,9-diaza-1,3(1,3)-dibenzenacyclododecaphane-5-carboxamide (1-03)

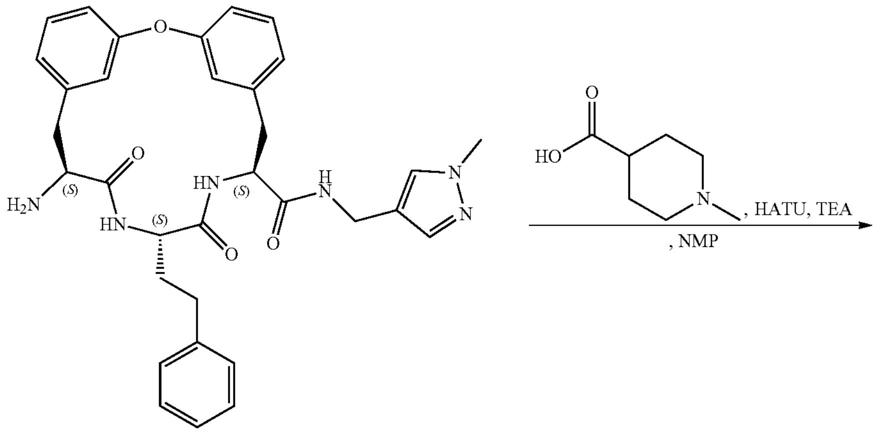

1-01-1

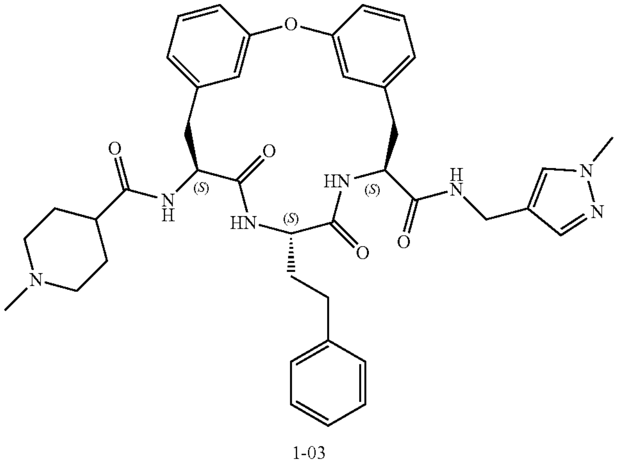

1-03

To the isolated 1-01-1 NMP (0.4 mL) was added followed by TEA (0.085 mmol). Then the N-methylisonipocotic acid (0.068 mmol) was added followed by HATU (0.068 mmol). The mixture was stirred for 60 minutes and then filtered through cotton wool. The product was purified by reverse phase HPLC to provide 1-03. LCMS of 1-03: RT=6.26 min, m/z 706.36 $[M+H]^+$.

The following compounds were made using a similar synthetic route as described for compound 1-03:

Compound 1-05; LCMS: RT=5.43 min, 639.72 m/z $[M+H]^+$

Compound 1-06; LCMS: RT=7.56 min, 599.28 m/z $[M+H]^+$

Compound 1-07; LCMS: RT=7.25 min, 597.30 m/z $[M+H]^+$

Compound 1-11; LCMS: RT=7.30 min, m/z 635.28 $[M+H]^+$

Compound 1-12; LCMS: RT=8.26 min, m/z 682.29 $[M+H]^+$

Compound 1-13; LCMS: RT=7.47 min, m/z 685.31 $[M+H]^+$

Compound 1-14; LCMS: RT=7.83 min, m/z 633.30 $[M+H]^+$

Compound 1-15; LCMS: RT=8.00 min, m/z 681.55 $[M+H]^+$

Compound 1-16; LCMS: RT=5.12 min, m/z 633.66 $[M+H]^+$

Compound 1-19; LCMS: RT=7.67 min, m/z 611.31 $[M+H]^+$

Compound 1-20; LCMS: RT=6.92 min, m/z 613.29 $[M+H]^+$

Compound 1-23; LCMS: RT=8.32 min, m/z 659.31 $[M+H]^+$

Compound 1-26; LCMS: RT=7.92 min, m/z 633.30 $[M+H]^+$

Compound 1-30; LCMS: RT=7.76 min, m/z 599.31 $[M+H]^+$

Compound 1-31; LCMS: RT=8.40 min, m/z 647.31 $[M+H]^+$

Compound 1-32; LCMS: RT=7.18 min, m/z 651.32 $[M+H]^+$

Compound 1-33; LCMS: RT=6.38 min, m/z 664.30 $[M+H]^+$

Compound 1-34; LCMS: RT=6.44 min, m/z 650.29 $[M+H]^+$

Compound 1-36; LCMS: RT=7.30 min, m/z 648.31 $[M+H]^+$

Compound 1-39; LCMS: RT=7.12 min, m/z 697.40 $[M+H]^+$

Compound 1-41; LCMS: RT=8.06 min, m/z 687.27 $[M+H]^+$

Compound 1-44; LCMS: RT=6.57 min, m/z 625.29 $[M+H]^+$

Compound 1-45; LCMS: RT=7.22 min, m/z 669.28 $[M+H]^+$

Compound 1-46; LCMS: RT=5.56 min, m/z 651.24 $[M+H]^+$

Compound 1-47; LCMS: RT=6.91 min, m/z 643.30 $[M+H]^+$

Compound 1-48; LCMS: RT=6.68 min, m/z 634.29 $[M+H]^+$

Compound 1-49; LCMS: RT=6.65 min, m/z 691.32 $[M+H]^+$

Compound 1-52; LCMS: RT=4.64 min, m/z 675.75 $[M+H]^+$

Example 3—Synthesis of (5S,8S,11S)-N-((1-Methyl-1H-pyrazol-4-yl)methyl)-11-(methylsulfonamido)-7,10-dioxo-8-phenethyl-2-oxa-6,9-diaza-1,3(1,3)-dibenzenacyclododecaphane-5-carboxamide (1-04)

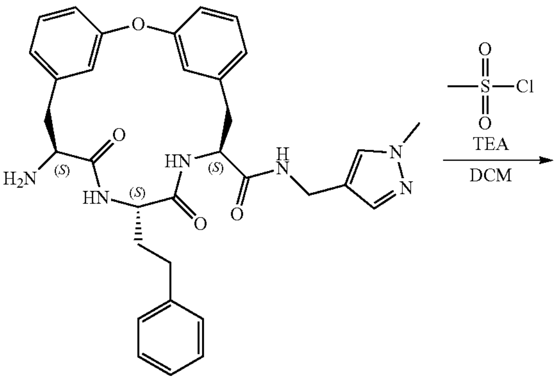

1-01-1

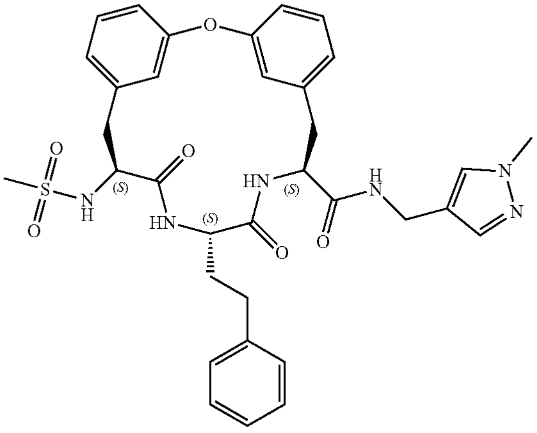

1-04

To the isolated 1-01-1 DCM (1 mL) was added followed by TEA (0.85 mmol). Then methane sulfonyl chloride (0.068 mmol) was added and the mixture was stirred for 60 minutes. Volatile organics were removed by evaporation and NMP (0.4 mL) was added. The mixture was filtered through cotton wool. The product was purified by reverse phase HPLC to provide 0.0145 g (22.1% yield) of 1-04. LCMS of 1-04: RT=6.18 min, m/z 659.78 $[M+H]^+$ The following compounds were made using a similar synthetic route as described for compound 1-04:

Compound 1-08; LCMS: RT=7.19 min, m/z 619.25 $[M+H]^+$

Compound 1-35; LCMS: RT=6.26 min, m/z 565.20 $[M+H]^+$

Compound 1-37; LCMS: RT=7.76 min, m/z 621.27 $[M+H]^+$

Compound 1-38; LCMS: RT=6.23 min, m/z 673.00$[M+H]^+$

Example 4—Synthesis of (5S,8S,11S)-N-Cyclopentyl-11-(methylamino)-7,10-dioxo-8-phenethyl-2-oxa-6,9-diaza-1,3(1,3)-dibenzenacyclododecaphane-5-carboxamide (1-24)

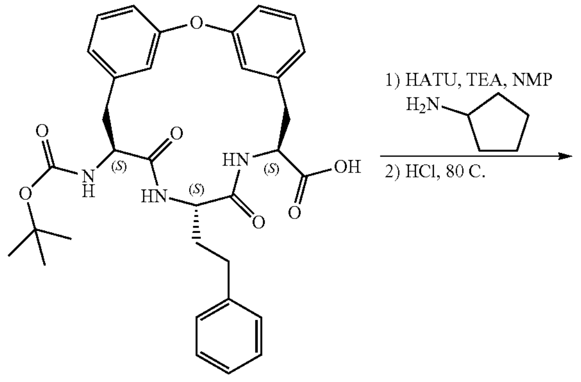

1-68-1

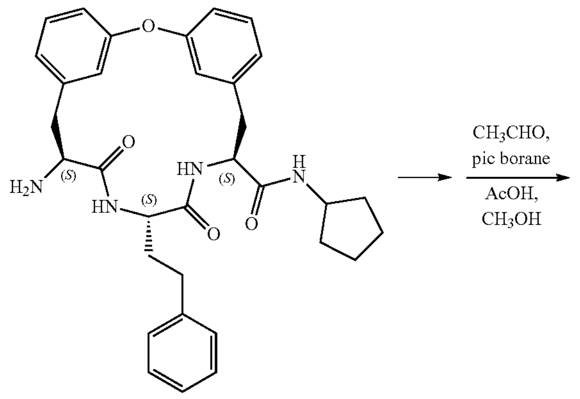

1-24-1

-continued

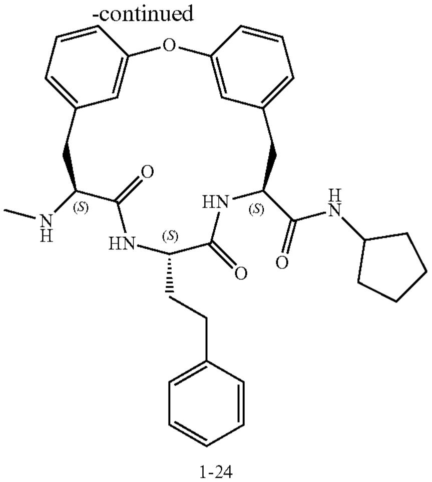

1-24

To a mixture of 1-68-1 (10 mg, 0.017 mmol) and NMP (0.4 mL) cyclopentylamine (0.017 mmol) was added followed by HATU (0.020 mmol) and TEA (0.020 mmol). The mixture was stirred at room temperature for 30 minutes and a 4M solution of HCl in dioxane (0.255 mL, 1.021 mmol) was added. The mixture was heated to 80° C. for 3 hours then cooled to room temperature and passed through a solid phase extraction column (scx-2 5 g), washed with MeOH (3*8 mL), and eluted with 2N ammonia in MeOH (3*8 mL). Volatile organics were removed by evaporation to provide 1-24-1 which was used immediately without purification.

To the isolated 1-24-1 was added MeOH (2 mL) followed by acetaldehyde (35 mg, 0.796 mmol) and pic borane (36 mg, 0.332 mmol), and a drop of AcOH. The mixture was stirred overnight. The product was purified by reverse phase HPLC to provide 1-24.

Example 5—Synthesis of Benzyl-(S,8S,11S)-11-((tert-butoxycarbonyl)amino)-7,10-dioxo-8-phenethyl-2-oxa-6,9-diaza-1,3(1,3)-dibenzenacyclododecaphane-5-carboxylate (1-50)

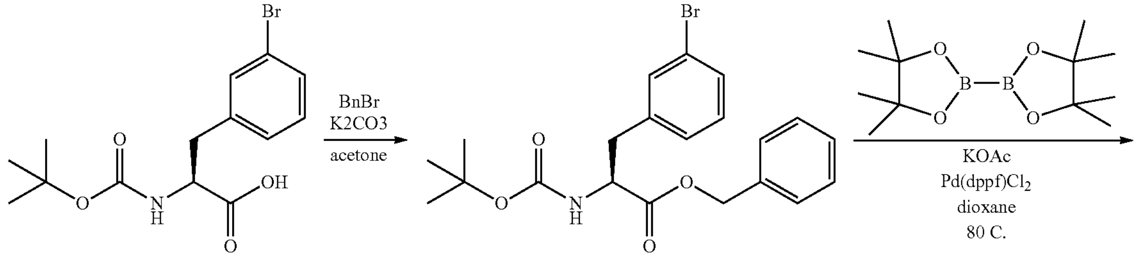

1-50-1

-continued
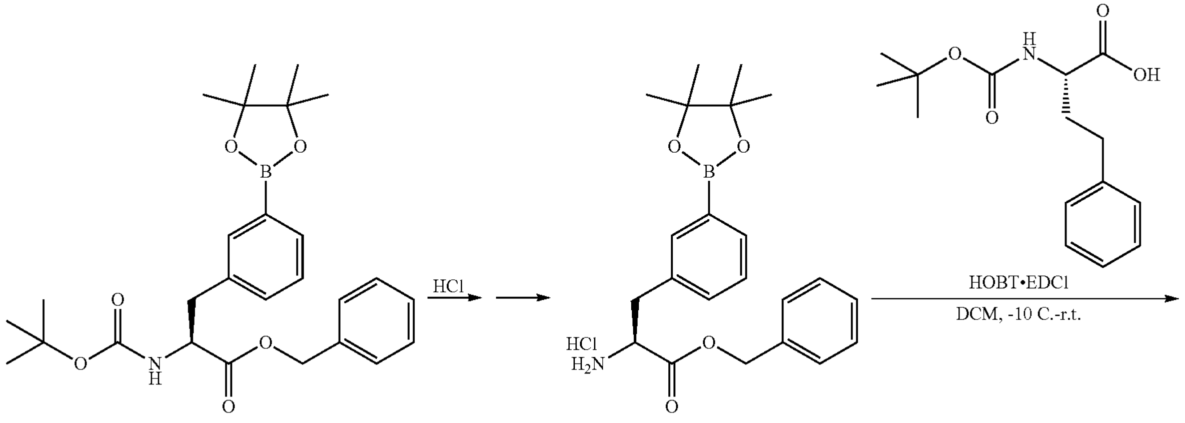
1-50-2 1-50-3
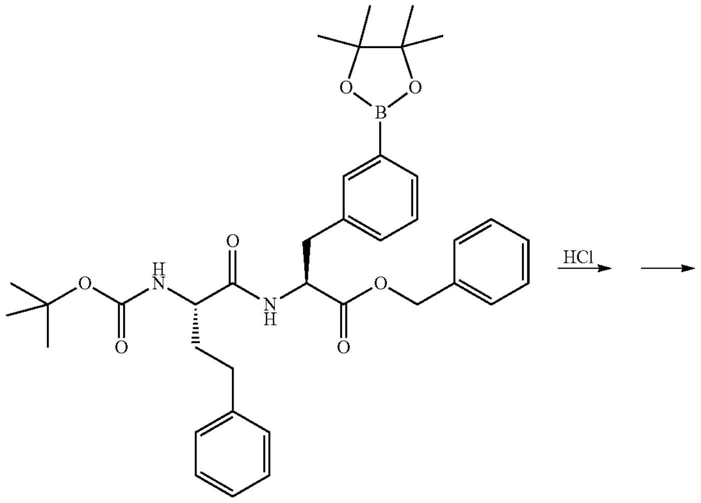
1-50-4
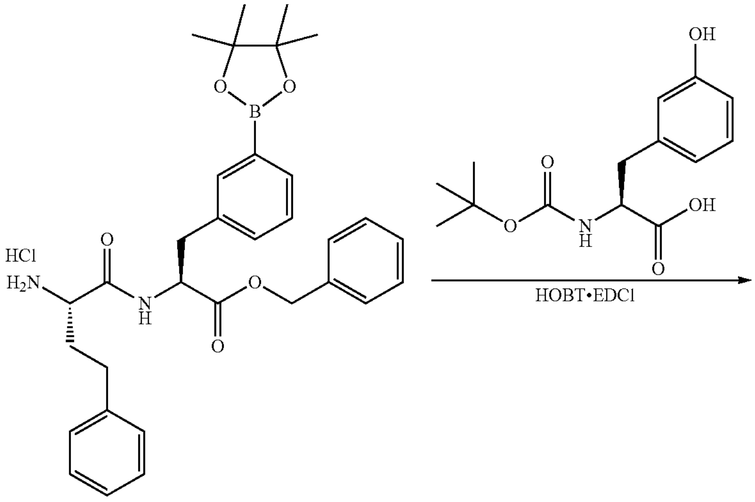
1-50-5

-continued

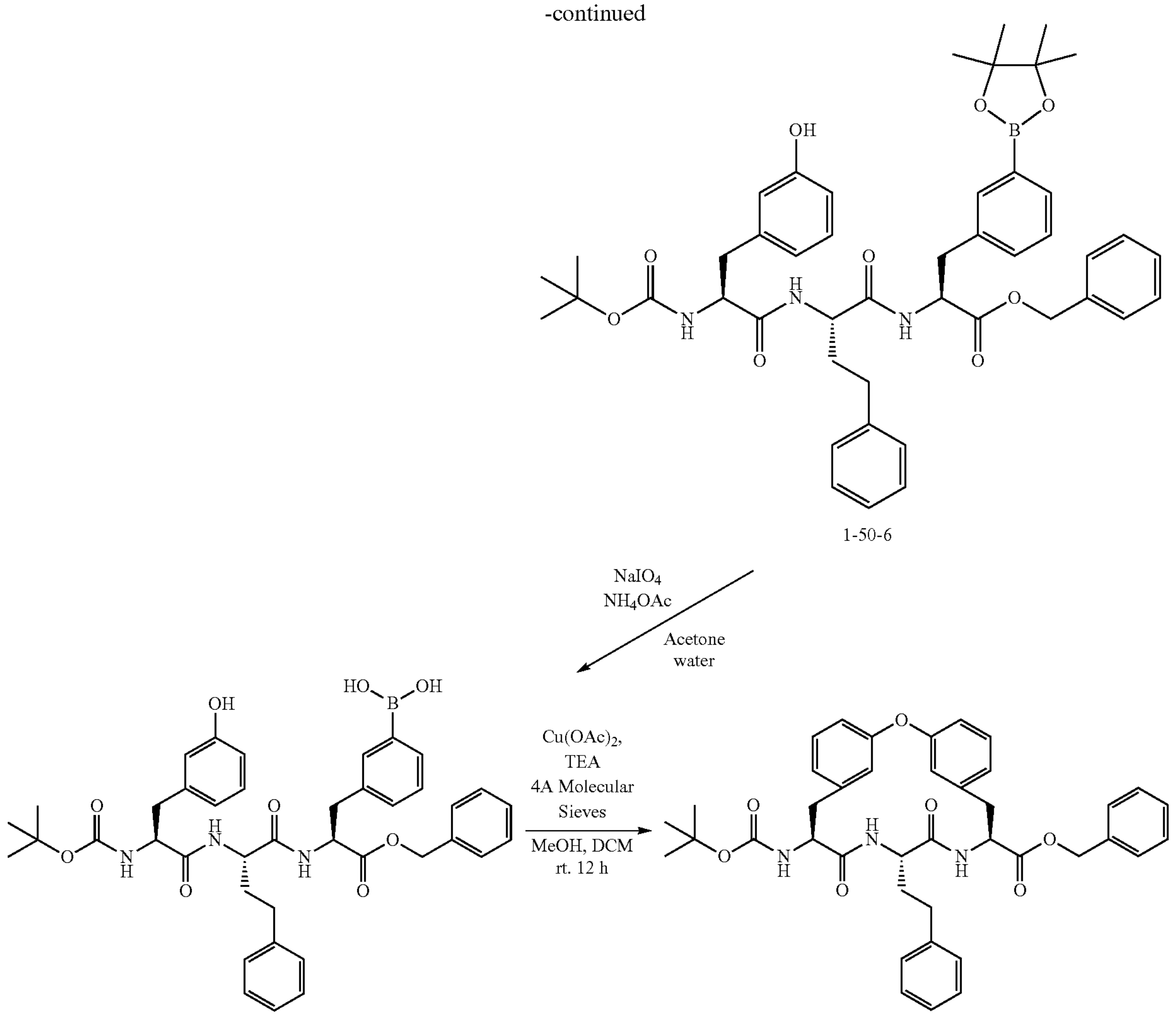

1-50-6

1-50-7

1-50

To a mixture of (S)-3-(3-bromophenyl)-2-((tert-butoxycarbonyl)amino)propanoic acid (8.0 g, 23 mmol) and potassium carbonate (3.37 g, 24.4 mmol) in acetone (800 mL) benzyl bromide (4.37 g, 25.6 mmol) was added at 25° C. The reaction mixture was stirred for 12 hours at 25° C. then filtered and the filtrate was concentrated under vacuum. The residue was purified by column chromatography (petroleum ether:ethyl acetate, 100:1 to 10:1) to afford 1-50-1 (10.0 g, 97.8% yield) as a white solid.

To a solution of compound 1-50-1 (10.0 g, 23.0 mmol), 4,4,4',4',5,5,5',5'-octamethyl-2,2'-bi(1,3,2-dioxaborolane) (9.35 g, 36.8 mmol), and potassium acetate (6.78 g, 69.1 mmol) in dioxane (250 mL) was added Pd(dppf)$Cl_2$ (1.68 g, 2.30 mmol) at 25° C. The reaction mixture was stirred at 80° C. for 12 hours under nitrogen then filtered and the filtrate was concentrated under vacuum. The residue was purified by column chromatography ($SiO_2$, petroleum ether:ethyl acetate=100:1 to 10:1) to afford 1-50-2 (10.0 g, 85.66% yield) as a yellow oil.

To a solution of compound 1-50-2 (35.0 g, 72.7 mmol) in dioxane (50 mL) was added a 4 M solution of hydrogen chloride in dioxane (300 mL, 1.2 mol) at 25° C. The reaction mixture was stirred at 25° C. for 0.5 hour then concentrated under vacuum to afford 1-50-3 (30.0 g, crude) as a yellow oil, which was used directly in the next step.

To a solution of (S)-2-((tert-butoxycarbonyl)amino)-4-phenylbutanoic acid (18.39 g, 65.84 mmol), 1-hydroxybenzotriazole (8.9 g, 66 mmol) in dichloromethane (250 mL) was added 1-ethyl-3-(3-dimethyl aminopropyl) carbodiimide hydrochloride (12.62 g, 65.84 mmol) at 0° C. and the reaction mixture was stirred for 30 mins at 0° C. The crude 1-50-3 (25 g, 60 mmol) and diisopropylethylamine (23.2 g, 179 mmol) in dichloromethane (120 mL) were added to above reaction mixture at 0° C. The resulting mixture was stirred at 25° C. for 11.5 hours. The reaction mixture was diluted with a 1M aqueous solution of hydrochloric acid (400 mL, 400 mmol) and extracted with dichloromethane (200 mL*2). The combined organic phases were washed with brine (400 mL*2), dried over sodium sulfate, and concentrated under reduced pressure. The residue was purified by column chromatography ($SiO_2$, petroleum ether: ethyl acetate=50:1 to 2:1) to afford 1-50-4 (29.00 g, 64.25% yield) as a yellow oil.

To a solution of compound 1-50-4 (31.0 g, 48.2 mmol) in dioxane (50 mL) was added a 4 M solution of hydrogen chloride in dioxane (250 mL, 1 mol) at 25° C. and the reaction mixture was stirred at 25° C. for 30 min. The reaction mixture was concentrated under reduced pressure to afford 1-50-5 (26.00 g, 78.79% yield) as a yellow oil.

To a solution of compound 1-50-5 (5.0 g, 9.2 mmol) and (S)-2-((tert-butoxycarbonyl)amino)-3-(3-hydroxyphenyl) propanoic acid (2.59 g, 9.22 mmol) in N,N-dimethylformamide (150 mL) was added diisopropylethylamine (5.96 g, 46.1 mmol), 1-hydroxybenzotriazole (1.37 g, 10.1 mmol), and 1-ethyl-3-(3-dimethylaminopropyl) carbodiimide hydrochloride (1.94 g, 10.1 mmol) at 0° C. The reaction was allowed to warm to 25° C. and stirred for 12 hours. The reaction mixture was acidified to pH=4 with a 0.5 M solution of hydrochloric acid and extracted with dichloromethane (150 mL*4). The organic layer was dried over anhydrous sodium sulfate, filtered, and concentrated under reduced pressure to afford 1-50-6 (13.60 g, 47.16% yield) as a red oil, which was used directly in the next step.

To a solution of 1-50-6 (30.0 g, 37.2 mmol) in acetone (300 mL) was added a solution of sodium periodate (23.89 g, 111.7 mmol) and ammonium acetate (8.61 g, 112 mmol) in water (240 mL) at 25° C. The reaction mixture was stirred at 25° C. for 12 hours. The reaction mixture was acidified to pH=4 with a 0.5M solution of hydrochloric acid and extracted with dichloromethane (300 mL*3). The organic layer was dried over anhydrous sodium sulfate, filtered, and concentrated in vacuum. The residue was purified by reverse phase flash chromatography (HCl condition) to afford 1-50-7 (9.30 g, 25.1% yield) as a brown solid.

To a solution of compound 1-50-7 (6.0 g, 8.3 mmol) in dichloromethane (600 mL), copper acetate (1.51 g, 8.29 mmol), triethylamine (8.39 g, 82.9 mmol), methanol (2.66 g, 82 mmol), and 4 Å molecular sieves (6.0 g) were added at 25° C. The reaction mixture was stirred at 25° C. for 12 hours under oxygen then filtered and concentrated under reduced pressure. The residue was purified by re-crystallization from ethyl acetate (100 mL) and then recrystallized again from acetonitrile (100 mL) to give 1-50 (2.60 g, 44% yield) as a yellow solid.

Example 6—Synthesis of (5S,8S,11S)-11-Acetamido-N-(4-methylbenzyl)-7,10-dioxo-8-phenethyl-2-oxa-6,9-diaza-1,3(1,3)-dibenzenacyclododecaphane-5-carboxamide (1-51)

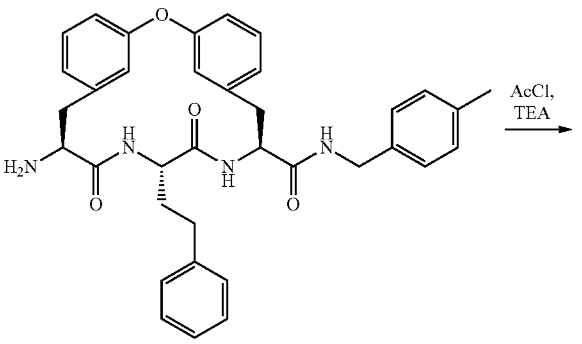

1-69

-continued

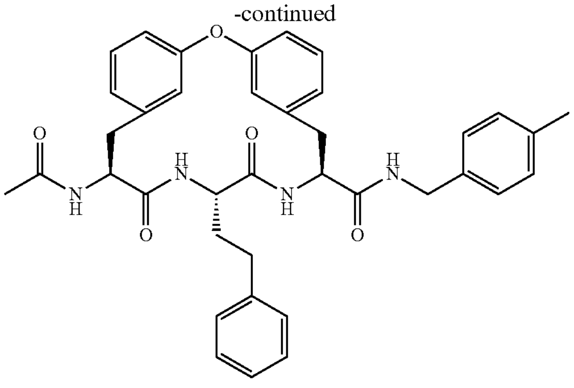

1-51

To a solution of 1-69 (80 mg, 110 μmol) and triethylamine (34 mg, 340 μmol) in N,N-dimethylformamide (3 mL) a solution of acetyl chloride (11 mg, 230 μmol) in dichloromethane (1 mL) was added at 0° C. The reaction mixture was stirred for 2 hours at 25° C. The reaction mixture was quenched with water (3 mL) causing a solid to precipitate out. The solid was collected by filtration, washed with acetonitrile (3 mL*3) followed by a mixture of dichloromethane/methanol (V:V=1:1, 2 mL*2). The solid was dried to afford 1-51 (8.5 mg, 11% yield) as a yellow solid.

Example 7—Synthesis of (5S,8S,11S)-11-Acetamido-7,10-dioxo-8-phenethyl-N-(2,2,2-trifluoroethyl)-2-oxa-6,9-diaza-1,3(1,3)-dibenzenacyclododecaphane-5-carboxamide (1-53)

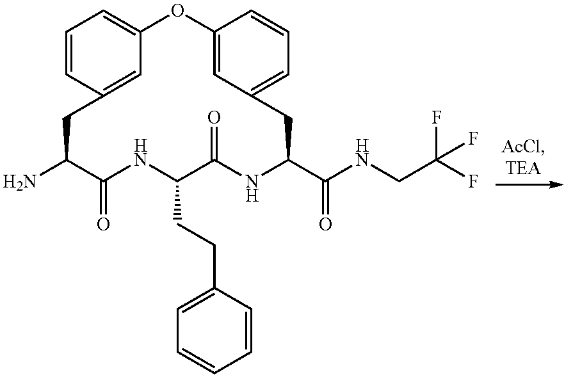

1-71

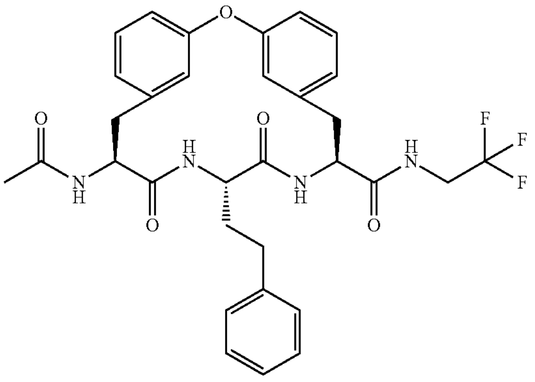

1-53

To a solution of 1-71 (100 mg, 176 μmol) and triethylamine (53 mg, 530 μmol) in N,N-dimethylformamide (4 mL) acetyl chloride (10 mg, 190 μmol) was added at 0° C. and then the reaction mixture was stirred for 3 hours at 25° C. The reaction was diluted with water (5 mL) causing a solid to precipitate from solution. The solid was collected by filtration and purified by prep-HPLC (TFA condition; column: PhenomenexSynergi C18 150 mm*25 mm*10 um, mobile phase: [water (0.1% TFA)-ACN]; B %: 38%-68%, 11 min) to afford 1-53 (9.50 mg, 8.76% yield) as a white solid. LCMS of 1-53: RT=2.177 min, m/z=611.2 [M+H]$^+$ Example 8—Synthesis of (5S,8S,11S)-11-(Cyclopropanecarboxamido)-7,10-dioxo-8-phenethyl-N-(2,2,2-trifluoroethyl)-2-oxa-6,9-diaza-1,3(1,3)-dibenzenacyclododecaphane-5-carboxamide (1-54)

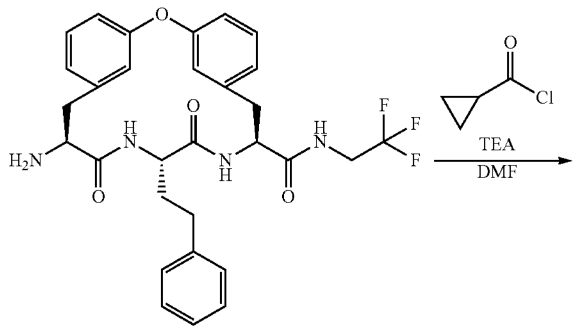

1-71

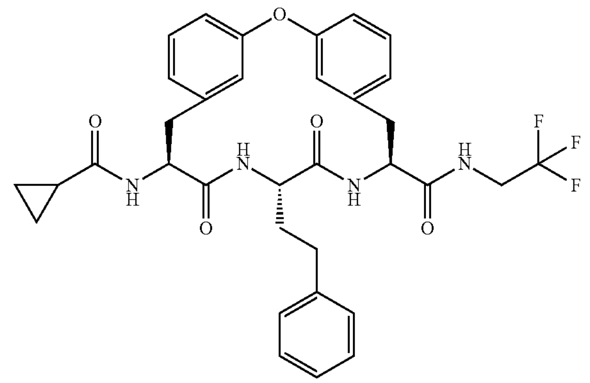

1-54

To a solution of 1-71 (100 mg, 176 mmol) and triethylamine (60 mg, 590 μmol) in N,N-dimethylformamide (4 mL) cyclopropanecarbonyl chloride (28 mg, 260 μmol) was added at 0° C. The mixture was stirred for 2 hours at 25° C. then concentrated under reduced pressure and the residue was purified by prep-HPLC (column: PhenomenexSynergi C18 150 mm*25 mm*10 um; mobile phase: [water (0.1% TFA)-ACN]; B %: 45%-75%, 11 min) to afford 1-54 (24.2 mg, 20.8% yield) as an off-white solid. LCMS of 1-54: RT=2.812 min, m/z=637.2 [M+H]$^+$.

Example 9—Synthesis of (5S,8S,11S)-7,10-Dioxo-8-phenethyl-N-(2,2,2-trifluoroethyl)-11-(3,3,3-trifluoropropanamido)-2-oxa-6,9-diaza-1,3(1,3)-dibenzenacyclododecaphane-5-carboxamide (1-55)

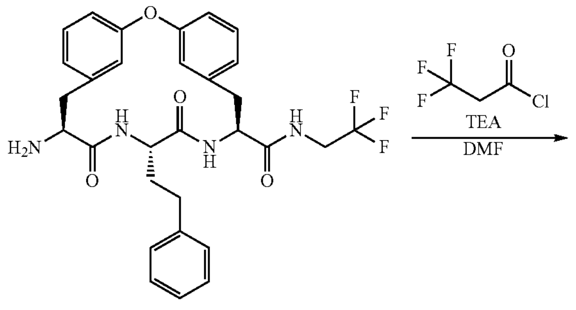

1-71

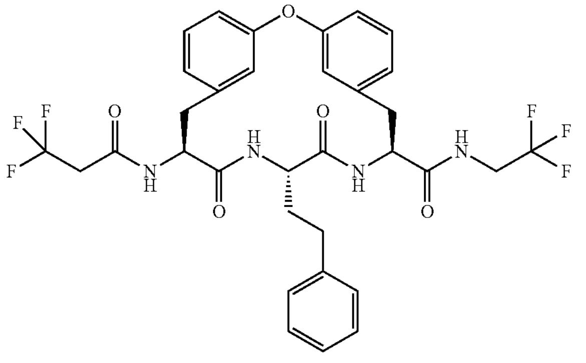

1-55

To a solution of 1-71 (100 mg, 176 μmol) and triethylamine (53 mg, 530 μmol) in N,N-dimethylformamide (5 mL) and 3,3,3-trifluoropropanoyl chloride (39 mg, 260 μmol) were added at 0° C. The mixture was stirred for 2 hours at 25° C. then concentrated under reduced pressure and the residue was purified by prep-HPLC (column: PhenomenexSynergi C18 150 mm*25 mm*10 um; mobile phase: [water (0.1% TFA)-ACN]; B %: 45%-75%, 11 min) to afford 1-55 (18.0 mg, 13.9% yield) as an off-white solid. LCMS of 1-55: RT=2.891 min, m/z=679.2 [M+H]$^+$.

Example 10—Synthesis of (5S,8S,11S)-7,10-Dioxo-11-(2-oxopyrrolidin-1-yl)-8-phenethyl-N-(2,2,2-trifluoroethyl)-2-oxa-6,9-diaza-1,3(1,3)-dibenzena-cyclododecaphane-5-carboxamide (1-56)
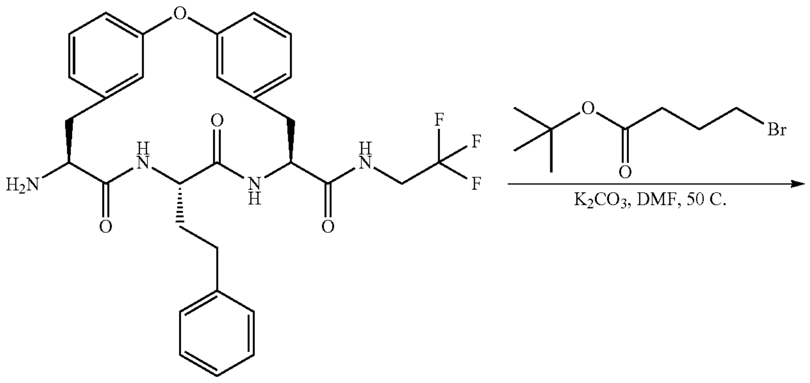
1-71
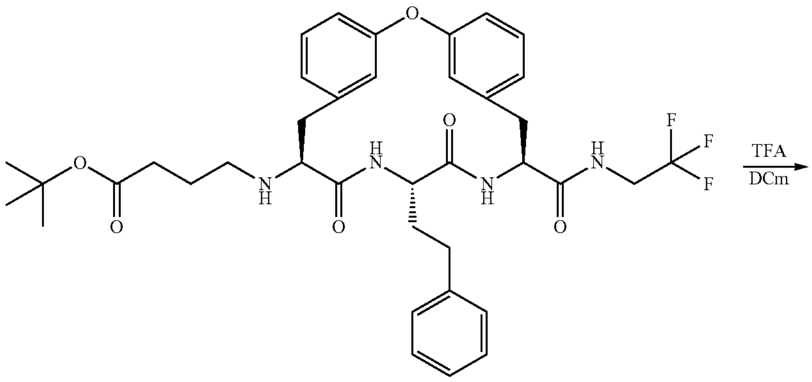
1-56-1
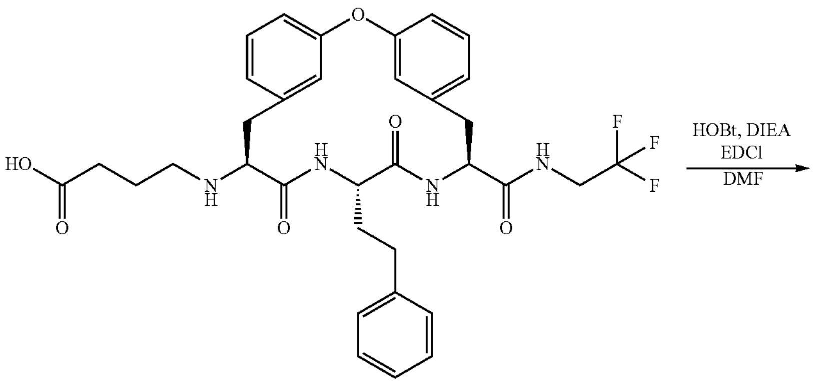
1-56-2

-continued

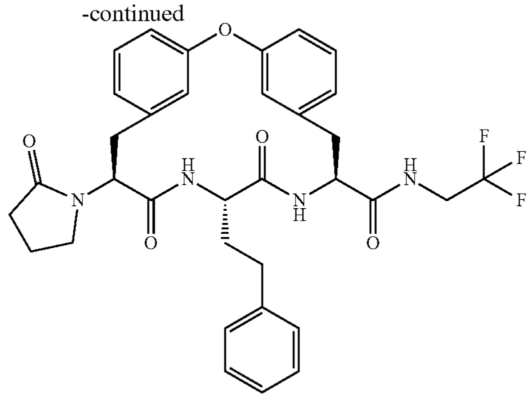

1-56

To a mixture of 1-71 (100 mg, 176 μmol), sodium iodide (3 mg, 20 μmol), and sodium carbonate (93 mg, 880 μmol) in N,N-dimethylformamide (3 mL) tert-butyl 4-bromobutanoate (51 mg, 230 μmol) was added at 25° C. The mixture was stirred for 12 hours at 50° C. and then diluted with water (20 mL) causing a solid to precipitate from solution. The solid was collected by filtration and dried under reduced pressure to afford compound 1-56-1 (110 mg, 155 μmol) as a yellow solid.

To a solution of compound 1-56-1 (50 mg, 70 μmol) in dichloromethane (2 mL) trifluoroacetic acid (1 mL) was added. The mixture was stirred for 2 hours at 25° C. then concentrated under reduced pressure to afford compound 1-56-2 (50 mg, crude) as a yellow solid, which was used in the next step without further purification.

To a solution of compound 1-56-2 (40 mg, 61 μmol), 1-hydroxybenzotriazole (12 mg, 92 μmol), and diisopropylethylamine (24 mg, 180 μmol) in N,N-dimethylformamide (2 mL) EDCI (18 mg, 92 μmol) was added at 25° C. The mixture was stirred for 12 hours at 25° C. The mixture was poured into water (10 mL) causing a solid to precipitate from solution. The solid was collected by filtration and purified by prep-HPLC (column: PhenomenexSynergi C18 150 mm*25 mm*10 um; mobile phase: [water (0.1% TFA)-ACN]; B %: 44%-74%, 12 min) to afford 1-56 (15.7 mg, 38.8% yield) as a white solid. LCMS of 1-56: RT=2.791 min, m/z=637.2 $[M+H]^+$.

Example 11—Synthesis of (5S,8S,11S)-11-(Dimethylamino)-7,10-dioxo-8-phenethyl-N-(2,2,2-trifluoroethyl)-2-oxa-6,9-diaza-1,3(1,3)-dibenzenacyclododecaphane-5-carboxamide (1-57)

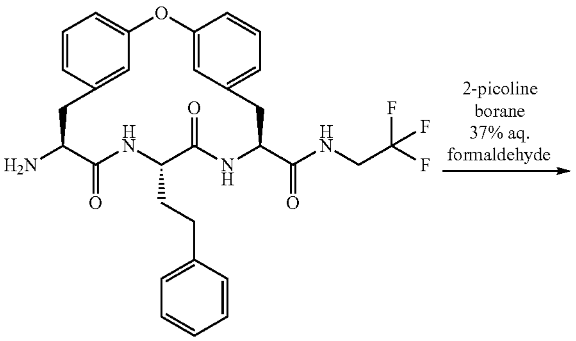

1-71

-continued

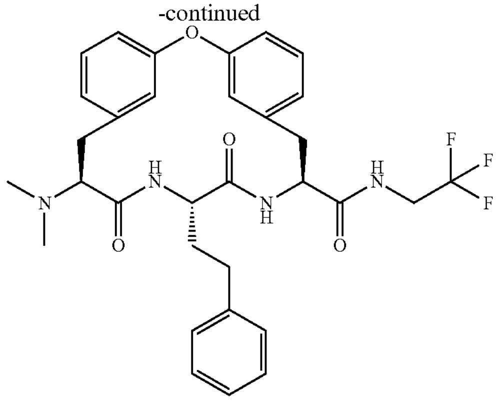

1-57

2-Picoline borane complex (47 mg, 430 μmol) was added to a mixture of 1-71 (83 mg, 140 μmol) and 37% formaldehyde solution (13 mg, 430 μmol) in MeOH (1.50 mL) and AcOH (150 μL) at room temperature. The mixture was stirred at room temperature for 3 hours. The solvent was removed in vacuo and the residue was dissolved with methylene chloride. The mixture was poured into sat. $NaHCO_3$ (aq.) and extracted with methylene chloride. The organic layer was washed with brine, dried with $Na_2SO_4$, and concentrated in vacuo. The residue was purified by recrystalization (EtOAc/hexanes) to afford 1-57 (28 mg, 32% yield) as a colorless solid. LCMS of 1-57: RT=1.845 min, m/z=597.44 $[M+H]^+$ Example 12—Synthesis of (5S,8S,11S)-11-Acetamido-8-isobutyl-7,10-dioxo-N-(2,2,2-trifluoroethyl)-2-oxa-6,9-diaza-1,3(1,3)-dibenzenacyclododecaphane-5-carboxamide (1-58)

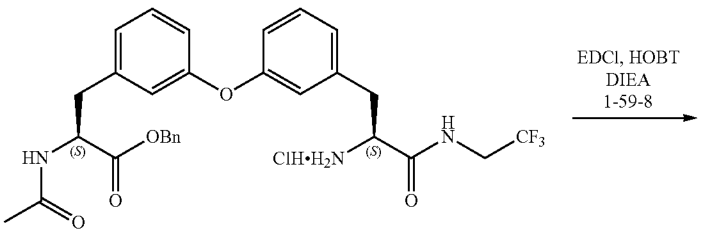

1-59-8

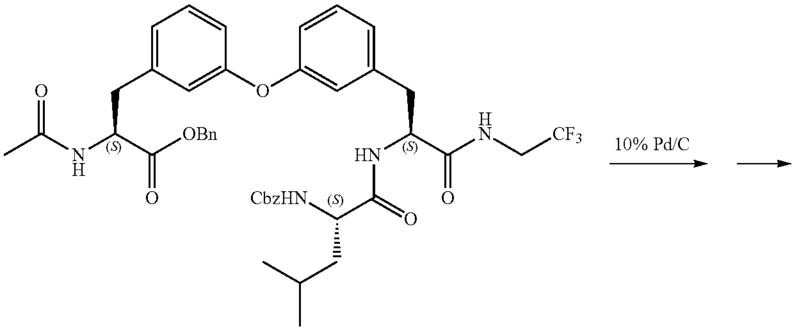

1-58-1

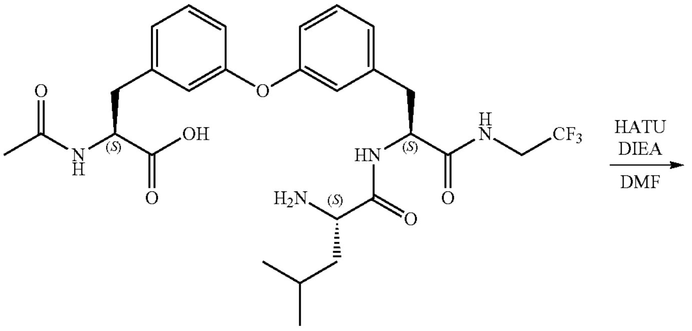

1-58-2

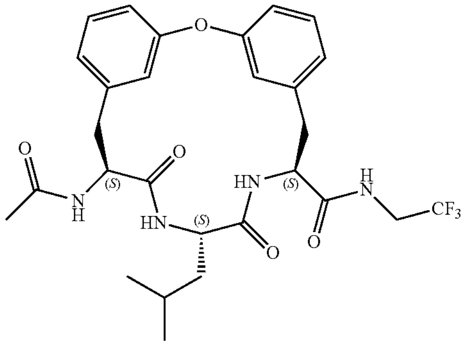

1-58

To a solution of ((benzyloxy)carbonyl)-L-leucine (45 mg, 170 μmol) in dimethyl formamide (3 mL) was added diisopropylethylamine (50 mg, 390 μmol), HOBt (27 mg, 200 μmol), and EDCI (38 mg, 200 μmol) at 0° C. under nitrogen and then compound 1-59-8 (100 mg, 155 μmol) was added. The mixture was stirred at 25° C. for 16 hours. The mixture was poured into water (10 mL) and then extracted with ethyl acetate (10 mL*3). The combined organic phase was washed with brine (10 mL) then dried over sodium sulfate. After filtration and concentration, the crude product was purified by reverse phase flash chromatography using a gradient of water/ACN with 0.1% TFA additive. The eluent was removed under reduced pressure to afford compound 1-58-1 (70 mg, 51% yield) as a yellow solid.

To a solution of compound 1-58-1 (300 mg, 373 μmol) in tetrahydrofuran (4 mL) 10% Pd/C (90 mg) was added. The mixture was degassed and purged with hydrogen for 3 times, and then the mixture was stirred at 25° C. for 23 hours under hydrogen balloon. Dichloromethane (10 mL) and methanol (5 mL) were added to the mixture. The mixture was filtered and the filtrat was concentrated. The crude product was triturated by acetonitrile (5 mL) to afford 1-58-2 (100 mg, 46% yield) as an off-white solid.

To a solution of compound 1-58-2 (97 mg, 167 μmol) in dimethyl formamide (7 mL) was added diisopropylethylamine (43 mg, 334 μmol) and HATU (95 mg, 250 μmol) at 0° C. under nitrogen. The mixture was stirred at 0° C. for 5 hours. The mixture was poured into water (10 mL) and then extracted by ethyl acetate (10 mL*3). The combined organic phase was washed with brine (20 mL) and dried over sodium sulfate. After filtration and concentration, the crude product was recrystallized by acetonitrile (4 mL) to afford 1-58 (20 mg, 21% yield) as a white solid. LCMS of 1-58: RT=3.040 min, m/z 563.2 [M+H]$^+$.

The following compound was made using a similar synthetic route as described for compound 1-58: Compound 1-62; LCMS: RT=2.666 min, m/z 507.1 [M+H]$^+$ Example 13—Synthesis of (5S,8S,11S)-11-Acetamido-7,10-dioxo-8-propyl-N-(2,2,2-trifluoroethyl)-2-oxa-6,9-diaza-1,3(1,3)-dibenzenacyclododecaphane-5-carboxamide (1-59)

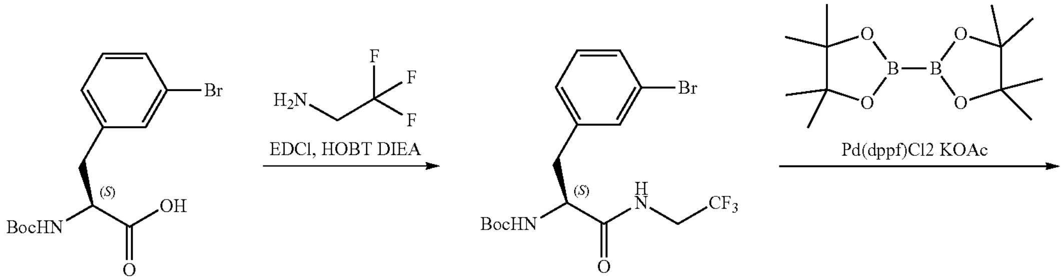

1-59-1

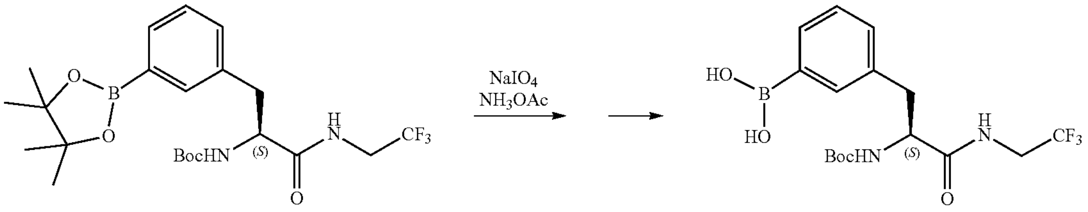

1-59-5

1-59-6

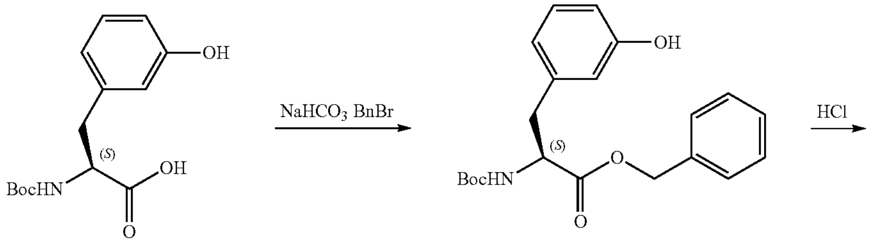

1-59-2

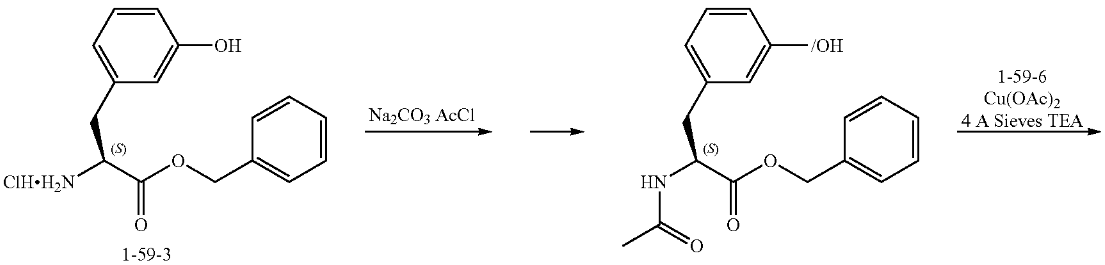

1-59-3

1-59-4

-continued
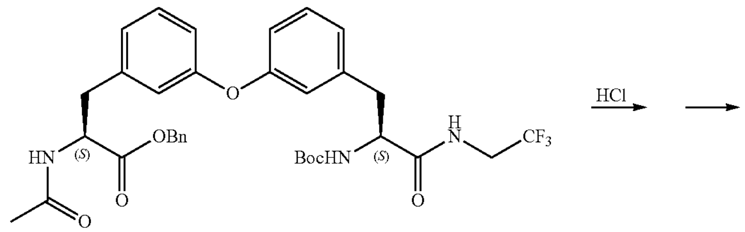
1-59-7
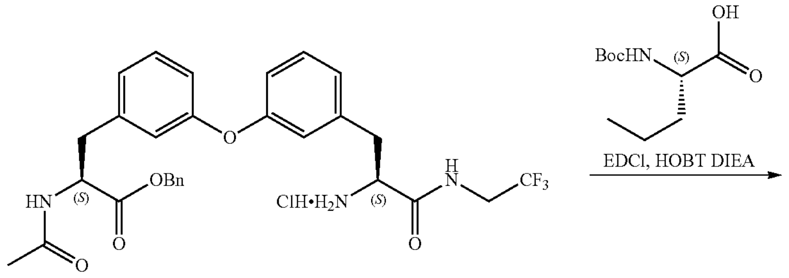
1-59-8
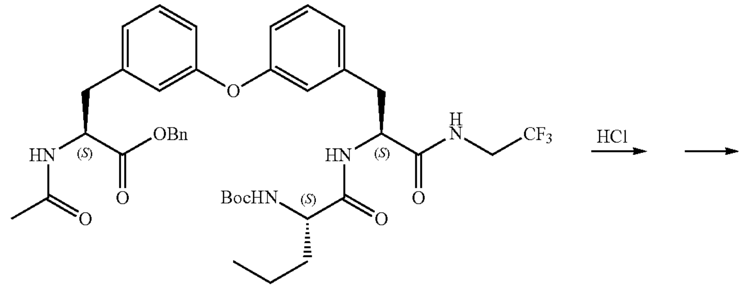
1-59-9
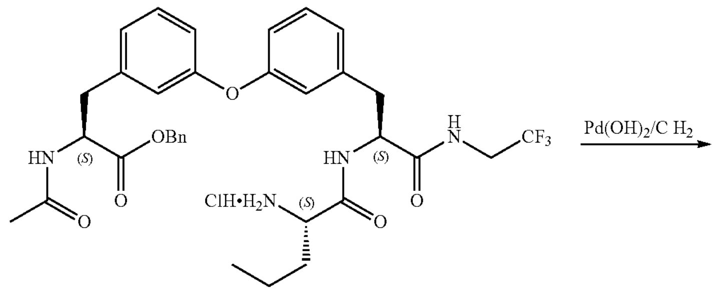
1-59-10
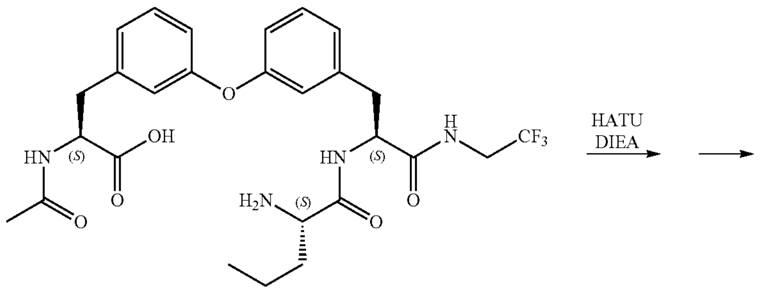
1-59-11

-continued

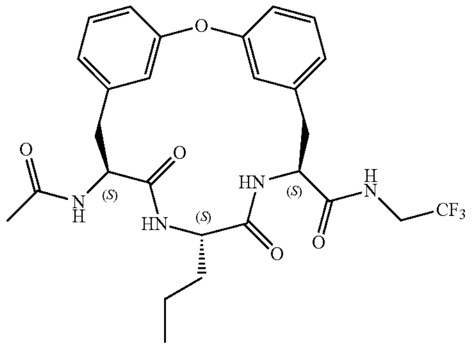

1-59

To a solution of (S)-3-(3-bromophenyl)-2-((tert-butoxycarbonyl)amino)propanoic acid (2.00 g, 5.81 mmol) in dichloromethane (15 mL) was added EDCI (1.45 g, 7.55 mmol), HOBT (1.02 g, 7.55 mmol), and diisopropylethylamine (2.25 g, 17.43 mmol) at 0° C. under nitrogen and then 2,2,2-trifluoroethan-1-amine·HCl (944.85 mg, 6.97 mmol) was added. The mixture was stirred at 25° C. for 16 hours. The mixture was poured into water (40 mL) and 1 N hydrochloric acid (10 mL). The mixture was extracted by dichloromethane (40 mL*3). The combined organic phase was washed by saturated sodium carbonate (40 mL*3), brine (20 mL) and dried over sodium sulfate. After filtration and concentration, compound 1-59-1 (2.01 g, 77.1% yield) was obtained as a light yellow solid.

To a solution of (tert-butoxycarbonyl)-L-tyrosine (2.00 g, 7.11 mmol) in dimethylformamide (5 mL) was added sodium bicarbonate (896 mg, 10.67 mmol) and benzylbromide (1.34 g, 7.82 mmol). The mixture was stirred at 40° C. for 16 hours. The mixture was cooled to 25° C. and then poured into water (50 mL). The mixture was extracted with ethyl acetate (50 mL*2). The combined organic phase was washed with brine (50 mL) and dried over sodium sulfate. After filtration and concentration, the crude product was purified by silica gel chromatography (petroleum ether:ethyl acetate=20:1 to 8:1) to afford compound 1-59-2 (1.18 g, 44.0% yield) as yellow oil.

To a solution of 1-59-2 (1.79 g, 4.82 mmol) in dioxane (10 mL) was added 4M HCl/dioxane (80.0 mmol, 20 mL). The mixture was stirred at 25° C. for 4 hours. The mixture was concentrated under vacuum to afford compound 1-59-3 (2.0 g, crude) as a yellow solid.

A solution of compound 1-59-3 (2.0 g, 6.5 mmol) and sodium carbonate (6.9 g, 65 mmol) in tetrahydrofuran (20 mL) and water (10 mL) was added dropwise a solution of acetyl chloride (2.55 g, 32.5 mmol) in tetrahydrofuran (5 mL) at 0° C. The mixture was stirred at 25° C. for 3 hours. The mixture was poured into water (10 mL) and the pH was adjusted with 1N hydrochloric acid (5 mL) until pH=6. The mixture was extracted by ethyl acetate (15 mL*3). The combined organic phase was washed by brine (20 mL) and dried over sodium sulfate. After filtration and concentration, compound 1-59-4 (840 mg, 40.62% yield) was obtained as yellow oil.

To a solution of 1-59-1 (1.55 g, 3.65 mmol) in dioxane (15 mL) was added bis(pinacolato)diboron (1.39 g, 5.48 mmol), Pd(dppf)$Cl_2$ (267 mg, 0.365 mmol), and potassium acetate (1.07 g, 10.9 mmol). The mixture was degassed and purged with nitrogen for 3 times. The mixture was stirred at 80° C. for 7 hours. The mixture was filtered and then the filtrat was concentrated to give compound 1-59-5 (1.8 g, crude) as black oil.

To a solution of 1-59-5 (1.8 g, 3.8 mmol) in acetone (8 mL) and water (4 mL) was added ammonium acetate (881 mg, 11.4 mmol) and sodium periodate (2.45 g, 11.4 mmol). The mixture was stirred at 25° C. for 40 hours. Ethyl acetate (10 mL) was added to the mixture and then the mixture was filtered. The filtrate was extracted by ethyl acetate (20 mL*2). The combined organic phase was washed by brine (20 mL) and dried over sodium sulfate. After filtration and concentration, the crude product was purified by reverse phase flash chromatography (0.1% TFA modifier) to afford compound 1-59-6 (900 mg, 59.3% yield) as a yellow solid.

To a solution of compound 1-59-6 (517 mg, 1.32 mmol) in dichloromethane (6.00 mL) was added 4A molecular sieves (1.5 g), copper acetate (278 mg, 1.53 mmol), triethylamine (1.41 mL, 10.2 mmol), and compound 1-59-4 (320 mg, 1.02 mmol). The mixture was stirred at 25° C. for 18 hours. The mixture was filtered and then filter liquor was concentrated. The mixture was purified by reverse phase flash chromatography (TFA) to afford compound 1-59-7 (360 mg, 51.3% yield) as a yellow brown solid.

To a solution of compound 1-59-7 (800 mg, 1.22 mmol) in dioxane (5 mL) was added a solution of hydrochloric acid in dioxane (4 M, 5 mL, 20 mmol). The mixture was stirred at 25° C. for 4 hours. The mixture was concentrated to give compound 1-59-8 (770 mg, crude) as a yellow brown solid.

To a solution of (S)-2-amino-5-((tert-butoxycarbonyl)amino)pentanoic acid (73 mg, 340 μmol) in dimethylformamide (3 mL) was added N,N-diisopropylethylamine (130 mg, 1.01 mmol), EDCI (97 mg, 500 μmol), and HOBT (68 mg, 500 μmol) at 0° C., then compound 1-59-8 (200 mg, 336 μmol) was added into the mixture and the reaction was stirred at 26° C. for 6 hours. Water (5 mL) was then added to the reaction mixture. The mixture was acidified by hydrochloric acid (1N) until pH=4 and extracted with ethyl acetate (3*20 mL). The combined organic layers were washed with brine (3*20 mL) and dried over anhydrous sodium sulfate. After filtration and concentration, compound 1-59-9 (240 mg, crude) was obtained as yellow oil.

To a solution of 1-59-9 (240 mg, 317 μmol) in dioxane (3 mL) was added a 4M solution of HCl in dioxane (4 mL, 16 mmol) the reaction was stirred at 26° C. for 1 hour. The mixture was concentrated under reduced pressure to afford compound 1-59-10 (270 mg, 85.4% yield) as yellow oil.

To a solution of 1-59-10 (270 mg, 411 μmol) in tetrahydrofuran (3 mL) was added Pd$(OH)_2$/C (29 mg, 210 μmol) under a hydrogen balloon (15 psi). Then the mixture was degassed under vacuum and purged with hydrogen for 3 times and the reaction was stirred at 26° C. for 1.5 hours. The reaction mixture was filtered and the filtrate was concentrated under reduced pressure to afford compound 1-59-11 (110 mg, crude) as yellow oil.

To a solution of 1-59-11 (110 mg, 194 μmol) in dimethyl formamide (2 mL) was added N,N-diisopropylethylamine (75 mg, 580 μmol) and HATU (111 mg, 291 μmol) at 0° C., the reaction was stirred at 0° C. for 2.5 hours. The reaction mixture was diluted with water (10 mL) and extracted with ethyl acetate (3*15 mL). The combined organic layers were washed with brine (3*20 mL), dried with anhydrous sodium sulfate, filtered, and concentrated under reduced pressure. The residue was triturated with methanol (1 mL), filtered and the filter cake was collected to afford 1-59 (21.0 mg, 18.7% yield) as an off-white solid. LCMS for 1-59: RT=1.947 min, m/z 549.2 $[M+H]^+$.

The following compounds were made using a similar synthetic route as described for compound 1-59:

Compound 1-60; LCMS: RT=2.919 min, m/z 551.2 $[M+H]^+$

Compound 1-61; LCMS: RT=3.261 min, m/z 603.2 $[M+H]^+$

Example 14—Synthesis of (5S,8S,11S)-6-Methyl-7,10-dioxo-11-(2-oxopyrrolidin-1-yl)-8-phenethyl-N-(2,2,2-trifluoroethyl)-2-oxa-6,9-diaza-1,3(1,3)-dibenzenacyclododecaphane-5-carboxamide (1-65)

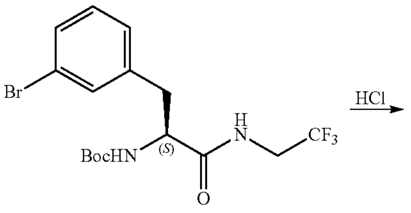

1-59-1

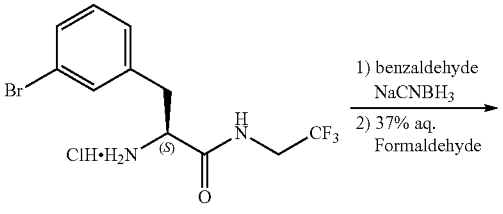

1-65-1

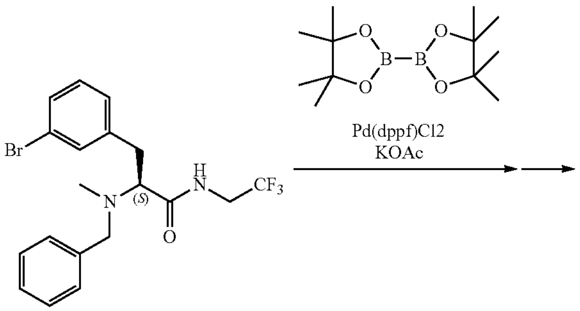

1-65-2

-continued

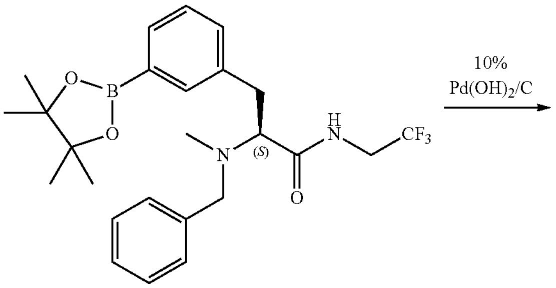

1-65-3

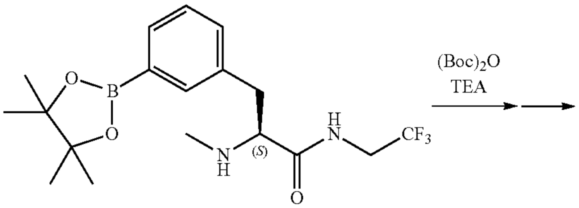

1-65-4

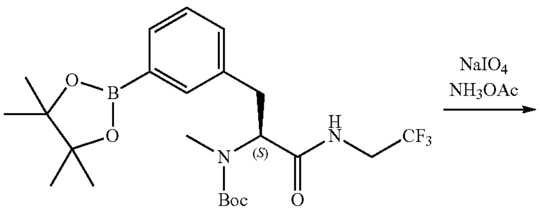

1-65-5

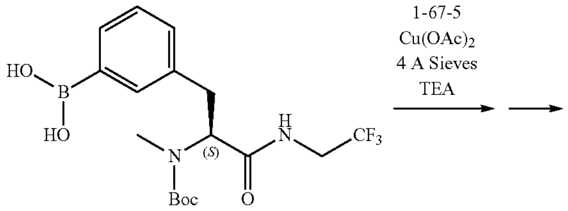

1-65-6

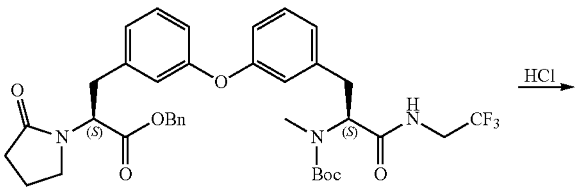

1-65-7

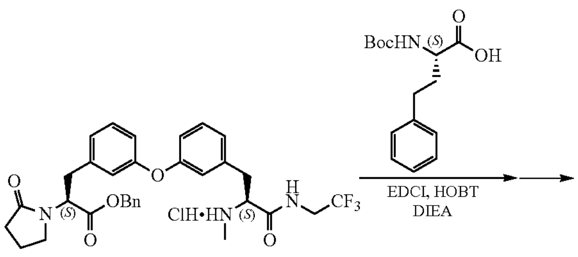

1-65-8

-continued

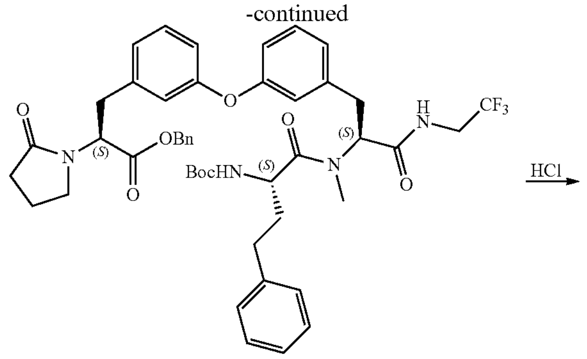

1-65-9

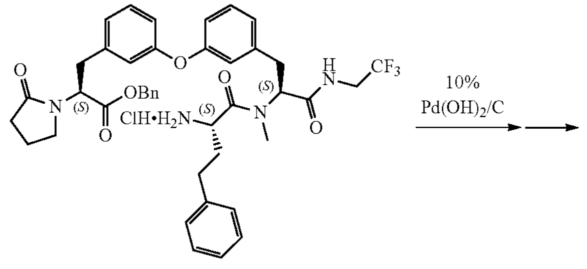

1-65-10

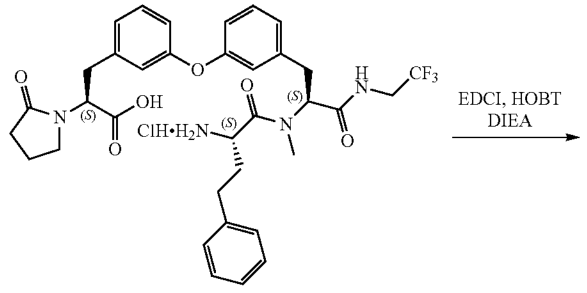

1-65-11

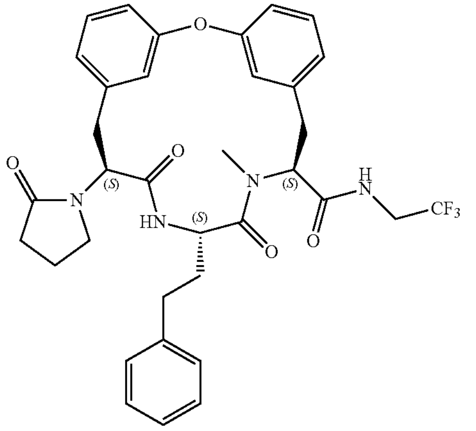

1-65

To a solution of 1-59-1 (710 mg, 1.67 mmol) in dioxane (5 mL) was added 4M hydrochloric acid/dioxane (10 mL). The mixture was stirred at 25° C. for 1.5 hours. The mixture was concentrated to afford compound 1-65-1 (600 mg, 99.4% yield) as yellow oil.

To a solution of 1-65-1 (1.33 g, 4.09 mmol) in methanol (10 mL) was added benzaldehyde (521 mg, 4.91 mmol). The mixture was stirred at 25° C. for 0.5 hour and then sodium cyanoborohydride (771 mg, 12.3 mmol) was added. The mixture was stirred at 25° C. for 16 hours then an aqueous solution of formaldehyde (498 mg, 6.14 mmol) was added. The mixture was stirred at 25° C. for 0.5 hour. The mixture was poured into water (20 mL) and then extracted with ethyl acetate (20 mL*3). The combined organic phase was washed with brine (20 mL) and dried over sodium sulfate. After filtration and concentration, the residue was purified by silica gel column chromatography (petroleum ether:ethyl acetate=5:1 to 4:1, TLC, petroleum ether:ethyl acetate=3:1) to afford compound 1-65-2 (800 mg, 28.2% yield) as light yellow oil.

To a solution of compound 1-65-2 (800 mg, 1.86 mmol) in dioxane (8 mL) was added 4,4,4',4',5,5,5',5'-octamethyl-2,2'-bi(1,3,2-dioxaborolane) (946 mg, 3.73 mmol), potassium acetate (549 mg, 5.59 mmol), and $Pd(dppf)Cl_2$ (136 mg, 186 μmol). The mixture was degassed and purged with nitrogen for 3 times and then the mixture was stirred at 80° C. for 3 hours under nitrogen atmosphere. The mixture was concentrated to give crude product. The crude product was purified by silica gel column chromatography (petroleum ether:ethyl acetate=8:1 to 5:1, TLC, petroleum ether:ethyl acetate=3:1) to afford compound 1-65-3 (1.12 g, crude) as light yellow oil.

To a solution of compound 1-65-3 (1.0 g, 2.1 mmol) was added 10% palladium hydroxide (200 mg). The mixture was degassed and purged with hydrogen for 3 times, and then the mixture was stirred at 25° C. for 6 hours under a hydrogen atmosphere. The mixture was concentrated to afford compound 1-65-4 (800 mg, 82.4% yield) as a black oil.

To a solution of compound 1-65-4 (800 mg, 2.07 mmol) in methanol (10 mL) was added triethylamine (629 mg, 6.21 mmol) and $(Boc)_2O$ (1.36 g, 6.21 mmol). The mixture was stirred at 25° C. for 2 hours. The mixture was concentrated and the crude product was purified by silica gel column chromatography (petroleum ether:ethyl acetate=15:1 to 15:1) to afford compound 1-65-5 (670 mg, 53.7% yield) as a colorless oil.

To a solution of tert-butyl 1-65-5 (650 mg, 1.34 mmol) in a mixture of acetone (5 mL) and water (5 mL) was added ammonium acetate (309 mg, 4.01 mmol) and sodium periodate (222 μL, 4.01 mmol). The mixture was stirred at 25° C. for 16 hours. The mixture was poured into water (40 mL) and then hydrochloric acid (1M) was added until the pH=8. The mixture was extracted with ethyl acetate (20 mL*3). The combined organic phase was washed by brine (20 mL) and dried over anhydrous sodium sulfate. After filtration and concentration, compound 1-65-6 (400 mg, 66.8% yield) was obtained as a yellow oil.

To a solution of compound 1-65-6 (400 mg, 989.64 umol) and compound 1-67-5 (250 mg, 737 μmol) in dichloromethane (5 mL) was added 4A MS (600 mg), triethylamine (745 mg, 7.37 mmol), and copper acetate (200 mg, 1.1 mmol). The mixture was stirred at 25° C. for 2 hours. The mixture was filtered and then the filtrate was concentrated. The crude product was purified by silica gel column chromatography (petroleum ether:ethyl acetate=10:1 to 3:1) to afford compound 1-65-7 (330 mg, 55.9% yield) as a yellow oil.

To a solution of 1-65-7 (300 mg, 430 μmol) in dioxane (4 mL) was added a 4M solution of hydrochloric acid in dioxane (10 mL, 40 mmol). The mixture was stirred at 25° C. for 0.5 hour. The mixture was concentrated to afford compound 1-65-8 (300 mg, 85.4% yield, crude) as a yellow solid.

To a solution of compound boc-L-homophenylalanine (145 mg, 520 μmol) in dimethyl formamide (5 mL) was added HOBt (83 mg, 610 μmol), EDCI (118 mg, 615 μmol), and diisopropylethylamine (183 mg, 1.42 mmol) at 0° C. under nitrogen. To this mixture was added 1-65-8 (300 mg, 473 umol) and the mixture was stirred at 25° C. for 16 hours. The mixture was poured into water (40 mL) and then 1 N hydrochloric acid (10 mL) was added. The mixture was extracted with ethyl acetate (20 mL*3). The combined organic phase was washed by brine (20 mL) and dried over anhydrous sodium sulfate. After filtration and concentration, the crude product was purified by prep-HPLC (column: Phenomenex Synergi C18 150*25*10 um; mobile phase: [water(0.1% TFA)-ACN]; B %: 62%-92%, 2 min) to afford compound 1-65-9 (120 mg, 26.8% yield) as a white solid.

To a solution of compound 1-65-9 (115 mg, 134 μmol) in dioxane (2 mL) was added a 4M solution of hydrochloric acid in dioxane (5 mL, 20 mmol). The mixture was stirred at 25° C. for 1.5 hours. The mixture was concentrated to afford compound 1-65-10 (100 mg, 86.1% yield, crude) as a black brown solid.

To a solution of 1-65-10 (100 mg, 126 umol) in tetrahydrofuran (5 mL) was added 10% palladium hydroxide (30 mg, 21 μmol). The mixture was degassed and purged with hydrogen 3 times and then the mixture was stirred at 25° C. for 8 hours under a hydrogen balloon. The mixture was filtered and filtrate was concentrated to afford compound 1-65-11 (100 mg, 99.1% yield) as an off-white solid.

To a solution of 1-65-11 (80 mg, 110 μmol) in dimethyl formamide (6 mL) was added diisopropylethylamine (44 mg, 340 μmol), EDCI (33 mg, 170 μmol), and HOBT (23 mg, 170 μmol) at 0° C. under nitrogen. The mixture was stirred at 25° C. for 16 hours. The mixture was poured into water (20 mL) and then 1 N hydrochloric acid (5 mL) was added. The mixture was extracted with ethyl acetate (20 mL*3). The combined organic phase was washed with brine (20 mL), dried over sodium sulfate, filtered, and concentrated under reduced pressure to give a residue. The crude product was purified by prep-HPLC (column: Phenomenex Synergi C18 150*25*10 um; mobile phase: [water(0.1% TFA)-ACN]; B %: 46%-76%, 13 min) to afford 1-65 (20 mg, 26% yield) as a white solid. LCMS for 1-65: RT=3.210 min, m/z 651.3[M+H]$^+$ The following compounds were made using a similar synthetic route as described for compound 1-65:

Compound 1-64; LCMS: RT=3.210 min, m/z 651.3 [M+H]$^+$

Compound 1-81; LCMS: RT=2.904 min, m/z 623.2 [M+H]$^+$

Example 15—Synthesis of (5S,8S,11S)-7,10-Dioxo-11-(2-oxopyrrolidin-1-yl)-8-(2-(piperidin-1-yl) ethyl)-N-(2,2,2-trifluoroethyl)-2-oxa-6,9-diaza-1,3 (1,3)-dibenzenacyclododecaphane-5-carboxamide (1-67)

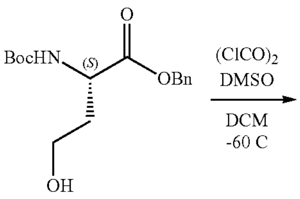

-continued

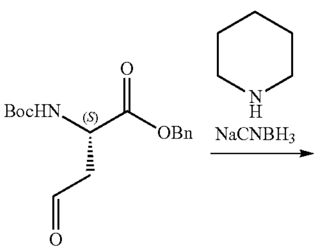

1-67-1

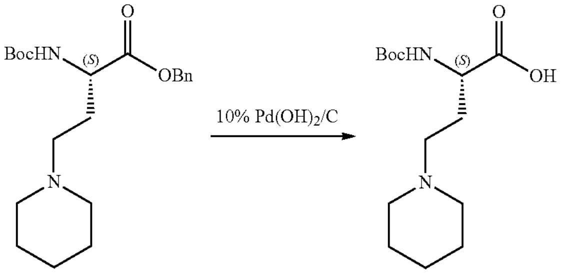

1-67-2

1-67-3

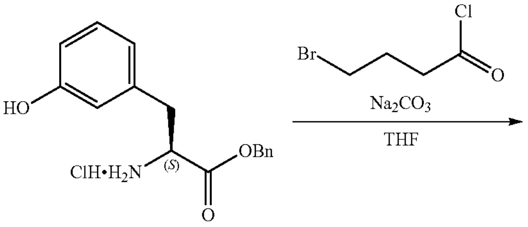

1-59-3

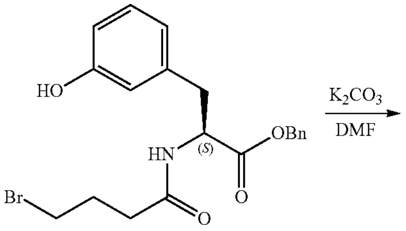

1-67-4

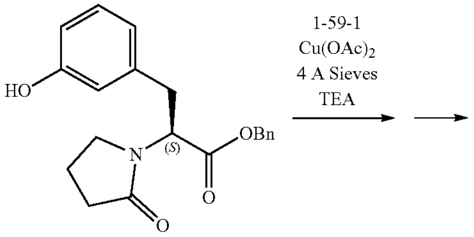

1-67-5

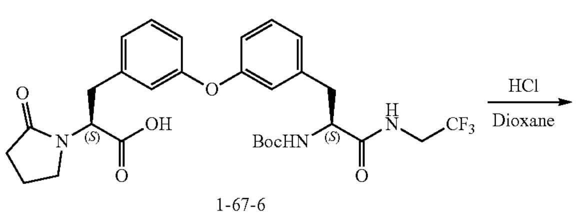

1-67-6

-continued

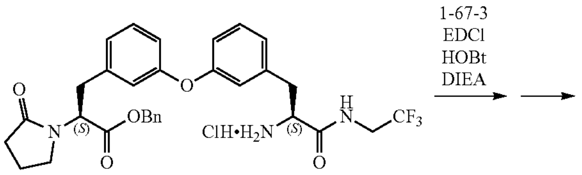

1-67-7

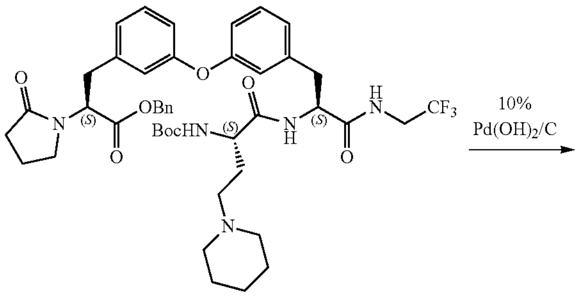

1-67-8

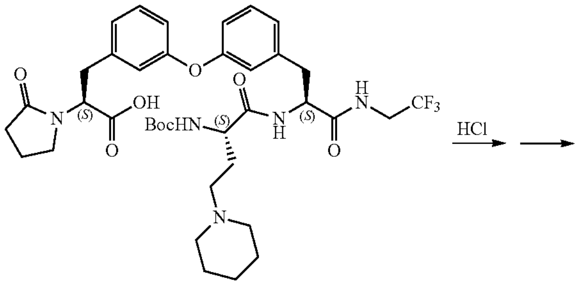

1-67-9

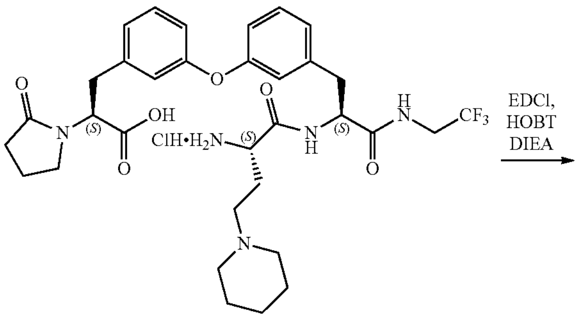

1-67-10

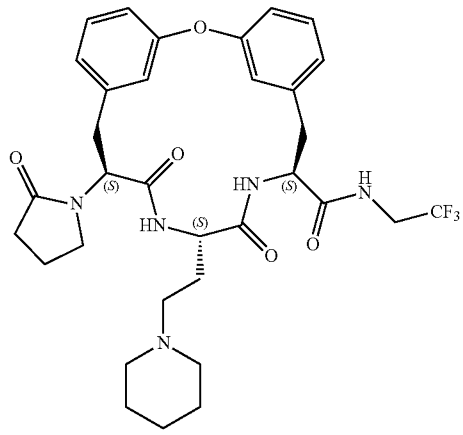

1-67

To a solution of oxalyl chloride (361 mg, 2.84 mmol) in dichloromethane (5 mL) was added a solution of dimethylsulfoxide (404 mg, 5.17 mmol) in dichloromethane (5 mL) at −60° C. and the mixture was stirred for 10 minutes at −60° C. (S)-Benzyl-2-((tert-butoxycarbonly)amino)-4-hydroxybutanoate (800 mg, 2.59 mmol) in dichloromethane (5 mL) was added into the mixture and the mixture was stirred at −60° C. for 30 minutes. Triethylamine (1.05 g, 10.3 mmol) was added into the mixture and the resulting mixture was allowed to warm up to 20° C. and stirred for 30 minutes. The mixture was concentrated under vacuum and the crude product was purified by column chromatography ($SiO_2$, petroleum ether:ethyl acetate=10:1 to 8:1) to afford compound 1-67-1 (600 mg, 75.5% yield) as a colorless oil.

To a solution of piperidine (140 mg, 1.64 mmol) in dichloromethane (4 mL) was added 1-67-1 (420 mg, 1.37 mmol) at 25° C. and the mixture was stirred at 25° C. for 30 minutes. Sodium cyanoborohydride (129 mg, 2.05 mmol) was added and the mixture was stirred at 25° C. for 30 minutes. The mixture was poured into water (20 mL) and then extracted with ethyl acetate (20 mL*3). The combined organic phase was washed with brine (20 mL) and dried over sodium sulfate. After filtration and concentration, the crude product was purified by prep-HPLC (column: Gemini 150*25 5 u; mobile phase: [water (0.05% ammonia hydroxide v/v)-ACN]; B %: 57%-87%, 12 min) to afford compound 1-67-2 (200 mg, 38.9% yield) as colorless oil.

To a solution of compound 1-67-2 (170 mg, 451 μmol) in tetrahydrofuran (4 mL) was added 10% palladium hydroxide (63 mg, 45 μmol). The mixture was degassed and purged with hydrogen 3 times. The mixture was stirred at 20° C. for 1 hour under a hydrogen balloon. The mixture was filtered and the filtrate was concentrated to afford compound 1-67-3 (135 mg, crude) as a white solid.

To a solution of compound 1-59-3 (1.5 g, 4.9 mmol) in tetrahydrofuran (20 mL) and water (10 mL) was added sodium carbonate (2.6 g, 24 mmol), then 4-bromobutanoyl chloride (1.35 g, 7.31 mmol) was added dropwise at 0° C. The mixture was stirred at 0° C. for 1.5 hours. The mixture was poured into water (20 mL) and then extracted with ethyl acetate (20 mL*3). The combined organic phase was washed with saturated sodium bicarbonate (20 mL*3), followed by brine (20 mL), and then dried over anhydrous sodium sulfate. After filtration and concentration, the crude product was purified by silica gel column chromatography (petroleum ether:ethyl acetate=3:1 to 3:1) to afford compound 1-67-4 (1.1 g, 50% yield) as a yellow oil.

To a solution of compound 1-67-4 (1.0 g, 2.5 mmol) in dimethyl formamide (10 mL) was added potassium carbonate (1.0 g, 7.5 mmol). The mixture was stirred at 25° C. for 2 hours. The mixture was poured into water (10 mL) and then 1 N hydrochloric acid (5 mL) was added. The mixture was extracted with ethyl acetate (20 mL*3). The combined organic phase was washed with brine (20 mL) and dried over anhdrous sodium sulfate. After filtration and concentration, the crude product was purified by silica gel column chromatography (petroleum ether:ethyl acetate=2:1 to 2:1) to afford compound 1-67-5 (165 mg, 16.1% yield) as light yellow oil.

To a solution of compound 1-67-5 (310 mg, 785 μmol) in dichloromethane (5 mL) was added compound 1-59-1 (674 mg, 1.73 mmol), copper acetate (214 mg, 1.18 mmol), triethylamine (795 mg, 7.86 mmol), and 4A molecular sieves (400 mg). The mixture was stirred at 25° C. in the air for 3 hours. The mixture was filtered and then the filtrat was concentrated. The crude product was purified by silica gel column chromatography (petroleum ether:ethyl acetate=3:1 to 3:1) to afford compound 1-67-6 (510 mg, 86.3% yield) as a yellow solid.

To a solution of compound 1-67-6 (320 mg, 468 μmol) in dioxane (5 mL) was added a 4M solution of hydrochloric acid in dioxane (10 mL, 40 mmol). The mixture was stirred at 25° C. for 1.5 hours. The mixture was concentrated to afford compound 1-67-7 (305 mg, 86.5% yield) as a yellow solid.

To a solution of compound 1-67-3 (95 mg, 330 μmol) in dimethyl formamide (3 mL) was added HOBT (58 mg, 430 μmol), EDCI (83 mg, 430 μmol), and diisopropylethylamine (107 mg, 829 μmol) at 0° C. under nitrogen. To this mixture was added 1-67-7 (300 mg, 484 μmol) and the mixture was stirred at 20° C. for 16 hours. The mixture was poured into water (20 mL) and then 1 N hydrochloric acid (4 mL) was added. The mixture was extracted with ethyl acetate (20 mL*3). The combined organic phase was washed with saturated sodium carbonate (20 mL*3) followed by brine (20 mL), and then dried over anhdrous sodium sulfate. After filtration and concentration, the crude product was purified by prep-HPLC (column: Phenomenex Synergi C18 150*25*10 um; mobile phase: [water(0.1% TFA)-ACN]; B %: 35%-65%, 13 min) to afford compound 1-67-8 (120 mg, 37.6% yield) as a yellow oil.

A solution of compound 1-67-8 in tetrahydrofuran (4 mL) was added 10% $Pd(OH)_2/C$ (40 mg). The suspension was degassed under vacuum and purged with hydrogen 3 times. The resulting mixture was stirred at 20° C. for 1 hour under a hydrogen balloon. The mixture was filtered and the filtrated liquid was concentrated to afford compound 1-67-9 (95 mg, crude) as a white solid.

To a mixture of compound 1-67-9 (130 mg, 0.171 mmol) in dioxane (5 mL) was added a 4M solution of HCl in dioxane (1.0 mL, 4.0 mmol). The mixture was stirred at 20° C. for 40 minutes. The mixture was concentrated under vacuum to afford compound 1-67-10 (115 mg, crude, HCl) as a light yellow solid.

To a solution of compound 1-67-10 (110 mg, 158 μmol) in dimethyl formamide (10 mL) was added diisopropylethylamine (51 mg, 390 μmol), HOBt (30 mg, 220 μmol), and EDCI (42 mg, 220 μmol) at 0° C. under nitrogen and the result mixture was stirred at 20° C. for 16 hours. The mixture was poured into water (10 mL) and then extracted with ethyl acetate (20 mL*3). The combined organic phase was washed by brine (20 mL) and dried over anhdrous sodium sulfate. After filtration and concentration, the crude product was purified by prep-HPLC (column: Phenomenex Gemini 150*25 mm*10 um; mobile phase: [water (0.05% ammonia hydroxide v/v)-ACN]; B %: 35%-65%, 12 min) to afford 1-67 (25.8 mg, 24.2% yield) as a white solid. LCMS for 1-67: RT=2.615 min, purity: 95.088%, m/z 644.3$[M+H]^+$.

The following compounds were made using a similar synthetic route as described for compound 1-67:

Compound 1-63; LCMS: RT=3.014 min, m/z 623.2 $[M+H]^+$

Compound 1-66; LCMS: RT=2.649 min, m/z 680.2$[M+H]^+$

Example 16—Synthesis of tert-Butyl-((5S,8S,11S)-5-((4-methylbenzyl)carbamoyl)-7,10-dioxo-8-phenethyl-2-oxa-6,9-diaza-1,3(1,3)-dibenzenacyclododecaphane-11-yl)carbamate (1-68)

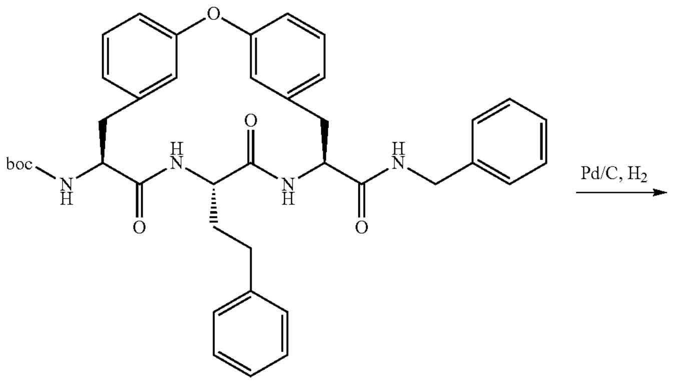

1-50

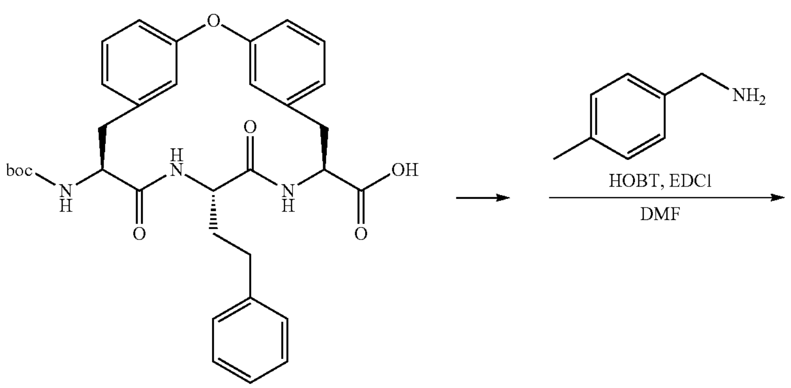

1-68-1

-continued

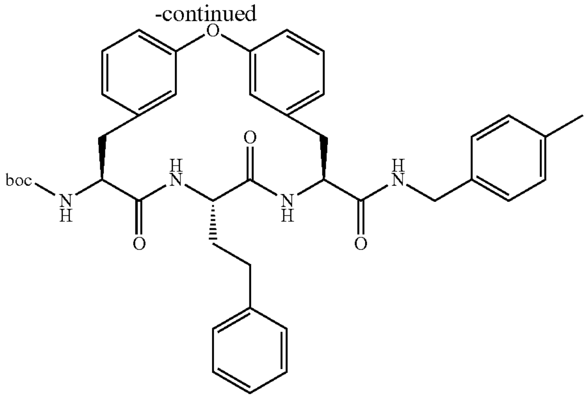

1-68

To a solution of 1-50 (250 mg, 369 μmol) in dichloromethane (10 mL) and isopropanol (20 mL) was added 5% palladium on carbon (100 mg) under nitrogen. The suspension was degassed under vacuum and purged with hydrogen several times. The mixture was stirred under hydrogen (15 psi) at 25° C. for 4 hours then filtered and the filtrate was concentrated under reduced pressure to afford compound 1-68-1 (150 mg, 49.8% yield) as a brown solid.

To a mixture of compound 1-68-1 (500 mg, 851 μmol), diisopropylethylamine (121 mg, 936 μmol), and 1-hydroxy benzotriazole (126 mg, 936 μmol) in tetrahydrofuran (10 mL) and N,N-dimethylformamide (10 mL) was added 1-ethyl-3-(3-dimethylaminopropyl) carbodiimide hydrochloride (179 mg, 935 μmol) at −10° C. The reaction mixture was stirred for 0.5 hour at −10° C. then p-tolylmethanamine (113 mg, 936 μmol) was added and the reaction mixture was stirred for 11.5 hours at 25° C. Water (20 mL) was added to the reaction mixture resulting in a precipitate formation. The formed solid was collected by filtration and purified by prep-HPLC (TFA condition, column: Agela ASB 150 mm*25 mm*5 um, mobile phase: [water (0.1% TFA)-ACN]; B %: 60%-85%, 11 min) to afford 1-68 (23 mg, 3.7% yield) as a white solid. LCMS of 1-68: RT=1.043 min, m/z=691.3 [M+H]$^+$.

Example 17—Synthesis of (5S,8S,11S)-11-Amino-N-(4-methylbenzyl)-7,10-dioxo-8-phenethyl-2-oxa-6,9-diaza-1,3(1,3)-dibenzenacyclododecaphane-5-carboxamide (1-69)

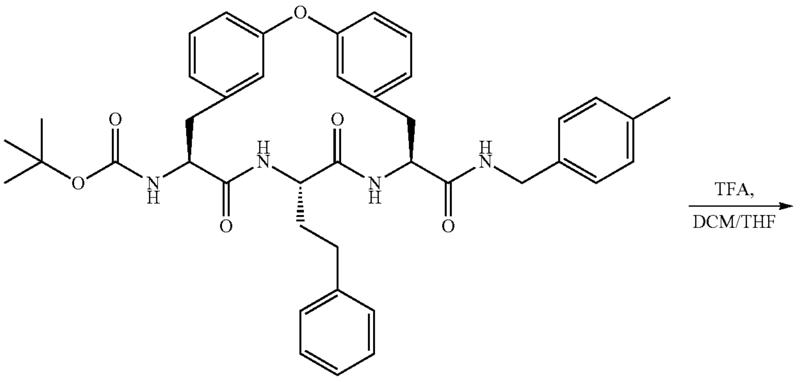

1-68

-continued

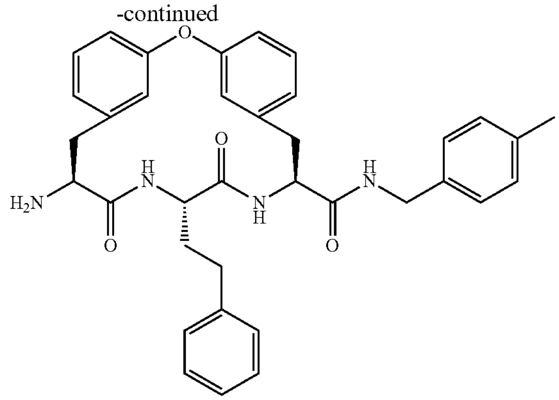

1-69

To a solution of 1-68 (150 mg, 217 μmol) in dichloromethane (10 mL) and tetrahydrofuran (10 mL) was added trifluoroacetic acid (7.7 g, 68 mmol, 5 mL) and the reaction mixture was stirred for 12 hours at 25° C. then concentrated under reduced pressure. The residue was purified by prep-HPLC (TFA condition; column: Phenomenex Synergi C18 150 mm*25 mm*10 um, mobile phase: [water (0.1% TFA)-ACN]; B %: 25%-55%, 12 min) to afford the product as a TFA salt. The product was redissolved in water (5 mL) and pH of the solution was adjusted to pH=9 with aqueous sodium bicarbonate causing a solid to precipitate from the solution. The formed solid was collected by filtration and dried to afford 1-69 (32 mg, 25% yield) as a white solid. LCMS of 1-69: RT=0.846 min, purity: 100%, m/z=591.2 $[M+H]^+$.

Example 18—Synthesis of tert-Butyl-((5S,8S,11S)-7,10-dioxo-8-phenethyl-5-((2,2,2-trifluoroethyl)carbamoyl)-2-oxa-6,9-diaza-1,3(1,3)-dibenzenacyclododecaphane-11-yl)carbamate (1-70)

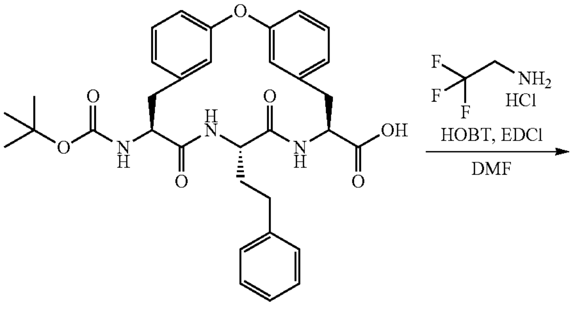

1-68-1

-continued

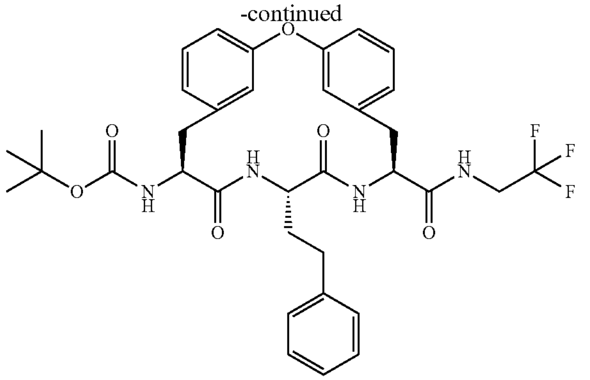

1-70

To a solution of compound 1-68-1 (800 mg, 1.36 mmol) and 1-hydroxybenzotriazole (202 mg, 1.50 mmol) in a mixture of tetrahydrofuran (15 mL) and N,N-dimethylformamide (15 mL) was added EDCI (287 mg, 1.50 mmol) and diisopropylethylamine (352 mg, 2.72 mmol) at −10° C. The reaction mixture was stirred for 0.5 hour at −10° C. then 2,2,2-trifluoroethan-1-amine hydrochloride (203 mg, 1.50 mmol) was added and the reaction mixture was stirred for 11.5 hours at 25° C. Water (30 mL) was added to the reaction mixture causing a solid to precipitate out of solution. The solid was collected by filtration and purified by prep-HPLC (TFA condition; column: Agela ASB 150 mm*25 mm*5 um, mobile phase: [water (0.1% TFA)-ACN]; B %: 55%-85%, 11 min). The isolated material was further purified by recrystallization from a mixture of isopropyl ether, methanol, and dichloromethane (V:V:V=3:1:1, 5 mL*3) to afford 1-70 (19 mg, 6.3% yield) as a white solid. LCMS of 1-70: RT=2.379 min, m/z=669.2 $[M+H]^+$.

Example 19—Synthesis of (5S,8S,11S)-11-Amino-7,10-dioxo-8-phenethyl-N-(2,2,2-trifluoroethyl)-2-oxa-6,9-diaza-1,3(1,3)-dibenzenacyclododecaphane-5-carboxamide (1-71)

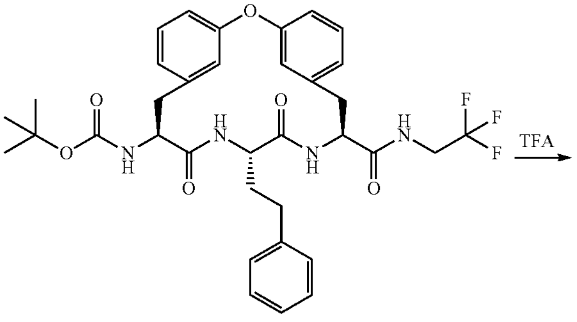

1-70

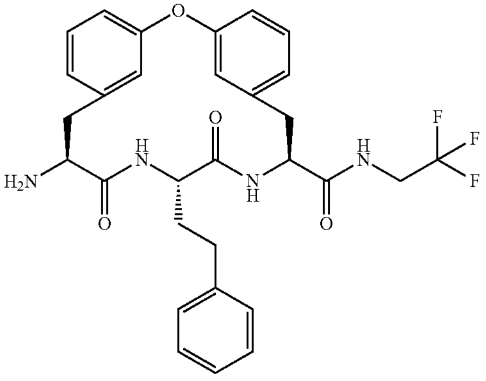

1-71

To a solution of 1-70 (300 mg, 449 μmol) in dichloromethane (10 mL) and N,N-dimethylformamide (10 mL) was added trifluoroacetic acid (5.0 mL, 68 mmol) at 25° C. and then the reaction mixture was stirred for 12 hours at 25° C. The reaction mixture was concentrated under reduced pressure at 30° C. and the residue was purified by prep-HPLC (TFA condition; column: Agela ASB 150 mm*25 mm*5 um, mobile phase: [water (0.1% TFA)-ACN]; B %: 25%-55%, 11 min). The isolated material was redissolved in water (5 mL) and the pH of the solution was adjusted to pH=9 with aqueous sodium bicarbonate solution causing a solid to precipitate from solution. The solid was collected by filtration and triturated with isopropyl ether (10 mL*2) to afford 1-71 (38 mg, 15% yield) as a white solid. LCMS of 1-71: RT=1.906 min, m/z=569.3 [M+H]+

Example 20—Synthesis of (5S,8S,11S)-N-(Cyclopropylmethyl)-7,10-dioxo-11-(2-oxopyrrolidin-1-yl)-8-(2-(piperidin-1-yl)ethyl)-2-oxa-6,9-diaza-1,3(1,3)-dibenzenacyclododecaphane-5-carboxamide (1-72)

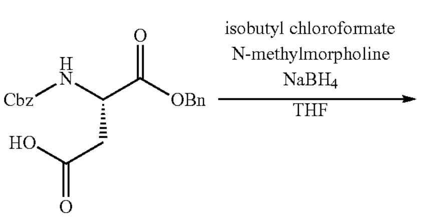

-continued

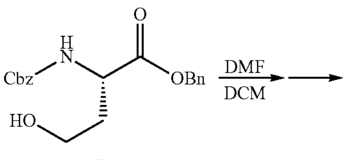

1-72-1

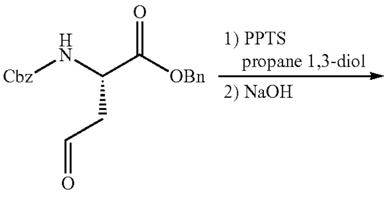

1-72-2

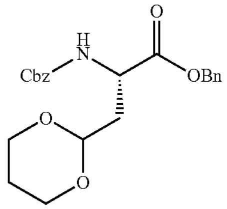

1-72-3

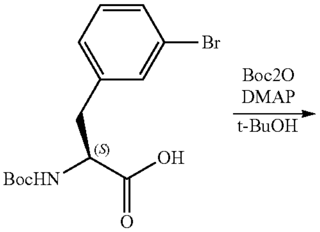

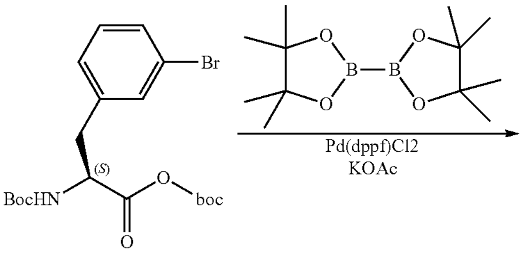

1-72-4

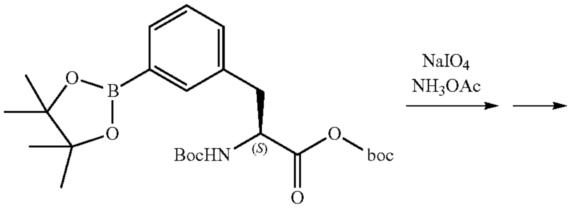

1-72-5

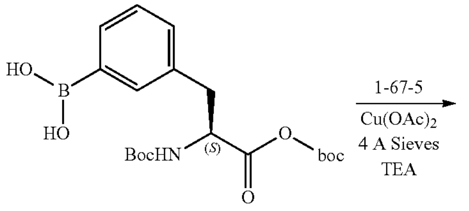

1-72-6

-continued
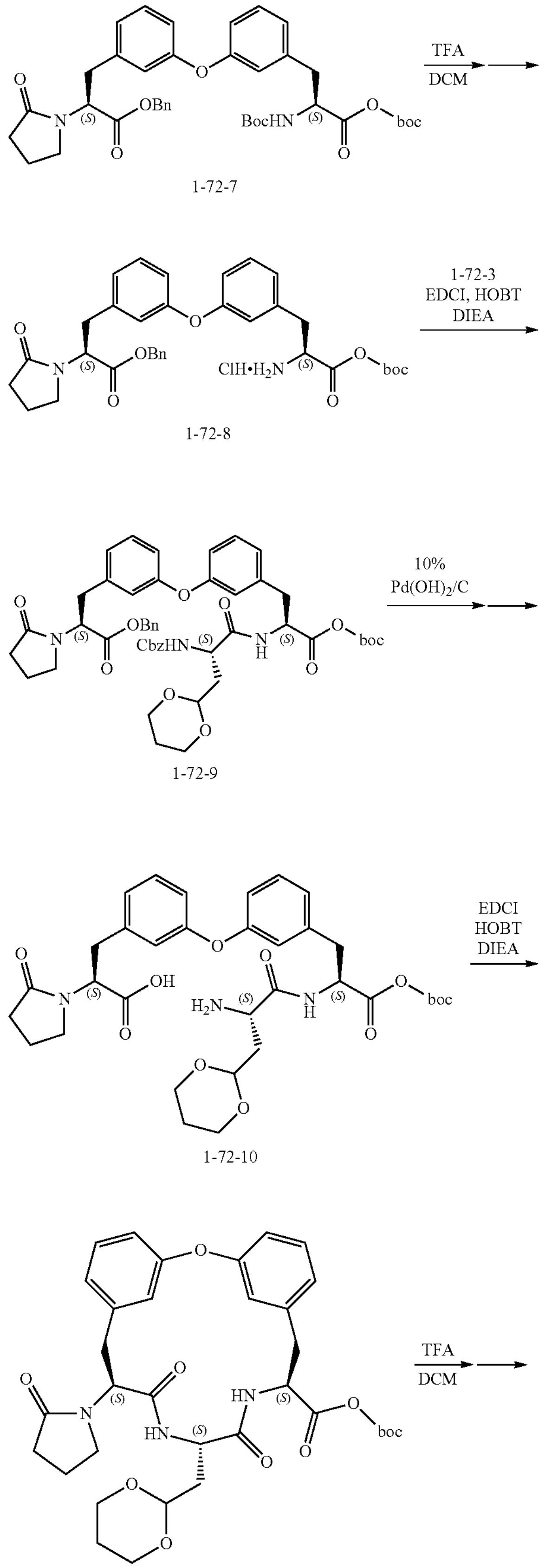
1-72-7
1-72-8
1-72-9
1-72-10
1-72-11
-continued
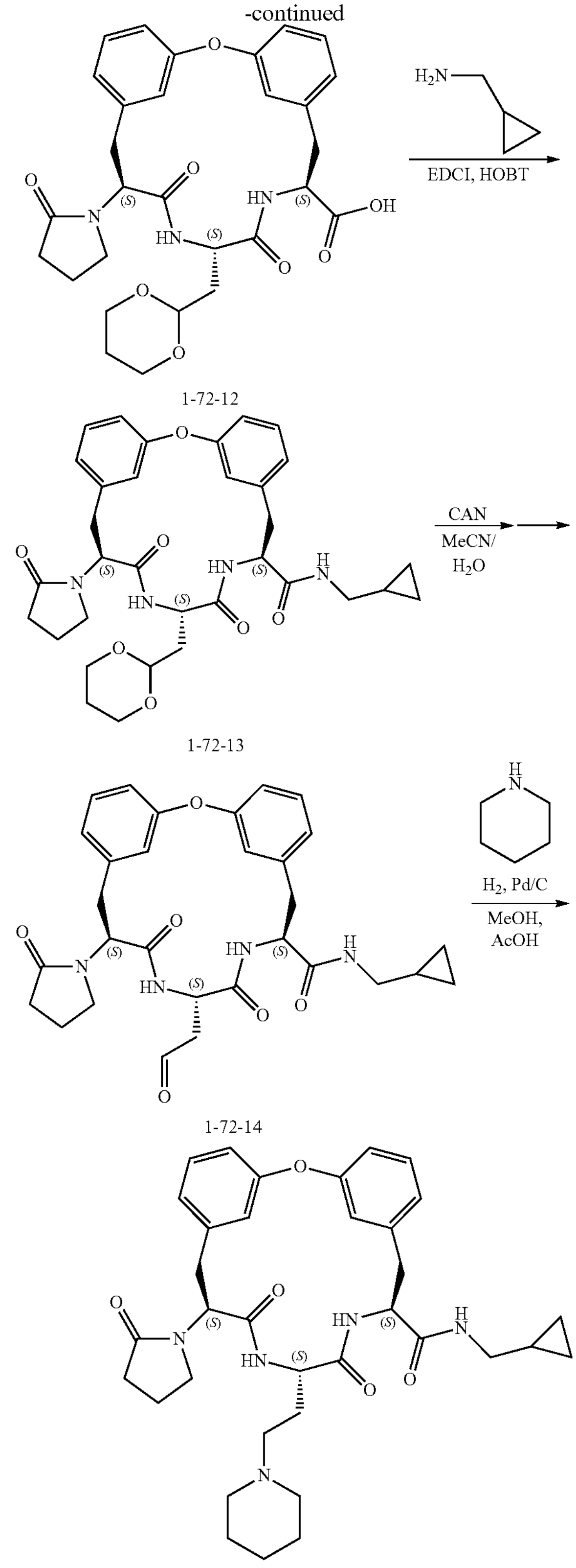
1-72-12
1-72-13
1-72-14
1-72
To a mixture of (S)-4-(benzyloxy)-3-(((benzyloxy)carbonyl)amino)-4-oxobutanoic acid (58 g, 130 mmol) and N-methylmorpholine (14.53 mL, 132.1 mmol) in tetrahydrofuran (500 mL) was added isobutyl carbonochloridate (17.34 mL, 132.1 mmol) dropwise at −20° C. under nitrogen atmosphere. The mixture was stirred at −20° C. for 2 hours then sodium borohydride (7.50 g, 198 mmol) in water (80 mL) was added dropwise. The mixture was stirred at −20° C. for 1 hour, then 1N hydrochloric acid (800 mL) was added. The aqueous phase was extracted with ethyl acetate. The combined organic phase was washed with brine, dried with anhydrous sodium sulfate, filtered, and concentrated under reduced pressure. The residue was purified by flash silica gel chromatography to afford 1-72-1 (46.5 g, 97.3 mmol, 73.7% yield) as a light yellow oil.

To a solution of 1-72-1 (23.5 g, 49.2 mmol) in dichloromethane (500 mL) was added Dess-Martin reagent (30.49 mL, 98.50 mmol) at 0° C. under a nitrogen atmosphere. The mixture was stirred at 20° C. for 3 hours. The mixture was concentrated under reduced pressure and the residue was purified by flash silica gel column chromatography to afford 1-72-2 (11 g, 48% yield) as a light yellow oil.

To a mixture of 1-72-2 (2.2 g, 4.8 mmol) and propane-1,3-diol (9.0 mL, 120 mmol) was added PPTS (324 mg, 1.29 mmol) and 4A MS (4.4 g) in one portion at 20° C. under a nitrogen atmosphere. The mixture was stirred at 80° C. for 12 hours then cooled to 20° C. and poured into water (100 mL). The aqueous phase was extracted with ethyl acetate and the combined organic phase was washed with brine then dried with anhydrous sodium sulfate, filtered, and concentrated in vacuum to give (11 g, crude) of a light yellow oil, which was used for the next step directly without further purification.

To a mixture of the above oil (5.5 g, 14 mmol) in tetrahydrofuran (50 mL) and water (50 mL) was added sodium hydroxide (3.86 g, 96.4 mmol) in one portion at 0° C. under a nitrogen atmosphere. The mixture was stirred at 0° C. for 30 min. The mixture was poured into ice-water (50 mL) and the aqueous phase was extracted with ethyl acetate. The combined organic phase was discarded, then the pH value of the aqueous phase was adjusted to 2 by the addition of aqueous 1 N hydrochloric acid. The mixture was extracted with ethyl acetate and the combined organic phase was washed with brine, dried over anhydrous sodium sulfate, filtered, and concentrated under reduced pressure to give 1-72-3 (4.6 g, 52% yield) as a light yellow oil.

To a solution of (S)-3-(3-bromophenyl)-2-((tert-butoxycarbonyl)amino)propanoic acid (20 g, 58 mmol) in tert-butyl alcohol (140 mL, 1.46 mol) was added dimethylaminopyridine (710 mg, 5.81 mmol) and di-tert-butyl dicarbonate (17.35 mL, 75.54 mmol). The mixture was stirred at 20° C. for 18 hours under a nitrogen atmosphere. The mixture was diluted with ethyl acetate and then washed with brine. The organic layer was dried over anhydrous sodium sulfate, filtered, and concentrated under reduced pressure. The residue was purified by flash silica gel column chromatography to afford 1-72-4 (14.9 g, 64.1% yield) as colorless gum.

To a solution of 1-72-4 (14.9 g, 37.2 mmol), 4,4,5,5-tetramethyl-2-(4,4,5,5-tetramethyl-1,3,2-dioxaborolan-2-yl)-1,3,2-dioxaborolane (12.29 g, 48.39 mmol) and potassium acetate (9.13 g, 93.0 mmol) in dry dioxane (200 mL) was added Pd(dppf)$Cl_2$ (1.09 g, 1.49 mmol) under a nitrogen atmosphere. The mixture was degassed and then stirred at 80° C. for 7 hours under a nitrogen atmosphere. The mixture was concentrated under reduced pressure and the residue was diluted with ethyl acetate (500 mL). The mixture was filtered and the solid was washed with ethyl acetate. The combined organic layers were combined and concentrated under reduced pressure to afford 1-72-5 (26.6 g, crude) as black gum, which was used into the next step without further purification.

To a solution of 1-72-5 (26.6 g, 37.2 mmol) and ammonium acetate (14.35 g, 186.1 mmol) in a mixture of acetone (300 mL) and water (150 mL) was added sodium periodate (8.25 mL, 149 mmol) over a period of 1 hour. The mixture was stirred at 25° C. for 18 hours then another batch of ammonium acetate (14.35 g, 186.1 mmol) and sodium periodate (8.25 mL, 149 mmol) was added. The reaction mixture was stirred at 25° C. for another 24 hours. The mixture was diluted with ethyl acetate and then filtered. The filtrate was extracted with ethyl acetate. The combined organic layers were washed with saturated sodium sulfite solution followed by brine, then dried over anhydrous sodium sulfate, filtered, and concentrated under reduced pressure. The residue was purified by flash silica gel column chromatography to afford 1-72-6 (12.73 g, 93.2% yield) as a red solid.

To a solution of 1-72-6 (8.07 g, 22.1 mmol), 1-67-5 (5.0 g, 14 mmol), 4A molecular sieve (5 g) and triethylamine (10.2 mL, 73.7 mmol) in dichloromethane (100 mL) was added copper acetate (4.01 g, 22.1 mmol). The mixture was stirred at 25° C. for 18 hours under an atmosphere of oxygen (15 psi). The mixture was filtered through a celite pad and the solid was washed with ethyl acetate. The combined filtrates were concentrated under reduced pressure. The residue was purified by flash silica gel column chromatography to provide 1-72-7 (5.68 g, 58.5% yield) as a light yellow gum.

To a solution of 1-72-7 (5.68 g, 8.62 mmol) in dichloromethane (120 mL) was added trifluoroacetic acid (24 mL, 320 mmol) at 0° C. The mixture was stirred at 0° C. for 4 hours then poured into a saturated aqueous sodium bicarbonate solution. The organic phase was separated and the aqueous layer was extracted with ethyl acetate. The combined organic layers were dried over anhydrous sodium sulfate, filtered, and concentrated under reduced pressure to provide compound 1-72-8 (4.18 g, 79.3% yield) as a yellow gum. The isolated material was used without further purification.

To a solution of 1-72-3 (2.56 g, 8.28 mmol) and N,N-diisopropylethylamine (4.77 mL, 27.4 mmol) in N,N-dimethylformamide (45 mL) was added HOBt (1.20 g, 8.89 mmol) at 0° C. The mixture was stirred at 0° C. for 10 minutes then EDCI (2.62 g, 13.7 mmol) was added followed by 1-72-8 (4.18 g, 6.84 mmol) as a solution in N,N-dimethylformamide (15 mL). The reaction mixture was stirred at 0° C. for 20 minutes and then stirred at 25° C. for another 1.5 hours under a nitrogen atmosphere. The mixture was poured into ice water and then extracted with ethyl acetate. The combined organic layers were washed with brine, dried over anhydrous sodium sulfate, filtered, and concentrated under reduced pressure. The residue was purified by flash silica gel column chromatography to provide 1-72-9 (4.08 g, 68.0% yield) as a colorless gum.

To a solution of 1-72-9 (4.08 g, 4.80 mmol) in tetrahydrofuran (60 mL) was added Pd/C (0.4 g, 10% purity) and $Pd(OH)_2$/C (0.4 g, 10% purity) under a nitrogen atmosphere. The mixture was degassed under vacuum and purged with hydrogen several times. The mixture was stirred under a hydrogen atmosphere (15 psi) at 25° C. for 14 hours. The mixture was filtered, the solid was washed with tetrahydrofuran and ethyl acetate. The combined filtrate was concentrated in vacuum to provide 1-72-10 (3.1 g, crude) as a white solid, which was used without further purification.

To a solution of 1-72-10 (1 g, 1.60 mmol) and N,N-diisopropylethylamine (1.39 mL, 7.99 mmol) in N,N-dimethylformamide (80 mL) was added HOBt (324 mg, 2.40 mmol) and EDCI (613 mg, 3.20 mmol) at 0° C. The mixture was stirred at 25° C. for 15 hours. The mixture was cooled to 0° C. and an additional batch of N,N-diisopropylethylamine (516 mg, 4.00 mmol) and EDCI (613 mg, 3.20 mmol) was added. The reaction mixture was stirred at 25° C. for another 15 hours. The mixture was poured into ice water and then extracted with ethyl acetate. The combined organic layers were washed with brine, dried over anhydrous sodium sulfate, filtered, and concentrated under reduced pressure. The residue was purified by flash silica gel column chromatography to provide 1-72-11 (410 mg, 35.3% yield) as a white solid.

To a solution of 1-72-11 (410 mg, 0.564 mmol) in dichloromethane (5 mL) was added trifluoroacetic acid (1.56 mL, 21.0 mmol). The mixture was stirred at 25° C. for 5.5 hours. The mixture was poured into water and the pH was adjusted to approximately pH=4-5 by addition of a saturated aqueous sodium bicarbonate solution. The mixture was extracted with ethyl acetate. The combined organic layers were washed with brine, dried over anhydrous sodium sulfate, filtered, and concentrated under reduced pressure to provide 1-72-12 (440 mg, crude) as a white solid, which was used without further purification.

To a solution of 1-72-12 (240 mg, 0.430 mmol) in pyridine (2.5 mL) was added HOBt (59 mg, 0.430 mmol, 1 eq) at 0° C. The mixture was stirred at 0° C. for 10 minutes and cyclopropylmethanamine (62 mg, 0.87 mmol) and EDCI (209 mg, 1.09 mmol) were added to this mixture at 0° C. The reaction mixture was stirred at 0° C. for 20 minutes and then stirred at 25° C. for 16 hours under a nitrogen atmosphere. To this mixture was added an additional batch of EDCI (209 mg, 1.09 mmol) and the reaction mixture was stirred at 25° C. for another 18 hours. The reaction mixture was poured into ice water, and the pH was adjusted to approximately pH=6-7 with a 1 N hydrochloric acid solution. The mixture was extracted with ethyl acetate. The combined organic layers were washed with 1 N hydrochloric acid solution followed by a saturated aqueous sodium bicarbonate solution and brine, then dried over anhydrous sodium sulfate, filtered, and concentrated under reduced pressure. The residue was purified by flash silica gel column chromatography to provide 1-72-13 (179 mg, 65.0% yield) as a light yellow solid.

To a solution of 1-72-13 (194 mg, 0.320 mmol) in acetonitrile (2 mL) was added CAN (440 mg, 0.80 mmol) in water (2 mL) at 25° C. The mixture was heated at 70° C. for 2.5 hours. The mixture was diluted with a saturated aqueous sodium bicarbonate solution and then extracted with ethyl acetate. The combined organic layers were washed with brine, dried over anhydrous sodium sulfate, and concentrated under reduced pressure to give 1-72-14 (140 mg, crude) as a light yellow solid. The material was used without further purification.

To a solution of 1-72-14 (140 mg, 0.256 mmol) and acetic acid (0.029 mL, 0.51 mmol) in methanol (5 mL) was added piperidine (0.13 mL, 1.3 mmol) and Pd/C (0.02 g, 10% purity) under a nitrogen atmosphere. The mixture was degassed and purged with hydrogen several times. The reaction mixture was stirred at 25° C. for 14 hours under an atmosphere of hydrogen (15 psi). The mixture was filtered and Pd/C (0.02 g, 10% purity) was added into the filtrate under a nitrogen atmosphere. The mixture was degassed and purged with hydrogen several times. The reaction mixture was stirred at 25° C. for another 2 hours under a hydrogen atmosphere (15 psi). The mixture was filtered through a celite pad and then the filter pad was washed with methanol. The combined filtrate was concentrated in vacuum and the residue was purified by preparative reverse phase HPLC using an eluent of water/acetonitrile with 0.1 trifluoroacetic acid additive. The fraction was adjusted to pH=7 with a saturated aqueous sodium bicarbonate solution. The mixture was concentrated under reduced pressure to remove volatile organics and then extracted with dichloromethane. The combined organic layers were washed with brine, dried over anhydrous sodium sulfate, filtrated, and concentrated under reduced pressure to provide 1-72 (22.5 mg, 13.7% yield) as a white solid. LCMS of 1-72: RT=2.277 min, m/z=616.3 $[M+H]^+$.

The following compounds were made using a similar synthetic route as described for compound 1-72:

Compound 1-73; LCMS: RT=2.380 min, m/z=630.3 $[M+H]^+$

Compound 1-75; LCMS: RT=2.153 min, m/z=656.3 $[M+H]^+$

Compound 1-76; LCMS: RT=2.249 min, m/z=618.3 $[M+H]^+$

Compound 1-77; LCMS: RT=2.297 min, m/z=662.2 $[M+H]^+$

Example 21—Synthesis of (5S,8S,11S)-N-((1-Methyl-1H-pyrazol-4-yl)methyl)-11-(methylsulfonamido)-7,10-dioxo-8-(2-(piperidin-1-yl)ethyl)-2-oxa-6,9-diaza-1,3(1,3)-dibenzenacyclododecaphane-5-carboxamide (1-74)

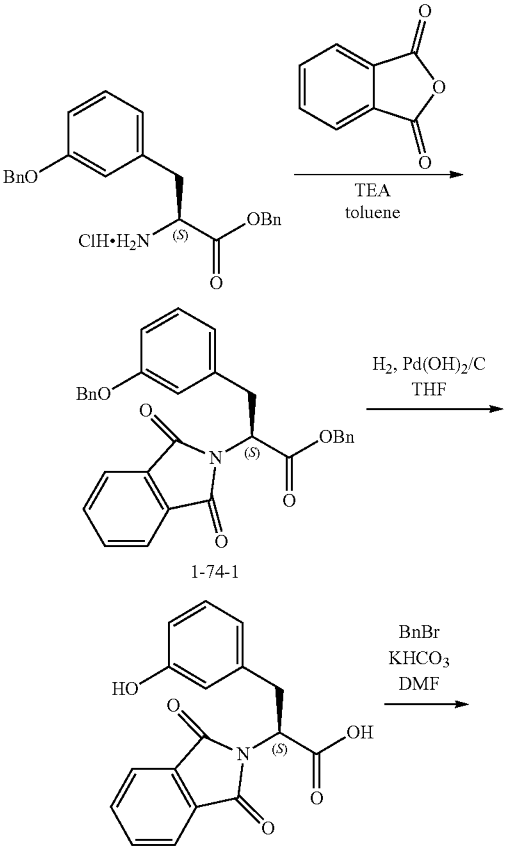

1-74-1

1-74-2

-continued
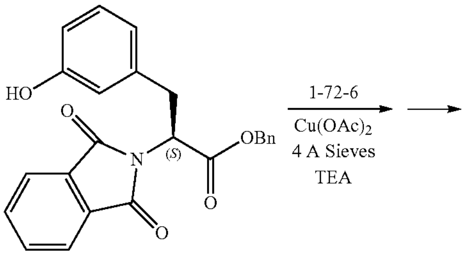
1-74-3
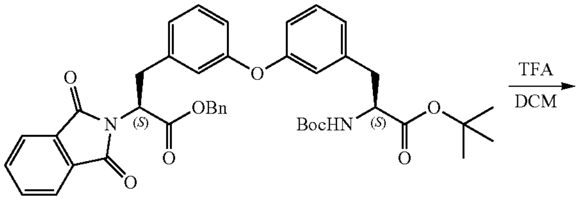
1-74-4
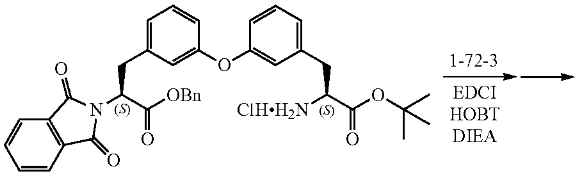
1-74-5
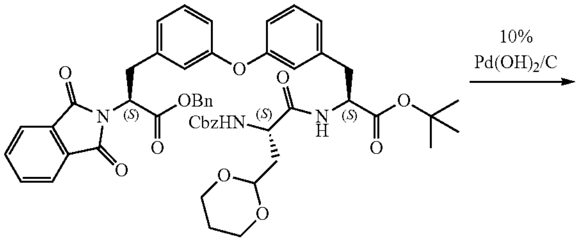
1-74-6
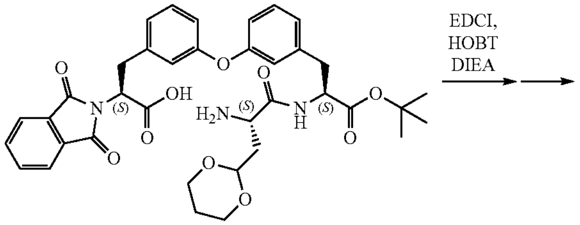
1-74-7
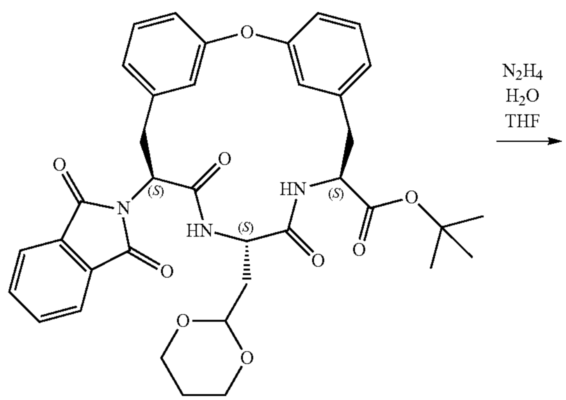
1-74-8
-continued
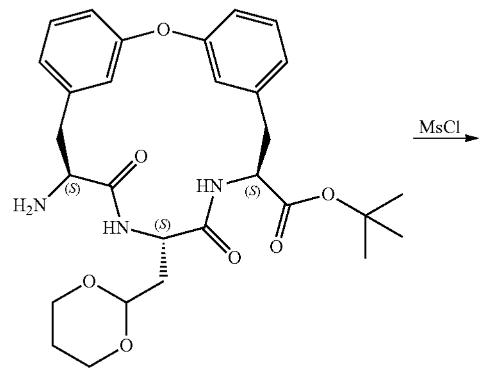
1-74-9
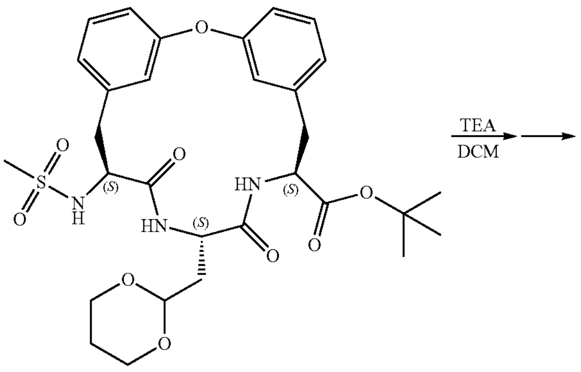
1-74-10
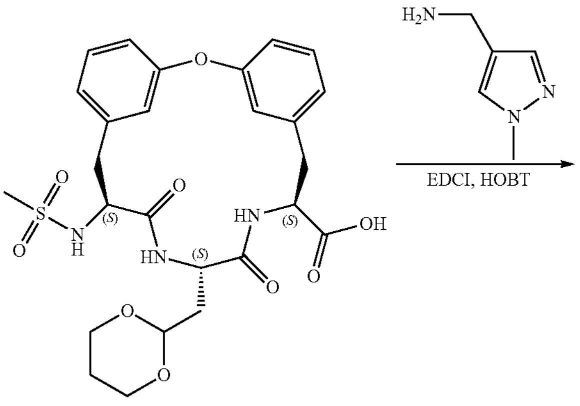
1-74-11
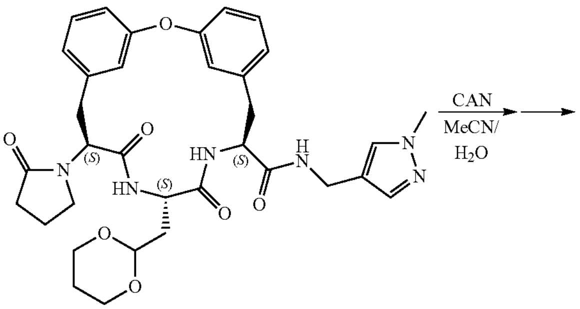
1-74-12

-continued

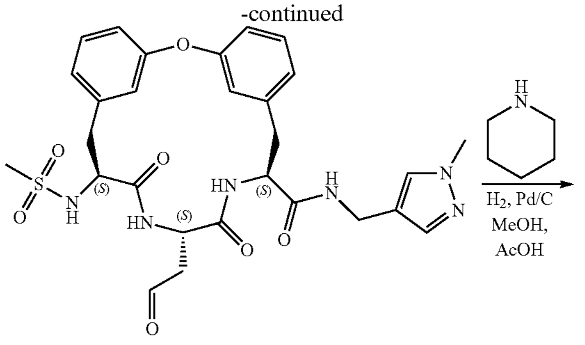

1-74-13

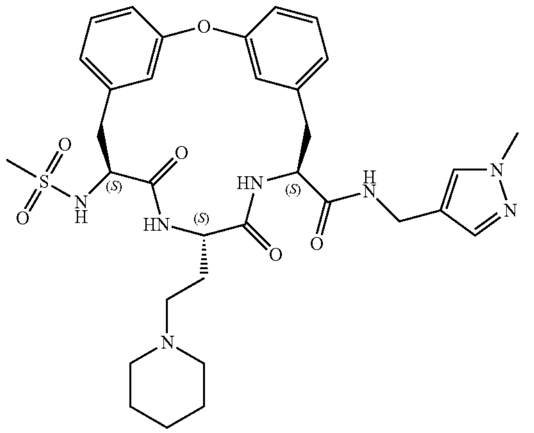

1-74

To a solution of benzyl (S)-2-amino-3-(3-(benzyloxy) phenyl)propanoate hydrochloride (3.8 g, 9.55 mmol, HCl salt) and triethylamine (24 mL, 29 mmol) in toluene (40 mL) was added isobenzofuran-1,3-dione (1.42 g, 9.62 mmol). The mixture was stirred at 20° C. for 1 hour, then heated to 100° C. and stirred for 12 hours. The reaction mixture was poured into ethyl acetate, washed with 1N hydrochloric acid followed by brine, dried over anhydrous sodium sulfate, filtered, and concentrated under reduced pressure to provide 1-74-1 (5.9 g, crude) as a yellow oil.

A solution of 1-74-1 (5.9 g, 10 mmol) in tetrahydrofuran (50 mL) was purged with nitrogen for 10 minutes, then $Pd(OH)_2/C$ (300 mg, 10% purity on carbon) was added in one portion. The mixture was stirred for 24 hours at 20° C. under a hydrogen atmosphere (15 psi). The mixture was filtered and concentrated under reduced pressure. The residue was dissolved in a mixture of methanol (20 mL) and tetrahydrofuran (20 mL) then purged with nitrogen for 10 minutes. To this was added then $Pd(OH)_2/C$ (300 mg, 10% purity on carbon) and the mixture was stirred for 12 hours at 20° C. under a hydrogen atmosphere (15 psi). The reaction mixture was filtered and the filtrate was concentrated under reduced pressure to afford 1-74-2 (2.6 g, 2.8% yield) as a white solid.

To a solution of 1-74-2 (2.6 g, 8.35 mmol) in N,N-dimethyl formamide (30 mL) potassium bicarbonate (1.00 g, 10.2 mmol) was added portion wise at 0° C. The mixture was stirred at 0° C. for 30 minutes. Benzyl bromide (1.09 mL, 9.19 mmol) was added drop wise to the mixture at 0° C. The mixture was stirred for 2 hours at 20° C. The reaction mixture was poured into water and extracted with ethyl acetate. The combined organic phase was washed with brine, dried over anhydrous sodium sulfate, filtered, and concentrated under reduced pressure. The residue was purified by flash silica gel column chromatography to afford 1-74-3 (3.5 g, 90.8% yield) as a colorless gum.

To a mixture of 1-74-3 (2 g, 4.33 mmol), 1-72-6 (2.37 g, 6.50 mmol), copper acetate (1.18 g, 6.50 mmol), and triethylamine (3.0 mL, 22 mmol) in dichloromethane (25 mL) was added 4A molecular sieves (5 g). The mixture was stirred at 20° C. for 16 hours under an oxygen atmosphere (15 psi). The reaction mixture was concentrated under reduced pressure. The residue was purified by flash silica gel column chromatography to provide 1-74-4 (2.3 g, 73% yield) as a yellow gum.

To a solution of 1-74-4 (2.3 g, 3.2 mmol) in dichloromethane (40 mL) was added trifluoroacetic acid (8.0 mL, 110 mmol, 8 mL) drop wise at 0° C. The mixture was stirred for 4 hours at 0° C. The reaction mixture was slowly added to a saturated aqueous solution of sodium bicarbonate and extracted with ethyl acetate. The combined organic phase was washed with brine, dried over anhydrous sodium sulfate, and concentrated under reduced pressure to provide 1-74-5 (2.0 g, crude) as a yellow gum.

To a solution of 1-72-3 (1.13 g, 3.22 mmol) and diisopropylethylamine (1.68 mL, 9.66 mmol) in N,N-dimethylformamide (13 mL) was added HBTU (1.59 g, 4.19 mmol) wise-portion at 0° C. The mixture was stirred for 10 minutes at 0° C. A solution of 1-74-5 (2.0 g, 3.2 mmol in N,N-dimethylformamide (8 mL) was added drop wise at 0° C. The mixture was stirred for 20 minutes at 20° C. then the reaction mixture was poured into water and extracted with ethyl acetate. The combined organic phase was washed with brine, dried over anhydrous sodium sulfate, filtered, and concentrated under reduced pressure. The residue was purified by flash silica gel column chromatography and then further purified by reverse phase flash column chromatography using a water/acetonitrile gradient with 0.1% trifluoroacetic acid additive to provide 1-74-6 (1.9 g, 65% yield) as a yellow gum.

A solution of 1-74-6 (1.9 g, 2.1 mmol) in tetrahydrofuran (30 mL) was purged with nitrogen for 10 minutes, $Pd(OH)_2/C$ (0.2 g, 10% purity on carbon) and Pd/C (0.2 g, 10% purity on carbon) were added in one-portion. The mixture was degassed with hydrogen three times, then stirred for 5 hours at 20° C. under a hydrogen atmosphere (15 psi). The reaction mixture was filtered and the filter pad washed with methanol to afford compound 1-74-7 (1.2 g, 84% yield).

To a solution of 1-74-7 (500 mg, 0.727 mmol) and diisopropylethylamine (0.50 mL, 2.9 mmol) in N,N-dimethyl formamide (50 mL) was added a mixture of EDCI (500 mg, 2.61 mmol) and HOBt (59 mg, 0.44 mmol) at 0° C. The mixture was stirred for 12 hours at 20° C. The reaction mixture was poured into a mixture of ice-water (50 mL) and hydrochloric acid (1N, 10 mL) and a white solid precipitated from solution. The formed solid was collected by filtration. The collected solid was dried under reduced pressure and the residue was purified by flash silica gel column chromatography to afford 1-74-8 (0.12 g, 25% yield) as a white solid.

To a solution of 1-74-8 (180 mg, 0.269 mmol) in tetrahydrofuran (2 mL) was added hydrazine hydrate (0.026, 0.54 mmol). The mixture was stirred for 1.5 hours at 25° C., then heated to 60° C. and stirred for 12 hours. The reaction mixture was concentrated under reduced pressure. The residue was triturated with ethyl acetate and the organic phase was concentrated under reduced pressure and then purified by reverse phase column chromatography (0.1% of trifluoroacetic acid in water/acetonitrile). The pH of the collected fractions was adjusted to approximately pH=8 with a saturated aqueous solution of sodium bicarbonate. The mixture was extracted with dichloromethane and the combined organic phase was washed with brine, dried over anhydrous sodium sulfate, filtered, and concentrated under reduced pressure to afford 1-74-9 (110 mg, 75.8% yield) as a white solid.

To a solution of 1-74-9 (230 mg, 0.426 mmol) in dichloromethane (3 mL) was added diisopropylethylamine (0.20 mL, 1.1 mmol), and then methylsufonyl chloride (0.39 mL, 5.1 mmol) was added at 0° C. drop wise. The mixture was stirred at 25° C. for 1 hour. The reaction mixture was poured into water then extracted with ethyl acetate. The combined organic phase was washed with brine, dried over anhydrous sodium sulfate, and concentrated under reduced pressure. The residue was purified by preparative TLC to afford 1-74-10 (120 mg, 45.6% yield) as a white solid.

To a solution of 1-74-10 (140 mg, 0.227 mmol) in dichloromethane (1.5 mL) was added trifluoroacetic acid (0.50 mL, 6.7 mmol) drop wise at 0° C. The mixture was stirred for 2 hours at 20° C. The reaction mixture was poured into water and the pH of the mixture was adjusted to approximately pH=5 with a saturated aqueous solution of sodium bicarbonate. The mixture was extracted with ethyl acetate and the combined organic phase was washed with brine, dried over anhydrous sodium sulfate, and concentrated under reduced pressure to afford 1-74-11 (120 mg, crude) as a white solid. No further purification was performed.

To a solution of 1-74-11 (120 mg, 0.214 mmol) and (1-methylpyrazol-4-yl)methanamine (47 mg, 0.43 mmol) in N,N-dimethyl formamide (3 mL) was added a mixture of EDCI (90 mg, 0.47 mmol) and HOBt (20 mg, 0.15 mmol) at 0° C. The mixture was stirred for 5 hours at 25° C. then the reaction mixture was concentrated under reduced pressure. The residue was dissolved in ethyl acetate, washed with a 0.01 N solution of hydrochloric acid followed by brine then dried over anhydrous sodium sulfate and concentrated under reduced pressure. The residue was triturated with a 1:100 (50 mL) mixture of ethyl acetate:petroleum ether to afford 1-74-12 (75 mg, 48% yield) as a white solid.

To a solution of 1-74-12 (75 mg, 0.11 mmol) in acetonitrile (1 mL) was added a solution of CAN (0.142 mL, 0.286 mmol) in water (1 mL). The mixture was stirred for 2 hours at 70° C. The reaction mixture was poured into ethyl acetate, washed with saturated sodium sulfite followed by brine then dried over anhydrous sodium sulfate, filtered, and concentrated under reduced pressure to afford 1-74-13 (70 mg, crude) as a white solid. No additional purification was performed.

A solution of 1-74-13 (70 mg, 0.12 mol), piperidine (1.4 mg, 0.017 mmol), and acetic acid (7.0 mg, 0.12 mmol) in methanol (2 mL) was degassed with nitrogen three times and then Pd/C (20 mg, 10% purity on carbon) was added in one portion. The mixture was degassed with hydrogen and stirred for 12 hours at 25° C. under a hydrogen atmosphere (15 psi). The reaction mixture was filtered and the filtrate was concentrated under reduced pressure. The residue was purified by preparative reverse phase HPLC using a water/acetonitrile gradient with 0.1% trifluoroacetic acid additive. The pH of the collected fractions was adjusted to approximately pH=8 with a saturated aqueous sodium bicarbonate solution then extracted with dichloromethane. The combined organic phase was washed with brine, dried over anhydrous sodium sulfate, and concentrated under reduced pressure. The residue was further purified by preparative reverse phase HPLC using a water/acetonitrile gradient with 0.05% ammonia hydroxide additive. The eluent was removed under reduced pressure to afford 1-74 (2.3 mg, 2.8% yield) as a white solid. LCMS of 1-74: RT=3.41 min, m/z 666.3 $[M+H]^+$.

Example 22—Synthesis of (5S,8S,11S)-7,10-Dioxo-11-(2-oxooxazolidin-3-yl)-8-(2-(piperidin-1-yl)ethyl)-N-(2,2,2-trifluoroethyl)-2-oxa-6,9-diaza-1,3(1,3)-dibenzenacyclododecaphane-5-carboxamide (1-78)

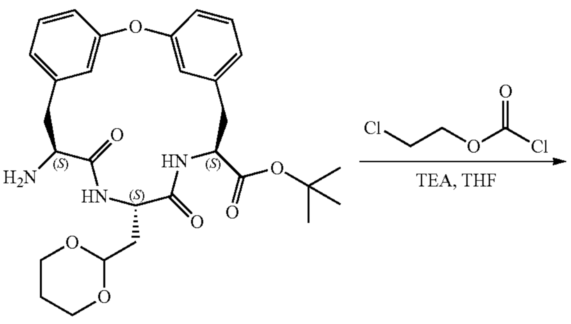

1-74-9

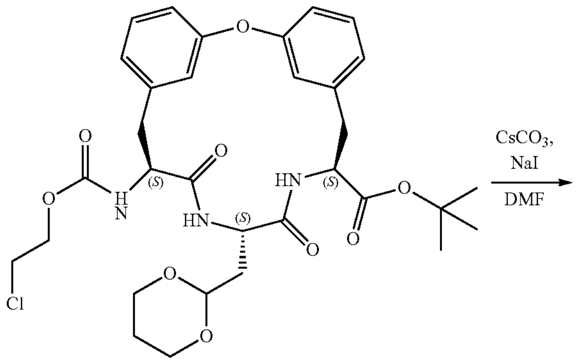

1-78-1

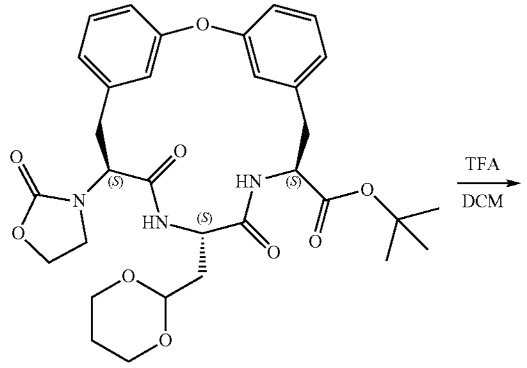

1-78-2

-continued

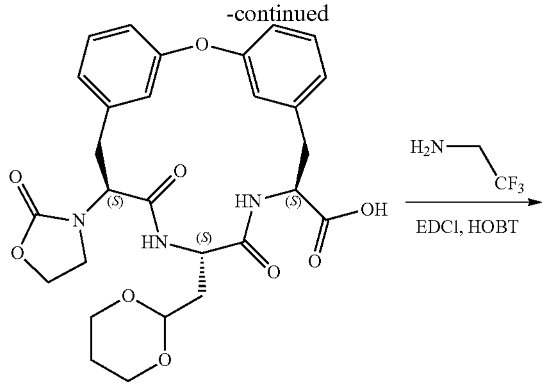

1-78-3

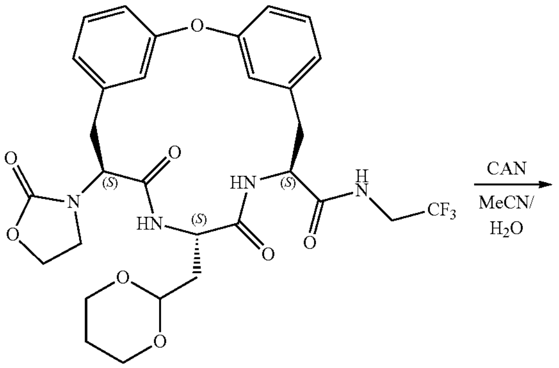

1-78-4

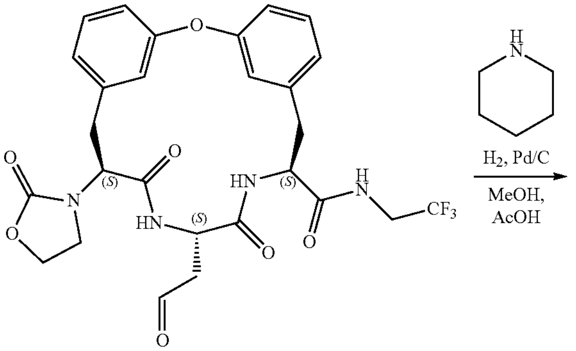

1-78-5

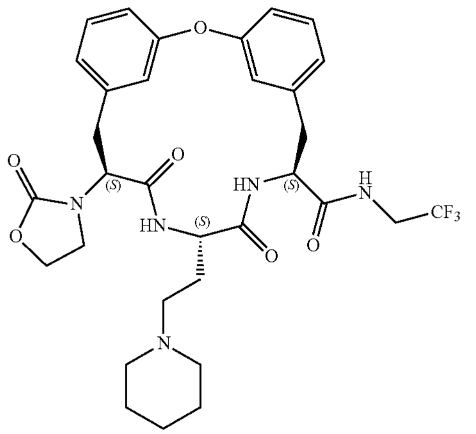

1-78

To a solution of 1-74-9 (280 mg, 0.519 mmol) and triethylamine (0.22 mL, 1.6 mmol) in tetrahydrofuran (3 mL) was added 2-chloroethyl carbonochloridate (0.080 mL, 0.78 mmol) at 0° C. The mixture was stirred for 30 minutes at 0° C. The reaction mixture was poured into water and extracted with ethyl acetate. The combined organic phase was washed with brine, dried over anhydrous sodium sulfate, filtered, and concentrated under reduced pressure. The residue was purified by reverse phase column chromatography using a water/acetonitrile gradient with 0.1% trifluoroacetic additive to afford 1-78-1 (230 mg, 68.6% yield) as a white solid.

To a solution of 1-78-1 (120 mg, 0.186 mmol) and sodium iodide (42 mg, 0.28 mmol) in N,N-dimethyl formamide (0.5 mL) was added cesium carbonate (151 mg, 0.464 mmol) at 0° C. The mixture was stirred for 2 hours at 25° C., poured into water, and extracted with ethyl acetate. The combined organic phase was washed with brine, dried over anhydrous sodium sulfate, filtered, and concentrated under reduced pressure. The residue was purified by flash silica gel column chromatography to afford 1-78-2 (70 mg, 56% yield) as a white solid.

To a solution of 1-78-2 (55 mg, 0.090 mmol) in dichloromethane (2 mL) was added trifluoroacetic acid (0.55 mL, 7.4 mmol) drop wise at 0° C. The mixture was stirred for 2 hours at 25° C. The reaction mixture was poured into water and the pH adjusted to pH=5 with a saturated aqueous sodium bicarbonate solution. The mixture was extracted with ethyl acetate and the combined organic phase was washed with brine, dried over anhydrous sodium sulfate, and concentrated under reduced pressure to afford 1-78-3 (50 mg, crude) as a white solid. No further purification was performed.

To a solution of 1-78-3 (50 mg, 0.090 mmol), diisopropylethylamine (0.047 mL, 0.27 mmol), and 2,2,2-trifluoroethanamine (0.007 mL, 0.090 mmol) in N,N-dimethyl formamide (1 mL) was added HOBt (7.0 mg, 0.054 mmol) and EDCI (26 mg, 0.13 mmol) at 0° C. The mixture was stirred for 12 hours at 25° C., then poured into water and extracted with ethyl acetate. The combined organic phase was washed with brine, dried over anhydrous sodium sulfate, and concentrated under reduced pressure to afford 1-78-4 (50 mg, crude) as yellow gum. No further purification was performed.

To a solution of 1-78-4 (50 mg, 0.079 mmol) in acetonitrile (0.8 mL) was added CAN (0.098 mL, 0.20 mmol) in water (0.8 mL). The mixture was stirred for 2 hours at 70° C., poured into water, and extracted with ethyl acetate. The combined organic phase was washed with a saturated sodium sulfite solution followed by brine, then dried over anhydrous sodium sulfate, and concentrated under reduced pressure to afford 1-78-5 (50 mg, crude) as a white solid. No further purification was performed.

To a solution of 1-78-5 (50 mg, 0.87 mmol) and piperidine (0.017 mL, 0.17 mmol) in methanol (1 mL) was added acetic acid (1.0 mg, 0.017 mmol). The mixture was purged with nitrogen atmosphere 10 minutes, then Pd/C (20 mg, 10% purity) was added in one portion. The mixture was degassed with hydrogen three times and stirred for 12 hours at 25° C. under a hydrogen atmosphere (15 psi). The reaction mixture was filtered and the filtrate was concentrated under reduced pressure. The residue was purified by preparative TLC followed by preparative reverse phase HPLC using a water/acetonitrile gradient with 0.04% $NH_3H_2O$+10 mM $NH_4HCO_3$ additive to afford 1-78 (3.5 mg, 6.0% yield) as a white solid. LCMS of 1-78: RT=1.697 min, m/z 646.3 $[M+H]^+$.

Example 23—Synthesis of (5S,8S,11S)-11-(1,1-Dioxidoisothiazolidin-2-yl)-N-((1-methyl-1H-pyrazol-4-yl)methyl)-7,10-dioxo-8-(2-(piperidin-1-yl)ethyl)-2-oxa-6,9-diaza-1,3(1,3)-dibenzenacyclododecaphane-5-carboxamide (1-79)
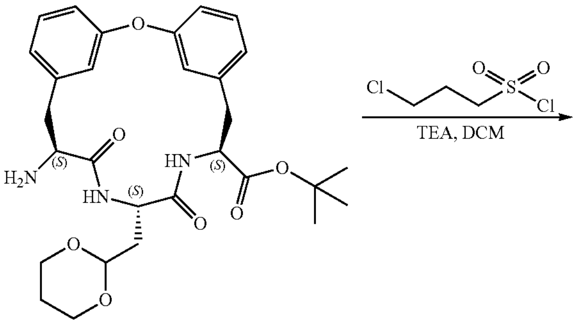
1-74-9
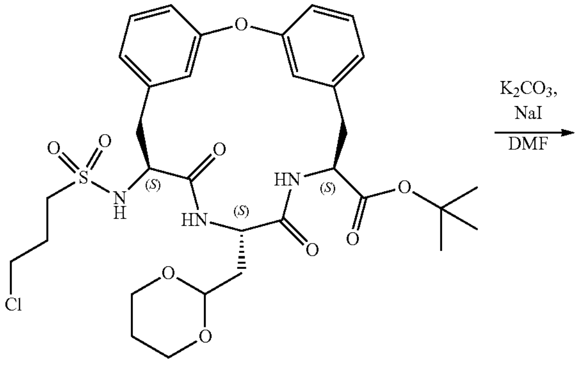
1-79-1
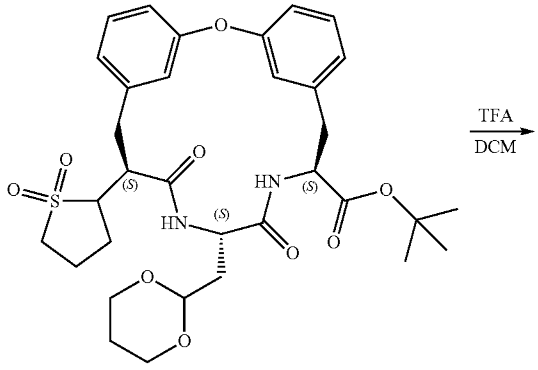
1-79-2
-continued
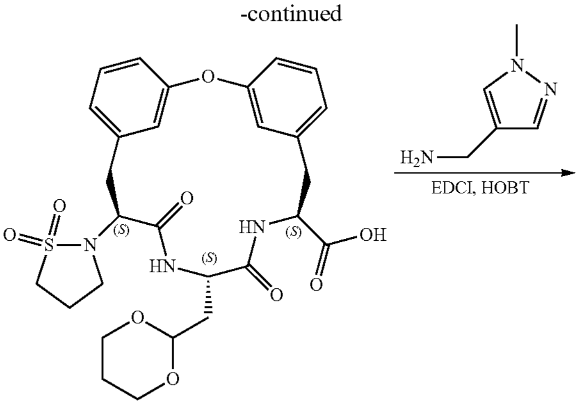
1-79-3
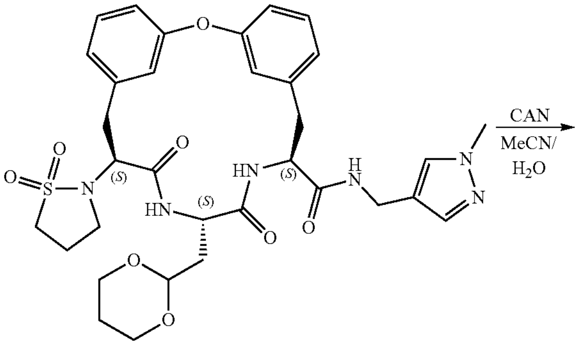
1-79-4
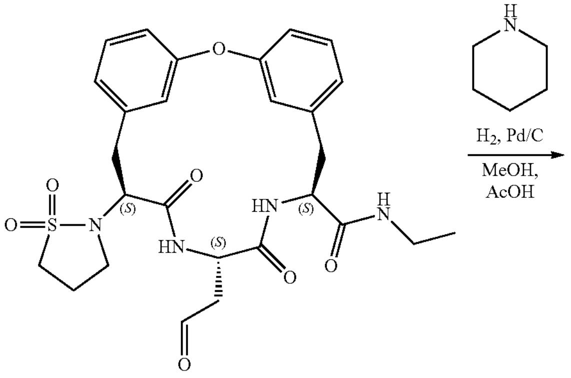
1-79-5
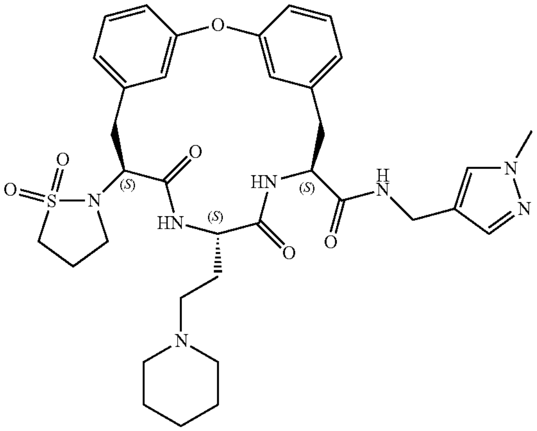
1-79
To a solution of 1-74-9 (250 mg, 0.463 mmol) and triethylamine (0.19 mL, 1.4 mmol) in dichloromethane (1 mL) was added 3-chloropropane-1-sulfonyl chloride (0.084 mL, 0.69 mmol) at 0° C. The mixture was stirred for 30 minutes at 0° C. then poured into water and extracted with ethyl acetate. The combined organic phase was washed with brine, dried over anhydrous sodium sulfate, filtered, and concentrated under reduced pressure to afford 1-79-1 (250 mg, crude) as a white solid. No further purification was performed.

To a solution of 1-79-1 (260 mg, 0.382 mmol) and sodium iodide (86 mg, 0.57 mmol) in N,N-dimethylformamide (3 mL) was added potassium carbonate (106 mg, 0.764 mmol) at 25° C. The mixture was stirred for 12 hours at 25° C. then poured into water and extracted with ethyl acetate. The combined organic phase was washed with brine, dried over anhydrous sodium sulfate, filtered, and concentrated under reduced pressure. The residue was purified by flash silica gel column chromatography to afford 1-79-2 (160 mg, 61.6% yield) as a white solid.

To a solution of 1-79-2 (160 mg, 0.248 mmol) in dichloromethane (4 mL) was added trifluoroacetic acid (1.0 mL, 13 mmol) at 0° C. The mixture was stirred for 3 hours at 25° C. then poured into water and extracted with ethyl acetate. The combined organic phase was washed with brine, dried over anhydrous sodium sulfate, filtered, and concentrated under reduced pressure to afford 1-79-3 (150 mg, crude) as a white solid. No further purification was performed.

To a solution of 1-79-3 (150 mg, 0.255 mmol), (1-methylpyrazol-4-yl) methanamine (75 mg, 0.51 mmol, HCl salt), and diisopropylethylamine (0.133 mL, 0.765 mmol) in N,N-dimethylformamide (2 mL) was added EDCI (73 mg, 0.38 mmol) and HOBt (21 mg, 0.15 mmol) at 0° C. The mixture was stirred for 12 hours at 25° C. then poured into water and extracted with ethyl acetate. The combined organic phase was washed with brine, dried over anhydrous sodium sulfate, and concentrated under reduced pressure to afford 1-79-4 (100 mg, crude) as a white solid. Compound 1-79-4 was used for the next step directly without further purification.

To a solution of 1-79-4 (100 mg, 0.145 mmol) in acetonitrile (1 mL) was added a solution of CAN (0.183 mL, 0.367 mmol) in water (1 mL). The mixture was stirred for 2 hours at 70° C. then poured into water and extracted with ethyl acetate. The combined organic phase was washed with saturated sodium sulfite followed by brine then dried over anhydrous sodium sulfate and concentrated under reduced pressure to afford 1-79-5 (100 mg, crude) as a white solid. No further purification was performed.

To a solution of 1-79-5 (100 mg, 0.160 mmol) and piperidine (0.031 mL, 0.32 mmol) in methanol (1.5 mL) was added acetic acid (5 mg, 0.8 mmol). The mixture was degassed with nitrogen for 10 minutes, then Pd/C (0.1 g, 10% purity) was added in one-portion. The mixture was degassed with hydrogen three times and stirred for 17 hours at 25° C. under a hydrogen atmosphere (15 psi). The reaction mixture was filtered and the filtrate was concentrated under reduced pressure. The residue was purified by preparative HPLC using a water/acetonitrile gradient with 0.1% trifluoroacetic acid additive. The pH of the collected fractions was adjusted to approximately pH=8 with a saturated sodium bicarbonate aqueous solution. The mixture was extracted with dichloromethane and the combined organic phase was washed with brine then dried over anhydrous sodium sulfate, filtered, and concentrated under reduced pressure to afford 1-79 (2.3 mg, 1.9% yield) as a white solid. LCMS 1-79: RT=1.706 min, m/z 692.3 $[M+H]^+$.

Example 24—Synthesis of (5S,8S,11S)-N-(Bicyclo[1.1.1]pentan-1-yl)-7,10-dioxo-11-(2-oxopyrrolidin-1-yl)-8-(2-(piperidin-1-yl)ethyl)-2-oxa-6,9-diaza-1,3(1,3)-dibenzenacyclododecaphane-5-carboxamide (1-80)

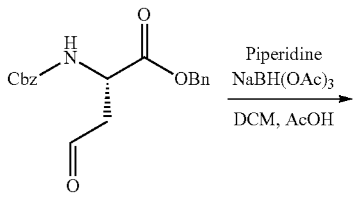

1-72-2

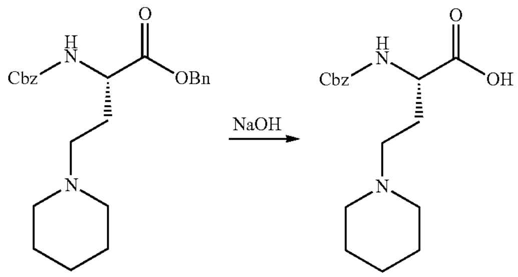

1-80-1

1-80-2

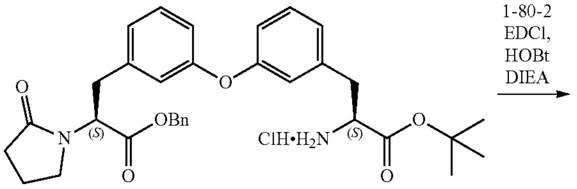

1-72-8

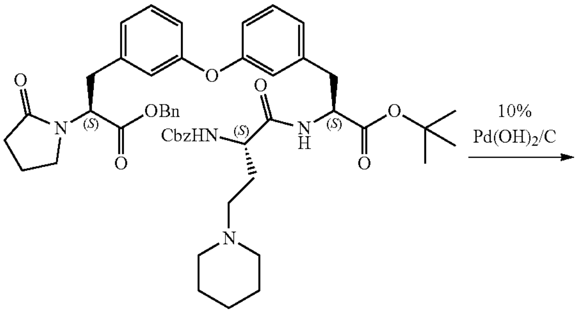

1-80-3

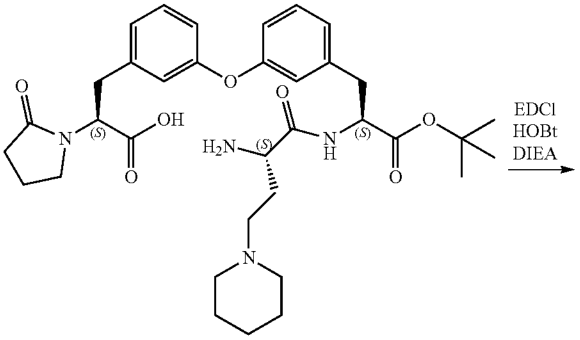

1-80-4

-continued

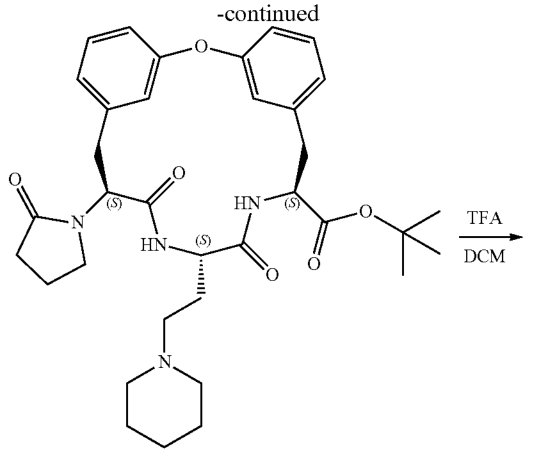

1-80-5

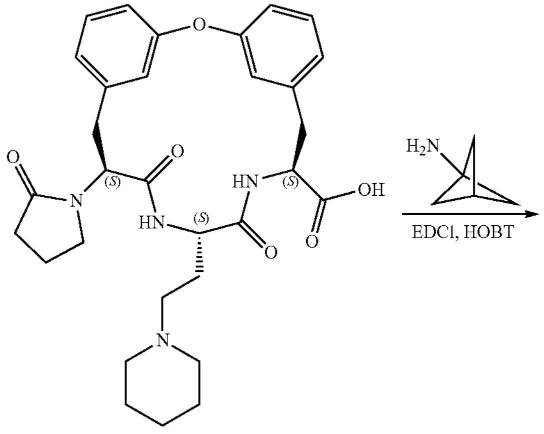

1-80-6

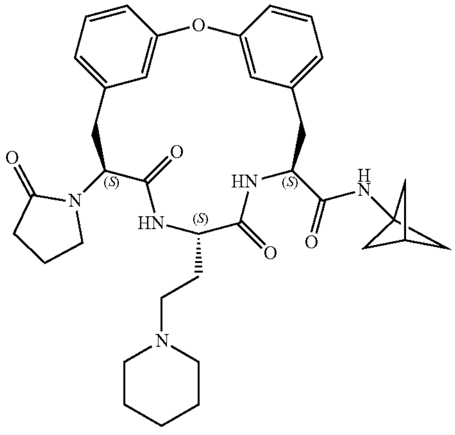

1-80

To a solution of 1-72-2 (1.00 g, 2.93 mmol) in dichloromethane (10 mL) was added piperidine (0.868 mL, 8.79 mmol), followed by acetic acid (0.167 mL, 2.93 mmol) and 4 Å molecular sieves (1 g, 1 mmol). The mixture was stirred at 25° C. for 10 minutes and then sodium triacetoxyborohydride (931 mg, 4.39 mmol) was added. The reaction mixture was stirred at 25° C. for 14 hours under a nitrogen atmosphere. The mixture was filtered through a Celite pad and the filter pad was washed with ethyl acetate. The combined filtrate was washed with brine and the organic layer was dried over anhydrous sodium sulfate, filtered, and concentrated under reduced pressure. The residue was purified by flash silica gel column chromatography to provide 1-80-1 (790 mg, 54.5% yield) as a yellow gum To a solution of 1-80-1 (790 mg, 1.60 mmol) in tetrahydrofuran (8 mL) was added sodium hydroxide (447 mg, 11.2 mmol) in water (8 mL) dropwise at 0° C. The mixture was stirred at 0° C. for 2 hours. An additional amount of sodium hydroxide (192 mg, 4.79 mmol) solution in water (1.5 mL) was added dropwise. The reaction mixture was stirred at 0° C. for another 1 hour. The pH of the mixture was adjusted to pH=2 with 1N hydrochloric acid solution. The mixture was extracted with ethyl acetate and the aqueous layer was lyophilized. The residue was purified by reverse phase flash chromatography using a water/acetonitrile gradient with 0.1% trifluoroacetic acid additive to provide 1-80-2 (750 mg, 99.2% yield, trifluoroacetic acid salt) as a light yellow gum.

To a solution of 1-80-2 (231 mg, 0.531 mmol) and N,N-diisopropylethylamine (0.54 mL, 3.1 mmol) in N,N-dimethylformamide (3 mL) was added HOBt (78 mg, 0.58 mmol) at 0° C., the mixture was stirred at 0° C. for 10 minutes. To this reaction mixture EDCI (340 mg, 1.77 mmol) was added followed by the drop wise addition of a solution of 1-72-8 (300 mg, 0.443 mmol) in N,N-dimethylformamide (1 mL) at 0° C. The reaction mixture was stirred at 0° C. for 20 minutes and then stirred at 25° C. for another 16 hours under a nitrogen atmosphere. The mixture was diluted with water and extracted with ethyl acetate. The combined organic phase was washed with brine, dried over anhydrous sodium sulfate, and concentrated under reduced pressure. The residue was purified by flash silica gel column chromatography to provide 1-80-3 as a yellow gum.

To a solution of 1-80-3 (300 mg, 0.305 mmol) in isopropyl alcohol (6 mL) was added Pd/C (50 mg, 10% purity) and $Pd(OH)_2/C$ (50 mg, 10% purity) under a nitrogen atmosphere. The suspension was degassed under vacuum and purged with hydrogen several times. The mixture was stirred under a hydrogen atmosphere (15 psi) at 25° C. for 8 hours. The mixture was filtered and the solid was washed with isopropyl alcohol. Pd/C (50 mg, 10% purity) and $Pd(OH)_2/C$ (50 mg, 10% purity) was added into the combined filtrate under a nitrogen atmosphere. The suspension was degassed under vacuum and purged with hydrogen several times. The mixture was stirred under a hydrogen atmosphere (15 psi) at 25° C. for 14 hours. The residue was purified by reverse phase flash chromatography using water/acetonitrile with 0.1% trifluoroacetic acid additive. The pH of the isolated fractions were adjusted to pH=7 with a saturated aqueous sodium bicarbonate solution. The mixture was lyophilized to provide 1-80-4 (280 mg, crude, sodium salt) as a white solid. No further purification was performed.

To a solution of 1-80-4 (280 mg, 0.315 mmol) in N,N-dimethylformamide (280 mL) was added N,N-diisopropylethylamine (0.38 mL, 2.2 mmol) followed by HOBt (64 mg, 0.47 mmol) at 0° C. The mixture was stirred at 0° C. for 10 minutes then EDCI (303 mg, 1.58 mmol) was added. The reaction mixture was stirred at 0° C. for 20 minutes and then stirred at 25° C. for another 16 hours. An additional portion of N,N-diisopropylethylamine (0.11 mL, 0.63 mmol) and EDCI (121 mg, 0.631 mmol) were added at 0° C. The mixture was stirred at 25° C. for another 24 hours. The mixture was poured into ice water (200 mL) and then extracted with ethyl acetate. The combined organic layers were washed with brine, dried over anhydrous sodium sulfate, filtered, and concentrated under reduced pressure. The residue was purified by reverse phase flash column chromatography using water/acetonitrile with 0.1% trifluoroacetic acid additive) and then further purified by preparative reverse phase HPLC using water/acetonitrile gradient with 0.1% trifluoroacetic acid additive to provide 1-80-5 (40 mg, 20% yield) as a light yellow solid.

To a solution of 1-80-5 (35 mg, 0.056 mmol) in dichloromethane (1 mL) was added trifluoroacetic acid (0.4 mL, 0.040 mmol) at 0° C. The mixture was stirred at 25° C. for 3 hours. The mixture was concentrated under reduced pressure to provide 1-80-6 (40 mg, crude, trifluoroacetic acid salt) as a light yellow gum. No further purification was performed.

To a solution of 1-80-6 (40 mg, 0.060 mmol, trifluoroacetic acid salt) in pyridine (0.5 mL) was added bicyclo [1.1.1]pentan-1-amine hydrochloride (21 mg, 0.18 mmol). The mixture was cooled to 0° C. HOBt (8 mg, 0.6 mmol) was added and the mixture was stirred at 0° C. for 10 minutes. EDCI (34 mg, 0.18 mmol) was added to this mixture at 0° C. The reaction mixture was stirred at 0° C. for 20 minutes and then stirred at 25° C. for another 1.5 hours under a nitrogen atmosphere. The mixture was diluted with water (5 mL) then concentrated under reduced pressure. The residue was diluted with water (20 mL) and then extracted with ethyl acetate. The combined organic layers were washed with brine, dried over anhydrous sodium sulfate, filtered, and concentrated under reduced pressure. The residue was purified by preparative reverse phase HPLC using a water/acetonitrile gradient with 0.1% trifluoroacetic acid additive. The isolated material was adjusted to pH=7 with a saturated aqueous sodium bicarbonate solution. The mixture was concentrated under reduced pressure to remove volatile organics, then extracted with dichloromethane. The combined organic layers were washed with brine, dried over anhydrous sodium sulfate, filtered, and concentrated in vacuum to provide 1-80 (15 mg) as a white solid. LCMS of 1-80: RT=2.420 min, m/z 628.3 $[M+H]^+$.

The following compounds were made using a similar synthetic route as described for compound 1-80:

Compound 1-82; LCMS: RT=2.857 min, m/z 630.4 $[M+H]^+$

Compound 1-84; LCMS: RT=2.681 min, m/z 630.3 $[M+H]^+$

Compound 1-85; LCMS: RT=2.683 min, m/z 630.3 $[M+H]^+$

Example 25—Synthesis of (5S,8S,11S)-6-Methyl-8-(2-morpholinoethyl)-7,10-dioxo-11-(2-oxopyrrolidin-1-yl)-N-(2,2,2-trifluoroethyl)-2-oxa-6,9-diaza-1,3(1,3)-dibenzenacyclododecaphane-5-carboxamide (1-86)

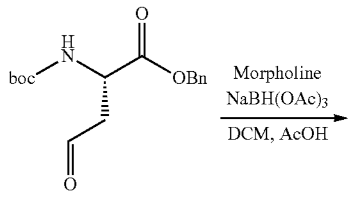

1-72-2

-continued

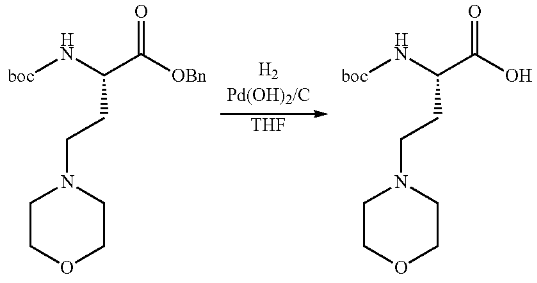

1-86-1 1-86-2

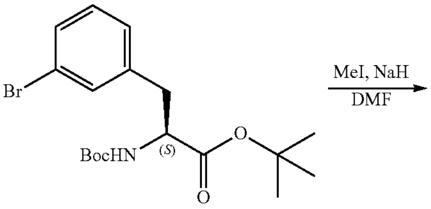

1-72-4

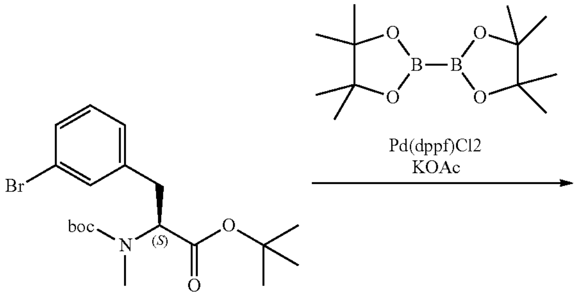

1-86-3

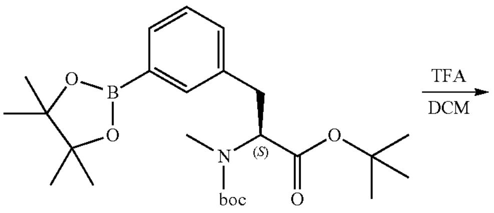

1-86-4

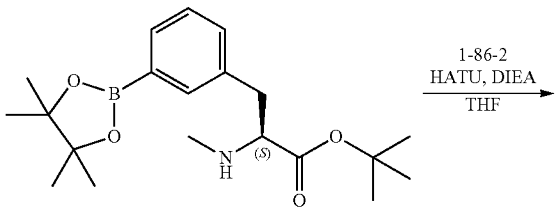

1-86-5

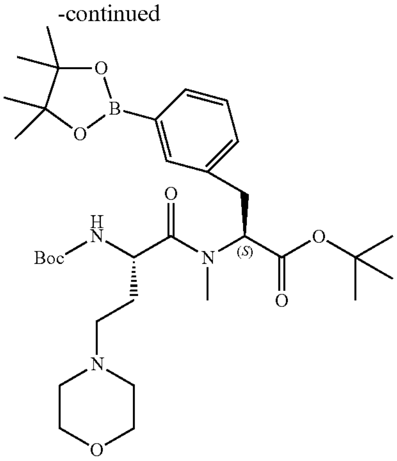
1-86-6
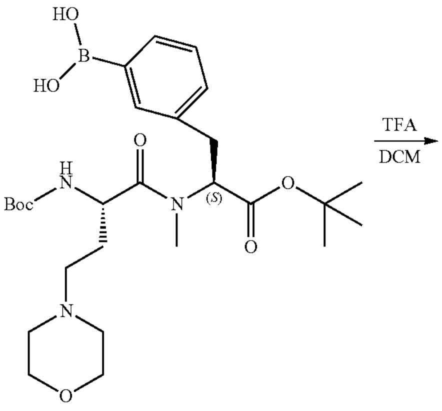
1-86-6a
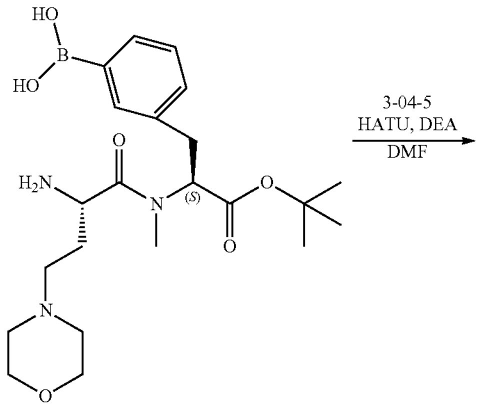
1-86-7
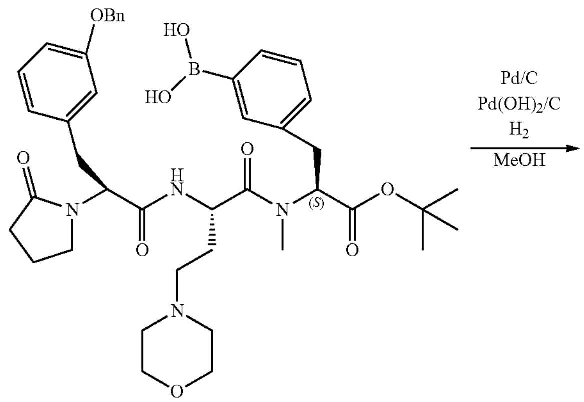
1-86-8
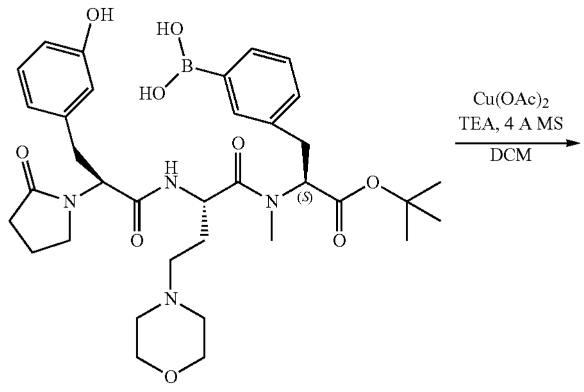
1-86-9
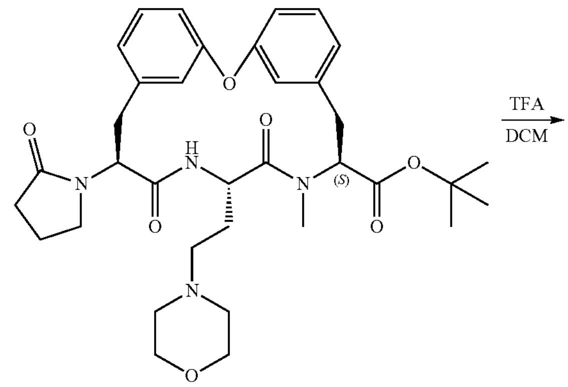
1-86-10
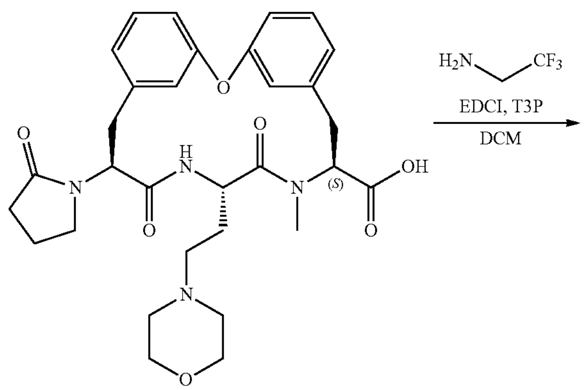
1-86-11

-continued

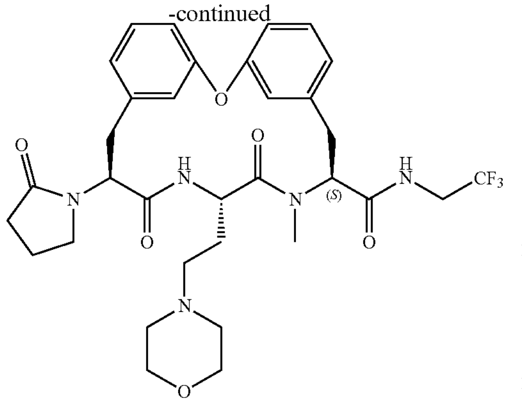

1-86

To a solution of 1-72-2 (23 g, 75 mmol), acetic acid (4.3 mL, 75 mmol) and 4 Å molecular sieves (23 g) in dichloromethane (230 mL) was added morpholine (13.2 mL, 150 mmol) at 0° C. The mixture was stirred at 25° C. for 15 minutes. Sodium triacetoxyborohydride (23.8 g, 112 mmol) was added at 0° C. The reaction mixture was stirred at 0° C. for 15 minutes and then stirred at 20° C. for another 14 hours. Additional batch of sodium triacetoxyborohydride (3.17 g, 15.0 mmol) was added to this reaction mixture and the reaction mixture was stirred at 20° C. for 14 hours. Excess reactants were consumed by the addition of a saturated aqueous sodium bicarbonate solution. The mixture was filtered through a Celite pad and the filter pad was washed with dichloromethane. The organic layer was separated from the filtrate and then washed with brine, dried over anhydrous sodium sulfate, filtered, and concentrated under reduced pressure. The residue was purified by reverse phase flash column chromatography (basic condition) to provide 1-86-1 (14.3 g, 44.3% yield) as a light yellow gum.

To a solution of 1-86-1 (14.3 g, 33.2 mmol) in tetrahydrofuran (150 mL) was added $Pd(OH)_2/C$ (0.5 g, 10% purity) under a nitrogen atmosphere. The suspension was degassed under reduced pressure and purged with hydrogen several times. The mixture was stirred under a hydrogen atmosphere (15 psi) at 20° C. for 16 hours. To this was added an additional portion of $Pd(OH)_2/C$ (0.5 g, 10% purity). The suspension was degassed under reduced pressure and purged with hydrogen several times. The mixture was stirred under a hydrogen atmosphere (15 psi) at 20° C. for 6 hours. The mixture was filtered through a Celite pad and the filter pad was washed with methanol. The combined filtrate was concentrated under reduced pressure. The residue was triturated with a mixture of ethyl acetate:methyl tert-butyl ether (30 mL/200 mL) to provide 1-86-2 (9.36 g, 97.9% yield) as a light yellow solid.

To a solution of 1-72-4 (13.55 g, 33.85 mmol) in N,N-dimethylformamide (140 mL) was added sodium hydride (2.03 g, 50.8 mmol, 60% purity in mineral oil) at 0° C. The mixture was stirred at 0° C. for 10 minutes. Methyl iodide (2.53 mL, 40.6 mmol) was added at 0° C. The reaction mixture was stirred at 0° C. for 3 hours then a further batch of sodium hydride (1.08 g, 27.1 mmol, 60% purity in mineral oil) was added. The reaction mixture was stirred at 0° C. for another 10 minutes. Methyl iodide (1.67 mL, 26.8 mmol) was added. The reaction mixture was stirred at 0° C. for another 1 hour. The mixture was poured into a saturated ammonium chloride solution and then extracted with ethyl acetate. The combined organic layers were washed with brine, dried over anhydrous sodium sulfate, filtered, and concentrated under reduced pressure. The residue was purified by flash silica gel column chromatography to provide 1-86-3 (14.3 g, 88.6% yield) as a colorless gum.

To a solution of 1-86-3 (6.0 g, 12 mmol), 4,4,4',4',5,5,5',5'-octamethyl-2,2'-bi(1,3,2-dioxaborolane) (3.84 g, 15.1 mmol), and potassium acetate (3.09 g, 31.5 mmol) in dry dioxane (60 mL) was added $Pd(dppf)Cl_2$ (921 mg, 1.26 mmol) under nitrogen atmosphere. The mixture was degassed and then stirred at 80° C. for 6 hours under nitrogen atmosphere. The mixture was concentrated under reduced pressure then the residue was diluted with ethyl acetate (200 mL), filtered, and the filter pad was washed with ethyl acetate. The combined organic phase was concentrated under reduced pressure. The residue was purified by flash silica gel column chromatography to provide 1-86-4 (7.7 g, crude) as light yellow gum. No further purification was performed.

To a solution of 1-86-4 (7.2 g, 12 mmol) in dichloromethane (610 mL) was added trifluoroacetic acid (61 mL, 830 mmol) drop-wise at 0° C. The mixture was stirred at 0° C. for 4 hours then poured into a mixture of ice and saturated sodium bicarbonate solution. The pH of the mixture adjusted to pH=7 with sodium bicarbonate. The mixture was stirred for 1 hour and then the organic layer was separated. The aqueous layer was extracted with dichloromethane and the combined organic layers were washed with brine then dried over anhydrous sodium sulfate, filtered, and concentrated under reduced pressure. The residue was purified by flash silica gel column chromatography to provide 1-86-5 (3.8 g, 86% yield) as a light yellow gum.

To a solution of 1-86-2 (1.2 g, 4.1 mmol), 1-86-5 (1.5 g, 4.1 mmol), and N,N-diisopropylethylamine (1.81 mL, 10.4 mmol) in tetrahydrofuran (25 mL) was added HATU (2.37 g, 6.23 mmol) at 0° C. The mixture was stirred at 0° C. for 3 hours and then concentrated under reduced pressure. The residue was purified by flash silica gel column chromatography and then further purified by reverse phase flash column using a gradient of water/acetonitrile with 0.1% trifluoroacetic acid additive to provide 1-86-6 (0.60 g, 19% yield, TFA salt) as a light yellow solid and compound 1-86-6a (0.90 g, 27% yield, TFA salt) as a light yellow solid.

To a solution of compound 1-86-6a (800 mg, 1.20 mmol) in dichloromethane (80 mL) was added trifluoroacetic acid (6.6 mL, 89 mmol) drop-wise at 0° C. The mixture was stirred at 0° C. for 4 hours then N,N-diisopropylethylamine (15.5 mL) was added into the mixture drop-wise at 0° C. to afford a solution of 1-86-7 in dichloromethane.

To a solution of 3-04-5 (428 mg, 1.26 mmol) and N,N-diisopropylethylamine (0.52 mL, 3.0 mmol) in tetrahydrofuran (10 mL) was added HATU (684 mg, 1.80 mmol) at 0° C. The mixture was stirred at 0° C. for 20 minutes then the above solution of 1-86-7 in dichloromethane (80 mL) was added into the mixture. The reaction mixture was stirred at 0° C. for 1 hour and then stirred at 20° C. for 12 hours. The mixture was diluted with water and then concentrated under reduced pressure. The residue was purified by reversed flash column chromatography using a water/acetonitrile gradient with 0.1% trifluoroacetic acid additive to provide 1-86-8 (730 mg, 68.8% yield, TFA salt) as a light yellow solid.

To a solution of 1-86-8 (730 mg, 0.825 mmol) in methanol (15 mL) was added Pd/C (50 mg, 10% purity) and $Pd(OH)_2/C$ (50 mg, 10% purity) under a nitrogen atmosphere. The suspension was degassed under vacuum and purged with hydrogen several times. The mixture was stirred under a hydrogen atmosphere (15 psi) at 20° C. for 20 hours. The mixture was filtered through a Celite pad and the filter pad was washed with methanol. The combined filtrate was concentrated under reduced pressure. The residue was purified by reverse phase flash column chromatography using a water/acetonitrile gradient with 0.1% trifluoroacetic acid additive to provide 1-86-9 (410 mg, 58.1% yield, TFA salt) as a white solid.

To a solution of 1-86-9 (200 mg, 0.252 mmol, 1 eq), 4 Å molecular sieves (400 mg), and triethylamine (0.17 mL, 1.3 mmol) in dichloromethane (20 mL) was added copper acetate (91 mg, 0.50 mmol). The mixture was stirred at 20° C. for 16 hours under an oxygen atmosphere (15 psi). The mixture was combined with two previous batches generated under the same conditions. The mixture was filtered through a Celite pad and the filter pad was washed with dichloromethane. The combined filtrate was washed with brine, dried over anhydrous sodium sulfate, filtered, and concentrated under reduced pressure. The residue was purified by preparative reverse phase HPLC using a water/acetonitrile gradient with 0.1% trifluoroacetic acid additive to provide 1-86-10 (130 mg, TFA salt) as a light yellow solid.

To a solution of 1-86-10 (60 mg, 0.080 mmol, 1 eq, TFA) in dichloromethane (2.4 mL) was added trifluoroacetic acid (1.2 mL, 16 mmol). The mixture was stirred at 20° C. for 5 hours then concentrated under reduced pressure to provide 1-86-11 (60 mg, crude, TFA salt) as a light yellow gum. No further purification was performed.

To a solution of 1-86-11 (60 mg, 0.087 mmol), 2,2,2-trifluoroethan-1-amine (0.034 uL, 0.43 mmol), and N,N-diisopropylethylamine (0.030 mL, 0.17 mmol) in dichloromethane (2 mL) was added propylphosphonic anhydride (T3P) (0.10 mL, 0.17 mmol, 50% in ethyl acetate) at 0° C. The mixture was stirred at 0 C for 3 hours. The mixture was diluted with water and then extracted with ethyl acetate. The combined organic layers were washed with brine, dried over anhydrous sodium sulfate, filtered, and concentrated under reduced pressure. The residue was purified by preparative reverse phase HPLC using a water/acetonitrile gradient with 0.05% ammonia hydroxide additive to provide 1-86 (10.2 mg, 17.8% yield) as a white solid. LCMS of 1-86: RT=2.313 min, m/z 660.3 [M+H]+.

The following compound was made using a similar synthetic route as described for compound 1-86: Example 1-83; LCMS: RT=2.370 min, m/z 658.3 [M+H]+.

Example 26—Synthesis of (5S,8S,11S)-11-(1,1-Dioxidoisothiazolidin-2-yl)-6-methyl-8-(2-morpholinoethyl)-7,10-dioxo-N-(2,2,2-trifluoroethyl)-2-oxa-6,9-diaza-1,3(1,3)-dibenzenacyclododecaphane-5-carboxamide (1-87)

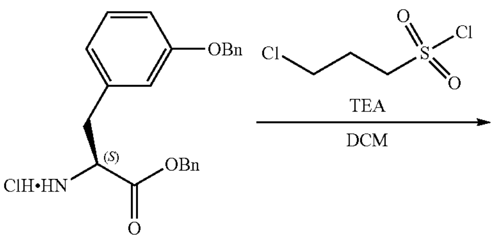

3-04-2

-continued

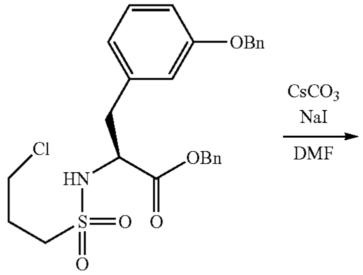

1-87-1

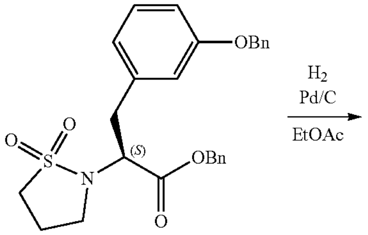

1-87-2

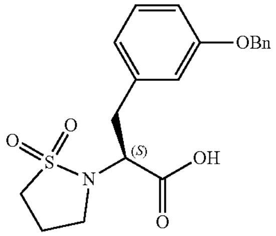

1-87-3

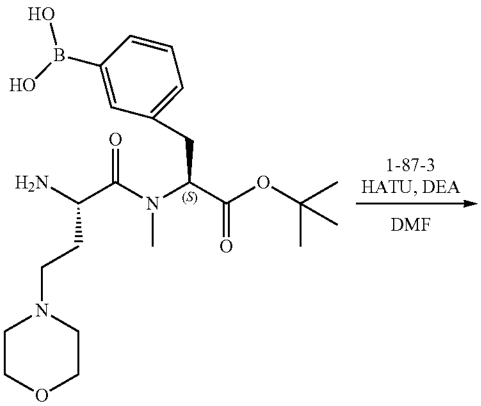

1-86-7

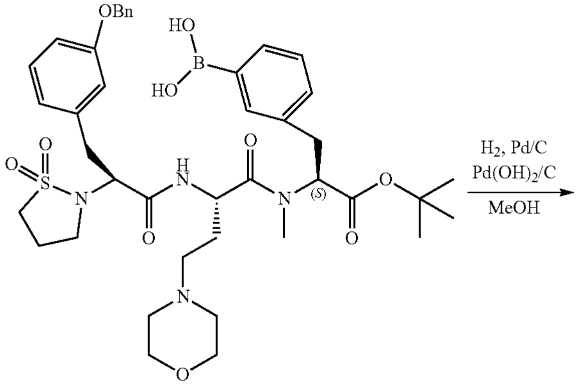

1-87-4

-continued

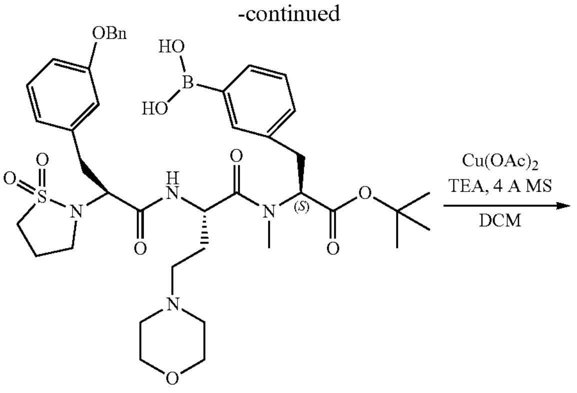

1-87-5

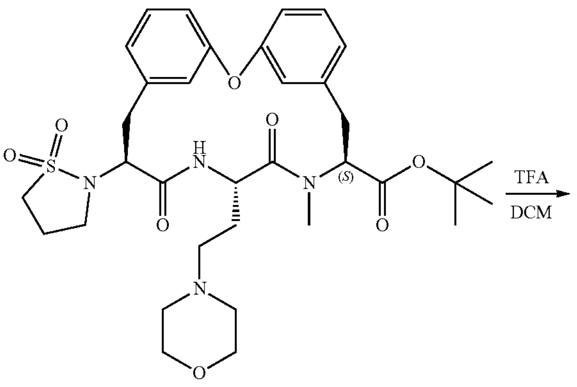

1-87-6

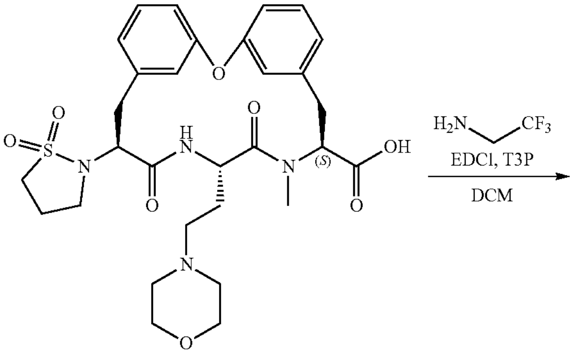

1-87-7

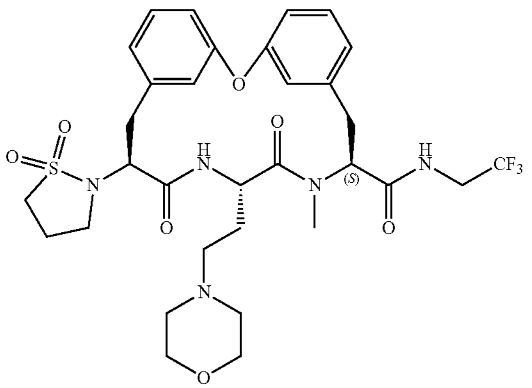

1-87

To a solution of 3-04-2 (14.5 g, 36.4 mmol, HCl salt) and triethylamine (15.2 mL, 109 mmol) in dichloromethane (150 mL) was added 3-chloropropane-1-sulfonyl chloride (5.3 mL, 44 mmol) at 0° C. The mixture was stirred for 1 hour at 15° C. The reaction mixture was poured into water, the pH of the mixture adjusted to pH=4 with 1N hydrochloric acid aqueous, then extracted with ethyl acetate. The combined organic phase was washed with brine, dried over anhydrous sodium sulfate, filtered, and concentrated under reduced pressure. The residue was purified by flash silica gel column chromatography to provide 1-87-1 (15 g, 79%) as yellow gum.

To a solution of 1-87-1 (15 g, 30 mmol) and sodium iodide (896 mg, 5.98 mmol) in N,N-dimethyl formamide (150 mL) was added cesium carbonate (19.5 g, 59.8 mmol) at 0° C. The mixture was stirred at 0° C. for 3 hours then poured into water and extracted with ethyl acetate. The combined organic phase was washed with brine, dried over anhydrous sodium sulfate, filtered, and concentrated under reduced pressure. The residue was purified by flash silica gel column chromatography to afford 1-87-2 (12.5 g, 82.9% yield) as a yellow solid.

A solution of 1-87-2 (5.5 g, 11.8 mmol) in ethyl acetate (50 mL) was purged with nitrogen for 10 minutes then Pd/C (0.5 g, 10% purity on carbon) was added in one portion. The mixture was degassed with hydrogen three times and stirred at 20° C. for 1 hour under a hydrogen atmosphere (15 psi). The mixture was filtered and the filtrate was concentrated under reduced pressure to afford 1-87-3 (8.0 g, 90% yield) as a white solid.

To a solution of 1-87-3 (342 mg, 0.912 mmol) and N,N-diisopropylethylamine (0.555 mL, 3.19 mmol) in tetrahydrofuran (10 mL) was added HATU (520 mg, 1.37 mmol) at 0° C. The mixture was stirred at 0° C. for 15 minutes. A solution of 1-86-7 (410 mg, 0.912 mmol) in dichloromethane (68 mL) was added at 0° C. The reaction mixture was stirred at 0° C. for 3 hours then excess reactants were consumed by diluting with water. The mixture was concentrated under reduced pressure and the residue was purified by reverse phase flash column using a water/acetonitrile gradient with 0.1% trifluoroacetic acid additive to provide 1-87-4 (450 mg, 53.6% yield) as a light yellow solid.

To a solution of 1-87-4 (450 mg, 0.489 mmol, TFA salt) in methanol (10 mL) was added Pd(OH)$_2$/C (50 mg, 10% purity) and Pd/C (50 mg, 10% purity) under a nitrogen atmosphere. The suspension was degassed under reduced pressure and purged with hydrogen several times. The mixture was stirred under a hydrogen atmosphere (15 psi) at 20° C. for 12 hours. The mixture was filtered and the filter pad was washed with methanol. The filtrate was concentrated under reduced pressure and the residue was purified by reverse phase flash column chromatography using a water/acetonitrile gradient with 0.1% trifluoroacetic acid additive to provide 1-87-5 (250 mg, 61.6% yield, TFA salt) as a white solid.

To a mixture of 1-87-5 (300 mg, 0.361 mmol, TFA salt), 4 Å molecular sieves (300 mg), and triethylamine (0.251 mL, 1.81 mmol) in dichloromethane (30 mL) was added copper acetate (131 mg, 0.722 mmol). The mixture was stirred at 20° C. for 16 hours under an oxygen atmosphere (15 psi). The mixture was filtered through a Celite pad and the filter pad was washed with dichloromethane. The combined filtrate was washed with brine, dried over anhydrous sodium sulfate, filtered, and concentrated under reduced pressure. The residue was purified by preparative reverse phase HPLC using a water/acetonitrile gradient with 0.1% trifluoroacetic acid additive to provide 1-87-6 (110 mg, 36.3% yield, TFA salt) as a light yellow solid.

To a solution of 1-87-6 (70 mg, 0.89 mmol, TFA salt) in dichloromethane (1.1 mL) was added trifluoroacetic acid (0.21 mL, 2.8 mmol) at 0° C. The mixture was stirred at 20° C. for 4 hours then N,N-diisopropylethylamine (0.51 mL) was added drop-wise at 0° C. to provide a solution of 1-87-7 in dichloromethane. The solution was added into a mixture of triethylamine (0.050 mL, 0.36 mmol), 2,2,2-trifluoro-ethan-1-amine (0.021 mL, 27 mmol), and T3P (0.106 mL, 178 mmol, 50% in EtOAc) in dichloromethane (1 mL) at 0° C. The mixture was stirred at 0° C. for 1 hour then diluted with water and extracted with ethyl acetate. The combined organic layers were washed with brine, dried over anhydrous sodium sulfate, filtered, and concentrated under reduced pressure. The residue was purified by preparative reverse phase HPLC using a water/acetonitrile gradient of 0.05% ammonia hydroxide additive followed by preparative SFC to provide 1-87 (5.8 mg, 9.2% yield) as a white solid. LCMS of 1-87: RT=2.313 min, m/z 696.2 $[M+H]^+$.

Example 27—Synthesis of (5S,8S,11S)-N-Cyclopentyl-11-(1,1-dioxidoisothiazolidin-2-yl)-8-(2-morpholinoethyl)-7,10-dioxo-2-oxa-6,9-diaza-1,3(1,3)-dibenzenacyclododecaphane-5-carboxamide (1-88)

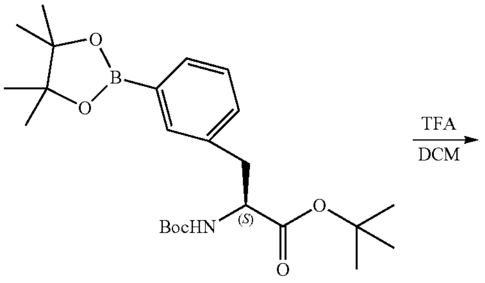

1-72-5

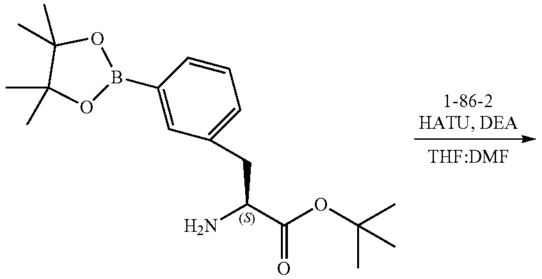

1-88-1

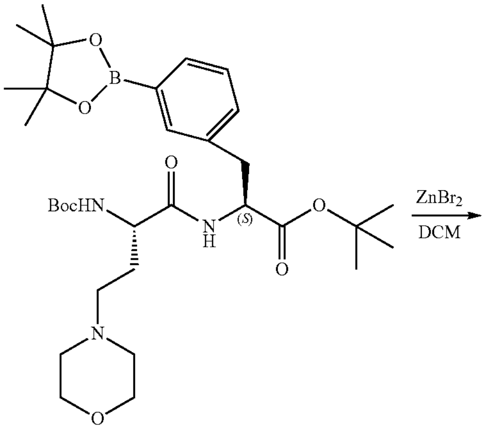

1-88-2

-continued

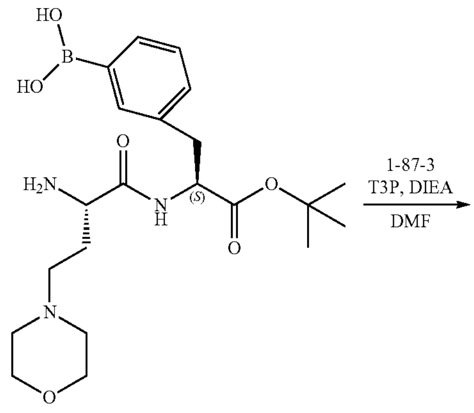

1-88-3

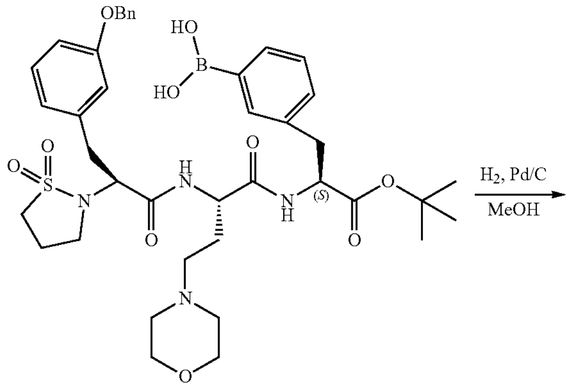

1-88-4

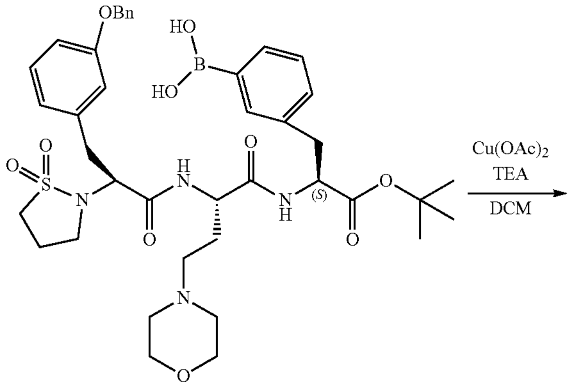

1-88-5

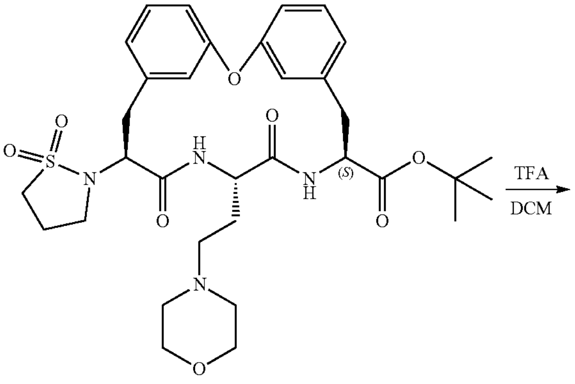

1-88-6

-continued

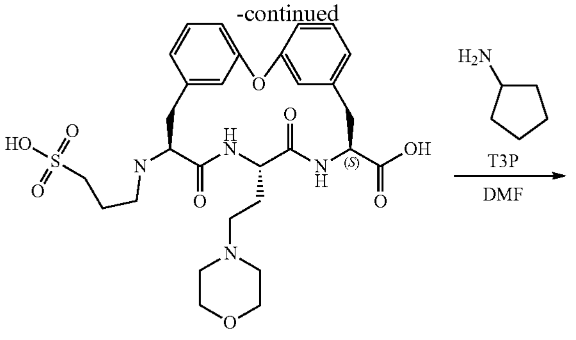

1-88-7

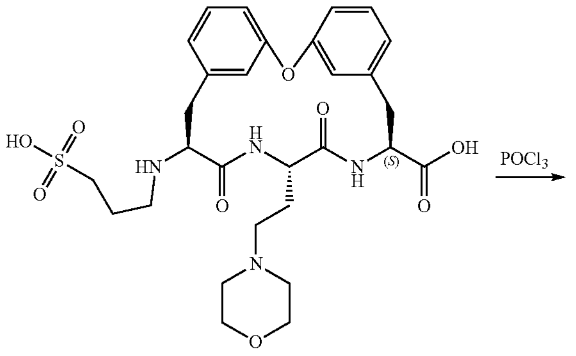

1-88-8

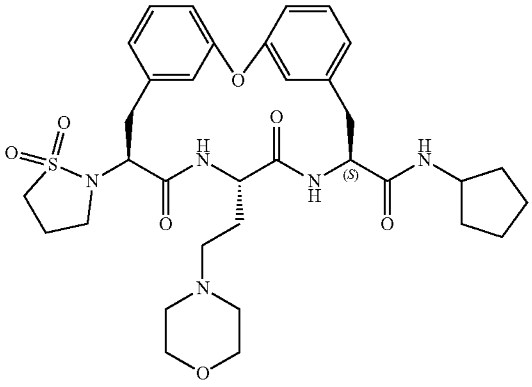

1-88

To a solution of 1-72-5 (5.0 g, 11 mmol) in dichloromethane (100 mL) was added trifluoroacetic acid (10.0 mL, 135 mmol) at 0° C. and the solution was stirred at 0° C. for 4 hours. The reaction was neutralized with a saturated aqueous sodium bicarbonate solution and extracted with dichloromethane. The combined organic layers were washed with brine, dried over anhydrous sodium sulfate, filtered, and concentrated under reduced pressure. The residue was purified by flash silica gel column chromatography to provide 1-88-1 (2.1 g, 54% yield) as a light yellow oil.

To a solution of 1-86-2 (1.1 g, 3.8 mmol) in tetrahydrofuran (10 mL) was added HATU (1.74 g, 4.58 mmol) and N,N-diisopropylethylamine (1.0 mL, 5.7 mmol) at 0° C. and the solution was stirred at 0° C. for 30 minutes. To this was added 1-88-1 (1.37 g, 3.96 mmol) at 0° C. and the solution was stirred at 0° C. for 2 hours. The reaction was diluted with a saturated aqueous ammonium chloride solution and extracted with ethyl acetate. The combined organic layers were washed with brine, dried over anhydrous sodium sulfate, filtered, and concentrated under reduced pressure. The residue was purified by reverse phase flash column chromatography using a water/acetonitrile gradient with 0.1% trifluoroacetic acid additive to provide 1-88-2 (2.2 g, 3.56 mmol, 93.38% yield) as a light yellow gum.

To a solution of 1-88-2 (2.2 g, 3.6 mmol) in dichloromethane (10 mL) and dioxane (1 mL) was added zinc bromide (4.0 g, 18 mmol) at 15° C. and the solution was stirred at 15° C. for 8 hours. The reaction was quenched with N,N-diisopropylethylamine (3 mL) and the mixture was concentrated to remove the solvent. The residue was purified by reverse phase flash column chromatography using a water/acetonitrile gradient with 0.1% trifluoroacetic acid additive to provide 1-88-3 (1.1 g, 53% yield, TFA salt) as an off-white solid.

To a solution of 1-87-3 (752 mg, 2.00 mmol) in N,N-dimethylacetamide (10 mL) was added T3P (2.4 mL, 4.0 mmol, 50% purity in ethyl acetate) and N,N-diisopropylethylamine (1.74 mL, 10.0 mmol) at 0° C. and the solution was stirred at 0° C. for 30 minutes. Then 1-88-3 (1.1 g, 2.0 mmol, TFA salt) was added to the solution at 0° C. and the solution was stirred at 0° C. for additional 1.5 hours. The reaction mixture was filtered and the crude product was purified by reverse phase flash column chromatography using a water/acetonitrile gradient with 0.1% trifluoroacetic acid additive to provide 1-88-4 (0.35 g, 22% yield) as a white solid.

To a solution of 1-88-4 (350 mg, 0.441 mmol) in methanol (3 mL) was added Pd/C (40 mg, 10% purity) and $Pd(OH)_2/C$ (40 mg, 10% purity) at 15° C. under a nitrogen atmosphere. The solution was stirred at 15° C. for 12 hours under a hydrogen atmosphere (15 psi). The reaction was filtered through a Celite and the filter cake was washed with methanol. °The filtrate was concentrated under reduced pressure to provide 1-88-5 (300 mg, crude) as a light yellow gum.

A mixture of 1-88-5 (200 mg, 0.285 mmol), copper acetate (103 mg, 0.569 mmol), 4 Å molecular sieve (500 mg), and triethylamine (0.198 mL, 1.42 mmol) in dichloromethane (15 mL) was stirred at 20° C. under an air balloon (15 psi) for 13 hours. The mixture was filtered though a Celite and the filter cake was washed with dichloromethane. The filtrate was concentrated under reduced pressure and the residue was purified by preparative reverse phase HPLC using a water/acetonitrile gradient with 0.1% trifluoroacetic acid additive to provide 1-88-6 (30 mg, 14% yield, TFA salt) as an off-white solid.

To a solution of 1-88-6 (15 mg, 0.023 mmol) in dichloromethane (0.4 mL) was added trifluoroacetic acid (0.100 mL, 1.35 mmol) at 0° C. The mixture was stirred for 12 hours at 20° C. The reaction mixture was concentrated under reduced pressure to afford 1-88-7 (20 mg, crude, TFA salt) as a yellow gum. No further purification was performed.

To a solution of the crude 1-88-7 (20 mg), diisopropylethylamine (0.023 mL, 0.13 mmol), and cyclopentyl amine (0.006 mL, 0.06 mmol) in dichloromethane (0.5 mL) was added a solution of T3P (0.38 mL, 0.065 mmol, 50% purity in ethyl acetate) drop wise at 0° C. The mixture was stirred for 1 hour at 0° C. then the reaction mixture was concentrated under reduced pressure to afford 1-88-8 (25 mg, crude) as a yellow gum. No further purification was performed.

A solution of 1-88-8 (22 mg, 0.032 mmol, split into two batches) in phosphorus oxychloride (2.3 mL, 25 mmol) was stirred at 0° C. for 2 hours. the reaction mixture was added to ice-water, and the pH adjusted to approximately pH=8 by the addition of a 1N sodium hydroxide solution. The mixture was extracted with ethyl acetate and the combined organic phase was washed with brine, dried over anhydrous sodium sulfate, filtered, and concentrated under reduced pressure.

The residue (two batches) was purified by preparative reverse phase HPLC using a water/acetonitrile gradient with 10 mM $NH_4HCO_3$ additive to afford 1-88 (4.9 mg, 5.4% yield) as a white solid. LCMS of 1-88: RT=1.673 min, m/z: 668.3 $[M+H]^+$.
Example 28—Synthesis of (5S,8S)-N-Cyclopentyl-8-(2-morpholinoethyl)-7,10-dioxo-2-oxa-6,9-diaza-1,3(1,3)-dibenzenacyclododecaphane-5-carboxamide (1-89)
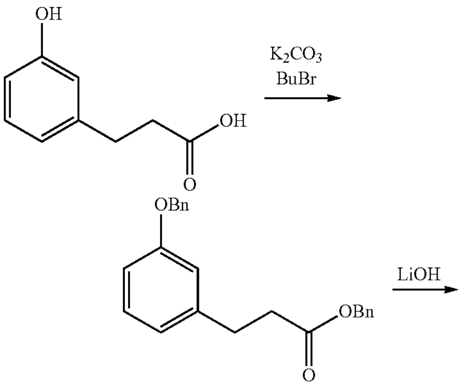
1-89-1
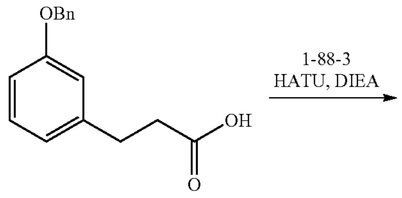
1-89-2
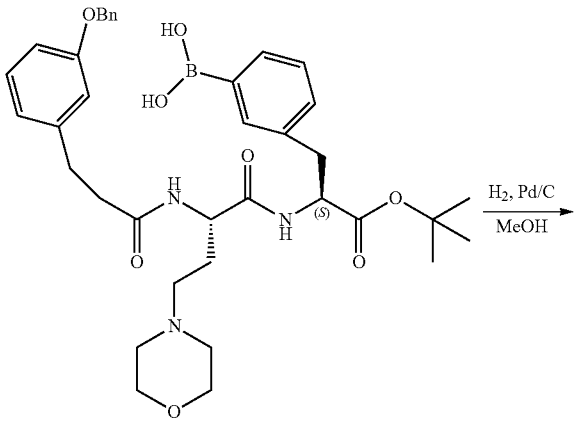
1-89-3
-continued
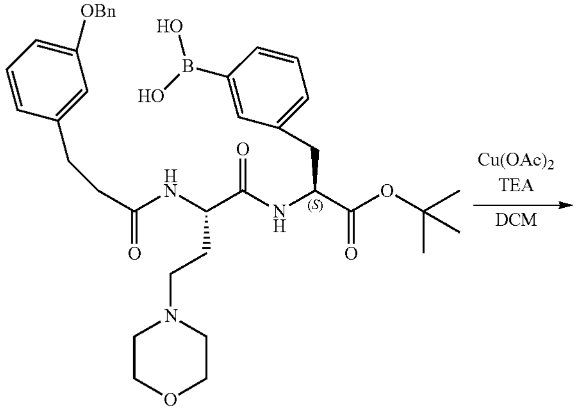
1-89-4
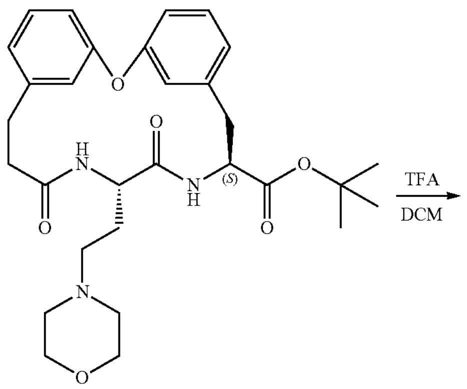
1-89-5
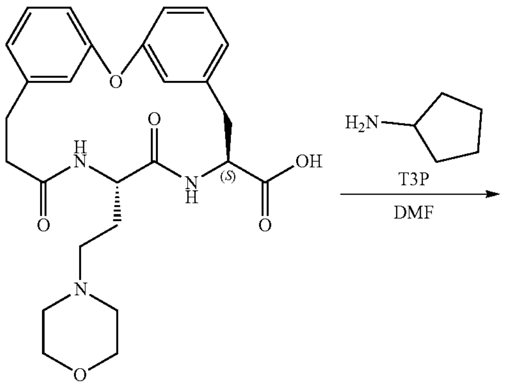
1-89-6
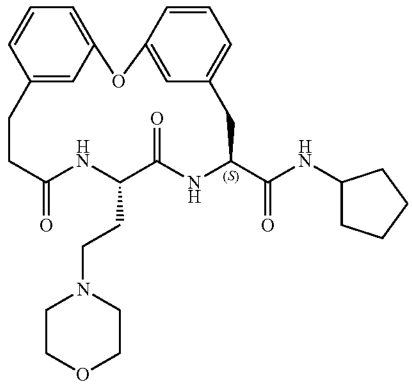
1-89

To a solution of compound 3-(3-hydroxyphenyl)propanoic acid (1.00 g, 6.02 mmol) in acetonitrile (10 mL) was added potassium carbonate (2.1 g, 15 mmol) and benzyl bromide (1.57 mL, 13.2 mmol) at 15° C. and the mixture was stirred at 80° C. for 10 hours. The reaction was poured into water (50 mL) and the solution was extracted with ethyl acetate. The combined organic layers were washed with brine, dried over anhydrous sodium sulfate, filtered, and concentrated under reduced pressure to provide 1-89-1 as a colorless oil (2.3 g, crude) which was used directly without further purification.

To a solution of 1-89-1 (2.3 g) in tetrahydrofuran (10 mL) and water (5 mL) was added lithium hydroxide monohydrate (0.477 g, 19.9 mmol) at 15° C. The solution was stirred at 15° C. for 3 hours then poured into water (100 mL) and the solution was washed with ethyl acetate. The organic layers were discarded. The pH of the aqueous phase was adjusted to pH=3 with a 1N HCl solution and the mixture was extracted with ethyl acetate. The combined organic layers were washed with brine, dried over anhydrous sodium sulfate, filtered, and concentrated under reduced pressure to provide 1-89-2 (1.36 g, 88.2% yield over 2 steps) as a white solid.

To a solution of 1-89-2 (0.300 g, 1.17 mmol) in N,N-dimethylacetamide (5 mL) was added N,N-diisopropylethylamine (0.611 mL, 3.51 mmol) and HATU (0.668 g, 1.76 mmol) at 0° C. The solution was stirred at 0° C. for 30 minutes then 1-88-3 (0.509 g, 1.17 mmol, TFA salt) was added to the solution at 0° C. and the solution was stirred at 0° C. for 1 hour. The solution was purified by reverse phase flash chromatography using water/acetonitrile with a TFA additive. The eluent was removed under reduced pressure to afford 1-89-3 (0.350 g, 35.3% yield, TFA salt) as a yellow solid.

To a solution of 1-89-3 (0.350 g, 0.520 mmol) in methanol (6 mL) was added 10% Pd/C (0.030 g) and 10% $Pd(OH)_2/C$ (0.030 g) at 20° C. under a nitrogen atmosphere. Then the mixture was stirred at 20° C. for 10 hours under a hydrogen atmosphere (15 psi). The reaction was filtered and the filter cake was washed with methanol. The solution was concentrated under reduced pressure to afford 1-89-4 (0.300 g, 98.9% yield) as a colorless gum.

To a solution of 1-89-4 (0.300 g, 0.514 mmol) in dichloromethane (30 mL) was added copper acetate (0.187 g, 1.03 mmol), triethylamine (0.36 mL, 2.6 mmol), and 4 Å molecular sieves (3 g) at 20° C. The mixture was stirred at 20° C. for 10 hours under an air atmosphere (15 psi). The reaction was filtered and the filter cake was washed with methanol (10 mL). The solution was concentrated under reduced pressure to remove volatile organics then the residue was diluted with water (10 mL) and the solution was extracted with ethyl acetate. The combined organic layers were washed with brine (10 mL), dried over anhydrous sodium sulfate, filtered, and concentrated under reduced pressure. The residue was purified by prep-HPLC using water/acetonitrile with an ammonium bicarbonate modifier to provide 1-89-5 (0.100 g, 36.0% yield) as a white solid.

To a solution of 1-89-5 (0.030 g, 0.056 mmol, split into 2 batches) in dichloromethane (2 mL) was added trifluoroacetic acid (1.0 mL, 13 mmol) at 25° C. and the solution was stirred at 25° C. for 7 hours. The reaction was concentrated under reduced pressure to provide 1-89-6 (0.031 g, crude, TFA salt) as a colorless gum.

To a solution of 1-89-6 (0.033 g, 0.055 mmol, TFA salt, split into 2 batches) in dichloromethane (1 mL) was added T3P (0.049 mL, 0.083 mmol, 50% solution in EtOAc) and N,N-diisopropylethylamine (0.029 mL, 0.17 mmol) at 0° C. The solution was stirred at 0° C. for 30 minutes then cyclopentylamine (0.008 mL, 0.080 mmol) was added to the solution at 0° C. and the solution was stirred at 0° C. for additional 2 hours. The reaction was concentrated under reduced pressure and the residue was purified by prep-HPLC using a gradient of acetonitrile in water with TFA additive. The pH of the isolated fractions was made alkaline using a saturated sodium bicarbonate solution and the solution was concentrated to remove volatile organics. The mixture was extracted with dichloromethane, dried over anhydrous sodium sulfate, filtered, and concentrated under reduced pressure to provide 1-89 (0.11 g, 35% yield) as a white solid. LCMS of 1-89: RT=2.316 min, m/z 549.3 $[M+H]^+$.

The following compounds were made using a similar synthetic route as described for compound 1-89:

Compound 1-90; LCMS: RT=2.227 min, m/z 565.3 $[M+H]^+$

Compound 1-91; LCMS: RT=2.323 min, m/z 589.3 $[M+H]^+$

Example 29—Synthesis of (5S,8S)-N-(2-Fluorobenzyl)-7,10-dioxo-8-(2-oxo-2-(pyrrolidin-1-yl)ethyl)-2-oxa-6,9-diaza-1(1,3),3(1,4)-dibenzenacyclododecaphane-5-carboxamide (2-01)

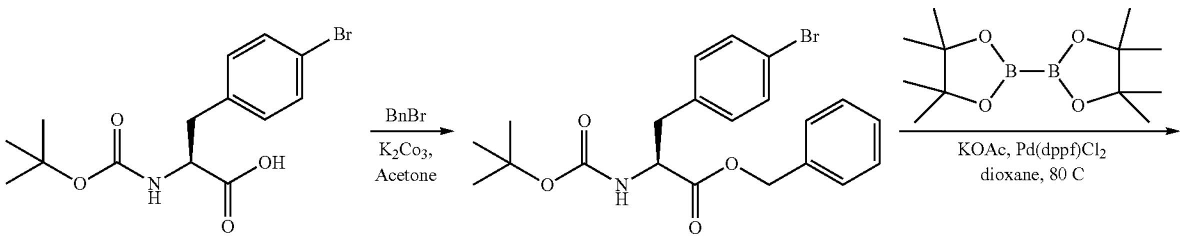

2-01-1

-continued
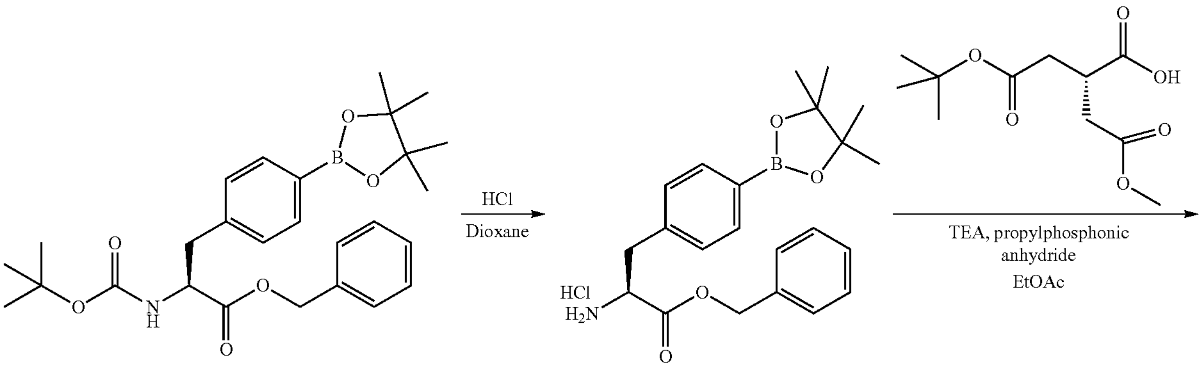
2-01-2 2-01-3
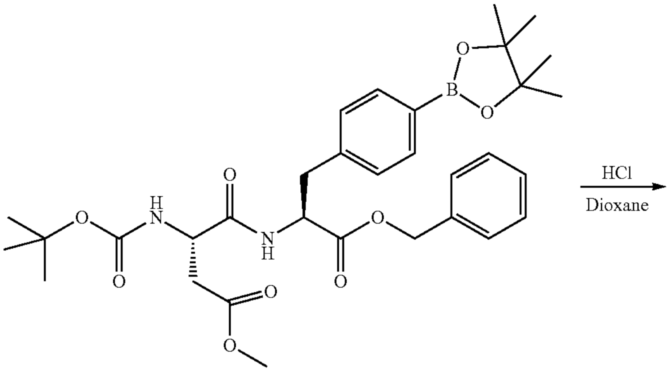
2-01-4
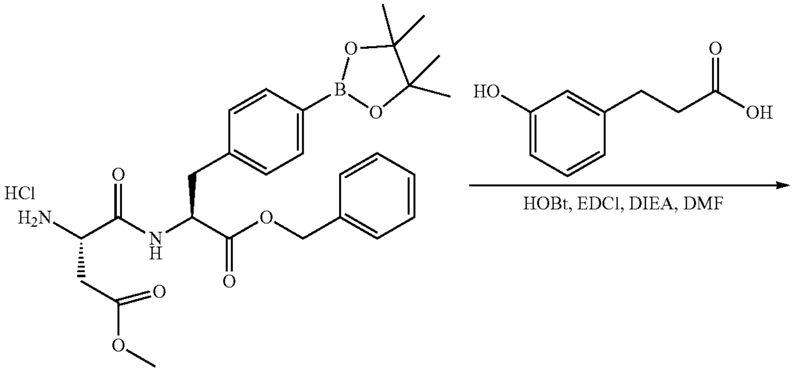
2-01-5
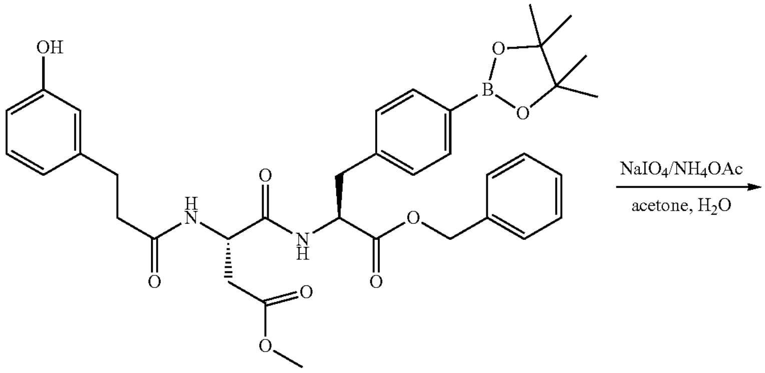
2-01-6

-continued
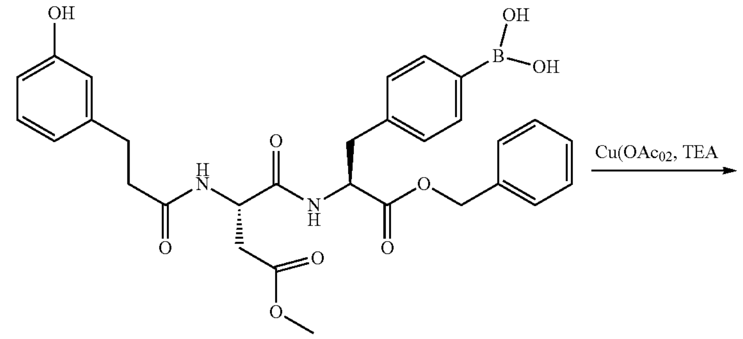
2-01-7
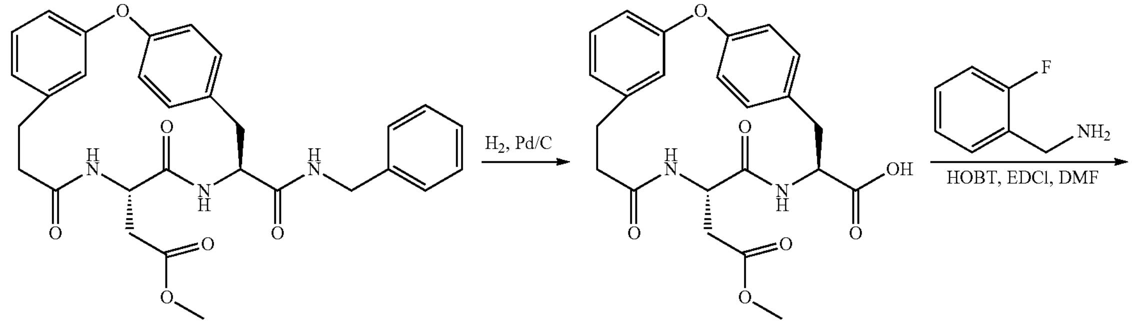
2-01-8 2-01-9
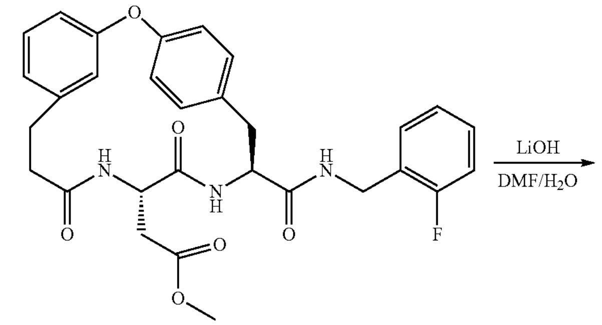
2-01-10
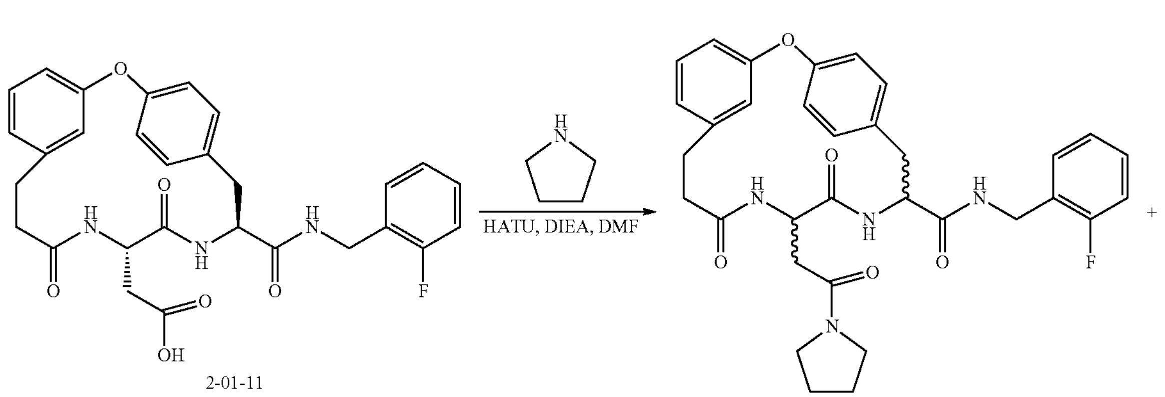
2-01-11 2-01-A -continued

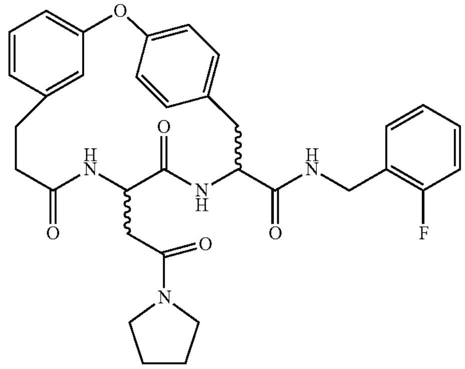

2-01-B

To a solution of (S)-3-(4-bromophenyl)-2-((tert-butoxycarbonyl)amino)propanoic acid (11 g, 32 mmol) in acetone (110 mL) was added potassium carbonate (4.86 g, 35.2 mmol) and benzyl bromide (6.01 g, 35.2 mmol). The reaction mixture was stirred at 26° C. for 48 hours. The residue was filtered and the filtrate was concentrated under reduced pressure to afford compound 2-01-1 (14 g, 96% yield) as a white solid.

To a mixture of compound 2-01-1 (21 g, 48 mmol), 4,4,4',4',5,5,5',5'-octamethyl-2,2'-bi(1,3,2-dioxaborolane) (12.28 g, 48.35 mmol), and potassium acetate (14.24 g, 145.1 mmol) in dioxane (210 mL) was added $Pd(dppf)Cl_2$ (3.54 g, 4.84 mmol) under nitrogen. The reaction mixture was degassed under vacuum, purged with nitrogen for 3 times then stirred at 80° C. for 12 hours under nitrogen. The reaction mixture was filtered and the filtrate was concentrated under reduced pressure. The residue was purified by silica gel chromatography (petroleum ether:ethyl acetate=10:1 to 3:1) to afford compound 2-01-2 (20 g, 82% yield) as a yellow oil.

To a mixture of compound 2-01-2 (5.3 g, 11 mmol) in dioxane (30 mL) was added a 4 M solution of hydrogen chloride in dioxane (50 mL, 200 mmol). The mixture was stirred at 26° C. for 4 hours then the reaction mixture was concentrated under reduced pressure to afford compound 2-01-3 (4.6 g, 85.1% yield, crude) as a yellow solid. No further purification was performed.

To a solution of (S)-2-((tert-butoxycarbonyl)amino)-4-methoxy-4-oxobutanoic acid (266 mg, 1.08 mmol) in ethyl acetate (5 mL) was added triethylamine (218 mg, 2.15 mmol) and propylphosphonic anhydride (914 mg, 1.44 mmol, 50% purity). Then compound 2-01-3 (300 mg, 718 μmol) was added into above reaction mixture and the resulting mixture was stirred at 26° C. for 4 hours. The reaction mixture was poured into water (15 mL), extracted with ethyl acetate (30 mL*3), dried over anhydrous sodium sulfate, filtered, and concentrated under reduced pressure. The residue was purified by silica gel chromatography (petroleum ether:ethyl acetate=10:1 to 3:1) to afford compound 2-01-4 (380 mg, 75.6% yield) as a yellow oil.

To a solution of compound 2-01-4 (3.0 g, 4.91 mmol) in dioxane (10 mL) was added a 4M solution of hydrogen chloride in dioxane (10 mL, 40 mmol). The reaction mixture was stirred at 25° C. for 2 hours then concentrated under reduced pressure to afford compound 2-01-5 (2.8 g, crude, HCl salt) as a white solid. No further purification was performed.

To a solution of 3-(3-hydroxyphenyl)propanoic acid (2.7 g, 4.9 mmol) in N,N-dimethylformamide (20 mL) was added 1-hydroxybenzotriazole (867 mg, 6.42 mmol), diisopropylethylamine (3.19 g, 24.7 mmol), and 1-(3-dimethylaminopropyl)-3-ethylcarbodiimide hydrochloride (1.23 g, 6.42 mmol). Then compound 2-01-5 (820 mg, 4.94 mmol) was added into above mixture at 0° C. After addition, the reaction mixture was stirred at 25° C. for 16 hours. The reaction mixture was poured into hydrochloric acid (1M, 50 mL) at 0° C. and extracted with EtOAc (50 mL*3). The combined organic phases were washed with brine (50 mL*3), dried over sodium sulphate, filtered, and concentrated under reduced pressure to afford compound 2-01-6 (3.2 g, crude) as yellow oil. No further purification was performed.

To a solution of compound 2-01-6 (3.2 g, 4.9 mmol) in acetone (15 mL) and water (10 mL) was added sodium periodate (3.12 g, 14.6 mmol) and ammonium acetate (1.12 g, 14.6 mmol). The mixture was stirred at 25° C. for 16 hours. The reaction mixture was poured into water (40 mL) and then extracted by ethyl acetate (40 mL*3). The combined organic phases were washed with brine (20 mL), dried over sodium sulfate, filtered, and concentrated under reduced pressure. The crude product was purified by reverse phase flash chromatography to afford compound 2-01-7 (920 mg, 32.1% yield) as a yellow solid.

To a solution of compound 2-01-7 (50 mg, 87 μmol) in dichloromethane (2 mL) was added triethylamine (9 mg, 90 μmol), copper acetate (16 mg, 87 μmol), and 4 Å molecular sieves (200 mg). The mixture was stirred at 20° C. for 16 hours under oxygen. The mixture was filtered and the filter cake was washed with isopropanol (5 mL). The filtrate was concentrated under reduced pressure and the residue was purified by silica gel chromatography column (petroleum ether:ethyl acetate=5:1 to 2:1) to afford compound 2-01-8 (36 mg, 68% yield) as a yellow brown solid.

To a solution of compound 2-01-8 (380 mg, 716 μmol) in dichloromethane (7 mL) and isopropanol (15 mL) was added 10% palladium on carbon (38 mg). The reaction mixture was degassed and purged with hydrogen three times and then the mixture was stirred at 25° C. for 2 hours under a hydrogen balloon. The mixture was filtered and then the filtrate was concentrated in vacuum to afford compound 2-01-9 (330 mg, crude) as a white solid. No further purification was performed.

To a solution of compound 2-01-9 (170 mg, 386 μmol) in N,N-dimethyl formamide (5 mL) was added diisopropylethylamine (100 mg, 772 μmol), 1-(3-dimethylaminopropyl)-

3-ethylcarbodiimide hydrochloride (96 mg, 502 μmol), and 1-hydroxybenzotriazole (68 mg, 502 μmol) at 0° C. under nitrogen. To the reaction mixture was added (2-fluorophenyl)methanamine (58 mg, 460 μmol) and the mixture was stirred at 25° C. for 6 hours. The mixture was poured into water (20 mL) and extracted with ethyl acetate (20 mL*3). The combined organic phases were washed with brine (20 mL), dried over sodium sulfate, filtered, and concentrated under reduced pressure to afford compound 2-01-10 (190 mg, 87% yield) as a yellow solid.

To a solution of compound 2-01-10 (180 mg, 329 μmol) in N,N-dimethyl formamide (3 mL) was added a solution of lithium hydroxide monohydrate (41 mg, 990 μmol) in water (3 mL) at 0° C. The reaction mixture was stirred at 26° C. for 3 hours. The reaction mixture was diluted with water (5 mL), acidified by hydrochloric acid (1M, 5 mL) at 0° C., and extracted with ethyl acetate (20 mL*3). The combined organic layer was washed with brine (20 mL*3), dried over anhydrous sodium sulfate, filtered, and concentrated under reduced pressure to afford compound 2-01-11 (190 mg, 71.4% yield) as a yellow solid. No further purification was performed.

To a solution of compound 2-01-11 (95 mg, 180 μmol) in N,N-dimethyl formamide (3 mL) was added N,N-diisopropylethylamine (69 mg, 530 μmol) and HATU (102 mg, 270 μmol) at 0° C. Then pyrrolidine (19 mg, 270 μmol) was added into above mixture and the reaction mixture was stirred at 26° C. for 3 hours. The reaction mixture was quenched with water (10 mL) and extracted with ethyl acetate (20 mL*3). The combined organic layer was washed with brine (20 mL*3), dried over anhydrous sodium sulfate, filtered, and concentrated under reduced pressure. The crude product was purified by prep-HPLC (column: Phenomenex Synergi C18, 150 mm*25 mm*10 um; mobile phase: [water (0.1% TFA)-ACN]; B %: 32%-62%, 13 min) to afford two diastereomer, 2-01-A (14.0 mg, 13.0% yield, $1^{st}$ eluting peak) as a yellow solid, and 2-01-B (19.0 mg, 18.2% yield, $2^{d}$ eluting peak) as a yellow solid. The relative stereochemistry was not determined. LCMS of 2-01-A: RT=1.999 min, m/z=587.3 $[MS+H]^+$ LCMS of 2-01-B: RT=2.144 min, m/z=587.2 $[M+H]^+$ Example 30—Synthesis of (5S,8S)-N-(2-Fluorobenzyl)-7,10-dioxo-8-(2-oxo-2-((R)-2-phenylpyrrolidin-1-yl)ethyl)-2-oxa-6,9-diaza-1(1,3),3(1,4)-dibenzenacyclododecaphane-5-carboxamide (2-02-A) and (5S,8S)-N-(2-Fluorobenzyl)-7,10-dioxo-8-(2-oxo-2-((R)-2-phenylpyrrolidin-1-yl)ethyl)-2-oxa-6,9-diaza-1(1,3),3(1,4)-dibenzenacyclododecaphane-5-carboxamide (2-02-B)

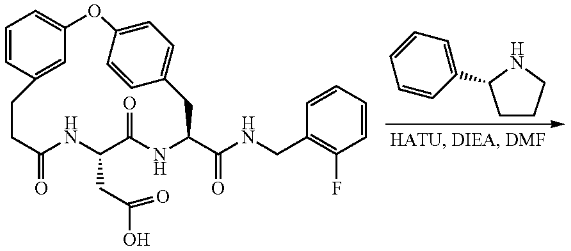

2-01-11

-continued

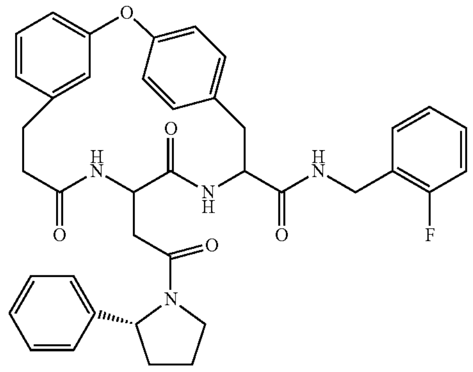

+

2-02-A

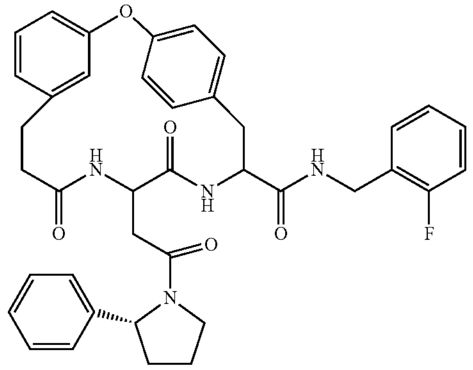

2-02-B

To a solution of compound 2-01-11 (95 mg, 178 μmol) in N,N-dimethyl formamide (3 mL) was added N,N-diisopropylethylamine (69 mg, 530 μmol) and HATU (102 mg, 267 μmol) at 0° C. Then (R)-2-phenylpyrrolidine (39 mg, 210 μmol) was added into above mixture and the resulting mixture was stirred at 26° C. for 3 hours. The reaction mixture was diluted with water (10 mL) and extracted with ethyl acetate (20 mL*3). The combined organic layers were washed with brine (20 mL*3), dried over anhydrous sodium sulfate, filtered, and concentrated under reduced pressure. The residue was purified by prep-HPLC (column: Phenomenex Synergi C18, 150 mm*25 mm*10 um; mobile phase: [water (0.1% TFA)-ACN]; B %: 40%-70%, 13 min) to afford a two diastereomers 2-02-A (3.0 mg, 2.4% yield, 1st eluting peak) as a yellow solid, and 2-02-B (15.0 mg, 12.7% yield, $2^{nd}$ eluting peak) as a yellow solid. The relative stereochemistry of was not assigned. LCMS of 2-02-A: RT=3.277 min, m/z=663.3 $[MS+H]^+$ LCMS of 2-02-B: RT=3.360 min, m/z=663.3 $[M+H]^+$.

Example 31—Synthesis of N-(Naphthalen-1-ylmethyl)-7,10-dioxo-8-(2-oxo-2-(pyrrolidin-1-yl)ethyl)-2-oxa-6,9-diaza-1(1,3),3(1,4)-dibenzenacyclododecaphane-5-carboxamide (2-03-A and 2-03-B)

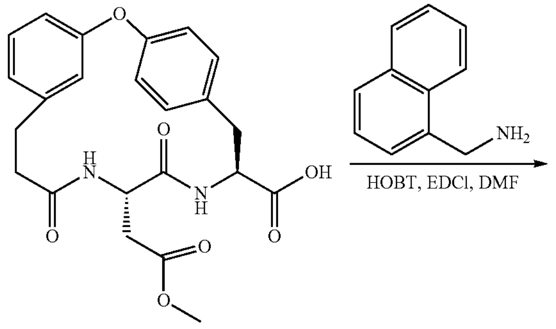

2-01-9

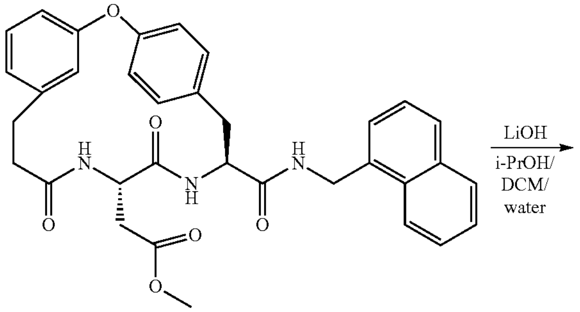

2-03-1

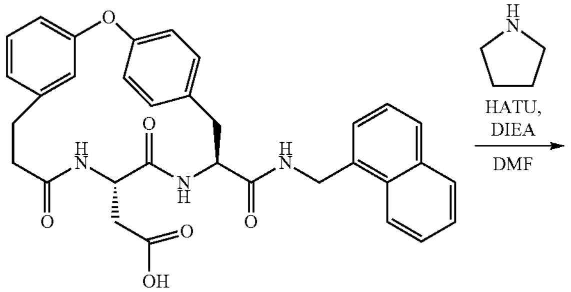

2-03-2

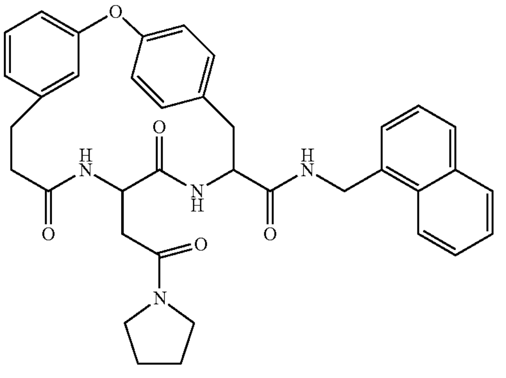

+

2-03-A

-continued

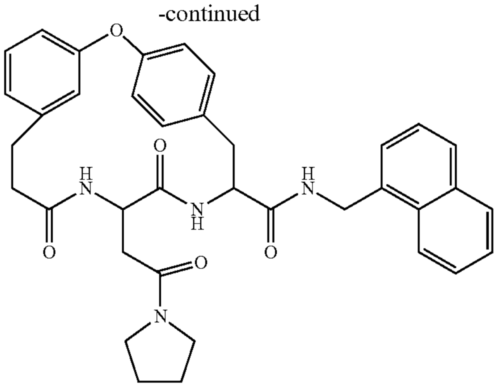

2-03-B

To a solution of compound 2-01-9 (200 mg, 454 μmol) in N,N-dimethyl formamide (5 mL) was added diisopropylethylamine (117 mg, 908 μmol), HOBt (80 mg, 590 μmol), and EDCI (113 mg, 590 μmol) at 0° C. under nitrogen. The mixture was degassed and purged with nitrogen 3 times. To this was added naphthalen-1-ylmethanamine (86 mg, 540 μmol) and the mixture was stirred at 25° C. for 5 hours. The mixture was poured into hydrochloric acid (1M, 20 mL) and then extracted by ethyl acetate (20 mL*3). The combined organic phases were washed by brine (20 mL), dried over sodium sulfate, filtered, and concentrated under reduced pressure to afford compound 2-03-1 (175 mg, 60.9% yield).

To a solution of compound 2-03-1 (170 mg, 290 μmol) in a mixture of dichloromethane (7 mL), isopropanol (15 mL) and water (1 mL) was added lithium hydroxide (28 mg, 1.2 mmol). The mixture was stirred at 25° C. for 3 hours. The mixture was poured into a solution of hydrochloric acid (1M, 5 mL) and water (20 mL) and then freeze dried to afford compound 2-03-2 (170 mg, 92% yield) as a white solid. No additional purification was performed.

To a solution of compound 2-03-2 (120 mg, 210 μmol) in N,N-dimethyl formamide (6 mL) was added diisopropylethylamine (82 mg, 640 μmol) and HATU (161 mg, 424 μmol). The mixture was stirred at 0° C. for 0.25 hour under nitrogen and then pyrrolidine (23 mg, 320 μmol) was added to above reaction mixture. The mixture was stirred at 0° C. for 0.5 hour then poured into a mixture of water (20 mL) and hydrochloric acid (1M, 2 mL). The mixture was extracted by ethyl acetate (20 mL*3) and the combined organic phases were washed by brine (20 mL), dried over sodium sulfate, filtered, and concentrated under reduced pressure. The residue was purified by prep-HPLC (column: Phenomenex Synergi C18 150 mm*25 mm*10 um; mobile phase: [water (0.10% TFA)-ACN]; B %: 38%-68%, 13 min) to afford two diasteromers 2-03-A (17 mg, 13% yield, 1st eluting peak) as a white solid, and 2-03-B (11 mg, 8.3% yield, 2nd eluting peak) as a white solid. The relative stereochemistry was not assigned. LCMS of 2-03-A: RT=3.076 min; m/z=619.3 $[MS+H]^+$. LCMS of 2-03-B: RT=3.175 min; m/z=619.3 $[M+H]^+$.

Example 32—Synthesis of (5S,8S,11S)-11-Acetamido-N-(2-fluorobenzyl)-7,10-dioxo-8-(2-oxo-2-((R)-2-phenylpyrrolidin-1-yl)ethyl)-2-oxa-6,9-diaza-1(1,3),3(1,4)-dibenzenacyclododecaphane-5-carboxamide (2-04)
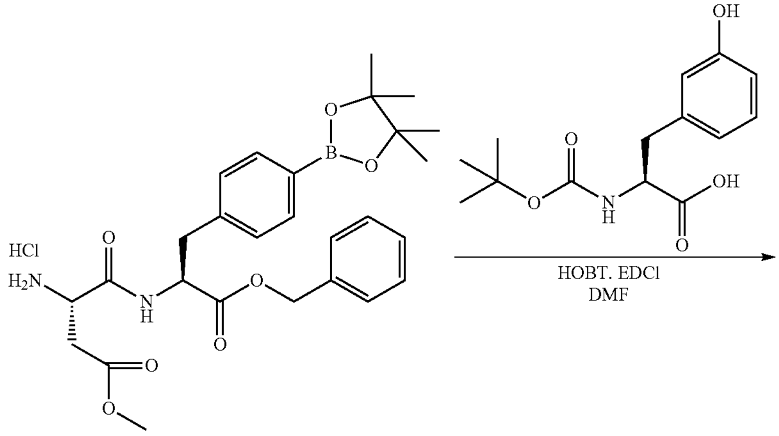
2-01-5
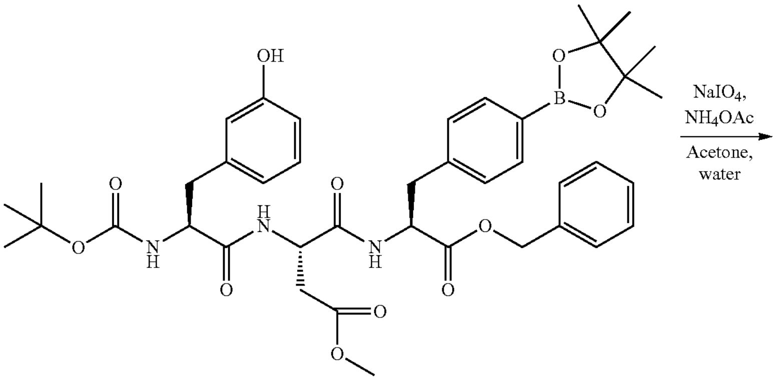
2-04-1
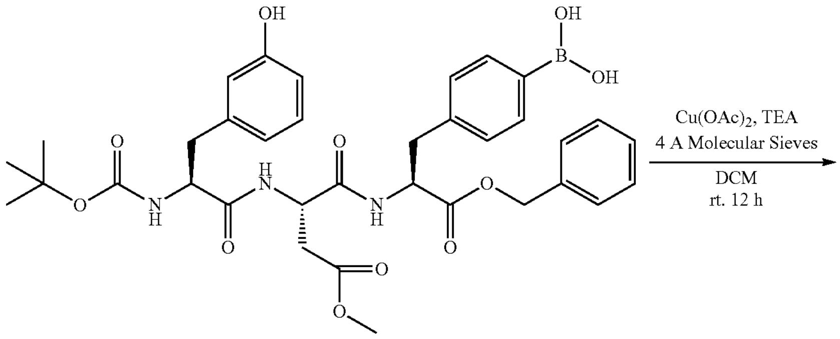
2-04-2

-continued
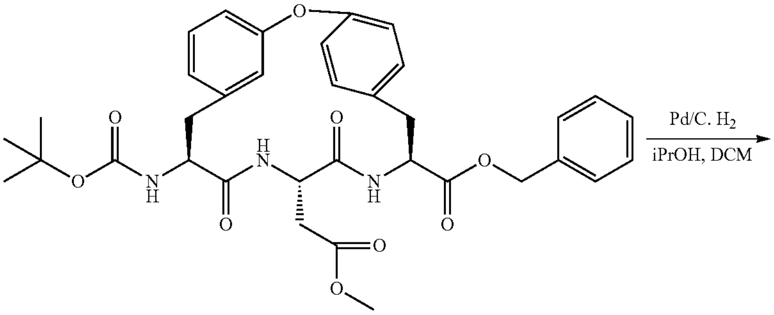
2-04-3
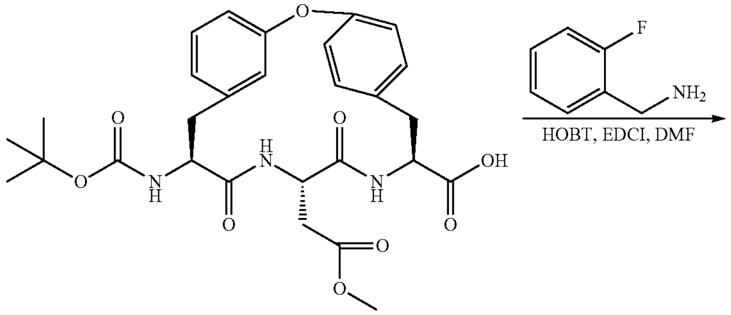
2-04-4
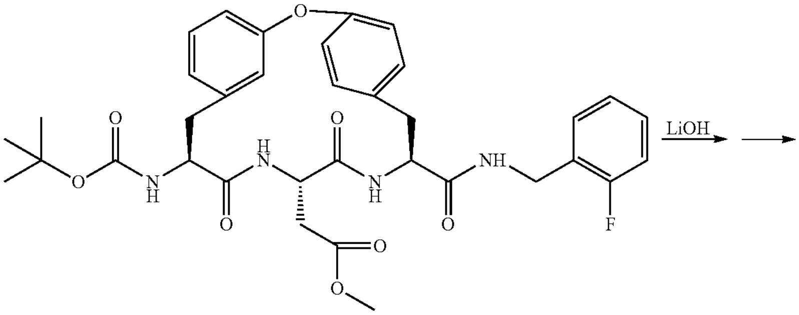
2-04-5
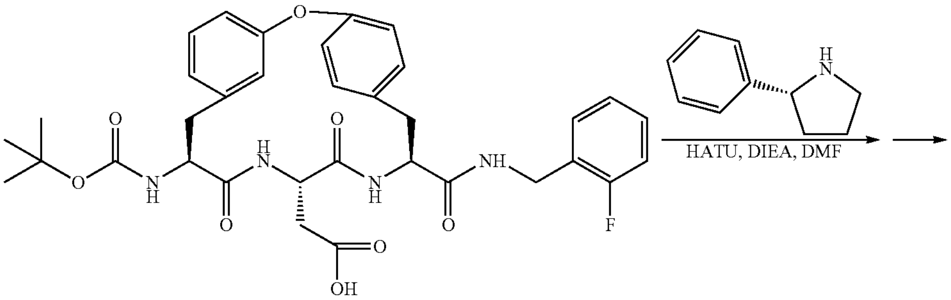
2-04-6

-continued

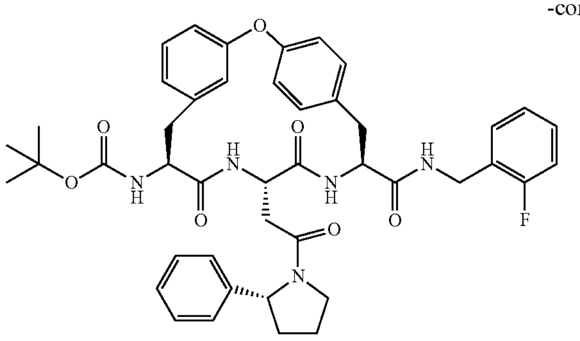

+

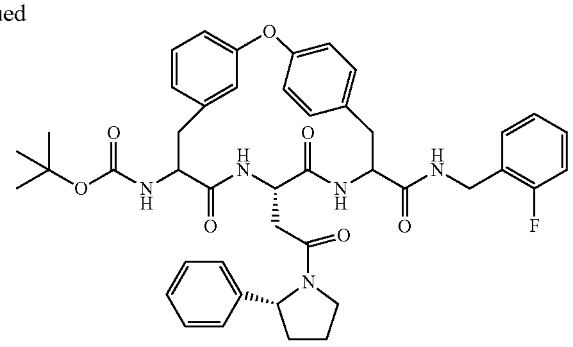

2-04-7

2-04-8

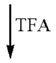

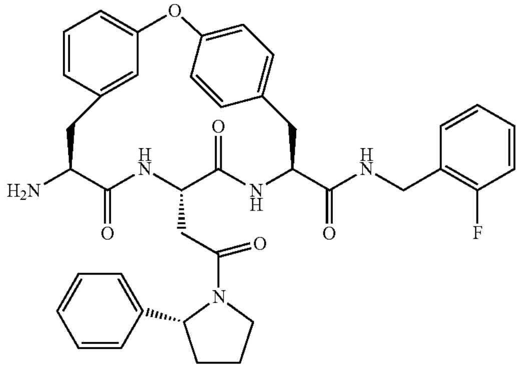

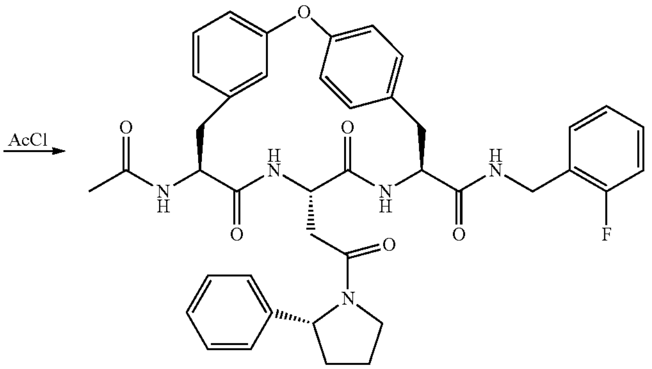

2-04-9

2-04

To a solution of compound boc-meta-tryrosine (3.52 g, 6.44 mmol), 1-ethyl-3-(3-dimethyl aminopropyl)carbodiimide hydrochloride (1.72 g, 8.95 mmol), 1-hydroxy benzotriazole (1.21 g, 8.95 mmol), and diisopropylethylamine (4.46 g, 34.5 mmol) in N,N-dimethylformamide (30 mL) was added compound 2-01-5 (2.14 g, 7.60 mmol, 1.18 eq) at 0° C. under nitrogen. The mixture was stirred at 25° C. for 16 hours then diluted with water (50 mL) and extracted by ethyl acetate (100 mL*3). The combined organic phases were washed with brine (50 mL), dried over sodium sulfate, filtered, and concentrated in vacuum to give compound 2-04-1 (6 g, crude) as red oil, which was used without further purification.

To a solution of compound 2-04-1 (5.0 g, 6.5 mmol) in acetone (50 mL) was added a mixture of sodium periodate (4.15 g, 19.4 mmol) and ammonium acetate (1.49 g, 19.4 mmol) in water (40 mL) at 25° C. and the reaction mixture was stirred for 12 hours at 25° C. The reaction mixture was diluted with water (50 mL) and extracted with ethyl acetate (100 mL*3). The combined organic phases were washed with brine (150 mL*2), dried over anhydrous sodium sulfate, filtered, and concentrated in vacuum. The residue was purified by reverse phase flash chromatography to afford compound 2-04-2 (1.4 g, 31% yield) as a yellow solid.

To a solution of compound 2-04-2 (1.5 g, 2.2 mmol) in dichloromethane (150 mL) was added copper acetate (394 mg, 2.17 mmol), triethylamine (2.2 g, 22 mmol), and 4 Å molecular sieves (2.0 g, 430 μmol) at 25° C. and the reaction mixture was stirred at 25° C. for 12 hours under oxygen. The reaction mixture was filtered and the filtrate was concentrated under reduced pressure. The residue was purified by silica gel chromatography to afford compound 2-04-3 (620 mg, 43.1% yield) as a yellow solid.

To a solution of compound 2-04-3 (600 mg, 929 μmol) in isopropanol (30 mL) and dichloromethane (5 mL) was added 5% palladium on carbon (200 mg) under nitrogen. The suspension was degassed under reduced pressure and purged with hydrogen several times. The mixture was stirred at 25° C. for 12 hours under hydrogen (15 psi). then filtered and the filtrate was concentrated under reduced pressure to afford compound 2-04-4 (385 mg, 73.5% yield) as a yellow solid. No further purification was performed.

To a solution of compound 2-04-4 (600 mg, 1.08 mmol) in N,N-dimethyl formamide (15 mL) was added 1-hydroxybenzotriazole (190 mg, 1.4 mmol), 1-ethyl-3-(3-dimethylaminopropyl)carbodiimide hydrochloride (269 mg, 1.40 mmol), and diisopropylethylamine (279 mg, 2.16 mmol) at 0° C. To this mixture (2-fluorophenyl)methanamine (162 mg, 1.30 mmol, 1.2 eq) was added and the reaction mixture was stirred at 25° C. for 12 hours. The mixture was diluted with water (40 mL) causing a solid to precipitate from solution. The formed solid was collected by filtration and dried to afford compound 2-04-5 (750 mg, 92.6% yield) as a yellow solid.

To a solution of compound 2-04-5 (1.2 g, 1.81 mmol) in N,N-dimethyl formamide (15 mL) and water (10 mL) was added lithium hydroxide (228 mg, 5.43 mmol) at 0° C. and the reaction mixture was stirred at 0° C. for 30 min. The reaction mixture was acidified with hydrochloric acid (0.5M) to pH=4-5. The reaction mixture was filtered and the cake was dried under reduced pressure to afford compound 2-04-6 (1.2 g, 97.8% yield) as a yellow solid.

To a solution of compound 2-04-6 (500 mg, 771 μmol) in N,N-dimethyl formamide (10 mL) was added 1-ethyl-3-(3-dimethylaminopropyl)carbodiimidehydrochloride (222 mg, 1.16 mmol), 1-hydroxybenzotriazole (156 mg, 1.16 mmol), and diisopropylethylamine (398 mg, 3.08 mmol) at 0° C. followed by (R)-2-phenylpyrrolidine (156 mg, 848 μmol). The reaction mixture was stirred at 25° C. for 12 hours and then acidified with hydrochloric acid (0.5M) until pH=4-5. The reaction mixture was filtered and the filter cake was dried under reduced pressure. The residue was purified by prep-HPLC (HCl condition, column: PhenomenexSynergi C18, 150 mm*25 mm*10 um, mobile phase: [water (0.05% HCl)-ACN]; B %: 56%-76%, 7.8 min) to give two diastereomers, compound 2-04-7 (260 mg, 43.4% yield) as a white solid, and 2-04-8 (130 mg, 21.7% yield) as a white solid. The relative stereochemistry of 2-07-7 was assigned based on isolated yield. The relative stereochemistry was not assigned.

To a solution of 2-04-7 (270 mg, 347 μmol) in dichloromethane (6 mL) was added trifluoroacetic acid (3.0 mL, 41 mmol) at 25° C. and the reaction mixture was stirred at 25° C. for 1 hour. The reaction mixture was concentrated in vacuum to afford compound 2-04-9 (300 mg, crude, TFA salt) as a yellow oil, which was used without further purification.

To a solution of compound 2-04-9 (120 mg, 152 μmol) and triethylamine (46 mg, 450 μmol) in dichloromethane (3 mL) was added acetyl chloride (15 mg, 300 μmol) at 0° C. and the reaction mixture was stirred at 25° C. for 0.5 hour. The reaction mixture was concentrated under reduced pressure and the residue was dissolved in water (10 mL) then extracted with ethyl acetate (20 mL*2). The combined organic phases were washed with brine (20 mL*2), dried over anhydrous sodium sulfate, filtered, and concentrated under reduced pressure. The residue was purified by prep-HPLC (HCl condition, column: PhenomenexSynergi C18 150 mm*25 mm*10 um, mobile phase: [water (0.05% HCl)-ACN]; B %: 45%-65%, 7.8 min) to afford 2-04 (60.00 mg, 55.00% yield) as a white solid. LCMS of 2-04: RT=2.244 min; m/z=720.3 [M+H]+.

Example 33—Synthesis of 11-Acetamido-N-(2-fluorobenzyl)-7,10-dioxo-8-(2-oxo-2-((R)-2-phenylpyrrolidin-1-yl)ethyl)-2-oxa-6,9-diaza-1(1,3),3(1,4)-dibenzenacyclododecaphane-5-carboxamide (2-05)

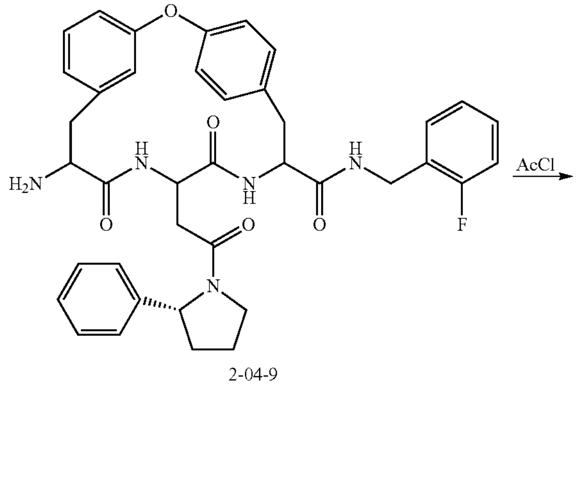

2-04-9

-continued

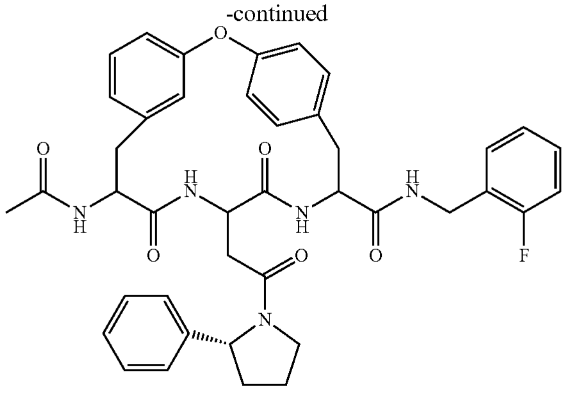

2-05

To a solution of compound 2-04-9 (60 mg, 76 μmol) and triethylamine (23 mg, 230 μmol) in N,N-dimethylformamide (500 uL) was added acetyl chloride (8.0 mg, 150 μmol) in dichloromethane (500 uL) at 0° C. and the reaction mixture was stirred for 20 min at 25° C. The reaction mixture was diluted with water (5 mL) and extracted with ethyl acetate (5 mL*3). The combined organic phases were washed with brine (10 mL*3), dried over anhydrous sodium sulfate, filtered, and concentrated under reduced pressure. The residue was purified by prep-HPLC (HCl condition, column: PhenomenexSynergi C18 150 mm*25 mm*10 um, mobile phase: [water (0.05% HCl)-ACN]; B %: 45%-65%, 7.8 min) to afford 2-05 (23.4 mg, 43% yield) as a white solid. LCMS of 2-05: RT=2.153 min; m/z=720.3 [M+H]+.

Example 34—Synthesis of (5S,8S,11S)-11-Benzamido-N-(2-fluorobenzyl)-7,10-dioxo-8-(2-oxo-2-((R)-2-phenylpyrrolidin-1-yl)ethyl)-2-oxa-6,9-diaza-1(1,3),3(1,4)-dibenzenacyclododecaphane-5-carboxamide (2-06)

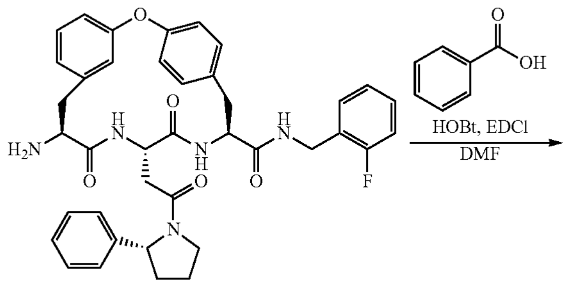

2-04-9

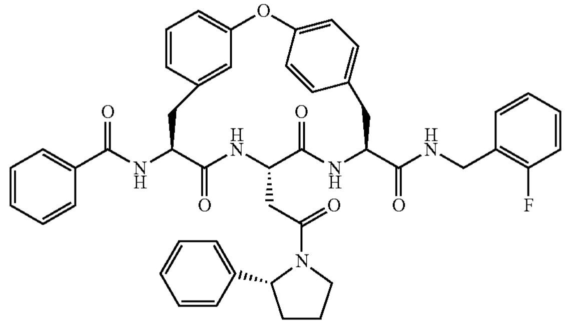

2-06

To a solution of benzoic acid (25 mg, 210 μmol), 1-hydroxybenzotriazole (38 mg, 280 μmol), 1-ethyl-3-(3-dimethylaminopropyl)carbodiimide hydrochloride (54 mg, 280 μmol), and diisopropylethylamine (73 mg, 570 μmol) in N,N-dimethylformamide (4 mL) was added compound 2-07-4 (150 mg, 189 μmol) at 25° C. and the reaction mixture was stirred at 25° C. for 12 hours. The reaction mixture was diluted with water (10 mL) and extracted with ethyl acetate (15 mL*3). The combined organic phases were washed with brine (20 mL*3), dried over anhydrous sodium sulfate, filtered, and concentrated under reduced pressure. The residue was purified by prep-HPLC (HCl condition, column: PhenomenexSynergi C18, 150 mm*25 mm*10 um, mobile phase: [water (0.05% HCl)-ACN]; B %: 52%-72%, 7.8 min) to afford 2-06 (69.2 mg, 46.5% yield) as a white solid. LCMS of 2-06: RT=2.484 min; m/z=782.3 [M+H]+.

Example 35—Synthesis of 11-Benzamido-N-(2-fluorobenzyl)-7,10-dioxo-8-(2-oxo-2-(-2-phenylpyrrolidin-1-yl)ethyl)-2-oxa-6,9-diaza-1(1,3),3(1,4)-dibenzenacyclododecaphane-5-carboxamide (2-07)

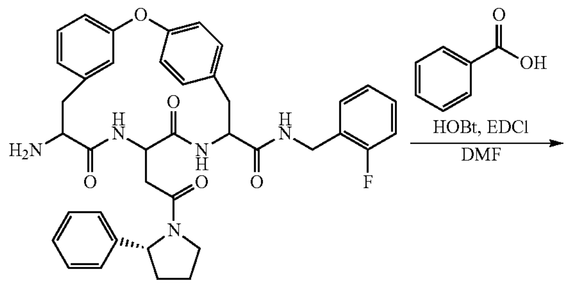

2-05-1

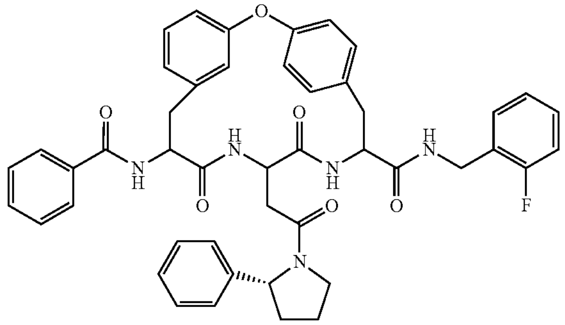

2-07

To a solution of benzoic acid (10 mg, 83 μmol), 1-hydroxybenzotriazole (15 mg, 110 μmol), 1-ethyl-3-(3-dimethylaminopropyl)carbodiimide hydrochloride (22 mg, 110 μmol), and diisopropylethylamine (29 mg, 230 μmol) in N,N-dimethylformamide (1 mL) was added compound 2-05-1 (60 mg, 76 μmol) at 25° C. and the reaction mixture was stirred at 25° C. for 12 hours. The reaction mixture was diluted with water (5 mL) and extracted with ethyl acetate (5 mL*3). The combined organic phases were washed with brine (10 mL*3), dried over anhydrous sodium sulfate, filtered, and concentrated under reduced pressure. The residue was purified by prep-HPLC (HCl condition, column: PhenomenexSynergi C18 150 mm*25 mm*10 um, mobile phase: [water (0.05% HCl)-ACN]; B %: 50%-70%, 7.8 min) to afford 2-07 (17.6 mg, 29.4% yield) as a white solid. LCMS of 2-07: RT=2.433 min; m/z=782.3 [M+H]+.

Example 36—Synthesis of (7S,10S,13S,E)-13-Acetamido-9,12-dioxo-10-phenethyl-N-(2,2,2-trifluoroethyl)-2-oxa-8,11-diaza-1(1,3)-benzenacyclotetradecaphan-4-ene-7-carboxamide (3-01)

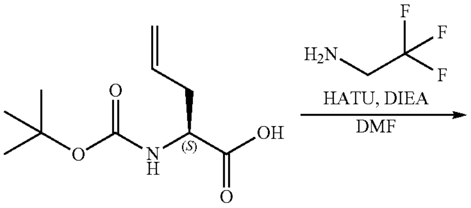

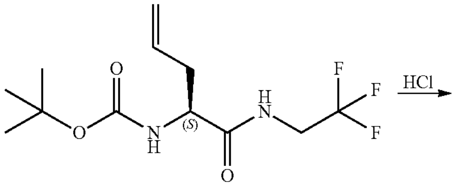

3-01-1

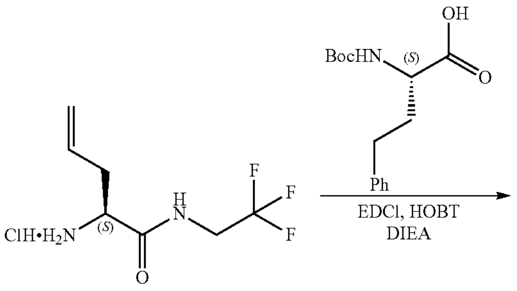

3-01-2

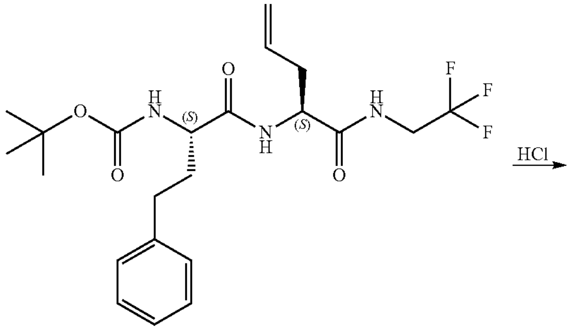

3-01-3

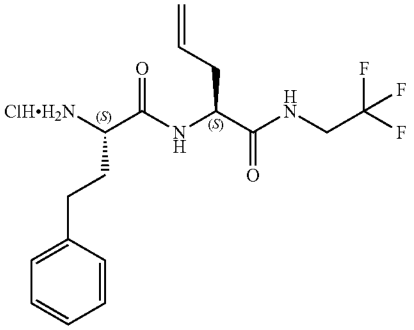

3-01-4

-continued

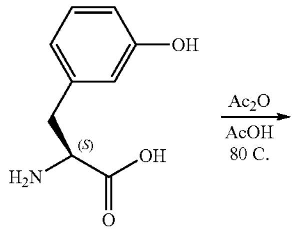

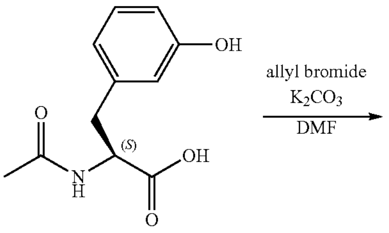

3-01-5

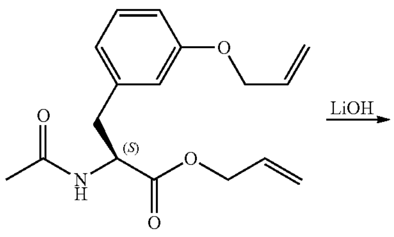

3-01-6

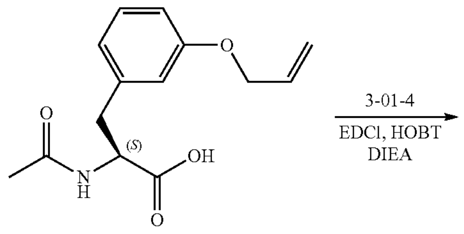

3-01-7

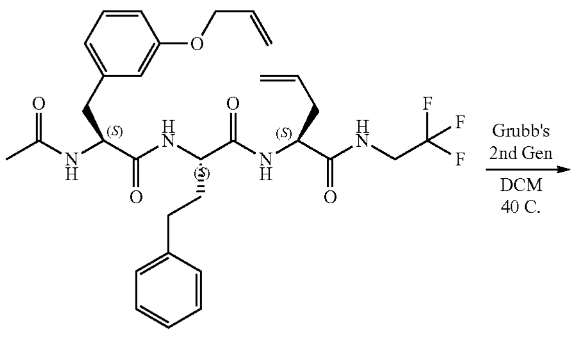

3-01-8

-continued

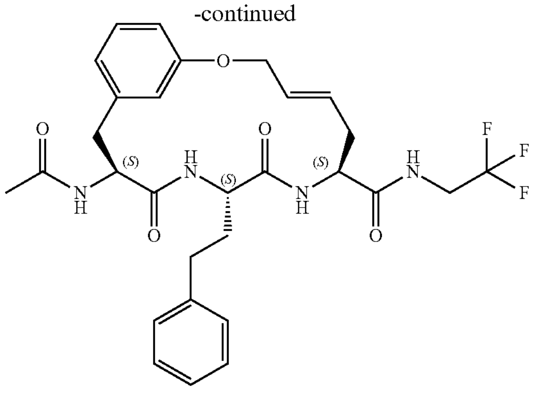

3-01

HATU (1.93 g, 5.12 mmol) was added to a mixture of (2S)-2-(tert-butoxycarbonylamino)pent-4-enoic acid (1.00 g, 4.65 mmol), 2,2,2-trifluoroethanamine (506 mg, 5.12 mmol), and Hunig's base (1.80 g, 13.95 mmol) in DMF (40.00 mL) at 0° C. The mixture was stirred at room temperature for 3 hours. DMF was removed under reduced pressure and the residue was dissolved with EtOAc. The organic layer was washed with water and brine, dried with anhydrous sodium sulfate and concentrated. The residue was collected by filtration, washed with water followed by hexanes, then dried under reduced pressure to afford 3-01-1 (762 mg, 55.3% yield) as a colorless solid.

A 4 M solution of HCl in dioxane (0.66 mL, 2.55 mmol) was added to 3-01-1 (762.00 mg, 2.57 mmol) at room temperature. The mixture was stirred for 2 hours then the solvent was removed under reduced pressure to afford 3-01-2 (571 mg, 113% yield, crude) as a slightly yellow solid. The crude product was subjected to the next reaction without further purification.

1-(3-Dimethylaminopropyl)-3-ethylcarbodiimide hydrochloride (542 mg, 2.83 mmol) was added to a mixture of (2S)-2-(tert-butoxycarbonylamino)-4-phenyl-butanoic acid (790 mg, 2.83 mmol), 3-01-2 (504 mg, 2.57 mmol), HOBt (382 mg, 2.83 mmol), and Hunig's base (1.35 mL, 7.71 mmol) in a mixture of DCM (10.00 mL) and DMF (10.00 mL) at room temperature. The mixture was stirred at room temperature overnight. The mixture was poured into water and extracted with DCM. The organic layer was washed with brine, dried over anhydrous sodium sulfate, and concentrated under reduced pressure. The residue was purified by column chromatography ($CH_2Cl_2$/EtOAc=90:10 to 10:90) to afford 3-01-3 (448 mg, 38.1% yield) as a colorless solid.

A 4 M solution of HCl in dioxane (979 umol) was added to a solution of 3-01-3 (448 mg, 979 μmol) at room temperature. The mixture was stirred for 1 hour and then the solvent was removed under reduced pressure to afford 3-01-4 (331 mg, 94.6% yield, crude) as a white solid. The crude product was used in the next reaction without further purification.

Acetic anhydride (1.40 g, 13.2 mmol) was added to a suspension of (2S)-2-amino-3-(3-hydroxyphenyl)propanoic acid (2.00 g, 11.0 mmol) in AcOH (60.00 mL) at room temperature. The mixture was stirred at 80° C. for 5 hours then concentrated under reduced pressure to afford 3-01-5 (2.46 g, 100% yield, crude) as an orange oil. The crude product was used in the next reaction without further purification.

Allyl bromide (4.01 g, 33.12 mmol) was added to a mixture of 3-01-5 (2.46 g, 11.0 mmol) and potassium carbonate (6.10 g, 44.2 mmol) in DMF (50 mL) at room temperature. The mixture was stirred at room temperature overnight then filtered and the filtrate was concentrated in vacuo. The residue was purified by flash silica gel column chromatography and the eluent was removed under reduced pressure to afford 3-01-6 (2.48 g, 74.1% yield) as an orange oil.

Lithium hydroxide (587 mg, 24.5 mmol) was added to a solution of 3-01-6 (2.48 g, 8.18 mmol) in a mixture of THF (200 mL) and water (50.00 mL) at room temperature. The mixture was stirred at room temperature for 5 hours. The THF was removed under reduced pressure and the aqueous solution was acidified to pH2 with 1N HCl (aq). The mixture was extracted with EtOAc. The organic layer was washed with brine, dried over anhydrous sodium sulfate, and concentrated under reduced pressure to afford 3-01-7 (1.96 g, 91.0% yield) as a colorless oil.

1-(3-Dimethylaminopropyl)-3-ethylcarbodiimide hydrochloride (195.31 mg, 1.02 mmol) was added to a solution of 3-01-7 (331 mg, 926 μmol), 3-01-4 (268 mg, 1.02 mmol), HOBt (138 mg, 1.02 mmol), and Hunig's base (485 μL, 2.78 mmol) in DMF (10 mL) at room temperature. The mixture was stirred at room temperature overnight. The reaction mixture was quenched with water at 0° C. and the precipitate was collected by filtration. The residue was purified by column chromatography ($CH_2Cl_2$:MeOH=100:0 to 80:20) to afford 3-01-8 (385 mg, 69.0% yield) as a white solid.

$2^{nd}$ generation Grubbs catalyst (28 mg, 33 μmol) was added to the suspension of 3-01-8 (98 mg, 160 μmol) in DCM (30 mL) at room temperature. The mixture was stirred at 40° C. for 4 hours. The solvent was removed under reduced pressure and the residue was purified by column chromatography (EtOAc/$CH_2Cl_2$=10:90 to 90:10). The eluent was concentrated under reduced pressure and the residue was collected by filtration then washed with EtOAc to afford 3-01 (44 mg, 47% yield) as a slightly purple solid. A portion (22 mg) was further purified by prep-HPLC (column: Bridge 18C 150*19 5 u; mobile phase: [water (0.1% formic acid)-MeCN(0.1% formic acid)]; B %: 5%-95%, 20 min) to afford the desired product (0.9 mg) as a white solid. LCMS for 3-01: RT: 1.96 min, m/z 575.44 $[M+H]^+$.

Example 37—Synthesis of (3S,6S,9S)-3-Acetamido-4,7-dioxo-6-(2-phenylethyl)-N-(2,2,2-trifluoroethyl)-14-oxa-5,8-diazabicyclo[13.3.1]nonadeca-1(19),15,17-triene-9-carboxamide (3-02)

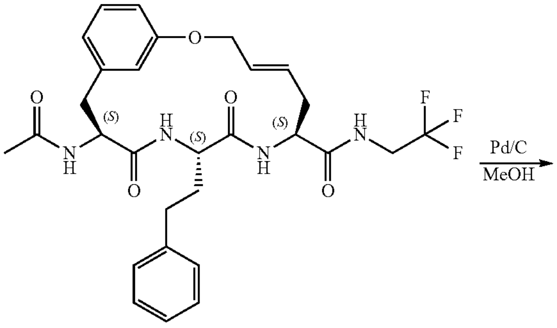

3-01

-continued

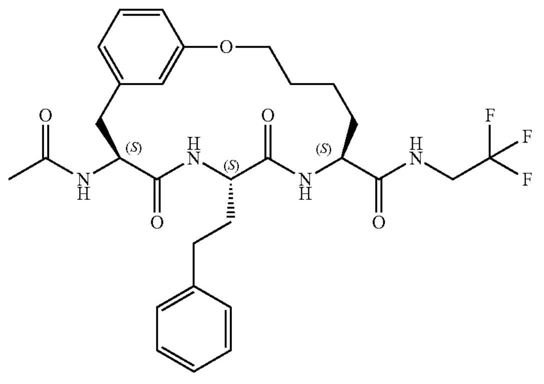

3-02

Solid Pd/C (5.01 mg, 47.1 umol) was added to a solution of 3-01 (22 mg, 38 μmol) in MeOH (1.00 mL) at room temperature. The mixture was stirred at room temperature for 4 hours under a hydrogen atmosphere. The catalyst was removed by filtration and the filtrate was concentrated under reduced pressure. The residue was purified by pre-HPLC (column: Bridge 18C 150*19 5 u; mobile phase: [water (0.1% formic acid)-MeCN(0.1% formic acid)]; B %: 5%-95%, 20 min) to afford 3-02 (3.10 mg, 14.0% yield) as a white solid. LCMS for 3-02: RT: 1.94 min, m/z 577.45 $[M+H]^+$.

Example 38—Synthesis of (3S,6S,9S)-9-Acetamido-5,8-dioxo-6-(2-phenylethyl)-N-(2,2,2-trifluoroethyl)-14-oxa-4,7-diazabicyclo[13.3.1]nonadeca-1(19),15,17-triene-3-carboxamide (3-03)

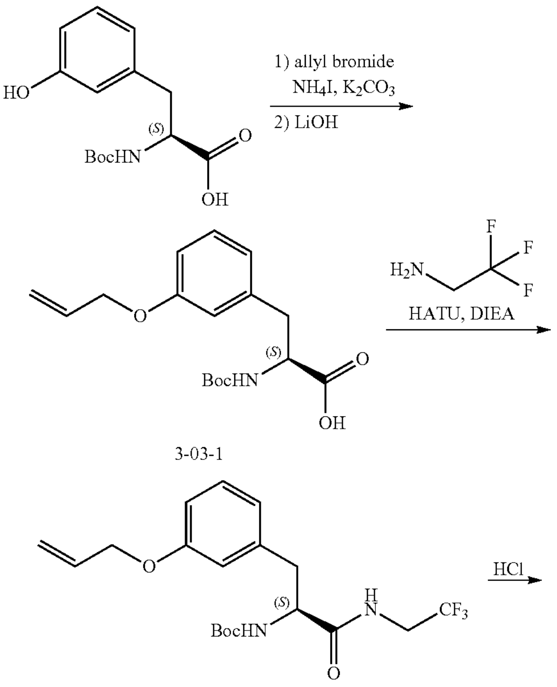

3-03-1

3-03-2

-continued

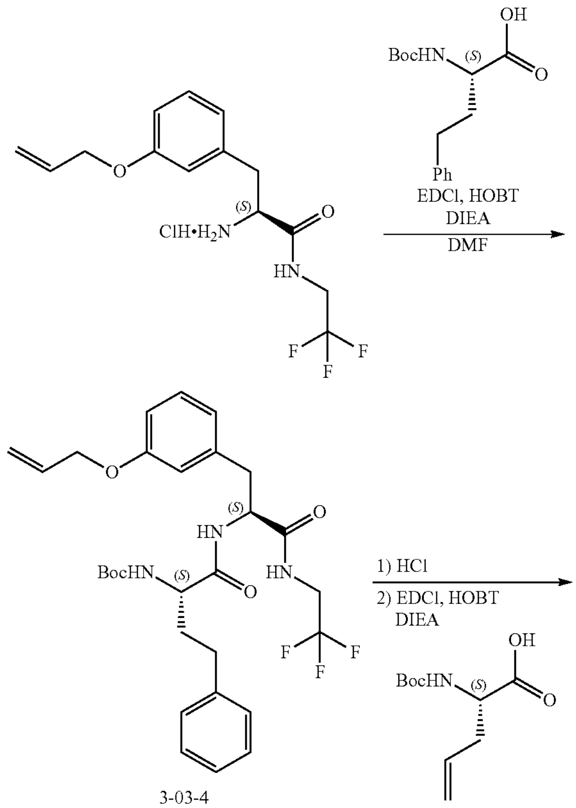

3-03-4

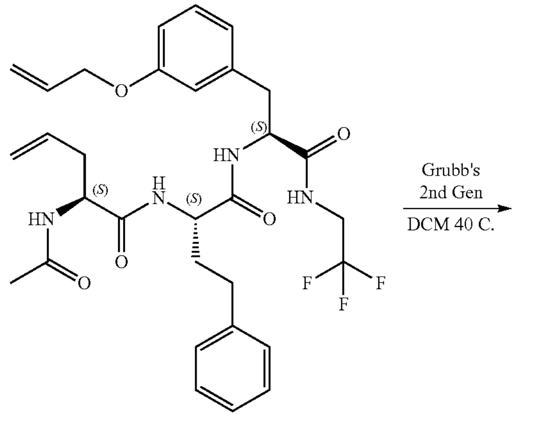

3-03-5

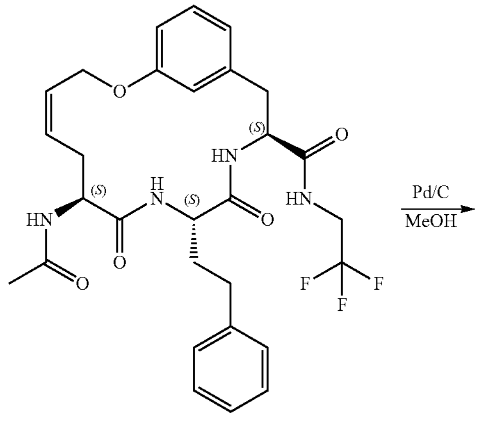

3-03-06

-continued

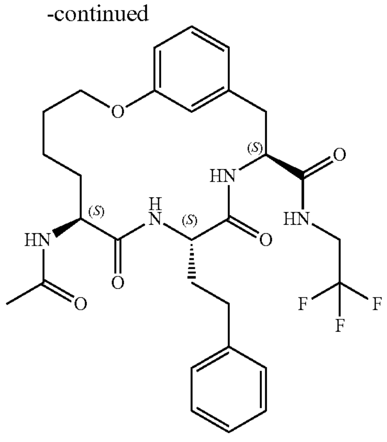

3-03

Allyl bromide (3.40 g, 28.1 mmol) was added to a mixture of (2S)-2-(tert-butoxycarbonylamino)-3-(3-hydroxyphenyl) propanoic acid (1.58 g, 5.62 mmol), tetrabutylammonium iodide (562 mg, 1.69 mmol), and potassium carbonate (2.33 g, 16.9 mmol) in DMF (20 mL) at 0° C. The mixture was stirred at room temperature for 6 hours. Solids were removed by filtration and the filtrate was concentrated under reduced pressure. The residue was taken up in a mixture of THE (15 mL) and water (5 mL) and lithium hydroxide monohydrate (1.18 g, 28.10 mmol) was added at room temperature. The mixture was stirred overnight then a saturated aqueous solution of sodium bicarbonate was added and the mixture was washed with EtOAc. The aqueous layer was acidified to pH3 with 1M HCl aq. and extracted with EtOAC. The organic layer was washed with brine, dried over anhydrous sodium sulfate, and concentrated under reduced pressure to afford 3-03-1 (286 mg, 15.8% yield) as a yellow oil.

HATU (504 mg, 1.33 mmol) was added to a solution of 3-03-1 (286 mg, 890 μmol), 2,2,2-trifluoroethanamine (84 μL, 1.07 mmol), and Hunig's base (466 μL, 2.67 mmol) in THE (10 mL) at 0° C. The mixture was stirred at room temperature for 1 hour. The mixture was poured into EtOAc and the organic layer was washed with saturated sodium bicarbonate followed by water and brine, then dried over anhydrous sodium sulfate and concentrated under reduced pressure. The residue was purified by column chromatography (EtOAc:hexanes=30:70 to 100:0) to afford 3-03-2 (311 mg, 86.8% yield) as a white solid.

A 4M solution of HCl in dioxane (1.00 mmol) was added to 3-03-2 (804 mg, 2.00 mmol) at room temperature. The mixture was stirred at room temperature for 1 hour. The solvent was removed under reduced pressure to afford 3-03-3 (714 mg, 118% yield, crude) as a colorless solid. The crude product was subjected to the next reaction without further purification.

1-(3-Dimethylaminopropyl)-3-ethylcarbodiimide hydrochloride (178 mg, 927 μmol) was added to a solution of (2S)-2-(tert-butoxycarbonylamino)-4-phenyl-butanoic acid (259 mg, 927 μmol), 3-03-3 (311 mg, 773 μmol), HOBt (125 mg, 927 μmol), and Hunig's base (405 μL, 2.32 mmol) in DMF (10 mL) at room temperature. The mixture was stirred at room temperature overnight. The mixture was diluted with water at 0° C. and extracted with EtOAc. The organic layer was washed with saturated aqueous sodium bicarbonate followed by brine, then dried over anhydrous sodium sulfate and concentrated under reduced pressure. The residue was purified with column chromatography (NH silica, EtOAC/hexane=10/90 to 90/10) to afford 3-03-4 (425 mg, 97.6% yield) as a white solid.

A solution of 4M HCl in dioxane (400 μmol, 0.10 mL) was added to tert-butyl N-[(1S)-1-[[(1S)-1-[(3-allyloxyphenyl)methyl]-2-oxo-2-(2,2,2-trifluoroethylamino)ethyl]carbamoyl]-3-phenyl-propyl]carbamate (225 mg, 399 μmol) at room temperature. The mixture was stirred for 30 min. The solvent was removed under reduced pressure. The residue was added to a flask containing a solution of 1-(3-dimethylaminopropyl)-3-ethylcarbodiimide hydrochloride (92 mg, 480 μmol), (2S)-2-acetamidopent-4-enoic acid (75 mg, 480 μmol), HOBt (65 mg, 480 μmol), and Hunig's base (209 μL, 1.20 mmol) in DMF (10 mL) at room temperature. The mixture was stirred at room temperature overnight then diluted with water at 0° C. and extracted with EtOAc. The organic layer was washed with saturated sodium bicarbonate followed by brine, then dried over anhydrous sodium sulfate and concentrated under reduced pressure. The residue was purified with column chromatography (silica gel, $CH_2Cl_2$/EtOAc=100/0 to 80/20) to afford 3-03-5 (150 mg, 62.3% yield) as a white solid.

2nd generation Grubbs catalyst (63 mg, 75 μmol) was added to the suspension of 3-03-5 (150 mg, 249 μmol) in DCM (10 mL) at room temperature. The mixture was stirred at 40° C. for 4 hours. The solvent was removed under reduced pressure and the residue was purified by column chromatography (EtOAc/$CH_2Cl_2$=10:90 to 90:10). The eluent was concentrated under reduced pressure and the residue was collected by filtration and washed with EtOAc to afford 3-03-6 (127 mg, 88.8% yield) as a slightly purple solid.

A mixture of (3-03-6 (127 mg, 221 μmol) and Pd/C (26.85 mg, 221.03 umol) in MeOH (10 mL) was stirred at room temperature for 2 hours under a hydrogen atmosphere. The catalyst was removed by filtration and the filtrate was concentrated under reduced pressure. The residue was purified by pre-HPLC (column: Bridge 18C 150*19 5 u; mobile phase: [water (0.1% formic acid)-MeCN(0.1% formic acid)]; B %: 5%-95%, 20 min) to afford 3-03 (9.80 mg, 7.69% yield) as a white solid. LCMS for 3-03: RT: 2.04 min, m/z 599.45 $[M+Na]^+$.

Example 39—Synthesis of (7S,10S,13S)-9,12-Dioxo-13-(2-oxopyrrolidin-1-yl)-10-phenethyl-N-(2,2,2-trifluoroethyl)-2-oxa-8,11-diaza-1(1,3)-benzenacyclotetradecaphane-7-carboxamide (3-04)

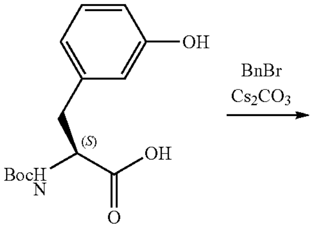

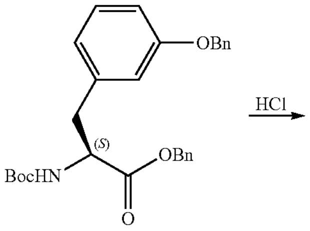

3-04-1

-continued

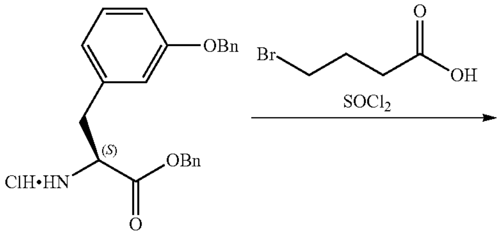

3-04-2

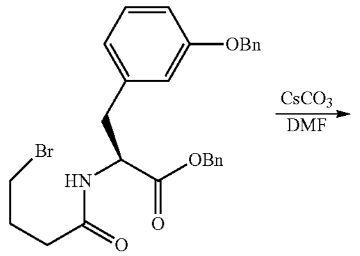

3-04-3

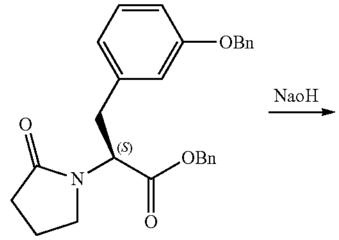

3-04-4

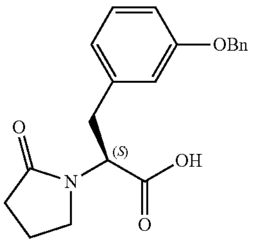

3-04-5

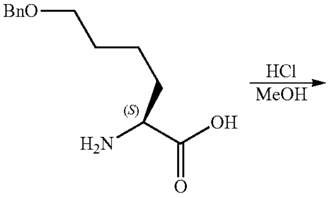

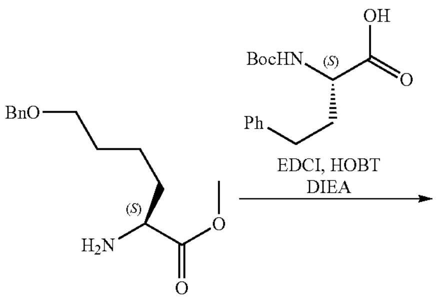

3-04-6

-continued
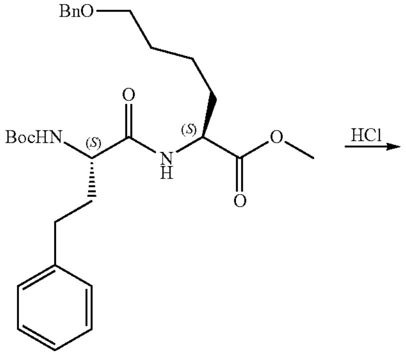
3-04-7
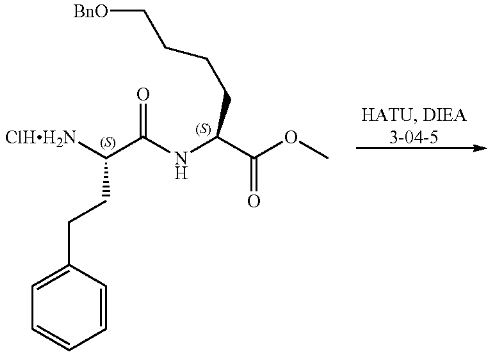
3-04-8
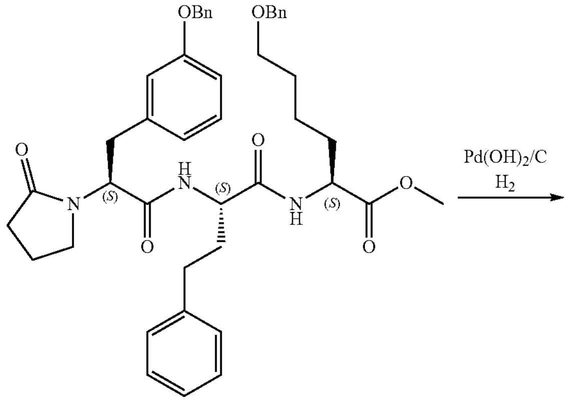
3-04-9
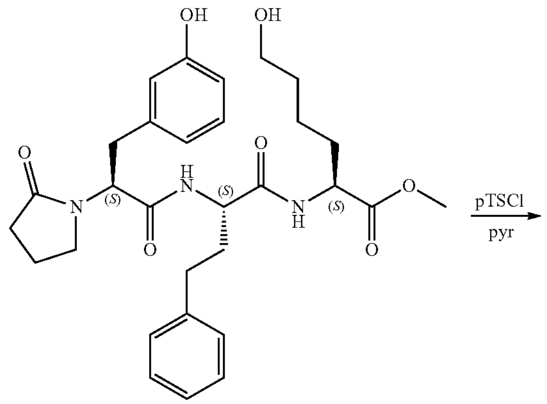
3-04-10
-continued
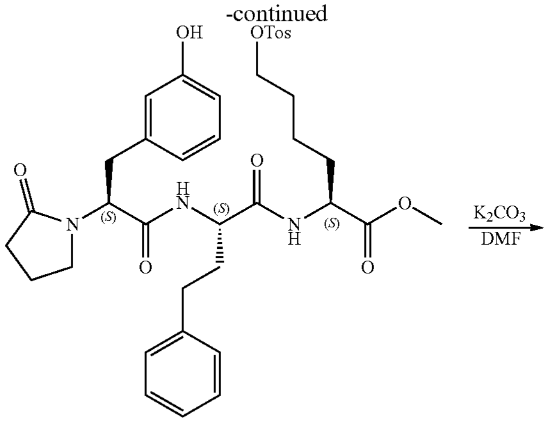
3-04-11
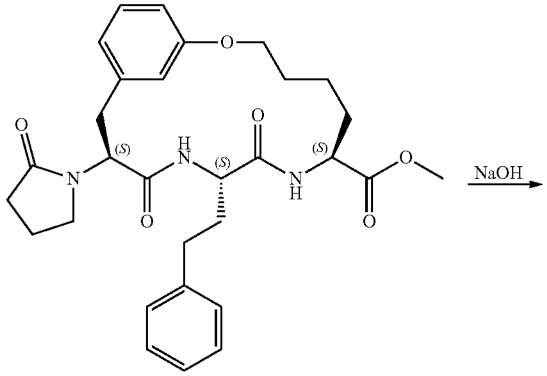
3-04-12
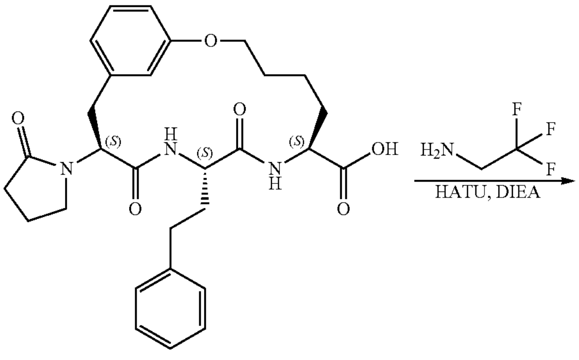
3-04-13
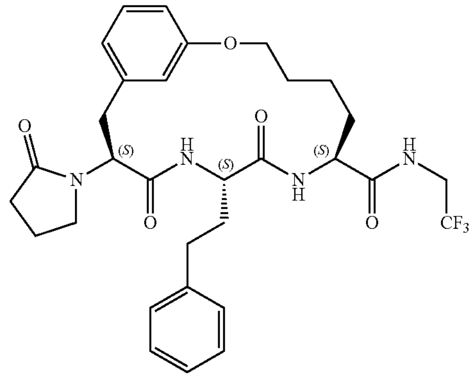
3-04
To a mixture of (S)-2-((tert-butoxycarbonyl)amino)-3-(3-hydroxyphenyl)propanoic acid (4.0 g, 14 mmol) and cesium carbonate (9.0 g, 28 mmol) in dimethylformamide (40 mL)

was added bromomethylbenzene (5.0 g, 31 mmol). The resulting mixture was stirred at 20° C. for 2 hours. The reaction was diluted with water (250 mL) and extracted with ethyl acetate (100 mL*3), the combined organic layer was dried over anhydrous sodium sulfate, filtered, and concentrated under reduced pressure. The residue was purified by column chromatography (petroleum ether:ethyl acetate=50:1-10:1) to afford compound 3-04-1 (6.4 g, 93% yield) as a yellow solid.

To a solution of benzyl 3-04-1 (7.0 g, 15 mmol) in dioxane (70 mL) was added a 4M solution of HCl in dioxane (100 mL, 400 mmol). The mixture was stirred at 20° C. for 12 hours. The reaction mixture was concentrated under reduced pressure to afford compound 3-04-2 (6.0 g, 99% yield, crude) as a white solid.

To a solution of 4-bromobutanoic acid (3.4 g, 21 mmol) in dichloromethane (30 mL) was added thionyl chloride (3.68 g, 30.9 mmol) and dimethyl formamide (75 mg, 1.0 mmol). The mixture was stirred for at 0° C. 1 hour. The mixture was concentrated under reduced pressure and the residue was dissolved in dichloromethane (10 mL). The resulting solution was added to a mixture of 3-04-2 and diisopropylethylamine (3.99 g, 30.9 mmol) in dichloromethane (30 mL). The mixture was stirred at 20° C. for 30 min then concentrated under reduced pressure. The residue was purified by column chromatography (petroleum ether:ethyl acetate=10:1-3:1) to afford compound 3-04-3 (4.8 g, 87.47% yield) as a white solid.

To a solution of 3-04-3 (12.8 g, 25.1 mmol) in dimethyl formamide (180 mL) was added cesium carbonate (24.51 g, 75.23 mmol) portion wise at 10° C. The mixture was stirred at 10° C. for 2 hours. The reaction mixture was poured into water (300 mL) and extracted with ethyl acetate (100 mL*2). The combined organic phase was washed with 0.5N hydrochloric acid (20 mL) followed by brine (200 mL*3), then dried over anhydrous sodium sulfate, filtered, and concentrated under reduced pressure. The residue was purified by column chromatography (petroleum ether:ethyl acetate=10:1-2:1) to afford compound 3-04-4 (7.6 g, 71% yield) as colorless gum.

To a solution of benzyl 3-04-4 (7.6 g, 18 mmol) in tetrahydrofuran (75 mL) was added a solution of sodium hydroxide (2.12 g, 53.1 mmol) in water (25 mL) at 0° C. The mixture was stirred at 0° C. for 20 min. The reaction mixture was poured into a mixture of water (50 mL) and ethyl acetate (50 mL). The aqueous phase was separated and adjusted to pH=6 with 1 N hydrochloric acid then extracted with ethyl acetate (100 mL*3). The combined organic phase was washed with brine (100 mL), dried over anhydrous sodium sulfate, filtered, and concentrated under reduced pressure to afford compound 3-04-5 (6.0 g, 100% yield) as a white solid.

To a solution of (S)-2-amino-6-(benzyloxy)hexanoic acid (5 g, 21.07 mmol) in methanol (20 mL) was added HCl/methanol (4 M, 50 mL). The mixture was stirred for at 20° C. 12 hours. The reaction mixture was concentrated in vacuo to afford compound 3-04-6 (6.1 g, crude, HCl salt) as a yellow solid.

To a solution of (S)-2-((tert-butoxycarbonyl)amino)-4-phenylbutanoic acid (7.0 g, 25 mmol) and diisopropylethylamine (9.9 g, 77 mmol) in dimethyl formamide (60 mL) was added HATU (9.67 g, 25.4 mmol) at 0° C. The mixture was stirred for 10 min at 0° C. A solution of 3-04-6 (6.1 g, 21 mmol) in dimethyl formamide (20 mL) was added to the mixture at 0° C. The mixture was stirred for 20 min at 20° C. The reaction mixture was poured into water (300 mL) and extracted with ethyl acetate (100 mL*2). The combined organic phase was washed with 0.5 N hydrochloric acid (20 mL) followed by brine (200 mL*3) then dried over anhydrous sodium sulfate, filtered, and concentrated under reduced pressure. The residue was purified by column chromatography (petroleum ether:ethyl acetate=10:1-2:1) to afford compound 3-04-7 (10.5 g, 90.4% yield) as a yellow gum.

To a solution of methyl 3-04-7 (10.5 g, 20.5 mmol) in dioxane (50 mL) was added a 4M solution of HCl in dioxane (80 mL, 320 mmol) at 0° C. The mixture was stirred at 20° C. for 3 hours. The reaction mixture was concentrated under reduced pressure to afford compound 3-04-8 (9.8 g, crude) as a colorless gum.

To a solution of 3-04-5 (5.0 g, 15 mmol) in dimethyl formamide (50 mL) was added diisopropylethylamine (7.62 g, 10.3 mL) and HATU (6.72 g, 17.7 mmol). The mixture was stirred for 10 min at 0° C., then 3-04-8 (6.67 g, 14.8 mmol) in dimethyl formamide (30 mL) was added. The mixture was stirred at 0° C. for 20 min. The reaction mixture was poured into water (200 mL) and extracted with ethyl acetate (200 mL*2). The combined organic phase was washed with brine (200 mL*3) then dried over anhydrous sodium sulfate, filtered, and concentrated under reduced pressure. The residue was purified by column chromatography (petroleum ether:ethyl acetate=10:1-1:1) to afford compound 3-04-9 (7.5 g, 66% yield) as a colorless gum.

To a solution of 3-04-9 (7.5 g, 10.2 mmol) in methanol (80 mL) was added 5% Pd/C (500 mg) and 10% $Pd(OH)_2/C$ (500 mg) under a nitrogen atmosphere. The mixture was degassed with argon three times and stirred for 40 hours at 25° C. under a hydrogen atmosphere (50 psi). The reaction mixture was filtered and concentrated under reduced pressure to afford compound 3-04-10 (5.15 g, 91.0% yield) as a white solid.

To a solution of 3-04-10 (0.50 g, 903 μmol) in pyridine (6 mL) was added p-toluenesulfonyl chloride (190 mg, 990 μmol) at 0° C. The mixture was stirred for 12 hours at 10° C. then concentrated under reduced pressure. The residue was purified by column chromatography (petroleum ether: ethyl acetate=5:1-0:1) to afford compound 3-04-11 (0.20 g, 28% yield) as colorless gum.

To a solution of 3-04-11 (0.60 g, 850 μmol) in dimethyl formamide (30 mL) was added potassium carbonate (468 mg, 3.39 mmol). The mixture was stirred at 50° C. for 2 hours. The reaction mixture was poured in water (20 mL) and extracted with ethyl acetate (30 mL*2). The combined organic phase was washed with brine (20 mL*3) then dried over anhydrous sodium sulfate, filtered, and concentrated under reduced pressure. The residue was purified by reverse phase column chromatography (TFA condition) to afford compound 3-04-12 (0.30 g, 66% yield) as a white solid.

To a solution of 3-04-12 (80 mg, 150 μmol) in tetrahydrofuran (2 mL) was added sodium hydroxide (30 mg, 750 μmol) in water (0.6 mL) at 0° C. The mixture was stirred for 10 min at 0° C. The reaction mixture was poured into a mixture of water (10 mL) and ethyl acetate (10 mL). The aqueous phase was adjusted to pH=4 with 1 N hydrochloric acid and extracted with ethyl acetate (20 mL*2). The combined organic phase was washed with brine (20 mL), dried over anhydrous sodium sulfate, filtered, and concentrated under reduced pressure to afford compound 3-04-13 (50 mg, 64% yield) as a white solid.

To a solution of 3-04-13 (60 mg, 110 μmol) and diisopropylethylamine (60 mg, 460 μmol) in dimethyl formamide (1 mL) was added HATU (60 mg, 160 μmol) at 0° C. The mixture was stirred at 0° C. for 5 min, then 2,2,2-trifluoroethanamine (24 mg, 240 μmol) in dimethyl formamide (0.5 mL) was added at 0° C. The mixture was stirred for 25 min at 0° C. The reaction mixture was poured into water (10 mL) and extracted with ethyl acetate (20 mL*2). The combined organic phase was washed with brine (20 mL*3), dried over anhydrous sodium sulfate, filtered, and concentrated under reduced pressure. The residue was purified by prep-HPLC (column: Phenomenex Synergi $C_{18}$ 150*25*10 um; mobile phase: [water(0.1% TFA)-ACN]; B %: 32%-62%, 12 min) to afford 3-04 (9.0 mg, 13% yield) as a white solid. LCMS for 3-04: RT=2.202 min, m/z 603.5 $[M+H]^+$.

The following compounds were made using a similar synthetic route as described for compound 3-04:

Compound 3-07; LCMS: RT=2.014 min, m/z 597.2 $[M+Na]^+$

Compound 3-08; LCMS: RT=2.131 min, m/z 589.2 $[M+H]^+$

Compound 3-10; LCMS: RT=2.591 min, m/z 585.3 $[M+H]^+$

Compound 3-11; LCMS: RT=2.385 min, m/z 615.3 $[M+H]^+$

Compound 3-15; LCMS: RT=2.681 min, m/z 629.2 $[M+H]^+$

Compound 3-16; LCMS: RT=1.839 min, m/z 602.2 $[M+H]^+$

Example 40—Synthesis of Methyl-(7S,10S)-9,12-dioxo-10-phenethyl-2,5-dioxa-8,11-diaza-1(1,3)-benzenacyclotetradecaphane-7-carboxylate (3-05)

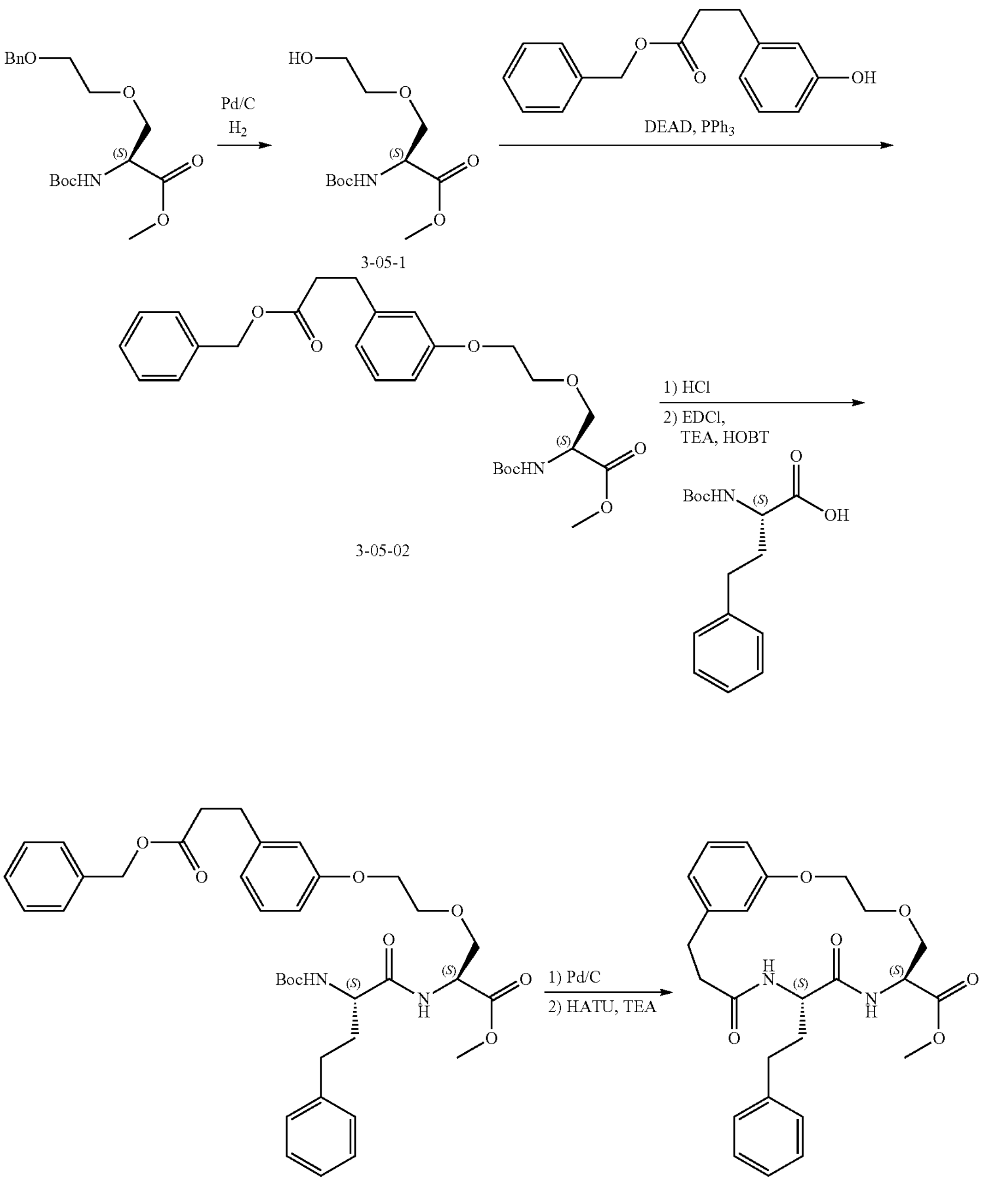

3-05-1

3-05-02

3-05-03

3-05

A mixture of methyl (2S)-3-(2-benzyloxyethoxy)-2-(tert-butoxycarbonylamino) propanoate (356 mg, 1.01 mmol) and Pd on carbon (30 mg, 1.0 mmol) in MeOH (10.00 mL) was stirred under a hydrogen atmosphere at room temperature for 2 hours. The catalyst was removed by filtration and concentrated under reduced pressure. The residue was purified with column chromatography (silica gel, EtOAc/hexanes=50:50 to 0:100) to afford methyl 3-05-1 (185 mg, 69.6% yield, crude) as a colorless oil.

Diethyl azodicarboxylate (134 μL, 855 umol) was added to a solution of benzyl 3-(3-hydroxyphenyl)propanoate (109 mg, 427 μmol), 3-05-1 (135.00 mg, 512.74 umol), and triphenylphosphine (224 mg, 855 μmol) in THE (5.00 mL) at room temperature. The reaction mixture was stirred at 50° C. overnight. The solvent was removed in vacuo and the residue was purified by column chromatography (silica gel, EtOAc/hexanes=10:90 to 50:50) to afford 3-05-2 (135 mg, 63% yield) as a colorless oil.

A 4M solution of HCl in dioxane (3.00 mL, 12 mmol) was added to 3-05-2 (135 mg, 269 μmol) at room temperature. The mixture was stirred for 1 hour and concentrated in vacuo to give amine as a colorless oil. To this was added a solution of 1-(3-dimethylaminopropyl)-3-ethylcarbodiimide hydrochloride (77 mg, 400 μmol), TEA (111 μL, 807 μmol), HOBt (54 mg, 400 μmol), and (2S)-2-(tert-butoxycarbonylamino)-4-phenyl-butanoic acid (90 mg, 320 μmol) in DMF. The mixture was stirred overnight. The mixture was diluted with water and extracted with a mixture of EtOAc/hexanes. The organic layer was washed with brine, dried over anhydrous sodium sulfate, and concentrated under reduced pressure. The residue was purified by column chromatography (silica gel, EtOAc/CH2C12=30:70 to 80:20) to afford 3-05-3 (177 mg, 99.2% yield) as a colorless oil.

A mixture of 3-05-3 (177 mg, 267 μmol) and Pd on carbon (30.00 mg, 270 μmol) in MeOH (3 mL) was stirred at room temperature for 1 hour under a hydrogen atmosphere. The catalyst was removed by filtration and the filtrate concentrated under reduced pressure. The reside was taken up in DCM and treated with a 4M solution of HCl in dioxane (5.00 mL, 20 mmol) at room temperature. The mixture was stirred at room temperature for 1 hour then the solvent was removed under reduced pressure. The residue was taken up in DMF (25 mL), TEA (111 μL, 320 μmol), and the mixture was cooled to 0° C. To this was added HATU (121 mg, 320 μmol) and the mixture was stirred at room temperature for 1 h our. The reaction mixture was diluted with water at 0° C. and extracted with a mixture of EtOAc/hexanes. The organic layer was washed with brine, dried over anhydrous sodium sulfate, and concentrated under reduced pressure. The residue was purified by column chromatography (silica gel, EtOAc/CH2C12=0:100 to 90:10) and concentrated under reduced pressure. The residue was collected by filtration and washed with IPE to afford 3-05 (95 mg, 78% yield) as a colorless solid. LCMS for 3-05: RT: 2.06 min, m/z 455.34 $[M+H]^+$.

Example 41—Synthesis of (7S,10S,13S)-7-(Hydroxymethyl)-13-(2-oxopyrrolidin-1-yl)-10-phenethyl-2-oxa-8,11-diaza-1(1,3)-benzenacyclotetradecaphane-9,12-dione (3-06)

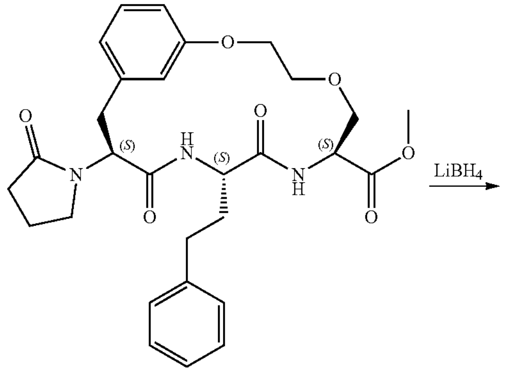

3-05

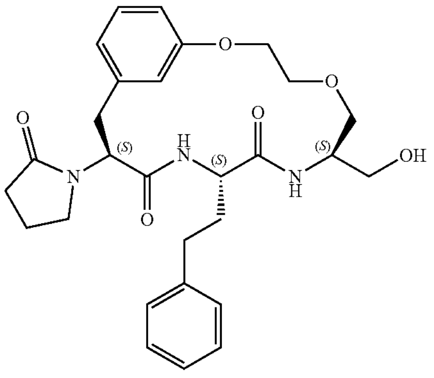

3-06

To a solution of 3-05 (80 mg, 149 μmol) in methanol (1 mL) was added lithium borohydride (13 mg, 600 μmol) at 0° C. The mixture was stirred at 0° C. for 1 hour then poured into a mixture of water (15 ml) and 1 N hydrochloric acid (10 mL). The mixture was extracted with ethyl acetate (10 mL*2). The combined organic phase was washed with brine (20 ml), dried over anhydrous sodium sulfate, filtered, and concentrated under reduced pressure. The residue was purified by prep-HPLC (column: Phenomenex Synergi $C_{18}$ 150*25*10 um; mobile phase: [water(0.1% TFA)-ACN]; B %: 28%-55%, 12 min) to afford 3-06 (51 mg, 67% yield) as a white solid. LCMS for 3-06: RT=2.329 min, m/z 508.3 $[M+H]^+$.

Example 42—Synthesis of (7S,10S,13S)-9,12-Dioxo-13-(2-oxopyrrolidin-1-yl)-10-phenethyl-N-(2,2,2-trifluoroethyl)-2,5-dioxa-8,11-diaza-1(1,3)-benzenacyclotetradecaphane-7-carboxamide (3-09)

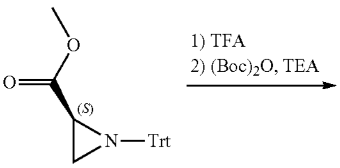

-continued
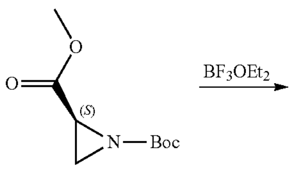
3-09-1
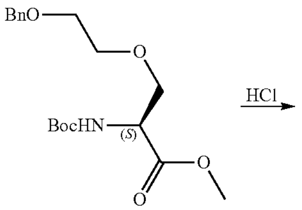
3-09-2
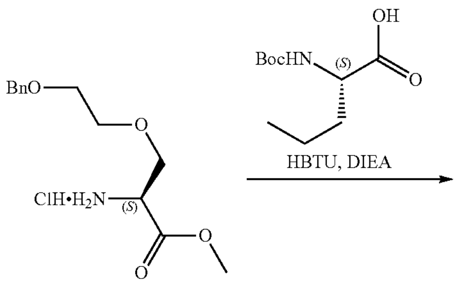
3-09-3
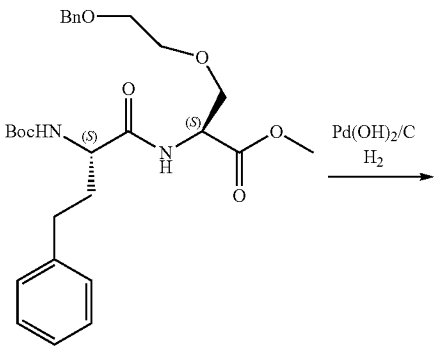
3-09-4
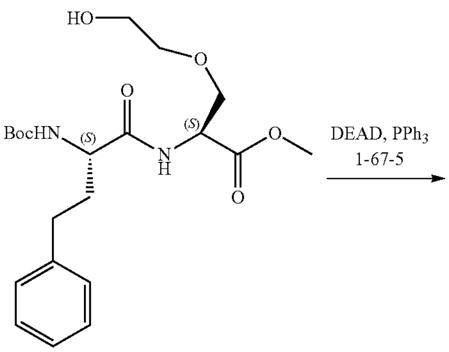
3-09-5
-continued
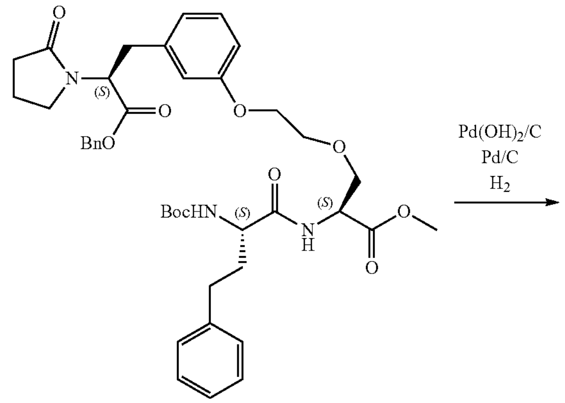
3-09-6
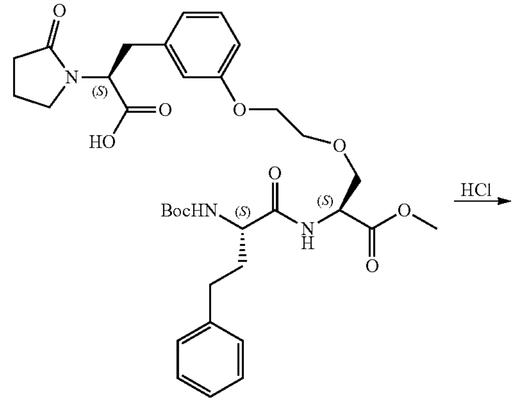
3-09-7
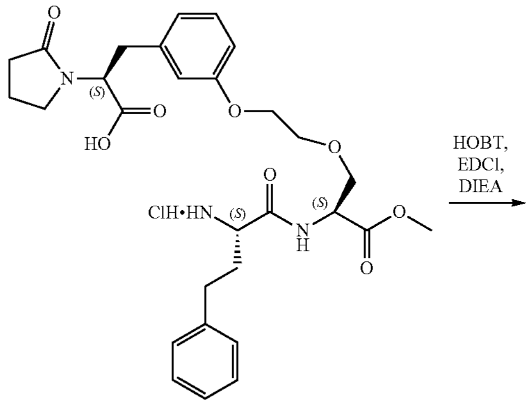
3-09-8
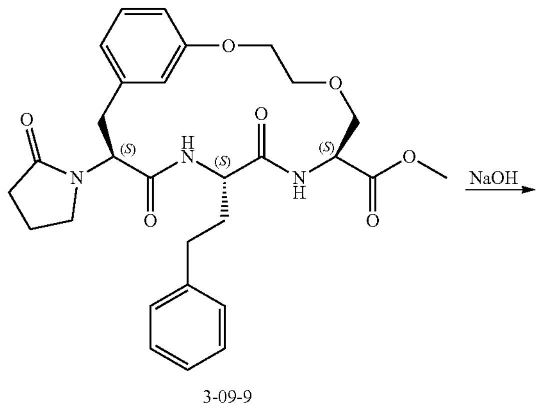
3-09-9

-continued

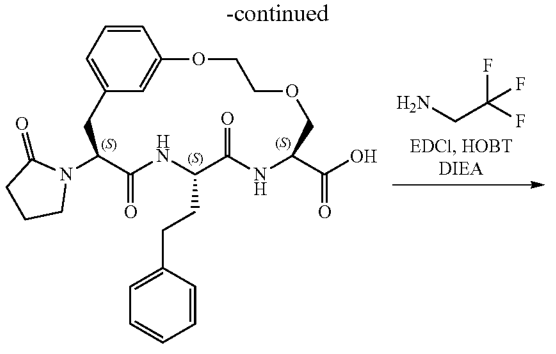

3-09-10

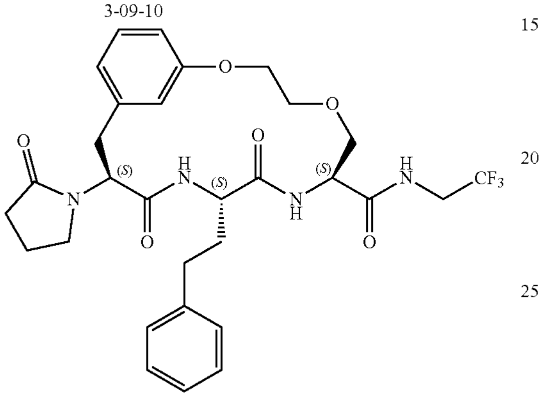

3-09

To a mixture of methyl (S)-1-tritylaziridine-2-carboxylate (20 g, 58 mmol) in dichloromethane (60 mL) and methanol (60 mL) was added trifluoroacetic acid (129 mL, 1.75 mol) drop wise at −30° C. The mixture was stirred at 0° C. for 4 hours and then at 10° C. for another 12 hours. The reaction mixture was concentrated under reduced pressure to afford a residue (12.5 g, crude) as a green solid. To the mixture of residue (12.5 g, 58.10 mmol) and triethylamine (29.4 g, 290 mmol) in acetonitrile (120 mL) was added di-tert-butyl dicarbonate (76 g, 350 mmol) drop wise at 0° C. The mixture was stirred at 25° C. for 12 hours then concentrated under reduced pressure to remove volatile organics. The residue was poured into water (200 mL) and extracted with ethyl acetate (200 mL*3). The combined organic phase was washed with brine (200 mL*2), dried over anhydrous sodium sulfate, filtered, and concentrated under reduced pressure. The residue was purified by chromatography column (petroleum ether:ethyl acetate=100:1-10:1) to afford compound 3-09-1 (5.0 g, 43% yield) as a colorless oil.

To a mixture of 3-09-1 (5.0 g, 25 mmol) and 2-(benzyloxy)ethan-1-ol (4.92 g, 32.3 mmol) in dichloromethane (70 mL) was added a solution of boron trifluoride diethyl ether complex (375 mg, 1.24 mmol) in dichloromethane (10 mL) drop wise at 0° C. The mixture was stirred at 0° C. for 10 minutes. The reaction mixture was poured into saturated aqueous sodium carbonate (200 mL) and extracted with dichloromethane (200 mL*3). The combined organic phase was washed with brine (200 mL*2), dried over anhydrous sodium sulfate, filtered, and concentrated under reduced pressure. The residue was purified chromatography column (petroleum ether:ethyl acetate=30:1-10:1) to afford compound 3-09-2 (3.8 g, 43% yield) as a colorless oil.

A mixture of methyl 3-09-2 (3.8 g, 11 mmol) in a 4M solution of HCl in methanol (95 mL) was stirred at 25° C. for 1 hour. The mixture was concentrated under reduced pressure to afford compound 3-09-3 (3.2 g, crude) as a white solid. No further purification was performed.

To a mixture of 3-09-3 (3.2 g, 11.04 mmol), (S)-2-((tert-butoxycarbonyl)amino)-4-phenylbutanoic acid (3.08 g, 11.0 mmol), and HBTU (4.19 g, 11.0 mmol) in dimethyl formamide (60 mL) was added N,N-diisopropylethylamine (4.28 g, 33.1 mmol) at 25° C. The mixture was stirred at 25° C. for 20 minutes then poured into water (200 mL) and extracted with dichloromethane (200 mL*3). The combined organic phase was washed with saturated aqueous sodium hydrosulfate (200 mL) followed by brine (200 mL), saturated aqueous sodium carbonate (200 mL) and brine (200 mL) again. The mixture was dried over anhydrous sodium sulfate, filtered, and concentrated under reduced pressure. The residue was purified by column chromatography (petroleum ether:ethyl acetate=20:1-5:1) to afford compound 3-09-4 (6.0 g, 59% yield) as a white solid.

To a solution of 3-09-4 (6.0 g, 12 mmol) in methanol (60 mL) was added 10% $Pd(OH)_2/C$ (600 mg, 10% purity on carbon) under nitrogen atmosphere. The suspension was degassed under vacuum and purged with hydrogen several times. The mixture was stirred under a hydrogen atmosphere (15 psi) at 25° C. for 12 hours. The mixture was filtered and concentrated under reduced pressure. The residue was purified by prep-HPLC (TFA, MeCN/water) followed by column chromatography (petroleum ether:ethyl acetate=10:1-1:1) to afford compound 3-09-5 (3.4 g, 66% yield) as a colorless oil.

To a 50 mL round bottom flask was added triphenylphosphine (371 mg, 1.41 mmol), a solution of 3-09-5 (200 mg, 471.16 umol), and compound 1-67-5 (160 mg, 471 μmol in tetrahydrofuran (2 mL) under a nitrogen atmosphere. A solution of DEAD (246 mg, 1.41 mmol) in tetrahydrofuran (2 mL) was added drop wise. The reaction mixture was stirred at 20° C. for 1 hour under a nitrogen atmosphere then mixture was concentrated under reduced pressure and the residue was purified by reverse phase column chromatography (water (0.05% HCl)-MeCN) to afford compound 3-09-6 (280 mg) as a colorless gum.

A solution of 3-09-6 (230 mg, 308 μmol) in methanol (6 mL) was purged with nitrogen, then 10% $Pd(OH)_2/C$ (20 mg) and 10% Pd/C (20 mg) were added in one portion under a nitrogen atmosphere. The mixture was stirred under a hydrogen atmosphere (20 psi) at 20° C. for 1 hour. The mixture was filtered through a celite pad and the filter pad washed with methanol (10 mL*3). The combined filtrate was concentrated under reduced pressure to afford compound 3-09-7 (220 mg, crude) as a white solid.

To a solution of 3-09-7 (220 mg, 335 μmol) in dioxane (3 mL) was added a 4 M solution of HCl in dioxane (3 mL, 12 mmol). The mixture was stirred at 20° C. for 1 hour then concentrated under reduced pressure to afford compound 3-09-8 (220 mg, crude) as a white solid.

To a solution of 3-09-8 (190 mg, 261 μmol) and N,N-diisopropylethylamine (152 mg, 1.17 mmol) in N,N-dimethyl formamide (19 mL) at 0° C., was added HOBt (53 mg, 390 μmol). The mixture was stirred at 0° C. for 10 minutes then EDCI (75 mg, 391 μmol) was added and the reaction mixture was stirred at 0° C. for an additional 20 minutes and then at 20° C. for another 23 hours. The mixture was diluted with water (30 mL) and then adjusted to pH=7 with an aqueous 1 N hydrochloric acid solution. The mixture was extracted with ethyl acetate (40 mL*3). The combined organic layers were washed with brine (50 mL*3), dried over anhydrous sodium sulfate, filtered, and concentrated under reduced pressure. The residue was purified by column chromatography ($SiO_2$, petroleum ether:ethyl acetate=2:1-2:3) to afford compound 3-09-9 (40 mg, 28% yield) as a light yellow solid.

To a solution of methyl 3-09-9 (40 mg, 74 μmol) in a mixture of tetrahydrofuran (0.4 mL) and water (0.2 mL) was added a solution of sodium hydroxide (21 mg, 520 μmol) in water (0.2 mL) drop wise at 0° C. The mixture was stirred at 0° C. for 4 hours. The mixture was adjusted pH=3 with an aqueous 1 N hydrochloric acid solution. The mixture was concentrated under reduced pressure. The mixture was filtered, washed with water (2 mL*3), and then dried under reduced pressure to afford compound 3-09-10 (36 mg, 90% yield) as a white solid.

To a solution of 3-09-10 (31 mg, 59 μmol) and 2,2,2-trifluoroethan-1-amine (12 μL, 150 umol) in pyridine (0.3 mL) was added EDCI (28 mg, 150 μmol) and HOBt (8 mg, 60 μmol) at 0° C. The mixture was stirred at 20° C. for 2 hours. The mixture was diluted with water (15 mL) and then adjusted pH=5 with an aqueous 1N hydrochloric acid solution. The mixture was extracted with ethyl acetate (30 mL*3). The combined organic layers were washed with brine (20 mL), dried over anhydrous sodium sulfate, filtered, concentrated under reduced pressure. The residue was purified by prep-HPLC (column: Phenomenex Synergi C18 150*25*10 um; mobile phase: [water (0.1% TFA)-ACN]; B %: 40%-66%, 12 mins) to afford 3-09 (32.3 mg, 77.6% yield) as a light yellow solid. LCMS for 3-09: RT=2.560 min, m/z 605.2 $[M+H]^+$.

Example 43—Synthesis of (7S,10S,13S)-13-(2-Oxopyrrolidin-1-yl)-10-phenethyl-7-(5-(trifluoromethyl)-4H-1,2,4-triazol-3-yl)-2-oxa-8,11-diaza-1(1,3)-benzenacyclotetradecaphane-9,12-dione (3-12)

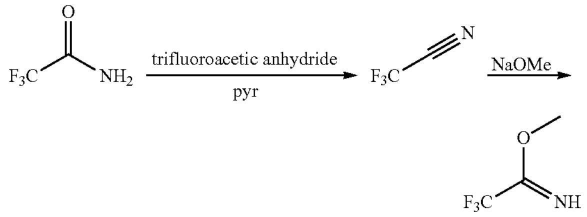

3-12-1

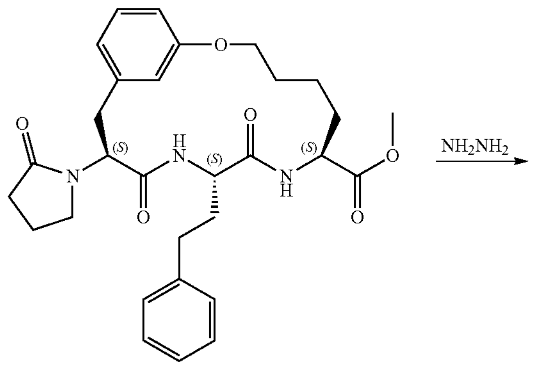

3-04-12

-continued

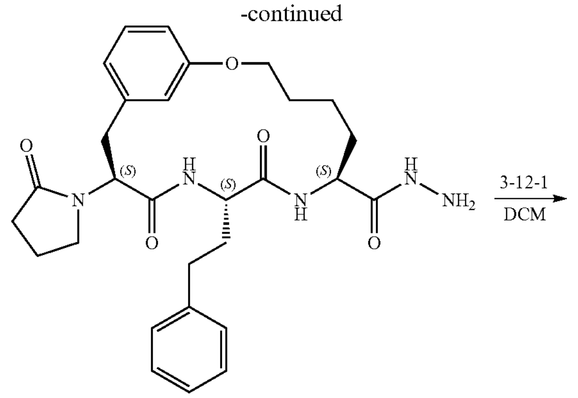

3-12-2

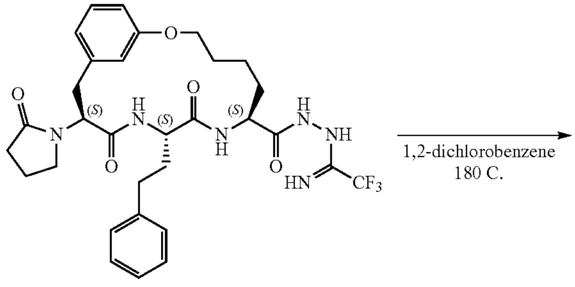

3-12-3

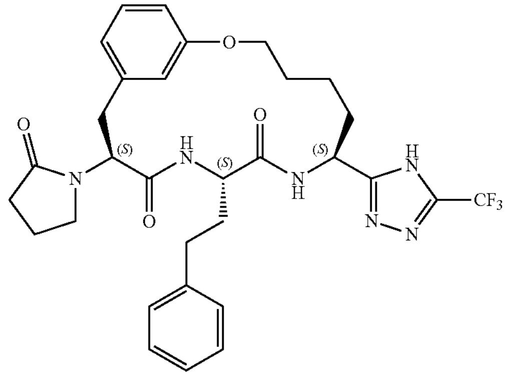

3-12

Sodium (710 mg, 31 mmol) was added to methanol (150 mL) portion wise at 20° C. The mixture was stirred at 20° C. for 30 min under nitrogen flow until the sodium was dissolved. To a solution of 2,2,2-trifluoroacetamide (35 g, 310 mmol) in pyridine (200 mL) was added trifluoroacetic anhydride (65 g, 310 mmol) in pyridine (60 mL) drop wise at 0° C. over 6 hours. The generated gas (BP: −60° C.) was bubbled into the sodium methoxide solution cooled to −70° C. The mixture was stirred at 20° C. for 1 hour until no additional gas evolution was observed. The mixture was transferred to a round bottom flask and distilled directly at 45° C. to afford compound 3-12-1 (5.0 g, 3.2% yield) as a colorless oil.

To a mixture of 3-04-12 (100 mg, 187 μmol) in methanol (1 mL) was added hydrazine hydrate (1.03 g, 20.6 mmol). The reaction mixture was stirred at 20° C. for 6 hours. The reaction mixture was diluted with 10 mL of water. A solid was collected by filtration and dried under reduced pressure to afford compound 3-12-2 (60 mg, 52% yield) as a white solid.

To a mixture of 3-12-2 (50 mg, 93 μmol) in dichloromethane (2 mL) was added compound 3-12-1 (474 mg, 933

μmol). The mixture was stirred at 20° C. for 3 hours. The mixture was concentrated under reduced pressure to afford compound 3-12-3 (60 mg, crude) as a white solid.

A mixture of 3-12-3 (55 mg, 87 μmol) in 1,2-dichlorobenzene (1 mL) was stirred at 180° C. for 3 hours then concentrated under reduced pressure. The residue was triturated with acetonitrile (10 mL) to afford 3-12 (15 mg) as an off-white solid. LCMS: RT=2.207 min, m/z 613.3 [M+H]$^+$.

Example 44—Synthesis of (7S,10S,13S)-13-(2-Oxopyrrolidin-1-yl)-10-phenethyl-7-(5-(trifluoromethyl)-1,3,4-oxadiazol-2-yl)-2-oxa-8,11-diaza-1(1,3)-benzenacyclotetradecaphane-9,12-dione (3-13)

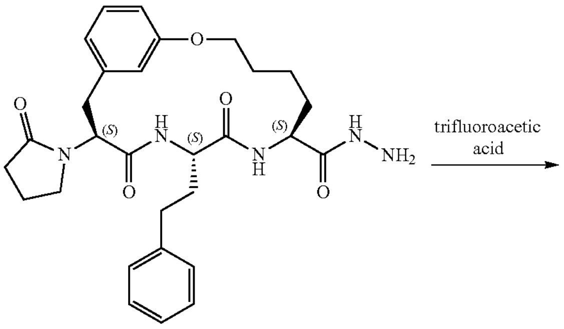

3-12-2

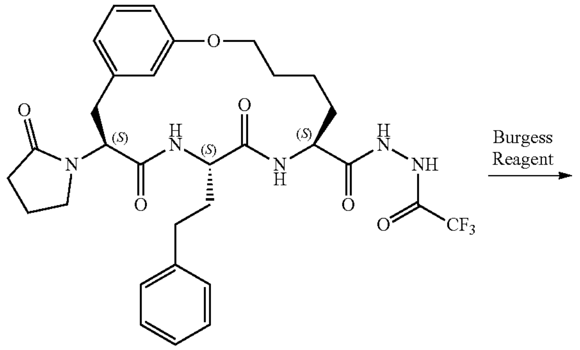

3-13-1

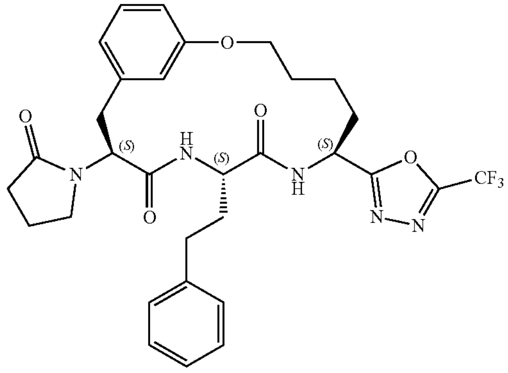

3-13

To a solution of 3-12-2 (45 mg, 71 μmol) in dichloromethane (1 mL) was added trifluoroacetic acid (308 mg, 2.70 mmol). The mixture was stirred at 20° C. for 3 hours then concentrated under reduced pressure. The residue was triturated with water (5 mL), filtered, and dried under reduced pressure to afford compound 3-13-1 (45 mg, crude) as a white solid.

To a solution of 3-13-1 (45 mg, 71 μmol) in tetrahydrofuran (1 mL) was added Burgess reagent (51 mg, 210 μmol). The mixture was stirred at 20° C. for 12 hours. Another 2 equivalents of Burgess reagent were added and the mixture and the mixture was stilled at 20° C. for 24 hours. The reaction mixture was poured into water (30 mL) and extracted with ethyl acetate (20 mL*2). The combined organic phase was washed with brine (20 mL), dried over anhydrous sodium sulfate, filtered, and concentrated under reduced pressure. The residue was triturated with ethyl acetate (5 mL) and filtered. The filtrate was concentrated under reduced pressure and purified by prep-HPLC (column: Phenomenex Synergi $C_{18}$ 150*25*10 um; mobile phase: [water(0.1% TFA)-ACN]; B %: 40%-70%, 13 min) to afford compound 3-13 (11.5 mg, 25.6% yield) as a white solid. LCMS for 3-13: RT=2.500 min, m/z 614.1 [M+H]$^+$.

Example 45—Synthesis of (7S,10S,13S)-13-(2-Oxopyrrolidin-1-yl)-10-phenethyl-7-(((2,2,2-trifluoroethyl)amino)methyl)-2-oxa-8,11-diaza-1(1,3)-benzenacyclotetradecaphane-9,12-dione (3-14)

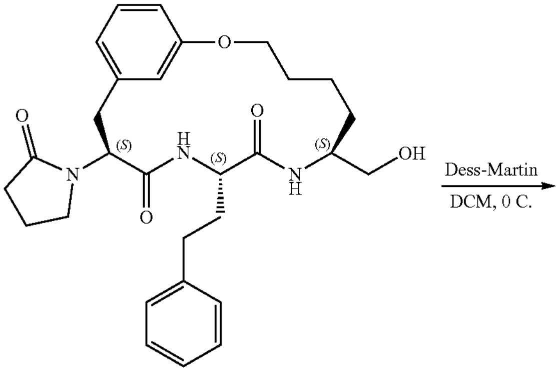

3-06

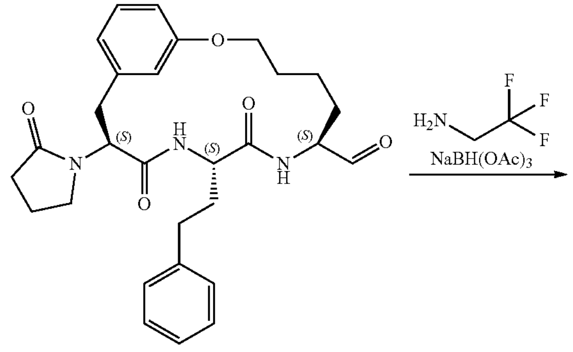

3-14-1

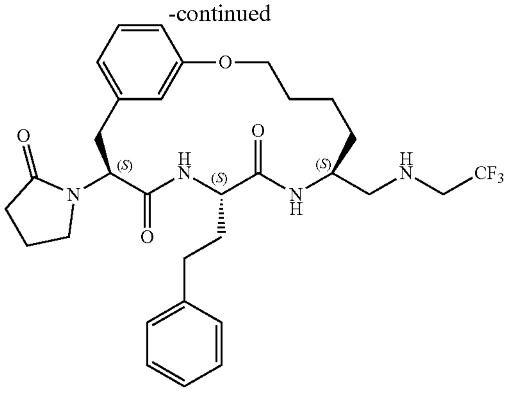

3-14

To a solution of 3-06 (80 mg, 160 μmol) in tetrahydrofuran (1 mL) was added Dess-Martin reagent (134 mg, 315 μmol) at 0° C. The mixture was stirred at 20° C. for 4 hours. The reaction mixture was poured into a mixture of water (20 mL) and ethyl acetate (20 mL). The organic phase was washed with brine (20 ml), dried over anhydrous sodium sulfate, filtrated, and concentrated under reduced pressure. The residue was purified by prep-TLC (petroleum ether: ethyl acetate=1:2) to afford compound 3-14-1 (20 mg, 23% yield) as a white solid.

To a mixture of 3-14-1 (20 mg, 40 μmol) and 2,2,2-trifluoroethanamine (12 mg, 120 μmol) in methanol (0.5 mL) was added 4 Å molecular sieves (100 mg). The mixture was stirred at 0° C. for 1 hour, then sodium triacetoxyborohydride (17 mg, 79 μmol) was added at 0° C. The mixture was stirred at 20° C. for 24 hours then filtered and the filter cake washed with ethyl acetate (30 mL). The organic phase was washed with brine (30 mL*2), dried over anhydrous sodium sulfate, filtered, and concentrated under reduced pressure. The residue was purified by prep-HPLC (column: Phenomenex Gemini 150*25 mm*10 um; mobile phase: [water (0.05% ammonia hydroxide v/v)-ACN]; B %: 35%-65%, 12 min) to afford compound 3-14 (4.6 mg, 18% yield) as a white solid. LCMS for 3-14: RT=1.833 min, m/z 589.2 $[M+H]^+$.

Example 46—Synthesis of (7S,10S,13S)-N-(Cyclopropylmethyl)-10-(2-morpholinoethyl)-9,12-dioxo-13-(2-oxopyrrolidin-1-yl)-2-oxa-8,11-diaza-1(1,3)-benzenacyclotetradecaphane-7-carboxamide (3-17)

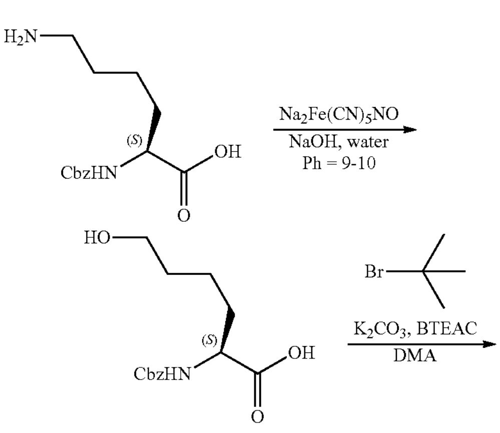

3-17-1

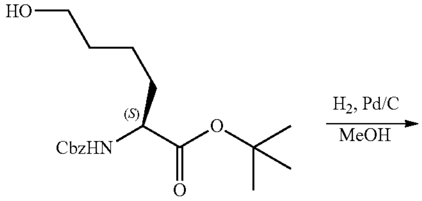

3-17-2

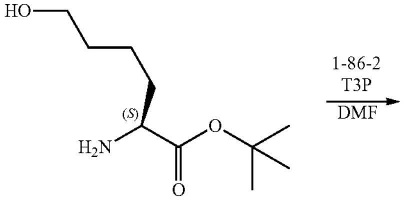

3-17-3

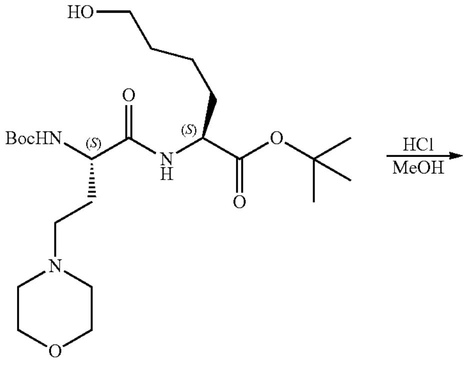

3-17-4

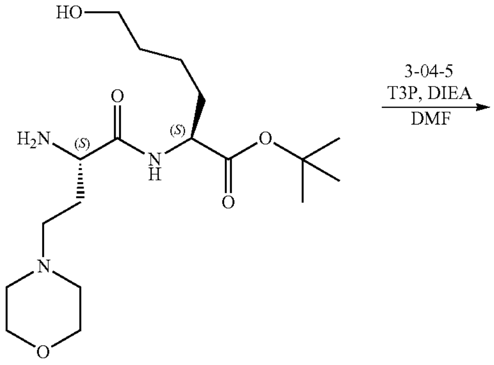

3-17-5

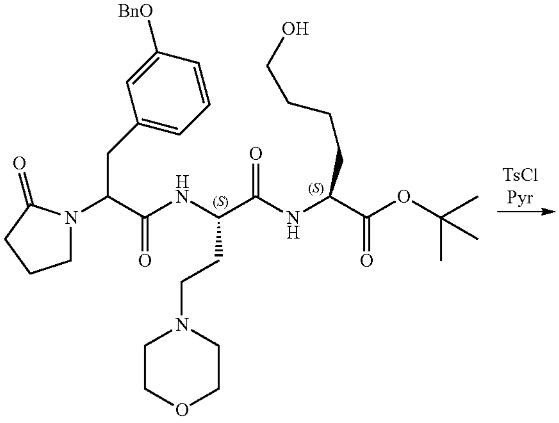

3-17-6

-continued

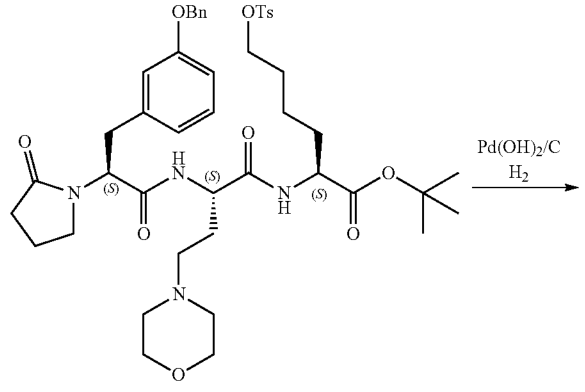

3-17-7

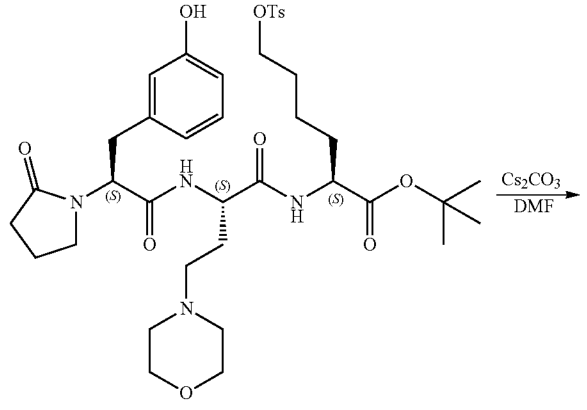

3-17-8

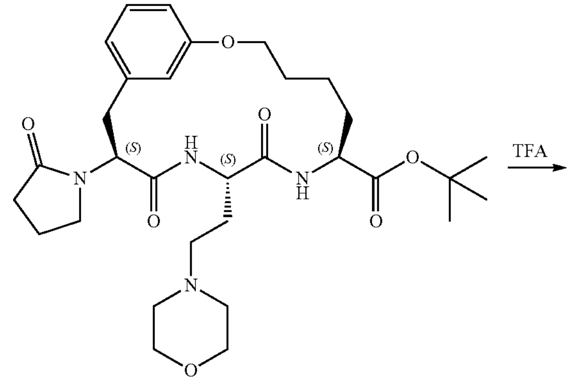

3-17-9

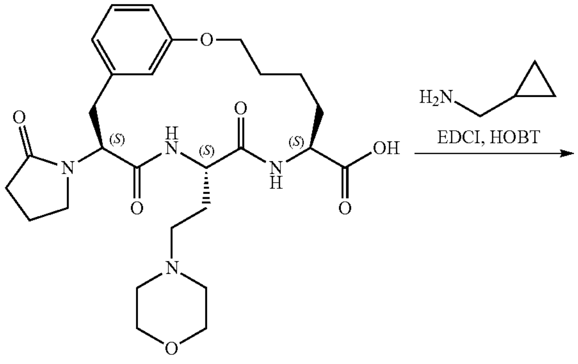

3-17-10

-continued

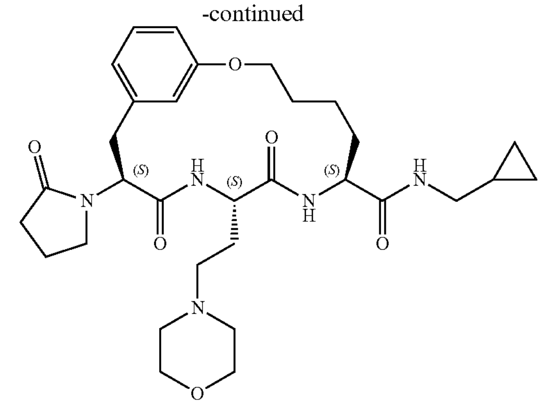

3-17

A sample of ((benzyloxy)carbonyl)-L-lysine (19 g, 68 mmol split into 2 batches) was dissolved in water (250 mL) and the pH adjusted to approximately pH 9-10 using an aqueous sodium hydroxide solution (4 M). The mixture was heated to 60-65° C. in an oil bath. To this was added sodium nitroprusside dihydrate (21.1 mL, 122 mmol) portion wise over a 1 hour period while maintaining the pH of the reaction mixture between 9-10 using a sodium hydroxide aqueous solution (4 M). The resulting mixture was heated for an additional 5 hours while maintaining the pH between 9-10 with occasional addition of a sodium hydroxide aqueous solution (4 M). The mixture was filtered and the pH of the filtrate was adjusted to pH=2 by the slow addition of 6M hydrochloric acid solution (Caution: HCN was released during the acidification, which can be monitored by HCN detector). The mixture was extracted with ethyl acetate and the combined organic layers were washed with brine, dried over anhydrous sodium sulfate, filtered, and concentrated under reduced pressure. The residue was purified by reverse phase flash column chromatography using a water/acetonitrile gradient with 0.1% trifluoroacetic acid additive to afford 3-17-1 (18 g, 42% yield) as a pink gum.

To a solution of 3-17-1 (7.00 g, 24.9 mmol) in N,N-dimethylacetamide (100 mL) was added potassium carbonate (89.4 g, 647 mmol), followed by the addition of 2-bromo-2-methyl-propane (139 mL, 1.19 mol). The mixture was stirred at 55° C. for 24 hours then the reaction mixture was filtered. The filtrate was poured into water and extracted with ethyl acetate. The combined organic phase was washed with brine, dried over anhydrous sodium sulfate, filtered, and concentrated under reduced pressure. The residue was purified by flash silica gel column chromatography to afford 3-17-2 (6.5 g, 70% yield) as a yellow gum.

A solution of 3-17-2 (6.4 g, 19 mmol) in methanol (60 mL) was degassed and purged with nitrogen for 10 minutes. To this was added Pd/C (0.6 g, 10% purity on carbon) in one portion. The mixture was degassed and purged with hydrogen three times and then stirred for 3 hours at 20° C. under a hydrogen atmosphere. The reaction mixture was filtered and the filtrate was concentrated under reduced pressure to afford 3-17-3 (3.5 g, 86% yield) as a colorless gum. No further purification was performed.

To a solution of 1-86-2 (3.19 g, 11.1 mmol), 3-17-3 (2.5 g, 12 mmol), and diisopropylethylamine (6.4 mL, 37 mmol) in N,N-dimethyl formamide (20 mL) was added a solution of T3P (11 mL, 18 mmol, 50% purity in ethyl acetate) drop wise at 0 C. The mixture was stirred for 1 hour at 0° C. then poured into water and extracted with ethyl acetate. The combined organic phase was washed with brine, dried over anhydrous sodium sulfate, filtered, and concentrated under reduced pressure. The residue was purified by flash silica gel column chromatography to afford 3-17-4 (4.0 g, 69% yield) as a colorless gum.

To a solution of 3-17-4 (4.0 g, 8.4 mmol) in methanol (40 mL) was added a solution of HCl in 1,4-dioxane (4 M, 9.33 mL, 37.3 mmol) at 0° C. The mixture was warmed to 20° C. and stirred for 12 hours. The reaction mixture was concentrated under reduced pressure to afford 3-17-5 (3.8 g, crude, 2HCl salt) as a white solid. No further purification was performed.

To a solution of 3-17-5 (3.6 g, 8.1 mmol, 2HCl salt), 3-04-5 (2.46 g, 7.26 mmol), and diisopropylethylamine (5.62 mL, 32.3 mmol) in N,N-dimethyl formamide (30 mL) was added a solution of T3P (5.76 mL, 9.68 mmol, 50% purity in ethyl acetate) at 0° C. The mixture was stirred for 1 hour at 0° C. then poured into water and extracted with ethyl acetate. The combined organic phase was washed with a saturated sodium bicarbonate aqueous solution followed by brine then dried over anhydrous sodium sulfate, filtered, and concentrated under reduced pressure. The residue was purified by flash siolica gel column chromatography to afford 3-17-6 (2.6 g, 46% yield) as a white solid.

To a solution of p-toluenesulfonyl chloride (856 mg, 4.49 mmol) in pyridine (30 mL) was added 3-17-6 (2.6 g, 3.7 mmol). The mixture was stirred for 2 hours at 15° C. then poured into water and the pH of the resulting mixture adjusted to approximately pH=7 using a 1 N hydrochloric acid aqueous solution. This mixture was extracted with ethyl acetate and the combined organic phase was washed with brine, dried over anhydrous sodium sulfate, filtered, and concentrated under reduced pressure to afford 3-17-7 (3.3 g, crude) as a yellow gum. No further purification was performed.

A solution of 3-17-7 (3.3 g, 3.9 mmol) in methanol (3 mL) was degassed and purged with nitrogen for 10 minutes. To this was added $Pd(OH)_2/C$ (0.1 g, 10% purity on carbon) in one portion. The mixture was degassed, purged with hydrogen three times, and stirred at 20° C. for 12 hours under a hydrogen atmosphere (15 psi). The mixture was filtered and the filtrate was concentrated under reduced pressure to afford 3-17-8 (2.7 g, crude) as a white solid. No further purification was performed.

To a solution of 3-17-8 (1.5 g, 2.0 mmol) in N,N-dimethyl formamide (15 mL) was added cesium carbonate (1.5 g, 4.6 mmol) at 20° C. The mixture was heated to 30° C. and stirred for 3 hours. The reaction mixture was poured into water and extracted with ethyl acetate. The combined organic phase was washed with brine, dried over anhydrous sodium sulfate, filtered, and concentrated under reduced pressure. The residue was purified by flash silica gel column chromatography followed by preparative reverse phase HPLC using a water/acetonitrile gradient with 0.1% trifluoroacetic acid additive to afford 3-17-9 (480 mg, 18.6% yield) as a colorless gum.

To a solution of 3-17-9 (40 mg, 0.68 mmol) in dichloromethane (0.6 mL) was added trifluoroacetic acid (0.3 mL, 4 mmol). The mixture was stirred for 1 hour at 20° C. then concentrated under reduced pressure. The residue was purified by preparative reverse phase HPLC using a water/acetonitrile gradient with 0.1% trifluoroacetic acid additive to afford 3-17-10 (22 mg, 49% yield, TFA salt) as a white solid.

To a solution of 3-17-10 (80 mg, 0.15 mmol) and cyclopropylmethanamine (22 mg, 0.30 mmol) in dimethyl formamide (1 mL) was added diisopropylethylamine (0.10 mL, 0.60 mmol) and a solution of T3P (0.18 mL, 0.30 mmol, 50% purity in ethyl acetate) at 0° C. The mixture was stirred for 1 hour at 0° C. then the reaction mixture was poured into water and extracted with ethyl acetate. The combined organic phase was washed with brine, dried over anhydrous sodium sulfate, filtered, and concentrated under reduced pressure. The residue was purified by preparative reverse phase HPLC (using a water/acetonitrile gradient with 0.1% trifluoroacetic acid additive to afford 3-17 (14 mg, 13% yield, TFA salt) as a white solid. LCMS of 3-17: RT=2.201 min, m/z 584.4[M+H]$^+$.

The following compounds were made using a similar synthetic route as described for compound 3-17:

Compound 3-19; LCMS: RT=1.624=min, m/z 648.3 [M+H]$^+$

Compound 3-20; LCMS: RT=2.104 min, m/z 598.3 [M+H]$^+$

Compound 3-21; LCMS: RT=1.501 min, m/z 589.4 [M+H]$^+$

Compound 3-22; LCMS: RT=1.487 min, m/z 589.41 [M+H]$^+$

Compound 3-23; LCMS: RT=1.976 min, m/z 614.4 [M+H]$^+$

Compound 3-24; LCMS: RT=0.645 min, m/z 602.3 [M+H]$^+$

Example 47—Synthesis of (7S,10S)-N-(2-Fluorobenzyl)-9,12-dioxo-10-(2-oxo-2-((R)-2-phenylpyrrolidin-1-yl)ethyl)-2-oxa-8,11-diaza-1(1,3)-benzenacyclotetradecaphane-7-carboxamide (3-18)

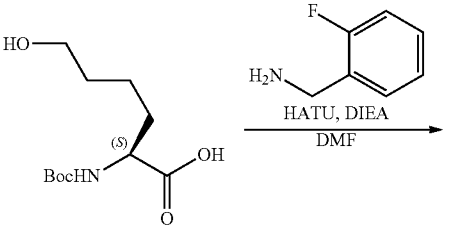

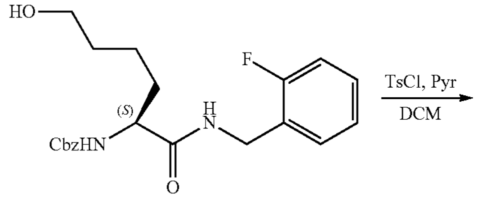

3-18-1

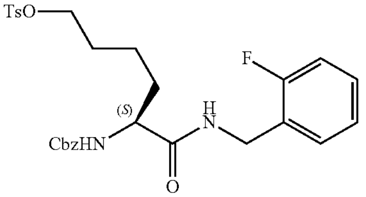

3-18-2

-continued

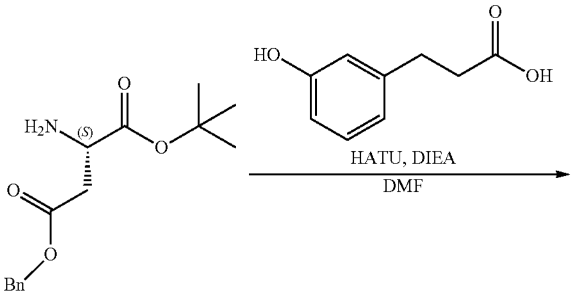

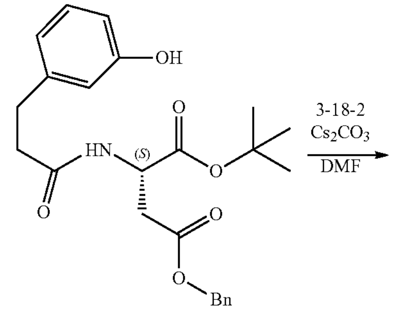

3-18-3

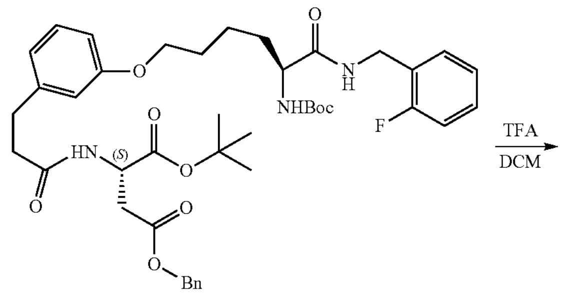

3-18-4

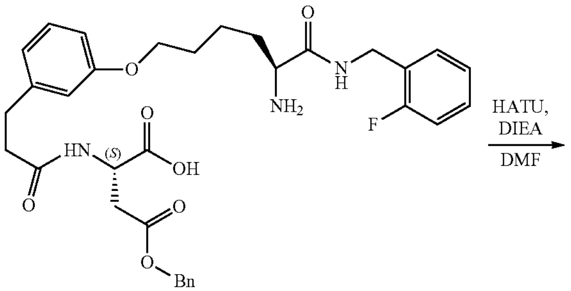

3-18-5

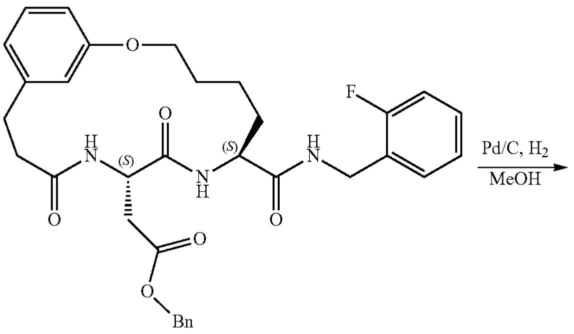

3-18-6

-continued

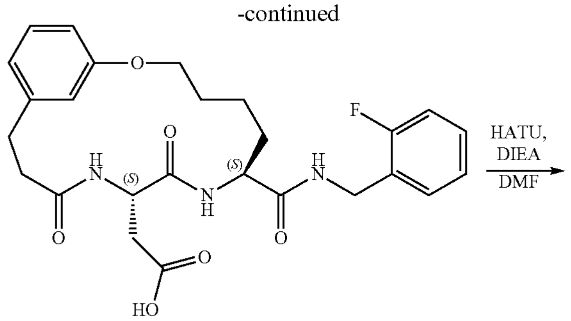

3-18-7

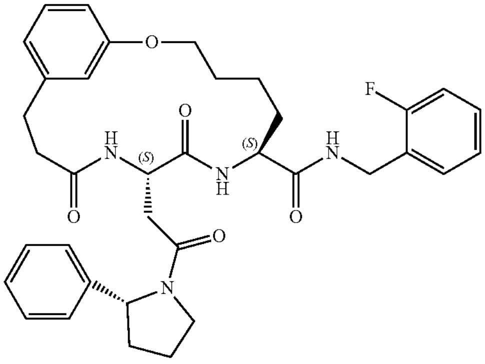

3-18

To a solution of (S)-2-((tert-butoxycarbonyl)amino)-6-hydroxyhexanoic acid (0.500 g, 2.02 mmol) in DMF (20 mL) was added (2-fluorophenyl)methanamine (0.28 mg, 2.2 mmol) followed by DIEA (1.0 mL, 0.58 mmol) and of HATU (0.85 g, 2.2 mmol). The mixture was stirred at room temperature for 3 hours then diluted with water and extracted with EtOAc. The combined organic phase was washed with a 1N hydrochloric acid solution followed by saturated aqueous solution of sodium bicarbonate and brine. The organic phase was dried over anhydrous sodium sulfate then concentrated under reduced pressure. The residue was purified by flash silica gel chromatography and the eluent was removed under reduced pressure to provide 3-18-1 (0.533 g, 74.3% yield) as a clear oil.

To a solution of 0.266 g (0.750 mmol) of 3-18-1 in DCM (4 mL) was added 0.17 g (0.89 mmol) of pTSA followed by 0.15 mL (1.9 mmol) of pyridine. The mixture was stirred overnight at room temperature then washed with a saturated aqueous solution of sodium bicarbonate. The organic phase was dried over anhydrous sodium sulfate and concentrated under reduced pressure to provide 3-18-2 (0.311 g, 81.5% yield) as a yellow oil. No further purification was performed.

To a solution of 0.250 g (1.50 mmol) of 3-(3-hydroxyphenyl)propanoic acid in DMF (7 mL) was added 0.500 g (1.58 mmol) of 4-benzyl 1-(tert-butyl) L-aspartate hydrochloride followed by 0.65 g (1.7 mmol) of HATU and 0.90 mL (5.2 mmol) of DIEA. The mixture was stirred at room temperature for 4 hours then diluted with water and extracted with EtOAc. The combined organic phase was washed with 1N HCl followed by saturated aqueous sodium bicarbonate and brine. The mixture was dried over anhydrous sodium sulfate and concentrated under reduced pressure. The residue was purified by flash silica gel chromatography and the eluent was concentrated under reduced pressure to provide 3-18-3 (0.587 g, 91%) as a clear oil.

To a solution of 0.290 g (0.678 mmol) of 3-18-3 in DMF (3 mL) was added 0.311 g (0.611 mmol) of 3-18-2 was added as a solution in DMF (3 mL). To this was added 1.0 g (3.1 mmol) of cesium carbonate. The mixture was stirred at room temperature for 3 days then diluted with water and extracted with DCM. The combined organic phase was washed with water followed by brine then dried over anhydrous sodium sulfate and concentrated under reduced pressure. The residue was purified by flash silica gel chromatography and the eluent was removed under reduced pressure to provide 3-18-4 (0.227 g, 43.8% yield) as a light yellow oil.

To a solution of 0.113 g (0.148 mmol) of 3-18-4 in DCM (1 mL) was added 0.20 mL (2.6 mmol) of TFA. The mixture was stirred overnight at room temperature then concentrated under reduced pressure. The residue was purified by C18 flash reverse phase column chromatography using a gradient of acetonitrile in water w/ 0.1% formic acid additive. The eluent was removed under reduced pressure to provide 3-18-5 (0.090 g, 93% yield) as a clear film.

To a solution of 0.068 g (0.10 mmol) of 3-18-5 in DMF (5 mL) was added 0.075 mL (0.43 mmol) of DIEA followed by 0.045 g (0.12 mmol) of HATU. The mixture was allowed to stir at room temperature for 4 days then purified by flash C18 reverse phase chromatography using a 5-95% gradient of acetonitrile in water w/ 0.1% formic acid additive. The solvent was removed under reduced pressure and the residue triturated with a 1:1 mixture of acetonitrile:water to provide 3-18-6 (0.021 g, 34% yield) as a white powder.

To a flask containing 0.020 g (0.034 mmol) of 3-18-6 was added 0.005 g (0.005 mmol) of 10% palladium on carbon. The flask was evacuated and refilled with nitrogen three times. To this was added a 1:1 mixture of methanol:ethyl acetate (5 mL). The atmosphere was replaced with hydrogen and the mixture was stirred at room temperature for 1 hour. The mixture was filtered through a syringe filter and concentrated under reduced pressure to provide 3-18-7 (0.017 g, quant) as a white powder. No further purification was performed.

To a solution of 0.017 g (0.034 mmol) of 3-18-7 in DMF (1 mL) was added 0.018 mL (0.10 mmol) of DIEA and 0.010 g (0.068 mmol) of (R)-2-phenylpyrrolidine. To the mixture was added 0.015 g (0.039 mmol) of HATU. The mixture was stirred overnight at room temperature then purified by preparative reverse phase chromatography using a 5-95% gradient of acetonitrile in water w/ 0.1% formic acid additive. The eluent was removed under reduced pressure to provide 3-18 (0.006 g, 28% yield) of as a white powder. LCMS of 3-18: RT=2.298 min, m/z 629.3 $[M+H]^+$.

Example 48—Synthesis of (6S,9S)-N-Cyclopentyl-9-(2-morpholinoethyl)-8,11-dioxo-2-oxa-7,10-diaza-1(1,3)-benzenacyclotridecaphane-6-carboxamide (3-25)

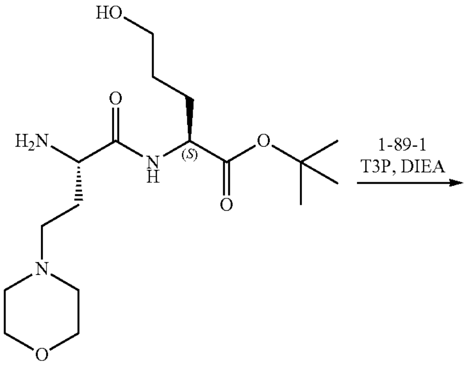

3-17-5

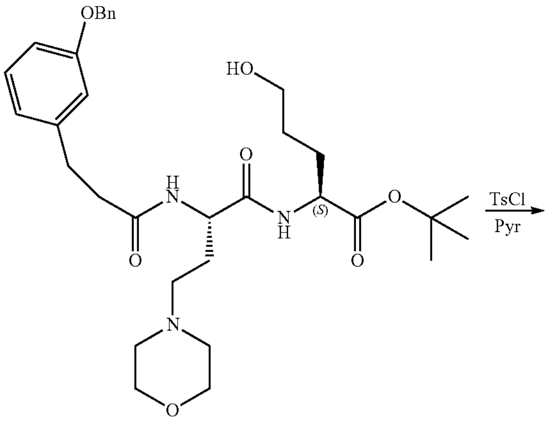

3-25-1

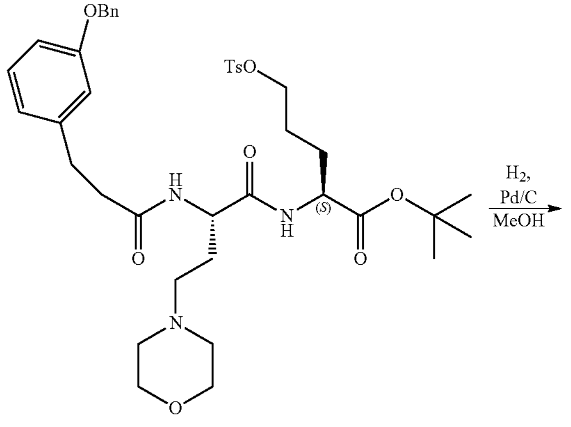

3-25-2

-continued

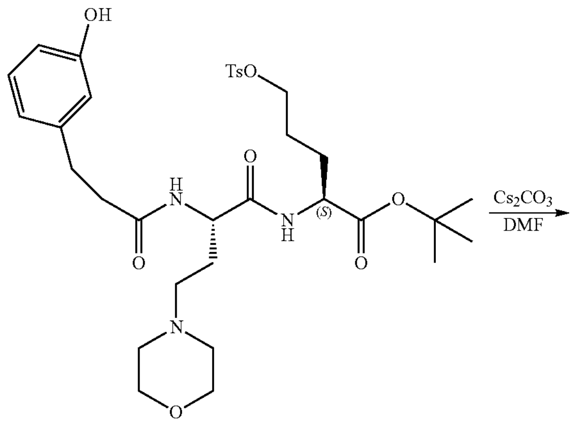

3-25-3

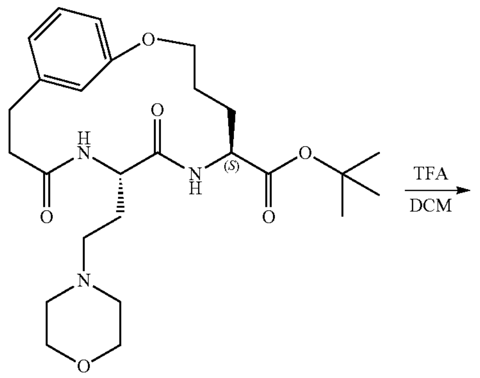

3-25-4

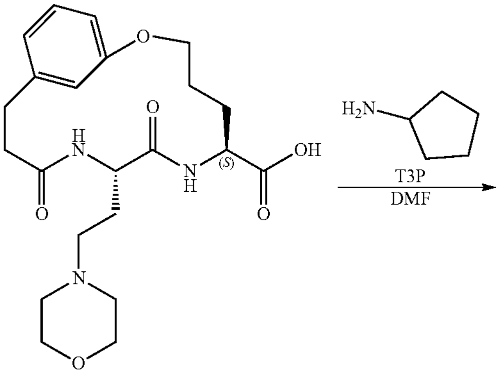

3-25-5

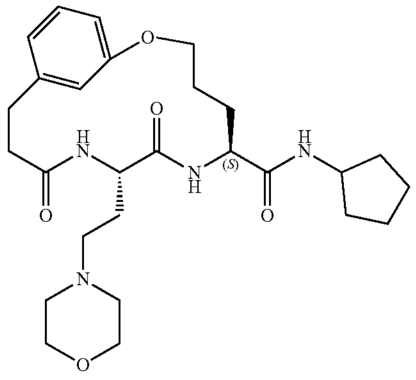

3-25

To a solution of 3-17-5 (3.00 g, 6.72 mmol, di-HCl salt), 1-89-1 (1.89 g, 7.39 mmol), and N,N-diisopropylethylamine (5.85 mL, 33.6 mmol) in N,N-dimethylformamide (30 mL) was added T3P (4.80 mL, 8.06 mmol, 50% purity in ethyl acetate) at 0° C. The mixture was stirred at 0° C. for 1 hour then the reaction mixture was poured into water (100 mL) and extracted with ethyl acetate. The combined organic phase was washed with brine, dried over anhydrous sodium sulfate, filtered, and the filtrate was concentrated under reduced pressure. The residue was purified by flash column chromatography to afford 3-25-1 (1.50 g, 36.5% yield) as yellow gum.

To a solution of 3-25-1 (1.50 g, 2.45 mmol) in pyridine (15 mL) was added para-toluensulfonyl chloride (0.935 g, 4.90 mmol). The mixture was stirred for 2 hour at 20° C. then poured into water and the pH adjusted to pH-7 with a 1N hydrochloric acid solution. The mixture was extracted with ethyl acetate and the combined organic phase was washed with brine, dried over anhydrous sodium sulfate, filtrated, and the filtrate was concentrated under reduced pressure. The residue was purified by flash column chromatography to afford 3-25-2 (1.50 g, 17.9% yield) as yellow gum.

To a solution of 3-25-2 (1.50 g, 1.96 mmol) in methanol (20 mL) was added 10% $Pd(OH)_2/C$ (0.150 g) under nitrogen. The mixture was degassed with hydrogen three times and stirred at 20° C. for 5 hours under a hydrogen atmosphere (15 psi). The reaction mixture was filtered and the filtrate was concentrated under reduced pressure to afford 3-25-3 (1.12 g, 84.6% yield) as colorless gum.

To a solution of 3-35-3 (1.12 g, 1.63 mmol) in dimethyl formamide (28 mL) was added cesium carbonate (1.26 g, 3.86 mmol). The mixture was stirred for at 30° C. 3 hours then poured into water (50 mL). The mixture was extracted with ethyl acetate and the combined organic phase was washed with brine, dried over anhydrous sodium sulfate, filtered, and concentrated under reduced pressure. The residue was purified by prep-HPLC using a mobile phase of water/acetonitrile with TFA buffer. The eluent was removed under reduced pressure to afford 3-25-4 (0.250 g, 30.0% yield) as a white solid.

To a solution of 3-25-4 (0.250 g, 0.496 mmol) in dichloromethane (3 mL) was added trifluoroacetic acid (0.5 mL, 7 mmol) drop-wise. The mixture was stirred for at 20° C. 24 hours then concentrated under reduced pressure to afford 3-25-5 (0.240 g, crude, TFA salt) as yellow gum. No further purification was performed.

To a solution of 3-25-5 (0.060 g, 0.13 mmol, TFA salt), cyclopentyl amine (0.040 mL, 0.40 mmol) and N,N-diisopropylethylamine (0.093 mL, 0.54 mmol) in dichloromethane (1 mL) was added T3P (0.12 mL, 0.20 mmol, 50% purity in ethyl acetate) drop-wise at 0° C. The mixture was stirred at 0° C. for 1 hour then poured into water (20 mL) and extracted with ethyl acetate. The combined organic phase was washed with brine (30 mL), dried over anhydrous sodium sulfate, filtered, and concentrated under reduced pressure. The residue was purified by prep-HPLC using an eluent of water/acetonitrile with ammonium bicarbonate buffer. The eluent was removed under reduced pressure to afford compound 3-25 (20.8 mg, 29.3% yield) as a white solid. LCMS of 3-25: RT=2.113 min, m/z: 515.3 $[M+H]^+$.

The following compounds were made using a similar synthetic route as described for compound 3-25:

Compound 3-26; LCMS: RT=2.156 min, m/z 555.3 $[M+H]^+$

Compound 3-27; LCMS: RT=1.402 min, m/z 515.3 $[M+H]^+$

Compound 3-31; LCMS: RT=1.874 min, m/z 531.3 $[M+H]^+$

Compound 3-32; LCMS: RT=1.849 min, m/z 531.3 $[M+H]^+$

Example 49—Synthesis of (7S,10S,13S)-N-Cyclopentyl-10-(4-fluorophenethyl)-9,12-dioxo-13-(2-oxopyrrolidin-1-yl)-2-oxa-8,11-diaza-1(1,3)-benzenacyclotetradecaphane-7-carboxamide (3-28)

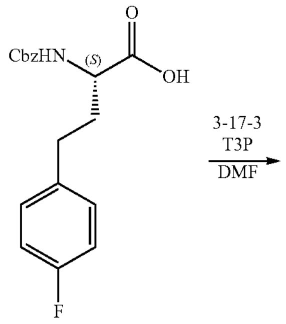

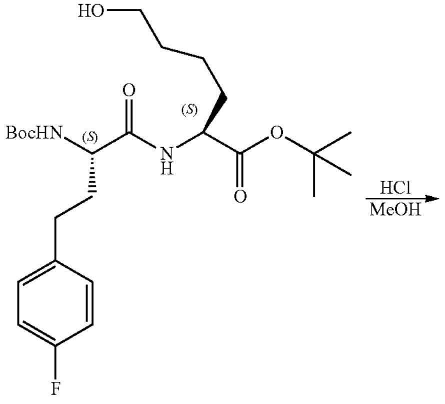

3-28-1

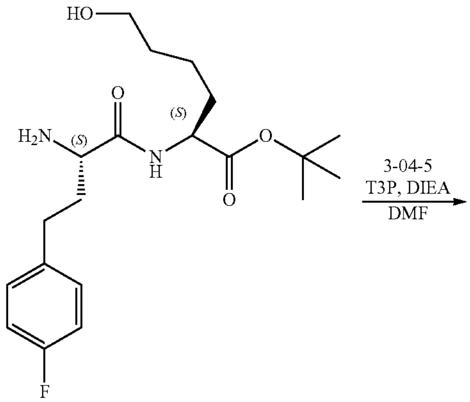

3-28-2

-continued

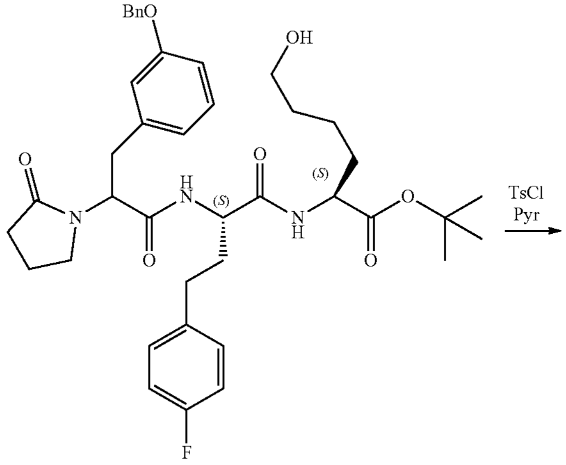

3-28-3

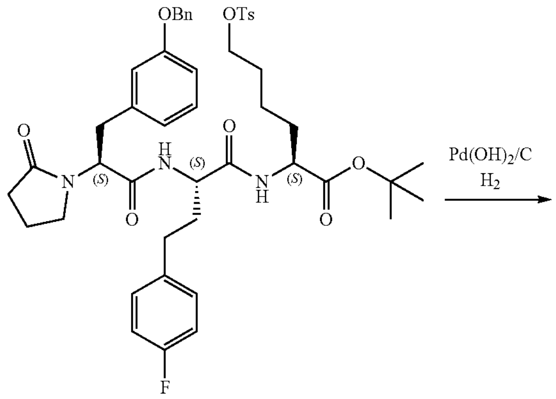

3-28-4

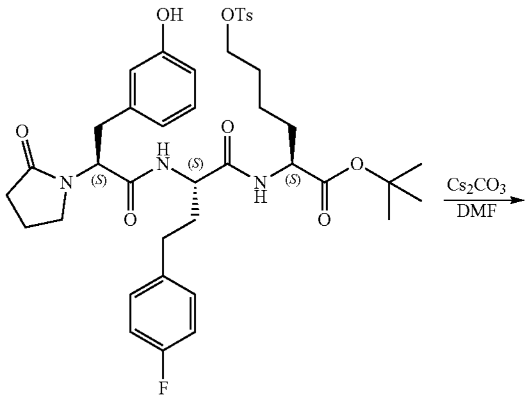

3-28-5

-continued

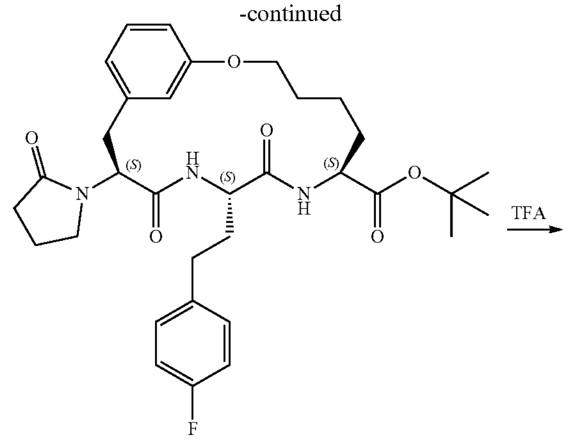

3-28-6

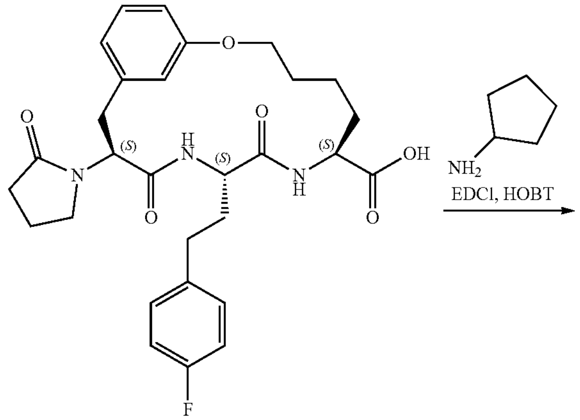

3-28-7

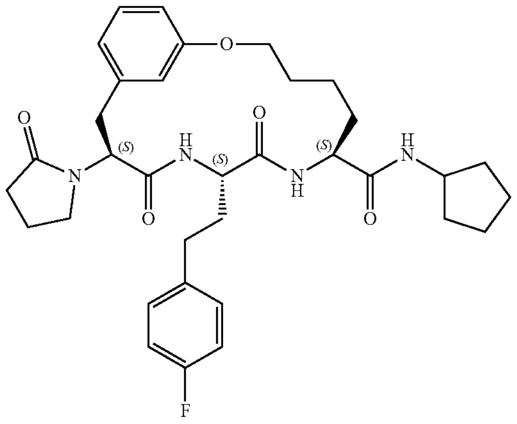

3-28

To a solution of 3-17-3 (1.30 g, 5.90 mmol), (S)-2-(((benzyloxy)carbonyl)amino)-4-(4-fluorophenyl)butanoic acid (1.92 g, 5.78 mmol), and T3P (5.27 mL, 8.85 mmol, 50% solution in EtOAc) in dichloromethane (30 mL) was added N,N-diisopropylethylamine (2.06 mL, 11.8 mmol) at −5° C. The mixture was stirred at −5° C. for 1 hour under nitrogen atmosphere then diluted with water (15 mL) and extracted with ethyl acetate. The combined organic layers were washed with 1N hydrochloric acid (20 mL) followed by a saturated sodium bicarbonate aqueous (20 mL) and then brine (20 mL). The solution was dried over anhydrous sodium sulfate, filtered, and the filtrate was concentrated under reduced pressure. The residue was purified by flash silica gel column chromatography and the eluent was removed under reduced pressure to give 3-28-1 (1.07 g, 32.1% yield) as light yellow gum.

A solution of 3-28-1 (1.07 g, 1.94 mmol) in tetrahydrofuran (10 mL) and trifluoroacetic acid (331.08 mg, 2.90 mmol, 214.99 uL, 1.5 eq) was degassed and purged with nitrogen three times, 10% Pd/C (0.2 g) was added, then degassed and purged with hydrogen three times. The reaction mixture was stirred at 20° C. for 1 hour under hydrogen (15 psi). The reaction mixture was filtrated to give a solution of 3-28-2 in tetrahydrofuran (10 mL), which was used directly without further purification.

To the above solution of 3-28-2 in tetrahydrofuran (10 mL) was added N,N-diisopropylethylamine (1.35 mL, 7.74 mmol), 3-04-5 (0.657 g, 1.93 mmol), and T3P (0.863 mL, 1.45 mmol, 50% solution in EtOAc) at −5° C. The reaction was stirred at −5° C. for 1 hour under nitrogen then diluted with water (20 mL). The mixture was extracted with ethyl acetate, washed with brine, dried over anhydrous sodium sulfate, filtrated, and the filtrate was concentrated under reduced pressure. The residue was purified by flash silica gel column chromatography. The eluent was removed under reduced pressure and the isolated material was combined with another batch (0.67 g scale) to provide 3-28-3 (1.16 g) as a white solid.

To a solution of 3-28-3 (1.16 g, 1.65 mmol) in pyridine (12 mL) was added p-toluenesulfonyl chloride (1.57 g, 8.24 mmol) at 20° C. and the reaction mixture was stirred at 20° C. for 3 hours under nitrogen atmosphere. The reaction was diluted with water (20 mL) and extracted with ethyl acetate. The combined organic phase was washed with 1N hydrochloric acid solution followed by a saturated sodium bicarbonate aqueous solution then brine. The solution was dried over anhydrous sodium sulfate, filtrated, and the filtrate was concentrated under reduced pressure. The residue was purified by flash silica gel column chromatography and the eluent removed under reduced pressure to provide 3-28-4 (0.90 g, 55% yield) as a white solid.

To a solution of 3-28-4 (0.90 g, 1.0 mmol) in methanol (20 mL) was added 10% $Pd(OH)_2/C$ (0.090 g) under nitrogen. The suspension was degassed under vacuum and purged with hydrogen several times. The mixture was stirred under a hydrogen atmosphere (15 psi) at 20° C. for 3 hours. The mixture was filtered and the filter pad was washed with methanol. The filtrate was concentrated under reduced pressure to afford 3-28-5 (crude, 0.780 g, 78.0% yield) as white solid, which was used directly without further purification.

To a solution of 3-28-5 (0.780 g, 1.02 mmol) in N,N-dimethylformamide (40 mL) was added cesium carbonate (0.993 g, 3.05 mmol). The mixture was stirred at 30° C. for 16 hours then poured into 1N hydrochloric acid aqueous solution (80 mL) cooled to 0° C. The mixture was extracted with ethyl acetate and the combined organic phase was washed with a saturated sodium bicarbonate solution followed by brine then dried over anhydrous sodium sulfate, filtered, and the filtrate was concentrated under reduced pressure. The residue was purified by flash silica gel column chromatography and the eluent removed under reduced pressure to afford 3-28-6 (0.330 g, 47.1% yield) as a white solid.

To a solution of 3-28-6 (0.33 g) in dichloromethane (4 mL) was added trifluoroacetic acid (1.25 mL, 16.9 mmol). The mixture was stirred at 20° C. for 3 hours then concentrated under reduced pressure to afford 3-28-7 (0.130 g, crude) as brown gum, which was used for the next step without further purification.

To a solution of 3-28-7 (0.040 g, 0.074 mmol), N,N-diisopropylethylamine (0.039 mL, 0.22 mmol), and cyclopentylamine (0.022 mL, 0.22 mmol) in dichloromethane (1 mL) was added T3P (0.088 mL, 0.15 mmol, 50% solution in EtOAc) at 0° C. The mixture was stirred at 0° C. for 1 hour then poured into water (10 mL) and extracted with ethyl acetate. The combined organic phase was washed with a 1N hydrochloric acid solution followed by a saturated sodium bicarbonate aqueous solution then brine. The solution was dried over anhydrous sodium sulfate, filtered, and the filtrate was concentrated under reduced pressure. The residue was purified by prep-HPLC using an eluent of water/acetonitrile with ammonium carbonate modifier. The eluent was removed under reduced pressure to afford 3-28 (0.012 g, 26% yield) as a white solid.

The following compounds were made using a similar synthetic route as described for compound 3-28:

Compound 3-29; LCMS: RT=2.525 min, m/z 623.3 $[M+H]^+$

Compound 3-30; LCMS: RT=2.525 min, m/z 623.3 $[M+H]^+$

Compound 3-44; LCMS: RT=2.807 min, m/z 643.3 $[M+H]^+$

Example 50—Synthesis of (7S,10S,13S)-9,12-Dioxo-13-(2-oxopyrrolidin-1-yl)-10-phenethyl-N-(2,2,2-trifluoroethyl)-2-oxa-8,11-diaza-1(1,3)-benzenacyclotetradecaphane-7-carboxamide (3-33)

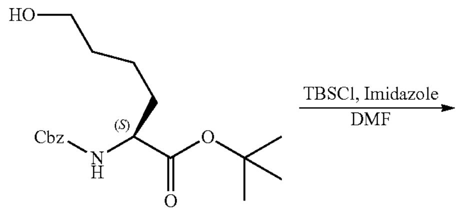

3-17-2

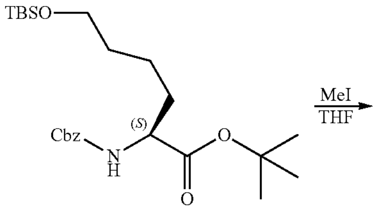

3-33-1

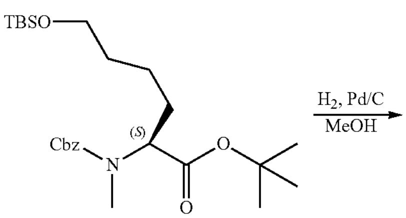

3-33-2

-continued

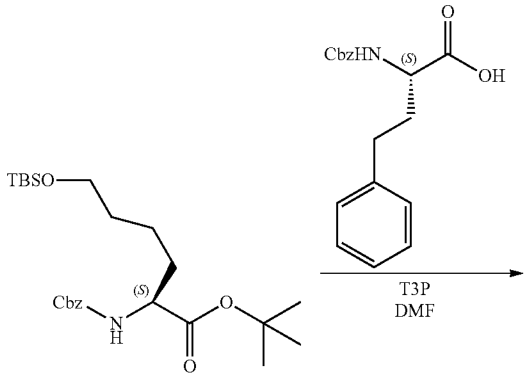

3-33-3

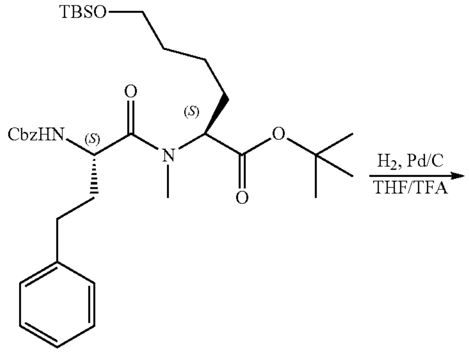

3-33-4

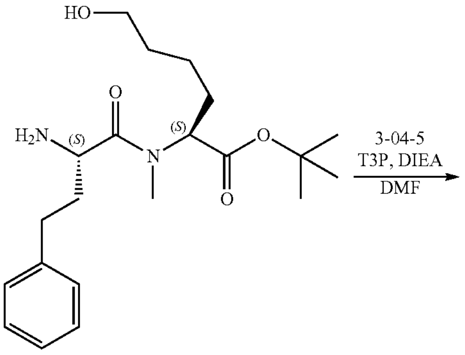

3-33-5

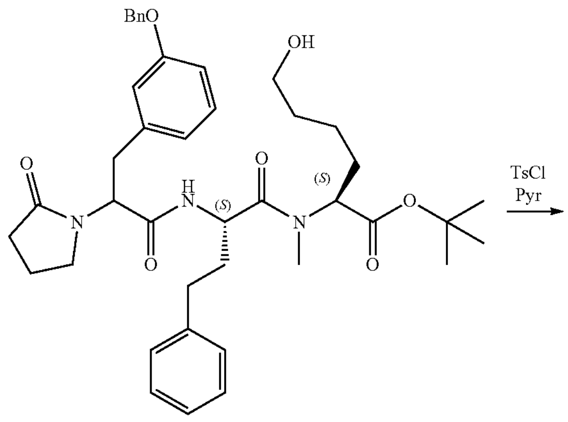

3-33-6

-continued

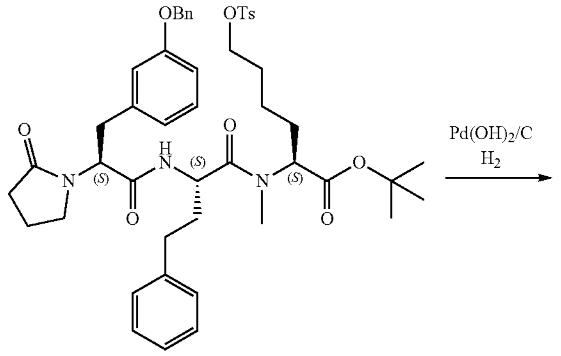

3-33-7

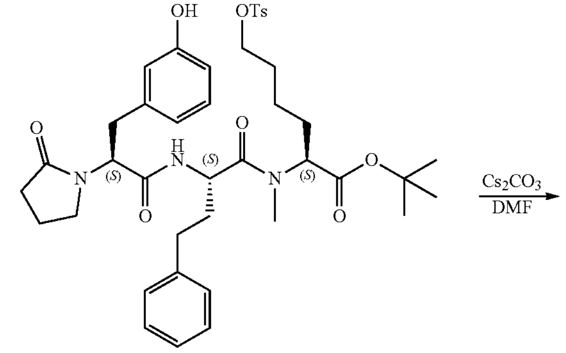

3-33-8

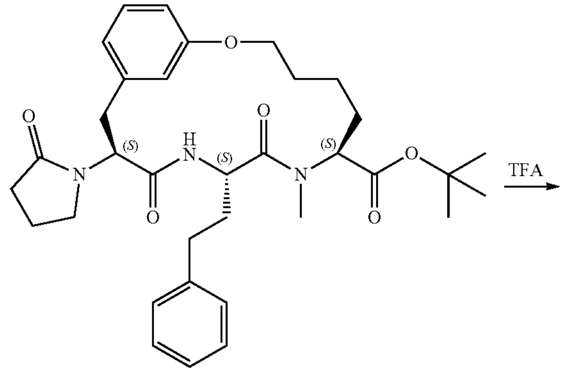

3-33-9

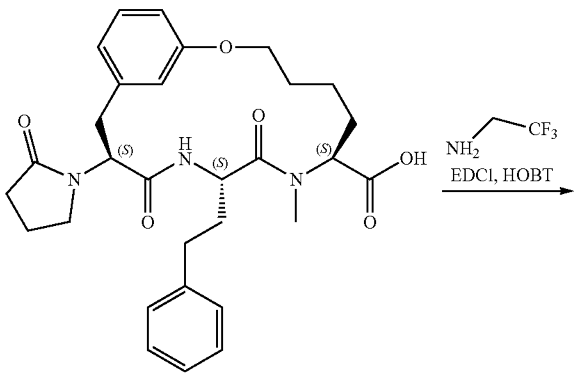

3-33-10

-continued

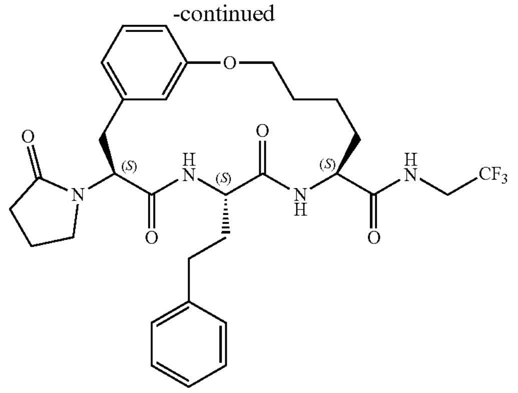

3-33

To a solution of 3-17-1 (8.0 g, 24 mmol) in dichloromethane (80 mL) was added imidazole (2.42 g, 35.6 mmol), followed by TBSCl (3.05 mL, 24.9 mmol) at 0° C. The mixture was stirred at 20° C. for 0.5 hour. The mixture was diluted with 200 mL of ethyl acetate, washed with water (50 mL*3), dried over anhydrous sodium sulfate, filtered, and the filtrate was concentrated under reduced pressure. The residue was purified by flash silica gel column chromatography which was combined with another batch (2 g scale) to afford 3-33-1 (10 g) as colorless oil.

To a solution of 3-33-1 (3.00 g, 6.64 mmol) in tetrahydrofuran (30 mL) was added sodium hydride (399 mg, 9.96 mmol, 60% purity, 1.5 eq) at 0° C. The mixture was stirred at 0° C. for 20 minutes. To this was added methyl iodide (12.5 mL, 201 mmol) and the reaction mixture was stirred at 20° C. for 30 minutes. The mixture was diluted with 55 mL of water and extracted with ethyl acetate. The combined organic phase was washed with brine, dried over anhydrous sodium sulfate, filtered, and the filtrate was concentrated under reduced pressure to afford 3-33-2 (9.0 g, 97% yield) as a colorless oil.

A solution of 3-33-2 (4.0 g, 8.6 mmol) in tetrahydrofuran (40 mL) was degassed and purged with nitrogen, 10% Pd/C (0.4 g) was added, then degassed and purged with hydrogen three times. The mixture was stirred at 20° C. under a hydrogen atmosphere (15 psi) for 2 hours. The mixture was filtered, and the filtrate was concentrated under reduced pressure. The residue was purified by flash silica gel column chromatography to afford 3-33-3 (5.6 g, 98% yield) as a colorless oil.

To a mixture of 3-33-3 (0.473 g, 1.51 mmol) in dichloromethane (6 mL) was added diisopropylethylamine (0.66 mL, 3.8 mmol) and T3P (1.35 mL, 2.26 mmol, 50% solution in EtOAc) at 0° C. To this was added (S)-2-(((benzyloxy)carbonyl)amino)-4-phenylbutanoic acid (0.500 g, 1.51 mmol) and the reaction mixture was stirred at 0° C. for 2 hours. The mixture was diluted with 30 mL of dichloromethane, washed with a saturated aqueous sodium carbonate solution then dried over anhydrous sodium sulfate, filtered, and the filtrate was concentrated under reduced pressure. The residue was purified by flash silica gel column chromatography and the eluent removed under reduced pressure to afford 3-33-4 (0.850 g, 1.36 mmol) as a colorless oil.

To a solution of 3-33-4 (0.850 g, 1.36 mmol) in tetrahydrofuran (10 mL) was added trifluoroacetic acid (0.150 mL, 2.03 mmol), the solution was degassed and purged with nitrogen three times, 10% Pd/C (0.085 g) was added. The mixture was degassed and purged with hydrogen three times, then stirred at 20° C. under a hydrogen atmosphere (15 psi) for 3 hours. The mixture was filtered and the filtrate was concentrated under reduced pressure to afford 3-33-5 (0.513 g, crude) as a yellow oil, which was used directly without further purification.

To a mixture of 3-33-5 (0.457 g, 1.35 mmol, 1 eq) in dichloromethane (9 mL) was added diisopropylethylamine (0.587 mL, 3.37 mmol) and 3-04-5 (510 mg, 1.35 mmol, 1 eq) at 0° C., then T3P (1.20 mL, 2.02 mmol, 50% solution in EtOAc) was added drop-wise and the mixture was stirred at 0° C. for 3 hours. The mixture was diluted with 60 mL of dichloromethane, washed with a saturated aqueous sodium carbonate solution then dried over anhydrous sodium sulfate, filtered, and the filtrate was concentrated under reduced pressure. The residue was purified by flash silica gel column chromatography and the eluent removed under reduced pressure to afford 3-33-6 (0.700 g, 74.2% yield) as a colorless oil.

To a solution of 3-33-6 (0.600 g, 0.857 mmol) in pyridine (7 mL) was added p-toluenesulfonyl chloride (1.00 g, 5.25 mmol) at 0° C. The mixture was allowed to warm to 20° C. and stirred for 3 hours. The mixture was diluted with 20 mL of ethyl acetate, washed with a 1N hydrochloride acid solution then dried over anhydrous sodium sulfate, filtered, and the filtrate was concentrated under reduced pressure. The residue was purified by flash silica gel column chromatography and the eluent removed under reduced pressure to afford 3-33-7 (0.450 g, 0.527 umol, 61.5% yield) as a colorless oil.

A solution of 3-33-7 (0.450 g, 0.527 mmol) in methanol (5 mL) was degassed with nitrogen three times. To this was added 10% $Pd(OH)_2/C$ (0.045 g) and the mixture was degassed and purged with hydrogen three times then stirred at 20° C. under hydrogen (15 psi) for 18 hours. The mixture was filtered and the filtrate was concentrated under reduced pressure. The residue was purified by flash silica gel column chromatography to provide 3-33-8 (0.300 g, 74.5% yield) as a colorless oil.

To a solution of 3-33-8 (0.300 g, 0.393 mmol) in dimethyl formamide (6 mL) was added cesium carbonate (0.256 g, 0.785 mmol) at 0° C. and the mixture was stirred at 0-20° C. for 3 hours. The mixture was poured into water (30 mL) and extracted with ethyl acetate. The combined organic layer was dried over anhydrous sodium sulfate, filtered, and the filtrate was concentrated under reduced pressure. The residue was purified by prep-HPLC using an eluent of water/acetonitrile with TFA additive. The eluent was removed under reduced pressure to provide 3-33-9 (0.070 g, 30% yield) as a colorless oil.

To a solution of 3-33-9 (0.070 g, 120 mmol) in dichloromethane (2 mL) was added trifluoroacetic acid (0.50 mL, 6.7 mmol) at 0° C. The mixture was stirred at 0-20° C. for 3 hours. The mixture was concentrated under reduced pressure to afford 3-33-10 (0.060 g, 95% yield) as a colorless oil, which was used without further purification.

To a solution of 3-33-10 (0.060 g, 112 mmol) and 2,2,2-trifluoroethylamine (0.011 mL, 0.130 mmol) in tetrahydrofuran (1 mL) was added diisopropylethylamine (0.049 mL, 0.280 mmol) at 0° C., followed by T3P (0.10 mL, 0.170 mmol, 50% solution in EtOAc) and the mixture was stirred at 0° C. for 1 hour. The mixture was diluted with 30 mL of water and extracted with ethyl acetate. The combined organic phase was washed with brine, dried over anhydrous sodium sulfate, filtered, and the filtrate was concentrated under reduced pressure. The residue was purified by prep-HPLC using and eluent of water/acetonitrile with an ammonium carbonate buffer. The eluent was removed under reduced pressure to afford 3-33 (0.020 mg, 28% yield) as a white solid. LCMS of 3-33: RT=2.758 min, m/z 617.3 $[M+H]^+$.

Example 51—Synthesis of (7S,10S,13S)-N-Cyclopentyl-13-(dimethylamino)-10-(2-morpholinoethyl)-9,12-dioxo-2-oxa-8,11-diaza-1(1,3)-benzenacyclotetradecaphane-7-carboxamide (3-34)

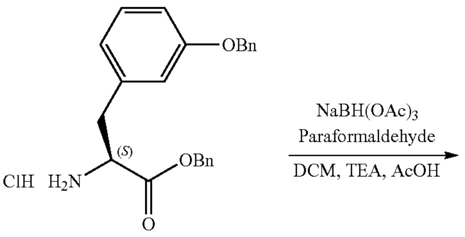

3-04-2

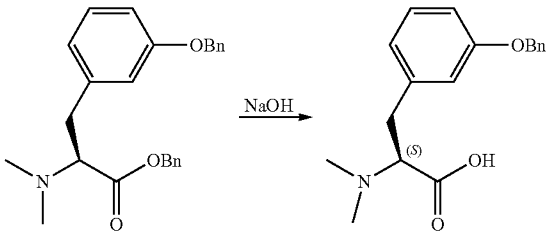

3-34-1

3-34-2

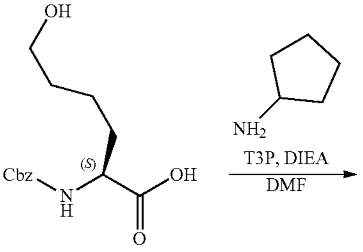

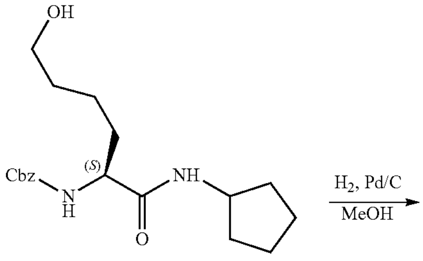

3-34-3

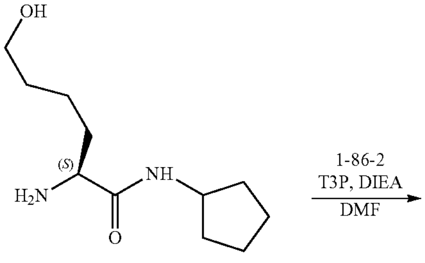

3-34-4

-continued

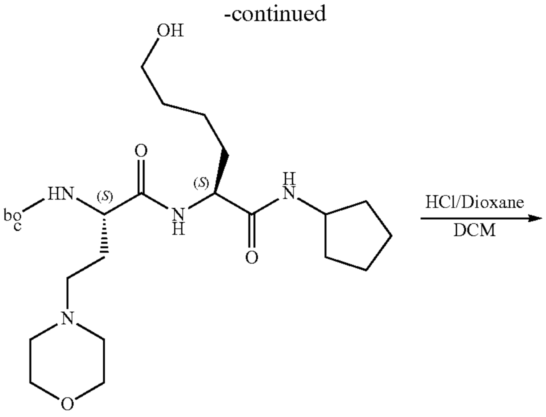

3-34-5

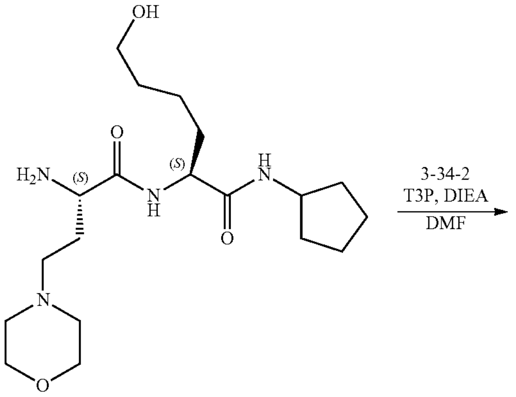

3-34-6

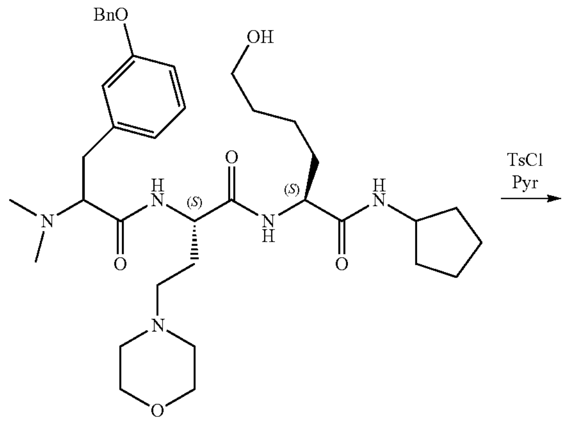

3-34-7

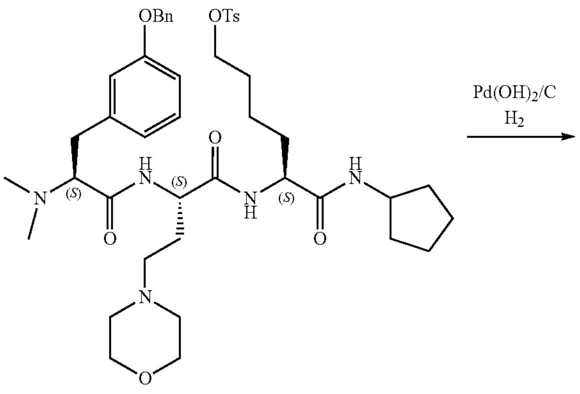

3-34-8

-continued

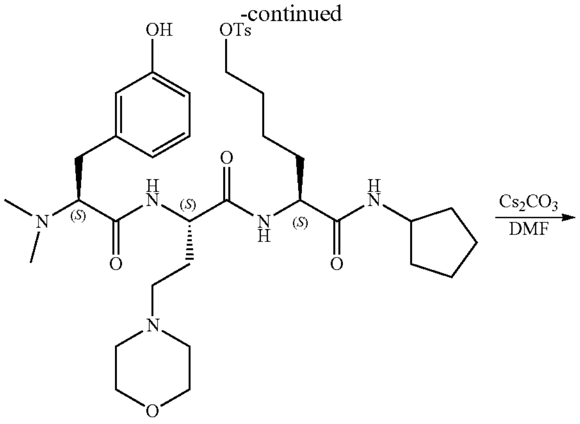

3-34-9

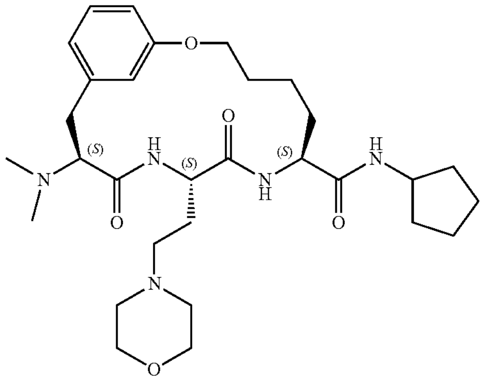

3-34

To a solution of 3-04-2 (5.00 g, 12.6 mmol, HCl salt) in dichloromethane (80 mL) was added triethylamine (3.50 mL, 25.1 mmol). The mixture was stirred at 20° C. for 15 min then acetic acid (1.80 mL, 31.4 mmol) and paraformaldehyde (5.66 g, 62.8 mmol) were added. The mixture was stirred for another 15 min at 20° C. then sodium triacetoxyborohydride (7.99 g, 37.7 mmol) was added and the mixture was stirred at 20° C. for 12 hours. The mixture was filtered and the filter cake was washed with dichloromethane (20 mL). The filtrate was concentrated under reduced pressure and the residue was purified by reversed-phase HPLC using an eluent of water/acetonitrile with 0.1% aqueous ammonia buffer. The eluent was concentrated under reduced pressure to obtain 3-34-1 (3.00 g, 61.3% yield) as a light yellow oil.

To a solution of 3-34-1 (1.50 g, 3.85 mmol) in water (15 mL) and methanol (15 mL) was added sodium hydroxide (0.924 g, 23.1 mmol) at 0° C. The mixture was stirred at 0-25° C. for 12 hour then concentrated under reduced pressure to remove volatile organics. The pH of the mixture was adjusted to approximately pH=7 with an aqueous hydrochloric acid solution (1 N). The resulting solution was purified by reversed-phase HPLC using an eluent of water/acetonitrile with 0.1% TFA buffer. The eluent was evaporated under reduced pressure to obtain 3-34-2 (1.1 g, 69%, TFA salt) as a light yellow gum.

To a solution of (S)-2-(((benzyloxy)carbonyl)amino)-6-hydroxyhexanoic acid (4.00 g, 14.2 mmol), cyclopentanamine (2.81 mL, 28.4 mmol), and diisopropylethylamine (7.43 mL, 42.7 mmol) in dimethyl formamide (40 mL) was added T3P (9.30 mL, 15.6 mmol, 50% solution in EtOAc) dropwise at 0° C. The mixture was stirred for 1 hour at 0° C. then poured into water (100 mL) and extracted with ethyl acetate. The combined organic phase was washed with a saturated sodium bicarbonate aqueous solution followed by a 1N solution of hydrochloric acid, then brine. The solution was dried over anhydrous sodium sulfate, filtered, and concentrated under reduced pressure to afford 3-34-3 (4.5 g, 91% yield) as a white solid.

To a solution of 3-34-3 (4.0 g, 11 mmol) in methanol (50 mL) was purged with nitrogen for 10 minutes, then 10% Pd/C (0.5 g) was added in one portion. The mixture was degassed with hydrogen three times then stirred for 4 hour at 20° C. under a hydrogen atmosphere (15 psi). The reaction mixture was filtered and concentrated under reduced pressure to afford 3-34-4 (2.5 g, crude) as colorless gum which was directly without further purification.

To a solution of 3-34-4 (1.2 g, 5.6 mmol), 1-86-2 (1.61 g, 5.60 mmol) and diisopropylethylamine (2.93 mL, 16.8 mmol) in dichloromethane (15 mL) was added T3P (4.00 mL, 6.72 mmol, 50% solution in EtOAc) drop-wise at 0° C. The mixture was stirred for 1 hour at 0° C. then poured into water and extracted with ethyl acetate. The combined organic layers were washed with brine, dried over anhydrous sodium sulfate, filtered, and concentrated under reduced pressure. The residue was purified by prep-HPLC using an eluent of water/acetonitrile with 0.1% TFAbuffer. The eluent was removed under reduced pressure to afford 3-34-5 (1.0 g, 34% yield) as a colorless gum.

To a solution of 3-34-5 (1.0 g, 2.1 mmol) in dioxane (10 mL) was added a solution of HCl/dioxane (4 M, 5 mL, 20 mmol) drop wise. The mixture was stirred for 3 hours at 20° C. then concentrated under reduced pressure to afford 3-34-6 (1.1 g, crude, di-HCl salt) as a colorless gum.

To a solution of 3-34-2 (0.40 g, 0.97 mmol, TFA salt) and 3-34-6 (0.487 g, 1.06 mmol, di-HCl salt) in dichloromethane (5 mL) was added T3P (1.15 mL, 1.94 mmol, 50% solution in EtOAc) and diisopropylethylamine (0.84 mL, 4.8 mmol). The mixture was stirred at 0° C. for 1 hour then diluted with water (2 mL) and evaporated under reduced pressure. The residue was purified by reversed-phase HPLC using an eluent of water/acetonitrile with 0.1% aqueous ammonia buffer. The eluent was evaporated under reduced pressure to provide 3-34-7 (0.25 g, 32% yield) as a white solid.

To a solution of 3-34-7 (0.17 g, 0.255 mmol) and triethylamine (0.35 mL, 2.5 mmol) in dichloromethane (0.5 mL) was added TosCl (0.292 g, 1.53 mmol) at 0° C. The mixture was stirred at 0° C. for 1 hour then the mixture was diluted with water (2 mL) at 0° C. and concentrated under reduced pressure. The residue was purified by reversed-phase HPLC using an eluent of water/acetonitrile with 0.1% TFA buffer. The eluent was concentrated under reduced pressure to afford 3-34-8 (0.150 g, 59% yield) as a white solid.

To a solution of 3-34-8 (0.120 g, 0.146 mmol) in methanol (1 mL) was added 10% $Pd(OH)_2/C$ (0.015 g) under nitrogen. The suspension was degassed under vacuum and purged with hydrogen several times. The mixture was stirred under a hydrogen atmosphere (15 psi) at 20-30° C. for 1 hour then filtered and the filtrate was concentrated under reduced pressure to provide 3-34-9 (0.100 g, 0.137 mmol) as a colorless oil.

To a solution of 3-34-9 (0.090 g, 0.123 mmol) in dimethyl formamide (3 mL) was added cesium carbonate (0.120 g, 0.370 mmol). The mixture was stirred at 20-30° C. for 3 hours then filtered. The filtrate was purified by prep-HPLC using an eluent of water/acetonitrile with 0.05% ammonia hydroxide buffer. The isolated fractions were lyophilization to afford 3-34 (0.15 g, 22% yield) as a white solid. LCMS of 3-34: RT=1.262 min, m/z: 558.3 $[M+H]^+$, 279.8 $[M/2+H]^+$.

The following compound was made using a similar synthetic route using (S)-2-(((benzyloxy)carbonyl)amino)-4-(4-fluorophenyl)butanoic acid: Compound 3-36; LCMS: RT=1.639 min, m/z 567.3 $[M+H]^+$ Example 52—Synthesis of (7S,10S,13S)-N-Cyclopentyl-9,12-dioxo-13-(2-oxopyrrolidin-1-yl)-10-(phenoxymethyl)-2-oxa-8,11-diaza-1(1,3)-benzenacyclotetradecaphane-7-carboxamide (3-35)

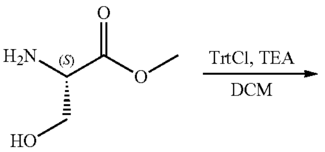

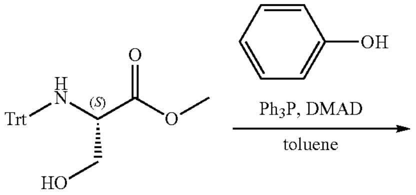

3-35-1

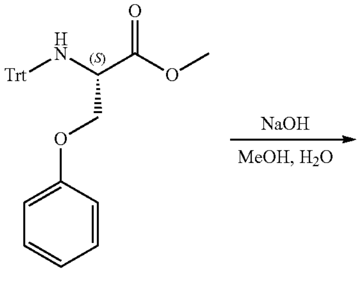

3-35-2

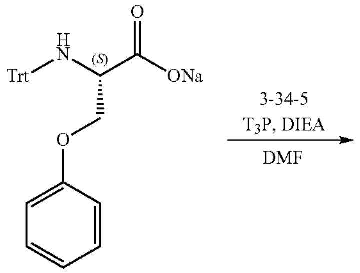

3-35-3

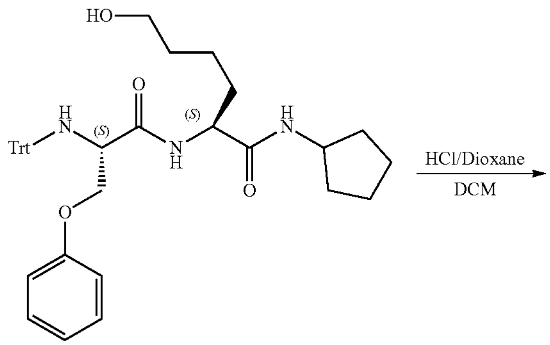

3-35-4

-continued

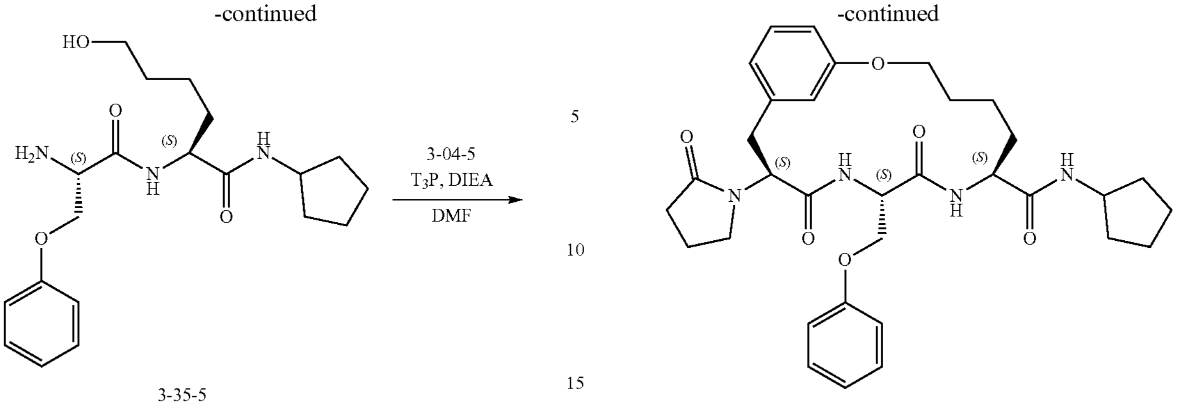

3-35-5

3-35

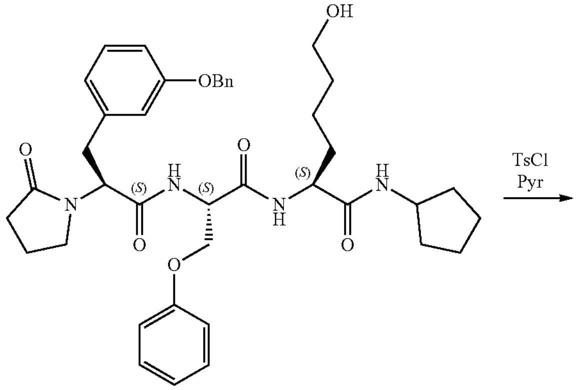

3-35-6

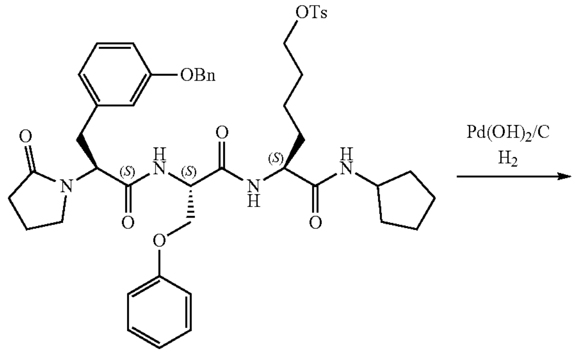

3-35-7

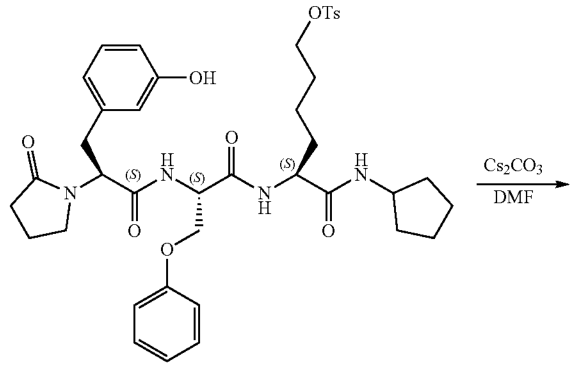

3-35-8

To a solution of methyl L-serinate (5.00 g, 32.1 mmol, HCl salt) in dichloromethane (50 mL) was added TrtCl (12.54 g, 44.99 mmol) and triethylamine (14.3 mL, 103 mmol). The mixture was stirred at 20-25° C. for 12 hours. The solvent was evaporated under reduced pressure and the residue was dissolved in ethyl acetate (50 mL), washed with water (50 mL) followed by brine (50 mL). The organic layer was dried over anhydrous sodium sulfate, filtered, and the filtrate was evaporated under reduced pressure. The residue was triturated in 50 mL mixed solvent (petroleum ether:ethyl acetate=20:1) for 0.5 hour, filtered, and the filter cake was dried to provide 3-35-1 (11.2 g, 31.0 mmol) as a white solid.

DIAD (5.91 mL, 30.4 mmol) was added drop-wise to a solution of 3-35-1 (10.00 g, 27.67 mmol), phenol (2.68 mL, 30.4 mmol), and $PPh_3$ (7.98 g, 30.4 mmol) in toluene (100 mL) at 100° C. under argon. The reaction mixture was stirred for 12 hours at 100° C. The mixture was concentrated under reduced pressure at 40° C. and the residue was diluted with water (100 mL) then extracted with ethyl acetate. The combined organic phase was washed with brine, dried over anhydrous sodium sulfate, filtered, and concentrated under reduced pressure. The residue was purified by flash silica gel chromatography and the eluent concentrated under reduced pressure to afford 3-35-2 (8.50 g, 18.5 mmol) as a white solid.

To a solution of 3-35-2 (1.00 g, 2.29 mmol) in methanol (20 mL) and water (5 mL) was added sodium hydroxide (0.274 g, 6.86 mmol) at 0° C. The mixture was stirred at 40-60° C. for 2 hours then cooled to room temperature and concentrated under reduced pressure. The crude product was purified by reversed-phase HPLC using an eluent of water/acetonitrile with 0.1% aqueous ammonia buffer. The collected fractions were lyophilized to provide 3-35-3 (0.50 g, 46.2% yield, Na salt) as a white solid.

To a solution of 3-35-3 (0.70 g, 1.57 mmol) and 3-34-5 (0.370 g, 1.73 mmol) in dimethyl formamide (8 mL) was added diisopropylethylamine (0.55 mL, 3.1 mmol) and $T_3P$ (1.87 mL, 3.14 mmol, 50% solution in EtOAc) at 0° C. The mixture was stirred at 0° C. for 1 hour then diluted with water (10 mL) and extracted with ethyl acetate. The combined organic phase was washed with brine, dried over anhydrous sodium sulfate, filtered, and the filtrate was concentrated under reduced pressure. The residue was purified by reversed-phase HPLC using an eluent of water/acetonitrile with 0.1% aqueous ammonia buffer. The eluent was concentrated under reduced pressure to afford 3-35-4 (0.40 g, 41% yield) as a white solid.

To a solution of 3-35-4 (0.40 g, 0.64 mmol) in dichloromethane (5 mL) was added HCl/dioxane (4 M, 0.16 mL, 0.64 mmol)). The mixture was stirred at 20-25° C. for 1 hour then concentrated under reduced pressure. The residue was triturated in ethyl acetate (10 mL) for 0.5 hr then filtered. The filter cake was collected and dried to afford 3-35-5 (0.260 g, 87.8% yield, HCl salt) as a white solid.

To a solution of 3-35-5 (0.260 g, 0.628 mmol, HCl salt) and 3-04-5 (0.214 g, 0.628 mmol) in dimethyl formamide (5 mL) was added diisopropylethylamine (0.55 mL, 3.1 mmol) and T3P (0.75 mL, 1.3 mmol, 50% solution in EtOAc). The mixture was stirred at 0° C. for 2 hours then diluted with water (10 mL) and extracted with ethyl acetate. The combined organic layer was washed with brine, dried over anhydrous sodium sulfate, filtered, and the filtrate was concentrated under reduced pressure. The residue was purified by prep-HPLC using an eluent of water/acetonitrile with 0.1% TFA buffer. The eluent was lyophilized to afford 3-35-6 (0.270 g, 58.4% yield) as a white solid.

To a solution of 3-35-6 (0.170 g, 0.243 mmol) in pyridine (1.5 mL) was added TosCl (1.16 g, 6.08 mmol) at 0° C. The mixture was stirred at 0° C. for 2 hours then volatile organics were removed by nitrogen gas flowed over the mixture. The crude product was purified by reversed-phase HPLC using an eluent of water/acetonitrile with 0.1% TFA buffer. The eluent was concentrated under reduced pressure to afford 3-35-7 (0.160 g, 74.9% yield) as a white solid.

To a solution of 3-35-7 (0.130 g, 0.152 mmol) in methanol (5 mL) was added 10% Pd/C (10 mg) under nitrogen. The suspension was degassed under vacuum and purged with hydrogen several times. The mixture was stirred under a hydrogen atmosphere (15 psi) at 25° C. for 2 hours. The mixture was filtered and the filtrate was concentrated under reduced pressure. The residue was purified by reversed-phase HPLC using an eluent of water/acetonitrile with 0.1% TFA buffer. The eluent was lyophilized to obtained 3-35-8 (0.110 g, 92.6% yield) as a colorless oil.

To a solution of 3-35-8 (0.110 g) in dimethyl formamide (5 mL) was added cesium carbonate (0.141 g, 0.432 mmol). The mixture was stirred at 20-30° C. for 2 hours then diluted with water (5 mL) and extracted with ethyl acetate. The combined organic phase was washed with brine, dried over anhydrous sodium sulfate, filtered, and the filtrate was concentrated under reduced pressure. The residue was purified by reversed-phase HPLC using an eluent of water/acetonitrile with 0.1% TFA buffer. The eluent was lyophilized to obtain compound 3-35 (0.13 g, 15% yield) as a white solid. LCMS of 3-35: RT=2.114 min, m/z: 591.2 [M+H]+.

Example 53—Synthesis of (7S,10S,13-Unassigned)-N-cyclopentyl-13-methyl-10-(2-morpholinoethyl)-9,12-dioxo-2-oxa-8,11-diaza-1(1,3)-benzenacyclotetradecaphane-7-carboxamide (3-37) and (7S,10S,13-Unassigned)-N-cyclopentyl-13-methyl-10-(2-morpholinoethyl)-9,12-dioxo-2-oxa-8,11-diaza-1(1,3)-benzenacyclotetradecaphane-7-carboxamide (3-38)

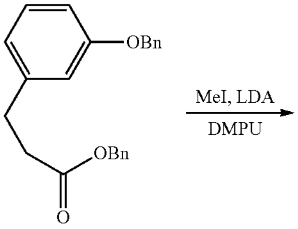

1-89-1

-continued

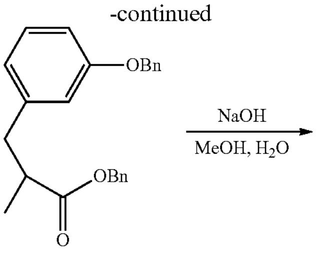

3-37-1

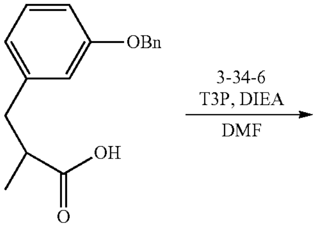

3-37-2

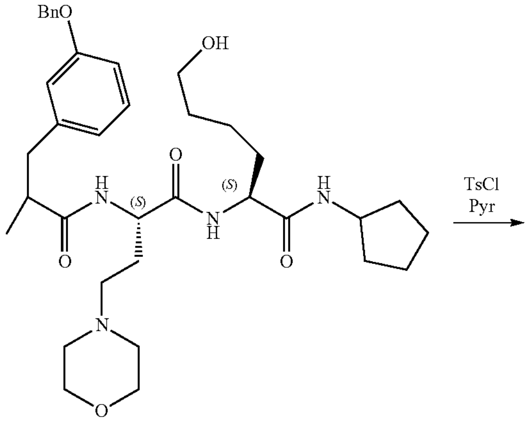

3-37-3

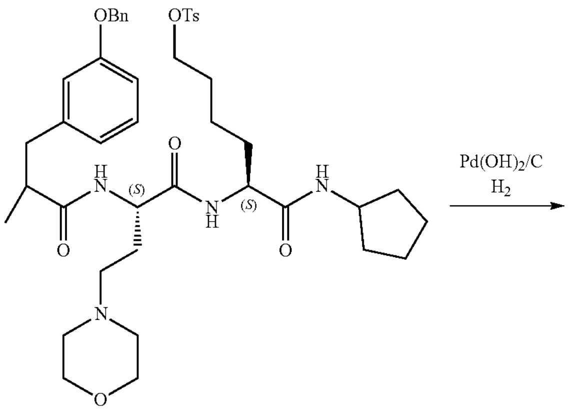

3-37-4

-continued

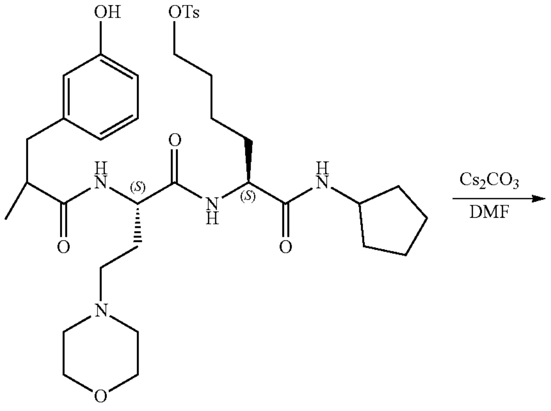

3-37-5

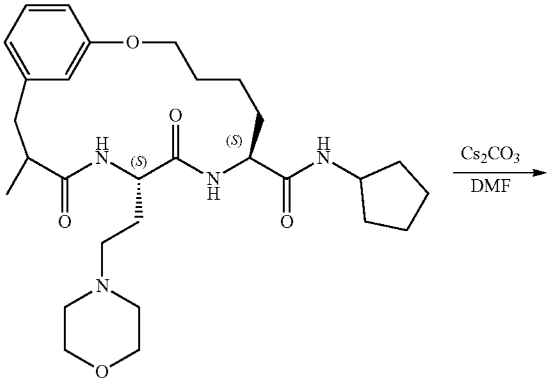

3-37-6

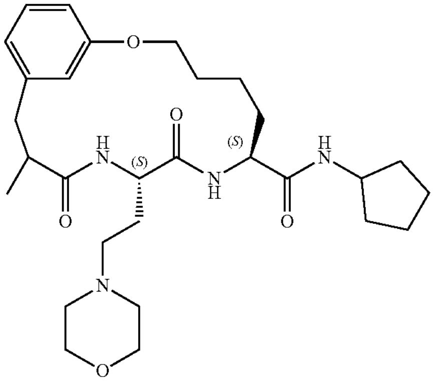

3-37

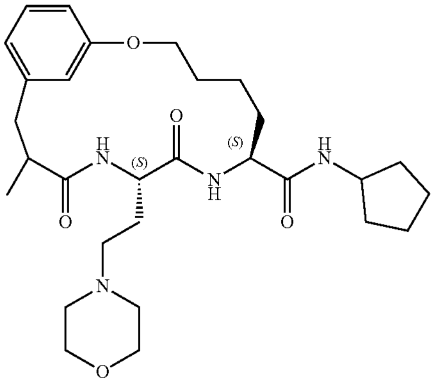

3-38

To a solution of 1-89-1 (10 g, 29 mmol) in tetrahydrofuran (100 mL) was added NaHMDS (1 M, 58 mL, 58 mmol) at −70° C. and the mixture was stirred for 0.5 hour. To this was added methyl iodide (7.19 mL, 115 mmol) and the reaction was stirred at −70° C. for 1 hour under nitrogen atmosphere. The reaction was diluted with a saturated ammonium chloride solution and extracted with ethyl acetate (200 mL*3). The combined organic phase was washed with brine, dried over anhydrous sodium sulfate, filtrated, and concentrated under reduced pressure. The residue was purified by flash silica gel column chromatography to afford 3-37-1 (3.0 g, 29% yield) as a light yellow oil.

To a solution of 3-37-1 (0.500 g, 1.39 mmol) in tetrahydrofuran (5 mL) was added a solution of sodium hydroxide (0.277 g, 6.94 mmol) in water (5 mL) at 0° C. The mixture was stirred at 0° C. for 3 hours and then stirred at 20° C. for 2 hours then another batch sodium hydroxide (0.166 g, 4.16 mmol) was added into the mixture and the reaction mixture was stirred at 20° C. for 14 hours. Methanol (5 mL) was added and the mixture was stirred at 40° C. for an additional 3 hours. The mixture was poured into a 1N hydrochloric acid solution (20 mL) and extracted with ethyl acetate. The combined organic layers were washed with brine, dried over anhydrous sodium sulfate, filtered, and concentrated under reduced pressure. The crude product was purified by reversed-phase HPLC using an eluent of water/acetonitrile with 0.1% TFA modifier and the eluent concentrated under reduced pressure to afford 3-37-2 (0.360 g, 90.5% yield) as a light yellow solid.

To a solution of 3-37-2 (0.190 g, 0.703 mmol), 3-34-6 (0.354 g, 0.773 mmol, di-HCl salt), and N,N-diisopropylethylamine (0.73 mL, 4.2 mmol) in dichloromethane (5 mL) was added drop-wise T3P (1.05 mL, 1.76 mmol, 50% solution in EtOAc) at −5° C.-0° C. The mixture was stirred at −5-0° C. for 1 hour then poured into ice water (20 mL) and then extracted with ethyl acetate. The combined organic layers were washed with brine, dried over anhydrous sodium sulfate, filtered, and concentrated under reduced pressure. The crude product was purified by reversed-phase HPLC using an eluent of water/acetonitrile with 0.1% TFA modifier and the eluent was concentrated under reduced pressure to afford 3-37-3 (0.270 g, 0.416 mmol) as a colorless gum.

To a solution of 3-37-3 (0.240 g, 0.377 mmol) and triethylamine (0.52 mL, 3.8 mmol) in dichloromethane (5 mL) was added p-toluenesulfonyl chloride (0.647 g, 3.39 mmol) at 0° C. The mixture was stirred at 20° C. for 2 hours then additional triethylamine (0.21 mL, 1.5 mmol) and p-toluenesulfonyl chloride (0.287 mg, 1.51 mmol) were added into the mixture at 0° C. The mixture was stirred at 20° C. for 2 hours then poured into ice-water (20 mL). A 1N hydrochloric acid solution was added until the pH was adjusted to approximately pH=7-8. The mixture was extracted with ethyl acetate and the combined organic phase was washed with brine, dried over anhydrous sodium sulfate, filtered, concentrated under reduced pressure. The residue was purified by flash silica gel column chromatography and the eluent concentrated under reduced pressure to afford 3-37-4 (0.267 g, 75.7%) as a light yellow gum.

To a solution of 3-37-4 (0.260 g, 0.329 mmol) in methanol (10 mL) was added 10% Pd/C (50 mg) and 10% $Pd(OH)_2/C$ (20 mg) under a nitrogen atmosphere. The suspension was degassed under vacuum and purged with hydrogen several times. The mixture was stirred under a hydrogen atmosphere (15 psi) at 25° C. for 2 hours then filtered and the filter cake was washed with methanol. The combined filtrate was concentrated under reduced pressure 3-37-5 (0.180 g, 78.1% yield) as a light yellow gum, which was used directly without further purification.

To a solution of 3-37-5 (0.180 g, 0.257 mmol) in N,N-dimethylformamide (15 mL) was added cesium carbonate (0.251 g, 0.770 mmol). The mixture was stirred at 25° C. for 12 hours then poured into ice water (20 mL) and extracted with ethyl acetate. The combined organic phase was washed with brine, dried over anhydrous sodium sulfate, filtered, and concentrated under reduced pressure. The residue was purified by prep-HPLC using an eluent of water/acetonitrile with a modifier or 0.04% $NH_3H_2O$+10 mm $NH_4HCO_3$ to afford, after concentration of the eluent under reduced pressure, two products, 3-37 (1st eluting peak, 0.021 g, 13%) and a $2^{nd}$ eluting compound. The $2^{nd}$ eluting compound was further purified by SFC (column: DAICEL CHIRALCEL OD (250 mm*30 mm*10 um); mobile phase: [Neu-MeOH]; B %: 30%-30%, 45 min) to afford, after concentration of the eluent under reduced pressure, 3-38 (0.12 g, 7.4% yield) as a white solid. The relative stereochemistry of 3-37 and 3-38 was not determined. LCMS of 3-37: RT=2.132 min, m/z 529.3 [M+H]$^+$. LCMS of 3-38: RT=2.148 min, m/z 529.3 [M+H]$^+$.

Example 54—Synthesis of (7S,10S)-N-Cyclopentyl-10-(4-fluorophenethyl)-9,12-dioxo-2-oxa-8,11-diaza-1(1,3)-benzenacyclotetradecaphane-7-carboxamide (3-39)

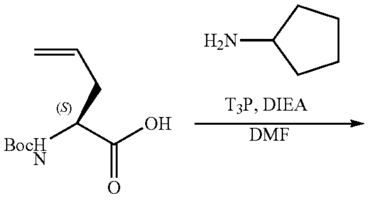

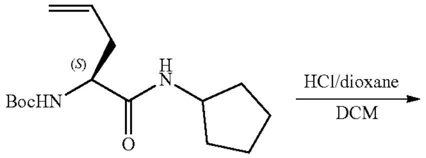

3-39-1

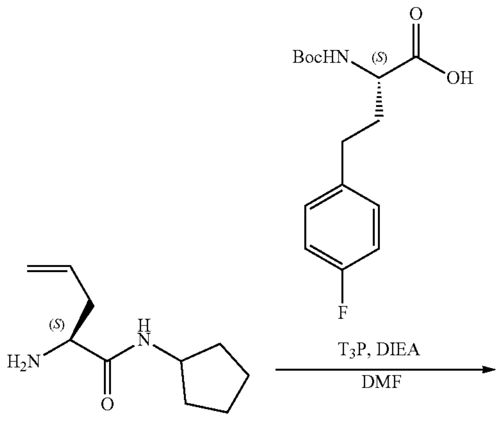

3-39-2

-continued

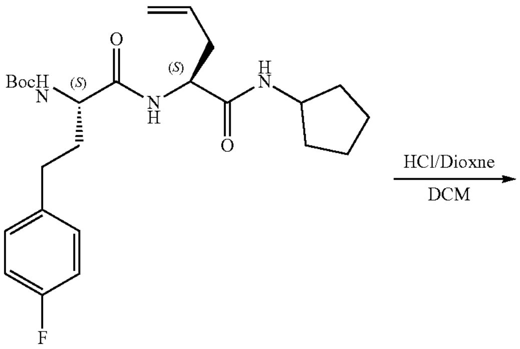

3-39-3

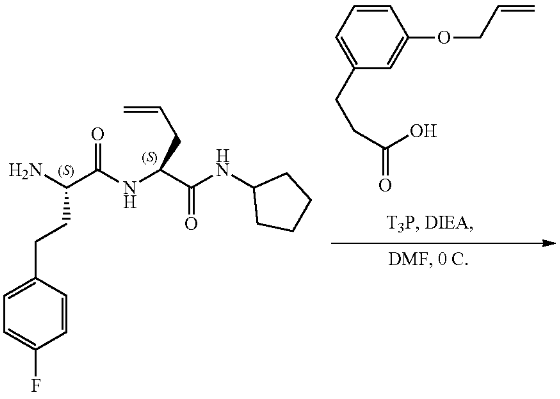

3-39-4

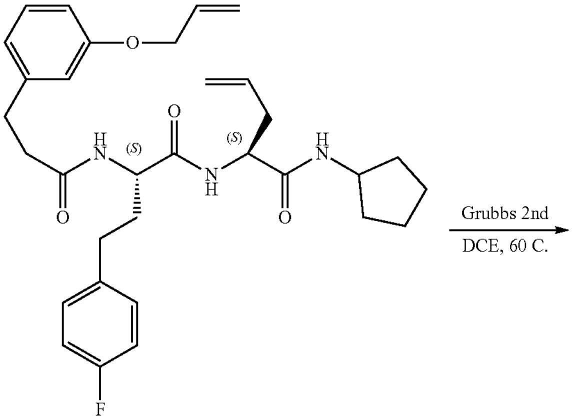

3-39-5

-continued

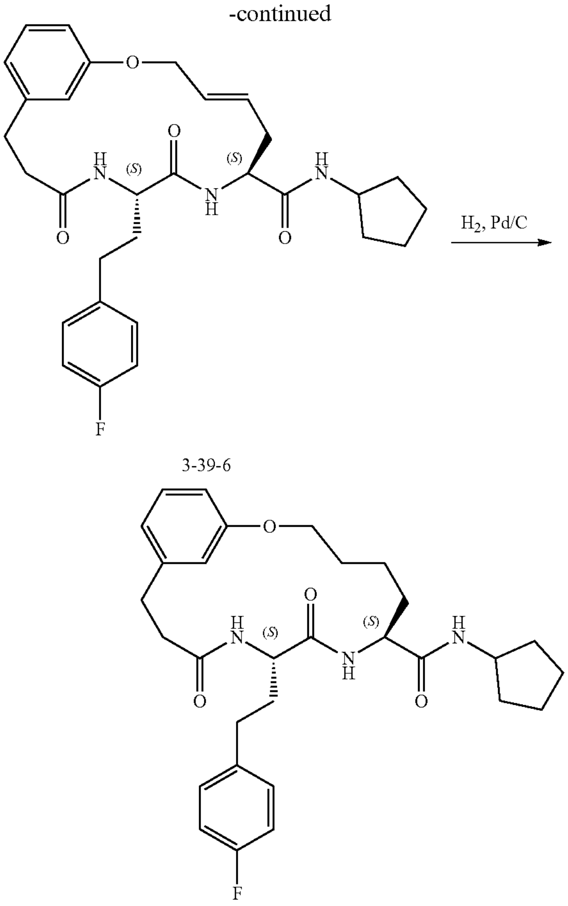

3-39-6

3-39

To a mixture of (S)-2-((tert-butoxycarbonyl)amino)pent-4-enoic acid (2.00 g, 9.29 mmol) and cyclopentyl amine (2.75 mL, 27.9 mmol) in N,N-dimethylformamide (20 mL) was added N,N-diisopropylethylamine (8.09 mL, 46.5 mmol) and T3P (11.05 mL, 18.58 mmol, 50% solution in EtOAc) at 0° C. The mixture was stirred at 25° C. for 12 hours then diluted with ethyl acetate and washed with a 1 M hydrochloric acid solution followed by a saturated sodium bicarbonate solution, and brine. The organic phase was dried over anhydrous sodium sulfate, filtered, and concentrated under reduced pressure to provide 3-39-1 (2.5 g, 92% yield) as a white solid.

To a solution of 3-39-1 (0.500 g, 1.77 mmol) in dioxane (2 mL) was added a solution of HCl/dioxane (4 M, 2 mL, 8 mmol) at 25° C. The reaction mixture was stirred at 25° C. for 1 hour then concentrated under reduced pressure to afford 3-39-2 (0.350 g, HCl salt) as a yellow gum.

To a solution of 3-39-2 (0.35 g, 1.92 mmol, HCl salt) in N,N-dimethylformamide (5 mL) was added (S)-2-((tert-butoxycarbonyl)amino)-4-(4-fluorophenyl)butanoic acid (0.571 g, 1.92 mmol), N,N-diisopropylethylamine (1.00 mL, 5.76 mmol), and T3P (2.28 mL, 3.84 mmol, 50% solution in EtOAc) at 0° C. The mixture was stirred at 25° C. for 2 hours then diluted with ethyl acetate (50 mL) and washed with a 1M hydrochloric acid solution followed by a saturated sodium bicarbonate solution then brine. The organic layer was dried over anhydrous sodium sulfate, filtered, and concentrated under reduced pressure. The residue was purified by flash silica gel column chromatography to afford 3-39-3 (0.40 g, 44% yield) as a yellow solid.

To a solution of 3-39-3 (0.400 g, 0.867 mmol) in dioxane (3 mL) was added a solution of HCl/dioxane (4 M, 3.70 mL, 14.8 mmol) at 25° C. The mixture was stirred at 25° C. for 12 hours then concentrated under reduced pressure to afford 3-39-4 (0.30 g, 87% yield, HCl salt) as a white solid.

To a solution of 3-39-4 (0.30 g, 0.75 mmol, HCl salt) in N,N-dimethylformamide (5 mL) was added 3-(3-(allyloxy) phenyl)propanoic acid (0.155 g, 0.750 mmol), T3P (0.90 mL, 1.5 mmol, 50% solution in EtOAc), and N,N-diisopropylethylamine (0.39 mL, 2.3 mmol) at 0° C. The mixture was stirred at 25° C. for 2 hours then diluted with ethyl acetate (50 mL) and washed with a 1M hydrochloric acid solution followed by a saturated sodium bicarbonate solution and brine. The organic phase was dried over anhydrous sodium sulfate, filtered, and concentrated under reduced pressure. The residue was purified by flash silica gel column chromatography and the eluent concentrated under reduced pressure to afford 3-39-5 (0.30 g, 72% yield) as a white solid.

To a solution of 3-39-5 (0.10 g, 0.18 mmol) in 1,2-dichloroethane (10 mL) was added Grubbs catalyst 2nd generation (0.046 g, 0.054 mmol). The mixture was degassed with nitrogen and stirred at 60° C. for 12 hours under nitrogen. The reaction mixture was purified by prep-TLC (petroleum ether:ethyl acetate, 1:3) to afford 3-39-6 (0.080 mg, 65% yield) as a black brown solid.

To a solution of 3-39-6 (0.080 g, 0.12 mmol) in methanol (5 mL) and dimethylsulfoxide (2 mL) was added 10% Pd/C (0.020 g) under nitrogen. The suspension was degassed under vacuum and purged with hydrogen several times. The mixture was then stirred under a hydrogen atmosphere (15 psi) at 25° C. for 12 hours then filtered and an additional 0.030 g of 10% Pd/C was added to the mixture. The suspension was degassed under vacuum and purged with hydrogen several times. The mixture was stirred under hydrogen (15 psi) at 25° C. for 4 hours then filtered and concentrated under reduced pressure. The residue was purified by prep-HPLC using an eluent of water/acetonitrile with 0.1% TFA additive. The eluent was concentrated under reduced pressure to afford 3-39 (0.017 mg, 22% yield) as a white solid. LCMS of 3-39: RT=2.730 min, m/z 524.3 $[M+H]^+$.

The following compound was made in a similar fashion to 3-39 using ortho-fluoro benzyl amine: Compound 3-41; RT=2.802 min, m/z 564.3 $[M+H]^+$.

The following compound was made in a similar fashion to 3-41 using 3-42-5: Compound 3-43; RT=2.491 min, m/z 549.3$[M+H]^+$.

Example 55—Synthesis of (7S,10S)-N-Cyclopentyl-13,13-dimethyl-10-(2-morpholinoethyl)-9,12-dioxo-2-oxa-8,11-diaza-1(1,3)-benzenacyclotetradecaphane-7-carboxamide (3-40)

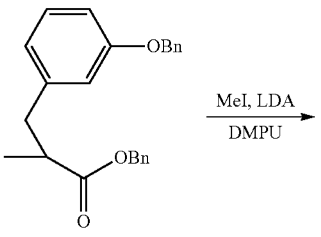

3-37-1

-continued

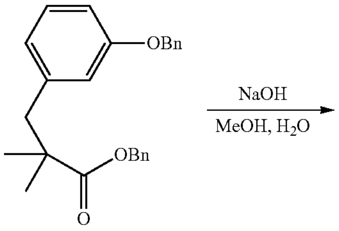

3-40-1

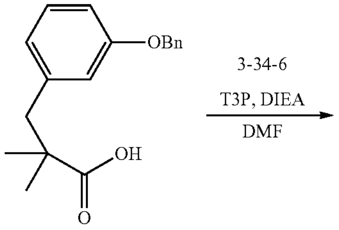

3-40-2

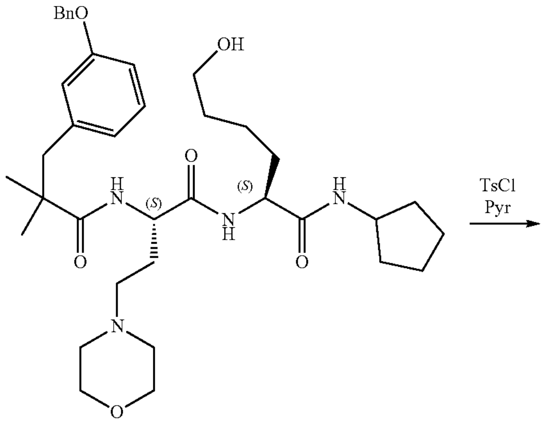

3-40-3

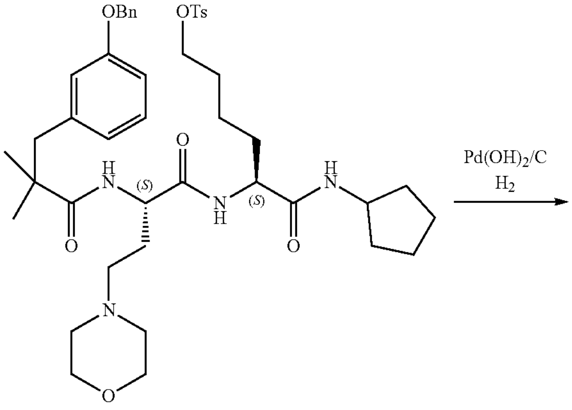

3-40-4

-continued

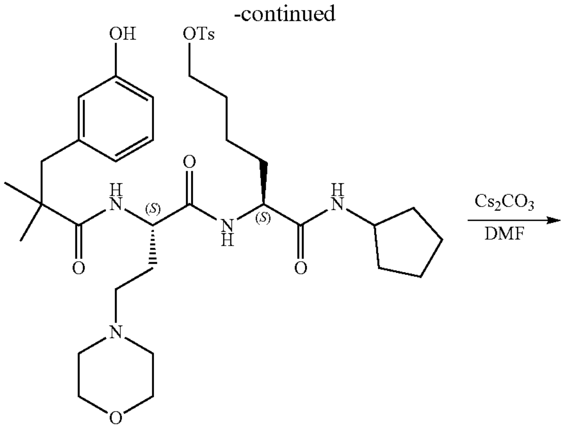

3-40-5

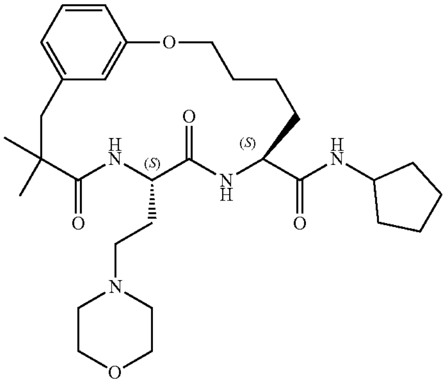

3-40

To a solution of N-isopropylpropan-2-amine (1.18 mL, 8.32 mmol) in tetrahydrofuran (12 mL) was added n-BuLi (2.5M, 3.50 mL) at −70° C., after stirred 10 min, 1,3-dimethylhexahydropyrimidin-2-one (0.50 mL, 4.2 mmol) was added, followed by a solution of 3-37-1 (1.5 g, 4.2 mmol) in tetrahydrofuran (3 mL) that was added dropwise. The reaction was stirred at −70° C. for 20 min and then methyl iodide (1.0 mL, 17 mmol) was added and stirred 12 hours as the mixture slowly warmed to room temperature. The reaction mixture was poured into a saturated ammonium chloride solution (50 mL) and extracted with ethyl acetate. The combined organic phase was washed with brine, dried over anhydrous sodium sulfate, filtered, and concentrated under reduced pressure. The residue was purified by flash silica gel column chromatography to afford 3-40-1 (0.3 g, crude) as a colorless gum.

To a solution of 3-40-1 (0.40 g, 1.0 mmol) in a mixture of methanol (4 mL) and water (1 mL) was added sodium hydroxide (0.128 g, 3.20 mmol). The mixture was stirred for 20 hours at 50° C. then poured into water (40 mL) and extracted with petroleum ether. The pH of the aqueous phase was adjusted to pH=5 with a 1N hydrochloride acid solution then extracted with ethyl acetate. The combined organic phase was washed with brine, dried over anhydrous sodium sulfate, filtered, and concentrated under reduced pressure to afford 3-40-2 (0.4 g, crude) as yellow gum.

To a solution of 3-40-2 (0.130 g, 0.46 mmol) and 3-34-6 (0.293 g, 0.640 mmol, di-HCl salt) in dichloromethane (2 mL) was added diisopropylethylamine (0.20 mL, 1.1 mmol) at 0° C. Then, T3P (0.41 mL, 0.68 mmol, 50% solution in EtOAc) was added drop-wise to the mixture and stirred at 0° C. for 1 hour. The mixture was diluted with 50 mL of ethyl acetate, washed with brine, dried over anhydrous sodium sulfate, filtered, and concentrated under reduced pressure. The residue was purified by prep-HPLC using an eluent of water/acetonitrile with 0.1% TFA additive. The eluent was removed under reduced pressure to provide 3-40-3 (0.20 mg, 67% yield) as colorless oil.

To a mixture of 3-40-3 (0.120 g, 0.18 mmol) in dichloromethane (2 mL) was added TosCl (0.105 g, 0.553 mmol) and triethyl amine (0.077 mL, 0.55 mmol) at 0° C. The mixture was allowed to warm to room temperature and stirred for 24 hours, diluted with 30 mL of water, and extracted with ethyl acetate. The combined organic phase was dried over anhydrous sodium sulfate, filtered, and concentrated under reduced pressure. The residue was purified by prep-HPLC using an eluent of water/acetonitrile with a modifier of 0.04% $NH_3H_2O$+10 mM $NH_4HCO_3$. The eluent was concentrated under reduced pressure to afford 3-40-4 (0.040 g, 27% yield) as a colorless oil.

A solution of 3-40-4 (0.040 g, 0.050 mmol) in methanol (2 mL) was degassed with nitrogen three times. To this was added 5% Pd/C (0.005 g) and 5% $Pd(OH)_2$/C (0.005 g) then the mixture was degassed with hydrogen three times. The mixture was stirred at 25° C. under hydrogen (15 psi) for 1 hour then filtered and concentrated under reduced pressure to provide 3-40-5 (0.033 g, 86% yield) as a white solid which was used directly without further purification.

To a solution of 3-40-5 (0.032 g, 0.045 mmol) in dimethyl formamide (1 mL) was added cesium carbonate (0.029 g, 0.089 mmol) at 0° C. The mixture was stirred at 0-25° C. for 12 hours and then stirred at 40° C. for another 12 hours. The mixture was diluted with 30 mL of water and extracted with ethyl acetate. The combined organic phase was washed with brine, dried over anhydrous sodium sulfate, filtered, and concentrated under reduced pressure. The residue was purified by prep-HPLC using an eluent of water/acetonitrile with 0.1% TFA additive. The collected fractions were lyophilized to afford 3-40 (0.003 mg, 10% yield, TFA salt) as a white solid. LCMS of 3-40: RT=1.654 min, m/z 543.3[M+H]+.

Example 56—Synthesis of (7S,10S,13S)-N-Cyclopentyl-10-(2-(4,4-difluoropiperidin-1-yl)ethyl)-9,12-dioxo-13-(2-oxopyrrolidin-1-yl)-2-oxa-8,11-diaza-1(1,3)-benzenacyclotetradecaphane-7-carboxamide (3-42)

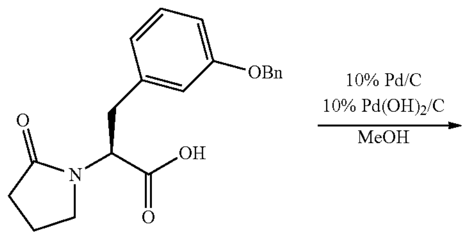

3-04-5

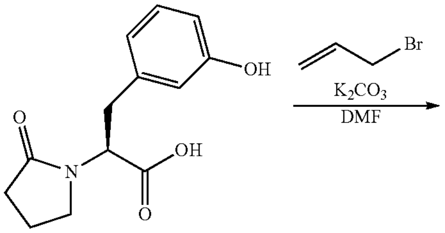

3-42-1

-continued

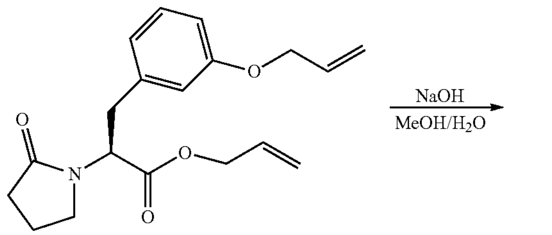

3-42-2

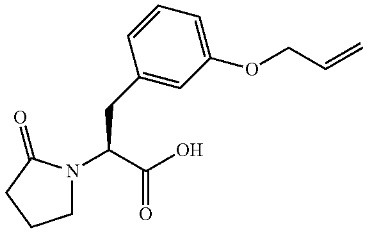

3-42-3

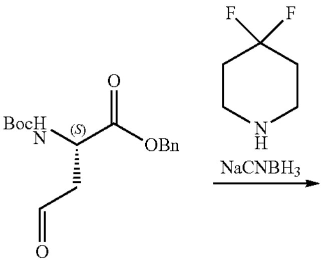

1-67-1

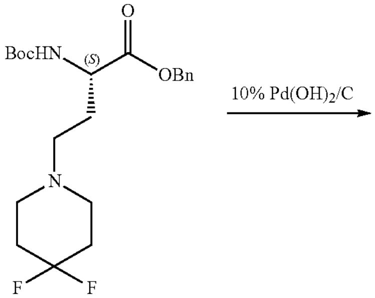

3-42-4

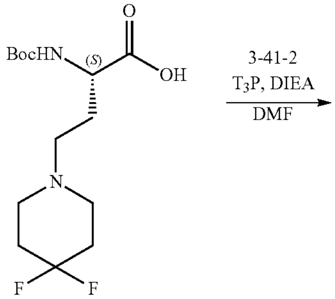

3-42-5

-continued

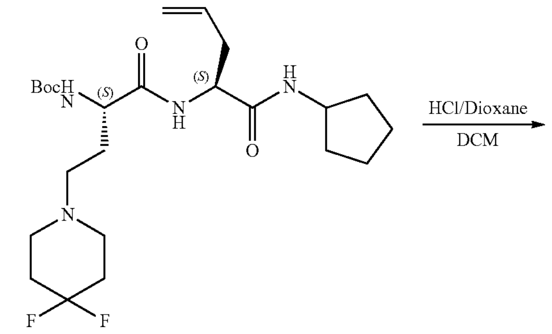

3-42-6

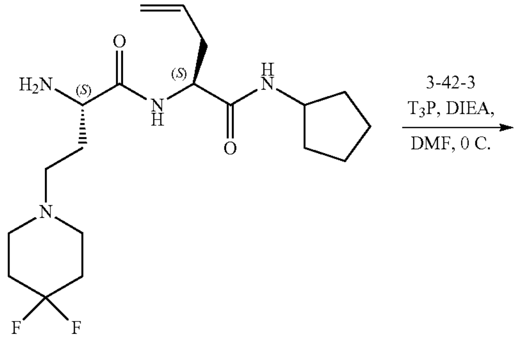

3-42-7

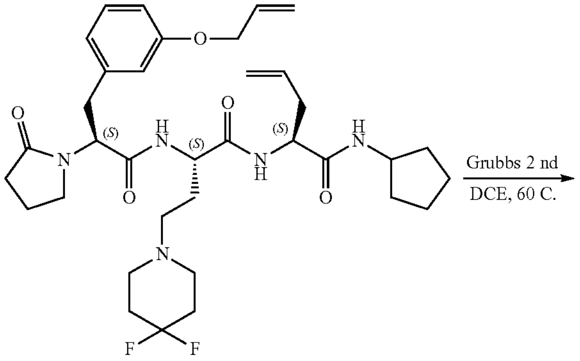

3-42-8

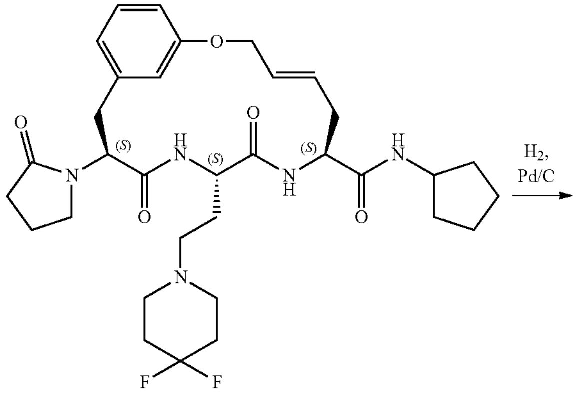

3-42-9

-continued

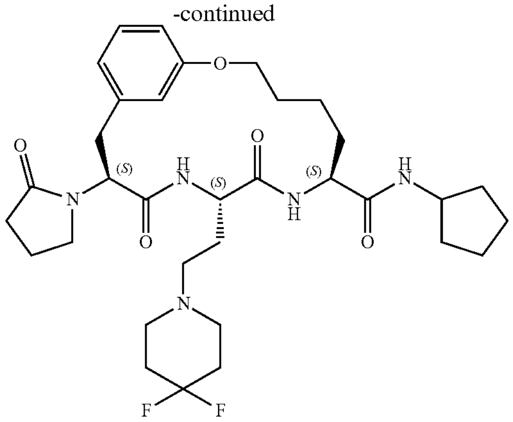

3-42

To a solution of 3-04-5 (0.740 g, 2.18 mmol) in methanol (15 mL) was added 10% Pd/C (0.070 g) and 10% $Pd(OH)_2/C$ (0.070 g) under nitrogen. The suspension was degassed under vacuum and purged with hydrogen several times. The mixture was stirred under a hydrogen atmosphere (15 psi) at 20° C. for 18 hours. Another batch of 10% Pd/C (0.070 g) and 10% $Pd(OH)_2/C$ (0.070 g) were added under a nitrogen atmosphere. The suspension was degassed under vacuum and purged with hydrogen several times. The mixture was stirred under a hydrogen atmosphere (15 psi) at 20° C. for 5 hours then filtered and the filter cake was washed with methanol. The combined filtrate was concentrated under reduced pressure to afford 3-42-1 (0.550 g) as a colorless gum, which was used directly without further purification.

To a mixture of 3-42-1 (0.550 g, 2.21 mmol) and potassium carbonate (0.916 g, 6.63 mmol) in N,N-dimethylformamide (10 mL) was added 3-bromoprop-1-ene (0.668 g, 5.53 mmol). The mixture was stirred at 20° C. for 14 hours then additional batch of 3-bromoprop-1-ene (0.267 g, 2.21 mmol) and potassium carbonate (0.305 g, 2.21 mmol) were added. The reaction mixture was stirred at 50° C. for another 4 hours then poured into a 1N hydrochloric acid aqueous solution and extracted with ethyl acetate. The combined organic phase was washed with brine, dried over anhydrous sodium sulfate, filtered, and the filtrate was concentrated under reduced pressure. The residue was purified by reverse-phase HPLC using an eluent of water/acetonitrile with 0.1% TFA modifier. The eluent was concentrated under reduced pressure to afford 3-42-2 (0.330 g, 45.3% yield) as a light yellow gum.

To a solution of 3-42-2 (0.330 g, 1.00 mmol) in methanol (4 mL) was added a solution of sodium hydroxide (0.160 g, 4.01 mmol) in water (2 mL) at 0° C. The mixture was stirred at 0° C. for 3 hours then poured into a 1N hydrochloric acid aqueous solution (20 mL) and extracted with ethyl acetate. The combined organic layers were washed with brine, dried over anhydrous sodium sulfate, filtered, and the filtrate was concentrated under reduced pressure. The residue was purified by reverse phase HPLC using an eluent of water/acetonitrile with 0.1% TFA additive to give 3-42-3 (0.260 g, 84.2% yield) as a light yellow gum.

To a solution of 1-67-1 (1.9 g, 6.2 mmol) in dichloromethane (15 mL) and methanol (15 mL) was added potassium acetate (1.52 g, 15.5 mmol) and 4,4-difluoropiperidine (1.02 g, 6.49 mmol, HCl salt) at 25° C. The mixture was stirred at 25° C. for 1 hour then $NaBH(OAc)_3$ (3.93 g, 18.5 mmol) was added the mixture and stirred at 25° C. for 11 hours. The mixture was added to an aqueous sodium bicarbonate solution (50 mL) and extracted with ethyl acetate. The combined organic phase was washed with brine, dried over anhydrous sodium sulfate, filtered, and concentrated under reduced pressure. The residue was purified by reverse flash column chromatography using an eluent of water/acetonitrile with 0.1% of TFA additive. The eluent was removed under reduced pressure to provide 3-42-4 (1.2 g, 46% yield) as a colorless oil.

To a solution of 3-42-4 (1.2 g, 2.9 mmol) in tetrahydrofuran (20 mL) was added 10% $Pd(OH)_2$ (0.20 g) under nitrogen. The suspension was degassed under vacuum and purged with hydrogen several times. The mixture was stirred under a hydrogen atmosphere (15 psi) at 25° C. for 12 hours then filtered and concentrated under reduced pressure to afford 3-42-5 (1.0 g, crude) as a white solid.

To a solution of 3-42-5 (0.500 g, 1.55 mmol) and 3-41-2 (0.509 g, 2.33 mmol, HCl salt) in N,N-dimethylformamide (10 mL) was added diisopropylethylamine (0.601 g, 4.65 mmol) at 0° C. To this was added T3P (1.48 g, 2.33 mmol, 50% solution in ethyl acetate) and the mixture was stirred at 0° C. for 1 hour then diluted with water (20 mL) and extracted with ethyl acetate. The combined organic phase was washed with an aqueous sodium bicarbonate solution, followed by brine then dried over anhydrous sodium sulfate, filtered, and concentrated under reduced pressure. The residue was purified by silica gel column chromatography and the eluent concentrated under reduced pressure to afford 3-42-6 (0.550 g, 72.9% yield) as a yellow oil.

To a solution of 3-42-6 (0.550 g, 1.13 mmol) in dioxane (5 mL) was added a solution of hydrochloric acid/dioxane (4 M, 10 mL, 40 mmol) at 25° C. and the mixture was stirred at 25° C. for 1 hour. The mixture was concentrated under reduced pressure to provide 3-42-7 (600 mg, crude, di-HCl salt) as yellow oil and the residue was used next step directly.

To a solution of 3-42-7 (0.588 g, 1.28 mmol, di-HCl salt) and 3-42-3 (0.370 g, 1.28 mmol) in N,N-dimethylformamide (10 mL) was added diisopropylethylamine (0.826 g, 6.39 mmol) at 0° C. followed by T3P (1.14 mL, 1.92 mmol, 50% solution in EtOAc). The mixture was stirred at 0° C. for 0.5 hour then diluted with water (20 mL) and extracted with ethyl acetate. The combined organic phase was washed with an aqueous sodium bicarbonate solution followed by brine then dried over anhydrous sodium sulfate, filtered, and concentrated under reduced pressure. The residue was purified by flash silica gel column chromatography and the eluent concentrated under reduced pressure to afford 3-42-8 (0.450 g, 50.8% yield) as a white solid.

To a solution of 3-42-8 (0.200 g, 0.304 mmol) in dichloroethane (40 mL) and dichloromethane (20 mL) was added Grubbs catalyst 2nd Generation (0.155 g, 0.182 mmol) at 25° C. under nitrogen and the mixture was stirred at 60° C. for 12 hours under nitrogen. The mixture was filtered and concentrated under reduced pressure and the residue was purified by prep-HPLC using an eluent of water/acetonitrile with 0.1% TFA additive. The eluent was concentrated under reduced pressure to provide 3-42-9 (0.120 mg, 61.6% yield) as a black brown solid.

To a solution of 3-42-9 (0.100 g, 0.159 mmol) in methanol (10 mL) was added 10/5 Pd/C (0.020 g) under nitrogen. The suspension was degassed under vacuum and purged with hydrogen several times. The mixture was stirred under a hydrogen atmosphere (15 psi) at 25° C. for 1 hour then concentrated under reduced pressure. The residue was purified by prep-HPLC using an eluent of water/acetonitrile with a modifier of 0.05% ammonia hydroxide. The eluent was removed under reduced pressure to provide 3-42 (0.045 g, 44% yield) as a white solid. LCMS of 3-42: RT=2.215 min, m/z 632.4 $[M+H]^+$.

Example 57—Synthesis of (7S,10S)-N-Cyclopentyl-10-(2-((unassigned)-2-cyclopropylpyrrolidin-1-yl)-2-oxoethyl)-9,12-dioxo-2-oxa-8,11-diaza-1(1,3)-benzenacyclotetradecaphane-7-carboxamide (3-45-A) and (7S,10S)-N-Cyclopentyl-10-(2-((unassigned)-2-cyclopropylpyrrolidin-1-yl)-2-oxoethyl)-9,12-dioxo-2-oxa-8,11-diaza-1(1,3)-benzenacyclotetradecaphane-7-carboxamide (3-45-B)

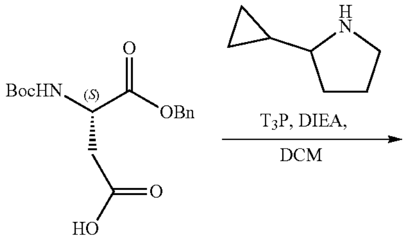

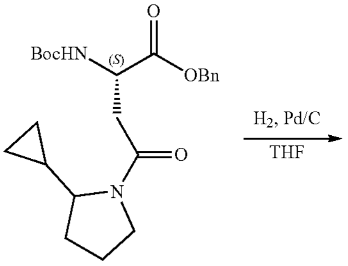

3-45-1

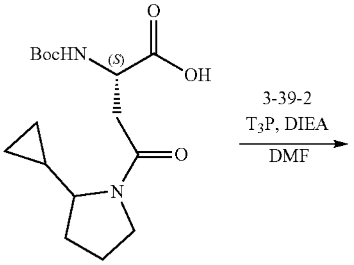

3-45-2

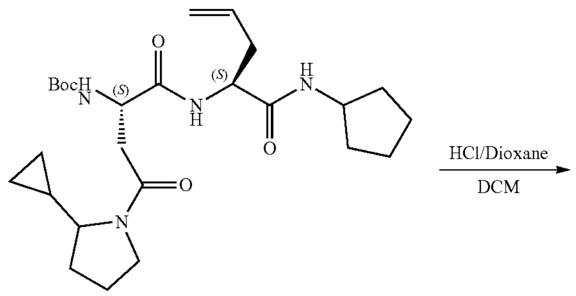

3-45-3

-continued

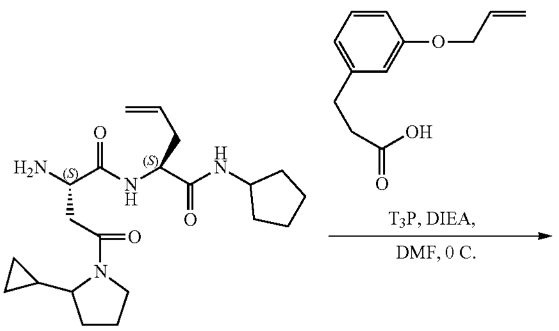

3-45-4

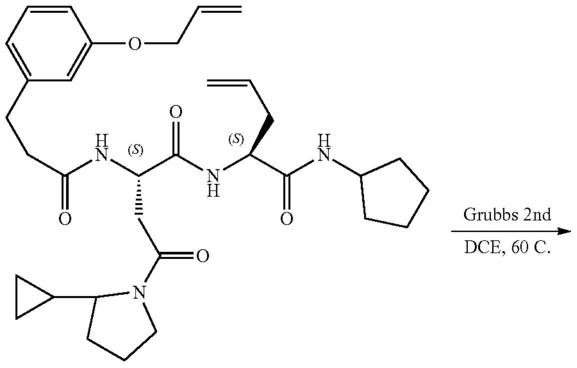

3-45-5

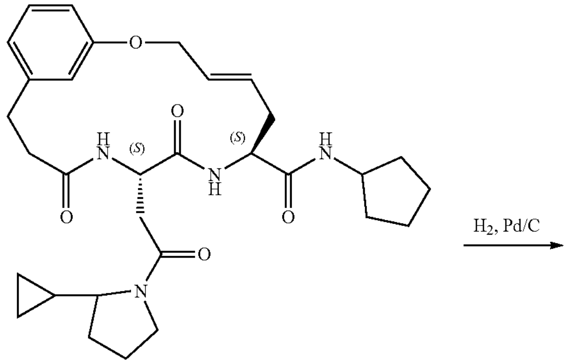

3-45-6

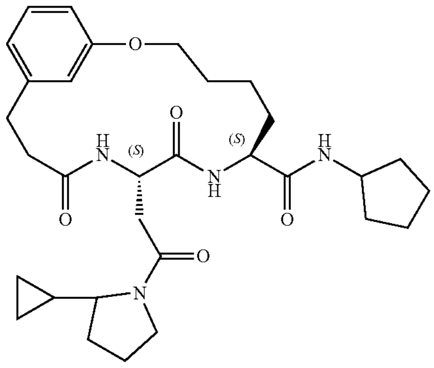

3-45-A

-continued

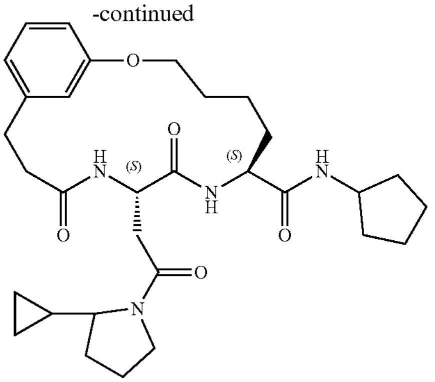

3-45-B

To a solution of (S)-4-(benzyloxy)-3-((tert-butoxycarbonyl)amino)-4-oxobutanoic acid (0.350 g, 1.08 mmol) and 2-cyclopropylpyrrolidine (0.109 g, 0.984 mmol) in dichloromethane (5 mL) was added diisopropylethylamine (0.514 mL, 2.95 mmol) at 0° C., followed by T3P (0.878 mL, 1.48 mmol, 50% solution in EtOAc) was added at 0° C. The mixture was stirred at 0-25° C. for 2 hours then diluted with a saturated aqueous sodium bicarbonate solution (50 mL) and extracted with ethyl acetate. The combined organic layer was dried over anhydrous sodium sulfate, filtered, and the filtrate was concentrated under reduced pressure to afford 3-45-1 (0.400 g, 97.6% yield) as a colorless oil. No further purification was performed.

A solution of 3-45-1 (0.400 g, 0.960 mmol) in tetrahydrofuran (1.5 mL) was degassed with nitrogen for three times then 10% Pd/C (0.01 g) was added. The mixture was degassed with hydrogen three times and the mixture was stirred at 25° C. for 1 hour under hydrogen atmosphere (15 psi). The mixture was filtered and concentrated under reduced pressure to afford 3-45-2 (0.300 g, 92.2% yield) as a colorless gum.

To a solution of 3-45-2 (0.500 g, 1.53 mmol) in ethyl acetate (6 mL) was added 3-39-2 (0.369 g, 1.69 mmol, HCl salt) followed by diisopropylethylamine (1.07 mL, 6.13 mmol) at 0° C. To this was added T3P (1.18 mL, 1.99 mmol, 50% solution in EtOAc), drop-wise, and the mixture was stirred at 0° C. for 2 hours. The mixture was diluted with ethyl acetate and washed with a saturate aqueous solution of ammonium chloride (20 mL*3) followed by a 1M solution of hydrochloride acid then dried over anhydrous sodium sulfate, filtered, and concentrated under reduced pressure. The residue was purified by flash silica gel column chromatography and the eluent concentrated under reduced pressure to afford 3-45-3 (0.500 g, 59.9% yield) as a colorless oil.

To a solution of 3-45-3 (0.500 g, 1.02 mmol) in dioxane (6 mL) was added a solution of hydrochloride acid in 1,4-dioxane (4 M, 5 mL, 20 mmol) at 0° C. The mixture was stirred at 0° C. for 2 hours then concentrated under reduced pressure to afford 3-45-4 (0.400 g, 91.9% yield, HCl salt) as a colorless oil.

To a solution of 3-45-4 (0.400 g, 0.937 mmol, HCl salt) and 3-(3-(allyloxy)phenyl)propanoic acid (0.225 g, 0.937 mmol) in ethyl acetate (5 mL) was added diisopropylethylamine (0.57 mL, 3.3 mmol) followed by T3P (0.36 mL, 1.2 mmol, 50% solution in EtOAc) at 0° C. The mixture was stirred at 0° C. for 1 hour then diluted with ethyl acetate, washed with a saturate aqueous solution of ammonium chloride followed by a 1M solution of hydrochloride (30 mL*3) then dried over anhydrous sodium sulfate, filtered, and concentrated under reduced pressure. The residue was purified by silica gel column chromatography and the eluent removed under reduced pressure to afford 3-45-5 (0.450 g, 83.0% yield) as colorless oil.

A solution of 3-45-5 (0.45 g, 0.777 mmol) in dichloromethane (70 mL) and 1,2-dichloroethane (120 mL) was degassed with nitrogen for three times then Grubbs catalyst (2nd generation, 0.264 g, 0.311 mmol) was added and the mixture stirred at 50° C. under nitrogen for 12 hours. The mixture was concentrated under reduced pressure and the residue purified by flash silica gel column chromatography. The isolated material was further purified by prep-HPLC using an eluent of water/acetonitrile to afford, after concentration of the eluent under reduced pressure, 3-45-6 (0.200 g, 46.7% yield) as a colorless oil.

A solution of 3-45-6 (0.200 g, 0.363 mmol) in methanol (4 mL) was degassed with nitrogen for three times then 10% Pd/C (0.020 g) was added and the mixture was degassed with hydrogen three times. The mixture was stirred at 25° C. under a hydrogen atmosphere (15 psi) for 1 hour. Then filtered and the filtrate was concentrated under reduced pressure. The residue and separated by SFC (column: daicel chiralpak ic (250 mm*30 mm, 5 um); mobile phase: [0.1% NH3H2O aqueous-MeOH]; B %: 40%-40%, 5.5 min; 160 min) to afford 3-45-A (0.028 g, 16% yield, $1^{st}$ eluting peak) as a white solid and 3-45-B (0.032 g, 18% yield, $2^{d}$ eluting peak) as a white solid. The relative stereochemistry of 3-45-A and 3-45-B was not established. LCMS of 3-45-A: RT=2.647 min, m/z 553.3 $[M+H]^+$. LCMS of 3-45-B: RT=2.638 min, m/z 553.3 $[M+H]^+$.

The following compound was made in a similar fashion to 3-45-A and 3-45-B using ortho-fluoro benzyl amine:

Compound 3-46-A; RT=2.238 min, m/z 593.4$[M+H]^+$

Compound 3-46-B; RT=2.224 min, m/z 593.4$[M+H]^+$

Example 58—Synthesis of 2-((2S,5S,15S)-15-Benzyl-5-(methoxycarbonyl)-3,16-dioxo-1,4-diazacyclohexadecan-2-yl)acetic Acid (4-01) and 2-((2S,5S,15R)-15-Benzyl-5-(methoxycarbonyl)-3,16-dioxo-1,4-diazacyclohexadecan-2-yl)acetic Acid (4-02)

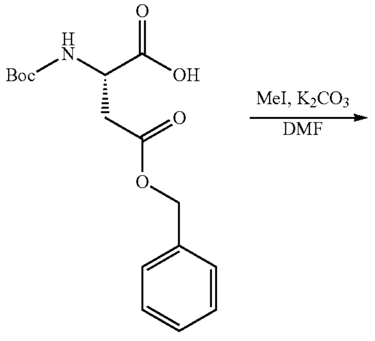

-continued

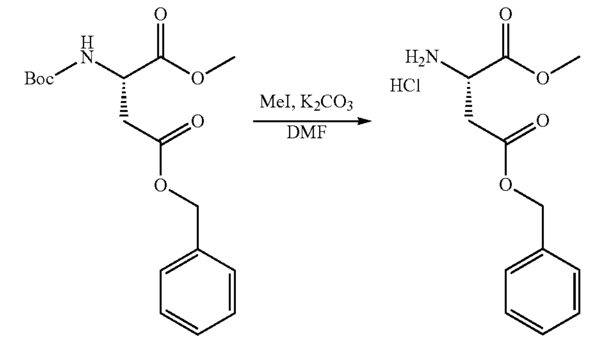

4-01-1

4-01-2

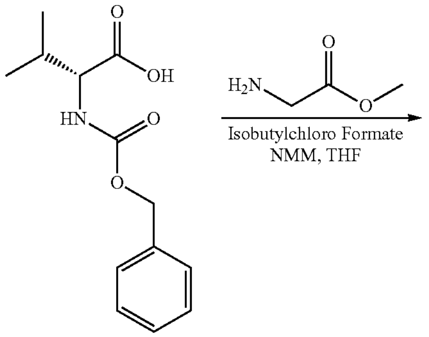

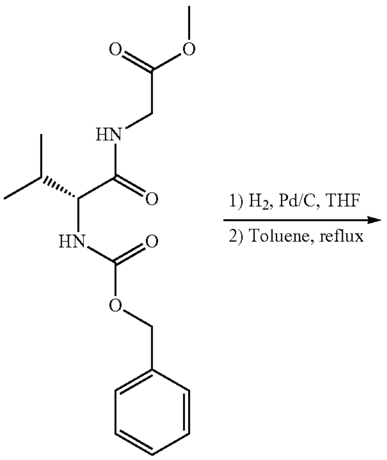

4-01-3

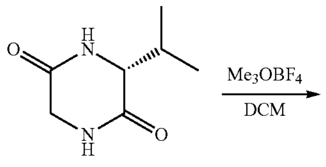

4-01-4

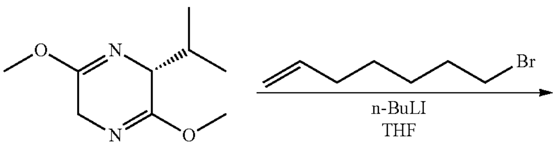

4-01-5

-continued
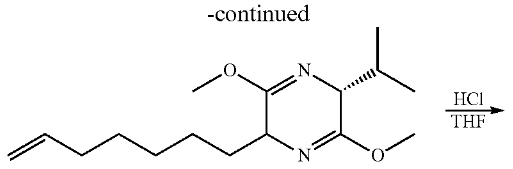
4-01-6
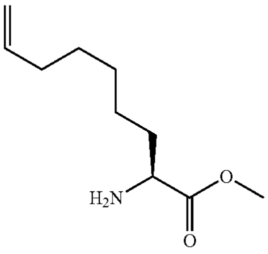
4-01-7
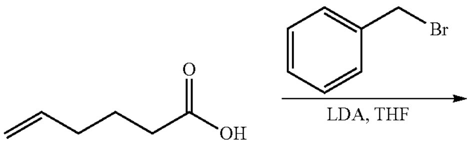
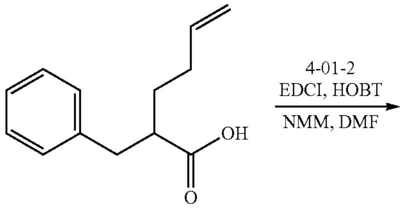
4-01-8
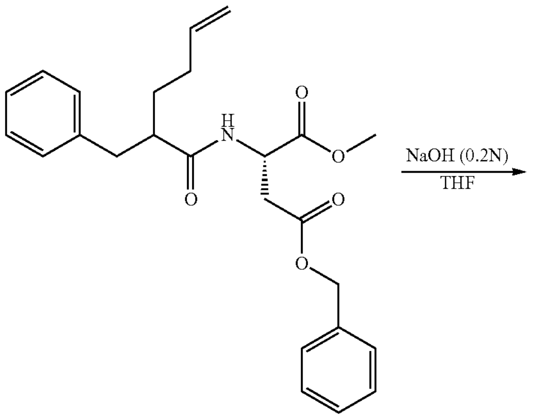
4-01-9
-continued
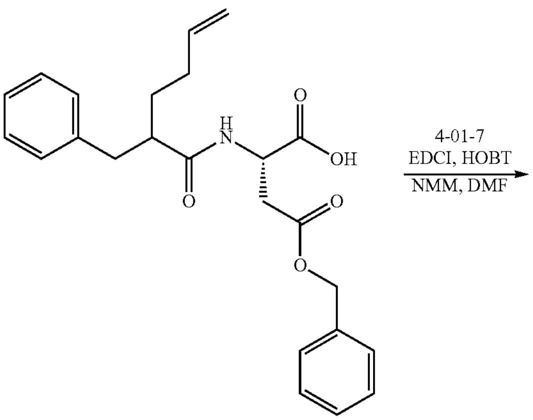
4-01-10
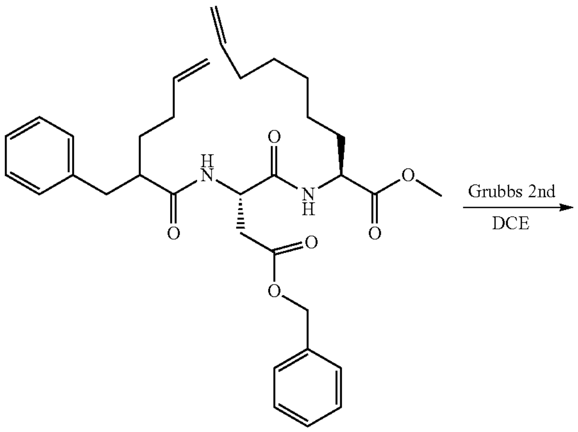
4-01-11
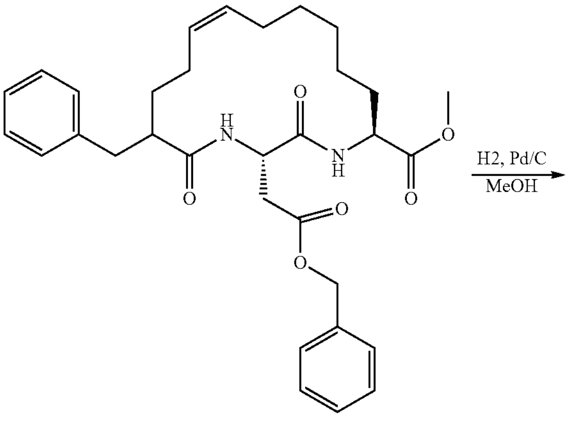
4-01-12
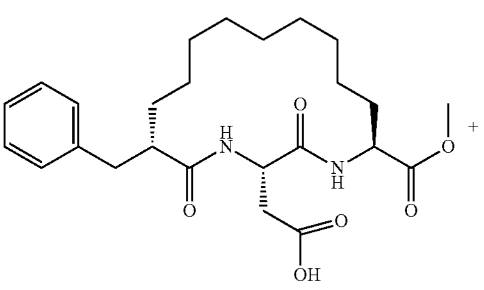
4-01

-continued

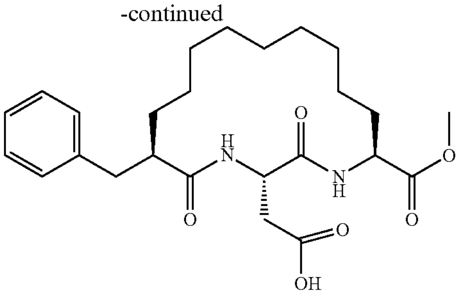

4-02

To a solution of 4-benzyl 1-methyl L-aspartate hydrochloride (11.5 g, 35.6 mmol, 2 paralleled batches) and potassium carbonate (7.9 g, 57 mmol) in dimethyl formamide (100 mL) was added iodomethane (6.03 mL, 96.9 mmol) drop wise. The mixture was stirred at 20° C. for 2 hours. The reaction mixture was poured into water (200 mL), extracted with ethyl acetate (300 mL*2). The combined organic phase was washed with brine (300 mL*2), dried over anhydrous sodium sulfate, and concentrated in reduced pressure to afford compound 4-01-1 (23.5 g, 98% yield) as a yellow solid. No further purification was performed.

To a solution of compound 4-01-1 (23.5 g, 67.0 mmol) in dioxane (100 mL) was added hydrochloric acid as a 4M solution in dioxane (100 mL, 400 mmol). The mixture was stirred at 20° C. for 1 hour. The reaction mixture was concentrated under reduced pressure to afford compound 4-01-2 (20 g, crude, hydrochloride salt) as a white solid. No further purification was performed.

To a solution of compound ((benzyloxy)carbonyl)-D-valine (45 g, 180 mmol) and N-methylmorpholine (64.97 mL, 591.0 mmol) in tetrahydrofuran (500 mL) was added isobutyl carbonochloridate (25.7 g, 188.03 mmol, 24.69 mL, 1.05 eq) at 0° C. The mixture was stirred at 20° C. for 1 hour, then methyl glycinate (22.5 g, 179 mmol) was added at 5° C. The mixture was stirred at 20° C. for 1 hour. The reaction mixture was poured into water (100 mL) and 1 N solution of hydrochloric acid (100 mL) was added. The mixture was extracted with ethyl acetate (200 mL*2). The combined organic phase was washed with brine (200 mL*2), dried over anhydrous sodium sulfate and concentrated in reduced pressure. The residue was purified by flash silica gel column chromatography (petroleum ether:ethyl acetate=10:1~1:1) to afford compound 4-01-3 (40 g, 69% yield) as a white solid.

To a solution of compound 4-01-3 (40.0 g, 120 mmol) in tetrahydrofuran (100 mL) was added 5% palladium on carbon (1 g). The mixture was degassed, purged with hydrogen, and stirred at 20° C. for 2 hours under hydrogen (15 psi) atmosphere. The solution was filtered through celite and concentrated under reduced pressure. The residue was dissolved in toluene (300 mL) and then stirred at 130° C. for 8 hours, then stirred at 110° C. for 12 hours. The suspension mixture was cooled to 0° C. The solid was filtered and washed with petroleum ether (500 mL*2) to afford compound 4-01-4 (11 g, 53% yield) as a white solid.

To a solution of compound 4-01-4 (11 g, 70 mmol) in dichloromethane (500 mL) was added trimethyloxonium tetrafluoroborate (41.7 g, 282 mmol). The slurry was stirred vigorously at 20° C. under a nitrogen atmosphere for 18 hours. The slurry became a clear solution with very viscous yellow oil settled on the bottom of the flask, then another 10.4 g (70 mmol) of trimethyloxonium tetrafluoroborate was added and the mixture was stirred at 20° C. for 24 hours. The mixture was cooled in an ice bath, and 200 g of ice and 100 mL of concentrated ammonium hydroxide solution (30%) were added. The reaction mixture was stirred in an ice bath for 1 hour. The layers were separated and aqueous layer was extracted with DCM (500 mL*2). The combined organic layers were washed with saturated sodium bicarbonate solution (300 mL*2) and brine (300 mL), dried over anhydrous sodium sulfate, filtered through a celite pad, and concentrated under reduced pressure. The residue was purified by column chromatography (petroleum ether to petroleum ether:ethyl acetate=10:1) to afford compound 4-01-5 (9 g, 69% yield) as yellow oil.

A solution of compound 4-01-5 (8.9 g, 48 mmol) in tetrahydrofuran (100 mL) was cooled to −70° C. and n-butyl lithium (2.5 M, 19.5 mL, 49 mmol) was added under nitrogen while the temperature was kept below −70° C. A solution of compound 7-bromohept-1-ene (8.0 g, 45 mmol) in tetrahydrofuran (15 mL) was added at −70° C. The reaction mixture was stirred at −70° C. for 2 hours, then slowly heated to 20° C. and stirred for 1 hour. The reaction mixture was poured into saturated ammonium chloride solution (50 mL) and extracted with ethyl acetate (200 mL*2). The combined organic phase was washed with brine (100 mL*2), dried over anhydrous sodium sulfate, and concentrated in reduced pressure. The residue was purified by column chromatography (petroleum ether to petroleum ether:ethyl acetate=50:1) to afford compound 4-01-6 (7 g, 55% yield) as a colorless oil.

To a solution of compound 4-01-6 (7.0 g, 25 mmol) in tetrahydrofuran (140 mL) was added a 1M aqueous solution of hydrochloric acid (140 mL, 140 mmol) drop wise. The reaction mixture was stirred at 20° C. for 6 hours. The reaction mixture was poured into saturated sodium bicarbonate (100 mL), extracted with ethyl acetate (100 mL*3). The combined organic phase was washed with brine (100 mL), dried over anhydrous sodium sulfate, and concentrated under reduced pressure. The residue was purified by column chromatography (petroleum ether:ethyl acetate=10:1~1:2) to afford compound 4-01-7 (3.6 g, 58% yield) as a colorless oil.

To a solution of diisopropyl amine (21.5 mL, 152 mmol) in tetrahydrofuran (100 mL) was added a solution of n-butyllithium (2.5 M, 63 mL, 157 mmol) drop wise at 0° C. and the mixture was stirred at 0° C. for 15 min. Hex-5-enoic acid (8.85 mL, 74.5 mmol) was added and the mixture was stirred for 15 min, then bromomethylbenzene (10.6 mL, 89.4 mmol) was added. The mixture was stirred at 25° C. for 10 hours. The reaction mixture was quenched with an aqueous 5% hydrochloric acid solution (50 mL) and extracted with ethyl acetate (25 mL*3). The combined organic extracts were washed with brine, dried over anhydrous sodium sulfate, filtered, and concentrated under reduced pressure. The crude product was purified by reversed phase flash column chromatography (trifluoroacetic acid/acetonitrile/water) to afford compound 4-01-8 (11.8 g, 76% yield) as a light yellow oil.

To a solution of compound 4-01-8 (7.5 g, 37 mmol) and N-methylmorpholine (16 mL, 147 mmol) in dimethyl formamide (130 mL) was added HOBt (2.5 g, 18 mmol) and EDCI (8.5 g, 44 mmol) portion wise at 0° C., then compound 4-01-2 (10.1 g, 36.7 mmol) was added portion wise at 0° C. The reaction mixture was slowly warmed to 20° C. and stirred for 2 hours. The reaction mixture was poured into a solution of 1 N hydrochloric acid (50 mL) and water (100 mL). The mixture was extracted with ethyl acetate (200 mL*2). The combined organic phase was washed with brine (100 mL*3), dried over anhydrous sodium sulfate and concentrated in reduced pressure. The residue was purified by column chromatography (petroleum ether:ethyl acetate=10:1~3:1) to afford compound 4-01-9 (11 g, 71% yield) as a yellow solid.

To a solution of compound 4-01-9 (14 g, 33 mmol) in tetrahydrofuran (100 mL) was added a 0.2 M solution of sodium hydroxide (200 mL, 40 mmol) drop wise at 0° C. The mixture was stirred at 0° C. for 2 hours. The reaction mixture was poured into a solution of 1 N hydrochloric acid (200 mL) and extracted with ethyl acetate (200 mL*3). The combined organic phase was washed with brine (100 mL*2), dried over anhydrous sodium sulfate, and concentrated in reduced pressure. The residue was purified by column chromatography (petroleum ether:ethyl acetate=10:1~1:1) to afford compound 4-01-10 (9 g, 66% yield) as a colorless gum.

To a solution of compound 4-01-10 (5.2 g, 13 mmol) and N-methylmorpholine (4.2 mL, 38 mmol) in dimethyl formamide (50 mL) was added EDCI (3.7 g, 19 mmol) and HOBt (1.0 g, 7.6 mmol) at 0° C., then compound 4-01-7 (2.4 g, 13 mmol) was added. The mixture was stirred at 20° C. for 1 hour. The reaction mixture was poured into a solution of 1 N hydrochloric acid (100 mL) and water (80 mL) then extracted with ethyl acetate (200 mL*2). The combined organic phase was washed with brine (100 mL*3), dried over anhydrous sodium sulfate, and concentrated in reduced pressure. The residue was purified by column chromatography (petroleum ether:ethyl acetate=30:1~3:1) to afford compound 4-01-11 (5 g, 68% yield) as a colorless gum.

A solution of compound 4-01-11 (2.5 g, 4.3 mmol, in 2 paralleled batches) in dichloroethane (400 mL) was degassed and purged with nitrogen three times, then Grubbs' 2nd catalyst (740 mg, 870 umol) was added in one portion. The mixture was stirred at 50° C. for 24 hours under nitrogen atmosphere then concentrated in reduced pressure. The residue was purified by column chromatography (Petroleum ether:ethyl acetate=10:1~3:1) to afford a gray solid containing compound 4-01-12 as a diastereoisomeric mixture (2.5 g, 53% yield). The two isomers were used directly without further separation.

A solution of compound 4-01-12 (3.2 g, 5.8 mmol) in methanol (30 mL) was degassed and purged with hydrogen three times. To this was added 5% palladium on carbon (400 mg) in one portion. The mixture was stirred at 20° C. for 4 hours under hydrogen (15 psi). The reaction mixture was filtered and concentrated under reduced pressure. The residue was purified by SFC (column: OD (250 mm*30 mm, 10 um); mobile phase: [0.1% ammonium hydroxide in methanol]; B %: 20%-20%, 3.55 min; 500 min), followed by prep-HPLC (Column: Daiso 150*25 5 u; mobile phase: [water(0.1% trifluoroacetic acid)-acetonitrile]; B %: 45%-70%, 27 min; 65 min) to afford 4-01 (550 mg, 59.6% yield) as a white solid and 4-02 (370 mg, 721.19 umol, 36.9% yield) as a white solid. The relative stereochemistry of 4-01 and 4-02 was arbitrarily assigned. LCMS for 4-01: RT=2.301 min, m/z 461.1 $[M+H]^+$. LCMS for 4-02: RT=2.276 min, m/z 461.1 $[M+H]^+$.

Example 59—Synthesis of Benzyl-(2S,5S,15S)-15-benzyl-N-(naphthalen-1-ylmethyl)-3,16-dioxo-2-(2-oxo-2-(pyrrolidin-1-yl)ethyl)-1,4-diazacyclohexadecane-5-carboxamide (4-03) and (2S,5S,15S)-15-Benzyl-N-(naphthalen-1-ylmethyl)-3,16-dioxo-2-(2-oxo-2-(pyrrolidin-1-yl)ethyl)-1,4-diazacyclohexadecane-5-carboxamide (4-04)

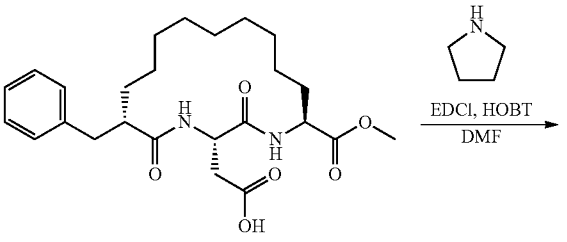

4-01

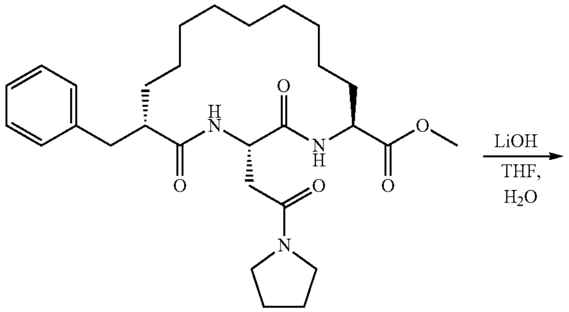

4-03-1

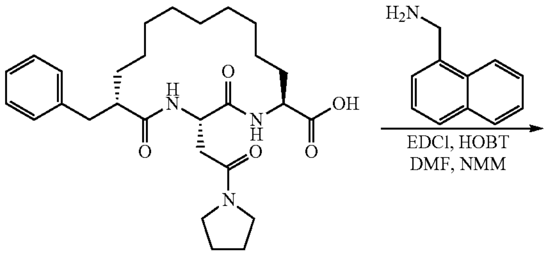

4-03-2

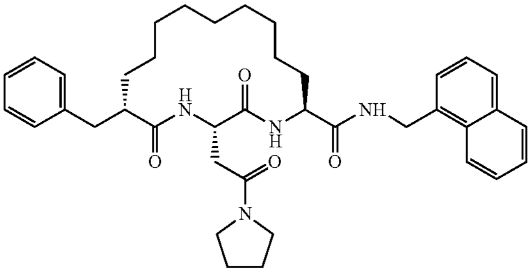

4-03

+

-continued

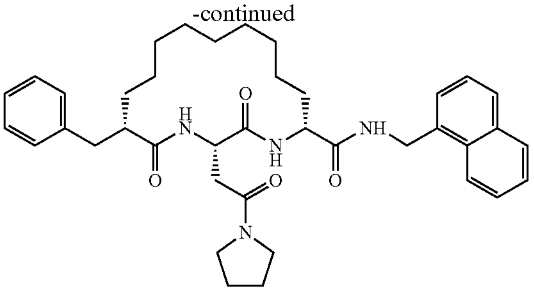

4-04

To a solution of 4-01 (100 mg, 217 μmol) and N-methylmorpholine (72 μL, 650 μmol) in dimethyl formamide (2 mL) was added EDCI (63 mg, 330 μmol) and HOBt (18 mg, 130 μmol) at 0° C., then pyrrolidine (36 μL, 430 μmol) was added. The mixture was stirred at 20° C. for 2.5 hours. The reaction mixture was poured into water (20 mL) and extracted with ethyl acetate (30 mL*2). The combined organic phase was washed with 1 N hydrochloric acid (30 mL) followed by brine (20 mL*2) then dried over anhydrous sodium sulfate and concentrated under reduced pressure to afford a diastereomeric mixture 4-03-1 (130 mg, 76% yield) as a white solid.

To a solution of 4-03-1 (130 mg, 164 umol) in tetrahydrofuran (3 mL) was added a solution of lithium hydroxide hydrate (14 mg, 330 umol) in water (1 mL) drop wise at 0° C. The mixture was stirred at 20° C. for 2 hours. The reaction mixture was concentrated under reduced pressure, then water (10 mL) was added and the pH adjusted to pH=3 with 1N hydrochloric acid causing a precipitate to formed. The material was collected by filtration and the solid was dried under vacuo to afford a mixture of diastereomers containing 4-03-2 (100 mg, crude) as a white solid. No further purification was performed.

To a solution of the diasteromeric mixture 4-03-2 (500 mg, 1.00 mmol) and N-methylmorpholine (320 μL, 3.00 mmol) in dimethyl formamide (6 mL) was added a mixture of EDCI (290 mg, 1.50 mmol) and HOBt (70 mg, 500 umol) portion wise at 0° C. Naphthalen-1-ylmethanamine (294 μL, 2.00 mmol) was added at 0° C. and the mixture was stirred at 20° C. for 1 hour. The reaction mixture was poured into water (20 mL), extracted with ethyl acetate (20 mL*2). The combined organic phase was washed with brine (20 mL*2), dried over anhydrous sodium sulfate, and concentrated in reduced pressure. The residue was purified by prep-TLC (petroleum ether:ethyl acetate=2:1), followed by prep-HPLC (Column: Phenomenex Synergi C18 150*25*10 um; mobile phase: [water (0.1% trifluoroacetic acid)-acetonitrile]; B %: 55%-85%, 13 min) to afford 4-03 (29 mg, 9.2% yield) as a white solid and 4-04 (18 mg, 5.6% yield) as a white solid. The relative stereochemistry at position C-2 was arbitrarily assigned. LCMS for 4-03: RT=2.639 min, m/z 639.2 $[M+H]^+$. LCMS for 4-04: RT=2.687 min, m/z 639.2 $[M+H]^+$ Example 60—Synthesis of (2S,5S,11Z)—N-(1-Naphthylmethyl)-3,16-dioxo-2-(2-oxo-2-pyrrolidin-1-yl-ethyl)-1,4-diazacyclohexadec-11-ene-5-carboxamide (4-05)

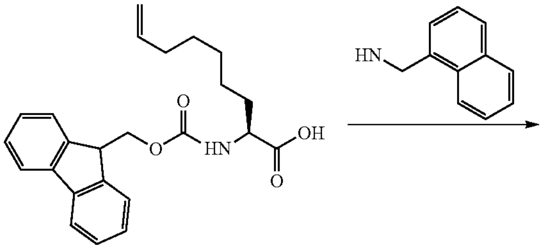

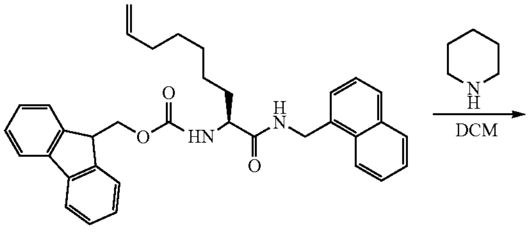

4-05-01

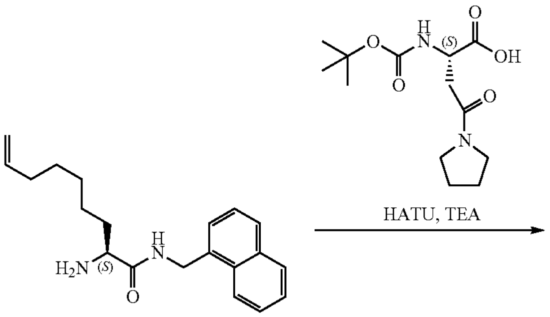

4-05-02

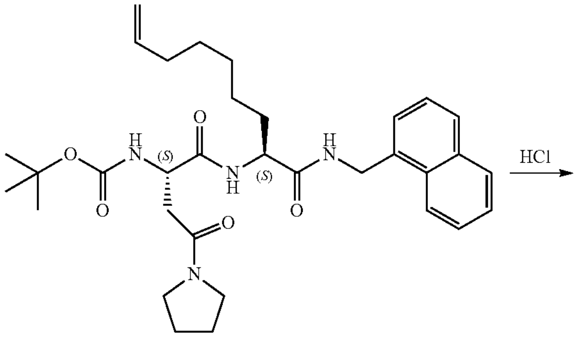

4-05-03

-continued

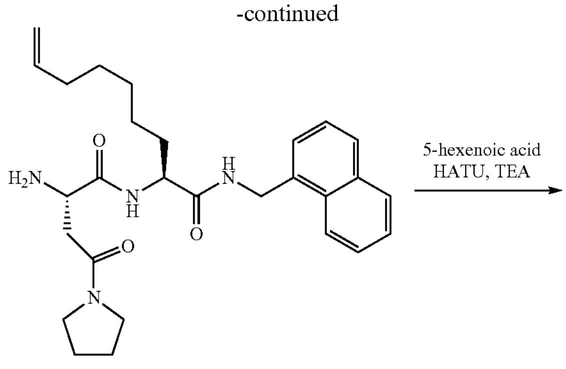

4-05-04

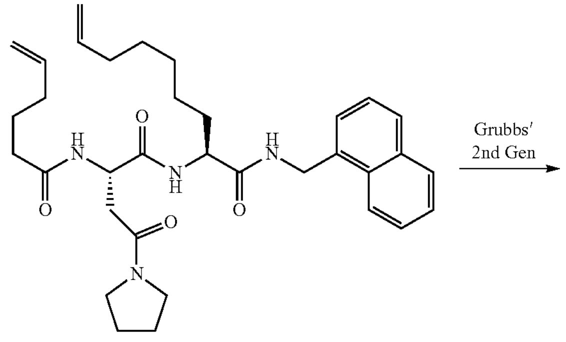

4-05-05

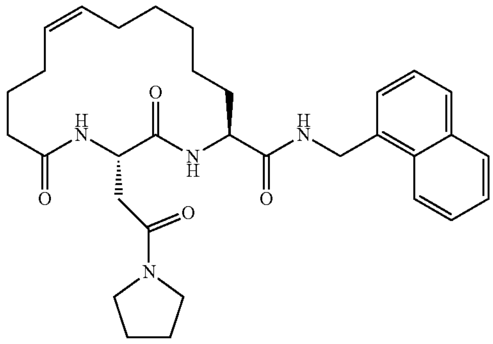

4-05

To a suspension of (2S)-2-(9H-fluoren-9-ylmethoxycarbonylamino)non-8-enoic acid (1.06 g, 2.69 mmol) and 1-naphthylmethanamine (465 mg, 2.96 mmol) in DMF (10 mL) was added HATU (1.12 g, 2.96 mmol) and DIEA (764.84 mg, 5.92 mmol, 1.03 mL) at room temperature. After being stirred for 16 hours, water was added to the solution. The mixture was extracted with EtOAc twice. The combined extract was washed with brine followed by water, then dried over anhydrous sodium sulfate, and concentrated under reduced pressure. The residue was purified by recrystallization from EtOAc to afford 4-05-1 (1.1 g, 77% yield) as white solid.

To a solution of 4-05-1 (1.10 g, 2.07 mmol) in $CH_2Cl_2$ (200.00 mL) was added piperidine (7.76 g, 91.1 mmol) at room temperature. After being stirred for 16 hours, the mixture was concentrated under reduced pressure. To the residue was added $CH_2Cl_2$ and insoluble material was filtered off. The filtrate was purified by column chromatography (40 g, ISCO, 10-20% MeOH in EtOAc) to afford 4-05-2 (380 mg, 59% yield) as a white solid.

To a solution of (2S)-2-(tert-butoxycarbonylamino)-4-oxo-4-pyrrolidin-1-yl-butanoic acid (390.00 mg, 1.36 mmol) and 4-05-2 (380 mg, 1.22 mmol) in DMF (10.00 mL) was added HATU (615 mg, 1.63 mmol) at room temperature. After being stirred for 15 min, TEA (413 mg, 4.08 mmol) was added at room temperature, and the mixture was stirred at room temperature for 16 hours. Water was added and the mixture was extracted with EtOAc. The extract was washed with brine followed by water then dried over anhydrous sodium sulfate, and concentrated under reduced pressure. The residue was purified by column chromatography (40 g, ISCO, 90-100% EtOAc in hexane) to afford 4-05-3 (580 mg, 73.7% yield) as a white solid.

A mixture of 4-05-3 (580 mg, 1.00 mmol) in a 4M solution of HCl in 1,4-dioxane (1.00 mmol) was stirred at room temperature for 1 hour. The mixture was concentrated under reduced pressure to afford 4-05-4 (660 mg, crude) as a pale brown solid. The isolated material was used without further purification.

To a solution of 4-05-4 (330.00 mg, 640.66 umol, CL) and 5-hexenoic acid (73 mg, 640 μmol) in DMF (4.00 mL) was added HATU (290 mg, 770 μmol) at room temperature. After being stirred for 15 min, TEA (194 mg, 1.92 mmol) was added at room temperature, and the mixture was stirred at room temperature for 16 hours. Water was added and the mixture extracted with EtOAc. The extract was washed with brine and water then dried over anhydrous sodium sulfate, and concentrated under reduced pressure. The residue was purified by column chromatography (40 g, ISCO, 0-5% MeOH in EtOAc) to afford 4-05-5 (200 mg, 54% yield) as a white solid.

A solution of 4-05-5 (160 mg, 278 μmol) in $CH_2Cl_2$ (250.00 mL) was first degassed by bubbling nitrogen through for 5 min and then Grubbs 2nd Generation catalyst (59 mg, 70 μmol) was added at room temperature. After being stirred for 4 hours at 50° C. and for 16 hours at room temperature under $N_2$ the mixture was concentrated under reduced pressure. The residue was purified by column chromatography (10-15% MeOH in EtOAc) then further purified by column chromatography using a NH $SiO_2$ column (28 g, 5-10% MeOH/EtOAc) to afford 4-05 (45 mg, 36% yield) as a white solid. LCMS for 4-05: RT: 2.22 min, m/z: 547.47 $[M-H]^+$ Example 61—Synthesis of (2S,5S)-N-(1-Naphthylmethyl)-3,16-dioxo-2-(2-oxo-2-pyrrolidin-1-ylethyl)-1,4-diazacyclohexadecane-5-carboxamide (4-06)

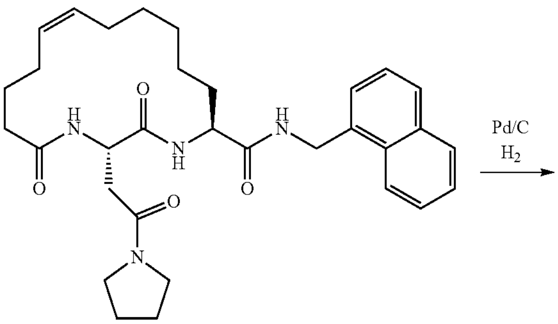

4-05

-continued

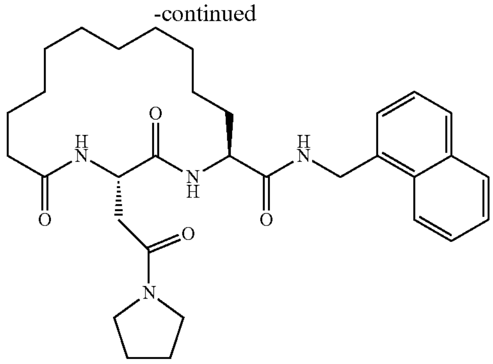

4-06

A mixture of 4-05 (40 mg, 73 μmol), 10% palladium on carbon (60 mg, 73 μmol), and MeOH (15.00 mL) was stirred under a balloon pressure of $H_2$. After being stirred for 2 hours, insoluble materials were removed by filtration and the filter cake was washed with MeOH. The filtrate was concentrated under reduced pressure and the residue was purified by column chromatography (12 g, ISCO, 5-10% MeOH in EtOAc) to afford 4-06 (17 mg, 42% yield) as a white solid. LCMS for 4-06: RT: 2.28 min, m/z: 549.57 $[M-H]^+$.

The following compound was generated in a similar fashion as Compound 4-06: Compound 4-07; LCMS: RT: 2.18 min, m/z: 535.47 $[M+H]^+$ Example 62—Synthesis of (3S,16S)-16-(7-Fluoro-1H-benzimidazol-2-yl)-3-[2-oxo-2-[(2R)-2-phenylpyrrolidin-1-yl]ethyl]-1,4-diazacyclohexadecane-2,5-dione (4-09)

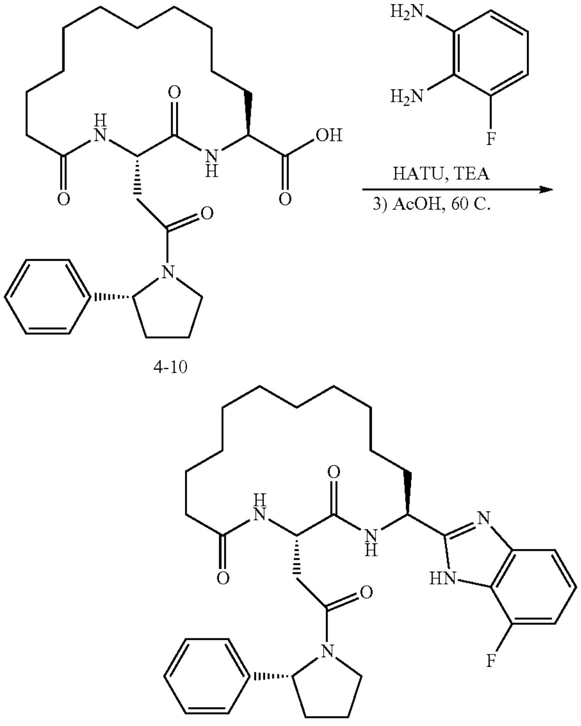

4-10

4-09

A mixture of 4-10 (240 mg, 494 umol), 3-fluorobenzene-1,2-diamine (74 mg, 0.59 mmol), HATU (280 mg, 0.74 mmol), and TEA (342 μL, 2.47 mmol) in DMF (4.0 mL) was stirred at room temperature for 16 hours. The reaction was diluted with water and EtOAc. The organic layer was separated, washed with brine, dried over anhydrous sodium sulfate, filtered, and concentrated under reduced pressure to give a black oil. A mixture of the isolated material in acetic acid (10.00 mL) was heated to 60° C., stirred for 3 hours, and then concentrated under reduced pressure. The residue was purified by column chromatography and then recrystallization from EtOAc to afford 4-09 (16 mg, 5.6% yield) as a pale brown solid. LCMS for 4-09: RT: 2.33 m/z: 576.55 $[M+H]^+$ Example 63—Synthesis of (2S,5S)-3,16-Dioxo-2-(2-oxo-2-((R)-2-phenylpyrrolidin-1-yl)ethyl)-1,4-diazacyclohexadecane-5-carboxylic acid (4-10)

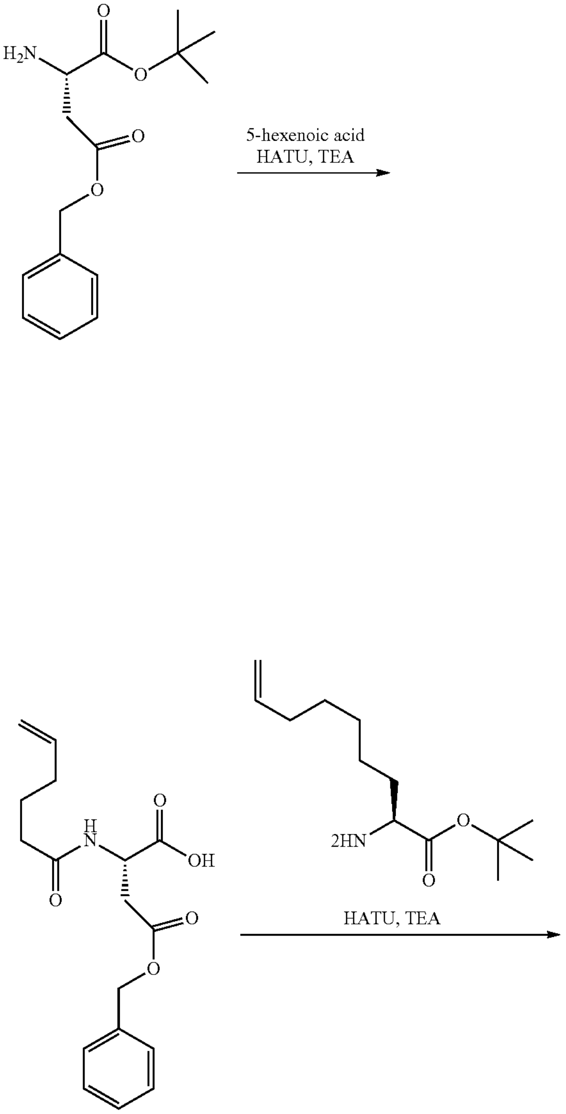

4-10-1

-continued

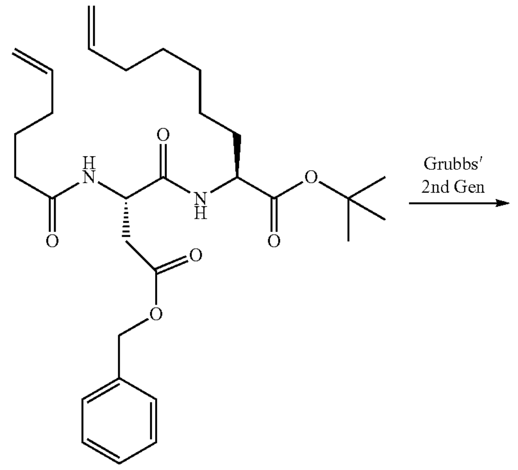

4-10-2

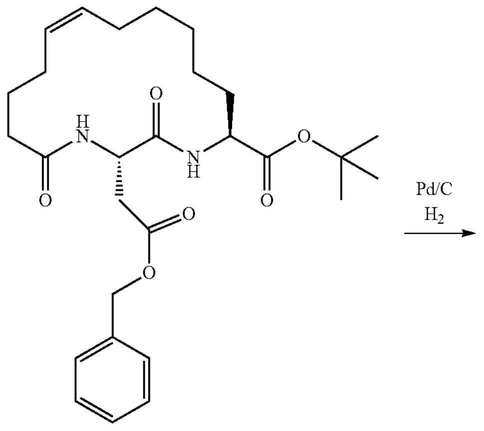

4-10-3

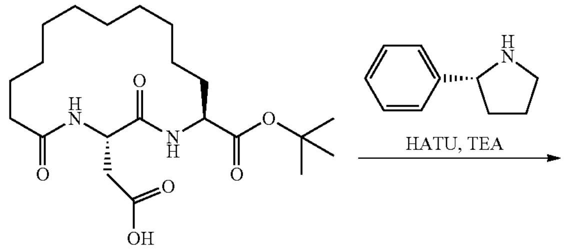

4-10-4

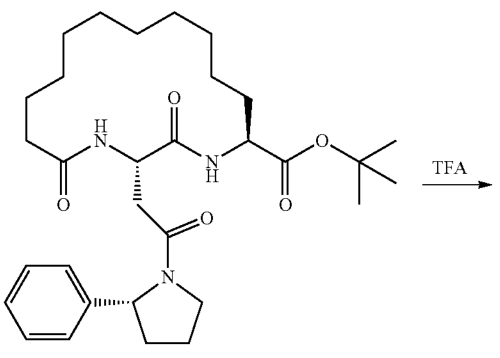

4-10-5

-continued

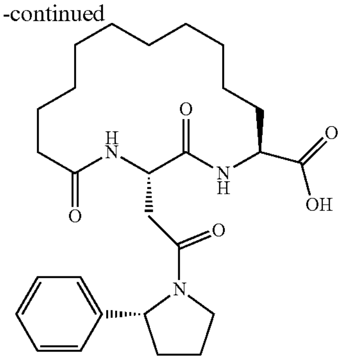

4-10

To a solution of O4-benzyl O1-tert-butyl (2S)-2-aminobutanedioate (25 g, 79 mmol, HCl salt) and 5-hexenoic acid (10 g, 91 mmol) in DMF (500.00 mL) was added HATU (37 g, 99 mmol) at room temperature. After being stirred for 5 min, TEA (43.9 mL, 320 mmol) was added at room temperature and the mixture was stirred at room temperature for 16 hours. Water was added and the mixture was extracted with EtOAc. The extract was washed with brine and water then dried over anhydrous sodium sulfate, and concentrated under reduced pressure. The residue was purified by column chromatography to afford a residue (26.7 g, 89.8% yield) as a pale brown oil which was used as is. To the residue was added 2,2,2-trifluoroacetic acid (121.62 g, 1.07 mol) in an ice-bath, and the mixture was stirred at room temperature for 16 hours. Then the reaction mixture was concentrated under reduced pressure and azeotroped with toluene 3 times to afford, 4-10-1 (23 g, 102% yield) as a pale brown oil which was used for next step without further purification.

To a solution of 4-10-1 (7.88 g, 24.7 mmol) and tert-butyl (2S)-2-aminonon-8-enoate (6.20 g, 23.5 mmol) in DMF (350 mL) was added HATU (10.6 g, 28.2 mmol) at room temperature. After being stirred for 5 min, TEA (7.13 g, 70.5 mmol) was added, and the mixture was stirred at room temperature for 1 hour. Water was added and the mixture was extracted with EtOAc. The extract was washed with brine and water, then dried over anhydrous sodium sulfate, and concentrated under reduced pressure. The residue was purified by column chromatography to afford 4-10-2 (8.63 g, 69.5% yield) as a pale brown oil, which was used in the next step without further purification.

A solution of tert-butyl 4-10-2 (2.0 g, 3.8 mmol) in toluene (3.00 L) was degassed by bubbling nitrogen through for 15 min then Grubbs 2nd Generation catalyst (0.80 g, 0.94 mmol) was added at room temperature. After being stirred for 16 hours at 40° C. under N2 the mixture was concentrated under reduced pressure. The residue was triturated with ether (200 mL) and filtrated. The filtrated was concentrated under reduced pressure and the residue was purified by column chromatography to afford 4-10-3 (610 mg, 92.6% yield).

A mixture of 4-10-3 (640 mg, 1.28 mmol), and 10% palladium on carbon (360 mg, 1.28 mmol), in MeOH (200 mL) was hydrogenated under a balloon pressure of $H_2$. After being stirred for 2 hours, insoluble materials were removed by filtration through celite and the filter pad was washed with MeOH. The filtrate was concentrated under reduced pressure to afford 4-10-4 (540 mg, 102% yield, crude) as a pale brown amorphous solid which was used in the next step without further purification.

To a solution of 4-10-4 (450 mg, 1.09 mmol) and (R)-2-phenylpyrrolidine (177 mg, 1.20 mmol) in DMF (5.00 mL) was added HATU (535 mg, 1.42 mmol) at room temperature. After being stirred for 5 min, triethylamine (552 mg, 5.45 mmol) was added, and the mixture was stirred at room temperature for 24 hours. Water was added and the mixture was extracted with EtOAc. The extract was washed with brine and water, then dried over anhydrous sodium sulfate, and concentrated under reduced pressure. The residue was purified by column chromatography to afford 4-10-5 (280 mg, 47% yield) as a white solid.

To 4-10-5 (250 mg, 461 μmol), cooled to 0 C, was added trifluoroacetic acid (1.05 g, 9.23 mmol). The mixture was stirred at room temperature for 3 hours then concentrated under reduced pressure. The residue was crystallized with ether to afford the acid (180 mg) as a pale brown solid. No further purification was performed. LCMS for 4-10: LCMS: RT: 2.19 m/z: 486.37 $[M+H]^+$ Example 64—Synthesis of (3S,16S)-16-(Hydroxymethyl)-3-[2-oxo-2-[(2R)-2-phenylpyrrolidin-1-yl]ethyl]-1,4-diazacyclohexadecane-2,5-dione (4-11)

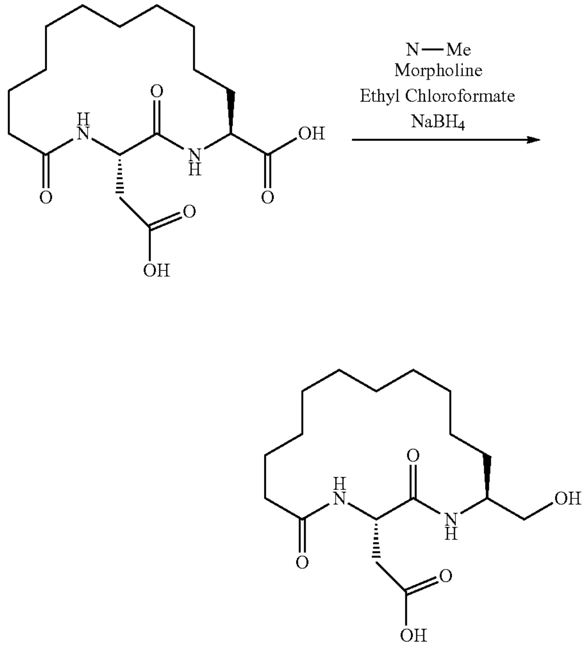

4-11

To a solution of (2S,5S)-3,16-dioxo-2-[2-oxo-2-[(2R)-2-phenylpyrrolidin-1-yl]ethyl]-1,4-diazacyclohexadecane-5-carboxylic acid (50 mg, 102 μmol) in THE (2.00 mL) chilled over ice-bath was added 4-methylmorpholine (12 mg, 120 μmol) and ethyl chloroformate (13 mg, 120 μmol). Sodium borohydride (19 mg, 510 μmol) was added in one portion. Methanol (2.00 mL) was added dropwise over 10 min. After being stirred for 1 hour in the ice-bath, the mixture was concentrated under reduced pressure. The residue was purified by column chromatography (40 g, ISCO, 0-5% MeOH in EtOAc) to afford 4-11 (20 mg, 41% yield) as a white solid. LCMS for 4-11: RT: 2.18 m/z: 473.5 $[M+H]^+$.

Example 65—Synthesis of (2S,5S)-N-(2-Fluorobenzyl)-3,16-dioxo-2-(2-oxo-2-((R)-2-phenylpyrrolidin-1-yl)ethyl)-1,4-diazacyclohexadecane-5-carboxamide (4-12)

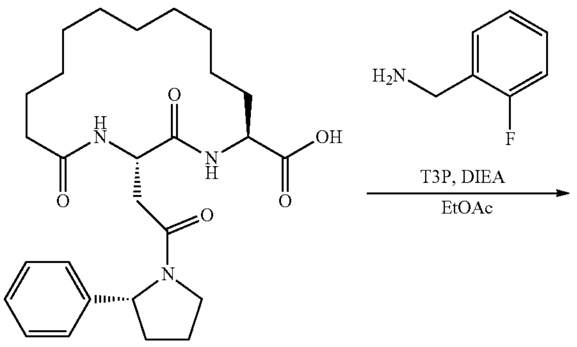

4-10

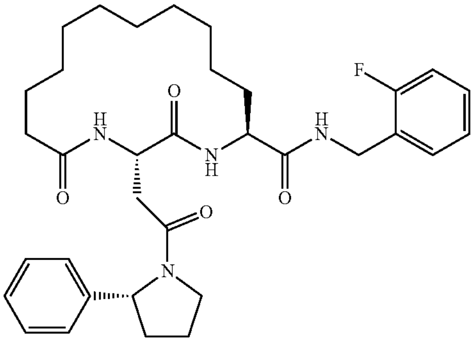

4-12

To a solution of 4-10 (34.4 mg, 0.708 mmol) and (2-fluorophenyl)methanamine (12.9 mg, 0.103 mmol) in ethyl acetate (1.00 mL), cooled to 0° C., was added, dropwise, a mixture of T3P (0.050 mL, 1.6 mmol, 50% in EtOAc) and DIEA (0.037 mL, 0.21 mmol) in ethyl acetate (1.00 mL). The reaction was removed from the ice bath and stirred for 4 hours as the mixture warmed to room temperature. The solvent was removed under reduced pressure and the residue purified by flash silica gel column chromatography to provide 4-12 (32 mg, 76% yield) as a brown solid. LCMS for 4-12: RT: 2.40 min, m/z: 593.5 $[M-H]^+$.

The following compounds were made using a similar synthetic route as described for compound 4-12:

Compound 4-08; LCMS: RT: 2.51 m/z: 625.6 $[M+H]^+$
Compound 4-13; LCMS: RT: 2.35 m/z: 557.5 $[M+H]^+$
Compound 4-14; LCMS: RT: 2.50 m/z: 625.6 $[M+H]^+$
Compound 4-17; LCMS: RT: 2.97 m/z: 573.1 $[M+H]^+$ Example 66—Synthesis of (3S,6S)-N-(Naphthalen-1-ylmethyl)-5,8-dioxo-6-(2-oxo-2-(pyrrolidin-1-yl)ethyl)-1-oxa-4,7-diazacyclohexadecane-3-carboxamide (4-15)

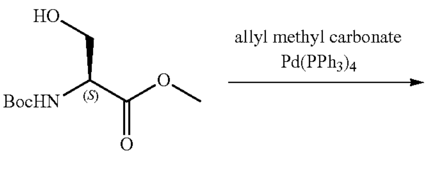

-continued
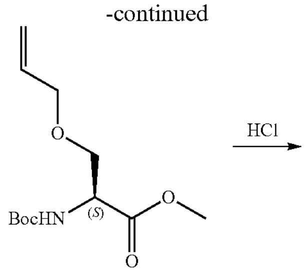
4-15-1
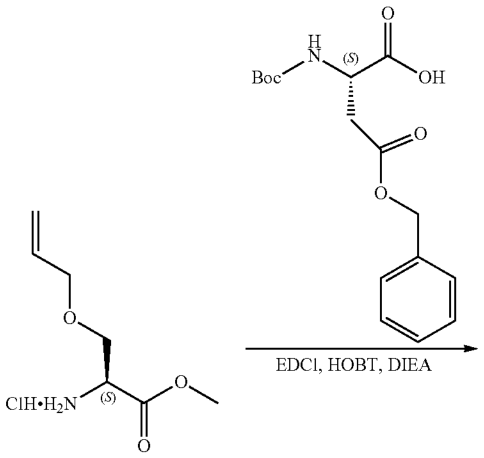
4-15-2
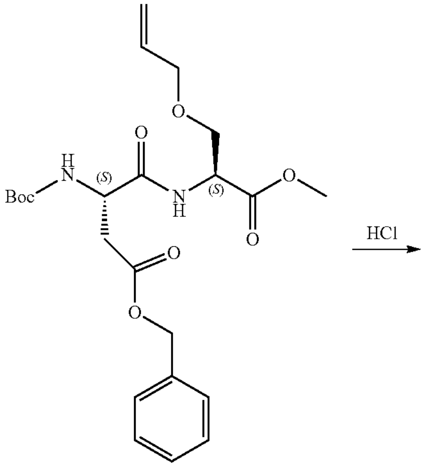
4-15-3
-continued
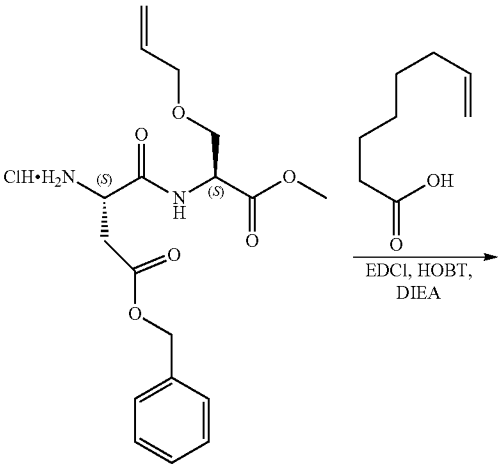
4-15-4
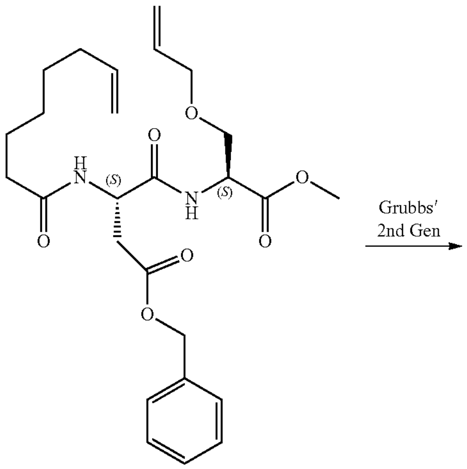
4-15-5
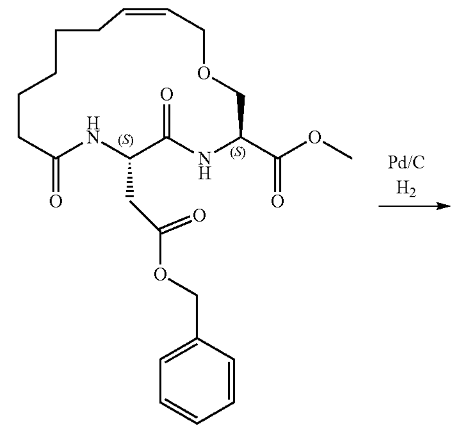
4-15-6

-continued

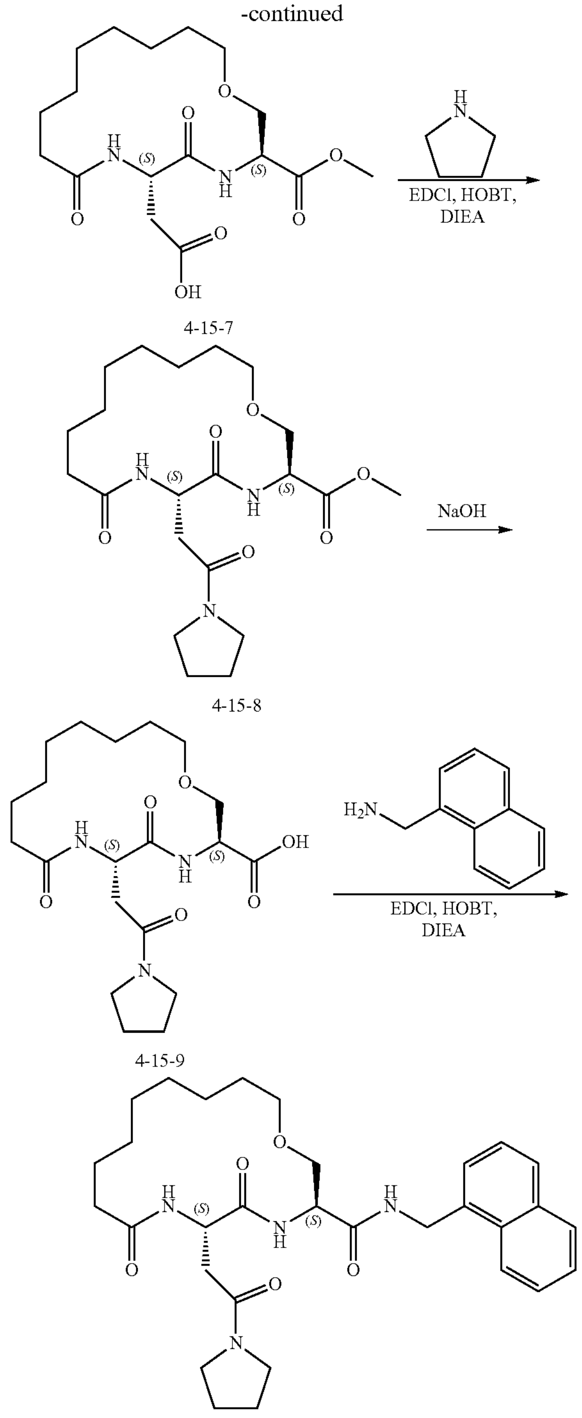

To a solution of compound methyl (tert-butoxycarbonyl)-L-serinate (5.0 g, 23 mmol) in tetrahydrofuran (50 mL) was added allyl methyl carbonate (3.97 g, 34.2 mmol) at followed by $Pd(PPh_3)_4$(527 mg, 456 μmol). The reaction mixture was degassed in vacuum and purged with nitrogen 3 times. The resulting mixture was stirred at 60° C. for 4 hours. The reaction mixture was diluted with water (20 mL) and extracted with ethyl acetate (50 mL*3). The combined organic layer was dried over anhydrous sodium sulfate. After filtration and concentration under reduced pressure, the residue was purified by silica gel chromatography (petroleum ether:ethyl acetate=20:1 to 10:1) to afford compound 4-15-1 (4 g, 58% yield) as yellow oil.

To a solution of compound methyl 4-15-1 (4.0 g, 15 mmol) in dioxane (20 mL) was added a 4M solution of hydrogen chloride in dioxane (30 mL, 120 mmol). The reaction mixture was stirred at 26° C. for 2 hours. The mixture was concentrated under reduced pressure to provide compound 4-15-2 (2.90 g, crude) as a yellow solid.

To a solution of N-(tert-butoxycarbonyl)-L-aspartic acid 4-benzyl ester (5.08 g, 15.7 mmol) in N,N-dimethylformamide (20 mL) was added diisopropylethylamine (6.09 g, 47.1 mmol), EDCI (4.52 g, 23.6 mmol), and HOBt (3.18 g, 23.6 mmol) at 0° C. Then a solution of compound 4-15-2 (2.5 g, 16 mmol) in DMF (10 mL) was added and the resulting mixture was stirred at 26° C. for 17 hours. The reaction mixture was diluted with water (20 mL), acidified by hydrochloric acid (1N) until pH=4, and extracted with ethyl acetate (30 mL*3). The combined organic layer was washed with brine (30 mL*3) and dried over anhydrous sodium sulfate. After filtration and concentration under reduced pressure, the residue was purified by silica gel column chromatography (petroleum ether:ethyl acetate=15:1 to 6:1) to provide compound 4-15-3 (5.3 g, 68% yield) as yellow oil.

To a solution of compound 4-15-3 (1.8 g, 3.9 mmol) in dioxane (10 mL) was added a 4M solution of hydrogen chloride in dioxane (10 mL, 40 mmol). The mixture was stirred at 25° C. for 2 hours. The mixture was concentrated under reduced pressure to provide compound 4-15-4 (2 g, crude) as a colorless oil.

To a solution of 7-octenoic acid (560 mg, 3.94 mmol) in N,N-dimethylformamide (10 mL) was added HOBt (692 mg, 5.12 mmol), EDCI (981 mg, 5.12 mmol), and N,N-diisopropylethylamine (2.55 g, 19.7 mmol) at 0° C. under nitrogen. Then compound 4-15-4 (2.01 g, 5.0 mmol) was added to above reaction mixture at 0° C. under nitrogen. The resulting mixture was stirred at 25° C. for 16 hours. The mixture was diluted with water (40 mL) and extracted with ethyl acetate (20 mL*3). The combined organic phases were washed with saturated aqueous sodium carbonate solution (20 mL*3) followed by brine (20 mL) and then dried over anhydrous sodium sulfate. After filtration and concentration under reduced pressure, the crude product was purified by silica gel chromatography (petroleum ether:ethyl acetate=15:1 to 2:1) to afford compound 4-15-5 (1.48 g, 64.2% yield) as a yellow oil.

To a solution of compound 4-15-5 (1.48 g, 3.03 mmol) in toluene (280 mL) was added Grubbs' $2^{nd}$ Generation Catalyst (2.57 g, 3.03 mmol) and then the mixture was degassed in vacuum and purged with nitrogen 3 times. The mixture was stirred at 60° C. for 16 hours under nitrogen concentrated under reduced pressure. The crude product was purified by silica gel chromatography (petroleum ether:ethyl acetate=3:1 to 3:1) and recrystallized in methanol (20 mL) to afford 4-15-6 (2.2 g, crude) as an off-white solid.

To a solution of methyl 4-15-6 (500 mg, 1.09 mmol) in tetrahydrofuran (4 mL) was added 10% Pd/C (200 mg) and the mixture was degassed and purged with hydrogen 3 times. The mixture was stirred at 25° C. for 1 hour under a hydrogen balloon. The mixture was diluted with dichloromethane (10 mL) and methanol (2 mL) and then filtered. The filtrate was concentrated under reduced pressure. The crude product was purified by prep-HPLC (column: Phenomenex Synergi C18 150 mm*25 mm*10 um; mobile phase: [water (0.1% TFA)-ACN]; B %: 18%-48%, 11 min.) to afford 4-15-7 (400 mg, 98.1% yield) as a white solid.

To a solution of 4-15-7 (180 mg, 483 μmol) in N,N-dimethylformamide (3 mL) was added HOBt (84 mg, 630 μmol), EDCI (120 mg, 628 μmol), N,N-diisopropylethylamine (124 mg, 967 μmol), and pyrrolidine (34 mg, 48 μmol) at 0° C. under nitrogen. The mixture was stirred at 25° C. for 16 hours. The mixture was diluted with water (20 mL) and extracted with ethyl acetate (20 mL*3). The combined organic phases were washed with brine (20 mL), dried over anhydrous sodium sulfate, filtered, and concentrated under reduced pressure. The residue was purified by reverse phase flash chromatography (TFA) to afford compound 4-15-8 (70 mg, 34% yield) as a white solid.

To a solution of 4-15-8 (20 mg, 47 μmol) in water (0.2 mL) and tetrahydrofuran (2 mL) was added sodium hydroxide (11 mg, 280 μmol). The mixture was stirred at 0° C. for 0.25 hour. The mixture was acidified with a 1N solution of hydrochloric acid until pH=3 and then adjusted to pH=8 with saturated aqueous sodium bicarbonate solution. The mixture was washed with ethyl acetate (10 mL*2) and the aqueous layer was acidified with 1N hydrochloric acid to pH=6 and then freeze-dried to afford compound 4-15-9 (15 mg, 73% yield) as a white solid.

To a solution of 4-15-9 (15 mg, 36 μmol) in N,N-dimethylformamide (3 mL) was added N,N-diisopropylethylamine (12 mg, 91 μmol), HOBt (6.0 mg, 47 μmol), and EDCI (9.0 mg, 47 μmol) at 0° C. under nitrogen. Then 1-naphthylmethylamine (7.0 mg, 47 μmol) was added to above mixture. The mixture was stirred at 25° C. for 16 hours. The mixture was diluted with water (20 mL) and extracted with ethyl acetate (20 mL*3). The combined organic phases were washed with brine (20 mL*3), dried over anhydrous sodium sulfate, filtered, and concentrated under reduced pressure. The crude product was recrystallized with acetonitrile (3 mL, twice) to afford 4-15 (31.2 mg, 155% yield) as a white solid. LCMS for 4-15: RT=2.983 min, m/z 551.3 $[M+H]^+$ The following compound was made using a similar synthetic route as described for compound 4-15: Compound 4-16; LCMS: RT=3.122 min, m/z 595.3 $[M+H]^+$ LCMS Conditions that was used are shown in Table 1. Analytical Data for the synthesized compounds is shown in Tale 2.

TABLE 1

| LCMS Conditions | | | | |
|---|---|---|---|---|
| Instrument | | SHIMADZU LCMS-2020; | | |
| Software | | LabSolution Version 5.72 | | |
| HPLC | Column | Chromolith@Flash RP-18E 25-2 MM | | |
| | Mobile Phase | A: 0.0375% TFA in water (v/v) | | |
| | | B: 0.01875% TFA in Acetonitrile (v/v) | | |
| | Gradient | Time(min) | B(%) | Flow(mL/min) |
| | | 0.0 | 5 | 1.5 |
| | | 0.80 | 95 | 1.5 |
| | | 1.20 | 95 | 1.5 |
| | | 1.21 | 5 | 1.5 |
| | | 1.55 | 5 | 1.5 |
| | Column Temp | 50° C. | | |
| | Detector | PDA (220 nm & 254 nm) | | |
| MS | Ionization source | ESI | | |
| | Drying Gas | N2 | | |
| | Drying Gas Flow | 15(L/min) | | |
| | DL Voltage | 120(v) | | |
| | Qarray DC Voltage | 20(V) | | |
| | MS Polarity | Positive | | |
| | MS Mode | Scan | | |
| | Mass range | 100-1000 | | |

TABLE 1-continued

| LCMS Conditions | | | | |
|---|---|---|---|---|
| Instrument | | SHIMADZU LCMS-2020; | | |
| Software | | LabSolution Version 5.72 | | |
| HPLC | Column | Chromolith@Flash RP-18E 25-2 MM | | |
| | Mobile Phase | A: 0.0375% TFA in water (v/v) | | |
| | | B: 0.01875% TFA in Acetonitrile (v/v) | | |
| | Gradient | Time(min) | B(%) | Flow(mL/min) |
| | | 0.0 | 5 | 0.8 |
| | | 3.0 | 95 | 0.8 |
| | | 3.50 | 95 | 0.8 |
| | | 3.51 | 5 | 0.8 |
| | | 4.00 | 5 | 0.8 |
| | Column Temp | 50° C. | | |
| | Detector | PDA (220 nm & 254 nm) | | |
| MS | Ionization source | ESI | | |
| | Drying Gas | N2 | | |
| | Drying Gas Flow | 15(L/min) | | |
| | DL Voltage | 120(v) | | |
| | Qarray DC Voltage | 20(V) | | |
| | MS Polarity | Positive | | |
| | MS Mode | Scan | | |
| | Mass range | 100-1000 | | |
| Instrument | | Agilent 1200\G1956A | | |
| Software | | Agilent ChemStation Rev. B. 04.03[52] | | |
| HPLC | Column | Chromolith@Flash RP-18E 25-2MM | | |
| | Mobile Phase | A: 0.0375% TFA in water (v/v) | | |
| | | B: 0.01875% TFA in Acetonitrile (v/v) | | |
| | Gradient | Time(min) | B(%) | Flow(mL/min) |
| | | 0.0 | 5 | 0.8 |
| | | 3.00 | 95 | 0.8 |
| | | 3.50 | 95 | 0.8 |
| | | 3.51 | 5 | 0.8 |
| | | 4.00 | 5 | 0.8 |
| | Column Temp | 50° C. | | |
| | Detector | DAD (220 nm & 254 nm) | | |
| MS | Ionization source | ESI | | |
| | Drying Gas | N2 | | |
| | Drying Gas Flow | 12(L/min) | | |
| | Nebulizer Pressure | 2070(Torr) | | |
| | Drying Gas Temp | 350(° C.) | | |
| | Capillary Voltage | 4000(V) | | |
| | MS Polarity | Positive | | |
| | MS Mode | Scan | | |
| | Mass range | 100-1000 | | |
| Instrument | | Agilent 1200 LC/G1956A MSD | | |
| Software | | Agilent ChemStation Rev.B.04.03 | | |
| HPLC | Column | Chromolith Flash RP-18e 25 * 2 mm | | |
| | Mobile Phase | A: 0.0375% TFA in Water (v/v) | | |
| | | B: 0.01875% TFA in Acetonitrile (v/v) | | |
| | Gradient | Time(min) | B (%) | Flow(mL/min) |
| | | 0.01 | 5 | 1.5 |
| | | 0.80 | 95 | 1.5 |
| | | 1.2 | 95 | 1.5 |
| | | 1.21 | 5 | 1.5 |
| | | 1.5 | 5 | 1.5 |
| | Column Temp | 50° C. | | |
| | Detector | DAD (220&254nm) | | |
| MS | Ionization source | ESI | | |
| | Drying Gas | N2 | | |
| | Drying Gas Flow | 10(L/min) | | |
| | Nebulizer Pressure | 35 (psig) | | |
| | Drying Gas Temp | 350(° C.) | | |
| | Capillary Voltage | 2500(V) | | |
| | MS Polarity | Positive | | |
| | MS Mode | Scan | | |
| | Mass range | 100-1000 | | |
| Instrument | | Agilent 1200 LC & Agilent 6110 MSD | | |
| Software | | Agilent Chemstation Rev. B. 04.03[54] | | |
| HPLC | Column | Agilent ZORBAX 5 μm SB-Aq, 2.1 * 50mm | | |
| | Mobile Phase | A: 0.0375% TFA in water (v/v) | | |
| | | B: 0.01875% TFA in Acetonitrile (v/v) | | |
| | Gradient | Time(min) | B(%) | Flow(mL/min) |
| | | 0.00 | 1 | 0.8 |
| | | 0.40 | 1 | 0.8 |
| | | 3.40 | 90 | 0.8 |

TABLE 1-continued

| LCMS Conditions | | | | |
|---|---|---|---|---|
| | | 3.90 | 100 | 0.8 |
| | | 3.91 | 1 | 0.8 |
| | | 4.00 | 1 | 1.0 |
| | | 4.50 | 1 | 1.0 |
| | Post time(min) | Off | | |
| | Column Temp | 50° C. | | |
| | Detector | DAD (210 nm, 215 nm, 220 nm, 254 nm) | | |
| MS | Ionization source | ESI | | |
| | Drying Gas | N2 | | |
| | Drying Gas Flow | 10(L/min) | | |
| | Nebulizer Pressure | 40(psi) | | |
| | Drying Gas Temperature | 350° C. | | |
| | Capillary Voltage | 2500(V) Positive | | |
| | MS Polarity | Positive | | |
| | MS Mode | Scan | | |
| | Mass Range | 100-1500 | | |
| Instrument | | Agilent 1200 LC & Agilent 6110 MSD | | |
| Software | | Agilent Chemstation Rev. B. 04.03[54] | | |
| HPLC | Column | Agilent ZORBAX 5 μm SB-Aq, 2.1 * 50 mm | | |
| | Mobile Phase | A: 0.0375% TFA in water (v/v) | | |
| | | B: 0.01875% TFA in Acetonitrile (v/v) | | |
| | Gradient | Time(min) | B(%) | Flow(mL/min) |
| | | 0.00 | 10 | 0.8 |
| | | 0.40 | 10 | 0.8 |
| | | 3.40 | 100 | 0.8 |
| | | 3.90 | 100 | 0.8 |
| | | 3.91 | 10 | 0.8 |
| | | 4.00 | 10 | 1.0 |
| | | 4.50 | 10 | 1.0 |
| | Post time(min) | Off | | |
| | Column Temp | 50° C. | | |
| | Detector | DAD (210 nm, 215 nm, 220 nm, 254 nm) | | |
| MS | Ionization source | ESI | | |
| | Drying Gas | N2 | | |
| | Drying Gas Flow | 10(L/min) | | |
| | Nebulizer Pressure | 40(psi) | | |
| | Drying Gas Temperature | 350° C. | | |
| | Capillary Voltage | 2500(V) Positive | | |
| | MS Polarity | Positive | | |
| | MS Mode | Scan | | |
| | Mass Range | 100-1500 | | |

TABLE 2

| Analytical Data | | |
|---|---|---|
| Example | $[M + H]^+$ | R.T. (min) |
| 1-01 | 649.34 | 7.67 |
| 1-02 | 637.34 | 6.71 |
| 1-03 | 706.36 | 6.26 |
| 1-04 | 659.78 | 6.18 |
| 1-05 | 639.72 | 5.43 |
| 1-06 | 599.28 | 7.56 |
| 1-07 | 597.3 | 7.25 |
| 1-08 | 619.25 | 7.19 |
| 1-09 | 661.37 | 9.77 |
| 1-10 | 645.34 | 8.64 |
| 1-11 | 635.28 | 7.30 |
| 1-12 | 682.29 | 8.26 |
| 1-13 | 685.31 | 7.47 |
| 1-14 | 633.3 | 7.83 |
| 1-15 | 681.55 | 8.00 |
| 1-16 | 633.66 | 5.12 |
| 1-17 | 631.77 | 5.06 |
| 1-18 | 609.34 | 8.29 |
| 1-19 | 611.31 | 7.67 |
| 1-20 | 613.29 | 6.92 |
| 1-21 | 639.38 | 9.77 |
| 1-22 | 611.35 | 9.09 |
| 1-23 | 659.31 | 8.32 |
| 1-24 | | |

TABLE 2-continued

| Analytical Data | | |
|---|---|---|
| Example | $[M + H]^+$ | R.T. (min) |
| 1-25 | 585.34 | 8.66 |
| 1-26 | 633.3 | 7.92 |
| 1-27 | 571.32 | 8.26 |
| 1-28 | 583.32 | 8.09 |
| 1-29 | 599.35 | 8.97 |
| 1-30 | 599.31 | 7.76 |
| 1-31 | 647.31 | 8.40 |
| 1-32 | 651.32 | 7.18 |
| 1-33 | 664.3 | 6.38 |
| 1-34 | 650.29 | 6.44 |
| 1-35 | 565.2 | 6.26 |
| 1-36 | 648.31 | 7.30 |
| 1-37 | 621.27 | 7.76 |
| 1-38 | 673.0 | 6.23 |
| 1-39 | 697.4 | 7.12 |
| 1-40 | | |
| 1-41 | 687.27 | 8.06 |
| 1-42 | | |
| 1-43 | | |
| 1-44 | 625.29 | 6.57 |
| 1-45 | 669.28 | 7.22 |
| 1-46 | 651.24 | 5.56 |
| 1-47 | 643.3 | 6.91 |
| 1-48 | 634.29 | 6.68 |
| 1-49 | 691.32 | 6.65 |
| 1-50 | 699.8 $[M + Na]^+$ | 2.64 |
| 1-51 | 637.0 | 2.29 |
| 1-52 | 675.75 | 4.64 |
| 1-53 | 611.2 | 2.177 |
| 1-54 | 637.2 | 2.812 |
| 1-55 | 679.2 | 2.891 |
| 1-56 | 637.2 | 2.791 |
| 1-57 | 597.44 | 1.845 |
| 1-58 | 563.2 | 3.040 |
| 1-59 | 549.2 | 1.947 |
| 1-60 | 551.2 | 2.919 |
| 1-61 | 603.2 | 3.261 |
| 1-62 | 507.1 | 2.666 |
| 1-63 | 623.2 | 3.014 |
| 1-64 | 651.3 | 3.21 |
| 1-65 | 651.3 | 3.21 |
| 1-66 | 680.2 | 2.649 |
| 1-67 | 644.3 | 2.615 |
| 1-68 | 691.3 | 1.043 |
| 1-69 | 591.2 | 0.846 |
| 1-70 | 669.2 | 2.379 |
| 1-71 | 569.3 | 1.906 |
| 1-72 | 616.3 | 2.277 |
| 1-73 | 630.3 | 2.380 |
| 1-74 | 666.3 | 3.410 |
| 1-75 | 656.3 | 2.153 |
| 1-76 | 618.3 | 2.249 |
| 1-77 | 662.2 | 2.297 |
| 1-78 | 646.3 | 1.697 |
| 1-79 | 692.3 | 1.706 |
| 1-80 | 628.3 | 2.420 |
| 1-81 | 2.904 | 623.2 |
| 1-82 | 630.4 | 2.857 |
| 1-83 | 2.370 | 658.3 |
| 1-84 | 630.3 | 2.681 |
| 1-85 | 630.3 | 2.683 |
| 1-86 | 660.3 | 2.313 |
| 1-87 | 696.2 | 2.313 |
| 1-88 | 668.3 | 1.673 |
| 1-89 | 549.3 | 2.316 |
| 1-90 | 565.3 | 2.227 |
| 1-91 | 589.3 | 2.323 |
| 2-01 | 587.2 | 2.144 |
| 2-02 | 663.3 | 3.360 |
| 2-03 | 619.3 | 3.076 |
| 2-04 | 619.3 | 3.175 |
| 2-05 | 663.3 | 3.36 |
| 2-06 | 587.3 | 1.999 |
| 2-07 | 720.3 | 2.244 |
| 2-08 | 720.3 | 2.153 |
| 2-09 | 782.3 | 2.484 |

TABLE 2-continued

| Analytical Data | | |
|---|---|---|
| Example | [M + H]+ | R.T. (min) |
| 2-10 | 782.3 | 2.433 |
| 3-01 | 575.44 | 1.96 |
| 3-02 | 577.45 | 1.94 |
| 3-03 | 599.45 | 2.04 |
| 3-04 | 603.5 | 2.202 |
| 3-05 | 455.34 | 2.06 |
| 3-06 | 508.3 | 2.329 |
| 3-07 | 597.2 | 2.014 |
| 3-08 | 589.2 | 2.131 |
| 3-09 | 605.2 | 2.560 |
| 3-10 | 585.3 | 2.591 |
| 3-11 | 615.3 | 2.385 |
| 3-12 | 613.3 | 2.207 |
| 3-13 | 614.1 | 2.500 |
| 3-14 | 589.2 | 1.833 |
| 3-15 | 629.2 | 2.681 |
| 3-16 | 602.2 | 1.839 |
| 3-17 | 584.4 | 2.201 |
| 3-18 | 6293.3 | 2.298 |
| 3-19 | 648.3 | 1.624 |
| 3-20 | 598.3 | 2.104 |
| 3-21 | 589.4 | 1.501 |
| 3-22 | 589.41 | 1.487 |
| 3-23 | 614.4 | 1.976 |
| 3-24 | 602.3 | 0.645 |
| 3-25 | 515.3 | 2.113 |
| 3-26 | 555.3 | 2.156 |
| 3-27 | 515.3 | 1.402 |
| 3-28 | 607.3 | 2.738 |
| 3-29 | 623.3 | 2.525 |
| 3-30 | 623.3 | 2.525 |
| 3-31 | 531.3 | 1.874 |
| 3-32 | 531.3 | 1.849 |
| 3-33 | 617.3 | 2.758 |
| 3-34 | 558.3 | 1.262 |
| 3-35 | 591.2 | 2.114 |
| 3-36 | 567.3 | 1.639 |
| 3-37 | 529.3 | 2.132 |
| 3-38 | 529.3 | 2.148 |
| 3-39 | 524.3 | 2.730 |
| 3-40 | 543.3 | 1.654 |
| 3-41 | 564.3 | 2.802 |
| 3-42 | 632.4 | 2.215 |
| 3-43 | 549.3 | 2.492 |
| 3-44 | 643.3 | 2.807 |
| 3-45-A | 553.3 | 2.647 |
| 3-45-B | 553.3 | 2.638 |
| 3-46-A | 593.4 | 2.238 |
| 3-46-B | 593.4 | 2.224 |
| 4-01 | 461.1 | 2.301 |
| 4-02 | 461.1 | 2.276 |
| 4-03 | 639.2 | 2.639 |
| 4-04 | 639.2 | 2.687 |
| 4-05 | 547.47 | 2.22 |
| 4-06 | 549.57 | 2.28 |
| 4-07 | 535.47 | 2.18 |
| 4-08 | 625.63 | 2.51 |
| 4-09 | 576.55 | 2.33 |
| 4-10 | 486.37 | 2.19 |
| 4-11 | 473.48 | 2.18 |
| 4-12 | 593.46 | 2.40 |
| 4-13 | 557.53 | 2.35 |
| 4-14 | 625.59 | 2.50 |
| 4-15 | 551.3 | 2.983 |
| 4-16 | 595.3 | 3.122 |
| 4-17 | 573.1 | 2.972 |

Example 67—$IC_{50}$ Determination

Experiments to determine $IC_{50}$ values against β5i and β5c for compounds were carried out in 96-well plates. In brief, 1 μL of compound in a 3× series dilution in DMSO at concentration ranging from 100 μM-0.0017 μM were spotted to the bottom of a black 96-well plate with solid bottom. 100 μL of reaction buffer (20 mM HEPES, 0.5 mM EDTA, pH7.5, 0.1% BSA) containing enzyme (final concentration was 0.2 nM for c-20S, and 0.4 nM for i-20S) and substrate (25 μM for suc-LLVY-AMC for β5c and 15 μM for Ac-ANW-AMC) were dispensed into each well, and the plate was then spun at 1000× rpm for 1 minute and then shaked on a shaker for 1 minute. Time course of the hydrolysis of each well was followed by recording the fluorescence of product AMC (Ex 360 nm and Em 460 nm) on a SpectraMax M5 plate reader for 1.5-2 hours. Initial reaction velocity of each well was fit to a dose-dependent inhibition equation using PRISM to determine the $IC_{50}$. $IC_{50}$s were determined only for β5i and β5c (Table 3). SDS was used as activator for both enzymes at concentration 0.0200.

TABLE 3

| $IC_{50}$ values | | | |
|---|---|---|---|
| Compound Number | Structure | IC50 (μM) hu c-20S | IC50 (μM) hu i-20S |
| 1-01 | 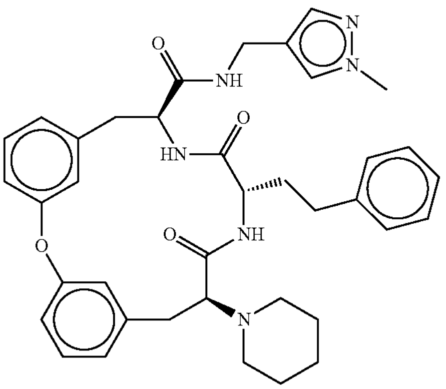 | 0.4020 | |

TABLE 3-continued
| IC50 values | | | |
|---|---|---|---|
| Compound Number | Structure | IC50 (μM) hu c-20S | IC50 (μM) hu i-20S |
| 1-02 | 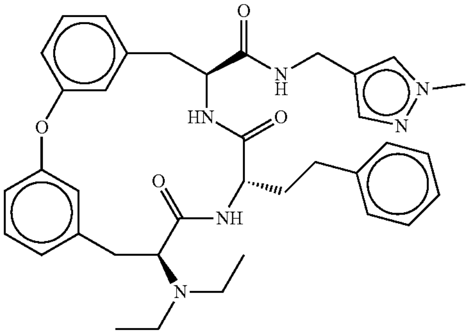 | 0.5500 | |
| 1-03 | 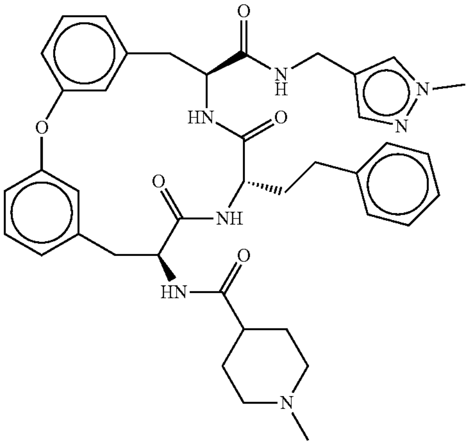 | 1.0000 | |
| 1-04 | 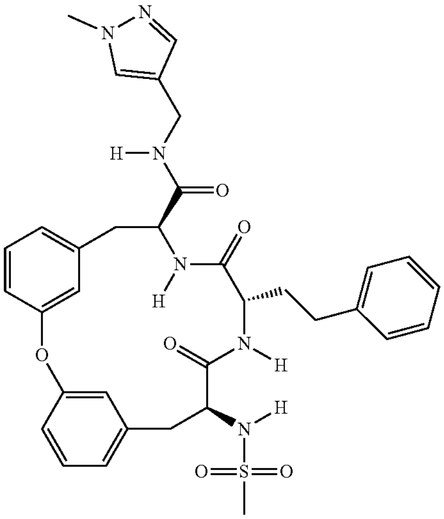 [SMILES: Cn1cc(CNC(=O)[C@@H]2Cc3cccc(c3)Oc3cccc(c3)C[C@H](NS(C)(=O)=O)C(=O)N[C@@H](CCc3ccccc3)C(=O)N2)cn1] | >100 | 7.22 |

TABLE 3-continued
| IC$_{50}$ values | | | |
|---|---|---|---|
| Compound Number | Structure | IC50 (μM) hu c-20S | IC50 (μM) hu i-20S |
| 1-05 | 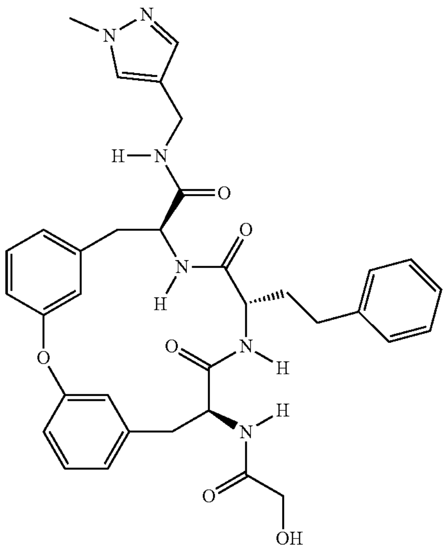 [SMILES: Cn1cc(CNC(=O)[C@@H]2Cc3cccc(c3)Oc3cccc(c3)C[C@H](NC(=O)CO)C(=O)N[C@@H](CCc3ccccc3)C(=O)N2)cn1] | >100 | 14.770 |
| 1-06 | 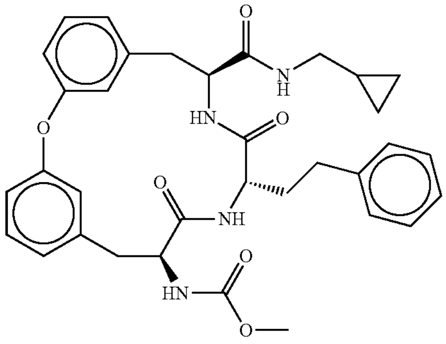 | 0.5420 | |
| 1-07 | 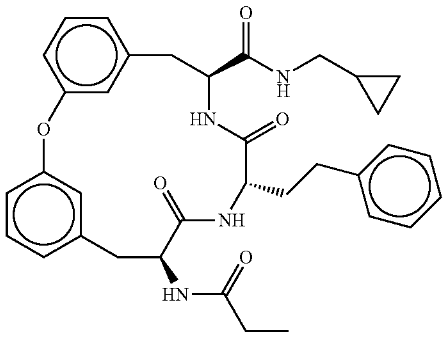 | 1.1200 | |

TABLE 3-continued
| IC$_{50}$ values | | | |
|---|---|---|---|
| Compound Number | Structure | IC50 (μM) hu c-20S | IC50 (μM) hu i-20S |
| 1-08 | 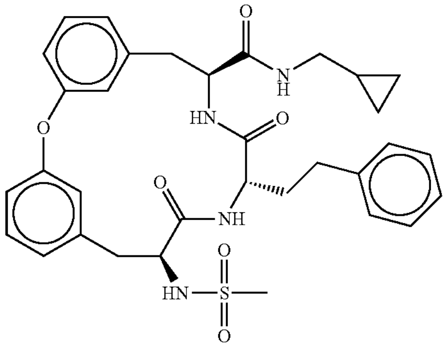 | 1.7800 | |
| 1-09 | 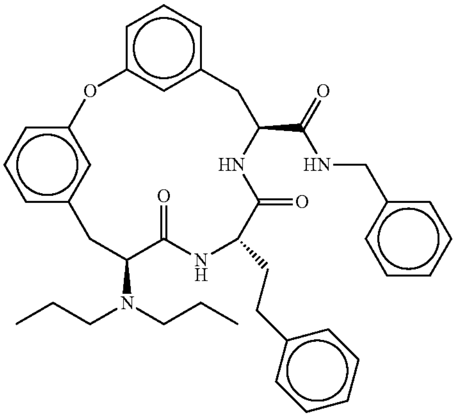 | 0.5030 | |
| 1-10 | 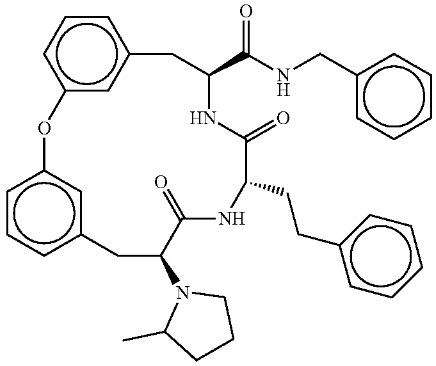 | 1.3000 | |
| 1-11 | 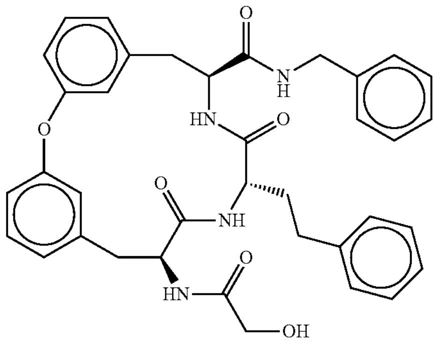 | 1.9270 | |

TABLE 3-continued
| IC$_{50}$ values | | | |
|---|---|---|---|
| Compound Number | Structure | IC50 (μM) hu c-20S | IC50 (μM) hu i-20S |
| 1-12 | 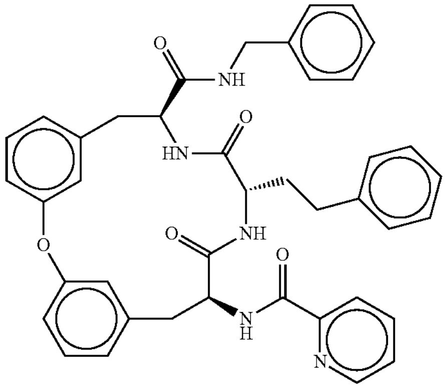 | 3.2000 | |
| 1-13 | 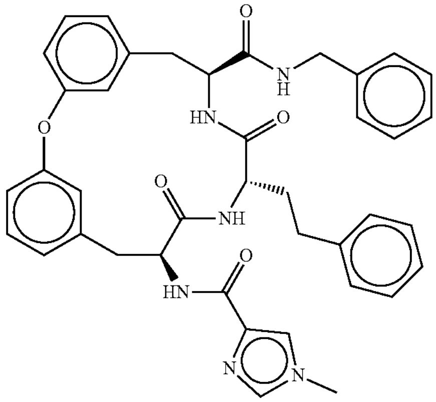 | 3.5200 | |
| 1-14 | 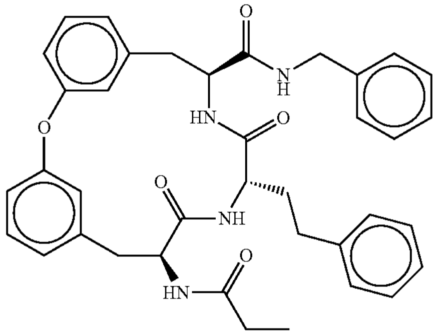 | 4.0100 | |

TABLE 3-continued
| IC$_{50}$ values | | | |
|---|---|---|---|
| Compound Number | Structure | IC50 (μM) hu c-20S | IC50 (μM) hu i-20S |
| 1-15 | 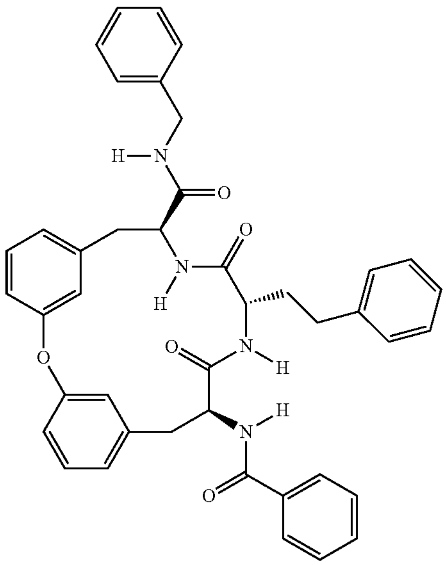 [SMILES: O=C(N[C@H]1Cc2cccc(c2)Oc2cccc(c2)C[C@@H](C(=O)NCc2ccccc2)NC(=O)[C@H](CCc2ccccc2)NC1=O)c1ccccc1] | 100 | |
| 1-16 | 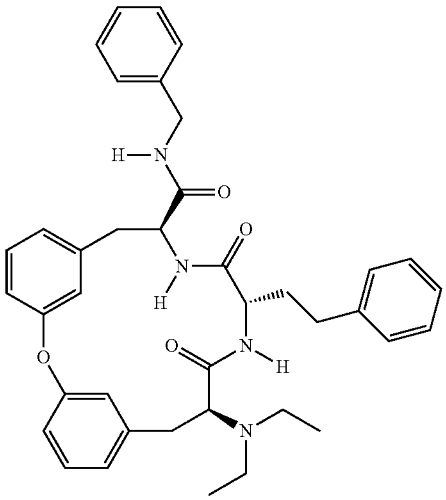 [SMILES: CCN(CC)[C@H]1Cc2cccc(c2)Oc2cccc(c2)C[C@@H](C(=O)NCc2ccccc2)NC(=O)[C@H](CCc2ccccc2)NC1=O] | 22.85 | 100.000 |
| 1-17 | 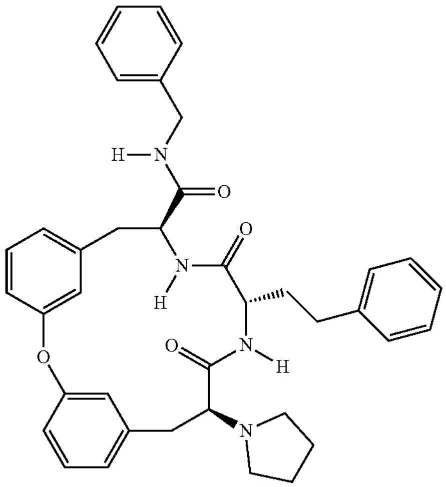 [SMILES: O=C(NCc1ccccc1)[C@@H]1Cc2cccc(c2)Oc2cccc(c2)C[C@H](N2CCCC2)C(=O)N[C@@H](CCc2ccccc2)C(=O)N1] | 42.5 | 6.601 |

TABLE 3-continued
| IC$_{50}$ values | | | |
|---|---|---|---|
| Compound Number | Structure | IC50 (μM) hu c-20S | IC50 (μM) hu i-20S |
| 1-18 | 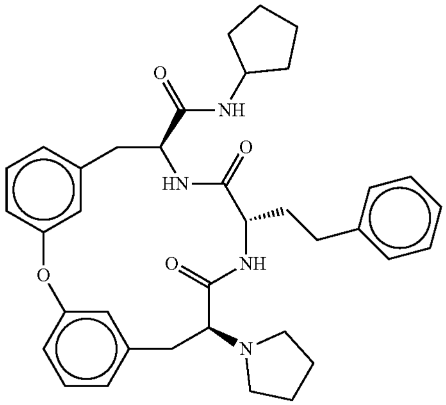 | 0.5720 | |
| 1-19 | 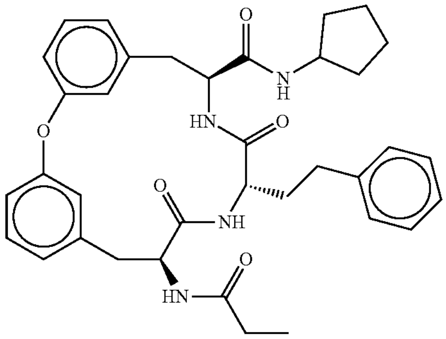 | 2.8000 | |
| 1-20 | 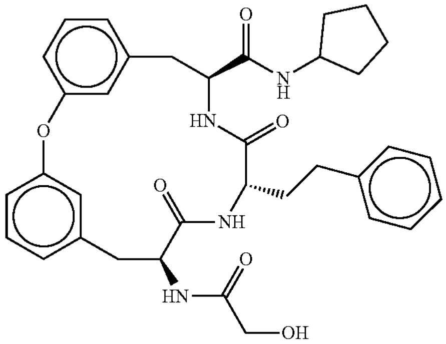 | 3.2500 | |
| 1-21 | 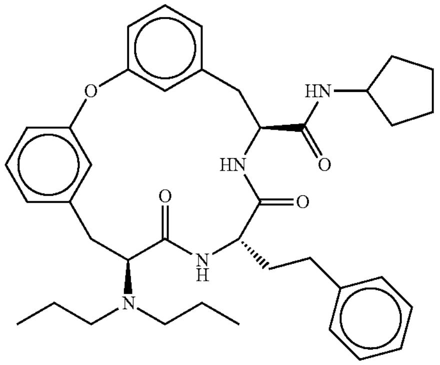 | 3.4000 | |

TABLE 3-continued
| IC$_{50}$ values | | | |
|---|---|---|---|
| Compound Number | Structure | IC50 (μM) hu c-20S | IC50 (μM) hu i-20S |
| 1-22 | 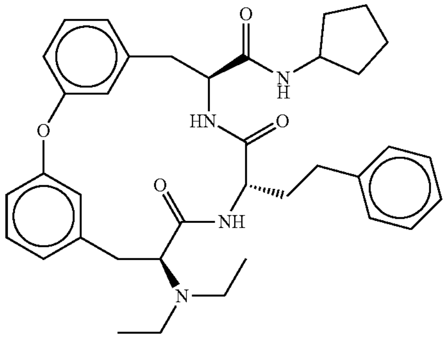 | 41.6300 | |
| 1-23 | 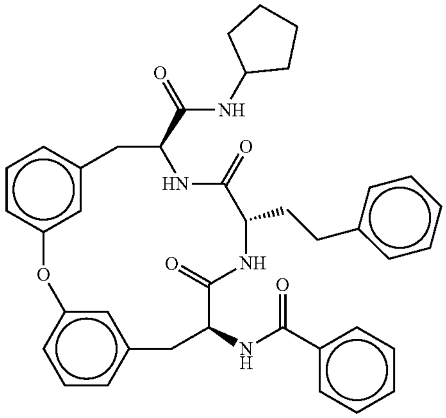 | 6.2100 | |
| 1-24 | 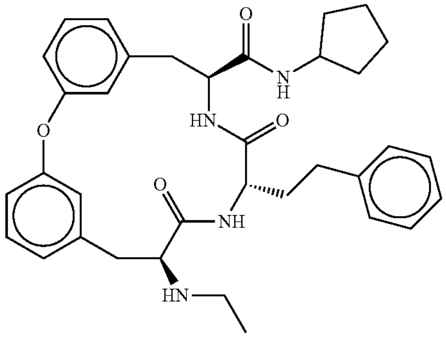 | 100.0000 | |
| 1-25 | 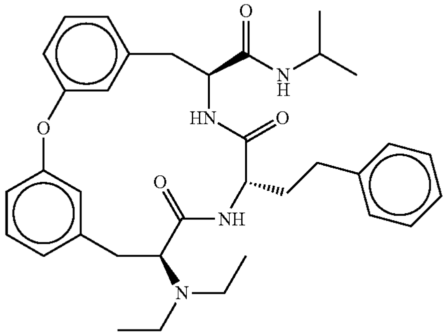 | 1.6300 | |

TABLE 3-continued
| IC$_{50}$ values | | | |
|---|---|---|---|
| Compound Number | Structure | IC50 (μM) hu c-20S | IC50 (μM) hu i-20S |
| 1-26 | 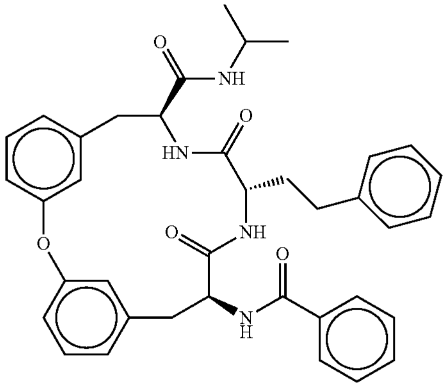 | 6.9300 | |
| 1-27 | 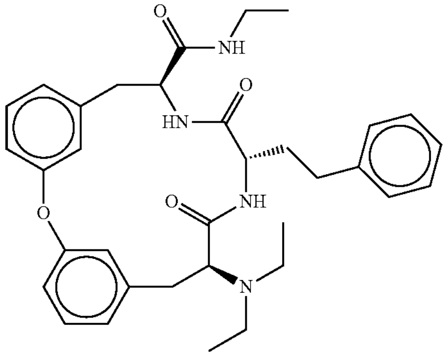 | 1.1400 | |
| 1-28 | 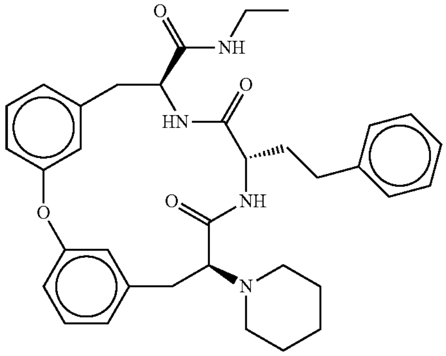 | 2.4700 | |
| 1-29 | 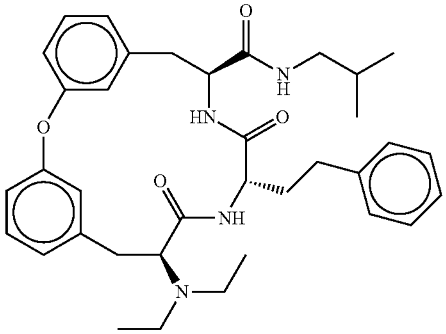 | 2.2000 | |

TABLE 3-continued
| IC$_{50}$ values | | | |
|---|---|---|---|
| Compound Number | Structure | IC50 (μM) hu c-20S | IC50 (μM) hu i-20S |
| 1-30 | 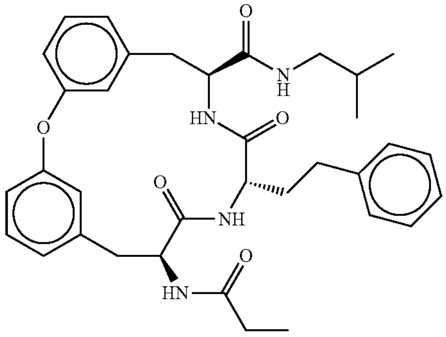 | 4.2100 | |
| 1-31 | 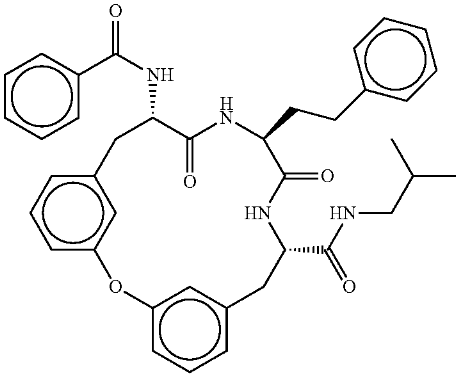 | 5.0000 | |
| 1-32 | 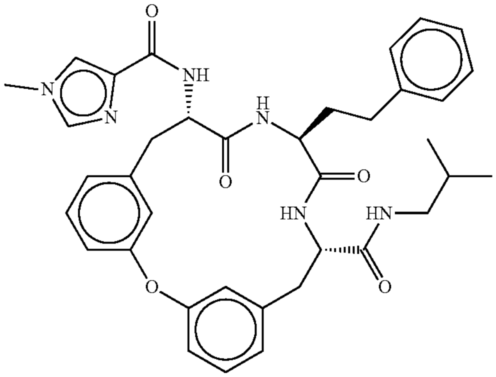 | 8.8600 | |
| 1-33 | 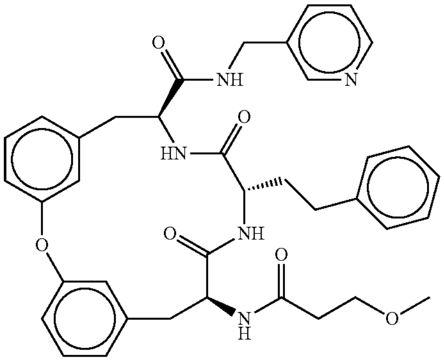 | 2.2500 | |

TABLE 3-continued
IC$_{50}$ values
| Compound Number | Structure | IC50 (μM) hu c-20S | IC50 (μM) hu i-20S |
|---|---|---|---|
| 1-34 | 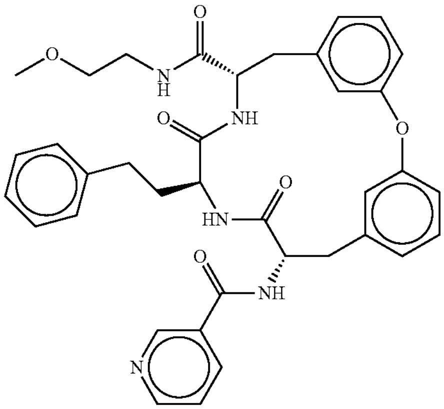 | 2.8500 | |
| 1-35 | 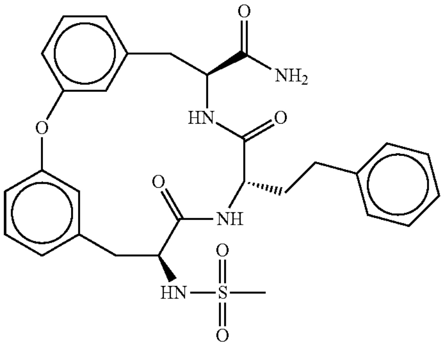 | 3.0000 | |
| 1-36 | 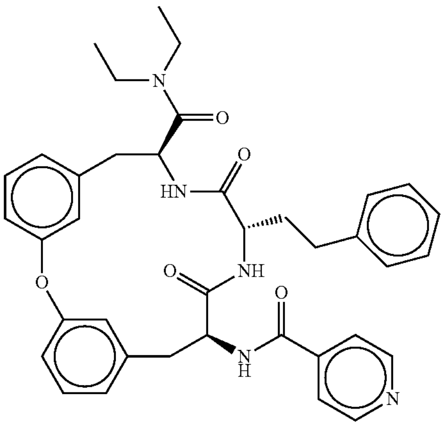 | 3.0400 | |
| 1-37 | 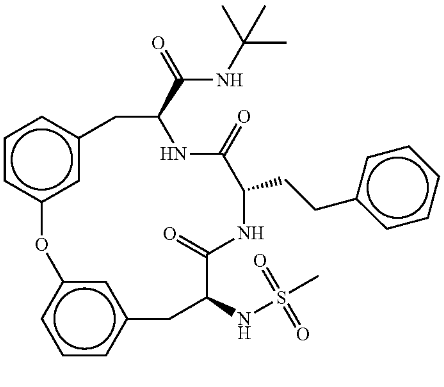 | 3.6000 | >100 |

TABLE 3-continued
| IC$_{50}$ values | | | |
|---|---|---|---|
| Compound Number | Structure | IC50 (μM) hu c-20S | IC50 (μM) hu i-20S |
| 1-38 | 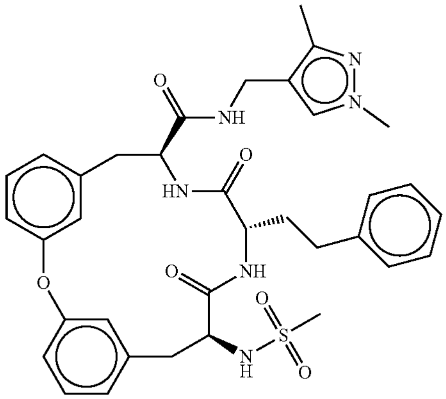 | 4.2900 | |
| 1-39 | 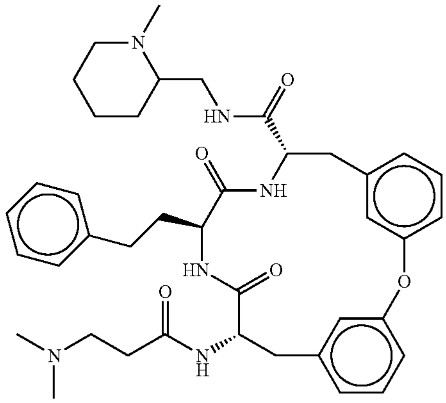 | 4.5700 | |
| 1-40 | 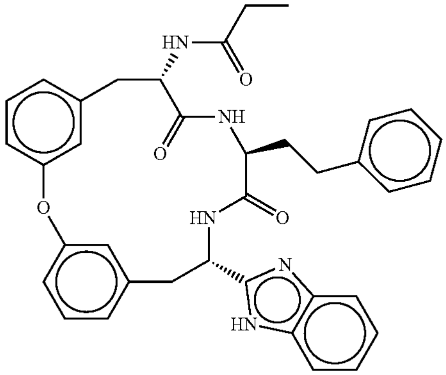 | 4.8500 | |

TABLE 3-continued
| IC$_{50}$ values | | | |
|---|---|---|---|
| Compound Number | Structure | IC50 (μM) hu c-20S | IC50 (μM) hu i-20S |
| 1-41 | 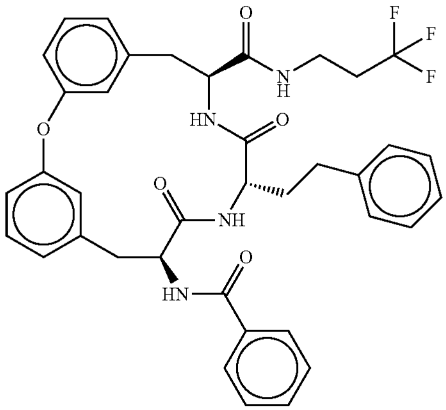 | 5.7000 | |
| 1-42 | 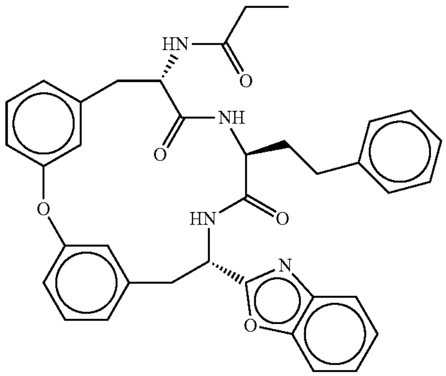 | 5.9300 | |
| 1-43 | 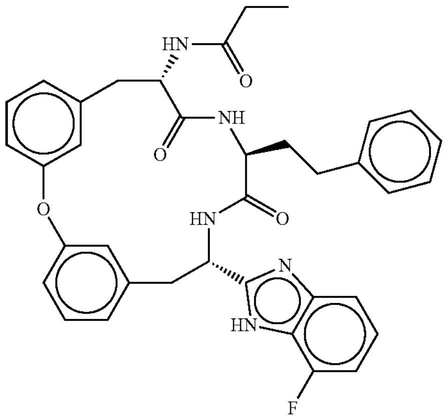 | 6.0800 | |

TABLE 3-continued
| IC$_{50}$ values | | | |
|---|---|---|---|
| Compound Number | Structure | IC50 (μM) hu c-20S | IC50 (μM) hu i-20S |
| 1-44 | 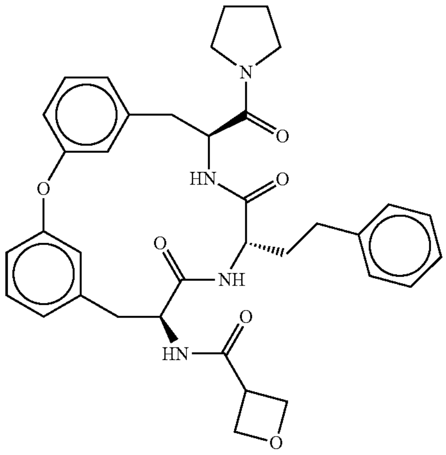 | 7.5200 | |
| 1-45 | 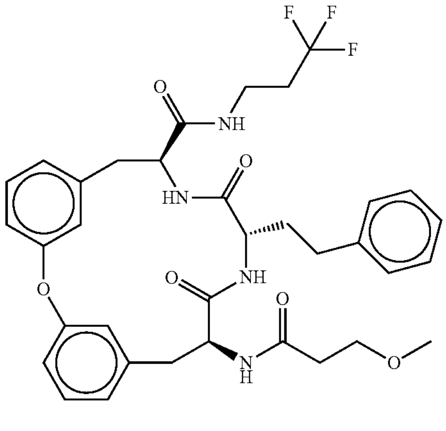 | 7.7000 | |
| 1-46 | 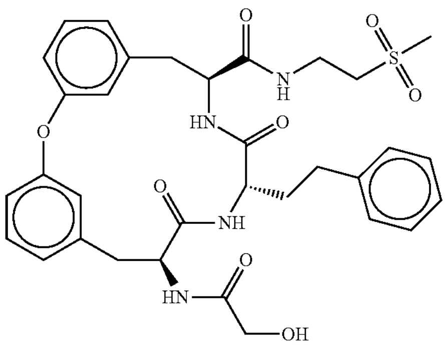 | 9.5000 | |

TABLE 3-continued
| IC₅₀ values | | | |
|---|---|---|---|
| Compound Number | Structure | IC50 (μM) hu c-20S | IC50 (μM) hu i-20S |
| 1-47 | 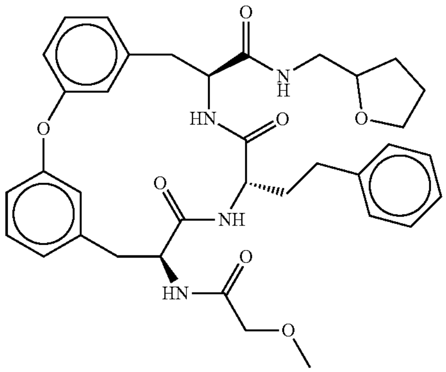 | 9.7000 | |
| 1-48 | 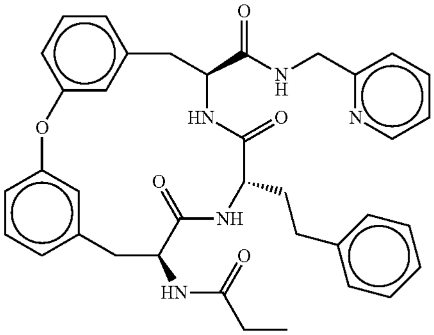 | 10.1900 | |
| 1-49 | 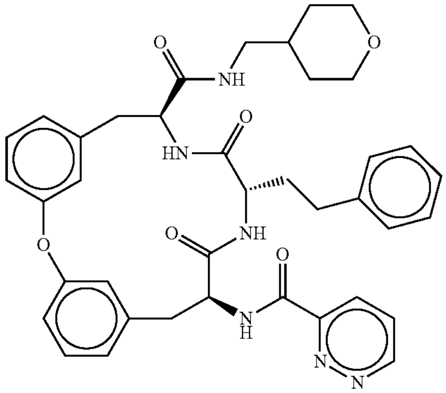 | 11.8600 | |
| 1-50 | 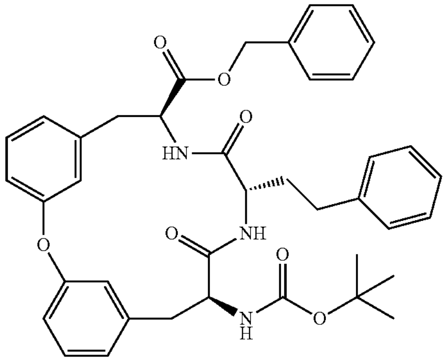 [SMILES: CC(C)(C)OC(=O)N[C@H]1Cc2cccc(c2)Oc2cccc(c2)C[C@@H](C(=O)OCc2ccccc2)NC(=O)[C@H](CCc2ccccc2)NC1=O] | >100 | >100 |

TABLE 3-continued
| IC$_{50}$ values | | | |
|---|---|---|---|
| Compound Number | Structure | IC50 (μM) hu c-20S | IC50 (μM) hu i-20S |
| 1-51 | 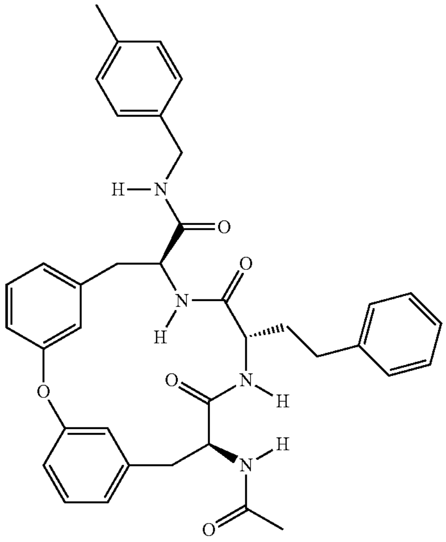 [SMILES: CC(=O)N[C@H]1Cc2cccc(c2)Oc2cccc(c2)C[C@@H](C(=O)NCc2ccc(C)cc2)NC(=O)[C@H](CCc2ccccc2)NC1=O] | 6.7 | |
| 1-52 | 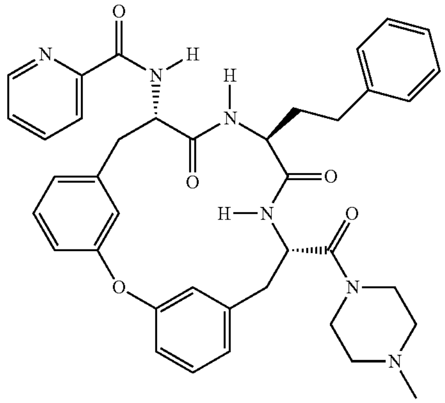 [SMILES: CN1CCN(C(=O)[C@@H]2Cc3cccc(c3)Oc3cccc(c3)C[C@H](NC(=O)c3ccccn3)C(=O)N[C@@H](CCc3ccccc3)C(=O)N2)CC1] | 30.74 | 33.9 |
| 1-53 | 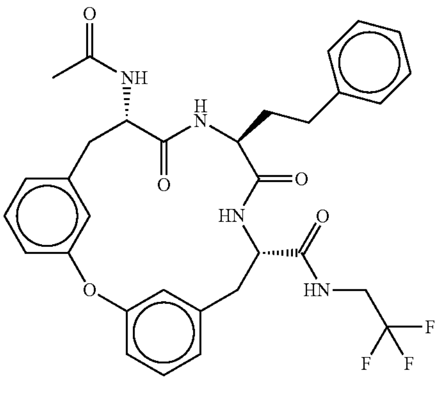 | >100 | >100 |

TABLE 3-continued
| IC$_{50}$ values | | | |
|---|---|---|---|
| Compound Number | Structure | IC50 (μM) hu c-20S | IC50 (μM) hu i-20S |
| 1-54 | 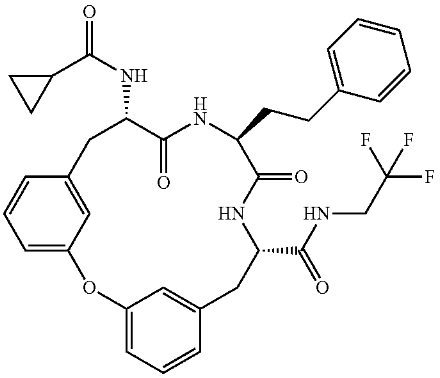 [SMILES: O=C(N[C@H]1Cc2cccc(c2)Oc2cccc(c2)C[C@@H](C(=O)NCC(F)(F)F)NC(=O)[C@H](CCc2ccccc2)NC1=O)C1CC1] | >100 | >100 |
| 1-55 | 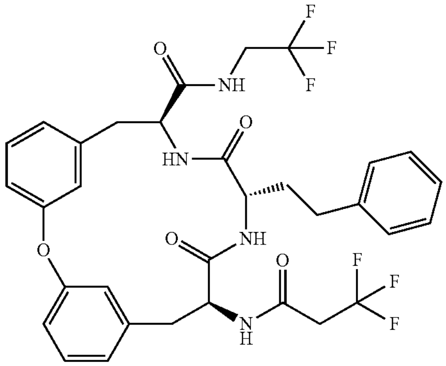 [SMILES: O=C(CC(F)(F)F)N[C@H]1Cc2cccc(c2)Oc2cccc(c2)C[C@@H](C(=O)NCC(F)(F)F)NC(=O)[C@H](CCc2ccccc2)NC1=O] | >100 | >100 |
| 1-56 | 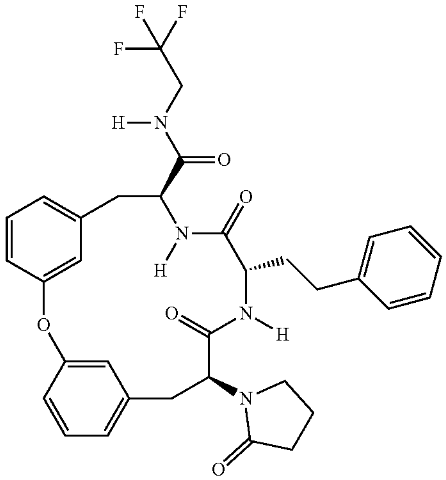 [SMILES: O=C(NCC(F)(F)F)[C@@H]1Cc2cccc(c2)Oc2cccc(c2)C[C@H](N2CCCC2=O)C(=O)N[C@@H](CCc2ccccc2)C(=O)N1] | 0.43 | 33.9 |

TABLE 3-continued
| IC$_{50}$ values | | | |
|---|---|---|---|
| Compound Number | Structure | IC50 (μM) hu c-20S | IC50 (μM) hu i-20S |
| 1-57 | 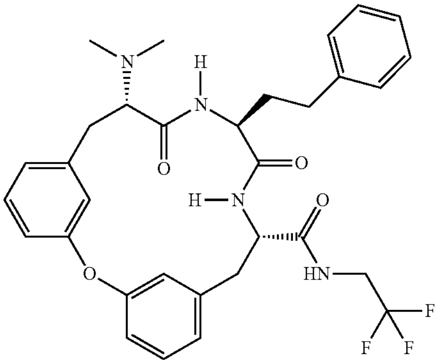 [SMILES: CN(C)[C@H]1Cc2cccc(c2)Oc2cccc(c2)C[C@@H](C(=O)NCC(F)(F)F)NC(=O)[C@H](CCc2ccccc2)NC1=O] | 1.1 | 18.670 |
| 1-58 | 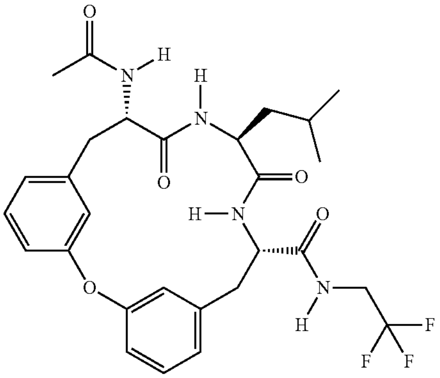 [SMILES: CC(=O)N[C@H]1Cc2cccc(c2)Oc2cccc(c2)C[C@@H](C(=O)NCC(F)(F)F)NC(=O)[C@H](CC(C)C)NC1=O] | 32% @ 33.3 uM | 31% @ 33.3 uM |
| 1-59 | 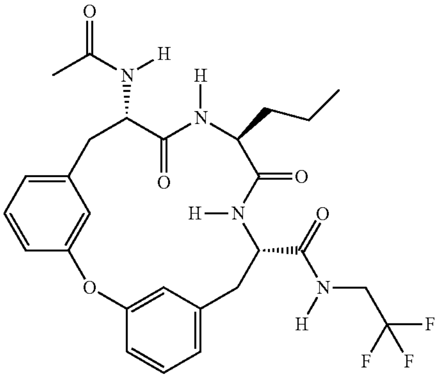 [SMILES: CCC[C@@H]1NC(=O)[C@@H](NC(C)=O)Cc2cccc(c2)Oc2cccc(c2)C[C@@H](C(=O)NCC(F)(F)F)NC1=O] | >100 | 29.73 |
| 1-60 | 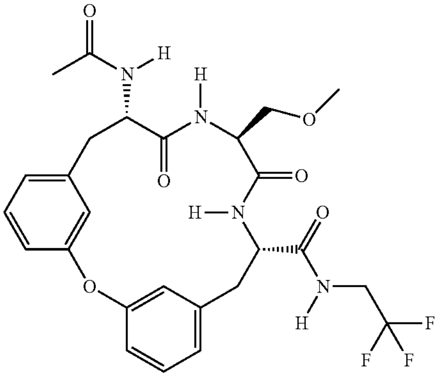 [SMILES: COC[C@@H]1NC(=O)[C@@H](NC(C)=O)Cc2cccc(c2)Oc2cccc(c2)C[C@@H](C(=O)NCC(F)(F)F)NC1=O] | >100 | >100 |

TABLE 3-continued
| IC$_{50}$ values | | | |
|---|---|---|---|
| Compound Number | Structure | IC50 (μM) hu c-20S | IC50 (μM) hu i-20S |
| 1-61 | 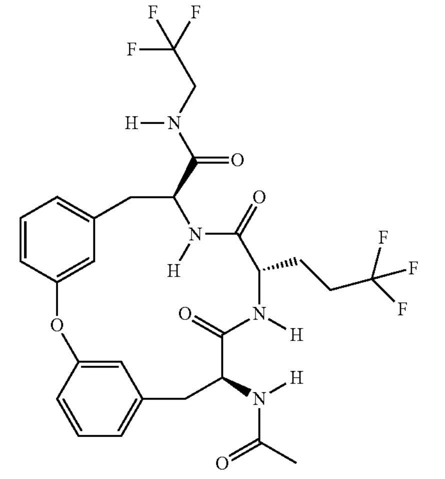 [SMILES: CC(=O)N[C@H]1Cc2cccc(c2)Oc2cccc(c2)C[C@@H](C(=O)NCC(F)(F)F)NC(=O)[C@H](CCC(F)(F)F)NC1=O] | >100 | >100 |
| 1-62 | 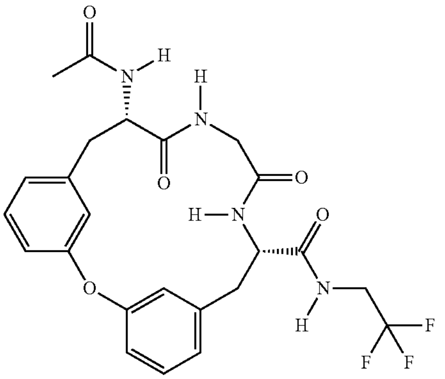 [SMILES: CC(=O)N[C@H]1Cc2cccc(c2)Oc2cccc(c2)C[C@@H](C(=O)NCC(F)(F)F)NC(=O)CNC1=O] | 3.7 | >100 |
| 1-63 | 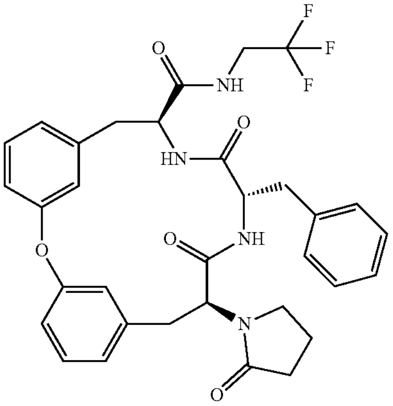 [SMILES: O=C(NCC(F)(F)F)[C@@H]1Cc2cccc(c2)Oc2cccc(c2)C[C@H](N2CCCC2=O)C(=O)N[C@@H](Cc2ccccc2)C(=O)N1] | 2.87 | 7.2 |

TABLE 3-continued
| IC$_{50}$ values | | | |
|---|---|---|---|
| Compound Number | Structure | IC50 (μM) hu c-20S | IC50 (μM) hu i-20S |
| 1-64 | 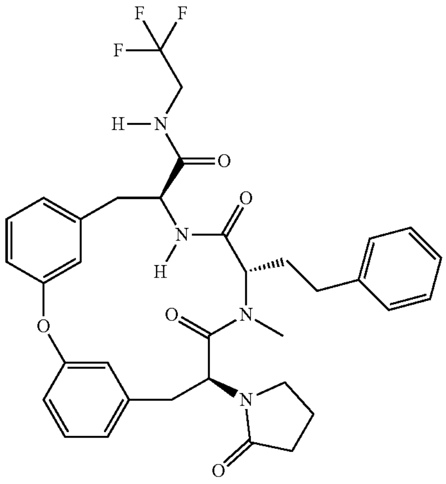 [SMILES: CN1C(=O)[C@@H](N2CCCC2=O)Cc2cccc(c2)Oc2cccc(c2)C[C@@H](C(=O)NCC(F)(F)F)NC(=O)[C@@H]1CCc1ccccc1] | >100 | 2.72 |
| 1-65 | 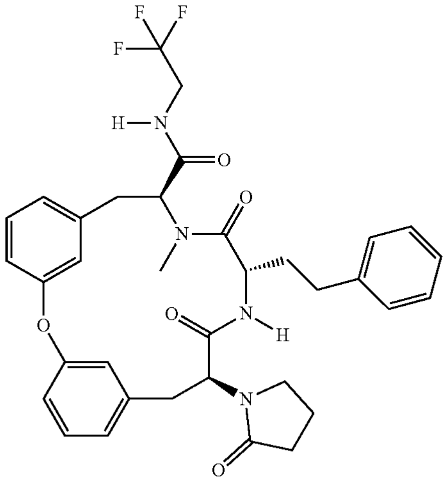 [SMILES: CN1C(=O)[C@H](CCc2ccccc2)NC(=O)[C@@H](N2CCCC2=O)Cc2cccc(c2)Oc2cccc(c2)C[C@H]1C(=O)NCC(F)(F)F] | 40% @ 33.3 μM | 45.1 |
| 1-66 | 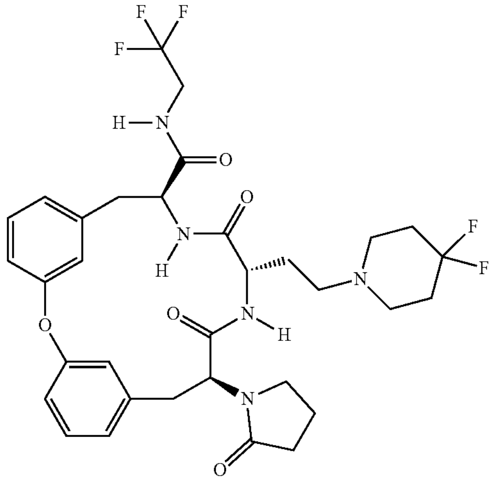 [SMILES: O=C(NCC(F)(F)F)[C@@H]1Cc2cccc(c2)Oc2cccc(c2)C[C@H](N2CCCC2=O)C(=O)N[C@@H](CCN2CCC(F)(F)CC2)C(=O)N1] | 0.14 | >100 |

TABLE 3-continued
| IC$_{50}$ values | | | |
|---|---|---|---|
| Compound Number | Structure | IC50 (μM) hu c-20S | IC50 (μM) hu i-20S |
| 1-67 | 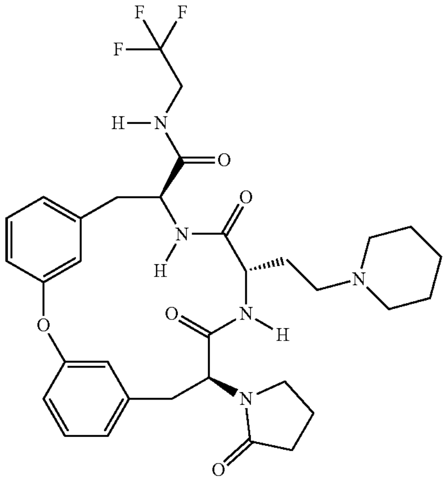 [SMILES: O=C(NCC(F)(F)F)[C@@H]1Cc2cccc(c2)Oc2cccc(c2)C[C@H](N2CCCC2=O)C(=O)N[C@@H](CCN2CCCCC2)C(=O)N1] | 0.57 | 3.65 |
| 1-68 | 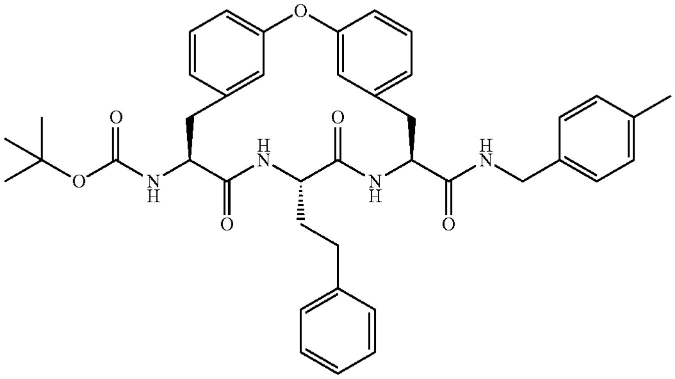 [SMILES: Cc1ccc(CNC(=O)[C@@H]2Cc3cccc(c3)Oc3cccc(c3)C[C@H](NC(=O)OC(C)(C)C)C(=O)N[C@@H](CCc3ccccc3)C(=O)N2)cc1] | 17.93 | >100 |
| 1-69 | 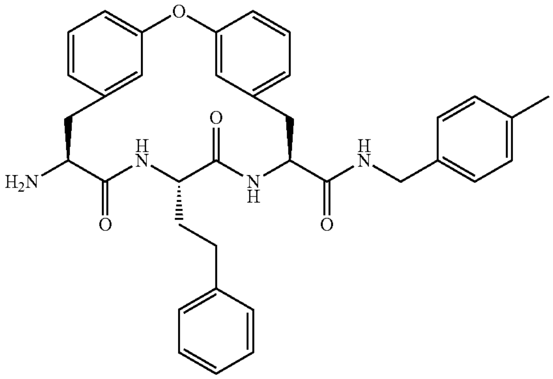 [SMILES: Cc1ccc(CNC(=O)[C@@H]2Cc3cccc(c3)Oc3cccc(c3)C[C@H](N)C(=O)N[C@@H](CCc3ccccc3)C(=O)N2)cc1] | >100 | >100 |

TABLE 3-continued
| IC$_{50}$ values | | | |
|---|---|---|---|
| Compound Number | Structure | IC50 (μM) hu c-20S | IC50 (μM) hu i-20S |
| 1-70 | 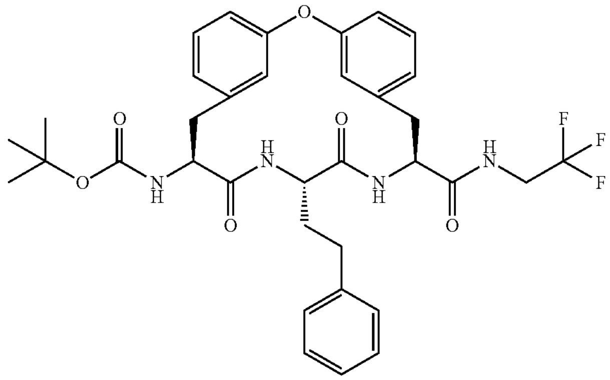 [SMILES: CC(C)(C)OC(=O)N[C@H]1Cc2cccc(c2)Oc2cccc(c2)C[C@@H](C(=O)NCC(F)(F)F)NC(=O)[C@H](CCc2ccccc2)NC1=O] | NT | NT |
| 1-71 | 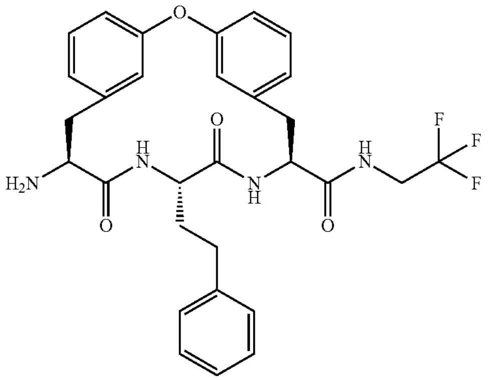 [SMILES: N[C@H]1Cc2cccc(c2)Oc2cccc(c2)C[C@@H](C(=O)NCC(F)(F)F)NC(=O)[C@H](CCc2ccccc2)NC1=O] | NT | NT |
| 1-72 | 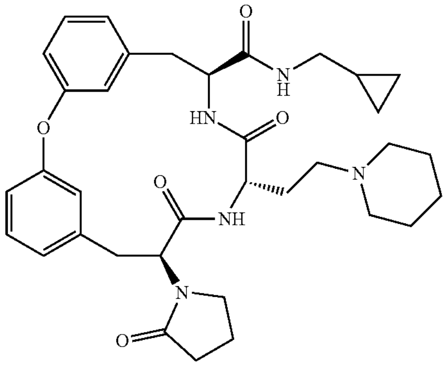 [SMILES: O=C(NCC1CC1)[C@@H]1Cc2cccc(c2)Oc2cccc(c2)C[C@H](N2CCCC2=O)C(=O)N[C@@H](CCN2CCCCC2)C(=O)N1] | 10% @ 33.3 μM | 30% @ 33.3 μM |
| 1-73 | 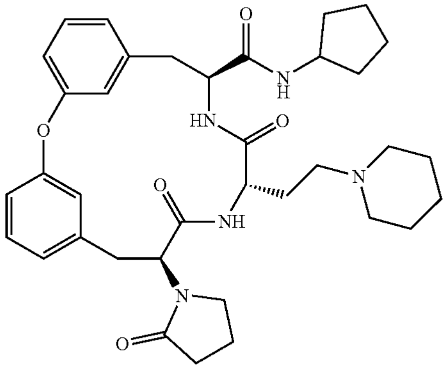 [SMILES: O=C(NC1CCCC1)[C@@H]1Cc2cccc(c2)Oc2cccc(c2)C[C@H](N2CCCC2=O)C(=O)N[C@@H](CCN2CCCCC2)C(=O)N1] | 26.9 | 30% @ 33.3 μM |

TABLE 3-continued
| IC$_{50}$ values | | | |
|---|---|---|---|
| Compound Number | Structure | IC50 (μM) hu c-20S | IC50 (μM) hu i-20S |
| 1-74 | 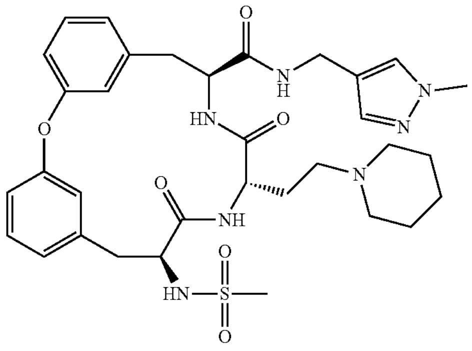 [SMILES: Cn1cc(CNC(=O)[C@@H]2Cc3cccc(c3)Oc3cccc(c3)C[C@H](NS(C)(=O)=O)C(=O)N[C@@H](CCN3CCCCC3)C(=O)N2)cn1] | 18% @ 33.3 μM | 9% @ 33.3 μM |
| 1-75 | 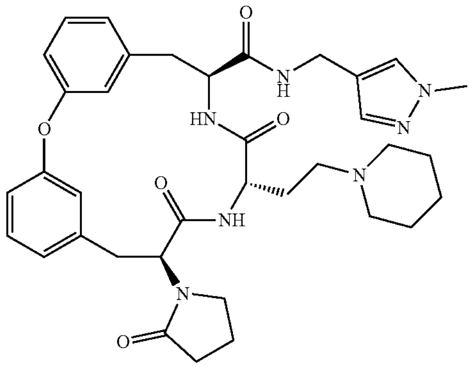 [SMILES: Cn1cc(CNC(=O)[C@@H]2Cc3cccc(c3)Oc3cccc(c3)C[C@H](N3CCCC3=O)C(=O)N[C@@H](CCN3CCCCC3)C(=O)N2)cn1] | 81.6 | 30% @ 33.3 μM |
| 1-76 | 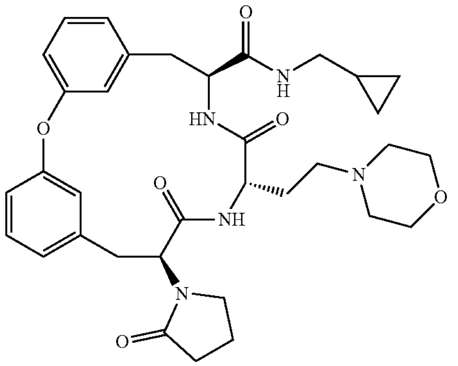 [SMILES: O=C(NCC1CC1)[C@@H]1Cc2cccc(c2)Oc2cccc(c2)C[C@H](N2CCCC2=O)C(=O)N[C@@H](CCN2CCOCC2)C(=O)N1] | 10.6 | 21% @ 33.3 μM |
| 1-77 | 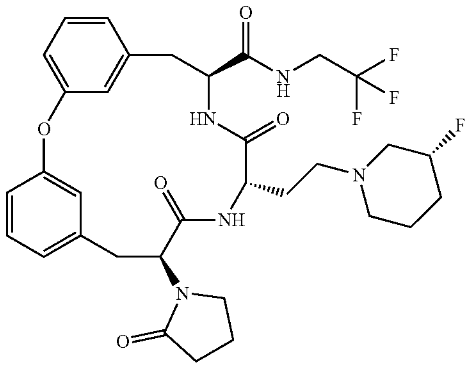 [SMILES: O=C(NCC(F)(F)F)[C@@H]1Cc2cccc(c2)Oc2cccc(c2)C[C@H](N2CCCC2=O)C(=O)N[C@@H](CCN2CCC[C@@H](F)C2)C(=O)N1] | 17 | 53.7 |

TABLE 3-continued
| IC$_{50}$ values | | | |
|---|---|---|---|
| Compound Number | Structure | IC50 (μM) hu c-20S | IC50 (μM) hu i-20S |
| 1-78 | 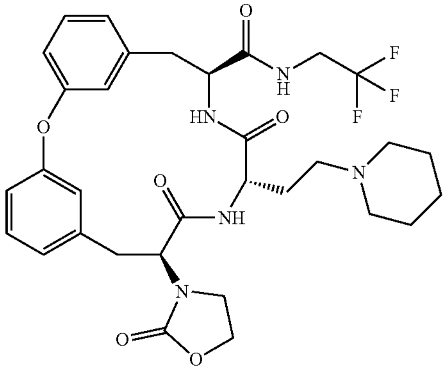 [SMILES: O=C(NCC(F)(F)F)[C@@H]1Cc2cccc(c2)Oc2cccc(c2)C[C@H](N2CCOC2=O)C(=O)N[C@@H](CCN2CCCCC2)C(=O)N1] | 23 | 22.3 |
| 1-79 | 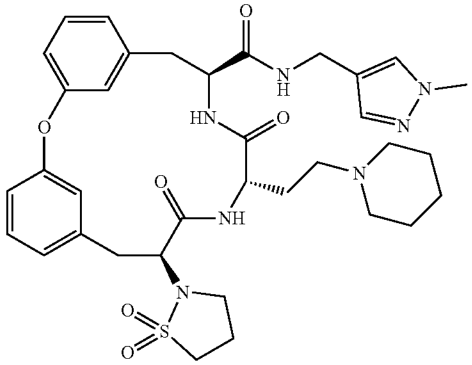 [SMILES: Cn1cc(CNC(=O)[C@@H]2Cc3cccc(c3)Oc3cccc(c3)C[C@H](N3CCCS3(=O)=O)C(=O)N[C@@H](CCN3CCCCC3)C(=O)N2)cn1] | 19% @ 33.3 μM | 59.8 |
| 1-80 | 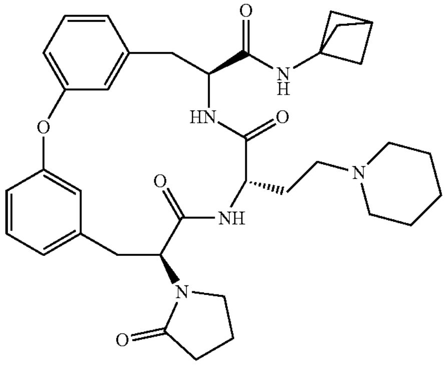 [SMILES: O=C(NC12CC(C1)C2)[C@@H]1Cc2cccc(c2)Oc2cccc(c2)C[C@H](N2CCCC2=O)C(=O)N[C@@H](CCN2CCCCC2)C(=O)N1] | 0% @ 33.3 μM | 26% @ 33.3 μM |
| 1-81 | 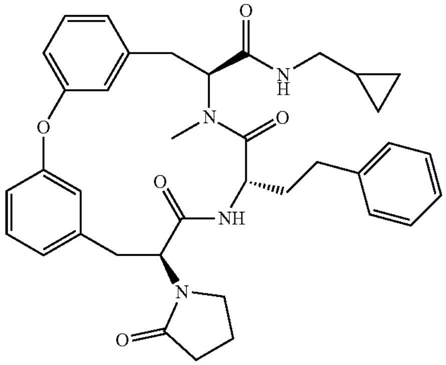 [SMILES: CN1C(=O)[C@H](CCc2ccccc2)NC(=O)[C@@H](N2CCCC2=O)Cc2cccc(c2)Oc2cccc(c2)C[C@H]1C(=O)NCC1CC1] | 0% @ 33.3 μM | 21% @ 33.3 μM |

TABLE 3-continued
| IC$_{50}$ values | | | |
|---|---|---|---|
| Compound Number | Structure | IC50 (μM) hu c-20S | IC50 (μM) hu i-20S |
| 1-82 | 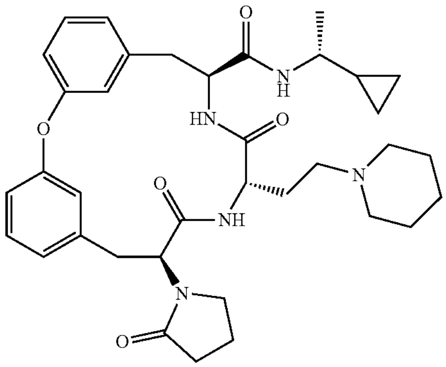 [SMILES: C[C@@H](NC(=O)[C@@H]1Cc2cccc(c2)Oc2cccc(c2)C[C@H](N2CCCC2=O)C(=O)N[C@@H](CCN2CCCCC2)C(=O)N1)C1CC1] | 23% @ 33.3 μM | 19% @ 33.3 μM |
| 1-83 | 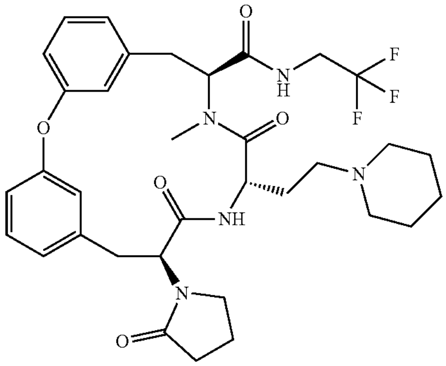 [SMILES: CN1C(=O)[C@H](CCN2CCCCC2)NC(=O)[C@@H](N2CCCC2=O)Cc2cccc(c2)Oc2cccc(c2)C[C@H]1C(=O)NCC(F)(F)F] | 0% @ 33.3 μM | 0% @ 33.3 μM |
| 1-84 | 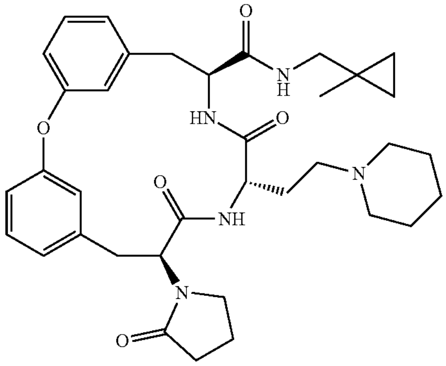 [SMILES: CC1(CNC(=O)[C@@H]2Cc3cccc(c3)Oc3cccc(c3)C[C@H](N3CCCC3=O)C(=O)N[C@@H](CCN3CCCCC3)C(=O)N2)CC1] | 13.1 | 45% @ 33.3 μM |
| 1-85 | 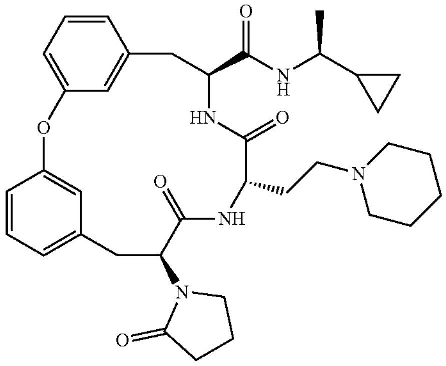 [SMILES: C[C@H](NC(=O)[C@@H]1Cc2cccc(c2)Oc2cccc(c2)C[C@H](N2CCCC2=O)C(=O)N[C@@H](CCN2CCCCC2)C(=O)N1)C1CC1] | 33.1 | 60.2 |

TABLE 3-continued
| IC$_{50}$ values | | | |
|---|---|---|---|
| Compound Number | Structure | IC50 (μM) hu c-20S | IC50 (μM) hu i-20S |
| 1-86 | 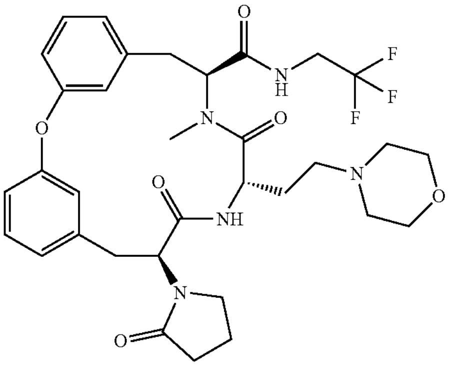 [SMILES: CN1C(=O)[C@H](CCN2CCOCC2)NC(=O)[C@@H](N2CCCC2=O)Cc2cccc(c2)Oc2cccc(c2)C[C@H]1C(=O)NCC(F)(F)F] | 31% @ 33.3 μM | 61 |
| 1-87 | 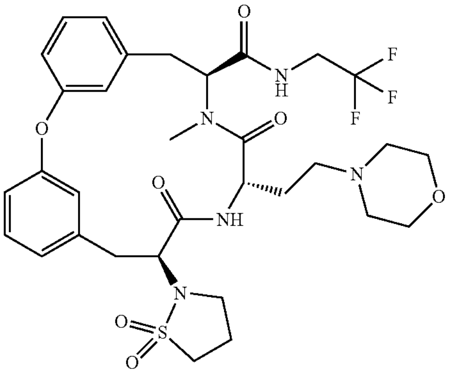 [SMILES: CN1C(=O)[C@H](CCN2CCOCC2)NC(=O)[C@@H](N2CCCS2(=O)=O)Cc2cccc(c2)Oc2cccc(c2)C[C@H]1C(=O)NCC(F)(F)F] | 0% @ 33.3 μM | 23% @ 33.3 μM |
| 1-88 | 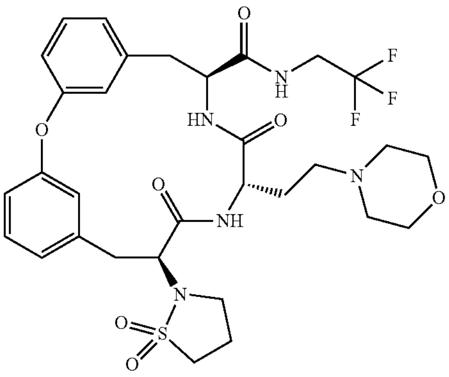 [SMILES: O=C(NCC(F)(F)F)[C@@H]1Cc2cccc(c2)Oc2cccc(c2)C[C@H](N2CCCS2(=O)=O)C(=O)N[C@@H](CCN2CCOCC2)C(=O)N1] | 3.7 | 15% @ 33.3 μM |
| 1-89 | 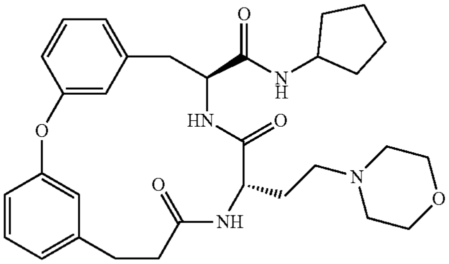 [SMILES: O=C1CCc2cccc(c2)Oc2cccc(c2)C[C@@H](C(=O)NC2CCCC2)NC(=O)[C@H](CCN2CCOCC2)N1] | 13% @ 33.3 μM | >100 |

TABLE 3-continued
| IC50 values | | | |
|---|---|---|---|
| Compound Number | Structure | IC50 (μM) hu c-20S | IC50 (μM) hu i-20S |
| 1-90 | 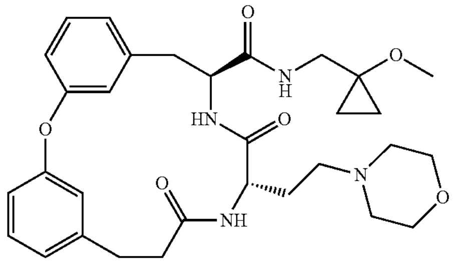 [SMILES: COC1(CNC(=O)[C@@H]2Cc3cccc(c3)Oc3cccc(c3)CCC(=O)N[C@@H](CCN3CCOCC3)C(=O)N2)CC1] | 68.1 | >100 |
| 1-91 | 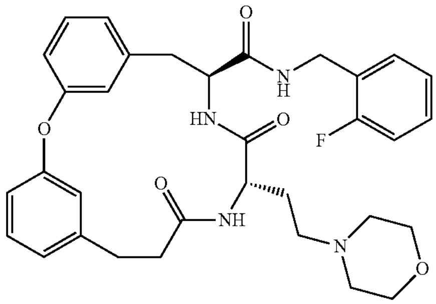 [SMILES: O=C1CCc2cccc(c2)Oc2cccc(c2)C[C@@H](C(=O)NCc2ccccc2F)NC(=O)[C@H](CCN2CCOCC2)N1] | 0.47 | 0% @ 33.3 μM |
| 2-01-B | 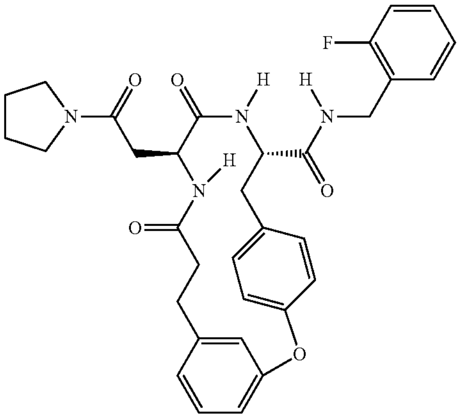 [SMILES: O=C1CCc2cccc(c2)Oc2ccc(cc2)C[C@@H](C(=O)NCc2ccccc2F)NC(=O)[C@H](CC(=O)N2CCCC2)N1] | 75.41 | 0.845 |
| 2-02-B | 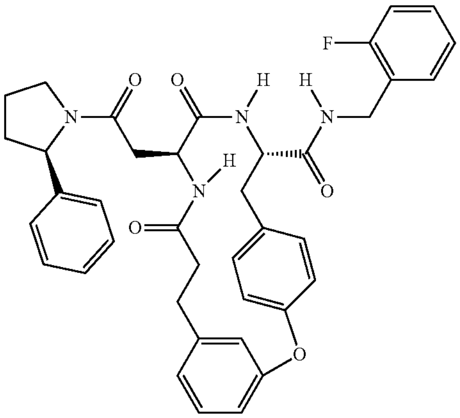 [SMILES: O=C1CCc2cccc(c2)Oc2ccc(cc2)C[C@@H](C(=O)NCc2ccccc2F)NC(=O)[C@H](CC(=O)N2CCC[C@@H]2c2ccccc2)N1] | >100 | 6.75 |

TABLE 3-continued
| IC$_{50}$ values | | | |
|---|---|---|---|
| Compound Number | Structure | IC50 (μM) hu c-20S | IC50 (μM) hu i-20S |
| 2-03-A | 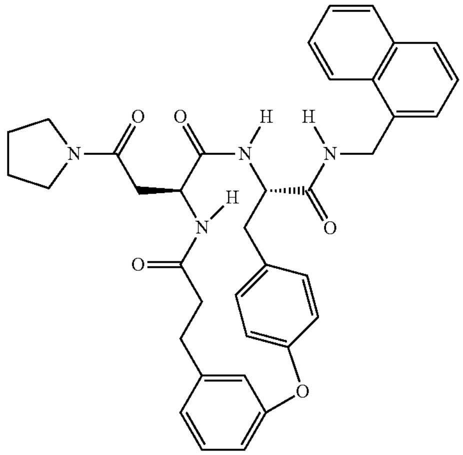 [SMILES: O=C1CCc2cccc(c2)Oc2ccc(cc2)C[C@@H](C(=O)NCc2cccc3ccccc23)NC(=O)[C@H](CC(=O)N2CCCC2)N1] | 18.48 | 10.14 |
| 2-03-B | 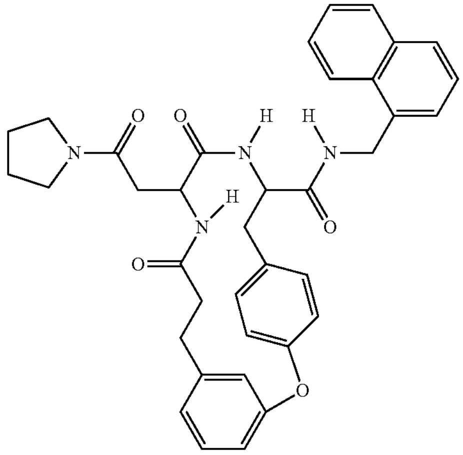 [SMILES: O=C1CCc2cccc(c2)Oc2ccc(cc2)CC(C(=O)NCc2cccc3ccccc23)NC(=O)C(CC(=O)N2CCCC2)N1] | >100 | 0.96 |
| 2-04 | 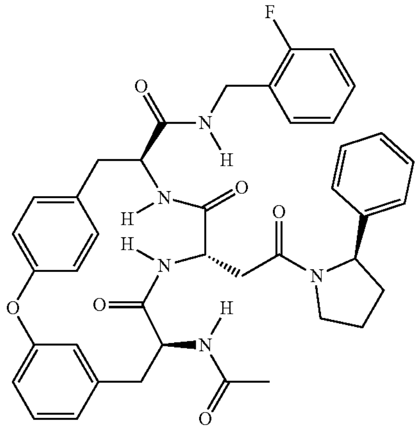 [SMILES: CC(=O)N[C@H]1Cc2cccc(c2)Oc2ccc(cc2)C[C@@H](C(=O)NCc2ccccc2F)NC(=O)[C@H](CC(=O)N2CCC[C@@H]2c2ccccc2)NC1=O] | 30.7 | 9.099 |

TABLE 3-continued
| IC$_{50}$ values | | | |
|---|---|---|---|
| Compound Number | Structure | IC50 (μM) hu c-20S | IC50 (μM) hu i-20S |
| 2-05 | 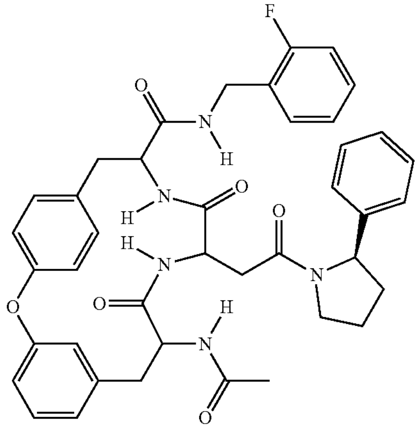 [SMILES: CC(=O)NC1Cc2cccc(c2)Oc2ccc(cc2)CC(C(=O)NCc2ccccc2F)NC(=O)C(CC(=O)N2CCC[C@@H]2c2ccccc2)NC1=O] | 88.4 | 35.94 |
| 2-06 | 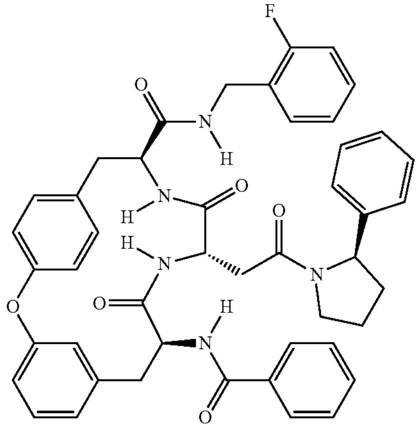 [SMILES: O=C(N[C@H]1Cc2cccc(c2)Oc2ccc(cc2)C[C@@H](C(=O)NCc2ccccc2F)NC(=O)[C@H](CC(=O)N2CCC[C@@H]2c2ccccc2)NC1=O)c1ccccc1] | >100 | 19.31 |
| 2-07 | 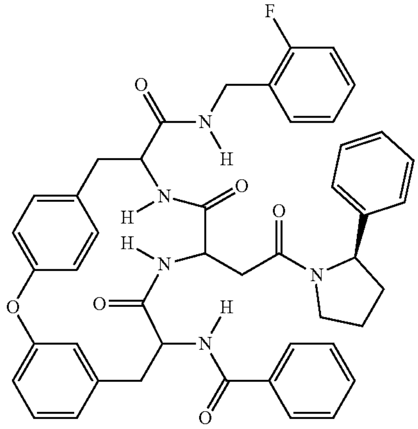 [SMILES: O=C(NC1Cc2cccc(c2)Oc2ccc(cc2)CC(C(=O)NCc2ccccc2F)NC(=O)C(CC(=O)N2CCC[C@@H]2c2ccccc2)NC1=O)c1ccccc1] | >100 | 26.84 |

TABLE 3-continued
| IC$_{50}$ values | | | |
|---|---|---|---|
| Compound Number | Structure | IC50 (μM) hu c-20S | IC50 (μM) hu i-20S |
| 3-01 | 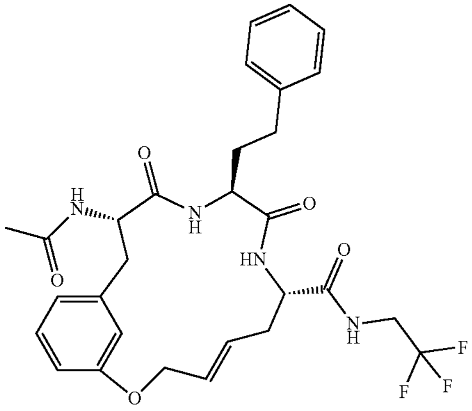 [SMILES: CC(=O)N[C@H]1Cc2cccc(c2)OC/C=C/C[C@@H](C(=O)NCC(F)(F)F)NC(=O)[C@H](CCc2ccccc2)NC1=O] | 0.78 | 15.59 |
| 3-02 | 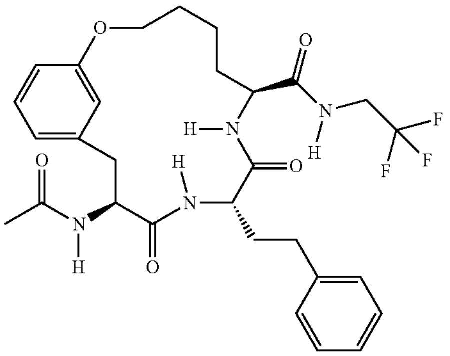 [SMILES: CC(=O)N[C@H]1Cc2cccc(c2)OCCCC[C@@H](C(=O)NCC(F)(F)F)NC(=O)[C@H](CCc2ccccc2)NC1=O] | 0.433 | 5.88 |
| 3-03 | 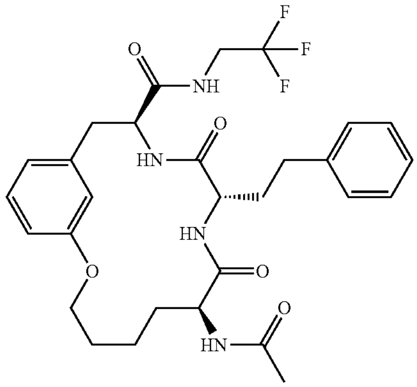 [SMILES: CC(=O)N[C@H]1CCCCOc2cccc(c2)C[C@@H](C(=O)NCC(F)(F)F)NC(=O)[C@H](CCc2ccccc2)NC1=O] | 11.9 | 10% @ 33.3 μM |
| 3-04 | 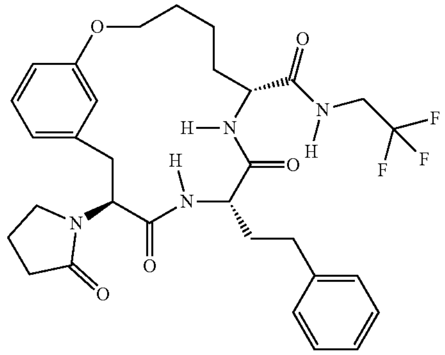 [SMILES: O=C1N[C@@H](C(=O)NCC(F)(F)F)CCCCOc2cccc(c2)C[C@H](N2CCCC2=O)C(=O)N[C@H]1CCc1ccccc1] | 1.1 | 32.76 |

TABLE 3-continued
| IC$_{50}$ values | | | |
|---|---|---|---|
| Compound Number | Structure | IC50 (μM) hu c-20S | IC50 (μM) hu i-20S |
| 3-05 | 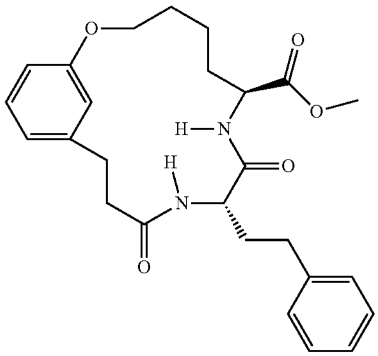 [SMILES: COC(=O)[C@@H]1CCCCOc2cccc(c2)CCC(=O)N[C@@H](CCc2ccccc2)C(=O)N1] | 23.11 | >10 |
| 3-06 | 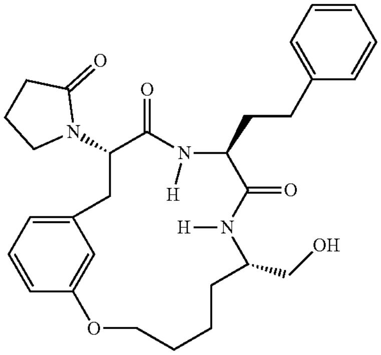 [SMILES: O=C1N[C@H](CO)CCCCOc2cccc(c2)C[C@H](N2CCCC2=O)C(=O)N[C@H]1CCc1ccccc1] | 22% @ 33.3 μM | 68 |
| 3-07 | 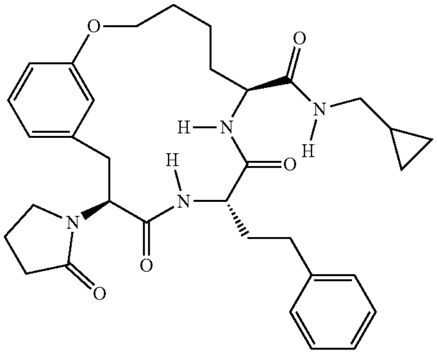 [SMILES: O=C(NCC1CC1)[C@@H]1CCCCOc2cccc(c2)C[C@H](N2CCCC2=O)C(=O)N[C@@H](CCc2ccccc2)C(=O)N1] | 3.140 | 40.46 |
| 3-08 | 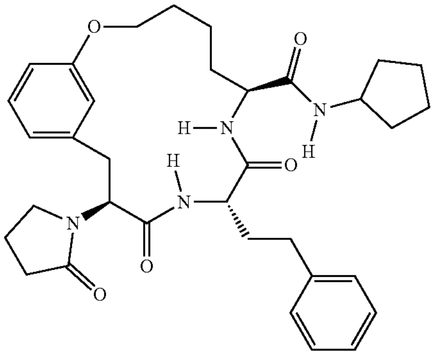 [SMILES: O=C(NC1CCCC1)[C@@H]1CCCCOc2cccc(c2)C[C@H](N2CCCC2=O)C(=O)N[C@@H](CCc2ccccc2)C(=O)N1] | 2.150 | >100 |

TABLE 3-continued
| IC$_{50}$ values | | | |
|---|---|---|---|
| Compound Number | Structure | IC50 (μM) hu c-20S | IC50 (μM) hu i-20S |
| 3-09 | 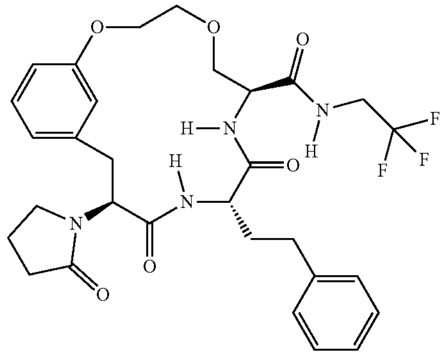 [SMILES: O=C(NCC(F)(F)F)[C@@H]1COCCOc2cccc(c2)C[C@H](N2CCCC2=O)C(=O)N[C@@H](CCc2ccccc2)C(=O)N1] | 10.810 | >100 |
| 3-10 | 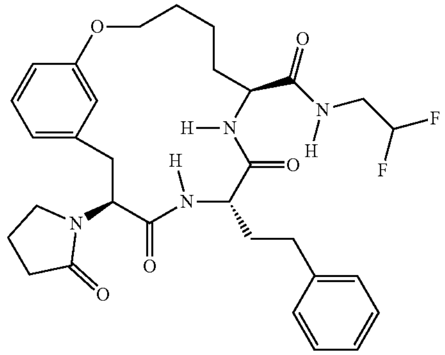 [SMILES: O=C(NCC(F)F)[C@@H]1CCCCOc2cccc(c2)C[C@H](N2CCCC2=O)C(=O)N[C@@H](CCc2ccccc2)C(=O)N1] | 7.060 | >100 |
| 3-11 | 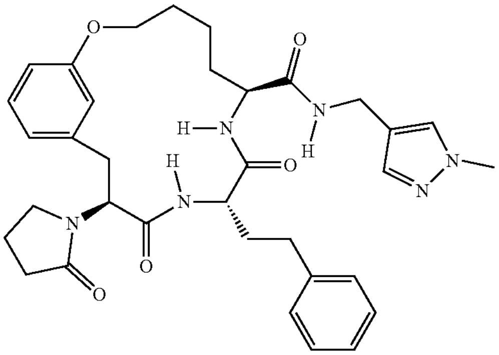 [SMILES: Cn1cc(CNC(=O)[C@@H]2CCCCOc3cccc(c3)C[C@H](N3CCCC3=O)C(=O)N[C@@H](CCc3ccccc3)C(=O)N2)cn1] | 2.48 | >100 |
| 3-12 | 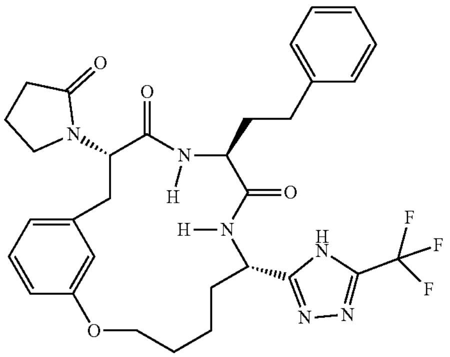 [SMILES: O=C1N[C@H](c2nnc(C(F)(F)F)[nH]2)CCCCOc2cccc(c2)C[C@H](N2CCCC2=O)C(=O)N[C@H]1CCc1ccccc1] | 0% @ 33.3 μM | 0% @ 33.3 μM |

TABLE 3-continued
| IC$_{50}$ values | | | |
|---|---|---|---|
| Compound Number | Structure | IC50 (μM) hu c-20S | IC50 (μM) hu i-20S |
| 3-13 | 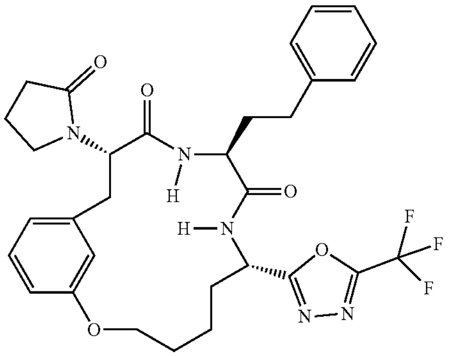 [SMILES: O=C1N[C@H](c2nnc(C(F)(F)F)o2)CCCCOc2cccc(c2)C[C@H](N2CCCC2=O)C(=O)N[C@H]1CCc1ccccc1] | 0% @ 33.3 μM | 0% @ 33.3 μM |
| 3-14 | 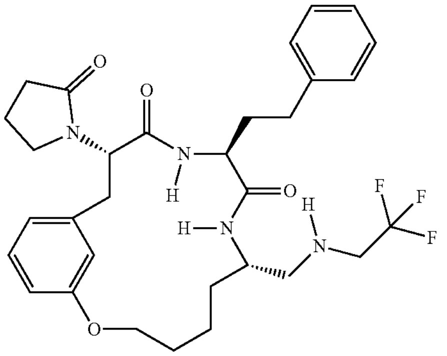 [SMILES: O=C1N[C@H](CNCC(F)(F)F)CCCCOc2cccc(c2)C[C@H](N2CCCC2=O)C(=O)N[C@H]1CCc1ccccc1] | 0% @ 33.3 μM | 0% @ 33.3 μM |
| 3-15 | 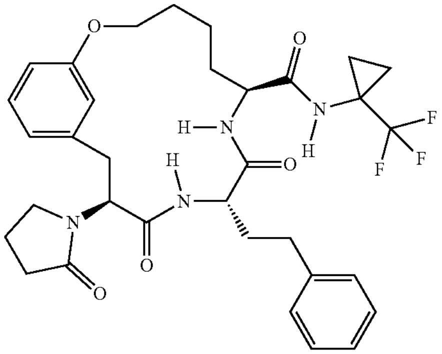 [SMILES: O=C(NC1(C(F)(F)F)CC1)[C@@H]1CCCCOc2cccc(c2)C[C@H](N2CCCC2=O)C(=O)N[C@@H](CCc2ccccc2)C(=O)N1] | 23% @ 33.3 μM | 0% @ 33.3 μM |
| 3-16 | 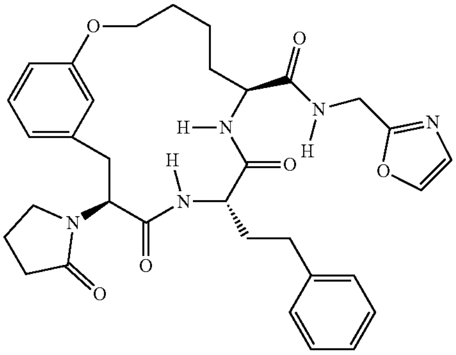 [SMILES: O=C(NCc1ncco1)[C@@H]1CCCCOc2cccc(c2)C[C@H](N2CCCC2=O)C(=O)N[C@@H](CCc2ccccc2)C(=O)N1] | 31.860 | 82 |

TABLE 3-continued
| IC$_{50}$ values | | | |
|---|---|---|---|
| Compound Number | Structure | IC50 (μM) hu c-20S | IC50 (μM) hu i-20S |
| 3-17 | 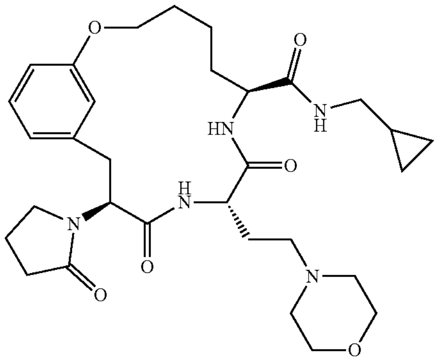 [SMILES: O=C(NCC1CC1)[C@@H]1CCCCOc2cccc(c2)C[C@H](N2CCCC2=O)C(=O)N[C@@H](CCN2CCOCC2)C(=O)N1] | 17.9 | 9% @ 33.3 μM |
| 3-18 | 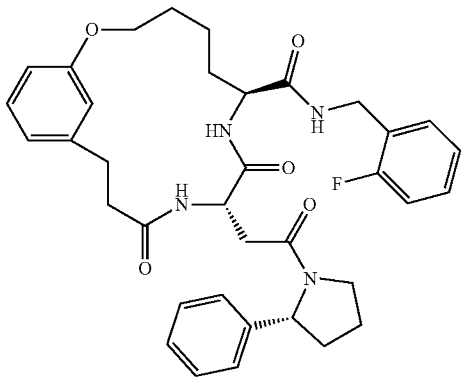 [SMILES: O=C1CCc2cccc(c2)OCCCC[C@@H](C(=O)NCc2ccccc2F)NC(=O)[C@H](CC(=O)N2CCC[C@@H]2c2ccccc2)N1] | 44.3 | 3.0 |
| 3-19 | 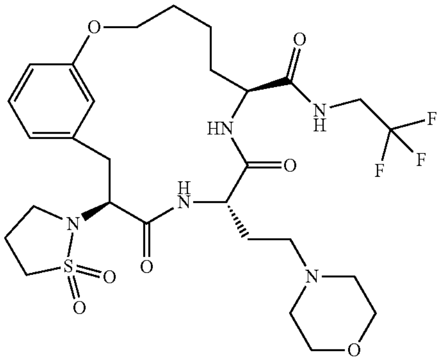 [SMILES: O=C(NCC(F)(F)F)[C@@H]1CCCCOc2cccc(c2)C[C@H](N2CCCS2(=O)=O)C(=O)N[C@@H](CCN2CCOCC2)C(=O)N1] | 45 | 0% @ 33.3 μM |
| 3-20 | 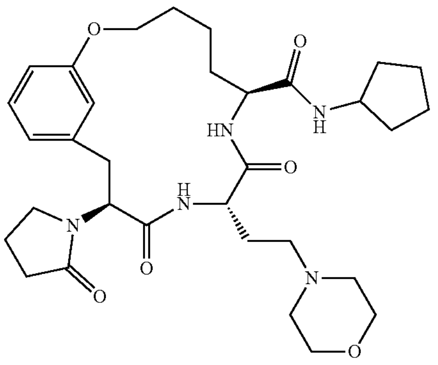 [SMILES: O=C(NC1CCCC1)[C@@H]1CCCCOc2cccc(c2)C[C@H](N2CCCC2=O)C(=O)N[C@@H](CCN2CCOCC2)C(=O)N1] | 81.8 | 2% @ 33.3 μM |

TABLE 3-continued
| IC$_{50}$ values | | | |
|---|---|---|---|
| Compound Number | Structure | IC50 (μM) hu c-20S | IC50 (μM) hu i-20S |
| 3-21 | 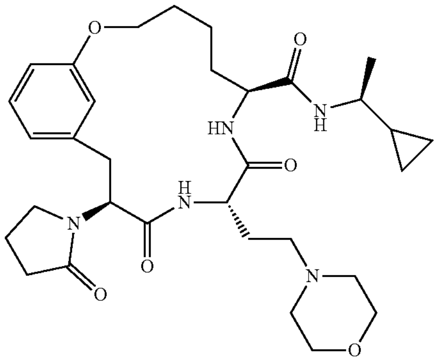 [SMILES: C[C@H](NC(=O)[C@@H]1CCCCOc2cccc(c2)C[C@H](N2CCCC2=O)C(=O)N[C@@H](CCN2CCOCC2)C(=O)N1)C1CC1] | 44.3 | >100 |
| 3-22 | 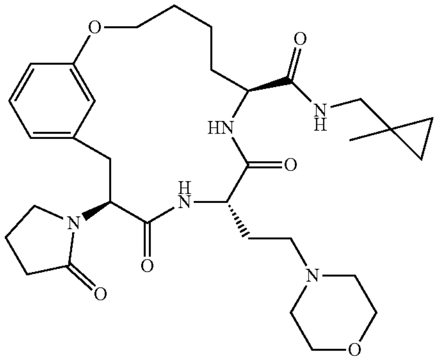 [SMILES: CC1(CNC(=O)[C@@H]2CCCCOc3cccc(c3)C[C@H](N3CCCC3=O)C(=O)N[C@@H](CCN3CCOCC3)C(=O)N2)CC1] | 4.2 | 24% @ 33.3 μM |
| 3-23 | 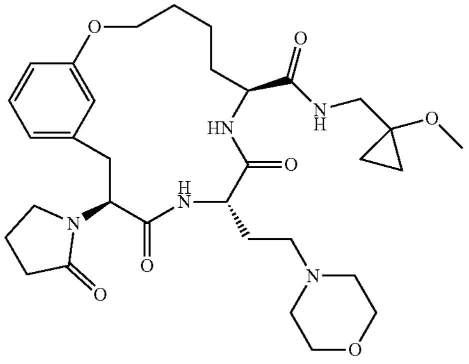 [SMILES: COC1(CNC(=O)[C@@H]2CCCCOc3cccc(c3)C[C@H](N3CCCC3=O)C(=O)N[C@@H](CCN3CCOCC3)C(=O)N2)CC1] | 4% @ 33.3 μM | 2% @ 33.3 μM |
| 3-24 | 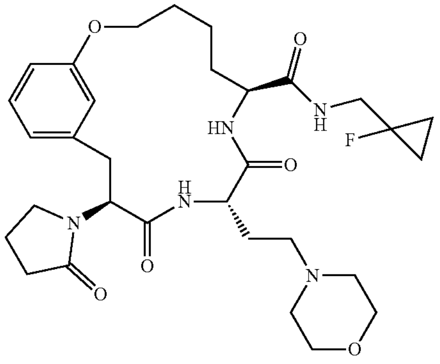 [SMILES: O=C(NCC1(F)CC1)[C@@H]1CCCCOc2cccc(c2)C[C@H](N2CCCC2=O)C(=O)N[C@@H](CCN2CCOCC2)C(=O)N1] | 0% @ 33.3 μM | 0% @ 33.3 μM |

TABLE 3-continued
| IC$_{50}$ values | | | |
|---|---|---|---|
| Compound Number | Structure | IC50 (μM) hu c-20S | IC50 (μM) hu i-20S |
| 3-25 | 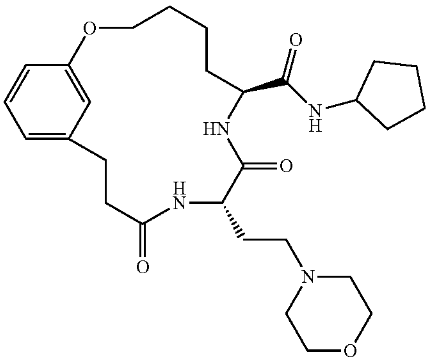 [SMILES: O=C1CCc2cccc(c2)OCCCC[C@@H](C(=O)NC2CCCC2)NC(=O)[C@H](CCN2CCOCC2)N1] | 24.1 | 7% @ 33.3 μM |
| 3-26 | 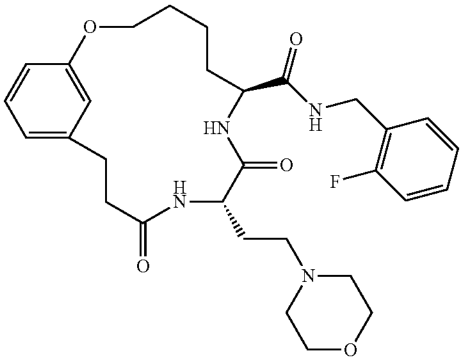 [SMILES: O=C1CCc2cccc(c2)OCCCC[C@@H](C(=O)NCc2ccccc2F)NC(=O)[C@H](CCN2CCOCC2)N1] | 3.4 | 3.5 |
| 3-27 | 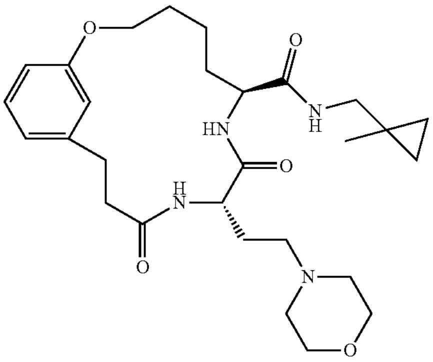 [SMILES: CC1(CNC(=O)[C@@H]2CCCCOc3cccc(c3)CCC(=O)N[C@@H](CCN3CCOCC3)C(=O)N2)CC1] | 34.6 | 25% @ 33.3 μM |
| 3-28 | 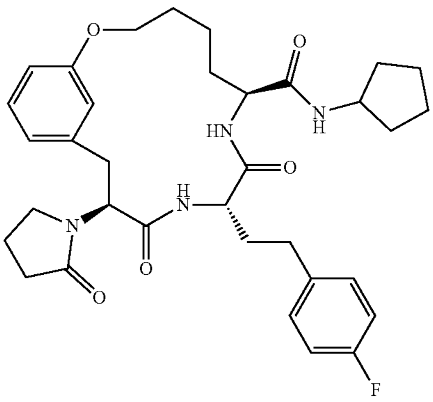 [SMILES: O=C(NC1CCCC1)[C@@H]1CCCCOc2cccc(c2)C[C@H](N2CCCC2=O)C(=O)N[C@@H](CCc2ccc(F)cc2)C(=O)N1] | 0.66 | 8.6 |

TABLE 3-continued
| IC$_{50}$ values | | | |
|---|---|---|---|
| Compound Number | Structure | IC50 (μM) hu c-20S | IC50 (μM) hu i-20S |
| 3-29 | 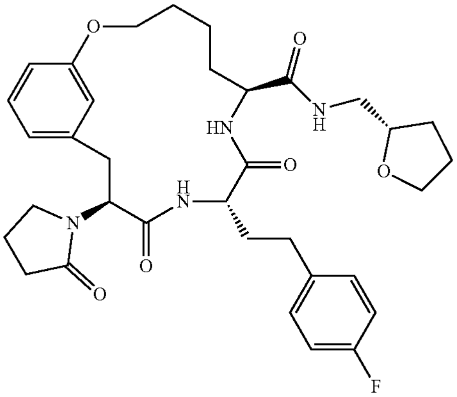 [SMILES: O=C(NC[C@@H]1CCCO1)[C@@H]1CCCCOc2cccc(c2)C[C@H](N2CCCC2=O)C(=O)N[C@@H](CCc2ccc(F)cc2)C(=O)N1] | 17% @ 33.3 μM | 2% @ 33.3 μM |
| 3-30 | 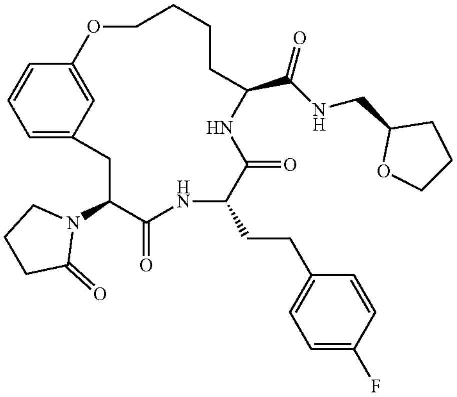 [SMILES: O=C(NC[C@H]1CCCO1)[C@@H]1CCCCOc2cccc(c2)C[C@H](N2CCCC2=O)C(=O)N[C@@H](CCc2ccc(F)cc2)C(=O)N1] | 85.3M | 4% @ 33.3 μM |
| 3-31 | 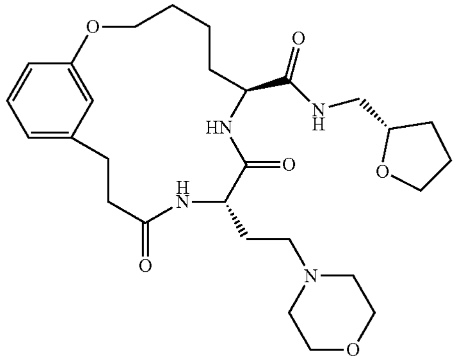 [SMILES: O=C1CCc2cccc(c2)OCCCC[C@@H](C(=O)NC[C@@H]2CCCO2)NC(=O)[C@H](CCN2CCOCC2)N1] | 0% @ 33.3 μM | 0% @ 33.3 μM |
| 3-32 | 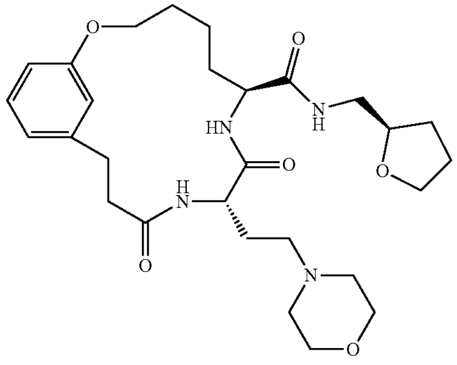 [SMILES: O=C1CCc2cccc(c2)OCCCC[C@@H](C(=O)NC[C@H]2CCCO2)NC(=O)[C@H](CCN2CCOCC2)N1] | 0% @ 33.3 μM | 0% @ 33.3 μM |

TABLE 3-continued
| IC$_{50}$ values | | | |
|---|---|---|---|
| Compound Number | Structure | IC50 (µM) hu c-20S | IC50 (µM) hu i-20S |
| 3-33 | 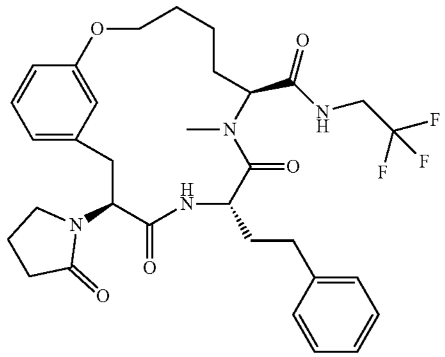 [SMILES: CN1C(=O)[C@H](CCc2ccccc2)NC(=O)[C@@H](N2CCCC2=O)Cc2cccc(c2)OCCCC[C@H]1C(=O)NCC(F)(F)F] | 25.8 | 0% @ 33.3 µM |
| 3-34 | 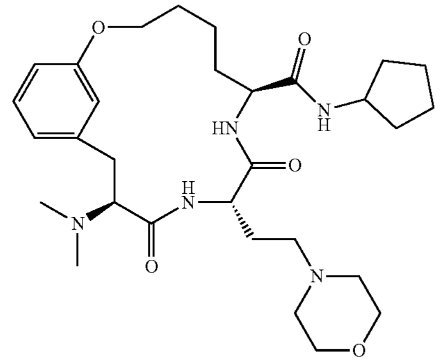 [SMILES: CN(C)[C@H]1Cc2cccc(c2)OCCCC[C@@H](C(=O)NC2CCCC2)NC(=O)[C@H](CCN2CCOCC2)NC1=O] | 30% @ 33.3 µM | >100 |
| 3-35 | 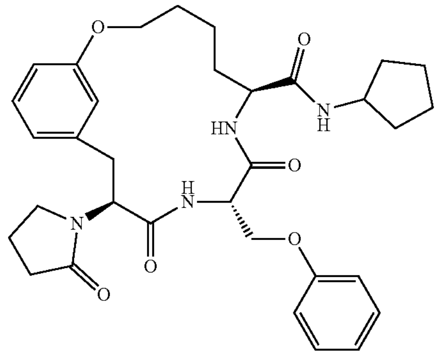 [SMILES: O=C(NC1CCCC1)[C@@H]1CCCCOc2cccc(c2)C[C@H](N2CCCC2=O)C(=O)N[C@@H](COc2ccccc2)C(=O)N1] | 9.7 | 88.4 |
| 3-36 | 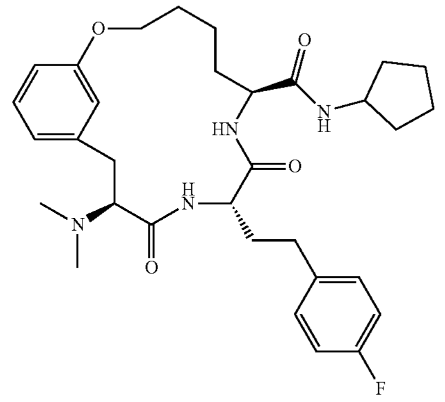 [SMILES: CN(C)[C@H]1Cc2cccc(c2)OCCCC[C@@H](C(=O)NC2CCCC2)NC(=O)[C@H](CCc2ccc(F)cc2)NC1=O] | 9.5 | >100 |

TABLE 3-continued
IC$_{50}$ values
| Compound Number | Structure | IC50 (μM) hu c-20S | IC50 (μM) hu i-20S |
|---|---|---|---|
| 3-37 | 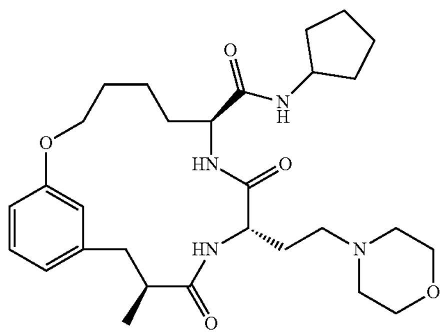 [SMILES: C[C@H]1Cc2cccc(c2)OCCCC[C@@H](C(=O)NC2CCCC2)NC(=O)[C@H](CCN2CCOCC2)NC1=O] | 56.7 | >100 |
| 3-38 | 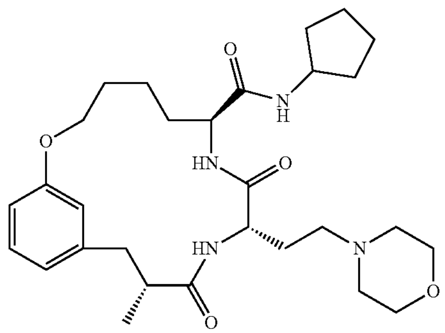 [SMILES: C[C@@H]1Cc2cccc(c2)OCCCC[C@@H](C(=O)NC2CCCC2)NC(=O)[C@H](CCN2CCOCC2)NC1=O] | 21.5 | >100 |
| 3-39 | 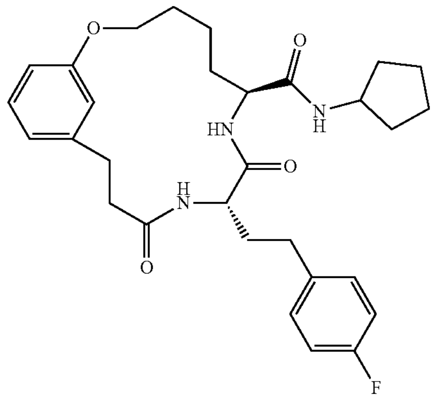 [SMILES: O=C1CCc2cccc(c2)OCCCC[C@@H](C(=O)NC2CCCC2)NC(=O)[C@H](CCc2ccc(F)cc2)N1] | 38.6 | >100 |
| 3-40 | 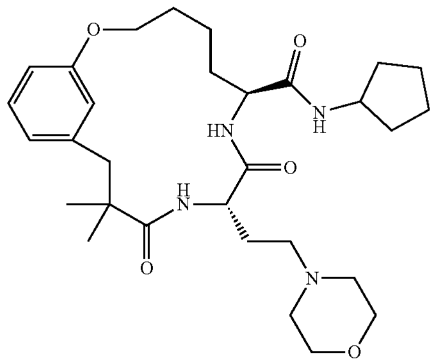 [SMILES: CC1(C)Cc2cccc(c2)OCCCC[C@@H](C(=O)NC2CCCC2)NC(=O)[C@H](CCN2CCOCC2)NC1=O] | 34.7 | >100 |

TABLE 3-continued
| IC$_{50}$ values | | | |
|---|---|---|---|
| Compound Number | Structure | IC50 (μM) hu c-20S | IC50 (μM) hu i-20S |
| 3-41 | 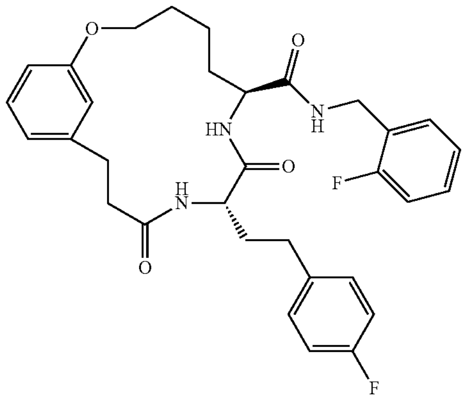 [SMILES: O=C1CCc2cccc(c2)OCCCC[C@@H](C(=O)NCc2ccccc2F)NC(=O)[C@H](CCc2ccc(F)cc2)N1] | 56 | >100 |
| 3-42 | 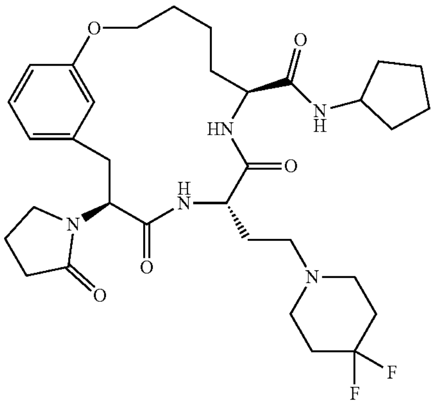 [SMILES: O=C(NC1CCCC1)[C@@H]1CCCCOc2cccc(c2)C[C@H](N2CCCC2=O)C(=O)N[C@@H](CCN2CCC(F)(F)CC2)C(=O)N1] | 2.92 | 56.4 |
| 3-43 | 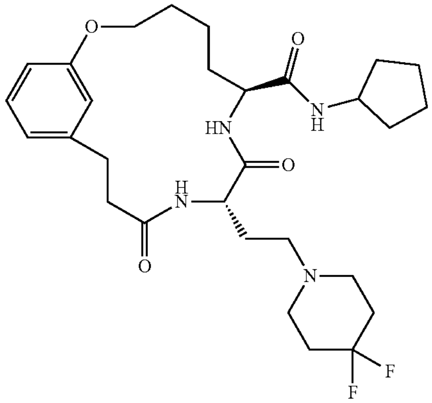 [SMILES: O=C1CCc2cccc(c2)OCCCC[C@@H](C(=O)NC2CCCC2)NC(=O)[C@H](CCN2CCC(F)(F)CC2)N1] | 75.5 | >100 |

TABLE 3-continued
| IC$_{50}$ values | | | |
|---|---|---|---|
| Compound Number | Structure | IC50 (μM) hu c-20S | IC50 (μM) hu i-20S |
| 3-44 | 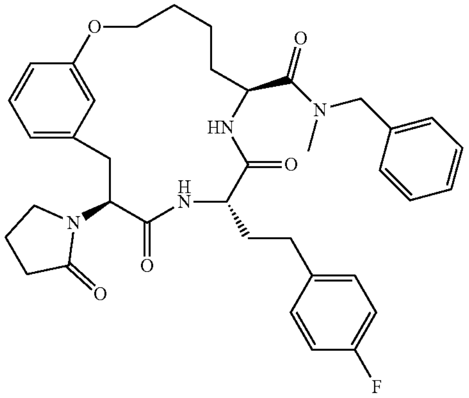 [SMILES: CN(Cc1ccccc1)C(=O)[C@@H]1CCCCOc2cccc(c2)C[C@H](N2CCCC2=O)C(=O)N[C@@H](CCc2ccc(F)cc2)C(=O)N1] | 5.15 | >100 |
| 3-45-A | 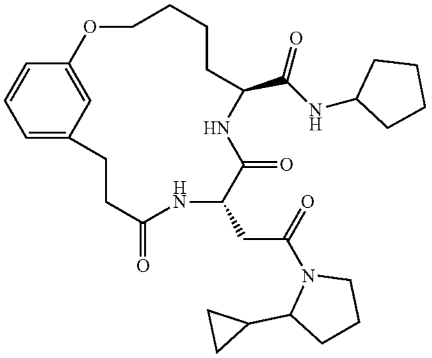 [SMILES: O=C1CCc2cccc(c2)OCCCC[C@@H](C(=O)NC2CCCC2)NC(=O)[C@H](CC(=O)N2CCCC2C2CC2)N1] | 12.29 | >100 |
| 3-45-B | 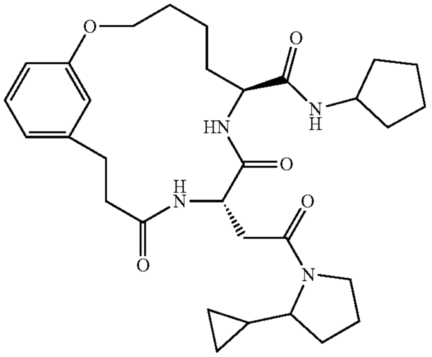 [SMILES: O=C1CCc2cccc(c2)OCCCC[C@@H](C(=O)NC2CCCC2)NC(=O)[C@H](CC(=O)N2CCCC2C2CC2)N1] | 3.6 | >100 |
| 3-46-A | 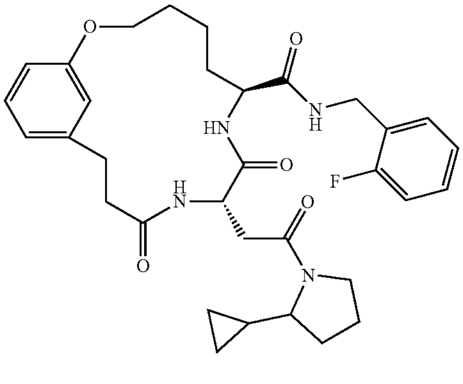 [SMILES: O=C1CCc2cccc(c2)OCCCC[C@@H](C(=O)NCc2ccccc2F)NC(=O)[C@H](CC(=O)N2CCCC2C2CC2)N1] | 0.0723 | 0.068 |

TABLE 3-continued
| IC$_{50}$ values | | | |
|---|---|---|---|
| Compound Number | Structure | IC50 (μM) hu c-20S | IC50 (μM) hu i-20S |
| 3-46-B | 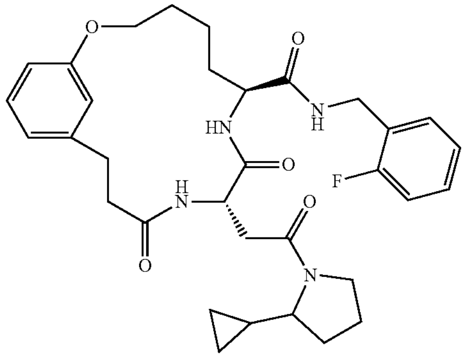 [SMILES: O=C1CCc2cccc(c2)OCCCC[C@@H](C(=O)NCc2ccccc2F)NC(=O)[C@H](CC(=O)N2CCCC2C2CC2)N1] | 1.35 | 0.312 |
| 4-01 | 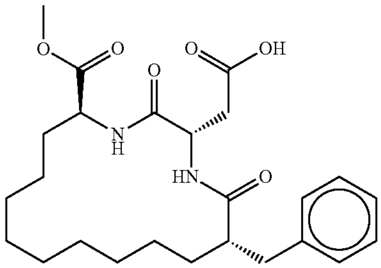 | 0% @ 33.3 μM | 0% @ 33.3 μM |
| 4-02 | 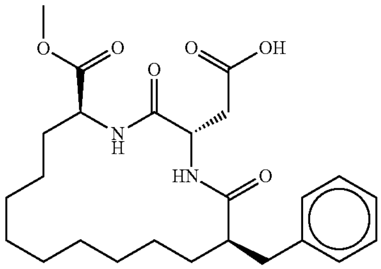 | 0% @ 33.3 μM | 0% @ 33.3 μM |
| 4-03 | 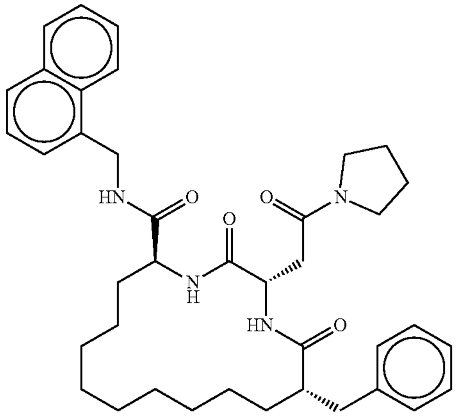 | >100 | 3.52 |

TABLE 3-continued
| IC$_{50}$ values | | | |
|---|---|---|---|
| Compound Number | Structure | IC50 (μM) hu c-20S | IC50 (μM) hu i-20S |
| 4-04 | 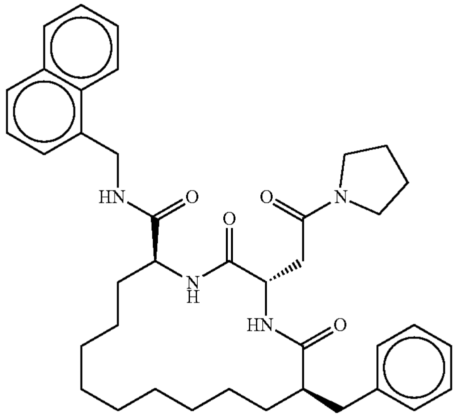 | 19.84 | 61.3 |
| 4-05 | 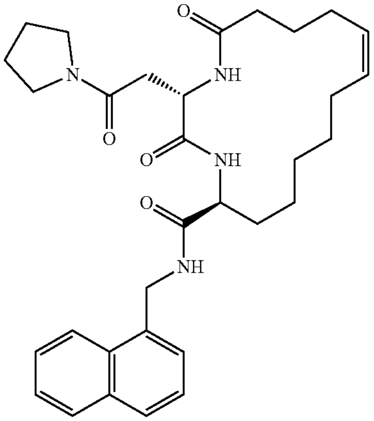 [SMILES: O=C1CCC/C=C\CCCCC[C@@H](C(=O)NCc2cccc3ccccc23)NC(=O)[C@H](CC(=O)N2CCCC2)N1] | >100 | 4.359 |
| 4-06 | 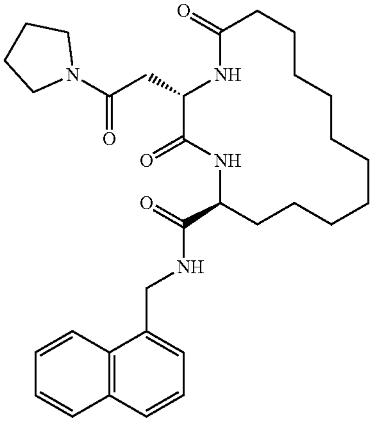 [SMILES: O=C1CCCCCCCCCC[C@@H](C(=O)NCc2cccc3ccccc23)NC(=O)[C@H](CC(=O)N2CCCC2)N1] | >100 | 3.515 |

TABLE 3-continued
| IC$_{50}$ values | | | |
|---|---|---|---|
| Compound Number | Structure | IC50 (μM) hu c-20S | IC50 (μM) hu i-20S |
| 4-07 | 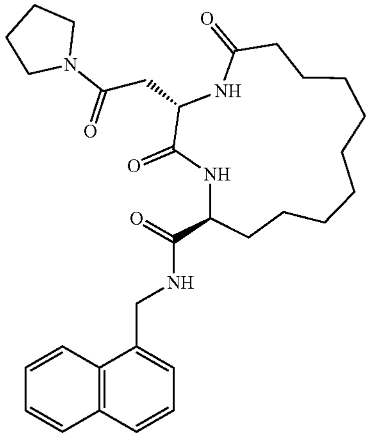 [SMILES: O=C1CCCCCCCCC[C@@H](C(=O)NCc2cccc3ccccc23)NC(=O)[C@H](CC(=O)N2CCCC2)N1] | >100 | 61.3 |
| 4-08 | 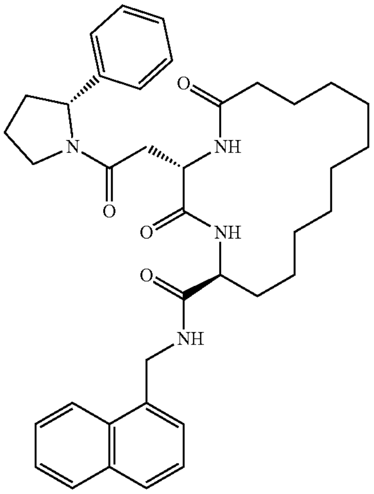 [SMILES: O=C1CCCCCCCCCC[C@@H](C(=O)NCc2cccc3ccccc23)NC(=O)[C@H](CC(=O)N2CCC[C@@H]2c2ccccc2)N1] | >100 | 33.37 |
| 4-09 | 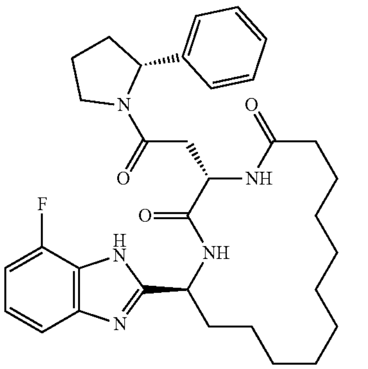 [SMILES: O=C1CCCCCCCCCC[C@@H](c2nc3cccc(F)c3[nH]2)NC(=O)[C@H](CC(=O)N2CCC[C@@H]2c2ccccc2)N1] | 0% @ 33.3 μM | 0% @ 33.3 μM |

TABLE 3-continued
| IC$_{50}$ values | | | |
|---|---|---|---|
| Compound Number | Structure | IC50 (μM) hu c-20S | IC50 (μM) hu i-20S |
| 4-10 | 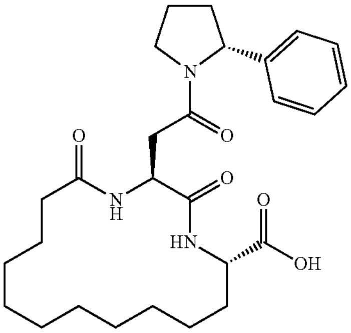 [SMILES: O=C1CCCCCCCCCC[C@@H](C(=O)O)NC(=O)[C@H](CC(=O)N2CCC[C@@H]2c2ccccc2)N1] | 21% @ 33.3 μM | 0% @ 33.3 μM |
| 4-11 | 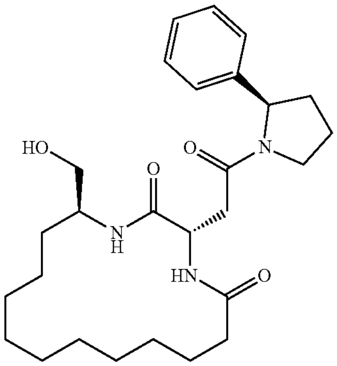 [SMILES: O=C1CCCCCCCCCC[C@@H](CO)NC(=O)[C@H](CC(=O)N2CCC[C@@H]2c2ccccc2)N1] | 14% @ 33.3 μM | 0% @ 33.3 μM |
| 4-12 | 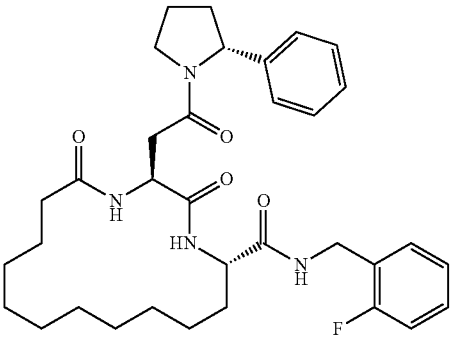 [SMILES: O=C1CCCCCCCCCC[C@@H](C(=O)NCc2ccccc2F)NC(=O)[C@H](CC(=O)N2CCC[C@@H]2c2ccccc2)N1] | 0% @ 33.3 μM | 0% @ 33.3 μM |
| 4-13 | 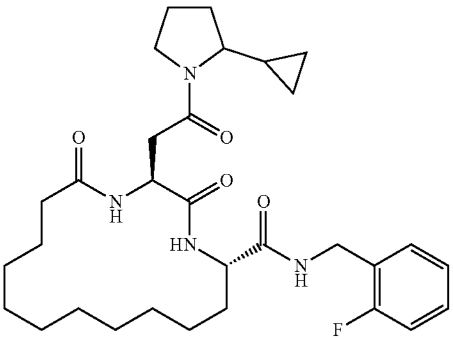 [SMILES: O=C1CCCCCCCCCC[C@@H](C(=O)NCc2ccccc2F)NC(=O)[C@H](CC(=O)N2CCCC2C2CC2)N1] | 0.274 | 0.018 |

TABLE 3-continued
| IC$_{50}$ values | | | |
|---|---|---|---|
| Compound Number | Structure | IC50 (μM) hu c-20S | IC50 (μM) hu i-20S |
| 4-14 | 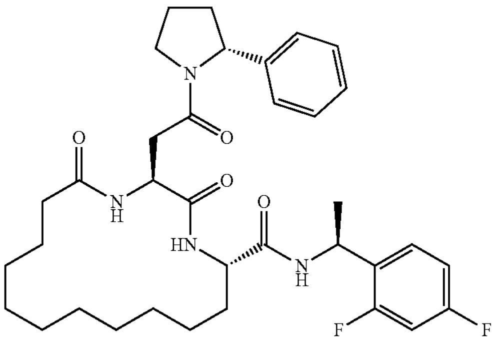 [SMILES: C[C@H](NC(=O)[C@@H]1CCCCCCCCCCC(=O)N[C@@H](CC(=O)N2CCC[C@@H]2c2ccccc2)C(=O)N1)c1ccc(F)cc1F] | 0% @ 33.3 μM | 68% @ 33.3 μM |
| 4-15 | 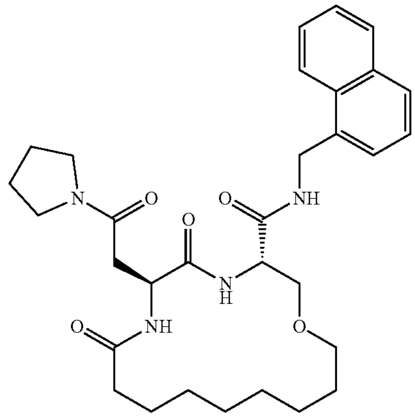 [SMILES: O=C1CCCCCCCCOC[C@@H](C(=O)NCc2cccc3ccccc23)NC(=O)[C@H](CC(=O)N2CCCC2)N1] | 3.67 | 4.71 |
| 4-16 | 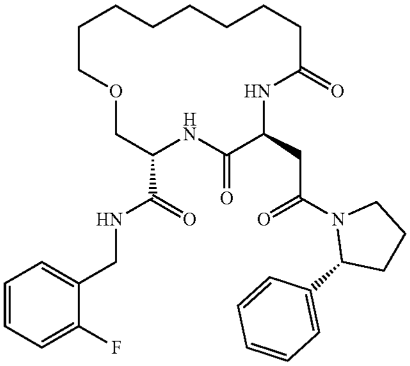 [SMILES: O=C1CCCCCCCCOC[C@@H](C(=O)NCc2ccccc2F)NC(=O)[C@H](CC(=O)N2CCC[C@@H]2c2ccccc2)N1] | 4.12 | 51.33 |
| 4-17 | 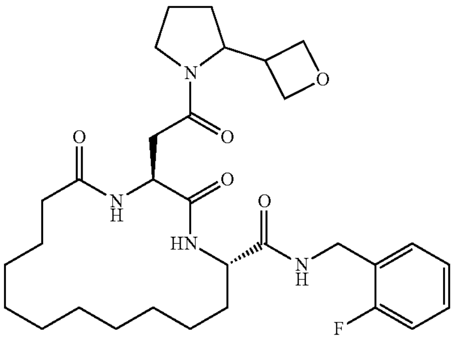 [SMILES: O=C1CCCCCCCCCC[C@@H](C(=O)NCc2ccccc2F)NC(=O)[C@H](CC(=O)N2CCCC2C2COC2)N1] | 0.88 | 0.11 |

Example 68—Inhibition of IL-6 in LPS-Stimulated Human Macrophages by 4-13

Monocytes were isolated from the blood of 2 healthy donors using CD14 magnetic beads and cultured with 20 ng/ml of MCSF for 24 hours to induce the differentiation into macrophages. 200,000 cells/wells in 96 wells plate were incubated with LPS (50 ng/ml) for 6 hours for RNA isolation and gene expression analysis (FIG. 1A) and 24 hours for ELISA (FIG. 1B). The proteasome inhibitor 4-13 used at the indicated concentration was added 15 minutes before adding LPS. At 6 hours, RNA were prepared using Qiagen RNA plus kit and cDNA were synthetized using the Thermofisher cDNA synthesis kit (FIG. 1A). Q-PCR was performed in duplicate and expression levels normalized to the level of the housekeeping gene ubiquitin. At 24 hours, supernatants were collected and IL-6 production quantified by ELISA (FIG. 1B).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A compound of Formula (I):

(I)

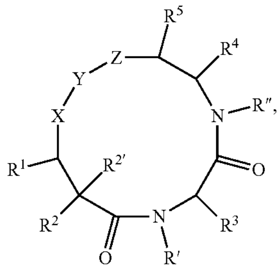

wherein

X is

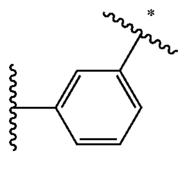

;

Y is O;

Z is $—(CH_2)_m—$, $—CH_2—CH_2—O—$, or $CH_2—CH{=}CH—$;

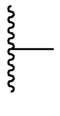

is the point of attachment to $—C(R^1)—$ moiety;

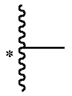

is the point of attachment to Y;

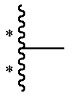

is the point of attachment to $—C(R^5)—$ moiety;

$R^1$ is H;

$R^2$ is independently selected at each occurrence thereof from the group consisting of H, $C_{1-6}$ alkyl, arylalkyl, $—NR^6R^7$, $—NHC(O)R^8$, $—NHS(O)_2R^8$, and $—NHC(O)(CH_2)_nNR^6R^7$;

$R^{2'}$ is H or $C_{1-6}$ alkyl;

$R^3$ is independently selected at each occurrence thereof from the group consisting of $C_{1-6}$ alkyl, $—(CH_2)_nNR^6R^7$, $—CH_2C(O)NR^6R^7$, $—CH_2C(O)OH$, and arylalkyl, wherein $C_{1-6}$ alkyl or arylalkyl can be optionally substituted from 1 to 3 times with halogen, $C_{1-6}$ alkoxy, —O-aryl, and $CF_3$;

$R^4$ is selected from the group consisting of $R^9$, $—C(O)R^9$, $—C(O)NH(CR^aR^b)_nR^8$, $—C(O)N(Me)(CR^aR^b)_nR^8$, $—C(O)OH$, $—C(O)CH_2Ph$, $—C(O)OR^9$, $—CH_2NHR^8$, and $—C(O)NR^6R^7$;

$R^5$ is H;

$R^6$ is selected from the group consisting of $C_{1-6}$ alkyl, $C_{3-8}$ cycloalkyl, and $C_{3-12}$ cycloalkylalkyl, or, wherein $C_{3-8}$ cycloalkyl and $C_{3-12}$ cycloalkylalkyl can be optionally substituted from 1 to 3 times with $CF_3$;

$R^7$ is selected from the group consisting of H, $C_{1-6}$ alkyl, $C_{3-8}$ cycloalkyl, and $C_{3-12}$ cycloalkylalkyl, or, wherein $C_{3-8}$ cycloalkyl and $C_{3-12}$ cycloalkylalkyl can be optionally substituted from 1 to 3 times with $CF_3$;

or $R^6$ and $R^7$ are taken together with the nitrogen to which they are attached to form a piperidine, pyrrolidine, morpholine ring, piperazine, oxazolidine, or isothiazolidine, wherein piperidine, pyrrolidine, morpholine, piperazine, oxazolidine, or isothiazolidine ring can be optionally substituted 1 to 3 times with halogen, $C_{1-6}$ alkyl, aryl, =O, $C_{3-8}$ cycloalkyl, or non-aromatic heterocycle;

$R^8$ is selected from the group consisting of H, OH, $CF_3$, $CHF_2$, $C_{1-12}$ alkyl, $C_{3-8}$ cycloalkyl, $C_{3-12}$ cycloalkylalkyl, monocyclic or bicyclic aryl, arylalkyl, and heteroaryl, heterocyclyl, and non-aromatic heterocycle, wherein $C_{1-12}$ alkyl, $C_{3-8}$ cycloalkyl, $C_{3-12}$ cycloalkylalkyl, monocyclic or bicyclic aryl, arylalkyl, and heteroaryl, heterocyclyl, and non-aromatic heterocycle can be optionally substituted from 1 to 3 times with OH, halogen, $C_{1-6}$ alkyl, $C_{1-6}$ alkoxy, $CHF_2$, $CF_3$, $—S(O)_2Me$;

$R^9$ is selected from the group consisting of OH, $CF_3$, $CHF_2$, $C_{1-12}$ alkyl, $C_{3-8}$ cycloalkyl, $C_{3-12}$ cycloalkylalkyl, $C_{1-12}$ alkoxy, monocyclic or bicyclic aryl, and heteroaryl, wherein $C_{1-12}$ alkyl, $C_{3-8}$ cycloalkyl, $C_{3-12}$ cycloalkylalkyl, monocyclic or bicyclic aryl, arylalkyl, and heteroaryl, can be optionally substituted from 1 to 3 times with OH, halogen, $C_{1-6}$ alkyl, $C_{1-6}$ alkoxy, $CHF_2$, $CF_3$, $—S(O)_2Me$;

$R^a$ and $R^b$ are each independently selected from the group consisting of H and $C_{1-6}$ alkyl;

R' and R" are each independently selected from the group consisting of H and $C_{1-6}$ alkyl;

n is 0, 1, 2, 3, or 4; and m is independently selected at each occurrence from the group consisting of 2, 3, 4, or 5, with the proviso that i) $R^2$ is not $NH_2$, ii) $R^4$ is not

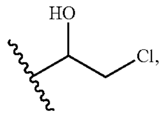
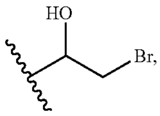
or
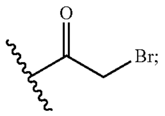

iii) when $R^4$ is COOH, then $R^3$ is not

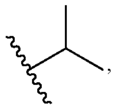
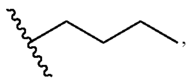
or
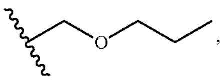

and iv) when $R^4$ is COOMe, then $R^3$ is not

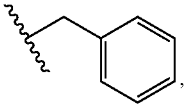

or an oxide thereof, a pharmaceutically acceptable salt thereof, or a solvate thereof.

2. The compound according to claim 1, wherein $R^2$ is selected from the group consisting of $CH_3$,

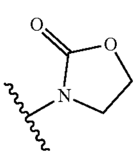
and
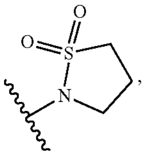

wherein

is the point of attachment to the corresponding carbon atom of the structure of Formula (I).

3. The compound according to claim 1, wherein $R^3$ is selected from the group consisting of

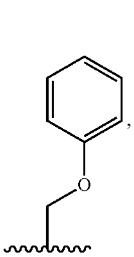
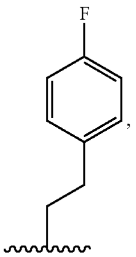
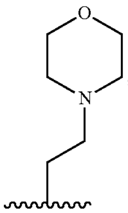
and
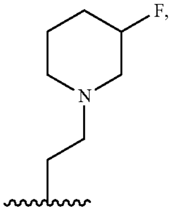

and wherein

is the point of attachment to the corresponding carbon atom of the structure of Formula (I).

4. The compound according to claim 1, wherein $R^4$ is selected from the group consisting of

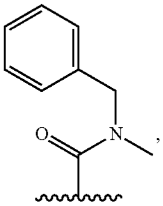
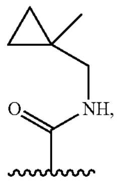
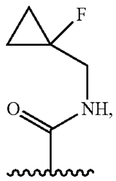
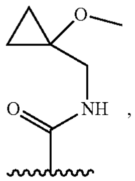
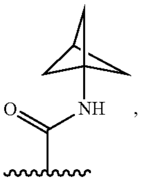
and
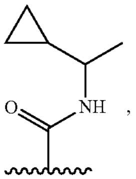

and wherein

is the point of attachment to the corresponding carbon atom of the structure of Formula (I).

5. The compound according to claim 1, wherein Z is $—CH_2—CH{=}CH—$.

6. The compound according to claim 1, wherein the compound of Formula (I) is selected from the group consisting of:
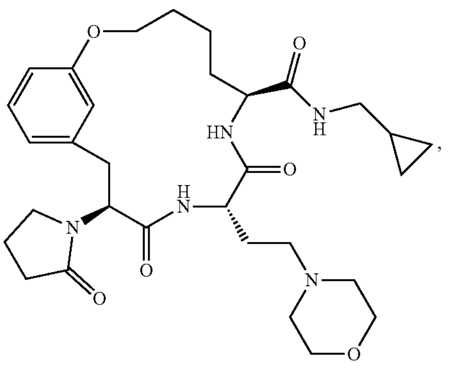
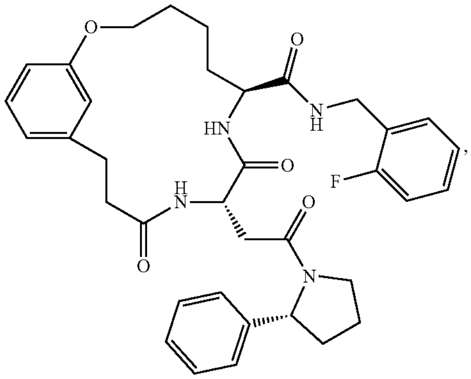
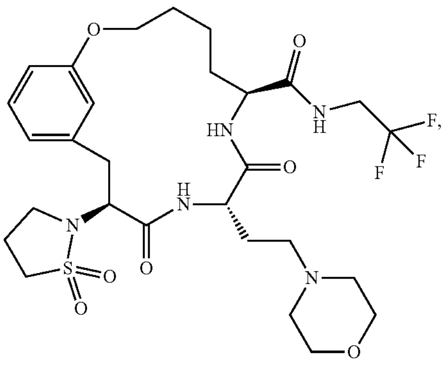
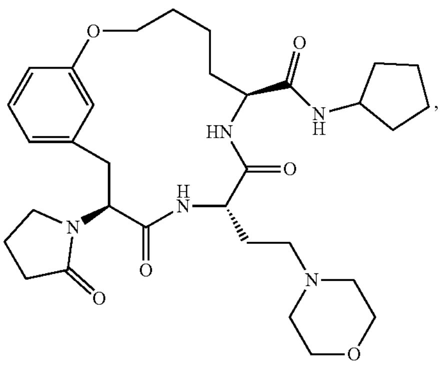
-continued
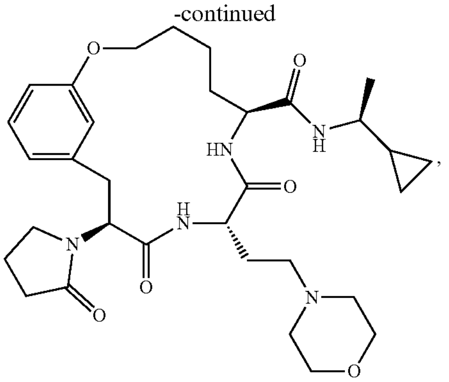
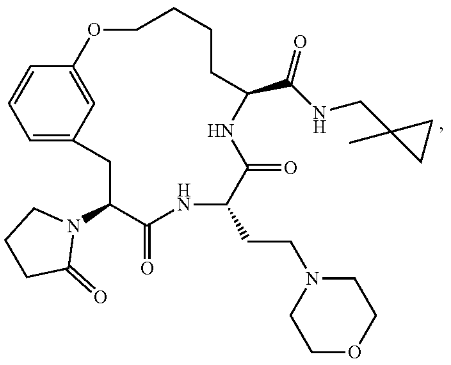
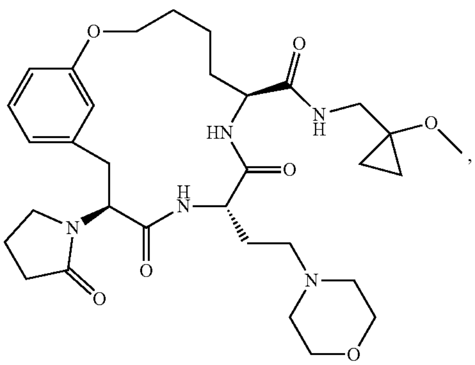
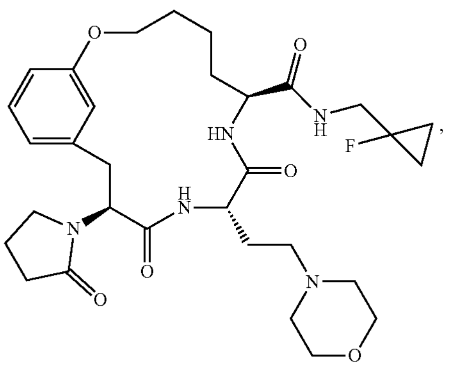

-continued
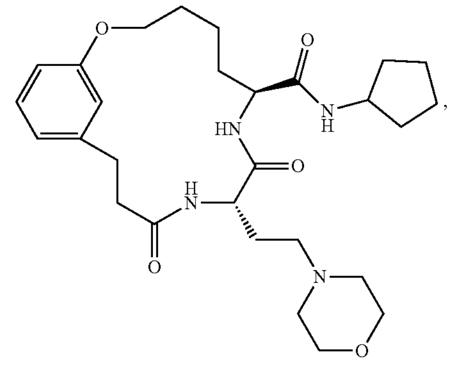
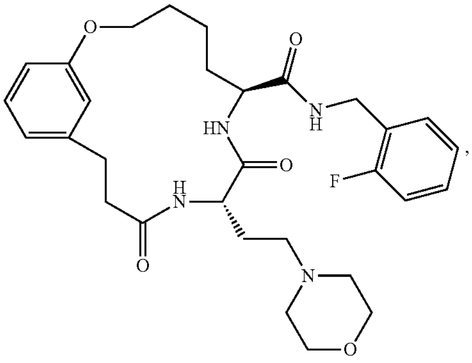
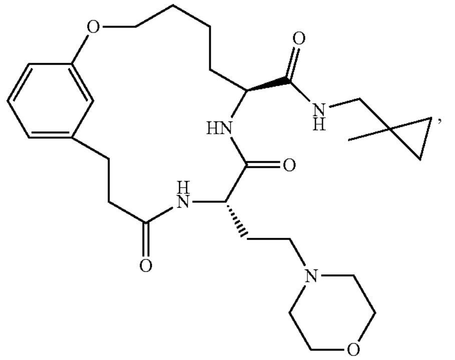
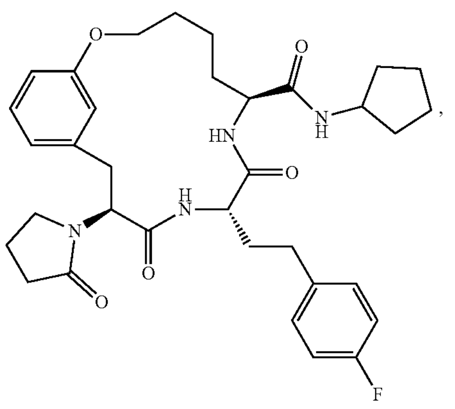
-continued
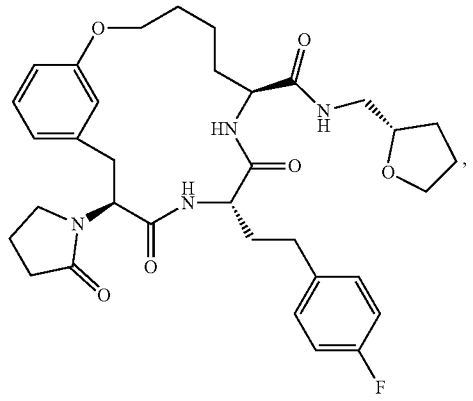
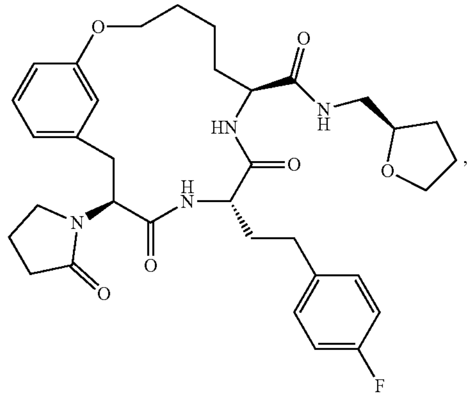
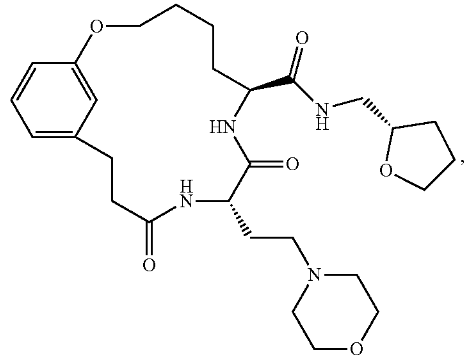
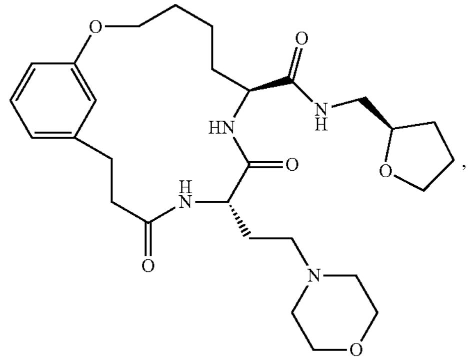

-continued
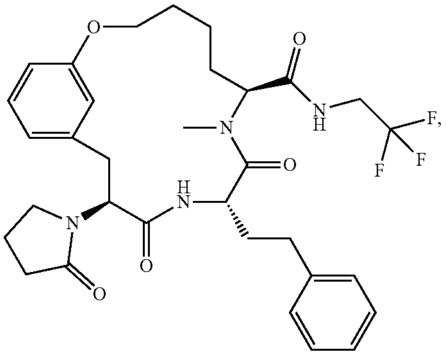
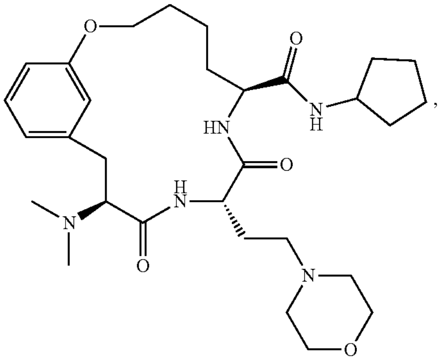
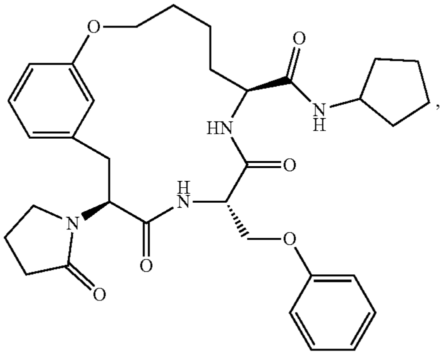
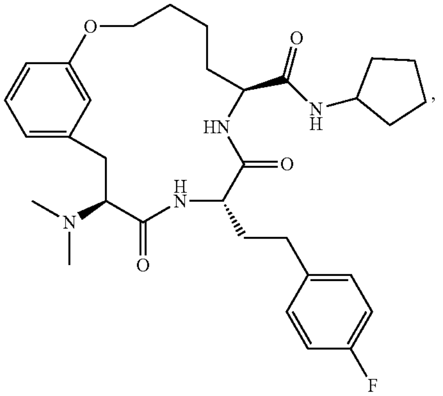
-continued
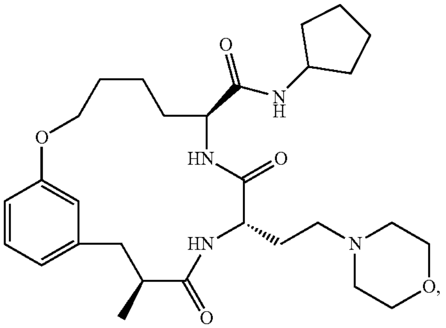
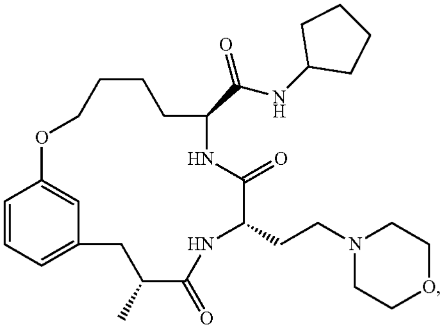
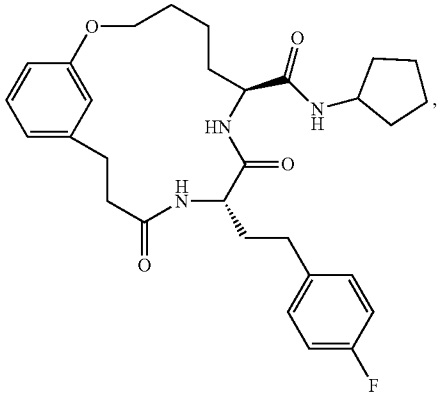
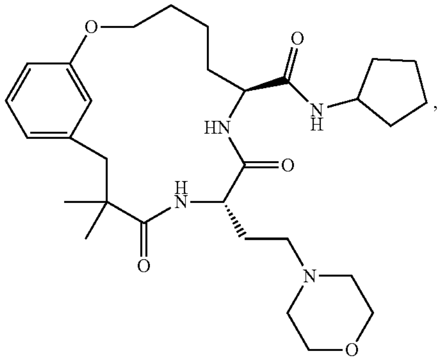

-continued
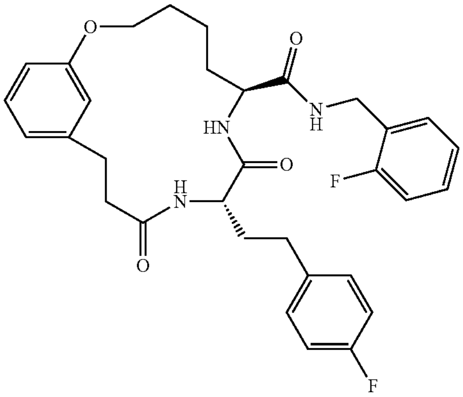
,
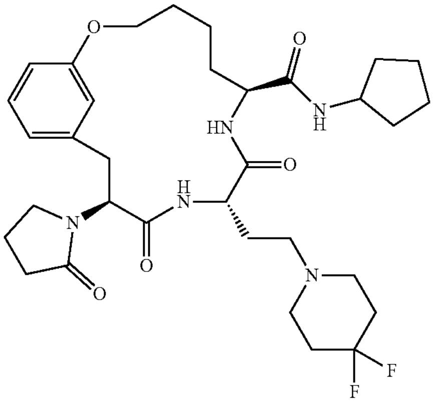
,
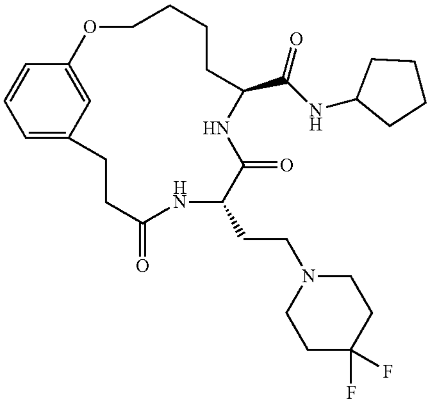
,
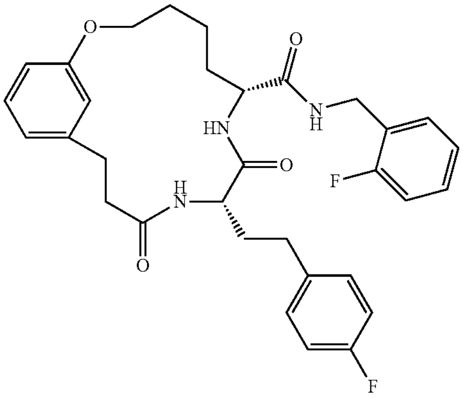
,
-continued
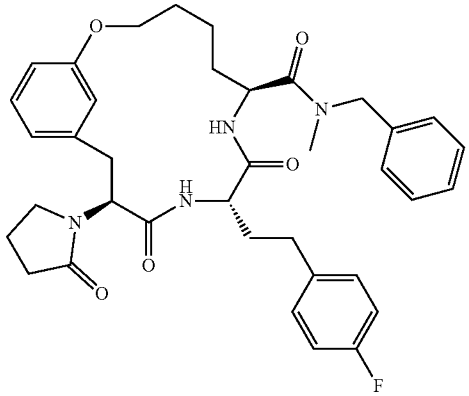
,
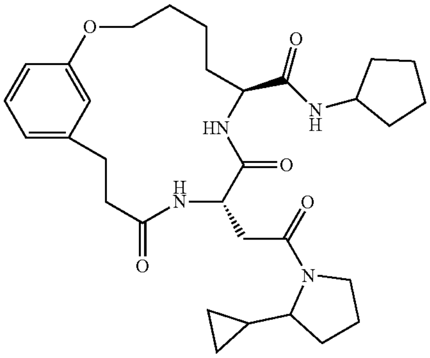
, and
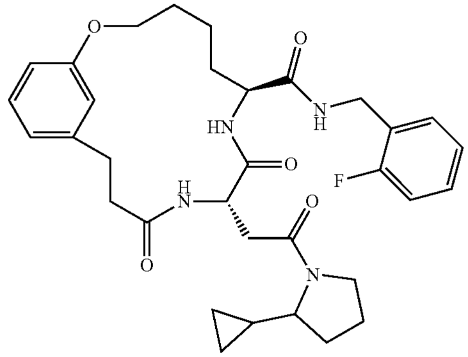
.
7. The compound according to claim 1 which has the Formula (I'):
(I')
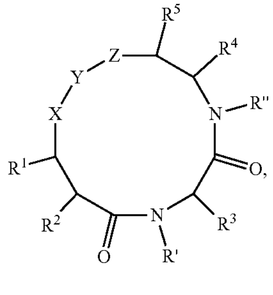

wherein

X is

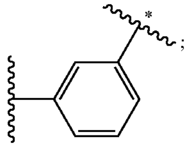 [SMILES: *c1cccc(*)c1]

Y is O;

Z is $—(CH_2)_m—$, or $—CH_2—CH_2—O—$;

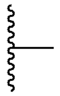

is the point of attachment to $—C(R^1)—$ moiety;

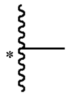

is the point of attachment to Y;

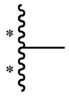

is the point of attachment to $—C(R^5)—$ moiety;

$R^1$ is H;

$R^2$ is independently selected at each occurrence thereof from the group consisting of H, arylalkyl, $—NR^6R^7$, $—NHC(O)R^8$, $—NHS(O)_2R^8$, and $—NHC(O)(CH_2)_nNR^6R^7$;

$R^3$ is independently selected at each occurrence thereof from the group consisting of $C_{1-6}$ alkyl, $—(CH_2)_nNR^6R^7$, $—CH_2C(O)NR^6R^7$, $—CH_2C(O)OH$, and arylalkyl, wherein $C_{1-6}$ alkyl can be optionally substituted from 1 to 3 times with $C_{1-6}$ alkoxy and $CF_3$;

$R^4$ is selected from the group consisting of $R^8$, $—C(O)R^8$, $—C(O)NH(CR^aR^b)_nR^8$, $—C(O)OR^8$, $—CH_2NHR^8$, and $—C(O)NR^6R^7$;

$R^5$ is H;

$R^6$ is selected from the group consisting of $C_{1-6}$ alkyl, $C_{3-8}$ cycloalkyl, and $C_{3-12}$ cycloalkylalkyl, or, wherein $C_{3-8}$ cycloalkyl and $C_{3-12}$ cycloalkylalkyl can be optionally substituted from 1 to 3 times with $CF_3$;

$R^7$ is selected from the group consisting of H, $C_{1-6}$ alkyl, $C_{3-8}$ cycloalkyl, and $C_{3-12}$ cycloalkylalkyl, or, wherein $C_{3-8}$ cycloalkyl and $C_{3-12}$ cycloalkylalkyl can be optionally substituted from 1 to 3 times with $CF_3$;

or $R^6$ and $R^7$ are taken together with the nitrogen to which they are attached to form a piperidine, pyrrolidine, or morpholine ring, wherein piperidine, pyrrolidine, or morpholine ring can be optionally substituted 1 to 3 times with halogen, $C_{1-6}$ alkyl, aryl, =O, $C_{3-8}$ cycloalkyl, or non-aromatic heterocycle;

$R^8$ is selected from the group consisting of H, OH, $CF_3$, $CHF_2$, $C_{1-12}$ alkyl, $C_{3-8}$ cycloalkyl, $C_{3-12}$ cycloalkylalkyl, monocyclic or bicyclic aryl, arylalkyl, heteroaryl, heterocyclyl, and non-aromatic heterocycle, wherein $C_{1-12}$ alkyl, monocyclic or bicyclic aryl, arylalkyl, heteroaryl, heterocyclyl, and non-aromatic heterocycle can be optionally substituted from 1 to 3 times with OH, halogen, $C_{1-6}$ alkyl, $C_{1-6}$ alkoxy, $CHF_2$, $CF_3$, $—S(O)_2Me$;

$R^a$ and $R^b$ are each independently selected from the group consisting of H and $C_{1-6}$ alkyl;

R' and R" are each independently selected from the group consisting of H and $C_{1-6}$ alkyl;

n is 0, 1, 2, 3, or 4; and m is 2, 3, 4, or 5.

8. The compound according to claim 1, wherein $R^2$ is selected from the group consisting of H,

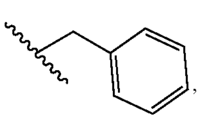, 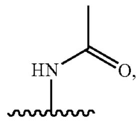, 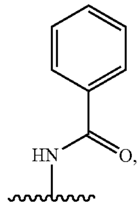, 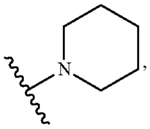, 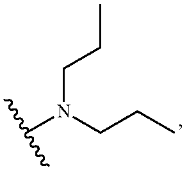, 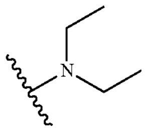, 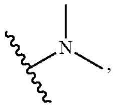, 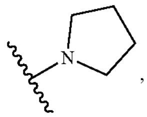, 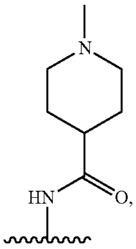, 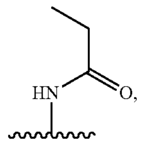, 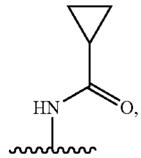, 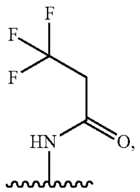, 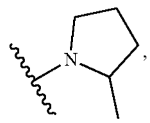, 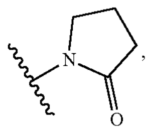, 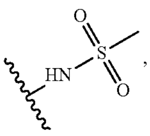, 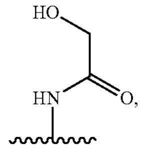, 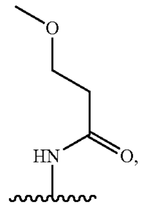, 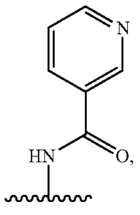, -continued

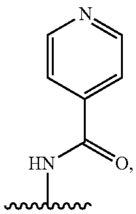, 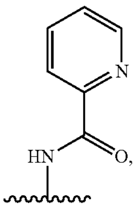, 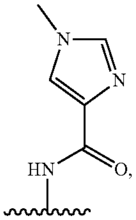,

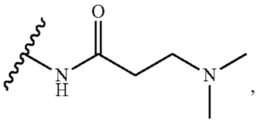, 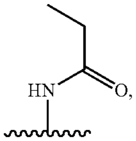,

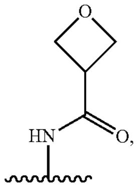, 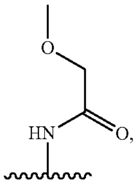, 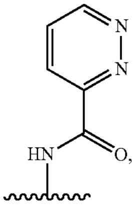, and

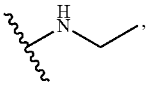 [SMILES: *NCC], wherein

is the point of attachment to the corresponding carbon atom of the structure of Formula (I).

9. The compound according to claim 1, wherein $R^3$ is selected from the group consisting of

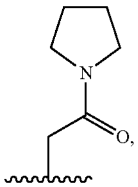, 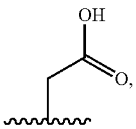, 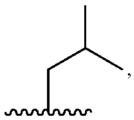, 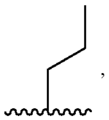,

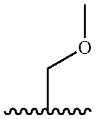, 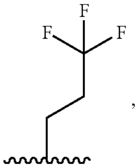, 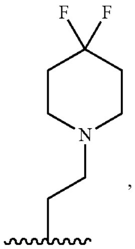, 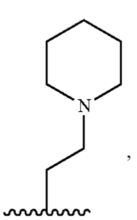,

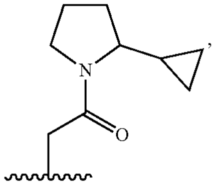, 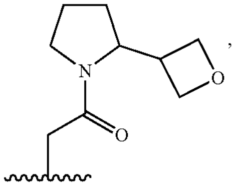,

-continued

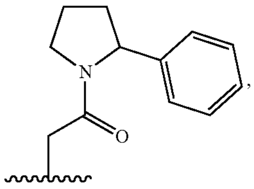, 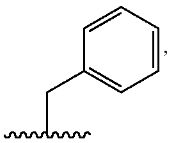, and

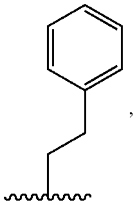, wherein

is the point of attachment to the corresponding carbon atom of the structure of Formula (I).

10. The compound according to claim 1, wherein $R^4$ is selected from the group consisting of

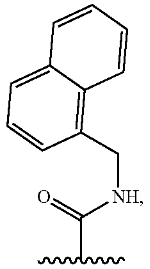, 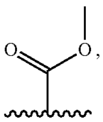, 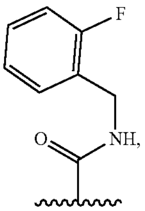,

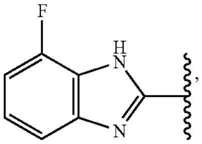, 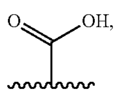, 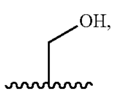,

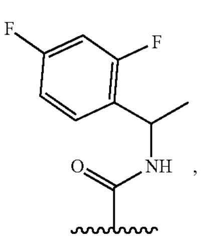, 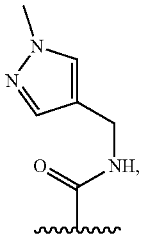, 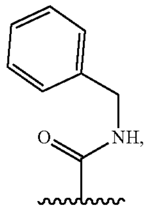,

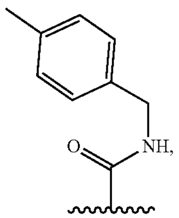, 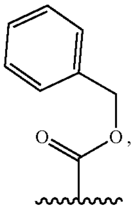, 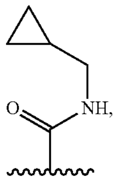

-continued
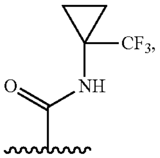 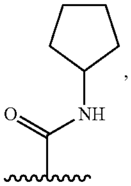, 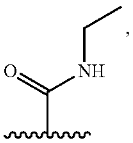,
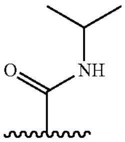, 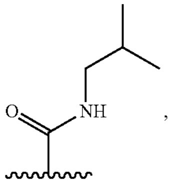, 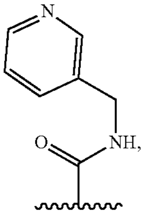
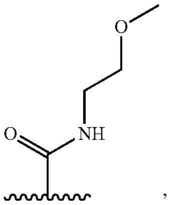, 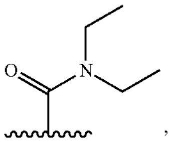, 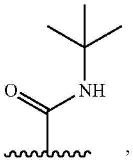,
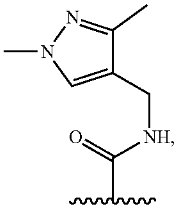 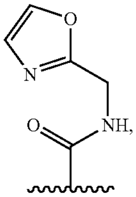 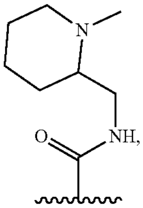
,
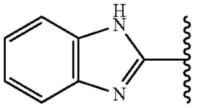 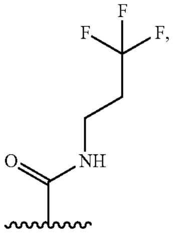
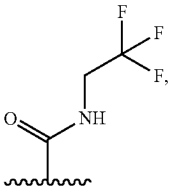 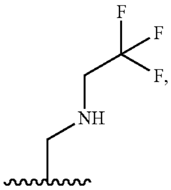 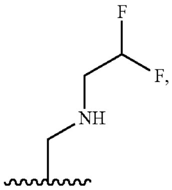
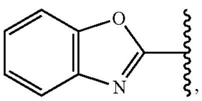 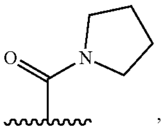,
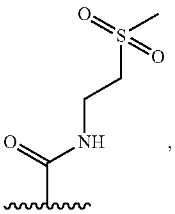, 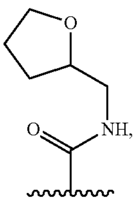 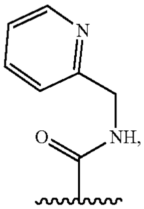
-continued
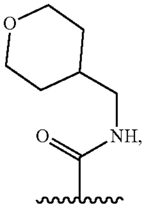 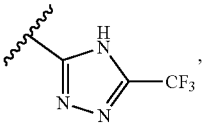,
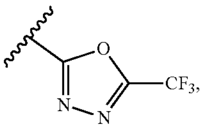 and 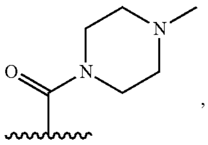,
wherein
is the point of attachment to the corresponding carbon atom of the structure of Formula (I).
11. The compound according to claim 1, wherein Z is selected from the group consisting of $-(CH_2)_3-$, and $-CH_2-CH_2-O-$.
12. The compound according to claim 1, wherein the compound of Formula (I) is selected from the group consisting of:
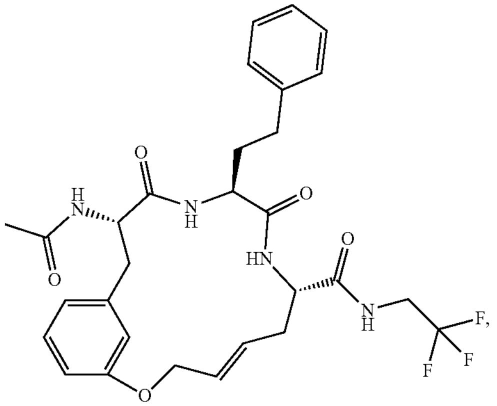
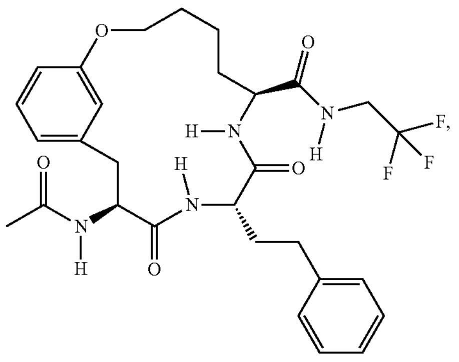

-continued
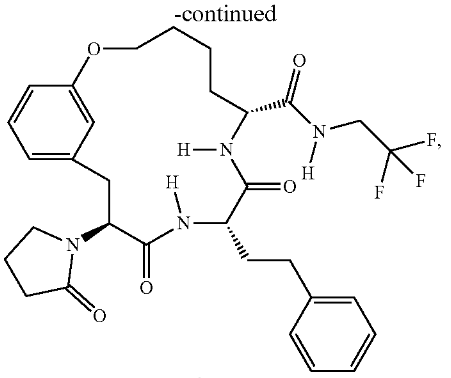
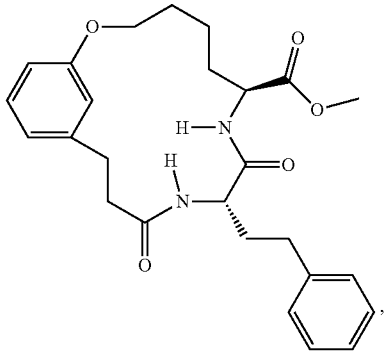
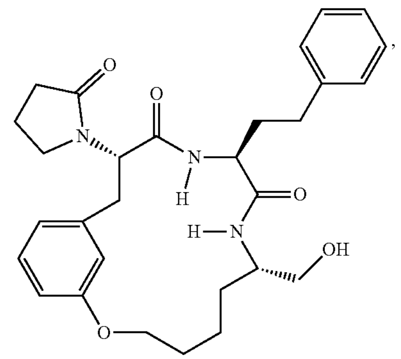
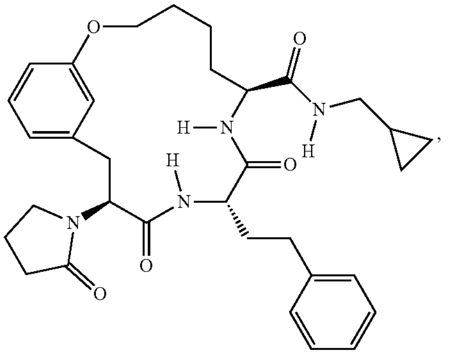
-continued
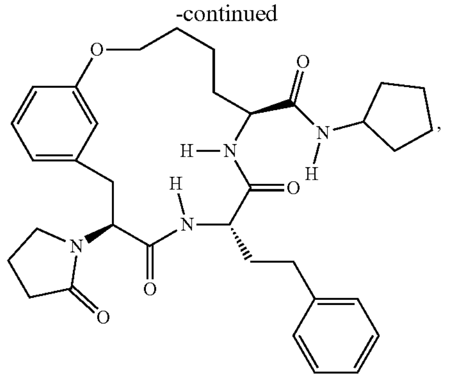
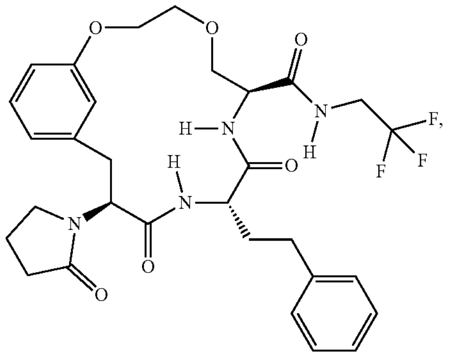
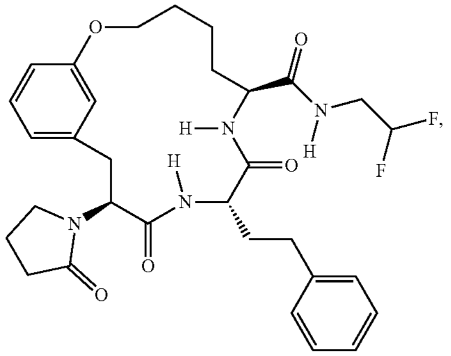
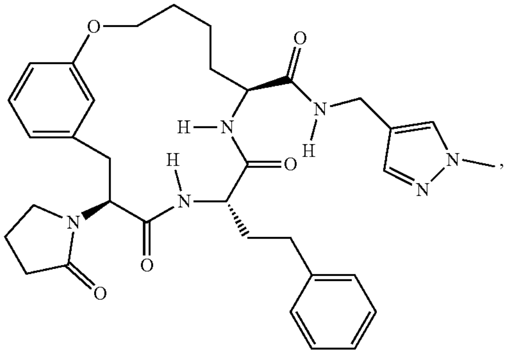

-continued
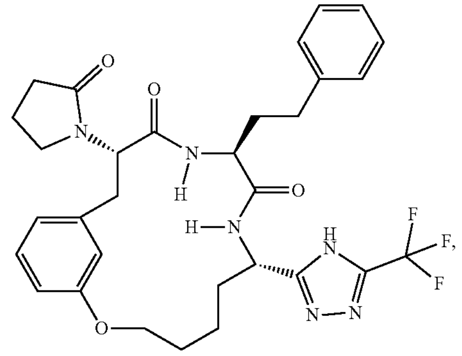
,
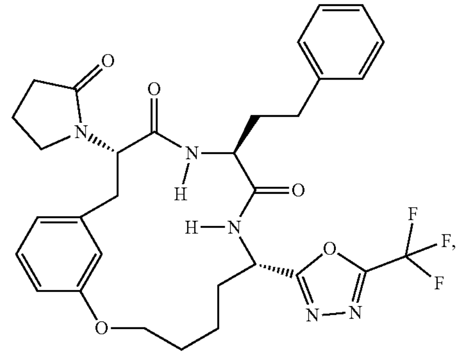
,
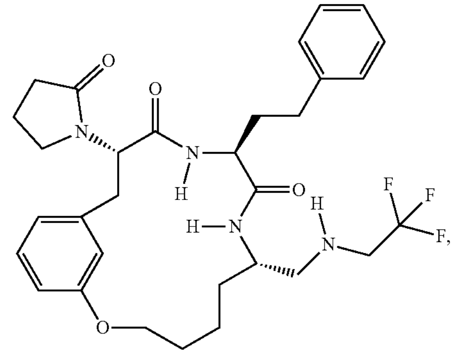
,
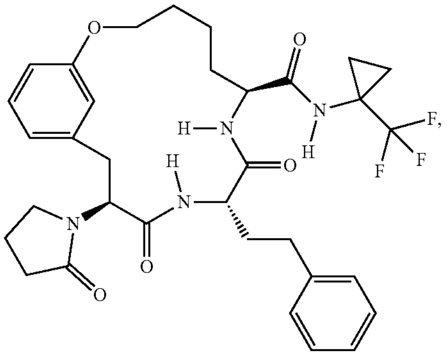
, and
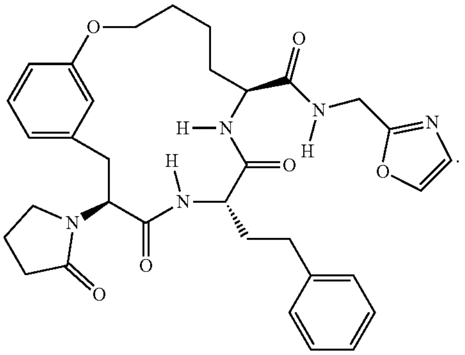
.
13. A pharmaceutical composition comprising a therapeutically effective amount of the compound according to claim 1 and a pharmaceutically acceptable carrier.
14. A compound selected from the group consisting of:
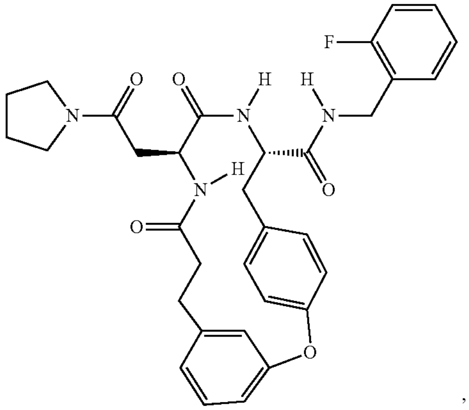
,
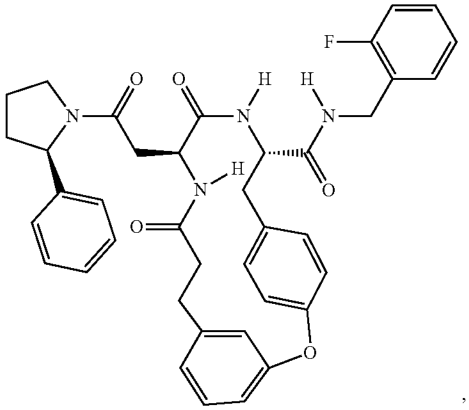
, -continued
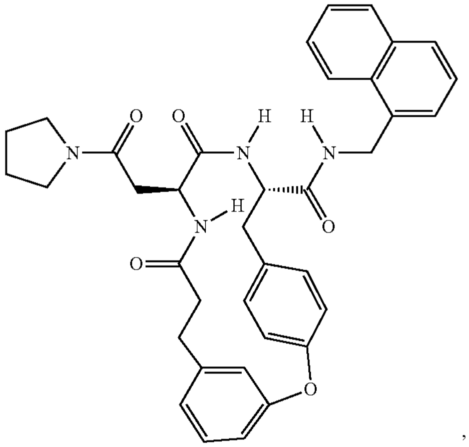
,
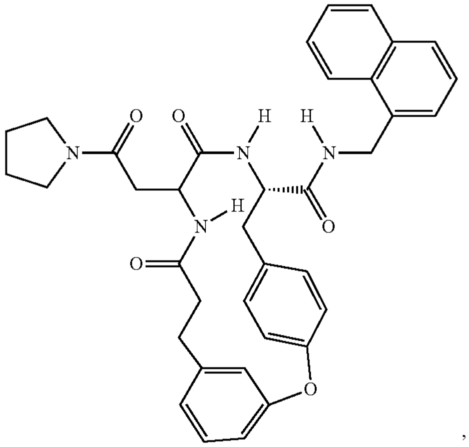
,
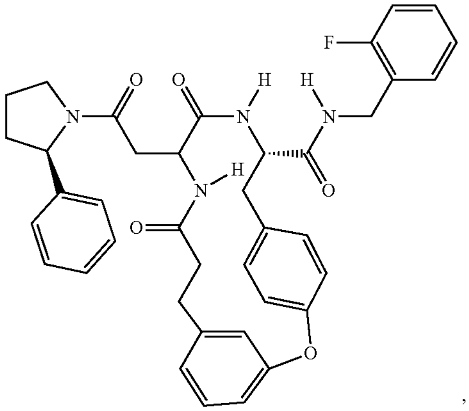
,
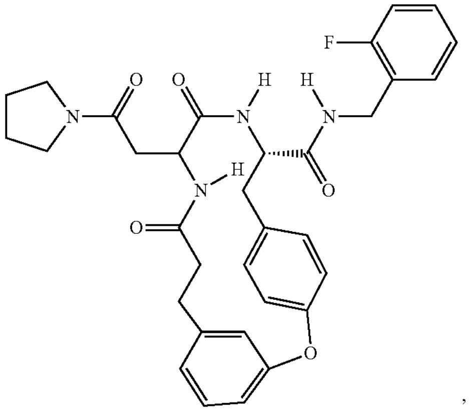
,
-continued
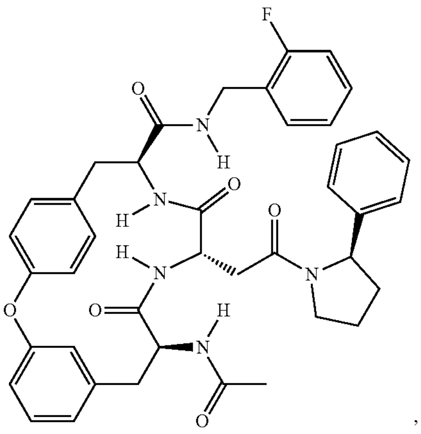
,
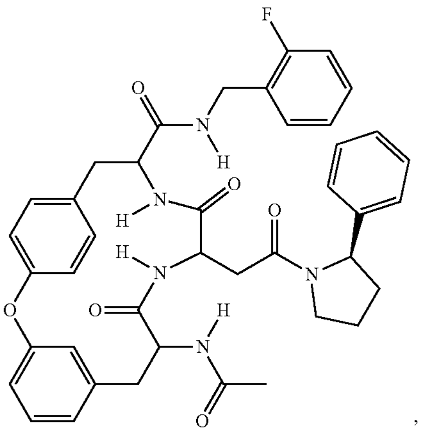
,
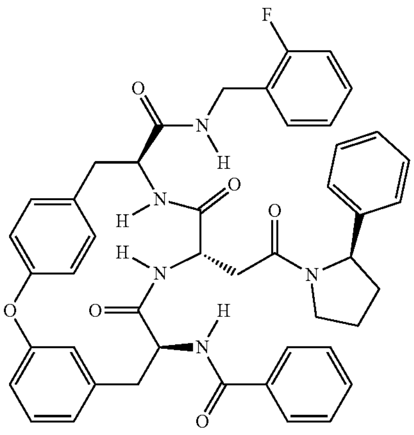
, and -continued
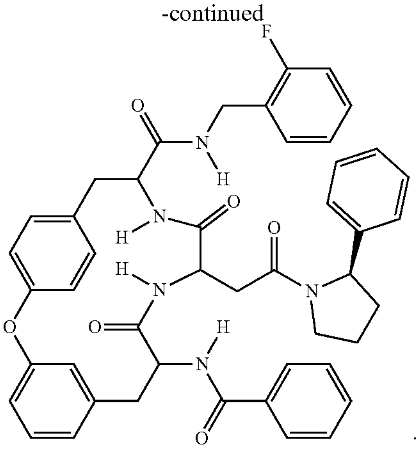
.
* * * * *